United States Patent
Benson et al.

(10) Patent No.: US 11,421,228 B2
(45) Date of Patent: *Aug. 23, 2022

(54) GENE-REGULATING COMPOSITIONS AND METHODS FOR IMPROVED IMMUNOTHERAPY

(71) Applicant: KSQ Therapeutics, Inc., Cambridge, MA (US)

(72) Inventors: Micah Benson, Cambridge, MA (US); Jason J. Merkin, Cambridge, MA (US); Gregory V. Kryukov, Cambridge, MA (US); Solomon Martin Shenker, Cambridge, MA (US); Michael R. Schlabach, Cambridge, MA (US); Noah Jacob Tubo, Cambridge, MA (US)

(73) Assignee: KSQ Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/357,400

(22) Filed: Jun. 24, 2021

(65) Prior Publication Data

US 2021/0388349 A1  Dec. 16, 2021

Related U.S. Application Data

(63) Continuation of application No. 16/791,273, filed on Feb. 14, 2020, now Pat. No. 11,111,493, which is a continuation of application No. 16/354,102, filed on Mar. 14, 2019.

(60) Provisional application No. 62/804,265, filed on Feb. 12, 2019, provisional application No. 62/768,458, filed on Nov. 16, 2018, provisional application No. 62/768,448, filed on Nov. 16, 2018, provisional application No. 62/768,428, filed on Nov. 16, 2018, provisional application No. 62/768,443, filed on Nov. 16, 2018, provisional application No. 62/692,010, filed on Jun. 29, 2018, provisional application No. 62/692,110, filed on Jun. 29, 2018, provisional
(Continued)

(51) Int. Cl.
| | |
|---|---|
| C12N 15/07 | (2006.01) |
| A61K 35/17 | (2015.01) |
| A61P 35/04 | (2006.01) |
| C12N 15/11 | (2006.01) |
| A61P 35/00 | (2006.01) |
| A61P 35/02 | (2006.01) |
| C12N 9/22 | (2006.01) |
| C12N 15/113 | (2010.01) |
| C12N 5/0783 | (2010.01) |
| C07K 16/28 | (2006.01) |
| C07K 16/32 | (2006.01) |
| C07K 14/725 | (2006.01) |
| C07K 14/705 | (2006.01) |
| A61K 38/00 | (2006.01) |
| A61K 35/12 | (2015.01) |
| A61K 39/00 | (2006.01) |

(52) U.S. Cl.
CPC ............. *C12N 15/11* (2013.01); *A61K 35/17* (2013.01); *A61P 35/00* (2018.01); *A61P 35/02* (2018.01); *A61P 35/04* (2018.01); *C07K 14/7051* (2013.01); *C07K 14/70517* (2013.01); *C07K 16/2803* (2013.01); *C07K 16/2863* (2013.01); *C07K 16/32* (2013.01); *C12N 5/0636* (2013.01); *C12N 9/22* (2013.01); *C12N 15/113* (2013.01); *C12N 15/1138* (2013.01); *A61K 38/00* (2013.01); *A61K 2035/124* (2013.01); *A61K 2039/505* (2013.01); *C07K 2317/622* (2013.01); *C07K 2319/03* (2013.01); *C07K 2319/30* (2013.01); *C12N 2310/122* (2013.01); *C12N 2310/14* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 5,126,132 A | 6/1992 | Rosenberg | |
| 5,222,982 A | 6/1993 | Ommaya | |

(Continued)

FOREIGN PATENT DOCUMENTS

| | | | |
|---|---|---|---|
| EP | 2 402 031 A1 | 1/2012 | |
| WO | WO 1990/004633 A1 | 5/1990 | |

(Continued)

OTHER PUBLICATIONS

U.S. Appl. No. 16/354,102, filed Mar. 14, 2019, Published, 2019-0284553.

(Continued)

*Primary Examiner* — Arthur S Leonard
(74) *Attorney, Agent, or Firm* — Wolf, Greenfield & Sacks, P.C.

(57) ABSTRACT

The present disclosure provides methods and compositions related to the modification of immune effector cells to increase therapeutic efficacy. In some embodiments, immune effector cells modified to reduce expression of one or more endogenous target genes, or to reduce one or more functions of an endogenous protein to enhance effector functions of the immune cells are provided. In some embodiments, immune effector cells further modified by introduction of transgenes conferring antigen specificity, such as exogenous T cell receptors (TCRs) or chimeric antigen receptors (CARs) are provided. Methods of treating a cell proliferative disorder, such as a cancer, using the modified immune effector cells described herein are also provided.

16 Claims, 27 Drawing Sheets
Specification includes a Sequence Listing.

Related U.S. Application Data application No. 62/692,100, filed on Jun. 29, 2018, provisional application No. 62/692,019, filed on Jun. 29, 2018, provisional application No. 62/643,597, filed on Mar. 15, 2018, provisional application No. 62/643,578, filed on Mar. 15, 2018, provisional application No. 62/643,587, filed on Mar. 15, 2018, provisional application No. 62/643,598, filed on Mar. 15, 2018.

(56) References Cited

U.S. PATENT DOCUMENTS

| | | | |
|---|---|---|---|
| 5,356,802 | A | 10/1994 | Chandrasegaran |
| 5,385,582 | A | 1/1995 | Ommaya |
| 5,436,150 | A | 7/1995 | Chandrasegaran |
| 5,487,994 | A | 1/1996 | Chandrasegaran |
| 5,858,358 | A | 1/1999 | June et al. |
| 5,883,223 | A | 3/1999 | Gray |
| 6,352,694 | B1 | 3/2002 | June et al. |
| 6,453,242 | B1 | 9/2002 | Eisenberg et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,962,810 | B2 | 11/2005 | Fraser et al. |
| 7,067,318 | B2 | 6/2006 | June et al. |
| 7,078,387 | B1 | 7/2006 | Leiden et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| RE39,788 | E | 8/2007 | Anderson et al. |
| 7,691,997 | B2 | 4/2010 | Khvorova et al. |
| 8,034,334 | B2 | 10/2011 | Dudley et al. |
| 8,287,857 | B2 | 10/2012 | Dudley et al. |
| 8,324,369 | B2 | 12/2012 | Chen |
| 8,383,099 | B2 | 2/2013 | Dudley et al. |
| 8,637,307 | B2 | 1/2014 | June et al. |
| 8,697,359 | B1 | 4/2014 | Zhang |
| 8,894,996 | B2 | 11/2014 | Akira et al. |
| 9,074,185 | B2 | 7/2015 | Dudley et al. |
| 9,233,125 | B2 | 1/2016 | Davila et al. |
| 9,597,357 | B2 | 3/2017 | Gregory et al. |
| 9,624,279 | B2 | 4/2017 | Nonaka et al. |
| 9,683,048 | B2 | 6/2017 | Freeman et al. |
| 9,782,437 | B2 | 10/2017 | Holmes et al. |
| 9,944,331 | B2 | 4/2018 | Weston |
| 10,125,361 | B2 | 11/2018 | May et al. |
| 10,130,659 | B2 | 11/2018 | Wardell et al. |
| 10,166,257 | B2 | 1/2019 | Wardell et al. |
| 10,266,850 | B2 | 4/2019 | Doudna et al. |
| 10,272,113 | B2 | 4/2019 | Wardell et al. |
| 10,286,066 | B2 | 5/2019 | Riley et al. |
| 10,363,273 | B2 | 7/2019 | Wardell et al. |
| 10,398,734 | B2 | 9/2019 | Wardell et al. |
| 10,420,799 | B2 | 9/2019 | Wardell et al. |
| 10,463,697 | B2 | 11/2019 | Wardell et al. |
| 10,537,595 | B2 | 1/2020 | Wardell et al. |
| 11,111,493 | B2 | 9/2021 | Benson et al. |
| 2003/0147869 | A1 | 8/2003 | Riley et al. |
| 2005/0233451 | A1 | 10/2005 | Liu et al. |
| 2006/0121005 | A1 | 6/2006 | Berenson et al. |
| 2007/0254842 | A1 | 11/2007 | Bankiewicz |
| 2008/0081064 | A1 | 4/2008 | Jelle et al. |
| 2009/0196903 | A1 | 8/2009 | Kliman |
| 2011/0052530 | A1 | 3/2011 | Dudley et al. |
| 2013/0287748 | A1 | 10/2013 | June et al. |
| 2014/0357530 | A1 | 12/2014 | Zhang et al. |
| 2015/0238631 | A1 | 8/2015 | Kim et al. |
| 2016/0083449 | A1 | 3/2016 | Schmitt et al. |
| 2016/0083728 | A1 | 3/2016 | Hu et al. |
| 2016/0175462 | A1 | 6/2016 | Zhang et al. |
| 2016/0237455 | A1 | 8/2016 | Glucksmann et al. |
| 2016/0251648 | A1 | 9/2016 | Wang et al. |
| 2016/0272965 | A1 | 9/2016 | Zhang et al. |
| 2016/0298096 | A1 | 10/2016 | Charpentier et al. |
| 2016/0355795 | A1 | 12/2016 | Ran et al. |
| 2016/0362464 | A1 | 12/2016 | Ghosh |
| 2016/0368995 | A1 | 12/2016 | Zlotnik et al. |
| 2017/0044496 | A1 | 2/2017 | Sarnaik et al. |
| 2017/0081635 | A1 | 3/2017 | Sarnaik et al. |
| 2017/0114413 | A1 | 4/2017 | Hahn et al. |
| 2017/0136063 | A1 | 5/2017 | Perez et al. |
| 2017/0152478 | A1 | 6/2017 | Rosenberg et al. |
| 2017/0152528 | A1 | 6/2017 | Zhang |
| 2017/0175128 | A1 | 6/2017 | Welstead et al. |
| 2017/0204407 | A1 | 7/2017 | Gilbert et al. |
| 2017/0224733 | A1 | 8/2017 | Badie et al. |
| 2017/0224734 | A1 | 8/2017 | Chapman et al. |
| 2017/0321214 | A1 | 11/2017 | Zhang et al. |
| 2018/0051347 | A1 | 2/2018 | Ribas et al. |
| 2018/0057810 | A1 | 3/2018 | Zhang et al. |
| 2018/0100201 | A1 | 4/2018 | Garraway et al. |
| 2018/0104354 | A1 | 4/2018 | Kim et al. |
| 2018/0112213 | A1 | 4/2018 | Welstead et al. |
| 2018/0112255 | A1 | 4/2018 | Chen et al. |
| 2018/0119174 | A1 | 5/2018 | Scharenberg et al. |
| 2018/0127715 | A1 | 5/2018 | Veerapathran et al. |
| 2018/0207201 | A1 | 7/2018 | Wardell et al. |
| 2018/0228841 | A1 | 8/2018 | Frank et al. |
| 2018/0255751 | A1 | 9/2018 | Regev et al. |
| 2018/0265531 | A1 | 9/2018 | Tremblay et al. |
| 2018/0273935 | A1 | 9/2018 | Lane et al. |
| 2018/0280436 | A1 | 10/2018 | Wardell et al. |
| 2018/0282694 | A1 | 10/2018 | Wardell et al. |
| 2018/0289771 | A1 | 10/2018 | Shan et al. |
| 2018/0298340 | A1 | 10/2018 | Zhao et al. |
| 2018/0325954 | A1 | 11/2018 | Wardell et al. |
| 2019/0106679 | A1 | 4/2019 | Regev et al. |
| 2019/0177693 | A1 | 6/2019 | Sarnaik et al. |
| 2019/0233814 | A1 | 8/2019 | Zhang et al. |
| 2019/0284553 | A1 | 9/2019 | Benson et al. |
| 2019/0345445 | A1 | 11/2019 | Veerapathran et al. |
| 2019/0358259 | A1 | 11/2019 | Wardell et al. |
| 2019/0358260 | A1 | 11/2019 | Wardell et al. |
| 2019/0358261 | A1 | 11/2019 | Wardell et al. |
| 2019/0388469 | A1 | 12/2019 | Marson et al. |
| 2020/0016202 | A1 | 1/2020 | Kuchroo et al. |
| 2020/0181610 | A1 | 6/2020 | Benson et al. |
| 2020/0347386 | A1 | 11/2020 | Benson et al. |
| 2020/0352999 | A1 | 11/2020 | Rao et al. |
| 2021/0071139 | A1 | 3/2021 | Wherry et al. |

FOREIGN PATENT DOCUMENTS

| | | |
|---|---|---|
| WO | WO 1994/028938 A1 | 12/1994 |
| WO | WO 1995/000655 A1 | 1/1995 |
| WO | WO 1995/011984 A2 | 5/1995 |
| WO | WO 1997/015669 A1 | 5/1997 |
| WO | WO 2001/035990 A2 | 5/2001 |
| WO | WO 2002/088346 A2 | 11/2002 |
| WO | WO 2003/057171 A2 | 7/2003 |
| WO | WO 2007/037780 A3 | 8/2007 |
| WO | WO 2007/103901 A3 | 4/2008 |
| WO | WO 2008/099088 A3 | 11/2008 |
| WO | WO 2009/069668 A1 | 6/2009 |
| WO | WO 2009/139921 A3 | 9/2010 |
| WO | WO 2010/138755 A1 | 12/2010 |
| WO | WO 2011/005566 A2 | 1/2011 |
| WO | WO 2012/127464 A3 | 3/2013 |
| WO | WO 2013/059343 A1 | 4/2013 |
| WO | WO 2014/055657 A1 | 4/2014 |
| WO | WO 2014/066137 A1 | 5/2014 |
| WO | WO 2014/201378 A9 | 1/2015 |
| WO | WO 2014/201021 A3 | 2/2015 |
| WO | WO 2015/039100 A1 | 3/2015 |
| WO | WO 2015/071474 A2 | 5/2015 |
| WO | WO 2015/090229 A1 | 6/2015 |
| WO | WO 2015/142675 A2 | 9/2015 |
| WO | WO 2015/154065 A1 | 10/2015 |

(56) References Cited

FOREIGN PATENT DOCUMENTS

| | | |
|---|---|---|
| WO | WO 2015/161276 A2 | 10/2015 |
| WO | WO 2015/188228 A1 | 12/2015 |
| WO | WO 2016/073748 A1 | 5/2016 |
| WO | WO 2016/106236 A1 | 6/2016 |
| WO | WO 2016/179283 A1 | 11/2016 |
| WO | WO 2016/191756 A1 | 12/2016 |
| WO | WO 2017/008019 A1 | 1/2017 |
| WO | WO 2017/015427 A1 | 1/2017 |
| WO | WO 2017/069958 A2 | 4/2017 |
| WO | WO 2017/070042 A1 | 4/2017 |
| WO | WO 2017/075465 A1 | 5/2017 |
| WO | WO 2017/076602 A1 | 5/2017 |
| WO | WO 2017/079113 A1 | 5/2017 |
| WO | WO 2017/120996 A1 | 7/2017 |
| WO | WO 2017/120998 A1 | 7/2017 |
| WO | WO 2017/140632 A1 | 8/2017 |
| WO | WO 2017/143171 A1 | 8/2017 |
| WO | WO 2017/156484 A1 | 9/2017 |
| WO | WO 2017/158153 A1 | 9/2017 |
| WO | WO 2017/174649 A1 | 10/2017 |
| WO | WO 2017/178572 A1 | 10/2017 |
| WO | WO 2017/191504 A1 | 11/2017 |
| WO | WO 2017/210677 A1 | 12/2017 |
| WO | WO 2018/005556 A1 | 1/2018 |
| WO | WO 2018/005559 A1 | 1/2018 |
| WO | WO 2018/006880 A1 | 1/2018 |
| WO | WO 2018/009894 A1 | 1/2018 |
| WO | WO 2018/013929 A1 | 1/2018 |
| WO | WO 2018/024895 A1 | 2/2018 |
| WO | WO 2018/035423 A1 | 2/2018 |
| WO | WO 2018/039333 A1 | 3/2018 |
| WO | WO 2018/049025 A2 | 3/2018 |
| WO | WO 2018/049226 A1 | 3/2018 |
| WO | WO 2018/053463 A1 | 3/2018 |
| WO | WO 2018/057447 A1 | 3/2018 |
| WO | 2018/071796 A2 | 4/2018 |
| WO | 2018/071873 A2 | 4/2018 |
| WO | WO 2018/064208 A1 | 4/2018 |
| WO | WO 2018/067991 A1 | 4/2018 |
| WO | WO 2018/075541 A1 | 4/2018 |
| WO | WO 2018/075664 A1 | 4/2018 |
| WO | WO 2018/081473 A1 | 5/2018 |
| WO | WO 2018/081476 A2 | 5/2018 |
| WO | WO 2018/081784 A1 | 5/2018 |
| WO | WO 2018/081789 A1 | 5/2018 |
| WO | WO 2018/085731 A2 | 5/2018 |
| WO | WO 2018/089518 A1 | 5/2018 |
| WO | WO 2018/089780 A1 | 5/2018 |
| WO | WO 2018/094167 A1 | 5/2018 |
| WO | WO 2018/120998 A1 | 7/2018 |
| WO | WO 2018/126205 A1 | 7/2018 |
| WO | WO 2018/129332 A1 | 7/2018 |
| WO | WO 2018/129336 A1 | 7/2018 |
| WO | WO 2018/137293 A1 | 8/2018 |
| WO | WO 2018/137295 A1 | 8/2018 |
| WO | WO 2018/148378 A1 | 8/2018 |
| WO | WO 2018/156886 A1 | 8/2018 |
| WO | WO 2018/182817 A1 | 10/2018 |
| WO | WO 2018/204761 A1 | 11/2018 |
| WO | WO 2018/209115 A1 | 11/2018 |
| WO | WO 2018/226714 A1 | 12/2018 |
| WO | WO 2019/036815 A1 | 2/2019 |
| WO | WO 2019/057102 A1 | 3/2019 |
| WO | WO 2018/081789 A8 | 5/2019 |
| WO | WO 2019/100023 A1 | 5/2019 |
| WO | WO 2019/104245 A1 | 5/2019 |
| WO | WO 2019/118873 A2 | 6/2019 |
| WO | WO 2019/136456 A1 | 7/2019 |
| WO | WO 2019/136459 A1 | 7/2019 |
| WO | WO 2019/190579 A1 | 10/2019 |
| WO | WO 2019/200306 A1 | 10/2019 |
| WO | WO 2019/210131 A1 | 10/2019 |
| WO | WO 2019/217753 A1 | 11/2019 |
| WO | WO 2019/235581 A1 | 12/2019 |
| WO | WO 2019/236681 A1 | 12/2019 |
| WO | WO 2019/236982 A1 | 12/2019 |
| WO | WO 2019/236998 A1 | 12/2019 |
| WO | WO 2019/246513 A1 | 12/2019 |
| WO | WO 2020/025706 A1 | 2/2020 |
| WO | WO 2020/061429 A1 | 3/2020 |
| WO | WO 2020/163365 A2 | 8/2020 |

OTHER PUBLICATIONS

PCT/US2019/022365, Aug. 7, 2019, International Search Report and Written Opinion.

PCT/US2019/022365, Sep. 24, 2020, International Preliminary Report on Patentability.

International Search Report and Written Opinion for PCT International Patent Application No. PCT/US2019/022365, dated Aug. 7, 2019.

International Preliminary Report on Patentability for Application No. PCT/US2019/022365, dated Sep. 24, 2020.

Abudayyeh et al., RNA targeting with CRISPR-Cas13. Nature (2017); 550(7675): 280-284. Epub Oct. 4, 2017.

Ahmed, et al., Human Epidermal Growth Factor Receptor 2 (HER2)-Specific Chimeric Antigen Receptor-Modified T Cells for the Immunotherapy of HER2-Positive Sarcoma. J Clin Oncol. (2015); 33(15): 1688-1696. Epub Mar. 23, 2015.

Ahmed, et al., Immunotherapy for osteosarcoma: genetic modification of T cells overcomes low levels of tumor antigen expression. Mol Ther. (2009); 17(10): 1779-1787. Epub Jun. 16, 2009.

Akira, Regnase-1, a Ribonuclease Involved in the Regulation of Immune Responses, Cold Spring Harbor Symposia on Quantitative Biology, 2013, vol. LXXVIII, pp. 51-60.

Akira, Shizuo, The endoribonuclease Regnase-1: key molecule in inflammatory and immune responses, Mar. 2019, Proceedings for the 92nd Annual Meeting of the Japanese Pharmacological Society, 1 page.

Ali, et al., Adeno-associated virus gene transfer to mouse retina. Hum Gene Ther. (1998); 9(1): 81-86.

Ali, et al., Bhattacharya SS. Gene transfer into the mouse retina mediated by an adeno-associated viral vector. Hum Mol Genet. (1996); 5(5): 591-594.

Altschul et al., Basic local alignment search tool. J Mol Biol. (1990); 215 (3): 403-410.

Altschul et al., Gapped BLAST and PSI-BLAST: a new generation of protein database search programs. Nucleic Acids Res. (1997); 25 (17): 3389-3402.

Aquino-Jarquin, Emerging role of CRISPR/Cas9 Technology for mRNAs Editing in Cancer Research, Cancer Research, 2017, vol. 77, No. 24, 7 pages.

Ashwood-Smith et al., Preservation of mouse bone marrow at -79 degrees C. with dimethyl sulphoxide. Nature (1961); 190: 1204-1205.

Ausubel et al., (eds.), DNA sequencing, Current Protocols in Molecular Biology (2003), Chapter 7, Supplement 47, p. 7.0.1-7.7.23; Contributed by Slatko, et al., Current Protocols in Molecular Biology (1999) 7.1.1-7.1.7, 163 pages.

Balazs and Godbey, Liposomes for Use in Gene Delivery. Journal of Drug Delivery (2011); Article ID 326497, 12 pages.

Balciunas et al., Harnessing a High Cargo-Capacity Transposon for Genetic Applications in Vertebrates. PLoS Genet. (Nov. 2006); 2(11): e169. Published online Nov. 10, 2006. Prepublished online Aug. 28, 2006.

Baumjohann et al., Posttranscriptional Gene Regulation of T Follicular Helper Cells by RNA-Binding Proteins and microRNAs, Frontiers in Immunology, Jul. 2018, vol. 9, Article 1794, 9 pages.

Beerli and Barbas, III, Engineering polydactyl zinc-finger transcription factors. Nat Biotechnol. (2002); 20(2): 135-141.

Behrens et al., A Translational Silencing Function of MCPIP1/Regnase-1 Specified by the Target Site Context, Nucleic Acids Research, 2018, 15 pages.

Belfort et al., Homing endonucleases: keeping the house in order. Nucleic Acids Res. (1997); 25(17): 3379-3788.

Bennett et al., Real-time, noninvasive in vivo assessment of adeno-associated virus-mediated retinal transduction. Invest Ophthalmol Vis Sci. (1997); 38(13): 2857-2863.

(56) References Cited

OTHER PUBLICATIONS

Bitinaite, et al., FokI dimerization is required for DNA cleavage. Proc. Natl. Acad. Sci. U.S.A. (1998); 95(18): 10570-10575.

Bitter et al., Expression and secretion vectors for yeast. Methods Enzymol. (1987); 153 (33): 516-544.

Blaeschke et al., TIM-3 Expression on CD4+ Bone Marrow T Cells Predicts Relapse of Pediatric B-Precursor Acute Lymphoblastic Leukemia, Blood, Nov. 29, 2018, vol. 132, Issue Supplement 1, 6 pages.

Bondanza et al., Suicide gene therapy of graft-versus-host disease induced by central memory human T lymphocytes. Blood (2006); 107(5): 1828-1836. Epub Nov. 17, 2005.

Bonini et al., HSV-TK gene transfer into donor lymphocytes for control of allogeneic graft-versus- leukemia. Science (1997); 276 (5319): 1719-1724.

Boratyn, MCPIP1 Exogenous Overexpression Inhibits Pathways Regulating MYCN Oncoprotein Stability in Neuroblastoma, 2017, Journal of Cellular Biochemistry, 118(7), 1741-1755. doi:10.1002/jcb.25832.

Borras et al., Adenoviral reporter gene transfer to the human trabecular meshwork does not alter aqueous humor outflow. Relevance for potential gene therapy of glaucoma. Gene Ther. (1999); 6(4): 515-524.

Brady, MCPIP1 (Zc3h12a) keeps inflammation in check by cleaving 3' UTRs, Immunology and Cell Biology, 2013, vol. 91, pp. 331-332.

Brown, et al., Bioactivity and Safety of IL13R?2-Redirected Chimeric Antigen Receptor CD8+ T Cells in Patients with Recurrent Glioblastoma. Clin Cancer Res. (2015); 21(18): 4062-4072. Epub Jun. 9, 2015.

Brudno and Kochenderfer, Chimeric antigen receptor T-cell therapies for lymphoma. Nat Rev Clin Oncol. (2018); 15 (1): 31-46. Epub Aug. 31, 2017.

Bugara et al., MCPIP1 contributes to the inflammatory response of UVB-treated keratinocytes, Journal of Dermatological Science, 2017, vol. 87, pp. 10-18.

Caruana et al., Heparanase promotes tumor infiltration and antitumor activity of CAR-redirected T lymphocytes. Nat Med. (2015); 21(5): 524-529. Epub Apr. 13, 2015.

Casucci and Bondanza, Suicide Gene Therapy to Increase the Safety of Chimeric Antigen Receptor-Redirected T Lymphocytes. Journal of Cancer (2011); 2: 378-382. Epub Jul. 1, 2011.

Cermak et al., Efficient design and assembly of custom TALEN and other TAL effector-based constructs for DNA targeting. Nucleic Acids Res. (2011); 39(12): e82. Epub Apr. 14, 2011.

Champlin et al., Selection of Autologous or Allogeneic Transplantation. Cancer Medicine. 6th ed. Kufe et al., eds. Hamilton, ON. BC Decker. 2003. 1 page.

Chen et al. MCPIP1 negatively regulate cellular antiviral innate immune responses through DUB and disruption ofTRAF3-TBK1-IKK£ complex, Biochemical and Biophysical Research Communications, 2018, vol. 503, pp. 830-836.

Chen et al., Dynamic imaging of genomic loci in living human cells by an optimized CRISPR/Cas system. Cell (2013); 155(7): 1479-1491.

Chen, et al., NR4A transcription factors limit CAR T cell function in solid tumours. NR4A transcription factors limit CAR T cell function in solid tumours. Nature (2019); 567: 530-534.

Choo, et al., Advances in zinc finger engineering. Curr. Opin. Struct. Biol. (2000); 10: 411-416.

Chylinski et al., The tracrRNA and Cas9 families of type II CRISPR-Cas immunity systems. RNA Biol. (2013); 10(5): 726-737. Epub Apr. 5, 2013.

Cianciotti et al., Generation of Memory Stem T Cells Specific for Tumor Antigens and Resistant to Inhibitory Signals by Genome Editing, Blood, Nov. 29, 2018, vol. 132, Supplement 1, 6 pages.

Ciceri et al., Antitumor effects of HSV-TK-engineered donor lymphocytes after allogeneic stem-cell transplantation. Blood. (2007); 109 (11): 4698-4707. Epub Feb. 27, 2007.

Cifuentes et al., ZC3H12A (MCPIP1): Molecular characteristics and clinical implications, Clinica Chimica Acta, 2010, vol. 411, pp. 1862-1868.

Cox et al., RNA editing with CRISPR-Cas13. Science (2017); 358(6366): 1019-1027. Epub Oct. 25, 2017.

Cui et al., Regnase-1 and Roquin Nonredundantly Regulate Th1 Differentiation Causing Cardiac Inflammation and Fibrosis, The Journal of Immunology, 2017, vol. 199, pp. 4066-4077.

De Lavallade et al., Tyrosine kinase inhibitors impair B-cell immune responses in CML through off-target inhibition of kinases important for cell signaling. Blood (2013);122: 227-238. Epub May 29, 2013.

Debets, et al., TCR-engineered T cells to treat tumors: Seeing but not touching? Semin Immunol. (2016); 28(1): 10-21. Epub Mar. 17, 2016.

Deltcheva, et al., CRISPR RNA maturation by trans-encoded small RNA and host factor RNase III. Nature (2011); 471(7340): 602-607.

Dempsey, Regnase-1 in the TME, Nature, 2019, vol. 576, pp. 471-476.

Deveau, et al., Phage response to CRISPR-encoded resistance in *Streptococcus thermophilus*. J Bacteriol. (2008); 190(4): 1390-1400. Epub Dec. 7, 2007.

Dobosz, MCPIP-1, Alias Regnase-1, Controls Epithelial Inflammation by Posttranscriptional Regulation of IL-8 Production, 2016, J Innate Immun., 8(6):564-578. doi: 10.1159/000448038.

Esvelt et al., A system for the continuous directed evolution of biomolecules. Nature (2011); 472(7344): 499-503. Epub Apr. 10, 2011.

Esvelt et al., Orthogonal Cas9 proteins for RNA-guided gene regulation and editing. Nat. Methods (2013); 10(11): 1116-1121. EpubSep. 29, 2013.

Fire et al., Potent and specific genetic interference by double-stranded RNA in Caenorhabditis elegans. Nature (Feb. 1998); 391(6669): 806-811.

Flannery et al., Efficient photoreceptor-targeted gene expression in vivo by recombinant adeno- associated virus. Proc Natl Acad Sci U.S.A. (1997); 94(13): 6916-6921.

Flotte et al., Stable in vivo expression of the cystic fibrosis transmembrane conductance regulator with an adeno-associated virus vector. Proc Natl Acad Sci U.S.A. (1993); 90(22): 10613-10617.

Forsberg et al., HER2 CAR-T Cells Eradicate Uveal Melanoma and T-cell Therapy-Resistant Human Melanoma in IL2 Transgenic NOD/SCIO IL2 Receptor Knockout Mice, Cancer Research, 2019, vol. 79, No. 5, pp. 899-905.

Fu et al., RNA-binding proteins in immune regulation: a focus on CCCH zinc finger proteins, Nat Rev Immunol., Feb. 2017, vol. 17, No. 2, pp. 130-143.

Garg et al., MCPIP1/Regnase-1 is a negative feedback inhibitor regulating IL-17 signaling and inflammation, AbstracUCytokine, 2015, vol. 76, p. 70.

Germer et al., RNA aptamers and their therapeutic and diagnostic applications. Int J Biochem Mol Biol (2013); 4(1): 27-40.

Grada, et al., TanCAR: A Novel Bispecific Chimeric Antigen Receptor for Cancer Immunotherapy. Mol Ther Nucleic Acids (2013); 2:e105.

Habacher. ZC3H12A/MCPIP1/Regnase-1-related endonucleases: An evolutionary perspective on molecular mechanisms and biological functions, 2017, Bioessays, Sep;39(9). doi: 10.1002/bies.201700051.

Hanieh, Arid5a stabilizes OX40 mRNA in murine CD4+ T cells by recognizing a stem-loop structure in its 3'UTR, 2018, Eur J Immunol, Apr;48(4):593-604. doi: 10.1002/eji.201747109.

Harel et al., Proteomics of Melanoma Response to Immunotherapy Reveals Mitochondrial Dependence, Cell, 2019, vol. 179, 1-15, 34 pages.

Hashim, Mutation of Regnase-1 Causes Primary Immunodeficiency Associated With Auto-Inflammatory Disease, Thesis, Nov. 10, 2017, https://www.repository.cam.ac.uk/handle/1810/269453.

Horvath and Barrangou, The immune system of bacteria and archaea. Science (2010); 327(5962): 167-170.

Hou et al., Efficient genome engineering in human pluripotent stem cells using Cas9 from Neisseria meningitidis. PNAS (Sep. 2013); 110(39): 15644-15649.

(56) References Cited

OTHER PUBLICATIONS

Huang et al., Monocyte Chemotactic Protein-induced Protein 1 and 4 Form a Complex but Act Independently in Regulation of Interleukin-6 mRNA Degradation, The Journal of Biological Chemistry, Aug. 21, 2015, vol. 290, No. 34, pp. 20782-20792.

Huang, et al., Monocyte Chemotactic Protein-induced Protein 1 and 4 Form a Complex but Act Independently in Regulation of Interleukin-6 mRNA Degradation. The Journal of Biological Chemistry (Aug. 21, 2015); 280(34): 20782-20792.

Introna et al., Genetic modification of human T cells with CD20: a strategy to purify and lyse transduced cells with anti-CD20 antibodies. Hum Gene Ther. (2000); 11(4): 611-620.

Isalan et al., A rapid, generally applicable method to engineer zinc fingers illustrated by targeting the HIV-1 promoter. Nat Biotechnol. (2001); 19(7): 656-660.

Isvák, et al., Sleeping Beauty, a wide host-range transposon vector for genetic transformation in vertebrates. J Mol Biol. (2000); 302(1): 93-102.

Iwasaki et al., The IKB kinase complex regulates the stability of cytokine-encoding mRNA induced by TLR-IL-1R by controlling degradation of regnase-1, Nature Immunology, Dec. 2011, vol. 12, No. 12, pp. 1167-1177.

Jeltsch et al. Cleavage of roquin and regnase-1 by the paracaspase MALT1 releases their cooperatively repressed targets to promote TH17 differentiation, Nature Immunology, Nov. 2014, vol. 15, No. 11, pp. 1079-1091.

Jeltsch et al., Regulation of T cell signaling and autoimmunity by RNA-binding proteins, Current Opinion in Immunology, 2016, vol. 39, pp. 127-135.

Jinek et al., A programmable dual RNA-guided DNA endonuclease in adaptive bacterial immunity, Science, Aug. 17, 2012, vol. 337, No. 6096, pp. 816-821.

Johnson et al., Gene therapy with human and mouse T-cell receptors mediates cancer regression and targets normal tissues expressing cognate antigen Blood (2009); 114(3): 535-546. Epub May 18, 2009.

Jomary et al., Rescue of photoreceptor function by AAV-mediated gene transfer in a mouse model of inherited retinal degeneration. Gene Ther. (1997); 4(7): 683-690.

June and Sadelain, Chimeric Antigen Receptor Therapy. N Engl J Med (Jul. 2018); 379(1): 64-73.

Jura et al., Monocyte chemotactic protein-1-induced protein-1 (MCPIP1) is a novel multifunctional modulator of inflammatory reactions, Biochemica et Biophysica Acta 1823, 2012, pp. 1905-1913.

Kahl, The Dictionary of Genomics, Transcriptomics and Proteomics—Regnase-1, 2015.

Katz, et al., Phase I Hepatic Immunotherapy for Metastases Study of Intra-Arterial Chimeric Antigen Receptor-Modified T-cell Therapy for CEA+ Liver Metastases. Clin Cancer Res. (2015); 21(14): 3149-3159. Epub Apr. 7, 2015.

Kawakami et al., Identification of a functional transposase of the Tol2 element, an Ac-like element from the Japanese medaka fish, and its transposition in the zebrafish germ lineage. PNAS (Oct. 2000); 97 (21): 11403-11408.

Kershaw et al., A phase I study on adoptive immunotherapy using gene-modified T cells for ovarian cancer. Clin Cancer Res. (2006); 12 (20 Pt 1): 6106-6115.

Kidoya et al., Regnase-1-mediated post-transcriptional regulation is essential for hematopoietic stem and progenitor cell homeostasis, Nature Communications, 2019, vol. 10, No. 1072, 16 pages.

Kim et al., Chimeric restriction endonuclease. Proc Natl Acad Sci U.S.A. (1994); 91(3): 883-887.

Kim, et al., Insertion and Deletion Mutants of FokI Restriction Endonuclease. The Journal of Biological Chemistry (1994); 269(50): 31978-31982.

Kimmel, AR. Identification and characterization of specific clones: strategy for confirming the validity of presumptive clones. Methods Enzymol. (1987); 152: 507-511.

Kishimoto, Discovery of IL-6 and Development of Anti-IL-6R Antibody, 2019, Keio J Med, 68(4):96. doi: 10.2302/kjm.68-007-ABST.

Kishimoto, Innovative Medicine, Basic Research and Development—IL-6: A New Era for the Treatment of Autoimmune Inflammatory Diseases, 2015.

Kishimoto, S-5 A novel IL-6 mRNA stability protein, Arid5A which is involved in IL-6 dependent autoimmunity, Sep. 2013, Cytokine, vol. 63, Issue 3, p. 242.

Kobold et al., Selective bispecific T cell recruiting antibody and antitumor activity of adoptive T cell transfer. J Natl Cancer Inst. (2014); 107(1): 364. Print Jan. 2015.

Kochenderfer et al., B-cell depletion and remissions of malignancy along with cytokine-associated toxicity in a clinical trial of anti-CD19 chimeric-antigen-receptor-transduced T cells. Blood (2012); 119 (12): 2709-2720. Epub Dec. 8, 2011.

Konermann et al., Transcriptome Engineering with RNA-Targeting Type VI-D CRISPR Effectors. Cell. (2018); 173(3): 665-676.e14 Epub Mar. 15, 2018.

Lamers et al., Treatment of metastatic renal cell carcinoma with CAIX CAR-engineered T cells: clinical evaluation and management of on-target toxicity. Mol Ther. (2013); 21 (4): 904-12. Epub Feb. 19, 2013.

Langer, R. New methods of drug delivery. Science (1990); 249 (4976): 1527-1533.

Li et al. Alteration of the cleavage distance of Fok I restriction endonuclease by insertion mutagenesis. Proc Natl Acad Sci U.S.A. (1993); 90(7): 2764-2768.

Li et al., Chimeric antigen receptor T cell (CAR-T) immunotherapy for solid tumors: lessons learned and strategies for moving forward. J Hematol Oncol. (2018); 11( 1): 22.

Li et al., Functional domains in Fok I restriction endonuclease. Proc Natl Acad Sci U.S.A. (1992); 89(10): 4275-4279.

Li et al., In vivo transfer of a reporter gene to the retina mediated by an adenoviral vector. Invest Ophthalmol Vis Sci. (1994); 35(5): 2543-2549.

Li et al., MCPIP1 down-regulates IL-2 expression through an ARE-independent pathway, PLOS ONE, Nov. 2012, vol. 7, No. 11, 11 pages.

Li et al., Pharmacological inhibition of MALT1 protease activity suppresses endothelial activation via enhancing MCPIP1 expression, Cell Signal, Oct. 2018, 50: 1-8, 18 pages.

Li et al., Phenotype correction in retinal pigment epithelium in murine mucopolysaccharidosis VII by adenovirus-mediated gene transfer. Proc Natl Acad Sci U.S.A. (1995); 92(17): 07700-07704.

Li, Characterization and Optimization of Antigen-Specific T Cell Responses During Ex Vivo Expansion of Melanoma Tumor-Infiltrating Lymphocytes, 2010, http://digitalcommons.library.tmc.edu/utgsbs dissertations/34.

Li, MCPIP1/regnase-1 inhibits simian immunodeficiency virus and is not counteracted by Vpx, 2016, J Gen Virol, Jul.;97(7):1693-1698. doi: 10.1099/jgv.0.000482.

Ligeza et al., MCPIP1 contributes to clear cell renal cell carcinomas development. Angiogenesis, Feb. 14, 2017, 16 pages.

Lippert, MCPIP1, alias Regnase-1 binds and cleaves mRNA of C/EBP13, Mar. 22, 2017, PLOS ONE, 12(3): e0174381. https://doi.org/10.1371/journal.pone.0174381.

Liu et al., A Chimeric Switch-Receptor Targeting PD1 Augments the Efficacy of Second-Generation CART Cells in Advanced Solid Tumors. Cancer Res. (2016); 76(6): 1578-1590.

Liu et al., Abstract LB-042-MCPIP1 suppresses breast tumor progression by targeting anti-tumor apoptosis pathway, Molecular and Cellular Biology, Aug. 2015, vol. 75, Issue 15 Supplement, 4 pages.

Liu et al., Poly(cationic lipid)-mediated in vivo gene delivery to mouse liver. Gene Ther. (2003); 10(2): 180-187.

Liu, et al., Regnase-1 in microglia negatively regulates high mobility group box 1-mediated inflammation and neuronal injury. Scientific Reports (Apr. 5, 2016); 6: 24073, pp. 1-9, and supplementary information.

Loakes et al., 5-Nitroindole as an universal base analogue. Nucleic Acids Res. (1994); 22 (20): 4039-4043.

(56) References Cited

OTHER PUBLICATIONS

Louis et al., Antitumor activity and long-term fate of chimeric antigen receptor-positive T cells in patients with neuroblastoma. Blood. (2011); 118(23): 6050-6056. Epub Oct. 7, 2011.
Lovelock et al., Prevention of freezing damage to living cells by dimethyl sulphoxide. Nature (1959); 183 (4672): 1394-1395.
Lu et al., MCPIP1 Selectively Destabilizes Transcripts Associated with an Antiapoptotic Gene Expression Program in Breast Cancer Cells That Can Elicit Complete Tumor Regression, Cancer Research, Mar. 15, 2016, vol. 76, No. 6, pp. 1429-1440.
Luo, et al., Bifunctional ?HER2/CD3 RNA-engineered CART-like human T cells specifically eliminate HER2(+) gastric cancer. Cell Res. (2016); 26(7): 850-853. Epub Jun. 24, 2016.
Maeda et al., Regulation of mRNA stability by CCCH-type zinc-finger proteins in immune cells, Japanese Society for Immunology, 2017, 20 pages.
Makki et al, MCPIP1 regulates the expression of interleukin-6 in human osteoarthritis chondrocytes, Abstracts/ Osteoarthritis and Cartilage 22, 2014, S57-S489.
Makki et al., Micro RNA-9 Promotion of Interleukin-6 Expression by Inhibiting Monocyte Chemoattractant Protein-Induced Protein 1 Expression in Interleukin-113-Stimulated Human Chondrocytes, Arthritis and Rheumatology, Aug. 2015, vol. 67, No. 8, pp. 2117-2128.
Mali et al., Church GM. RNA-guided human genome engineering via Cas9. Science. (2013); 339(6121): 823-826. Epub Jan. 3, 2013.
Mao et al., Regnase-1, a rapid response ribonuclease regulating inflammation and stress responses, Cellular & Molecular Immunology, 2017, vol. 14, pp. 412-422.
Masuda, AridSa controls IL-6 mRNA stability, which contributes to elevation of IL-6 level in vivo, 2013, Proc Natl Acad Sci US A, Jun. 4;110(23):9409-14. doi: 10.1073/pnas.1307419110.
Matsushita, Regnase-1 degradation is crucial for interleukin-33- and interleukin-25-mediated ILC2 activation, 2020, C1 Insight. 5. 10.1172/jci.insight.131480.
Mendelson et al., Expression and rescue of a nonselected marker from an integrated AAV vector. Virology. (1988); 166(1): 154-165.
Meuer et al., An alternative pathway of T-cell activation: a functional role for the 50 kd T11 sheep erythrocyte receptor protein. Cell (1984); 36(4): 897-906.
Miao et al., Targeted Disruption of MCPIP1/Zc3h12a Results in Fatal Inflammatory Disease, May 2013, Immunol Cell Biol., 91(5): 368-376.
Miekus, Activity of MCPIP1 RNase in tumor associated processes, 2019, Journal of Experimental & Clinical Cancer Research vol. 38, Article No. 421.
Miller et al. Repetitive zinc-binding domains in the protein transcription factor IIIA from Xenopus oocytes. EMBO J. (1985); 4(6):1609-1614.
Mino et al., Post-transcriptional regulation of immune responses by RNA binding proteins, Proc. Jpn. Acad., Ser. B 94, 2018, vol. 94, pp. 248-258.
Mino et al., Regnase-1 and Roquin Regulate a Common Element in Inflammatory mRNAs by Spatiotemporally Distinct Mechanisms, Cell 161, May 21, 2015, pp. 1058-1073.
Mino et al., Translation-dependent unwinding of stem-loops by UPF1 licenses Regnase-1 to degrade inflammatory mRNAs, Nucleic Acids Research, 2019, 22 pages.
Mino, et al., Regnase-1 and Roquin Regulate a Common Element in Inflammatory mRNAs by Spatiotemporally Distinct Mechanisms. Cell (May 21, 2015); 161(5): 1058-1073.
Miskey et al., The Frog Prince: a reconstructed transposon from Rana pipiens with high transpositional activity in vertebrate cells. Nucleic Acids Res. (2003); 31(23): 6873-6881.
Miyoshi et al., Stable and efficient gene transfer into the retina using an HIV-based lentiviral vector. Proc Natl Acad Sci U.S.A.(1997); 94(19): 10319-10323.
Monin, MCPIP1/Regnase-1 Restricts IL-17A- and IL-17C-Dependent Skin Inflammation, 2017, J Immunol, 198(2):767-775, doi: 10.4049/jimmunol.1601551.
Moon et al., Expression of a functional CCR2 receptor enhances tumor localization and tumor eradication by retargeted human T cells expressing amesothelin-specific chimeric antibody receptor. Clin Cancer Res. (2011); 17(14): 4719-4730. Epub May 24, 2011.
Moon, et al., 520. A PD1-CD28 Switch Receptor Is Able to Augment Mesothelin-Directed Chimeric Antigen Receptor T Cell Therapy in a Resistant In Vivo Model of Human Tumor. Cancer-Immunotherapy I Molecular Therapy vol. 22, Supplement 1, May 2014, p. S201.
Moon, et al., Blockade of Programmed Death 1 Augments the Ability of Human T Cells Engineered to Target NY-ESO-1 to Control Tumor Growth after AdoptiveTransfer. Clin Cancer Res. (2016); 22(2): 436-447. Epub Aug. 31, 2015.
Morgan et al., Case report of a serious adverse event following the administration of T cells transduced with a chimeric antigen receptor recognizing ERBB2. Mol Ther. (2010); 18(4): 843-851. Epub Feb. 23, 2010.
Morgan, et al. Cancer regression in patients after transfer of genetically engineered lymphocytes. Science (2006); 314(5796): 126-129. Epub Aug. 31, 2006.
Morgan, et al., Cancer regression and neurological toxicity following anti-MAGE-A3 TCR gene therapy. J Immunother. (2013); 36(2): 133-151.
Muromoto et al., IKB-1; Expression Requires Both TYK2/STAT3 Activity and IL-17-Regulated mRNA Stabilization, ImmunoHorizons, 2019, vol. 3, No. 5, pp. 172-185.
Nagahama et al., Regnase-1 controls colon epithelial regeneration via regulation of mTOR and purine metabolism, PNAS Latest Articles, 2018, 6 pages.
Nakatsuka et al., Pulmonary Regnase-1 orchestrates the interplay of epithelium and adaptive immune systems to protect against pneumonia, Mucosal Immunology, 2018, 16 pages.
Nakazawa et al., PiggyBac-mediated cancer immunotherapy using EBV-specific cytotoxic T-cells expressing HER2-specific chimeric antigen receptor. Mol Ther. (2011); 19(12): 2133-2143. Epub Jul. 19, 2011.
Needleman and Wunsch, A general method applicable to the search for similarities in the amino acid sequence of two proteins. J Mol Biol. (1970); 48 (3): 443-453.
Nichols et al., A universal nucleoside for use at ambiguous sites in DNA primers. Nature (1994); 369 (6480): 492-4933.
Oda et al., A CD200R-CD28 fusion protein appropriates an inhibitory signal to enhance T-cell function and therapy of murine leukemia. Blood (2017); 130 (22): 2410-2419. Epub Oct. 17, 2017.
Oh et al., Monocyte chemotactic protein-induced protein-1 enhances DRS degradation and negatively regulates DRS activation-induced apoptosis through its deubiquitinase function, Oncogene, 2018, 11 pages.
Ohgakiuchi et al., Dimethyl fumarate dampens IL-17-ACT1-TBK1 axis-mediated phosphorylation of Regnase-1 and suppresses IL-17-induced IKB-1; expression, Biochemical and Biophysical Research Communications, 2019, 7 pages.
Omiya, Cytokine mRNA Degradation in Cardiomyocytes Restrains Sterile Inflammation in Pressure Overloaded Hearts, Circulation. 2020;141:667-677.
Omiya, Regnase-1, a ribonuclease, in cardiomyocytes regulates immune responses in the heart, 2018, Journal of Molecular and Cellular Cardiology, Abstract# 119, vol. 120, Supplement, pp. 44-45.
Pabo et al., Design and selection of novel Cys2His2 zinc finger proteins. Annu. Rev. Biochem. (2001); 70: 313-340.
Panyam and Labhasetwar, Biodegradable nanoparticles for drug and gene delivery to cells and tissue. Advanced Drug Delivery Reviews (Feb. 2003); 55(3): 329-347.
Park et al., Adoptive transfer of chimeric antigen receptor redirected cytolytic T lymphocyte clones in patients with neuroblastoma. Mol Ther. (2007); 15(4): 825-833. Epub Feb. 13, 2007.
Parkhurst et al., T cells targeting carcinoembryonic antigen can mediate regression of metastatic colorectal cancer but induce severe transient colitis. Mol Ther. (2011); 19(3): 620-626. Epub Dec. 14, 2010.
Pearson et al., Improved tools for biological sequence comparison. ProcNatl Acad Sci U.S.A. (1988); 85 (8): 2444-2448.

(56) References Cited

OTHER PUBLICATIONS

Peng et al., Monocyte chemotactic protein-induced protein 1 controls allergic airway inflammation by suppressing IL-5-producing TH2 cells through the Notch/Gata3 pathway, Journal of Allergy and Clinical Immunology, Aug. 2018, vol. 142, No. 2, pp. 582-594.
Pydyn et al., MCPIP1—an important RNase controlling intracellular RNA pool, Advances in Hygiene and Experimental Medicine, 2018, vol. 72, 3 pages.
Pyzocha and Chen, Diverse Class 2 CRISPR-Cas Effector Proteins for Genome Engineering Applications. ACS Chem Biol. (2018); 13(2): 347-356. Epub Dec. 5, 2017.
Qi et al., MCP induced protein 1 suppresses TNFa-induced VCAM1 expression in human endothelial cells, FEBS Letters 584, 2010, pp. 3065-3072.
Radvanyi, et al., Specific lymphocyte subsets predict response to adoptive cell therapy using expanded autologous tumor-infiltrating lymphocytes in metastatic melanoma patients. Clin Cancer Res. (2012); 18 (24): 6758-6770. Epub Oct. 2, 2012.
Rapoport et al., NY-ESO-1-specific TCR-engineered T cells mediate sustained antigen-specific antitumor effects in myeloma. Nat Med. (2015); 21(8): 914-921. Epub Jul. 20, 2015.
Rhodes and Klug, Zinc fingers. Scientific American (1993); 268(2): 56-65, 12 pages.
Rinfret et al., Factors affecting the erythrocyte during rapid freezing and thawing. Ann NY Acad Sci. (1960); 85: 576-594.
Robbins et al., A pilot trial using lymphocytes genetically engineered with an NY-ESO-1-reactive T-cell receptor: long-term follow-up and correlates with response. Clin Cancer Res. (2015); 21(5): 1019-1027. Epub Dec. 23, 2014.
Robbins et al., Tumor regression in patients with metastatic synovial cell sarcoma and melanoma using genetically engineered lymphocytes reactive with NY-ESO-1. J Clin Oncol. (2011); 29(7): 917-924. Epub Jan. 31, 2011.
Robbins, et al, Single and dual amino acid substitutions in TCR CDRs can enhance antigen-specific T cell functions. J Immunol. (2008); 180(9): 6116-6131.
Rolling, et al., Evaluation of adeno-associated virus-mediated gene transfer into the rat retina by clinical fluorescence photography. Hum Gene Ther. (1999); 10(4): 641-648.
Safari et al., New Developments in CRISPR Technology_ Improvements in Specificity and Efficiency. Current Pharmaceutical Biotechnology, 2017, vol. 18, pp. 1038-1054.
Sakamoto, et al., A vitrectomy improves the transfection efficiency of adenoviral vector-mediated gene transfer to Müller cells. Gene Ther. (1998); 5(8): 1088-1097.
Samulski et al., Helper-free stocks of recombinant adeno-associated viruses: normal integration does not require viral gene expression. J Virol. (1989); 63(9): 3822-3828.
Segal and Barbas III, Custom DNA-binding proteins come of age: polydactyl zinc-finger proteins. Curr Opin Biotechnol. (2001); 12(6): 632-637.
Seno, Aggregation of Human Trophoblast Cells into Three-Dimensional Culture System Enhances Anti-Inflammatory Characteristics through Cytoskeleton Regulation, Int J Mol Sci, Aug. 8, 2018;19(8):2322. doi: 10.3390/ijms19082322.
Serafini et al., Characterization of CD20-transduced T lymphocytes as an alternative suicide gene therapy approach for the treatment of graft-versus-host disease. Hum Gene Ther. (2004); 15(1): 63-76.
Singer et al., A Distinct Gene Module for Dysfunction Uncoupled from Activation in Tumor-Infiltrating T Cells, Cell, 2016, vol. 166, pp. 1500-1511.
Sirin et al., Regulating gene expression using self-inactivating lentiviral vectors containing the mifepristone-inducible system. Gene (2003); 323: 67-77.
Sloviler et al., Recovery and transfusion of human erythrocytes after freezing in polyglycol solutions. Nature. (1962); 196: 899-900.
Straathof et al, An inducible caspase 9 safety switch for T-cell therapy. Blood. (2005); 105(11): 4247-4254. Epub Feb. 22, 2005.

Swarts et al., DNA-guided DNA interference by a prokaryotic Argonaute. Nature (2014); 507(7491): 258-261. Epub Feb. 16, 2014.
Takahashi et al., Rescue from Photoreceptor Degeneration in the rd Mouse by Human Immunodeficiency Virus Vector-Mediated Gene Transfer. J Virol. (1999); 73(9): 7812-7816.
Takaishi, 579 111 a is a target gene of regnase-1 in epidermal keratinocytes, 2017, Innate Immunity, Microbiology, Inflammation, vol. 137, Issue 5, Supplement 1, S100, May 1, 2017.
Takaishi, Regnase-1, an Immunomodulator, Limits the IL-36/IL-36R Autostimulatory Loop in Keratinocytes to Suppress Skin Inflammation, J Invest Dermatol, Jun. 2018;138(6):1439-1442. doi: 10.1016/j.jid.2017.12.033.
Takeuchi et al., Laboratory of Infection and Prevention. Department of Virus Research. Annual Report of the Institute for Frontier Life and medical Sciences. Kyoto University. 2016;1:38-43.
Takeuchi, Endonuclease Regnase-1/Monocyte chemotactic protein-1-induced protein-1 (MCPIP1) in controlling immune responses and beyond, WIREs RNA, 2018, 90:e1449, 14 pages.
Takeuchi, Osamu, Post-transcriptional control of immune responses via RNA binding proteins, Jul. 2018, Proceedings for Annual Meeting of The Japanese Pharmacological Society (18th World Congress of Basic and Clinical Pharmacology), Institute for Frontier Life and Medical Sciences, 1 page.
Takeuchi, Posttranscriptional control of inflammation by an RNase Regnase-1, Nihon Yakurigaku Zasshi. Mar. 2015; 145(3):129-33. doi: 10.1254/fpj.145.129.
Tanaka et al., Phosphorylation-dependent Regnase-1 release from endoplasm reticulum is critical in IL-17 response, Journal of Experimental Medicine, 2019, vol. 216, No. 6, pp. 1431-1449.
Thomis et al., A Fas-based suicide switch in human T cells for the treatment of graft-versus-host disease. Blood. (2001); 97(5): 1249-1257.
Uehata et al., Malt1-Induced Cleavage of Regnase1 in CD4+ Helper T Cells Regulates Immune Activation, Cell, May 23, 2013, vol. 153, pp. 1036-1049.
Uehata et al., mRNA degradation by the endoribuneclease Regnase—1/ZC3H12a/MCPIP-1, Biochimica et Biophysica Acta 1829, 2013, pp. 708-713.
Uehata et al., Regnase-1 Is an Endoribonuclease Essential for the Maintenance of Immune Homeostasis Journal of Interferon & Cytokine Research, 2017, vol. 37, No. 5, pp. 220-230.
Van Den Berg et al., Case Report of a Fatal Serious Adverse Event Upon Administration of T Cells Transduced With a MART-1-specific T-cell Receptor. Mol Ther. (2015); 23(9): 1541-1550. Epub Apr. 21, 2015.
Van Meerten et al., The CD20/alphaCD20' suicide' system: novel vectors with improved safety and expression profiles and efficient elimination of CD20-transgenic T cells. Gene Ther. (2006); 13(9): 789-797.
Vanseggelen et al., T Cells Engineered With Chimeric Antigen Receptors Targeting NKG2D Ligands Display Lethal Toxicity in Mice. Mol Ther. (2015); 23(10): 1600-1610. Epub Jun. 30, 2015.
Von Gamm, Immune homeostasis and regulation of the interferon pathway require myeloid-derived Regnase-3, J Exp Med, Jul. 1, 2019; 216(7):1700-1723. doi: 10.1084/jem.20181762.
Wahl, et al., Molecular hybridization of immobilized nucleic acids: theoretical concepts and practical considerations. Methods Enzymol. (1987); 152: 399-407.
Wang et al., TRAF Family Member-associated NF-kB Activator (TANK) Inhibits Genotoxic Nuclear Factor kB Activation by Facilitating Deubiquitinase USP10- dependent deubiquiutination of TRAF6 Ligase, Journal of Biological Chemistry, May 22, 2015, vol. 290, No. 21, 15 pages.
Wang, et al., Targeting fibroblast activation protein in tumor stroma with chimeric antigen receptor Tcells can inhibit tumor growth and augment host immunity without severe toxicity. Cancer Immunol Res. (2014); 2(2): 154-166. Epub Nov. 12, 2013.
Warren, O-3. Clinical Studies of regional and systemic gene therapy with autologous CC49-? modified T cells in colorectal cancer metastatic to the liver. 7th International Conference on Gene Therapy of Cancer, San Diego, California, USA. Nov. 19-21, 1998. Abstracts. Cancer Gene Ther. Nov.-Dec. 1998;5(6Suppl):S1-35, 37 pages.

(56) References Cited

OTHER PUBLICATIONS

Watkins et al., Nearest-neighbor thermodynamics of deoxyinosine pairs in DNA duplexes. Nucleic Acids Res. (2005); 33 (19): 6258-6267.

Wawro, ZC3H12B/MCPIP2, a new active member of the ZC3H12 family, RNA,. Jul. 2019;25(7):840-856. doi: 10.1261/rna.071381. 119.

Wei et al., Targeting Regnase-1 programs long-lived effector T cells for cancer therapy, Nature, Dec. 11, 2019, 29 pages.

Wherry, T cell exhaustion. Nature Immunology (Jun. 2011); 12(6): 492-499. Epub May 18, 2011.

Wilkie, et al., Dual targeting of ErbB2 and MUC1 in breast cancer using chimeric antigen receptors engineered to provide complementary signaling. J Clin Immunol. (2012); 32(5): 1059-1070. Epub Apr. 17, 2012.

Xu et al., MCP-1-induced protein-1, an immune regulator, Protein Cell, 2012, vol. 3, No. 12, pp. 903-910.

Xu et al., Structural study of MCPIP1 N-terminal conserved domain reveals a PIN-like RNase, Nucleic Acids Research, May 2012, vol. 40, No. 14, pp. 6957-6965.

Yang et al., A super-enhancer maintains homeostatic expression of Regnase-1, Gene, 2018, vol. 669, pp. 35-41.

Yang et al., Emerging roles of CCCH-type zinc finger proteins in destabilizing mRNA encoding inflammatory factors and regulating immune responses, May 2015, Critical Reviews in Eukaryotic Gene Expression, vol. 25, No. 1, pp. 77-89.

Yang, et al., A common pathway for T lymphocyte activation involving both the CD3-Ti complex and CD2 sheep erythrocyte receptor determinants. J Immunol. (1986); 137(4): 1097-1100.

Yokogawa et al., Structural basis for the regulation of enzymatic activity of Regnase-1 by domain-domain interactions, Nature, 2016, 6:22324, 10 pages.

Yong, et al., CAR T-cell therapy of solid tumors. Immunol Cell Biol. (2017); 95 (4): 356-363. Epub Dec. 22, 2016.

Yoshinaga et al., Post-transcriptional control of immune responses and its potential application, Clinical & Translational Immunology, 2019, 8: e1063, 13 pages.

Yoshinaga et al., RNA binding proteins in the control of autoimmune diseases, Immunological Medicine, 2019, vol. 42, No. 2, pp. 53-64.

Yoshinaga, Regnase-1 Maintains Iron Homeostasis via the Degradation of Transferrin Receptor 1 and Prolyl-Hydroxylase-Domain-Containing Protein 3 mRNAs, Cell Rep, May 23, 2017; 19(8):1614-1630. doi: 10.1016/j.celrep.2017.05.009.

Yu et al., Bone marrow deficiency of MCPIP1 results in severe multi-organ inflammation but diminishes atherogenesis in hyperlipidemic mice, PLOS ONE, 2013, vol. 8, No. 11, 12 pages.

Zhang et al., Structural Basis for the RNA-Guided Ribonuclease Activity of CRISPR-Cas13d. Cell (2018); 175(1): 212-223.e17.

Zhou et al., MCPIP1 Deficiency in Mice Results in Severe Anemia Related to Autoimmune Mechanisms, PLOS ONE, 2013, vol. 8, No. 11, e82542, 11 pages.

Zhu, *Drosophila* Regnase-1 RNase is required for mRNA and miRNA profile remodelling during larva-to-adult metamorphosis, 2019 RNA Biol, Oct. 2019;16(10):1386-1400. doi: 10.1080/15476286.2019.1630799.

EP 19767975.6, Nov. 24, 2021, Extended European Search Report. Extended European Search Report dated Nov. 24, 2021 for Application No. EP 19767975.6.

Li et al., MCPIP1 inhibits coxsackievirus B3 replication by targeting viral RNA and negatively regulates virus-induced inflammation. Med Microbiol Immunol. Feb. 2018;207(1):27-38. Epub Oct. 17, 2017.

Mizgalska et al., Interleukin-1-inducible MCPIP protein has structural and functional properties of RNase and participates in degradation of IL-1beta mRNA. FEBS J. Dec. 2009;276(24):7386-99.

Yao et al., MiR-9 promotes microglial activation by targeting MCPIP1. Nat Commun. Jul. 14, 2014;5:4386.

|        | Ikzf1 | Ikzf3 | Gata3 | Bcl3 | Tnip1 | Tnfaip3 | Nfkbia | Smad2 | Tgfbr1 | Tgfbr2 | Tank | Foxp3 | Ikzf2 | Rc3h1 | Traf6 |
|--------|-------|-------|-------|------|-------|---------|--------|-------|--------|--------|------|-------|-------|-------|-------|
| Ikzf1  |       | 25    | 49    | 73   | 97    | 121     | 145    | 169   | 193    | 217    | 241  | 265   | 289   | 313   | 337   |
| Ikzf3  | 1     |       | 50    | 74   | 98    | 122     | 146    | 170   | 194    | 218    | 242  | 266   | 290   | 314   | 338   |
| Gata3  | 2     | 26    |       | 75   | 99    | 123     | 147    | 171   | 195    | 219    | 243  | 267   | 291   | 315   | 339   |
| Bcl3   | 3     | 27    | 51    |      | 100   | 124     | 148    | 172   | 196    | 220    | 244  | 268   | 292   | 316   | 340   |
| Tnip1  | 4     | 28    | 52    | 76   |       | 125     | 149    | 173   | 197    | 221    | 245  | 269   | 293   | 317   | 341   |
| Tnfaip3| 5     | 29    | 53    | 77   | 101   |         | 150    | 174   | 198    | 222    | 246  | 270   | 294   | 318   | 342   |
| Nfkbia | 6     | 30    | 54    | 78   | 102   | 126     |        | 175   | 199    | 223    | 247  | 271   | 295   | 319   | 343   |
| Smad2  | 7     | 31    | 55    | 79   | 103   | 127     | 151    |       | 200    | 224    | 248  | 272   | 296   | 320   | 344   |
| Tgfbr1 | 8     | 32    | 56    | 80   | 104   | 128     | 152    | 176   |        | 225    | 249  | 273   | 297   | 321   | 345   |
| Tgfbr2 | 9     | 33    | 57    | 81   | 105   | 129     | 153    | 177   | 201    |        | 250  | 274   | 298   | 322   | 346   |
| Tank   | 10    | 34    | 58    | 82   | 106   | 130     | 154    | 178   | 202    | 226    |      | 275   | 299   | 323   | 347   |
| Foxp3  | 11    | 35    | 59    | 83   | 107   | 131     | 155    | 179   | 203    | 227    | 251  |       | 300   | 324   | 348   |
| Ikzf2  | 12    | 36    | 60    | 84   | 108   | 132     | 156    | 180   | 204    | 228    | 252  | 276   |       | 325   | 349   |
| Rc3h1  | 13    | 37    | 61    | 85   | 109   | 133     | 157    | 181   | 205    | 229    | 253  | 277   | 301   |       | 350   |
| Traf6  | 14    | 38    | 62    | 86   | 110   | 134     | 158    | 182   | 206    | 230    | 254  | 278   | 302   | 326   |       |
| Cblb   | 15    | 39    | 63    | 87   | 111   | 135     | 159    | 183   | 207    | 231    | 255  | 279   | 303   | 327   | 351   |
| Ppp2r2d| 16    | 40    | 64    | 88   | 112   | 136     | 160    | 184   | 208    | 232    | 256  | 280   | 304   | 328   | 352   |
| Nrp1   | 17    | 41    | 65    | 89   | 113   | 137     | 161    | 185   | 209    | 233    | 257  | 281   | 305   | 329   | 353   |
| Havcr2 | 18    | 42    | 66    | 90   | 114   | 138     | 162    | 186   | 210    | 234    | 258  | 282   | 306   | 330   | 354   |
| Lag3   | 19    | 43    | 67    | 91   | 115   | 139     | 163    | 187   | 211    | 235    | 259  | 283   | 307   | 331   | 355   |
| Tigit  | 20    | 44    | 68    | 92   | 116   | 140     | 164    | 188   | 212    | 236    | 260  | 284   | 308   | 332   | 356   |
| Ctla4  | 21    | 45    | 69    | 93   | 117   | 141     | 165    | 189   | 213    | 237    | 261  | 285   | 309   | 333   | 357   |
| Ptpn6  | 22    | 46    | 70    | 94   | 118   | 142     | 166    | 190   | 214    | 238    | 262  | 286   | 310   | 334   | 358   |
| Pdcd1  | 23    | 47    | 71    | 95   | 119   | 143     | 167    | 191   | 215    | 239    | 263  | 287   | 311   | 335   | 359   |
| Bcor   | 24    | 48    | 72    | 96   | 120   | 144     | 168    | 192   | 216    | 240    | 264  | 288   | 312   | 336   | 360   |

Fig. 1A

|  | Cblb | Ppp2r2d | Nrp1 | Havcr2 | Lag3 | Tigit | Ctla4 | Ptpn6 | Pdcd1 | Bcor |
|---|---|---|---|---|---|---|---|---|---|---|
| Ikzf1 | 361 | 385 | 409 | 433 | 457 | 481 | 505 | 529 | 553 | 577 |
| Ikzf3 | 362 | 386 | 410 | 434 | 458 | 482 | 506 | 530 | 554 | 578 |
| Gata3 | 363 | 387 | 411 | 435 | 459 | 483 | 507 | 531 | 555 | 579 |
| Bcl3 | 364 | 388 | 412 | 436 | 460 | 484 | 508 | 532 | 556 | 580 |
| Tnip1 | 365 | 389 | 413 | 437 | 461 | 485 | 509 | 533 | 557 | 581 |
| Tnfaip3 | 366 | 390 | 414 | 438 | 462 | 486 | 510 | 534 | 558 | 582 |
| Nfkbia | 367 | 391 | 415 | 439 | 463 | 487 | 511 | 535 | 559 | 583 |
| Smad2 | 368 | 392 | 416 | 440 | 464 | 488 | 512 | 536 | 560 | 584 |
| Tgfbr1 | 369 | 393 | 417 | 441 | 465 | 489 | 513 | 537 | 561 | 585 |
| Tgfbr2 | 370 | 394 | 418 | 442 | 466 | 490 | 514 | 538 | 562 | 586 |
| TANK | 371 | 395 | 419 | 443 | 467 | 491 | 515 | 539 | 563 | 587 |
| FOXP3 | 372 | 396 | 420 | 444 | 468 | 492 | 516 | 540 | 564 | 588 |
| IKZF2 | 373 | 397 | 421 | 445 | 469 | 493 | 517 | 541 | 565 | 589 |
| Rc3h1 | 374 | 398 | 422 | 446 | 470 | 494 | 518 | 542 | 566 | 590 |
| Traf6 | 375 | 399 | 423 | 447 | 471 | 495 | 519 | 543 | 567 | 591 |
| Cblb | | 400 | 424 | 448 | 472 | 496 | 520 | 544 | 568 | 592 |
| Ppp2r2d | 376 | | 425 | 449 | 473 | 497 | 521 | 545 | 569 | 593 |
| Nrp1 | 377 | 401 | | 450 | 474 | 498 | 522 | 546 | 570 | 594 |
| Havcr2 | 378 | 402 | 426 | | 475 | 499 | 523 | 547 | 571 | 595 |
| Lag3 | 379 | 403 | 427 | 451 | | 500 | 524 | 548 | 572 | 596 |
| Tigit | 380 | 404 | 428 | 452 | 476 | | 525 | 549 | 573 | 597 |
| Ctla4 | 381 | 405 | 429 | 453 | 477 | 501 | | 550 | 574 | 598 |
| Ptpn6 | 382 | 406 | 430 | 454 | 478 | 502 | 526 | | 575 | 599 |
| Pdcd1 | 383 | 407 | 431 | 455 | 479 | 503 | 527 | 551 | | 600 |
| Bcor | 384 | 408 | 432 | 456 | 480 | 504 | 528 | 552 | 576 | |

*Fig. 1B*

| | Bcl2l11 | Fli1 | Calm2 | Dhodh | Umps | Rbm39 | Sema7A | Chic2 | Pcbp1 | Pbrm1 | Wdr6 | E2f8 | Serpina3 | Gnas |
|---|---|---|---|---|---|---|---|---|---|---|---|---|---|---|
| Ikzf1 | 601 | 626 | 651 | 676 | 701 | 726 | 751 | 776 | 801 | 826 | 851 | 876 | 901 | 926 |
| Ikzf3 | 602 | 627 | 652 | 677 | 702 | 727 | 752 | 777 | 802 | 827 | 852 | 877 | 902 | 927 |
| Gata3 | 603 | 628 | 653 | 678 | 703 | 728 | 753 | 778 | 803 | 828 | 853 | 878 | 903 | 928 |
| Bcl3 | 604 | 629 | 654 | 679 | 704 | 729 | 754 | 779 | 804 | 829 | 854 | 879 | 904 | 929 |
| Tnip1 | 605 | 630 | 655 | 680 | 705 | 730 | 755 | 780 | 805 | 830 | 855 | 880 | 905 | 930 |
| Tnfaip3 | 606 | 631 | 656 | 681 | 706 | 731 | 756 | 781 | 806 | 831 | 856 | 881 | 906 | 931 |
| Nfkbia | 607 | 632 | 657 | 682 | 707 | 732 | 757 | 782 | 807 | 832 | 857 | 882 | 907 | 932 |
| Smad2 | 608 | 633 | 658 | 683 | 708 | 733 | 758 | 783 | 808 | 833 | 858 | 883 | 908 | 933 |
| Tgfbr1 | 609 | 634 | 659 | 684 | 709 | 734 | 759 | 784 | 809 | 834 | 859 | 884 | 909 | 934 |
| Tgfbr2 | 610 | 635 | 660 | 685 | 710 | 735 | 760 | 785 | 810 | 835 | 860 | 885 | 910 | 935 |
| Tank | 611 | 636 | 661 | 686 | 711 | 736 | 761 | 786 | 811 | 836 | 861 | 886 | 911 | 936 |
| Foxp3 | 612 | 637 | 662 | 687 | 712 | 737 | 762 | 787 | 812 | 837 | 862 | 887 | 912 | 937 |
| Ikzf2 | 613 | 638 | 663 | 688 | 713 | 738 | 763 | 788 | 813 | 838 | 863 | 888 | 913 | 938 |
| Rc3h1 | 614 | 639 | 664 | 689 | 714 | 739 | 764 | 789 | 814 | 839 | 864 | 889 | 914 | 939 |
| Traf6 | 615 | 640 | 665 | 690 | 715 | 740 | 765 | 790 | 815 | 840 | 865 | 890 | 915 | 940 |
| Cblb | 616 | 641 | 666 | 691 | 716 | 741 | 766 | 791 | 816 | 841 | 866 | 891 | 916 | 941 |
| Ppp2r2d | 617 | 642 | 667 | 692 | 717 | 742 | 767 | 792 | 817 | 842 | 867 | 892 | 917 | 942 |
| Nrp1 | 618 | 643 | 668 | 693 | 718 | 743 | 768 | 793 | 818 | 843 | 868 | 893 | 918 | 943 |
| Havcr2 | 619 | 644 | 669 | 694 | 719 | 744 | 769 | 794 | 819 | 844 | 869 | 894 | 919 | 944 |
| Lag3 | 620 | 645 | 670 | 695 | 720 | 745 | 770 | 795 | 820 | 845 | 870 | 895 | 920 | 945 |
| Tigit | 621 | 646 | 671 | 696 | 721 | 746 | 771 | 796 | 821 | 846 | 871 | 896 | 921 | 946 |
| Ctla4 | 622 | 647 | 672 | 697 | 722 | 747 | 772 | 797 | 822 | 847 | 872 | 897 | 922 | 947 |
| Ptpn6 | 623 | 648 | 673 | 698 | 723 | 748 | 773 | 798 | 823 | 848 | 873 | 898 | 923 | 948 |
| Pdcd1 | 624 | 649 | 674 | 699 | 724 | 749 | 774 | 799 | 824 | 849 | 874 | 899 | 924 | 949 |
| Bcor | 625 | 650 | 675 | 700 | 725 | 750 | 775 | 800 | 825 | 850 | 875 | 900 | 925 | 950 |

Fig. 2A

| | Zc3h12a | Map4k1 | Nr4a3 |
|---|---|---|---|
| Ikzf1 | 951 | 976 | 1001 |
| Ikzf3 | 952 | 977 | 1002 |
| Gata3 | 953 | 978 | 1003 |
| Bcl3 | 954 | 979 | 1004 |
| Tnip1 | 955 | 980 | 1005 |
| Tnfaip3 | 956 | 981 | 1006 |
| Nfkbia | 957 | 982 | 1007 |
| Smad2 | 958 | 983 | 1008 |
| Tgfbr1 | 959 | 984 | 1009 |
| Tgfbr2 | 960 | 985 | 1010 |
| Tank | 961 | 986 | 1011 |
| Foxp3 | 962 | 987 | 1012 |
| Ikzf2 | 963 | 988 | 1013 |
| Rc3h1 | 964 | 989 | 1014 |
| Traf6 | 965 | 990 | 1015 |
| Cblb | 966 | 991 | 1016 |
| Ppp2r2d | 967 | 992 | 1017 |
| Nrp1 | 968 | 993 | 1018 |
| Havcr2 | 969 | 994 | 1019 |
| Lag3 | 970 | 995 | 1020 |
| Tigit | 971 | 996 | 1021 |
| Ctla4 | 972 | 997 | 1022 |
| Ptpn6 | 973 | 998 | 1023 |
| Pdcd1 | 974 | 999 | 1024 |
| Bcor | 975 | 1000 | 1025 |

*Fig. 2B*

|  | Bcl2l11 | Fli1 | Calm2 | Dhodh | Umps | Rbm39 | Sema7A | Chic2 | Pcbp1 | Pbrm1 | Wdr6 | E2f8 | Serpina3 | Gnas |
|---|---|---|---|---|---|---|---|---|---|---|---|---|---|---|
| Bcl2l11 |  | 1042 | 1058 | 1074 | 1090 | 1106 | 1122 | 1138 | 1154 | 1170 | 1186 | 1202 | 1218 | 1234 |
| Fli1 | 1026 |  | 1059 | 1075 | 1091 | 1107 | 1123 | 1139 | 1155 | 1171 | 1187 | 1203 | 1219 | 1235 |
| Calm2 | 1027 | 1043 |  | 1076 | 1092 | 1108 | 1124 | 1140 | 1156 | 1172 | 1188 | 1204 | 1220 | 1236 |
| Dhodh | 1028 | 1044 | 1060 |  | 1093 | 1109 | 1125 | 1141 | 1157 | 1173 | 1189 | 1205 | 1221 | 1237 |
| Umps | 1029 | 1045 | 1061 | 1077 |  | 1110 | 1126 | 1142 | 1158 | 1174 | 1190 | 1206 | 1222 | 1238 |
| Rbm39 | 1030 | 1046 | 1062 | 1078 | 1094 |  | 1127 | 1143 | 1159 | 1175 | 1191 | 1207 | 1223 | 1239 |
| Sema7A | 1031 | 1047 | 1063 | 1079 | 1095 | 1111 |  | 1144 | 1160 | 1176 | 1192 | 1208 | 1224 | 1240 |
| Chic2 | 1032 | 1048 | 1064 | 1080 | 1096 | 1112 | 1128 |  | 1161 | 1177 | 1193 | 1209 | 1225 | 1241 |
| Pcbp1 | 1033 | 1049 | 1065 | 1081 | 1097 | 1113 | 1129 | 1145 |  | 1178 | 1194 | 1210 | 1226 | 1242 |
| Pbrm1 | 1034 | 1050 | 1066 | 1082 | 1098 | 1114 | 1130 | 1146 | 1162 |  | 1195 | 1211 | 1227 | 1243 |
| Wdr6 | 1035 | 1051 | 1067 | 1083 | 1099 | 1115 | 1131 | 1147 | 1163 | 1179 |  | 1212 | 1228 | 1244 |
| E2f8 | 1036 | 1052 | 1068 | 1084 | 1100 | 1116 | 1132 | 1148 | 1164 | 1180 | 1196 |  | 1229 | 1245 |
| Serpina3 | 1037 | 1053 | 1069 | 1085 | 1101 | 1117 | 1133 | 1149 | 1165 | 1181 | 1197 | 1213 |  | 1246 |
| Gnas | 1038 | 1054 | 1070 | 1086 | 1102 | 1118 | 1134 | 1150 | 1166 | 1182 | 1198 | 1214 | 1230 |  |
| Zc3h12a | 1039 | 1055 | 1071 | 1087 | 1103 | 1119 | 1135 | 1151 | 1167 | 1183 | 1199 | 1215 | 1231 | 1247 |
| Map4k1 | 1040 | 1056 | 1072 | 1088 | 1104 | 1120 | 1136 | 1152 | 1168 | 1184 | 1200 | 1216 | 1232 | 1248 |
| Nr4a3 | 1041 | 1057 | 1073 | 1089 | 1105 | 1121 | 1137 | 1153 | 1169 | 1185 | 1201 | 1217 | 1233 | 1249 |

Fig. 3A

|         | Zc3h12a | Map4k1 | Nr4a3 |
|---------|---------|--------|-------|
| Bcl2l11 | 1250    | 1266   | 1282  |
| Fli1    | 1251    | 1267   | 1283  |
| Calm2   | 1252    | 1268   | 1284  |
| Dhodh   | 1253    | 1269   | 1285  |
| Umps    | 1254    | 1270   | 1286  |
| Rbm39   | 1255    | 1271   | 1287  |
| Sema7A  | 1256    | 1272   | 1288  |
| Chic2   | 1257    | 1273   | 1289  |
| Pcbp1   | 1258    | 1274   | 1290  |
| Pbrm1   | 1259    | 1275   | 1291  |
| Wdr6    | 1260    | 1276   | 1292  |
| E2f8    | 1261    | 1277   | 1293  |
| Serpina3| 1262    | 1278   | 1294  |
| Gnas    | 1263    | 1279   | 1295  |
| Zc3h12a |         | 1280   | 1296  |
| Map4k1  | 1264    |        | 1297  |
| Nr4a3   | 1265    | 1281   |       |

Fig. 3B

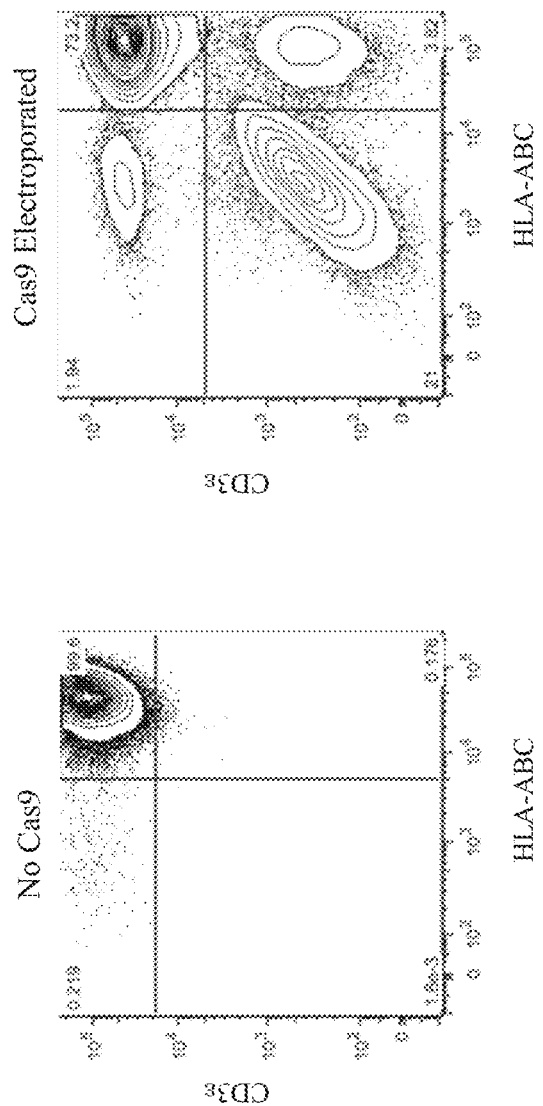

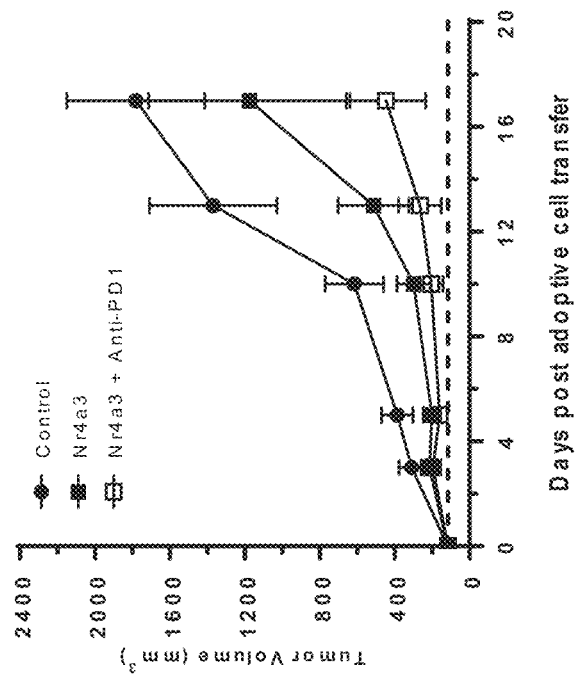
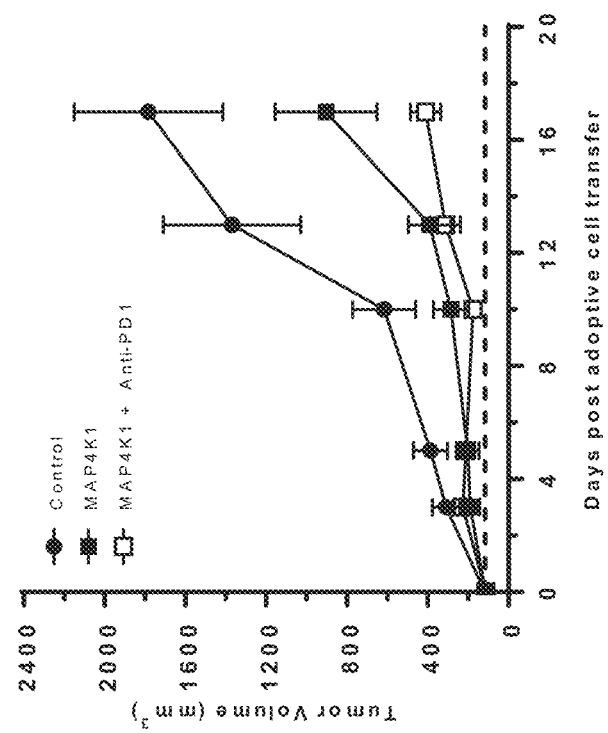
Fig. 8A
Fig. 8B

SEQUENCE LISTING

<160> NUMBER OF SEQ ID NOS: 1575

<210> SEQ ID NO 1
<211> LENGTH: 22
<212> TYPE: PRT
<213> ORGANISM: Artificial Sequence
<220> FEATURE:
<223> OTHER INFORMATION: P2A linker sequence

<400> SEQUENCE: 1

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 2
<211> LENGTH: 8
<212> TYPE: PRT
<213> ORGANISM: Human

<400> SEQUENCE: 2

Ser Leu Leu Met Trp Ile Thr Gln
1               5

<210> SEQ ID NO 3
<211> LENGTH: 9
<212> TYPE: PRT
<213> ORGANISM: Human

<400> SEQUENCE: 3

Ala Ala Gly Ile Gly Ile Leu Thr Val

<210> SEQ ID NO 4
<211> LENGTH: 310
<212> TYPE: PRT
<213> ORGANISM: Human

<400> SEQUENCE: 4

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 5
<211> LENGTH: 270
<212> TYPE: PRT
<213> ORGANISM: Human

<400> SEQUENCE: 5

Met Thr Ser Ile Arg Ala Val Phe Ile Phe Leu Trp Leu Gln Leu Asp

```
            1               5                  10                 15
Leu Val Asn Gly Glu Asn Val Glu Gln His Pro Ser Thr Leu Ser Val
            20                 25                 30

Gln Glu Gly Asp Ser Ala Val Ile Lys Cys Thr Tyr Ser Asp Ser Ala
            35                 40                 45

Ser Asn Tyr Phe Pro Trp Tyr Lys Gln Glu Leu Gly Lys Arg Pro Gln
            50                 55                 60

Leu Ile Ile Asp Ile Arg Ser Asn Val Gly Glu Lys Lys Asp Gln Arg
65                  70                 75                 80

Ile Ala Val Thr Leu Asn Lys Thr Ala Lys His Phe Ser Leu His Ile
            85                 90                 95

Thr Glu Thr Gln Pro Glu Asp Ser Ala Val Tyr Phe Cys Ala Ala Thr
            100                105                110

Glu Asp Tyr Gln Leu Ile Trp Gly Ala Gly Thr Lys Leu Ile Ile Lys
            115                120                125

Pro Asp Ile Gln Asn Pro Asp Pro Ala Val Tyr Gln Leu Arg Asp Ser
            130                135                140

Lys Ser Ser Asp Lys Ser Val Cys Leu Phe Thr Asp Phe Asp Ser Gln
145                 150                155                160

Thr Asn Val Ser Gln Ser Lys Asp Ser Asp Val Tyr Ile Thr Asp Lys
            165                170                175

Cys Val Leu Asp Met Arg Ser Met Asp Phe Lys Ser Asn Ser Ala Val
            180                185                190

Ala Trp Ser Asn Lys Ser Asp Phe Ala Cys Ala Asn Ala Phe Asn Asn
            195                200                205

Ser Ile Ile Pro Glu Asp Thr Phe Phe Pro Ser Pro Glu Ser Ser Cys
            210                215                220

Asp Val Lys Leu Val Glu Lys Ser Phe Glu Thr Asp Thr Asn Leu Asn
225                 230                235                240

Phe Gln Asn Leu Ser Val Ile Gly Phe Arg Ile Leu Leu Leu Lys Val
            245                250                255

Ala Gly Phe Asn Leu Leu Met Thr Leu Arg Leu Trp Ser Ser
            260                265                270

<210> SEQ ID NO 6
<211> LENGTH: 602
<212> TYPE: PRT
<213> ORGANISM: Artificial Sequence
<220> FEATURE:
<223> OTHER INFORMATION: DLT TCR

<400> SEQUENCE: 6

Met Ser Asn Gln Val Leu Cys Cys Val Val Leu Cys Phe Leu Gly Ala
1               5                  10                 15

Asn Thr Val Asp Gly Gly Ile Thr Gln Ser Pro Lys Tyr Leu Phe Arg
            20                 25                 30

Lys Glu Gly Gln Asn Val Thr Leu Ser Cys Glu Gln Asn Leu Asn His
            35                 40                 45

Asp Ala Met Tyr Trp Tyr Arg Gln Asp Pro Gly Gln Gly Leu Arg Leu
            50                 55                 60

Ile Tyr Tyr Ser Gln Ile Val Asn Asp Phe Gln Lys Gly Asp Ile Ala
65                  70                 75                 80

Glu Gly Tyr Ser Val Ser Arg Glu Lys Lys Glu Ser Phe Pro Leu Thr
            85                 90                 95

Val Thr Ser Ala Gln Lys Asn Pro Thr Ala Phe Tyr Leu Cys Ala Ser
```

```
                100                 105                 110
Ser Pro Gly Ala Leu Tyr Glu Gln Tyr Phe Gly Pro Gly Thr Arg Leu
            115                 120                 125
Thr Val Thr Glu Asp Leu Lys Asn Val Phe Pro Pro Glu Val Ala Val
        130                 135                 140
Phe Glu Pro Ser Glu Ala Glu Ile Ser His Thr Gln Lys Ala Thr Leu
145                 150                 155                 160
Val Cys Leu Ala Thr Gly Phe Tyr Pro Asp His Val Glu Leu Ser Trp
                165                 170                 175
Trp Val Asn Gly Lys Glu Val His Ser Gly Val Cys Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
            260                 265                 270
Val Leu Ser Ala Thr Ile Leu Tyr Glu Ile Leu Leu Gly Lys Ala Thr
        275                 280                 285
Leu Tyr Ala Val Leu Val Ser Ala Leu Val Leu Met Ala Met Val Lys
    290                 295                 300
Arg Lys Asp Ser Arg Gly Gly Ser Gly Ala Thr Asn Phe Ser Leu Leu
305                 310                 315                 320
Lys Gln Ala Gly Asp Val Glu Glu Asn Pro Gly Pro Met Thr Ser Ile
                325                 330                 335
Arg Ala Val Phe Ile Phe Leu Trp Leu Gln Leu Asp Leu Val Asn Gly
            340                 345                 350
Glu Asn Val Glu Gln His Pro Ser Thr Leu Ser Val Gln Glu Gly Asp
        355                 360                 365
Ser Ala Val Ile Lys Cys Thr Tyr Ser Asp Ser Ala Ser Asn Tyr Phe
    370                 375                 380
Pro Trp Tyr Lys Gln Glu Leu Gly Lys Arg Pro Gln Leu Ile Ile Asp
385                 390                 395                 400
Ile Arg Ser Asn Val Gly Glu Lys Lys Asp Gln Arg Ile Ala Val Thr
                405                 410                 415
Leu Asn Lys Thr Ala Lys His Phe Ser Leu His Ile Thr Glu Thr Gln
            420                 425                 430
Pro Glu Asp Ser Ala Val Tyr Phe Cys Ala Ala Thr Glu Asp Tyr Gln
        435                 440                 445
Leu Ile Trp Gly Ala Gly Thr Lys Leu Ile Ile Lys Pro Asp Ile Gln
    450                 455                 460
Asn Pro Asp Pro Ala Val Tyr Gln Leu Arg Asp Ser Lys Ser Ser Asp
465                 470                 475                 480
Lys Ser Val Cys Leu Phe Thr Asp Phe Asp Ser Gln Thr Asn Val Ser
                485                 490                 495
Gln Ser Lys Asp Ser Asp Val Tyr Ile Thr Asp Lys Cys Val Leu Asp
            500                 505                 510
Met Arg Ser Met Asp Phe Lys Ser Asn Ser Ala Val Ala Trp Ser Asn
        515                 520                 525
```

```
Lys Ser Asp Phe Ala Cys Ala Asn Ala Phe Asn Asn Ser Ile Ile Pro
        530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
            580                 585                 590

Leu Leu Met Thr Leu Arg Leu Trp Ser Ser
        595                 600

<210> SEQ ID NO 7
<211> LENGTH: 310
<212> TYPE: PRT
<213> ORGANISM: Homo sapiens

<400> SEQUENCE: 7

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
```

Arg Lys Asp Ser Arg Gly
305                 310

<210> SEQ ID NO 8
<211> LENGTH: 270
<212> TYPE: PRT
<213> ORGANISM: Homo sapiens

<400> SEQUENCE: 8

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Leu Thr Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Cys Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 9
<211> LENGTH: 602
<212> TYPE: PRT
<213> ORGANISM: Artificial Sequence
<220> FEATURE:
<223> OTHER INFORMATION: High affinity DLT TCR

<400> SEQUENCE: 9

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

```
Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
 50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
                100                 105                 110

Ser Pro Gly Ala Leu Tyr Glu Gln Tyr Phe Gly Pro Gly Thr Arg Leu
                115                 120                 125

Thr Val Thr Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                    165                 170                 175

Trp Val Asn Gly Lys Glu Val His Ser Gly Val Cys Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Thr Ser Ile
                325                 330                 335

Arg Ala Val Phe Ile Phe Leu Trp Leu Gln Leu Asp Leu Val Asn Gly
                340                 345                 350

Glu Asn Val Glu Gln His Pro Ser Thr Leu Ser Val Gln Glu Gly Asp
            355                 360                 365

Ser Ala Val Ile Lys Cys Thr Tyr Ser Asp Ser Ala Ser Asn Tyr Phe
        370                 375                 380

Pro Trp Tyr Lys Gln Glu Leu Gly Lys Arg Pro Gln Leu Ile Ile Asp
385                 390                 395                 400

Ile Arg Ser Asn Val Gly Glu Lys Lys Asp Gln Arg Ile Ala Val Thr
                405                 410                 415

Leu Asn Lys Thr Ala Lys His Phe Ser Leu His Ile Thr Glu Thr Gln
            420                 425                 430

Pro Glu Asp Ser Ala Val Tyr Phe Cys Ala Ala Thr Glu Asp Leu Thr
        435                 440                 445
```

Leu Ile Trp Gly Ala Gly Thr Lys Leu Ile Ile Lys Pro Asp Ile Gln
            450                 455                 460

Asn Pro Asp Pro Ala Val Tyr Gln Leu Arg Asp Ser Lys Ser Ser Asp
465                 470                 475                 480

Lys Ser Val Cys Leu Phe Thr Asp Phe Asp Ser Gln Thr Asn Val Ser
                485                 490                 495

Gln Ser Lys Asp Ser Asp Val Tyr Ile Thr Asp Lys Cys Val Leu Asp
            500                 505                 510

Met Arg Ser Met Asp Phe Lys Ser Asn Ser Ala Val Ala Trp Ser Asn
            515                 520                 525

Lys Ser Asp Phe Ala Cys Ala Asn Ala Phe Asn Asn Ser Ile Ile Pro
530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
            580                 585                 590

Leu Leu Met Thr Leu Arg Leu Trp Ser Ser
            595                 600

<210> SEQ ID NO 10
<211> LENGTH: 311
<212> TYPE: PRT
<213> ORGANISM: Human

<400> SEQUENCE: 10

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

```
His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 11
<211> LENGTH: 274
<212> TYPE: PRT
<213> ORGANISM: Human

<400> SEQUENCE: 11

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
            85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
            115                 120                 125

Leu Ile Val His Pro Tyr Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
            165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
            210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
            260                 265                 270

Ser Ser
```

<210> SEQ ID NO 12
<211> LENGTH: 607
<212> TYPE: PRT
<213> ORGANISM: Artificial Sequence
<220> FEATURE:
<223> OTHER INFORMATION: IG4 TCR

<400> SEQUENCE: 12

```
Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Glu Thr
                325                 330                 335

Leu Leu Gly Leu Leu Ile Leu Trp Leu Gln Leu Gln Trp Val Ser Ser
            340                 345                 350

Lys Gln Glu Val Thr Gln Ile Pro Ala Ala Leu Ser Val Pro Glu Gly
        355                 360                 365
```

Glu Asn Leu Val Leu Asn Cys Ser Phe Thr Asp Ser Ala Ile Tyr Asn
            370                 375                 380

Leu Gln Trp Phe Arg Gln Asp Pro Gly Lys Gly Leu Thr Ser Leu Leu
385                 390                 395                 400

Leu Ile Gln Ser Ser Gln Arg Glu Gln Thr Ser Gly Arg Leu Asn Ala
            405                 410                 415

Ser Leu Asp Lys Ser Ser Gly Arg Ser Thr Leu Tyr Ile Ala Ala Ser
            420                 425                 430

Gln Pro Gly Asp Ser Ala Thr Tyr Leu Cys Ala Val Arg Pro Thr Ser
            435                 440                 445

Gly Gly Ser Tyr Ile Pro Thr Phe Gly Arg Gly Thr Ser Leu Ile Val
            450                 455                 460

His Pro Tyr Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
            485                 490                 495

Gln Thr Asn Val Ser Gln Ser Lys Asp Ser Asp Val Tyr Ile Thr Asp
            500                 505                 510

Lys Cys Val Leu Asp Met Arg Ser Met Asp Phe Lys Ser Asn Ser Ala
            515                 520                 525

Val Ala Trp Ser Asn Lys Ser Asp Phe Ala Cys Ala Asn Ala Phe Asn
            530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
            565                 570                 575

Asn Phe Gln Asn Leu Ser Val Ile Gly Phe Arg Ile Leu Leu Leu Lys
            580                 585                 590

Val Ala Gly Phe Asn Leu Leu Met Thr Leu Arg Leu Trp Ser Ser
            595                 600                 605

<210> SEQ ID NO 13
<211> LENGTH: 311
<212> TYPE: PRT
<213> ORGANISM: Artificial Sequence
<220> FEATURE:
<223> OTHER INFORMATION: 95L TCRb

<400> SEQUENCE: 13

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
            85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
            115                 120                 125

```
Leu Thr Val Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
                195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 14
<211> LENGTH: 274
<212> TYPE: PRT
<213> ORGANISM: Artificial Sequence
<220> FEATURE:
<223> OTHER INFORMATION: 95L TCRa

<400> SEQUENCE: 14

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Gly Arg Ser Thr Leu Tyr Ile
                85                  90                  95

Ala Ala Ser Gln Pro Gly Asp Ser Ala Thr Tyr Leu Cys Ala Val Arg
                100                 105                 110

Pro Leu Tyr Gly Gly Ser Tyr Ile Pro Thr Phe Gly Arg Gly Thr Ser
            115                 120                 125

Leu Ile Val His Pro Tyr Ile Gln Asn Pro Asp Pro Ala Val Tyr Gln
            130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175
```

```
Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 15
<211> LENGTH: 607
<212> TYPE: PRT
<213> ORGANISM: Artificial Sequence
<220> FEATURE:
<223> OTHER INFORMATION: 95L IG4 TCR

<400> SEQUENCE: 15

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255
```

```
Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Glu Thr
            325                 330                 335

Leu Leu Gly Leu Leu Ile Leu Trp Leu Gln Leu Gln Trp Val Ser Ser
        340                 345                 350

Lys Gln Glu Val Thr Gln Ile Pro Ala Ala Leu Ser Val Pro Glu Gly
    355                 360                 365

Glu Asn Leu Val Leu Asn Cys Ser Phe Thr Asp Ser Ala Ile Tyr Asn
        370                 375                 380

Leu Gln Trp Phe Arg Gln Asp Pro Gly Lys Gly Leu Thr Ser Leu Leu
385                 390                 395                 400

Leu Ile Gln Ser Ser Gln Arg Glu Gln Thr Ser Gly Arg Leu Asn Ala
            405                 410                 415

Ser Leu Asp Lys Ser Ser Gly Arg Ser Thr Leu Tyr Ile Ala Ala Ser
        420                 425                 430

Gln Pro Gly Asp Ser Ala Thr Tyr Leu Cys Ala Val Arg Pro Leu Tyr
    435                 440                 445

Gly Gly Ser Tyr Ile Pro Thr Phe Gly Arg Gly Thr Ser Leu Ile Val
        450                 455                 460

His Pro Tyr Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
            485                 490                 495

Gln Thr Asn Val Ser Gln Ser Lys Asp Ser Asp Val Tyr Ile Thr Asp
        500                 505                 510

Lys Cys Val Leu Asp Met Arg Ser Met Asp Phe Lys Ser Asn Ser Ala
    515                 520                 525

Val Ala Trp Ser Asn Lys Ser Asp Phe Ala Cys Ala Asn Ala Phe Asn
        530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
            565                 570                 575

Asn Phe Gln Asn Leu Ser Val Ile Gly Phe Arg Ile Leu Leu Leu Lys
        580                 585                 590

Val Ala Gly Phe Asn Leu Leu Met Thr Leu Arg Leu Trp Ser Ser
    595                 600                 605

<210> SEQ ID NO 16
<211> LENGTH: 311
<212> TYPE: PRT
<213> ORGANISM: Homo sapiens

<400> SEQUENCE: 16

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30
```

```
Glu Thr Gly Thr Pro Val Thr Leu Arg Cys His Gln Thr Glu Asn His
            35                  40                  45

Arg Tyr Met Tyr Trp Tyr Arg Gln Asp Pro Gly His Gly Leu Arg Leu
 50                  55                  60

Ile His Tyr Ser Tyr Gly Val Lys Asp Thr Asp Lys Gly Glu Val Ser
 65                  70                  75                  80

Asp Gly Tyr Ser Val Ser Arg Ser Lys Thr Glu Asp Phe Leu Leu Thr
                 85                  90                  95

Leu Glu Ser Ala Thr Ser Ser Gln Thr Ser Val Tyr Phe Cys Ala Ile
                100                 105                 110

Ser Glu Val Gly Val Gly Gln Pro Gln His Phe Gly Asp Gly Thr Arg
                115                 120                 125

Leu Ser Ile Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 17
<211> LENGTH: 268
<212> TYPE: PRT
<213> ORGANISM: Homo sapiens

<400> SEQUENCE: 17

Met Leu Leu Glu His Leu Leu Ile Ile Leu Trp Met Gln Leu Thr Trp
  1               5                  10                  15

Val Ser Gly Gln Gln Leu Asn Gln Ser Pro Gln Ser Met Phe Ile Gln
             20                  25                  30

Glu Gly Glu Asp Val Ser Met Asn Cys Thr Ser Ser Ser Ile Phe Asn
             35                  40                  45

Thr Trp Leu Trp Tyr Lys Gln Glu Pro Gly Glu Gly Pro Val Leu Leu
         50                  55                  60

Ile Ala Leu Tyr Lys Ala Gly Glu Leu Thr Ser Asn Gly Arg Leu Thr
 65                  70                  75                  80

Ala Gln Phe Gly Ile Thr Arg Lys Asp Ser Phe Leu Asn Ile Ser Ala
```

```
                        85                  90                  95
Ser Ile Pro Ser Asp Val Gly Ile Tyr Phe Cys Ala Gly Gly Thr Gly
                100                 105                 110

Asn Gln Phe Tyr Phe Gly Thr Gly Thr Ser Leu Thr Val Ile Pro Asn
            115                 120                 125

Ile Gln Asn Pro Asp Pro Ala Val Tyr Gln Leu Arg Asp Ser Lys Ser
        130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Cys Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 18
<211> LENGTH: 601
<212> TYPE: PRT
<213> ORGANISM: Artificial Sequence
<220> FEATURE:
<223> OTHER INFORMATION: DMF4 TCR

<400> SEQUENCE: 18

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
                20                  25                  30

Glu Thr Gly Thr Pro Val Thr Leu Arg Cys His Gln Thr Glu Asn His
            35                  40                  45

Arg Tyr Met Tyr Trp Tyr Arg Gln Asp Pro Gly His Gly Leu Arg Leu
        50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Glu Val Gly Val Gly Gln Pro Gln His Phe Gly Asp Gly Thr Arg
        115                 120                 125

Leu Ser Ile Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
```

```
                    180                 185                 190
Gln Pro Leu Lys Glu Pro Ala Leu Asn Asp Ser Arg Tyr Cys Leu
            195                 200                 205
Ser Ser Arg Leu Arg Val Ser Ala Thr Phe Trp Gln Asn Pro Arg Asn
        210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
                260                 265                 270
Gly Val Leu Ser Ala Thr Ile Leu Tyr Glu Ile Leu Gly Lys Ala
            275                 280                 285
Thr Leu Tyr Ala Val Leu Val Ser Ala Leu Val Leu Met Ala Met Val
        290                 295                 300
Lys Arg Lys Asp Ser Arg Gly Gly Ser Gly Ala Thr Asn Phe Ser Leu
305                 310                 315                 320
Leu Lys Gln Ala Gly Asp Val Glu Glu Asn Pro Gly Pro Met Leu Leu
                325                 330                 335
Glu His Leu Leu Ile Ile Leu Trp Met Gln Leu Thr Trp Val Ser Gly
                340                 345                 350
Gln Gln Leu Asn Gln Ser Pro Gln Ser Met Phe Ile Gln Glu Gly Glu
            355                 360                 365
Asp Val Ser Met Asn Cys Thr Ser Ser Ile Phe Asn Thr Trp Leu
        370                 375                 380
Trp Tyr Lys Gln Glu Pro Gly Glu Gly Pro Val Leu Leu Ile Ala Leu
385                 390                 395                 400
Tyr Lys Ala Gly Glu Leu Thr Ser Asn Gly Arg Leu Thr Ala Gln Phe
                405                 410                 415
Gly Ile Thr Arg Lys Asp Ser Phe Leu Asn Ile Ser Ala Ser Ile Pro
                420                 425                 430
Ser Asp Val Gly Ile Tyr Phe Cys Ala Gly Gly Thr Gly Asn Gln Phe
            435                 440                 445
Tyr Phe Gly Thr Gly Thr Ser Leu Thr Val Ile Pro Asn Ile Gln Asn
        450                 455                 460
Pro Asp Pro Ala Val Tyr Gln Leu Arg Asp Ser Lys Ser Ser Asp Lys
465                 470                 475                 480
Ser Val Cys Leu Phe Thr Asp Phe Asp Ser Gln Thr Asn Val Ser Gln
                485                 490                 495
Ser Lys Asp Ser Asp Val Tyr Ile Thr Asp Lys Cys Val Leu Asp Met
                500                 505                 510
Arg Ser Met Asp Phe Lys Ser Asn Ser Ala Val Ala Trp Ser Asn Lys
            515                 520                 525
Ser Asp Phe Ala Cys Ala Asn Ala Phe Asn Asn Ser Ile Ile Pro Glu
        530                 535                 540
Asp Thr Phe Phe Pro Ser Pro Glu Ser Ser Cys Asp Val Lys Leu Val
545                 550                 555                 560
Glu Lys Ser Phe Glu Thr Asp Thr Asn Leu Asn Phe Gln Asn Leu Ser
                565                 570                 575
Val Ile Gly Phe Arg Ile Leu Leu Leu Lys Val Ala Gly Phe Asn Leu
                580                 585                 590
Leu Met Thr Leu Arg Leu Trp Ser Ser
            595                 600
```

```
<210> SEQ ID NO 19
<211> LENGTH: 310
<212> TYPE: PRT
<213> ORGANISM: Homo sapiens

<400> SEQUENCE: 19

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
        35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Leu Ser Phe Gly Thr Glu Ala Phe Phe Gly Gln Gly Thr Arg Leu
        115                 120                 125

Thr Val Val Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 20
<211> LENGTH: 272
<212> TYPE: PRT
<213> ORGANISM: Homo sapiens

<400> SEQUENCE: 20

Met Lys Ser Leu Arg Val Leu Leu Val Ile Leu Trp Leu Gln Leu Ser
1               5                   10                  15
```

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe Gly Gly Gly Lys Leu Ile Phe Gly Gln Gly Thr Glu Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 21
<211> LENGTH: 604
<212> TYPE: PRT
<213> ORGANISM: Artificial Sequence
<220> FEATURE:
<223> OTHER INFORMATION: DMF5 TCR

<400> SEQUENCE: 21

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
        35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

```
Ser Leu Ser Phe Gly Thr Glu Ala Phe Phe Gln Gly Thr Arg Leu
    115                 120                 125

Thr Val Val Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Lys Ser Leu
                325                 330                 335

Arg Val Leu Leu Val Ile Leu Trp Leu Gln Leu Ser Trp Val Trp Ser
                340                 345                 350

Gln Gln Lys Glu Val Glu Gln Asn Ser Gly Pro Leu Ser Val Pro Glu
    355                 360                 365

Gly Ala Ile Ala Ser Leu Asn Cys Thr Tyr Ser Asp Arg Gly Ser Gln
370                 375                 380

Ser Phe Phe Trp Tyr Arg Gln Tyr Ser Gly Lys Ser Pro Glu Leu Ile
385                 390                 395                 400

Met Phe Ile Tyr Ser Asn Gly Asp Lys Glu Asp Gly Arg Phe Thr Ala
                405                 410                 415

Gln Leu Asn Lys Ala Ser Gln Tyr Val Ser Leu Leu Ile Arg Asp Ser
            420                 425                 430

Gln Pro Ser Asp Ser Ala Thr Tyr Leu Cys Ala Val Asn Phe Gly Gly
    435                 440                 445

Gly Lys Leu Ile Phe Gly Gln Gly Thr Glu Leu Ser Val Lys Pro Asn
    450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
                485                 490                 495

Val Ser Gln Ser Lys Asp Ser Asp Val Tyr Ile Thr Asp Lys Cys Val
            500                 505                 510

Leu Asp Met Arg Ser Met Asp Phe Lys Ser Asn Ser Ala Val Ala Trp
    515                 520                 525
```

Ser Asn Lys Ser Asp Phe Ala Cys Ala Asn Ala Phe Asn Asn Ser Ile
    530                 535                 540

Ile Pro Glu Asp Thr Phe Phe Pro Ser Pro Glu Ser Ser Cys Asp Val
545                 550                 555                 560

Lys Leu Val Glu Lys Ser Phe Glu Thr Asp Thr Asn Leu Asn Phe Gln
                565                 570                 575

Asn Leu Ser Val Ile Gly Phe Arg Ile Leu Leu Leu Lys Val Ala Gly
            580                 585                 590

Phe Asn Leu Leu Met Thr Leu Arg Leu Trp Ser Ser
    595                 600

<210> SEQ ID NO 22
<211> LENGTH: 142
<212> TYPE: PRT
<213> ORGANISM: Human

<400> SEQUENCE: 22

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 23
<211> LENGTH: 142
<212> TYPE: PRT
<213> ORGANISM: Artificial Sequence
<220> FEATURE:
<223> OTHER INFORMATION: cys modified TRAC

<400> SEQUENCE: 23

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Cys Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn

```
                100              105              110
Phe Gln Asn Leu Ser Val Ile Gly Phe Arg Ile Leu Leu Lys Val
            115              120              125
Ala Gly Phe Asn Leu Leu Met Thr Leu Arg Leu Trp Ser Ser
       130              135              140

<210> SEQ ID NO 24
<211> LENGTH: 178
<212> TYPE: PRT
<213> ORGANISM: Human

<400> SEQUENCE: 24

Asp Leu Lys Asn Val Phe Pro Pro Glu Val Ala Val Phe Glu Pro Ser
 1               5                  10                  15
Glu Ala Glu Ile Ser His Thr Gln Lys Ala Thr Leu Val Cys Leu Ala
             20                  25                  30
Thr Gly Phe Tyr Pro Asp His Val Glu Leu Ser Trp Trp Val Asn Gly
         35                  40                  45
Lys Glu Val His Ser Gly Val Ser Thr Asp Pro Gln Pro Leu Lys Glu
     50                  55                  60
Gln Pro Ala Leu Asn Asp Ser Arg Tyr Cys Leu Ser Ser Arg Leu Arg
 65                  70                  75                  80
Val Ser Ala Thr Phe Trp Gln Asn Pro Arg Asn His Phe Arg Cys Gln
                 85                  90                  95
Val Gln Phe Tyr Gly Leu Ser Glu Asn Asp Glu Trp Thr Gln Asp Arg
            100                 105                 110
Ala Lys Pro Val Thr Gln Ile Val Ser Ala Glu Ala Trp Gly Arg Ala
        115                 120                 125
Asp Cys Gly Phe Thr Ser Glu Ser Tyr Gln Gln Gly Val Leu Ser Ala
    130                 135                 140
Thr Ile Leu Tyr Glu Ile Leu Leu Gly Lys Ala Thr Leu Tyr Ala Val
145                 150                 155                 160
Leu Val Ser Ala Leu Val Leu Met Ala Met Val Lys Arg Lys Asp Ser
                165                 170                 175
Arg Gly

<210> SEQ ID NO 25
<211> LENGTH: 178
<212> TYPE: PRT
<213> ORGANISM: Artificial Sequence
<220> FEATURE:
<223> OTHER INFORMATION: cys modified TRBC

<400> SEQUENCE: 25

Asp Leu Lys Asn Val Phe Pro Pro Glu Val Ala Val Phe Glu Pro Ser
 1               5                  10                  15
Glu Ala Glu Ile Ser His Thr Gln Lys Ala Thr Leu Val Cys Leu Ala
             20                  25                  30
Thr Gly Phe Tyr Pro Asp His Val Glu Leu Ser Trp Trp Val Asn Gly
         35                  40                  45
Lys Glu Val His Ser Gly Val Cys Thr Asp Pro Gln Pro Leu Lys Glu
     50                  55                  60
Gln Pro Ala Leu Asn Asp Ser Arg Tyr Cys Leu Ser Ser Arg Leu Arg
 65                  70                  75                  80
Val Ser Ala Thr Phe Trp Gln Asn Pro Arg Asn His Phe Arg Cys Gln
                 85                  90                  95
```

```
Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
            115                 120                 125

Asp Cys Gly Phe Thr Ser Glu Ser Tyr Gln Gln Gly Val Leu Ser Ala
            130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 26
<211> LENGTH: 444
<212> TYPE: PRT
<213> ORGANISM: Artificial Sequence
<220> FEATURE:
<223> OTHER INFORMATION: KSQ CAR017

<400> SEQUENCE: 26

Met Leu Leu Leu Val Thr Ser Leu Leu Leu Cys Glu Leu Pro His Pro
1               5                   10                  15

Ala Phe Leu Leu Ile Pro Asp Ile Leu Leu Thr Gln Ser Pro Val Ile
            20                  25                  30

Leu Ser Val Ser Pro Gly Glu Arg Val Ser Phe Ser Cys Arg Ala Ser
        35                  40                  45

Gln Ser Ile Gly Thr Asn Ile His Trp Tyr Gln Gln Arg Thr Asn Gly
    50                  55                  60

Ser Pro Arg Leu Leu Ile Lys Tyr Ala Ser Glu Ser Ile Ser Gly Ile
65                  70                  75                  80

Pro Ser Arg Phe Ser Gly Ser Gly Ser Gly Thr Asp Phe Thr Leu Ser
                85                  90                  95

Ile Asn Ser Val Glu Ser Glu Asp Ile Ala Asp Tyr Tyr Cys Gln Gln
            100                 105                 110

Asn Asn Asn Trp Pro Thr Thr Phe Gly Ala Gly Thr Lys Leu Glu Leu
            115                 120                 125

Lys Gly Gly Gly Ser Gly Gly Gly Ser Gly Gly Gly Gly Ser
130                 135                 140

Gln Val Gln Leu Lys Gln Ser Gly Pro Gly Leu Val Gln Pro Ser Gln
145                 150                 155                 160

Ser Leu Ser Ile Thr Cys Thr Val Ser Gly Phe Ser Leu Thr Asn Tyr
                165                 170                 175

Gly Val His Trp Val Arg Gln Ser Pro Gly Lys Gly Leu Glu Trp Leu
            180                 185                 190

Gly Val Ile Trp Ser Gly Gly Asn Thr Asp Tyr Asn Thr Pro Phe Thr
            195                 200                 205

Ser Arg Leu Ser Ile Asn Lys Asp Asn Ser Lys Ser Gln Val Phe Phe
            210                 215                 220

Lys Met Asn Ser Leu Gln Ser Asn Asp Thr Ala Ile Tyr Tyr Cys Ala
225                 230                 235                 240

Arg Ala Leu Thr Tyr Tyr Asp Tyr Glu Phe Ala Tyr Trp Gly Gln Gly
                245                 250                 255

Thr Leu Val Thr Val Ser Ala Thr Thr Thr Pro Ala Pro Arg Pro Pro
            260                 265                 270

Thr Pro Ala Pro Thr Ile Ala Ser Gln Pro Leu Ser Leu Arg Pro Glu
```

```
         275                 280                 285
Ala Cys Arg Pro Ala Ala Gly Gly Ala Val His Thr Arg Gly Leu Asp
         290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Arg Val Lys Phe
                325                 330                 335
Ser Arg Ser Ala Asp Ala Pro Ala Tyr Gln Gln Gly Gln Asn Gln Leu
            340                 345                 350
Tyr Asn Glu Leu Asn Leu Gly Arg Arg Glu Glu Tyr Asp Val Leu Asp
            355                 360                 365
Lys Arg Arg Gly Arg Asp Pro Glu Met Gly Gly Lys Pro Arg Arg Lys
        370                 375                 380
Asn Pro Gln Glu Gly Leu Tyr Asn Glu Leu Gln Lys Asp Lys Met Ala
385                 390                 395                 400
Glu Ala Tyr Ser Glu Ile Gly Met Lys Gly Glu Arg Arg Arg Gly Lys
                405                 410                 415
Gly His Asp Gly Leu Tyr Gln Gly Leu Ser Thr Ala Thr Lys Asp Thr
            420                 425                 430
Tyr Asp Ala Leu His Met Gln Ala Leu Pro Pro Arg
            435                 440
```

<210> SEQ ID NO 27
<211> LENGTH: 1328
<212> TYPE: DNA
<213> ORGANISM: Artificial Sequence
<220> FEATURE:
<223> OTHER INFORMATION: KSQ CAR017

<400> SEQUENCE: 27

```
atgctcctcc tggttactag cttgcttttg tgcgaactgc cgcatcctgc cttccttctc      60
atcccagata tacttctgac acaatctccg gtaatacttt ccgtctcacc ggggagcga     120
gtgtcatttt catgccgggc gagtcaatcc atcgggacga atattcactg gtatcagcaa     180
aggactaacg gctcaccacg ccttctcatc aagtatgcca gtgagtccat aagtggcatt     240
ccctctagat tctcaggatc aggcagtggc acggacttca cattgtcaat taatagcgta     300
gaaagtgagg acatagcaga ttattattgc caacaaaaca taactggcc taccacattc     360
ggtgcaggca ccaagcttga gttgaagggg gtggtggtt ctggaggcgg tgggagcggt     420
ggtggtgggt cacaagtgca gcttaagcaa agcggaccag gtctggtcca acctagccag     480
tcactgtcaa tcacatgtac ggtatccggc tttagtctga caaattatgg cgtccactgg     540
gtaaggcaat cccctggaaa gggcctcgag tggttggggg tgatttggag cggaggaaac     600
accgactata taccccttt cacctccaga ctgtccataa acaaggacaa ctctaaaagt     660
caggtattct tcaaaatgaa cagtctgcaa agtaatgaca cagcgatata ttattgcgcg     720
agagccctta catactacga ttacgagttc gcttattggg acaaggaac gttggtgacg     780
gtgtctgcca caaccactcc tgctcccagg ccaccaacac cggcgcctac catagcgtca     840
cagccgctta gtctcaggcc ggaagcgtgt cgccccgcag ccggtggggc ggtccacaca     900
cgcgggctgg atttcgcatg cgatatatac atctgggcac ccttgccgg gacctgcggt     960
gttttgctct tgtctctcgt aatcacgctg tactgtcggg ttaagttttc aagatctgcg    1020
gatgccccgg cataccaaca aggcagaat cagttgtaca cgaactgaa cttgggcaga    1080
cgcgaggagt atgatgtctt ggacaagagg cgggggcgcg acccggaaat gggtggcaaa    1140
```

```
ccacggcgca agaacccaca agagggggctt tacaacgaat tgcagaaaga caagatggcc    1200
gaggcataca gcgagattgg catgaaagga gagaggagga gggggaaaggg gcatgatggc    1260 ctttatcagg gcctttctac tgccaccaag gacacatacg acgcactgca catgcaggca    1320
ttgccacc                                                              1328
```

<210> SEQ ID NO 28
<211> LENGTH: 446
<212> TYPE: PRT
<213> ORGANISM: Artificial Sequence
<220> FEATURE:
<223> OTHER INFORMATION: KSQ CAR1909

<400> SEQUENCE: 28

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320
```

```
Gly Val Leu Leu Leu Ser Leu Val Ile Thr Leu Tyr Cys Leu Arg Val
            325                 330                 335

Lys Phe Ser Arg Ser Ala Asp Ala Pro Ala Tyr Gln Gln Gly Gln Asn
        340                 345                 350

Gln Leu Tyr Asn Glu Leu Asn Leu Gly Arg Arg Glu Glu Tyr Asp Val
            355                 360                 365

Leu Asp Lys Arg Arg Gly Arg Asp Pro Glu Met Gly Gly Lys Pro Arg
    370                 375                 380

Arg Lys Asn Pro Gln Glu Gly Leu Tyr Asn Glu Leu Gln Lys Asp Lys
385                 390                 395                 400

Met Ala Glu Ala Tyr Ser Glu Ile Gly Met Lys Gly Glu Arg Arg Arg
                405                 410                 415

Gly Lys Gly His Asp Gly Leu Tyr Gln Gly Leu Ser Thr Ala Thr Lys
            420                 425                 430

Asp Thr Tyr Asp Ala Leu His Met Gln Ala Leu Pro Pro Arg
            435                 440                 445

<210> SEQ ID NO 29
<211> LENGTH: 1338
<212> TYPE: DNA
<213> ORGANISM: Artificial Sequence
<220> FEATURE:
<223> OTHER INFORMATION: KSQ CAR1909

<400> SEQUENCE: 29
atgctccttc ttgtgacgtc actcctgctt tgtgagctgc cgcacccggc ctttctgctc      60
ataccccgaca tacaaatgac acagacgaca agttcccttt ccgcctcctt gggcgaccga    120
gtgacaatca gttgccgagc ttcccaggac atatctaaat atttgaattg gtatcagcaa    180
aagccagatg gtacggttaa acttcttatc taccacacct ccaggctcca ttctgggggtt    240
ccgagccgat tctctggatc tggctcaggg accgattatt ctttgactat tccaatttg    300
gagcaggaag acatcgcaac ctatttctgc caacaaggaa atacgctgcc atacaccttc    360
ggcgggggca ccaaactcga gattactggg ggtgggggga gtggaggagg gggttccggt    420
ggaggtgggt cagaagtcaa gctgcaagag agtgggcccg ggttggttgc tcctagccaa    480
tccttgagtg taacatgcac cgttagcgga gtttcacttc ctgactacgg tgttagctgg    540
ataagacagc ccccgaggaa gggtctggaa tggctggggg tcatttgggg cagtgagacg    600
acatattaca acagtgcctt gaaatccagg cttacgatca taaagacaa tagtaaaagc    660
caagtgttcc tcaagatgaa ctctcttcag accgacgaca cagccatcta ctattgcgca    720
aaacattatt attatggagg tagttacgct atggactatt ggggccaggg gacttcagtg    780
acggtgagta gtaccacgac tccggcaccg agaccaccaa caccagcccc aacaattgcc    840
tcacagccct tgagccttag acccgaggcc tgtaggcccg ccgcaggagg ggcagttcat    900
acgcgaggat tggactttgc atgtgacatc tatatctggg cgccacttgc gggaacttgc    960
ggtgtccttt tgctctcatt ggtcattacc ctctattgtt tgagagtaaa atttcccgc    1020
tccgctgatg cgcctgcata ccagcaaggt cagaaccaac tctacaatga gcttaacctc    1080
ggtagaagag aggaatatga cgtcttggat aagaggagag ccgagaccc agaaatgggg    1140
ggaaagccgc gccgcaagaa tccacaagaa ggtctttaca tgaactgca gaaggacaaa    1200
atggccgaag cgtatagcga gataggaatg aaaggcgaac ggagacgggg caaggggcat    1260
gacgggcttt accaaggact tagcacagcg acgaaggata catacgacgc actgcatatg    1320
caagcgctgc caccgcgc                                                   1338
```

<210> SEQ ID NO 30
<211> LENGTH: 496
<212> TYPE: PRT
<213> ORGANISM: Artificial Sequence
<220> FEATURE:
<223> OTHER INFORMATION: KSQ CAR010

<400> SEQUENCE: 30

```
Met Asp Phe Gln Val Gln Ile Phe Ser Phe Leu Leu Ile Ser Ala Ser
1               5                   10                  15

Val Ile Met Ser Arg Gly Ala Thr Gly Gly Ala Thr Thr Thr Thr Cys
            20                  25                  30

Ala Gly Gly Thr Gly Cys Ala Gly Ala Thr Thr Thr Thr Cys Ala Gly
            35                  40                  45

Cys Thr Thr Cys Cys Thr Gly Cys Thr Ala Ala Thr Cys Ala Gly Thr
        50                  55                  60

Gly Cys Cys Thr Cys Ala Asp Ile Gln Met Thr Gln Ser Pro Ser Ser
65                  70                  75                  80

Leu Ser Ala Ser Val Gly Asp Arg Val Thr Ile Thr Cys Arg Ala Ser
                85                  90                  95

Gln Asp Val Asn Thr Ala Val Ala Trp Tyr Gln Lys Pro Gly Lys
            100                 105                 110

Ala Pro Lys Leu Leu Ile Tyr Ser Ala Ser Phe Leu Tyr Ser Gly Val
            115                 120                 125

Pro Ser Arg Phe Ser Gly Ser Arg Ser Gly Thr Asp Phe Thr Leu Thr
            130                 135                 140

Ile Ser Ser Leu Gln Pro Glu Asp Phe Ala Thr Tyr Tyr Cys Gln Gln
145                 150                 155                 160

His Tyr Thr Thr Pro Pro Thr Phe Gly Gln Gly Thr Lys Val Glu Ile
                165                 170                 175

Lys Arg Thr Gly Ser Thr Ser Gly Ser Gly Lys Pro Gly Ser Gly Glu
                180                 185                 190

Gly Ser Glu Val Gln Leu Val Glu Ser Gly Gly Gly Leu Val Gln Pro
            195                 200                 205

Gly Gly Ser Leu Arg Leu Ser Cys Ala Ala Ser Gly Phe Asn Ile Lys
        210                 215                 220

Asp Thr Tyr Ile His Trp Val Arg Gln Ala Pro Gly Lys Gly Leu Glu
225                 230                 235                 240

Trp Val Ala Arg Ile Tyr Pro Thr Asn Gly Tyr Thr Arg Tyr Ala Asp
                245                 250                 255

Ser Val Lys Gly Arg Phe Thr Ile Ser Ala Asp Thr Ser Lys Asn Thr
                260                 265                 270

Ala Tyr Leu Gln Met Asn Ser Leu Arg Ala Glu Asp Thr Ala Val Tyr
            275                 280                 285

Tyr Cys Ser Arg Trp Gly Gly Asp Gly Phe Tyr Ala Met Asp Val Trp
        290                 295                 300

Gly Gln Gly Thr Leu Val Thr Val Ser Ser Thr Thr Thr Pro Ala Pro
305                 310                 315                 320

Arg Pro Pro Thr Pro Ala Pro Thr Ile Ala Ser Gln Pro Leu Ser Leu
                325                 330                 335

Arg Pro Glu Ala Cys Arg Pro Ala Ala Gly Gly Ala Val His Thr Arg
            340                 345                 350

Gly Leu Asp Phe Ala Cys Asp Ile Tyr Ile Trp Ala Pro Leu Ala Gly
        355                 360                 365
```

```
Thr Cys Gly Val Leu Leu Ser Leu Val Ile Thr Leu Tyr Cys Leu
            370                 375                 380
Arg Val Lys Phe Ser Arg Ser Ala Asp Ala Pro Ala Tyr Gln Gln Gly
385                 390                 395                 400
Gln Asn Gln Leu Tyr Asn Glu Leu Asn Leu Gly Arg Arg Glu Glu Tyr
                405                 410                 415
Asp Val Leu Asp Lys Arg Arg Gly Arg Asp Pro Glu Met Gly Gly Lys
            420                 425                 430
Pro Arg Arg Lys Asn Pro Gln Glu Gly Leu Tyr Asn Glu Leu Gln Lys
            435                 440                 445
Asp Lys Met Ala Glu Ala Tyr Ser Glu Ile Gly Met Lys Gly Glu Arg
            450                 455                 460
Arg Arg Gly Lys Gly His Asp Gly Leu Tyr Gln Gly Leu Ser Thr Ala
465                 470                 475                 480
Thr Lys Asp Thr Tyr Asp Ala Leu His Met Gln Ala Leu Pro Pro Arg
                485                 490                 495

<210> SEQ ID NO 31
<211> LENGTH: 1488
<212> TYPE: DNA
<213> ORGANISM: Artificial Sequence
<220> FEATURE:
<223> OTHER INFORMATION: KSQ CAR010

<400> SEQUENCE: 31
```

| | | | | | |
|---|---|---|---|---|---|
| atggactttc | aggtgcagat | cttctcattc | ctccttatca | gtgcgagtgt | aattatgtca | 60 |
| agaggtgcta | caggcggtgc | taccacgacg | acatgcgcag | ggggtaccgg | ttgtgcagga | 120 |
| gcgaccacga | ctacctgcgc | aggttgtacc | acctgttgta | ctggatgtac | tgctgcgaca | 180 |
| tgtgcgggga | cgggttgttg | cacttgtgcg | acatacaaa | tgacgcaaag | cccgtccagc | 240 |
| ctgtctgcat | cagttgggga | tagagtgacg | attacatgta | gagcaagcca | ggatgttaac | 300 |
| accgccgtag | cgtggtacca | acaaaaacca | ggtaaagccc | cgaagctgct | catatactcc | 360 |
| gccagctttc | tgtattcagg | cgttcccagt | cggttcagcg | gcagcagatc | agggacggat | 420 |
| tttacgctca | ctatctcttc | ccttcagcct | gaagattttg | ctacctatta | ttgtcagcag | 480 |
| cattacacga | ctcccccaac | ttttggtcag | gggactaaag | ttgaaatcaa | cgaacgggc | 540 |
| tccacctcag | gtagcggtaa | gccaggcagc | ggagaagggt | ctgaagtcca | gttggttgag | 600 |
| agtggaggcg | tcttgtgca | acccggtggc | agcttgcgac | tgagctgtgc | agcgtctggc | 660 |
| ttcaacataa | aagatactta | tattcattgg | gtaagacagg | ctcctggtaa | agggctggaa | 720 |
| tgggtggcac | gaatatatcc | gactaacggt | tataccagat | acgccgattc | tgttaagggc | 780 |
| aggttcacaa | taagcgccga | cacaagtaag | aatacgcgt | atctgcagat | gaattcactt | 840 |
| cgagctgaag | acacagcggt | atactactgc | tccaggtggg | gtggggatgg | tttttatgcg | 900 |
| atggacgttt | ggggtcaagg | aacactggta | actgttagtt | ctaccacgac | acctgctcct | 960 |
| aggcccccca | caccggcacc | tacgatcgct | tcccagccgc | ttagcctccg | cccggaggca | 1020 |
| tgccggcccg | ctgcgggggg | agcggtacat | actcgcgggt | tggacttcgc | ttgcgacatc | 1080 |
| tacatttggg | caccactggc | aggcacatgt | ggcgttctgt | tgcttagtct | ggttattaca | 1140 |
| ctgtattgcc | tgcgagttaa | attctcccgc | agcgctgatg | cgcccgccta | tcagcaaggt | 1200 |
| caaaaccagc | tgtataatga | gcttaatttg | ggacgccgag | aagagtatga | cgtccttgac | 1260 |
| aagaggcgcg | ggcgcgatcc | ggagatgggt | ggtaaaccgc | gccggaaaaa | cccccaggaa | 1320 |

```
ggcctttaca atgagctcca aaaagataaa atggcagagg catactctga aataggaatg    1380
aagggcgaga gacgccgggg taagggacac gatggccttt atcaagggct tagtacagcc    1440
acgaaggata cgtatgacgc tctgcacatg caggctcttc ccccgaga                 1488
```

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32

```
ccacctccag ttgttgcatt                                                  20
```

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33

```
tgctgcttca aagggaggta                                                  20
```

<210> SEQ ID NO 34
<211> LENGTH: 83
<212> TYPE: DNA
<213> ORGANISM: Artificial Sequence
<220> FEATURE:
<223> OTHER INFORMATION: tracrRNA

<400> SEQUENCE: 34

```
gttttagagc tagaaatagc aagttaaaat aaggctagtc cgttatcaac ttgaaaaagt    60
ggcaccgagt cggtgctttt ttt                                              83
```

<210> SEQ ID NO 35
<211> LENGTH: 65
<212> TYPE: DNA
<213> ORGANISM: Artificial Sequence
<220> FEATURE:
<223> OTHER INFORMATION: tracrRNA

<400> SEQUENCE: 35

```
gggcttcatg ccgaaatcaa caccctgtca ttttatggca gggtgttttc gttatttaat    60
ttttt                                                                  65
```

<210> SEQ ID NO 36
<211> LENGTH: 39
<212> TYPE: DNA
<213> ORGANISM: Artificial Sequence
<220> FEATURE:
<223> OTHER INFORMATION: tracrRNA

<400> SEQUENCE: 36

```
aaatcaacac cctgtcattt tatggcaggg tgtttttt                              39
```

<210> SEQ ID NO 37
<211> LENGTH: 170
<212> TYPE: DNA
<213> ORGANISM: Artificial Sequence
<220> FEATURE:
<223> OTHER INFORMATION: tracrRNA

<400> SEQUENCE: 37

```
gtattaagta ttgttttatg gctgataaat ttctttgaat ttctccttga ttatttgtta        60
taaaagttat aaataatct tgttggaacc attcaaaaca gcatagcaag ttaaaataag         120
gctagtccgt tatcaacttg aaaaagtggc accgagtcgg tgctttttt                    170

<210> SEQ ID NO 38
<211> LENGTH: 89
<212> TYPE: DNA
<213> ORGANISM: Artificial Sequence
<220> FEATURE:
<223> OTHER INFORMATION: tracrRNA

<400> SEQUENCE: 38
gttggaacca ttcaaaacag catagcaagt taaataagg ctagtccgtt atcaacttga         60
aaaagtggca ccgagtcggt gctttttt                                           89

<210> SEQ ID NO 39
<211> LENGTH: 76
<212> TYPE: DNA
<213> ORGANISM: Artificial Sequence
<220> FEATURE:
<223> OTHER INFORMATION: tracrRNA

<400> SEQUENCE: 39
aaaacagcat agcaagttaa aataaggcta gtccgttatc aacttgaaaa agtggcaccg         60
agtcggtgct tttttt                                                        76

<210> SEQ ID NO 40
<211> LENGTH: 93
<212> TYPE: DNA
<213> ORGANISM: Artificial Sequence
<220> FEATURE:
<223> OTHER INFORMATION: tracrRNA

<400> SEQUENCE: 40
gtttaagagc tatgctggaa acagcatagc aagtttaaat aaggctagtc cgttatcaac         60
ttgaaaaagt ggcaccgagt cggtgctttt ttt                                     93

<210> SEQ ID NO 41
<211> LENGTH: 141
<212> TYPE: DNA
<213> ORGANISM: Artificial Sequence
<220> FEATURE:
<223> OTHER INFORMATION: CBLB shRNA

<400> SEQUENCE: 41
gaaggctcga aaggtatat tgctgttgac agtgagcgat cagtgagaat gagtactta          60 tagtgaagcc acagatgtat aaagtactca ttctcactga gtgcctactg cctcggactt        120 caagggcta gaattcgagc a                                                   141

<210> SEQ ID NO 42
<211> LENGTH: 141
<212> TYPE: DNA
<213> ORGANISM: Artificial Sequence
<220> FEATURE:
<223> OTHER INFORMATION: CBLB shRNA

<400> SEQUENCE: 42
gaaggctcga aaggtatat tgctgttgac agtgagcgaa ggtgaaaatg tcaaaactaa         60
tagtgaagcc acagatgtat tagttttgac attttcacct gtgcctactg cctcggactt        120
```
caaggggcta gaattcgagc a                                                     141

<210> SEQ ID NO 43
<211> LENGTH: 141
<212> TYPE: DNA
<213> ORGANISM: Artificial Sequence
<220> FEATURE:
<223> OTHER INFORMATION: CBLB shRNA

<400> SEQUENCE: 43
gaaggctcga gaaggtatat tgctgttgac agtgagcgcc cagaaattca ccacagaaaa         60
tagtgaagcc acagatgtat tttctgtggt gaatttctgg ttgcctactg cctcggactt        120
caaggggcta gaattcgagc a                                                    141

<210> SEQ ID NO 44
<211> LENGTH: 141
<212> TYPE: DNA
<213> ORGANISM: Artificial Sequence
<220> FEATURE:
<223> OTHER INFORMATION: CBLB shRNA

<400> SEQUENCE: 44
gaaggctcga gaaggtatat tgctgttgac agtgagcgac cagaactgta gacaccaaaa        60
tagtgaagcc acagatgtat tttggtgtct acagttctgg ctgcctactg cctcggactt       120
caaggggcta gaattcgagc a                                                    141

<210> SEQ ID NO 45
<211> LENGTH: 21
<212> TYPE: DNA
<213> ORGANISM: Artificial Sequence
<220> FEATURE:
<223> OTHER INFORMATION: CBLB shRNA

<400> SEQUENCE: 45
gtcaattcca gggagataac t                                                    21

<210> SEQ ID NO 46
<211> LENGTH: 21
<212> TYPE: DNA
<213> ORGANISM: Artificial Sequence
<220> FEATURE:
<223> OTHER INFORMATION: CBLB shRNA

<400> SEQUENCE: 46
gcctggaagc aatggctcta a                                                    21

<210> SEQ ID NO 47
<211> LENGTH: 21
<212> TYPE: DNA
<213> ORGANISM: Artificial Sequence
<220> FEATURE:
<223> OTHER INFORMATION: CBLB shRNA

<400> SEQUENCE: 47
gcaccaaacc cggaagctat a                                                    21

<210> SEQ ID NO 48
<211> LENGTH: 21
<212> TYPE: DNA
<213> ORGANISM: Artificial Sequence
<220> FEATURE:
<223> OTHER INFORMATION: CBLB shRNA

<400> SEQUENCE: 48
gttgcactcg attgggacag t                                     21

<210> SEQ ID NO 49
<211> LENGTH: 21
<212> TYPE: DNA
<213> ORGANISM: Artificial Sequence
<220> FEATURE:
<223> OTHER INFORMATION: CBLB shRNA

<400> SEQUENCE: 49
ggattatgtg aacctacacc t                                     21

<210> SEQ ID NO 50
<211> LENGTH: 21
<212> TYPE: DNA
<213> ORGANISM: Artificial Sequence
<220> FEATURE:
<223> OTHER INFORMATION: CBLB shRNA

<400> SEQUENCE: 50
ggaatcacag cgagttcaaa t                                     21

<210> SEQ ID NO 51
<211> LENGTH: 21
<212> TYPE: DNA
<213> ORGANISM: Artificial Sequence
<220> FEATURE:
<223> OTHER INFORMATION: CBLB shRNA

<400> SEQUENCE: 51
gcaaggcata gtctcattga a                                     21

<210> SEQ ID NO 52
<211> LENGTH: 21
<212> TYPE: DNA
<213> ORGANISM: Artificial Sequence
<220> FEATURE:
<223> OTHER INFORMATION: CBLB shRNA

<400> SEQUENCE: 52
ggtgaagaga gccttagaga t                                     21

<210> SEQ ID NO 53
<211> LENGTH: 21
<212> TYPE: DNA
<213> ORGANISM: Artificial Sequence
<220> FEATURE:
<223> OTHER INFORMATION: CBLB shRNA

<400> SEQUENCE: 53
gtgaagagag ccttagagat a                                     21

<210> SEQ ID NO 54
<211> LENGTH: 23
<212> TYPE: RNA
<213> ORGANISM: Artificial Sequence
<220> FEATURE:
<223> OTHER INFORMATION: CBLB siRNA

<400> SEQUENCE: 54
aggagcuaag gucuuuucca aug                                   23

<210> SEQ ID NO 55
<211> LENGTH: 23
<212> TYPE: RNA

```
<213> ORGANISM: Artificial Sequence
<220> FEATURE:
<223> OTHER INFORMATION: CBLB siRNA

<400> SEQUENCE: 55
augucgaugc aaaaauugca aaa                                              23

<210> SEQ ID NO 56
<211> LENGTH: 23
<212> TYPE: RNA
<213> ORGANISM: Artificial Sequence
<220> FEATURE:
<223> OTHER INFORMATION: CBLB siRNA

<400> SEQUENCE: 56
gucacaugcu ggcagaaauc aaa                                              23

<210> SEQ ID NO 57
<211> LENGTH: 23
<212> TYPE: RNA
<213> ORGANISM: Artificial Sequence
<220> FEATURE:
<223> OTHER INFORMATION: CBLB siRNA

<400> SEQUENCE: 57
uccagguuac auggcauuuc uca                                              23

<210> SEQ ID NO 58
<211> LENGTH: 23
<212> TYPE: RNA
<213> ORGANISM: Artificial Sequence
<220> FEATURE:
<223> OTHER INFORMATION: CBLB siRNA

<400> SEQUENCE: 58
uugaacuuug aaccugugaa aug                                              23

<210> SEQ ID NO 59
<211> LENGTH: 23
<212> TYPE: RNA
<213> ORGANISM: Artificial Sequence
<220> FEATURE:
<223> OTHER INFORMATION: CBLB siRNA

<400> SEQUENCE: 59
uccacaucaa cagcuaaauc auu                                              23

<210> SEQ ID NO 60
<211> LENGTH: 23
<212> TYPE: RNA
<213> ORGANISM: Artificial Sequence
<220> FEATURE:
<223> OTHER INFORMATION: CBLB siRNA

<400> SEQUENCE: 60
augcuggcag aaaucaaagc aau                                              23

<210> SEQ ID NO 61
<211> LENGTH: 23
<212> TYPE: RNA
<213> ORGANISM: Artificial Sequence
<220> FEATURE:
<223> OTHER INFORMATION: CBLB siRNA

<400> SEQUENCE: 61
ugcagagaau gacaaagaug uca                                              23
```

<210> SEQ ID NO 62
<211> LENGTH: 23
<212> TYPE: RNA
<213> ORGANISM: Artificial Sequence
<220> FEATURE:
<223> OTHER INFORMATION: CBLB siRNA

<400> SEQUENCE: 62
ggcagaacuc accagucaca uca                                              23

<210> SEQ ID NO 63
<211> LENGTH: 23
<212> TYPE: RNA
<213> ORGANISM: Artificial Sequence
<220> FEATURE:
<223> OTHER INFORMATION: CBLB siRNA

<400> SEQUENCE: 63
ucgguccugu gauaaugguc acu                                              23

<210> SEQ ID NO 64
<211> LENGTH: 23
<212> TYPE: RNA
<213> ORGANISM: Artificial Sequence
<220> FEATURE:
<223> OTHER INFORMATION: CBLB siRNA

<400> SEQUENCE: 64
aggagcuaag gucuuuucca aug                                              23

<210> SEQ ID NO 65
<211> LENGTH: 23
<212> TYPE: RNA
<213> ORGANISM: Artificial Sequence
<220> FEATURE:
<223> OTHER INFORMATION: CBLB siRNA

<400> SEQUENCE: 65
augucgaugc aaaaauugca aaa                                              23

<210> SEQ ID NO 66
<211> LENGTH: 23
<212> TYPE: RNA
<213> ORGANISM: Artificial Sequence
<220> FEATURE:
<223> OTHER INFORMATION: CBLB siRNA

<400> SEQUENCE: 66
gucacaugcu ggcagaaauc aaa                                              23

<210> SEQ ID NO 67
<211> LENGTH: 23
<212> TYPE: RNA
<213> ORGANISM: Artificial Sequence
<220> FEATURE:
<223> OTHER INFORMATION: CBLB siRNA

<400> SEQUENCE: 67
uccagguuac auggcauuuc uca                                              23

<210> SEQ ID NO 68
<211> LENGTH: 23
<212> TYPE: RNA
<213> ORGANISM: Artificial Sequence
<220> FEATURE:

```
<223> OTHER INFORMATION: CBLB siRNA

<400> SEQUENCE: 68
uugaacuuug aaccugugaa aug                                          23

<210> SEQ ID NO 69
<211> LENGTH: 23
<212> TYPE: RNA
<213> ORGANISM: Artificial Sequence
<220> FEATURE:
<223> OTHER INFORMATION: CBLB siRNA

<400> SEQUENCE: 69
uccacaucaa cagcuaaauc auu                                          23

<210> SEQ ID NO 70
<211> LENGTH: 23
<212> TYPE: RNA
<213> ORGANISM: Artificial Sequence
<220> FEATURE:
<223> OTHER INFORMATION: CBLB siRNA

<400> SEQUENCE: 70
augcuggcag aaaucaaagc aau                                          23

<210> SEQ ID NO 71
<211> LENGTH: 23
<212> TYPE: RNA
<213> ORGANISM: Artificial Sequence
<220> FEATURE:
<223> OTHER INFORMATION: CBLB siRNA

<400> SEQUENCE: 71
ugcagagaau gacaaagaug uca                                          23

<210> SEQ ID NO 72
<211> LENGTH: 23
<212> TYPE: RNA
<213> ORGANISM: Artificial Sequence
<220> FEATURE:
<223> OTHER INFORMATION: CBLB siRNA

<400> SEQUENCE: 72
ggcagaacuc accagucaca uca                                          23

<210> SEQ ID NO 73
<211> LENGTH: 23
<212> TYPE: RNA
<213> ORGANISM: Artificial Sequence
<220> FEATURE:
<223> OTHER INFORMATION: CBLB siRNA

<400> SEQUENCE: 73
ucgguccugu gauaaugguc acu                                          23

<210> SEQ ID NO 74
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 74
agacacacgc aactttaaa                                               19
```

```
<210> SEQ ID NO 75
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 75
cagacacacg caactttaa                                                 19

<210> SEQ ID NO 76
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 76
acacacgcaa ctttaaatt                                                 19

<210> SEQ ID NO 77
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 77
acgaatgctt tcagttcaa                                                 19

<210> SEQ ID NO 78
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 78
atactcggaa ctggaatga                                                 19

<210> SEQ ID NO 79
<211> LENGTH: 19
<212> TYPE: DNA
<213> ORGANISM: Artificial Sequence
<220> FEATURE:
<223> OTHER INFORMATION: TNFAIP3 shRNA

<400> SEQUENCE: 79
gaagcttgtg gcgctgaaa                                                 19

<210> SEQ ID NO 80
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 80
aaagccggct gcgtgtattt t                                              21

<210> SEQ ID NO 81
<211> LENGTH: 21
<212> TYPE: DNA
<213> ORGANISM: Artificial Sequence
<220> FEATURE:
<223> OTHER INFORMATION: TNFAIP3 shRNA
```

```
<400> SEQUENCE: 81
aaagggagct ctagtcctttt t                                              21

<210> SEQ ID NO 82
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 82
aagggagctc tagtcctttt t                                               21

<210> SEQ ID NO 83
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 83
aagccctcat cgacagaaac a                                               21

<210> SEQ ID NO 84
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 84
aaacgaacgg tgacggcaat t                                               21

<210> SEQ ID NO 85
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 85
aaacagacac acgcaacttt a                                               21

<210> SEQ ID NO 86
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 86
aacagacaca cgcaacttta a                                               21

<210> SEQ ID NO 87
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 87
aatgtgcagc acaacggatt t                                               21

<210> SEQ ID NO 88
<211> LENGTH: 21
```

```
<212> TYPE: DNA
<213> ORGANISM: Artificial Sequence
<220> FEATURE:
<223> OTHER INFORMATION: TNFAIP3 shRNA

<400> SEQUENCE: 88
aaaagccggc tgcgtgtatt t                                              21

<210> SEQ ID NO 89
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 89
aaactcaacc agctgccttt t                                              21

<210> SEQ ID NO 90
<211> LENGTH: 20
<212> TYPE: DNA
<213> ORGANISM: Artificial Sequence
<220> FEATURE:
<223> OTHER INFORMATION: TNFAIP3 shRNA

<400> SEQUENCE: 90
aaactcaacc agctgccttt                                                20

<210> SEQ ID NO 91
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 91
aagtccttcc tcaggctttg t                                              21

<210> SEQ ID NO 92
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 92
aaagccagaa gaaactcaac t                                              21

<210> SEQ ID NO 93
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 93
aatccgagct gttccacttg t                                              21

<210> SEQ ID NO 94
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 94
```

```
aaggctggga ccatggcaca a                                              21

<210> SEQ ID NO 95
<211> LENGTH: 21
<212> TYPE: DNA
<213> ORGANISM: Artificial Sequence
<220> FEATURE:
<223> OTHER INFORMATION: TNFAIP3 shRNA

<400> SEQUENCE: 95
aatgccgcaa agttggatga a                                              21

<210> SEQ ID NO 96
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 96
uccucaguuu cgggagauca ucc                                            23

<210> SEQ ID NO 97
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 97
gagucucuca aaucucagga auu                                            23

<210> SEQ ID NO 98
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 98
agcucuaguc cuuuugugu aau                                             23

<210> SEQ ID NO 99
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 99
cacuggaaau guucagaacu ugc                                            23

<210> SEQ ID NO 100
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 100
augaugaaug ggacaaucuu auc                                            23

<210> SEQ ID NO 101
<211> LENGTH: 23
<212> TYPE: RNA
<213> ORGANISM: Artificial Sequence
```

```
<220> FEATURE:
<223> OTHER INFORMATION: TNFAIP3 siRNA

<400> SEQUENCE: 101
cacacugugu uucaucgagu aca                                              23

<210> SEQ ID NO 102
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 102
gcagaaccau ccauggacug uga                                              23

<210> SEQ ID NO 103
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 103
aaagaugugg ccuuuuguga ugg                                              23

<210> SEQ ID NO 104
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 104
uucagaacuu gccaguuuug ucc                                              23

<210> SEQ ID NO 105
<211> LENGTH: 23
<212> TYPE: RNA
<213> ORGANISM: Artificial Sequence
<220> FEATURE:
<223> OTHER INFORMATION: TNFAIP3 siRNA

<400> SEQUENCE: 105
augagacugg caauggucac agg                                              23

<210> SEQ ID NO 106
<211> LENGTH: 21
<212> TYPE: DNA
<213> ORGANISM: Artificial Sequence
<220> FEATURE:
<223> OTHER INFORMATION: PDCD1 shRNA

<400> SEQUENCE: 106
ggccaggatg gttcttagac t                                                21

<210> SEQ ID NO 107
<211> LENGTH: 21
<212> TYPE: DNA
<213> ORGANISM: Artificial Sequence
<220> FEATURE:
<223> OTHER INFORMATION: PDCD1 shRNA

<400> SEQUENCE: 107
ggatttccag tggcgagaga a                                                21
```

<210> SEQ ID NO 108
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 108
gccuguguuc ucguggacu aug                                              23

<210> SEQ ID NO 109
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 109
ggugcugcua gucugggucc ugg                                             23

<210> SEQ ID NO 110
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 110
gacagagaga agggcagaag ugc                                             23

<210> SEQ ID NO 111
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 111
cagcuucucc aacacaucgg aga                                             23

<210> SEQ ID NO 112
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 112
ccgugucaca caacugccca acg                                             23

<210> SEQ ID NO 113
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 113
uaugccacca uugucuuucc uag                                             23

<210> SEQ ID NO 114
<211> LENGTH: 23
<212> TYPE: RNA
<213> ORGANISM: Artificial Sequence
<220> FEATURE:
<223> OTHER INFORMATION: PDCD1 siRNA

```
<400> SEQUENCE: 114
ugcuaaacug guaccgcaug agc                                        23

<210> SEQ ID NO 115
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 115
gugacagaga gaagggcaga agu                                        23

<210> SEQ ID NO 116
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 116
cugaggaugg acacugcucu ugg                                        23

<210> SEQ ID NO 117
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 117
aucggagagc uucgugcuaa acu                                        23

<210> SEQ ID NO 118
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 118
gccuguguuc ucuguggacu aug                                        23

<210> SEQ ID NO 119
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 119
ggugcugcua gucuggqucc ugg                                        23

<210> SEQ ID NO 120
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 120
gacagagaga agggcagaag ugc                                        23

<210> SEQ ID NO 121
```

```
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 121
cagcuucucc aacacaucgg aga                                              23

<210> SEQ ID NO 122
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 122
ccgugucaca caacugccca acg                                              23

<210> SEQ ID NO 123
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 123
uaugccacca uugucuuucc uag                                              23

<210> SEQ ID NO 124
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 124
ugcuaaacug guaccgcaug agc                                              23

<210> SEQ ID NO 125
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 125
gugacagaga gaagggcaga agu                                              23

<210> SEQ ID NO 126
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 126
cugaggaugg acacugcucu ugg                                              23

<210> SEQ ID NO 127
<211> LENGTH: 23
<212> TYPE: RNA
<213> ORGANISM: Artificial Sequence
<220> FEATURE:
<223> OTHER INFORMATION: PDCD1 siRNA

<400> SEQUENCE: 127
```
aucggagagc uucgugcuaa acu                                          23

<210> SEQ ID NO 128
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 128
ggcaacggaa cccagattta t                                            21

<210> SEQ ID NO 129
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 129
ggaacccaaa ttacgtgtac t                                            21

<210> SEQ ID NO 130
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 130
gaacccaaat tacgtgtact a                                            21

<210> SEQ ID NO 131
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 131
gggagaagac tatattgtac a                                            21

<210> SEQ ID NO 132
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 132
gacgtttata gccgaaatga t                                            21

<210> SEQ ID NO 133
<211> LENGTH: 21
<212> TYPE: DNA
<213> ORGANISM: Artificial Sequence
<220> FEATURE:
<223> OTHER INFORMATION: CTLA4 shRNA

<400> SEQUENCE: 133
gacactaata caccaggtag a                                            21

<210> SEQ ID NO 134
<211> LENGTH: 23
<212> TYPE: RNA

```
<213> ORGANISM: Artificial Sequence
<220> FEATURE:
<223> OTHER INFORMATION: CTLA4 siRNA

<400> SEQUENCE: 134
accucacuau ccaaggacug agg                                              23

<210> SEQ ID NO 135
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 135
augaguugac cuuccuagau gau                                              23

<210> SEQ ID NO 136
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 136
ggggaaugag uugaccuucc uag                                              23

<210> SEQ ID NO 137
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 137
cucuggaucc uugcagcagu uag                                              23

<210> SEQ ID NO 138
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 138
cuccucugga uccuugcagc agu                                              23

<210> SEQ ID NO 139
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 139
uuugugugug aguaugcauc ucc                                              23

<210> SEQ ID NO 140
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 140
caccuccagu ggaaaucaag uga                                              23
```

<210> SEQ ID NO 141
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 141
cacgggacuc uacaucugca agg                                           23

<210> SEQ ID NO 142
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 142
uucugacuuc cuccucugga ucc                                           23

<210> SEQ ID NO 143
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 143
aagucugugc ggcaaccuac aug                                           23

<210> SEQ ID NO 144
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 144
accucacuau ccaaggacug agg                                           23

<210> SEQ ID NO 145
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 145
augaguugac cuuccuagau gau                                           23

<210> SEQ ID NO 146
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 146
ggggaaugag uugaccuucc uag                                           23

<210> SEQ ID NO 147
<211> LENGTH: 23
<212> TYPE: RNA
<213> ORGANISM: Artificial Sequence
<220> FEATURE:

<223> OTHER INFORMATION: CTLA4 siRNA

<400> SEQUENCE: 147
cucuggaucc uugcagcagu uag                                             23

<210> SEQ ID NO 148
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 148
cuccucugga uccuugcagc agu                                             23

<210> SEQ ID NO 149
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 149
uuugugugug aguaugcauc ucc                                             23

<210> SEQ ID NO 150
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 150
caccuccagu ggaaaucaag uga                                             23

<210> SEQ ID NO 151
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 151
cacgggacuc uacaucugca agg                                             23

<210> SEQ ID NO 152
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 152
uucugacuuc cuccucugga ucc                                             23

<210> SEQ ID NO 153
<211> LENGTH: 23
<212> TYPE: RNA
<213> ORGANISM: Artificial Sequence
<220> FEATURE:
<223> OTHER INFORMATION: CTLA4 siRNA

<400> SEQUENCE: 153
aagucugugc ggcaaccuac aug                                             23

```
<210> SEQ ID NO 154
<211> LENGTH: 20
<212> TYPE: DNA
<213> ORGANISM: Murine

<400> SEQUENCE: 154
gccgcaggag gttgcctttc                                              20

<210> SEQ ID NO 155
<211> LENGTH: 20
<212> TYPE: DNA
<213> ORGANISM: Murine

<400> SEQUENCE: 155
tccaagagtg atcgaggcat                                              20

<210> SEQ ID NO 156
<211> LENGTH: 20
<212> TYPE: DNA
<213> ORGANISM: Murine

<400> SEQUENCE: 156
agtgcagctt gatgtgccgc                                              20

<210> SEQ ID NO 157
<211> LENGTH: 20
<212> TYPE: DNA
<213> ORGANISM: Murine

<400> SEQUENCE: 157
cggtgagggc gtccctccgg                                              20

<210> SEQ ID NO 158
<211> LENGTH: 20
<212> TYPE: DNA
<213> ORGANISM: Murine

<400> SEQUENCE: 158
ggccacctga ggacgcactc                                              20

<210> SEQ ID NO 159
<211> LENGTH: 20
<212> TYPE: DNA
<213> ORGANISM: Murine

<400> SEQUENCE: 159
gttgcaaaga tggcatttga                                              20

<210> SEQ ID NO 160
<211> LENGTH: 20
<212> TYPE: DNA
<213> ORGANISM: Murine

<400> SEQUENCE: 160
cctttccagt gcaaccagtg                                              20

<210> SEQ ID NO 161
<211> LENGTH: 20
<212> TYPE: DNA
<213> ORGANISM: Murine

<400> SEQUENCE: 161
caactatgcc tgccgccgga                                              20
```

```
<210> SEQ ID NO 162
<211> LENGTH: 20
<212> TYPE: DNA
<213> ORGANISM: Human

<400> SEQUENCE: 162
gttggtaaac ctcacaaatg                                          20

<210> SEQ ID NO 163
<211> LENGTH: 20
<212> TYPE: DNA
<213> ORGANISM: Human

<400> SEQUENCE: 163
cgtgatccag gaagagcacc                                          20

<210> SEQ ID NO 164
<211> LENGTH: 20
<212> TYPE: DNA
<213> ORGANISM: Human

<400> SEQUENCE: 164
tctggagtat cgcttacagg                                          20

<210> SEQ ID NO 165
<211> LENGTH: 20
<212> TYPE: DNA
<213> ORGANISM: Human

<400> SEQUENCE: 165
ggaagccgtg gcagcccatg                                          20

<210> SEQ ID NO 166
<211> LENGTH: 20
<212> TYPE: DNA
<213> ORGANISM: Human

<400> SEQUENCE: 166
gcgtgcctgt gaaatgaatg                                          20

<210> SEQ ID NO 167
<211> LENGTH: 20
<212> TYPE: DNA
<213> ORGANISM: Human

<400> SEQUENCE: 167
cgcgtgcggg gcgatgtggt                                          20

<210> SEQ ID NO 168
<211> LENGTH: 20
<212> TYPE: DNA
<213> ORGANISM: Human

<400> SEQUENCE: 168
tgagcccatg ccgatccccg                                          20

<210> SEQ ID NO 169
<211> LENGTH: 20
<212> TYPE: DNA
<213> ORGANISM: Human

<400> SEQUENCE: 169
ctcttaccaa gaaatttctg                                          20
```

```
<210> SEQ ID NO 170
<211> LENGTH: 20
<212> TYPE: DNA
<213> ORGANISM: Human

<400> SEQUENCE: 170
catatggggc tgatgacttt                                              20

<210> SEQ ID NO 171
<211> LENGTH: 20
<212> TYPE: DNA
<213> ORGANISM: Human

<400> SEQUENCE: 171
ggggcctcat tcacccagaa                                              20

<210> SEQ ID NO 172
<211> LENGTH: 20
<212> TYPE: DNA
<213> ORGANISM: Human

<400> SEQUENCE: 172
gcctcgggag agaaaatgaa                                              20

<210> SEQ ID NO 173
<211> LENGTH: 20
<212> TYPE: DNA
<213> ORGANISM: Human

<400> SEQUENCE: 173
cgcgcagcag gtcgtaggcg                                              20

<210> SEQ ID NO 174
<211> LENGTH: 20
<212> TYPE: DNA
<213> ORGANISM: Human

<400> SEQUENCE: 174
tctctgatcc tatcttgcac                                              20

<210> SEQ ID NO 175
<211> LENGTH: 20
<212> TYPE: DNA
<213> ORGANISM: Human

<400> SEQUENCE: 175
ggacaggccc ttgtcccctg                                              20

<210> SEQ ID NO 176
<211> LENGTH: 20
<212> TYPE: DNA
<213> ORGANISM: Human

<400> SEQUENCE: 176
ccgcgtggtc agcaccagcg                                              20

<210> SEQ ID NO 177
<211> LENGTH: 20
<212> TYPE: DNA
<213> ORGANISM: Human

<400> SEQUENCE: 177
```
aagatttggg aattattgca                                              20

<210> SEQ ID NO 178
<211> LENGTH: 20
<212> TYPE: DNA
<213> ORGANISM: Human

<400> SEQUENCE: 178
cttccagtgc aatcagtgcg                                              20

<210> SEQ ID NO 179
<211> LENGTH: 20
<212> TYPE: DNA
<213> ORGANISM: Human

<400> SEQUENCE: 179
cctcacaaat gtggatattg                                              20

<210> SEQ ID NO 180
<211> LENGTH: 20
<212> TYPE: DNA
<213> ORGANISM: Murine

<400> SEQUENCE: 180
cctcgaaagt ctcggagctc                                              20

<210> SEQ ID NO 181
<211> LENGTH: 20
<212> TYPE: DNA
<213> ORGANISM: Murine

<400> SEQUENCE: 181
ctgcgtcaag actgctacac                                              20

<210> SEQ ID NO 182
<211> LENGTH: 20
<212> TYPE: DNA
<213> ORGANISM: Murine

<400> SEQUENCE: 182
tgctcacagg caagatgtag                                              20

<210> SEQ ID NO 183
<211> LENGTH: 20
<212> TYPE: DNA
<213> ORGANISM: Murine

<400> SEQUENCE: 183
ccggacagcc ctccaccttg                                              20

<210> SEQ ID NO 184
<211> LENGTH: 20
<212> TYPE: DNA
<213> ORGANISM: Murine

<400> SEQUENCE: 184
agacctacca ttgtagttgg                                              20

<210> SEQ ID NO 185
<211> LENGTH: 20
<212> TYPE: DNA
<213> ORGANISM: Murine

<400> SEQUENCE: 185
ccaagtgctc cacgatggcc                                         20

<210> SEQ ID NO 186
<211> LENGTH: 20
<212> TYPE: DNA
<213> ORGANISM: Murine

<400> SEQUENCE: 186
agcctctatc cacggctacc                                         20

<210> SEQ ID NO 187
<211> LENGTH: 20
<212> TYPE: DNA
<213> ORGANISM: Murine

<400> SEQUENCE: 187
gccccaggta agctggtagg                                         20

<210> SEQ ID NO 188
<211> LENGTH: 20
<212> TYPE: DNA
<213> ORGANISM: Murine

<400> SEQUENCE: 188
gcaagcagcg cacctgctgc                                         20

<210> SEQ ID NO 189
<211> LENGTH: 20
<212> TYPE: DNA
<213> ORGANISM: Murine

<400> SEQUENCE: 189
tcaagactgc tacactggcc                                         20

<210> SEQ ID NO 190
<211> LENGTH: 20
<212> TYPE: DNA
<213> ORGANISM: Murine

<400> SEQUENCE: 190
gcaggttgtt ctggaagttg                                         20

<210> SEQ ID NO 191
<211> LENGTH: 20
<212> TYPE: DNA
<213> ORGANISM: Murine

<400> SEQUENCE: 191
gggtgctgat gtcaacgctc                                         20

<210> SEQ ID NO 192
<211> LENGTH: 20
<212> TYPE: DNA
<213> ORGANISM: Murine

<400> SEQUENCE: 192
ccacgatggc caggtagccg                                         20

<210> SEQ ID NO 193
<211> LENGTH: 20
<212> TYPE: DNA
<213> ORGANISM: Murine

```
<400> SEQUENCE: 193
tggtcagcgg cttctcttcg                                          20

<210> SEQ ID NO 194
<211> LENGTH: 20
<212> TYPE: DNA
<213> ORGANISM: Murine

<400> SEQUENCE: 194
aatgtggggc tgatgtcaac                                          20

<210> SEQ ID NO 195
<211> LENGTH: 20
<212> TYPE: DNA
<213> ORGANISM: Murine

<400> SEQUENCE: 195
atttcaacaa gagcgaaacc                                          20

<210> SEQ ID NO 196
<211> LENGTH: 20
<212> TYPE: DNA
<213> ORGANISM: Murine

<400> SEQUENCE: 196
cacctgacca atgacttcca                                          20

<210> SEQ ID NO 197
<211> LENGTH: 20
<212> TYPE: DNA
<213> ORGANISM: Murine

<400> SEQUENCE: 197
gccctggaag cagcagctca                                          20

<210> SEQ ID NO 198
<211> LENGTH: 20
<212> TYPE: DNA
<213> ORGANISM: Murine

<400> SEQUENCE: 198
gctcacaggc aagatgtaga                                          20

<210> SEQ ID NO 199
<211> LENGTH: 20
<212> TYPE: DNA
<213> ORGANISM: Human

<400> SEQUENCE: 199
cgtccgcgcc atgttccagg                                          20

<210> SEQ ID NO 200
<211> LENGTH: 20
<212> TYPE: DNA
<213> ORGANISM: Human

<400> SEQUENCE: 200
tggtttcagg agccctgtaa                                          20

<210> SEQ ID NO 201
<211> LENGTH: 20
<212> TYPE: DNA
<213> ORGANISM: Human
```

<400> SEQUENCE: 201
acccggatac agcagcagct                                              20

<210> SEQ ID NO 202
<211> LENGTH: 20
<212> TYPE: DNA
<213> ORGANISM: Human

<400> SEQUENCE: 202
ttccagggct ccgagccgcg                                              20

<210> SEQ ID NO 203
<211> LENGTH: 20
<212> TYPE: DNA
<213> ORGANISM: Human

<400> SEQUENCE: 203
ctgaaggcta ccaactacaa                                              20

<210> SEQ ID NO 204
<211> LENGTH: 20
<212> TYPE: DNA
<213> ORGANISM: Human

<400> SEQUENCE: 204
gggtatttcc tcgaaagtct                                              20

<210> SEQ ID NO 205
<211> LENGTH: 20
<212> TYPE: DNA
<213> ORGANISM: Human

<400> SEQUENCE: 205
gagccgcagg aggtgccgcg                                              20

<210> SEQ ID NO 206
<211> LENGTH: 20
<212> TYPE: DNA
<213> ORGANISM: Human

<400> SEQUENCE: 206
ctgagtcagg actcccacgc                                              20

<210> SEQ ID NO 207
<211> LENGTH: 20
<212> TYPE: DNA
<213> ORGANISM: Human

<400> SEQUENCE: 207
cacttacgag tccccgtcct                                              20

<210> SEQ ID NO 208
<211> LENGTH: 20
<212> TYPE: DNA
<213> ORGANISM: Human

<400> SEQUENCE: 208
ctcaaattcc ttttggtttc                                              20

<210> SEQ ID NO 209
<211> LENGTH: 20
<212> TYPE: DNA

```
<213> ORGANISM: Human

<400> SEQUENCE: 209
ggttggtgat cacagccaag                                          20

<210> SEQ ID NO 210
<211> LENGTH: 20
<212> TYPE: DNA
<213> ORGANISM: Human

<400> SEQUENCE: 210
gcaggttgtt ctggaagttg                                          20

<210> SEQ ID NO 211
<211> LENGTH: 20
<212> TYPE: DNA
<213> ORGANISM: Murine

<400> SEQUENCE: 211
cacaggtcat tgatatctta                                          20

<210> SEQ ID NO 212
<211> LENGTH: 20
<212> TYPE: DNA
<213> ORGANISM: Murine

<400> SEQUENCE: 212
catggtgcaa ctcctgctgc                                          20

<210> SEQ ID NO 213
<211> LENGTH: 20
<212> TYPE: DNA
<213> ORGANISM: Murine

<400> SEQUENCE: 213
gtgaacgctc agatgtattc                                          20

<210> SEQ ID NO 214
<211> LENGTH: 20
<212> TYPE: DNA
<213> ORGANISM: Murine

<400> SEQUENCE: 214
atacatctga gcgttcacgt                                          20

<210> SEQ ID NO 215
<211> LENGTH: 20
<212> TYPE: DNA
<213> ORGANISM: Murine

<400> SEQUENCE: 215
gtgcgcagcg gggctgacag                                          20

<210> SEQ ID NO 216
<211> LENGTH: 20
<212> TYPE: DNA
<213> ORGANISM: Murine

<400> SEQUENCE: 216
tcacaatgac acacctctca                                          20

<210> SEQ ID NO 217
<211> LENGTH: 20
```

```
<212> TYPE: DNA
<213> ORGANISM: Murine

<400> SEQUENCE: 217
tagacgtcca taacaacctg                                               20

<210> SEQ ID NO 218
<211> LENGTH: 20
<212> TYPE: DNA
<213> ORGANISM: Murine

<400> SEQUENCE: 218
acgatccagg gccatggggc                                               20

<210> SEQ ID NO 219
<211> LENGTH: 20
<212> TYPE: DNA
<213> ORGANISM: Human

<400> SEQUENCE: 219
gctggaccgc catggccaga                                               20

<210> SEQ ID NO 220
<211> LENGTH: 20
<212> TYPE: DNA
<213> ORGANISM: Human

<400> SEQUENCE: 220
gttcactgcc acgtgcaggg                                               20

<210> SEQ ID NO 221
<211> LENGTH: 20
<212> TYPE: DNA
<213> ORGANISM: Human

<400> SEQUENCE: 221
gctggtcaac ctcttccagc                                               20

<210> SEQ ID NO 222
<211> LENGTH: 20
<212> TYPE: DNA
<213> ORGANISM: Human

<400> SEQUENCE: 222
acaaggcccg cagcgccgcg                                               20

<210> SEQ ID NO 223
<211> LENGTH: 20
<212> TYPE: DNA
<213> ORGANISM: Human

<400> SEQUENCE: 223
caggcctctc catattgctg                                               20

<210> SEQ ID NO 224
<211> LENGTH: 20
<212> TYPE: DNA
<213> ORGANISM: Human

<400> SEQUENCE: 224
gccacccgtg cagatgagga                                               20

<210> SEQ ID NO 225
```

```
<211> LENGTH: 20
<212> TYPE: DNA
<213> ORGANISM: Human

<400> SEQUENCE: 225
tcgacatcta caacaaccta                                               20

<210> SEQ ID NO 226
<211> LENGTH: 20
<212> TYPE: DNA
<213> ORGANISM: Human

<400> SEQUENCE: 226
atgtggtgat cacagccagg                                               20

<210> SEQ ID NO 227
<211> LENGTH: 20
<212> TYPE: DNA
<213> ORGANISM: Human

<400> SEQUENCE: 227
gcgcttgcgg agcggcagcg                                               20

<210> SEQ ID NO 228
<211> LENGTH: 20
<212> TYPE: DNA
<213> ORGANISM: Human

<400> SEQUENCE: 228
acaggtcatc gacatcctga                                               20

<210> SEQ ID NO 229
<211> LENGTH: 20
<212> TYPE: DNA
<213> ORGANISM: Human

<400> SEQUENCE: 229
gaccgagcct cacctgccgt                                               20

<210> SEQ ID NO 230
<211> LENGTH: 20
<212> TYPE: DNA
<213> ORGANISM: Human

<400> SEQUENCE: 230
ataccccatg atgtgcccca                                               20

<210> SEQ ID NO 231
<211> LENGTH: 20
<212> TYPE: DNA
<213> ORGANISM: Human

<400> SEQUENCE: 231
gtgaacgcgc aaatgtactc                                               20

<210> SEQ ID NO 232
<211> LENGTH: 20
<212> TYPE: DNA
<213> ORGANISM: Murine

<400> SEQUENCE: 232
ttttctatct catgaggttt                                               20
```

```
<210> SEQ ID NO 233
<211> LENGTH: 20
<212> TYPE: DNA
<213> ORGANISM: Murine

<400> SEQUENCE: 233
aggcatccca ttgcgggcct                                              20

<210> SEQ ID NO 234
<211> LENGTH: 20
<212> TYPE: DNA
<213> ORGANISM: Murine

<400> SEQUENCE: 234
tcggcccgag taagtgctat                                              20

<210> SEQ ID NO 235
<211> LENGTH: 20
<212> TYPE: DNA
<213> ORGANISM: Murine

<400> SEQUENCE: 235
gcgatcctcg tggttgctgt                                              20

<210> SEQ ID NO 236
<211> LENGTH: 20
<212> TYPE: DNA
<213> ORGANISM: Murine

<400> SEQUENCE: 236
ttctttgttg atcactttga                                              20

<210> SEQ ID NO 237
<211> LENGTH: 20
<212> TYPE: DNA
<213> ORGANISM: Murine

<400> SEQUENCE: 237
ttcttccaaa ccagcaagtg                                              20

<210> SEQ ID NO 238
<211> LENGTH: 20
<212> TYPE: DNA
<213> ORGANISM: Murine

<400> SEQUENCE: 238
gacagatgct cacttcaaca                                              20

<210> SEQ ID NO 239
<211> LENGTH: 20
<212> TYPE: DNA
<213> ORGANISM: Murine

<400> SEQUENCE: 239
tgatgttcac catccacatg                                              20

<210> SEQ ID NO 240
<211> LENGTH: 20
<212> TYPE: DNA
<213> ORGANISM: Human

<400> SEQUENCE: 240
catagtccag gaagaggacg                                              20
```

```
<210> SEQ ID NO 241
<211> LENGTH: 20
<212> TYPE: DNA
<213> ORGANISM: Human

<400> SEQUENCE: 241
gataactgga accatctccg                                              20

<210> SEQ ID NO 242
<211> LENGTH: 20
<212> TYPE: DNA
<213> ORGANISM: Human

<400> SEQUENCE: 242
caagcagaga agttcccttg                                              20

<210> SEQ ID NO 243
<211> LENGTH: 20
<212> TYPE: DNA
<213> ORGANISM: Human

<400> SEQUENCE: 243
aaagacctga tgttacctgc                                              20

<210> SEQ ID NO 244
<211> LENGTH: 20
<212> TYPE: DNA
<213> ORGANISM: Human

<400> SEQUENCE: 244
ttcggcgcca agatagctga                                              20

<210> SEQ ID NO 245
<211> LENGTH: 20
<212> TYPE: DNA
<213> ORGANISM: Human

<400> SEQUENCE: 245
gctcatacag acccgcatga                                              20

<210> SEQ ID NO 246
<211> LENGTH: 20
<212> TYPE: DNA
<213> ORGANISM: Human

<400> SEQUENCE: 246
agtgatcaac aaggaagggg                                              20

<210> SEQ ID NO 247
<211> LENGTH: 20
<212> TYPE: DNA
<213> ORGANISM: Human

<400> SEQUENCE: 247
acccgggctg agatgtcaaa                                              20

<210> SEQ ID NO 248
<211> LENGTH: 20
<212> TYPE: DNA
<213> ORGANISM: Human

<400> SEQUENCE: 248
tgtgattctg gcgttcttca                                              20
```

<210> SEQ ID NO 249
<211> LENGTH: 20
<212> TYPE: DNA
<213> ORGANISM: Human

<400> SEQUENCE: 249
ggtcagtgaa gccgacacca                                               20

<210> SEQ ID NO 250
<211> LENGTH: 20
<212> TYPE: DNA
<213> ORGANISM: Human

<400> SEQUENCE: 250
cttgcagtct tatgccgaga                                               20

<210> SEQ ID NO 251
<211> LENGTH: 20
<212> TYPE: DNA
<213> ORGANISM: Human

<400> SEQUENCE: 251
atgccccaca ctgattacac                                               20

<210> SEQ ID NO 252
<211> LENGTH: 20
<212> TYPE: DNA
<213> ORGANISM: Human

<400> SEQUENCE: 252
attccagtgt aatcagtgtg                                               20

<210> SEQ ID NO 253
<211> LENGTH: 20
<212> TYPE: DNA
<213> ORGANISM: Human

<400> SEQUENCE: 253 aagttcccctt gaggagcaca                                              20

<210> SEQ ID NO 254
<211> LENGTH: 20
<212> TYPE: DNA
<213> ORGANISM: Human

<400> SEQUENCE: 254
ggacagatta gcaagcaatg                                               20

<210> SEQ ID NO 255
<211> LENGTH: 20
<212> TYPE: DNA
<213> ORGANISM: Human

<400> SEQUENCE: 255
cttcccaaca ggtctcttga                                               20

<210> SEQ ID NO 256
<211> LENGTH: 20
<212> TYPE: DNA
<213> ORGANISM: Human

<400> SEQUENCE: 256
agcagtctct tcacaactgg                                                    20

<210> SEQ ID NO 257
<211> LENGTH: 20
<212> TYPE: DNA
<213> ORGANISM: Human

<400> SEQUENCE: 257
tcacagtcat catgaactca                                                    20

<210> SEQ ID NO 258
<211> LENGTH: 20
<212> TYPE: DNA
<213> ORGANISM: Human

<400> SEQUENCE: 258
caactctctg atagtggtaa                                                    20

<210> SEQ ID NO 259
<211> LENGTH: 20
<212> TYPE: DNA
<213> ORGANISM: Human

<400> SEQUENCE: 259
aatcggcaat atataacatg                                                    20

<210> SEQ ID NO 260
<211> LENGTH: 20
<212> TYPE: DNA
<213> ORGANISM: Human

<400> SEQUENCE: 260
agcacttgct ctgaaatttg                                                    20

<210> SEQ ID NO 261
<211> LENGTH: 20
<212> TYPE: DNA
<213> ORGANISM: Human

<400> SEQUENCE: 261
ctaaatgtgt taccatacca                                                    20

<210> SEQ ID NO 262
<211> LENGTH: 20
<212> TYPE: DNA
<213> ORGANISM: Human

<400> SEQUENCE: 262
attattgaat ccatacctgg                                                    20

<210> SEQ ID NO 263
<211> LENGTH: 20
<212> TYPE: DNA
<213> ORGANISM: Human

<400> SEQUENCE: 263
agaatgggca ggaagaaaag                                                    20

<210> SEQ ID NO 264
<211> LENGTH: 20
<212> TYPE: DNA
<213> ORGANISM: Murine

<400> SEQUENCE: 264
aaggtcggtt tggagaagtt 20

<210> SEQ ID NO 265
<211> LENGTH: 20
<212> TYPE: DNA
<213> ORGANISM: Murine

<400> SEQUENCE: 265
attgttcttt gaacaagcag 20

<210> SEQ ID NO 266
<211> LENGTH: 20
<212> TYPE: DNA
<213> ORGANISM: Murine

<400> SEQUENCE: 266
tggccttggt cctgtggagc 20

<210> SEQ ID NO 267
<211> LENGTH: 20
<212> TYPE: DNA
<213> ORGANISM: Murine

<400> SEQUENCE: 267
acaacatcag ggtctggatc 20

<210> SEQ ID NO 268
<211> LENGTH: 20
<212> TYPE: DNA
<213> ORGANISM: Murine

<400> SEQUENCE: 268
atttatgata tgacaacatc 20

<210> SEQ ID NO 269
<211> LENGTH: 20
<212> TYPE: DNA
<213> ORGANISM: Murine

<400> SEQUENCE: 269
tttatagcag cagacaacaa 20

<210> SEQ ID NO 270
<211> LENGTH: 20
<212> TYPE: DNA
<213> ORGANISM: Murine

<400> SEQUENCE: 270
gcaatgcaga cgaagcagac 20

<210> SEQ ID NO 271
<211> LENGTH: 20
<212> TYPE: DNA
<213> ORGANISM: Murine

<400> SEQUENCE: 271
agtttggcga ggcaaatggc 20

<210> SEQ ID NO 272
<211> LENGTH: 20
<212> TYPE: DNA
<213> ORGANISM: Murine

```
<400> SEQUENCE: 272
gagctggcag ctgtcattgc                                          20

<210> SEQ ID NO 273
<211> LENGTH: 20
<212> TYPE: DNA
<213> ORGANISM: Murine

<400> SEQUENCE: 273
tctgataaat ctctgcctct                                          20

<210> SEQ ID NO 274
<211> LENGTH: 20
<212> TYPE: DNA
<213> ORGANISM: Murine

<400> SEQUENCE: 274
gaatagatac actgttactg                                          20

<210> SEQ ID NO 275
<211> LENGTH: 20
<212> TYPE: DNA
<213> ORGANISM: Murine

<400> SEQUENCE: 275
gttacgccat gaaaatatcc                                          20

<210> SEQ ID NO 276
<211> LENGTH: 20
<212> TYPE: DNA
<213> ORGANISM: Murine

<400> SEQUENCE: 276
gtcagctggc cttggtcctg                                          20

<210> SEQ ID NO 277
<211> LENGTH: 20
<212> TYPE: DNA
<213> ORGANISM: Murine

<400> SEQUENCE: 277
aatgctttct tgtaacacaa                                          20

<210> SEQ ID NO 278
<211> LENGTH: 20
<212> TYPE: DNA
<213> ORGANISM: Murine

<400> SEQUENCE: 278
gatatgacaa catcagggtc                                          20

<210> SEQ ID NO 279
<211> LENGTH: 20
<212> TYPE: DNA
<213> ORGANISM: Human

<400> SEQUENCE: 279
tggcagaaac actgtaacgc                                          20

<210> SEQ ID NO 280
<211> LENGTH: 20
<212> TYPE: DNA
<213> ORGANISM: Human
```

<400> SEQUENCE: 280
attgttctct gaacaagcaa                                          20

<210> SEQ ID NO 281
<211> LENGTH: 20
<212> TYPE: DNA
<213> ORGANISM: Human

<400> SEQUENCE: 281
catacaaacg gcctatctcg                                          20

<210> SEQ ID NO 282
<211> LENGTH: 20
<212> TYPE: DNA
<213> ORGANISM: Human

<400> SEQUENCE: 282
gagatgcaga cgaagcacac                                          20

<210> SEQ ID NO 283
<211> LENGTH: 20
<212> TYPE: DNA
<213> ORGANISM: Human

<400> SEQUENCE: 283
attgtgttac aagaaagcat                                          20

<210> SEQ ID NO 284
<211> LENGTH: 20
<212> TYPE: DNA
<213> ORGANISM: Human

<400> SEQUENCE: 284
agaacgttcg tggttccgtg                                          20

<210> SEQ ID NO 285
<211> LENGTH: 20
<212> TYPE: DNA
<213> ORGANISM: Human

<400> SEQUENCE: 285
gtttggagag gaaagtggcg                                          20

<210> SEQ ID NO 286
<211> LENGTH: 20
<212> TYPE: DNA
<213> ORGANISM: Human

<400> SEQUENCE: 286
atttatgata tgacaacgtc                                          20

<210> SEQ ID NO 287
<211> LENGTH: 20
<212> TYPE: DNA
<213> ORGANISM: Human

<400> SEQUENCE: 287
gttgtgtata actttgtctg                                          20

<210> SEQ ID NO 288
<211> LENGTH: 20
<212> TYPE: DNA

<213> ORGANISM: Human

<400> SEQUENCE: 288
gtgcaccctc ttcaaaaact                                        20

<210> SEQ ID NO 289
<211> LENGTH: 20
<212> TYPE: DNA
<213> ORGANISM: Murine

<400> SEQUENCE: 289
gaccccaagc tcacctacca                                        20

<210> SEQ ID NO 290
<211> LENGTH: 20
<212> TYPE: DNA
<213> ORGANISM: Murine

<400> SEQUENCE: 290
ttctcccaag tgtgtcatga                                        20

<210> SEQ ID NO 291
<211> LENGTH: 20
<212> TYPE: DNA
<213> ORGANISM: Murine

<400> SEQUENCE: 291
ttccagagtg aagccgtggt                                        20

<210> SEQ ID NO 292
<211> LENGTH: 20
<212> TYPE: DNA
<213> ORGANISM: Murine

<400> SEQUENCE: 292
acggccacgc agacttcatg                                        20

<210> SEQ ID NO 293
<211> LENGTH: 20
<212> TYPE: DNA
<213> ORGANISM: Murine

<400> SEQUENCE: 293
ttcatgcggc ttctcacaga                                        20

<210> SEQ ID NO 294
<211> LENGTH: 20
<212> TYPE: DNA
<213> ORGANISM: Murine

<400> SEQUENCE: 294
ggacttctgg ttgtcgcaag                                        20

<210> SEQ ID NO 295
<211> LENGTH: 20
<212> TYPE: DNA
<213> ORGANISM: Murine

<400> SEQUENCE: 295
catgagcaac tgcagcatca                                        20

<210> SEQ ID NO 296
<211> LENGTH: 20

```
<212> TYPE: DNA
<213> ORGANISM: Murine

<400> SEQUENCE: 296
ccagaggccc ccttaccaca                                      20

<210> SEQ ID NO 297
<211> LENGTH: 20
<212> TYPE: DNA
<213> ORGANISM: Murine

<400> SEQUENCE: 297
caacaacagg tcgggactgc                                      20

<210> SEQ ID NO 298
<211> LENGTH: 20
<212> TYPE: DNA
<213> ORGANISM: Murine

<400> SEQUENCE: 298
cagcttggcc ttgtagacct                                      20

<210> SEQ ID NO 299
<211> LENGTH: 20
<212> TYPE: DNA
<213> ORGANISM: Murine

<400> SEQUENCE: 299
catgacacac ttgggagaag                                      20

<210> SEQ ID NO 300
<211> LENGTH: 20
<212> TYPE: DNA
<213> ORGANISM: Murine

<400> SEQUENCE: 300
gttcttgtcg ttcttcctcc                                      20

<210> SEQ ID NO 301
<211> LENGTH: 20
<212> TYPE: DNA
<213> ORGANISM: Murine

<400> SEQUENCE: 301
gctggacacg ctggtgggga                                      20

<210> SEQ ID NO 302
<211> LENGTH: 20
<212> TYPE: DNA
<213> ORGANISM: Human

<400> SEQUENCE: 302
ccagaataaa gtcatggtag                                      20

<210> SEQ ID NO 303
<211> LENGTH: 20
<212> TYPE: DNA
<213> ORGANISM: Human

<400> SEQUENCE: 303
cacatgaaga aagtctcacc                                      20

<210> SEQ ID NO 304
```

-continued

```
<211> LENGTH: 20
<212> TYPE: DNA
<213> ORGANISM: Human

<400> SEQUENCE: 304
ttgagctgga caccctggtg                                              20

<210> SEQ ID NO 305
<211> LENGTH: 20
<212> TYPE: DNA
<213> ORGANISM: Human

<400> SEQUENCE: 305
gcttctgctg ccggttaacg                                              20

<210> SEQ ID NO 306
<211> LENGTH: 20
<212> TYPE: DNA
<213> ORGANISM: Human

<400> SEQUENCE: 306
gaacatactc cagttcctga                                              20

<210> SEQ ID NO 307
<211> LENGTH: 20
<212> TYPE: DNA
<213> ORGANISM: Human

<400> SEQUENCE: 307
gggcagtcct attacagctg                                              20

<210> SEQ ID NO 308
<211> LENGTH: 20
<212> TYPE: DNA
<213> ORGANISM: Human

<400> SEQUENCE: 308
ttctccaaag tgcattatga                                              20

<210> SEQ ID NO 309
<211> LENGTH: 20
<212> TYPE: DNA
<213> ORGANISM: Human

<400> SEQUENCE: 309
tggatgacct ggctaacagt                                              20

<210> SEQ ID NO 310
<211> LENGTH: 20
<212> TYPE: DNA
<213> ORGANISM: Human

<400> SEQUENCE: 310
cctgggaaac cggcaagacg                                              20

<210> SEQ ID NO 311
<211> LENGTH: 20
<212> TYPE: DNA
<213> ORGANISM: Human

<400> SEQUENCE: 311
gaagccacag gaagtctgtg                                              20
```

```
<210> SEQ ID NO 312
<211> LENGTH: 20
<212> TYPE: DNA
<213> ORGANISM: Human

<400> SEQUENCE: 312
acagatatgg caactcccag                                          20

<210> SEQ ID NO 313
<211> LENGTH: 20
<212> TYPE: DNA
<213> ORGANISM: Human

<400> SEQUENCE: 313
gcagaagctg agttcaacct                                          20

<210> SEQ ID NO 314
<211> LENGTH: 20
<212> TYPE: DNA
<213> ORGANISM: Human

<400> SEQUENCE: 314
tcatctgccc cagctgtaat                                          20

<210> SEQ ID NO 315
<211> LENGTH: 20
<212> TYPE: DNA
<213> ORGANISM: Human

<400> SEQUENCE: 315
ggggaaaggt cgctttgctg                                          20

<210> SEQ ID NO 316
<211> LENGTH: 20
<212> TYPE: DNA
<213> ORGANISM: Human

<400> SEQUENCE: 316
gcaggatttc tggttgtcac                                          20

<210> SEQ ID NO 317
<211> LENGTH: 20
<212> TYPE: DNA
<213> ORGANISM: Murine

<400> SEQUENCE: 317
ccagctcctc tgccttctgc                                          20

<210> SEQ ID NO 318
<211> LENGTH: 20
<212> TYPE: DNA
<213> ORGANISM: Murine

<400> SEQUENCE: 318
cagccagatc ccgctgttcc                                          20

<210> SEQ ID NO 319
<211> LENGTH: 20
<212> TYPE: DNA
<213> ORGANISM: Murine

<400> SEQUENCE: 319
ggccctcgag ttcaacaggt                                          20
```

```
<210> SEQ ID NO 320
<211> LENGTH: 20
<212> TYPE: DNA
<213> ORGANISM: Murine

<400> SEQUENCE: 320
gtgaagagct ggctgtggtc                                              20

<210> SEQ ID NO 321
<211> LENGTH: 20
<212> TYPE: DNA
<213> ORGANISM: Murine

<400> SEQUENCE: 321
ggccaagctg gacaagggcc                                              20

<210> SEQ ID NO 322
<211> LENGTH: 20
<212> TYPE: DNA
<213> ORGANISM: Murine

<400> SEQUENCE: 322
ccaggagaat gaagccctga                                              20

<210> SEQ ID NO 323
<211> LENGTH: 20
<212> TYPE: DNA
<213> ORGANISM: Murine

<400> SEQUENCE: 323
tgctggcctc acctgcagga                                              20

<210> SEQ ID NO 324
<211> LENGTH: 20
<212> TYPE: DNA
<213> ORGANISM: Murine

<400> SEQUENCE: 324
ccagagggtg ctggcaagaa                                              20

<210> SEQ ID NO 325
<211> LENGTH: 20
<212> TYPE: DNA
<213> ORGANISM: Human

<400> SEQUENCE: 325
gatccagcgg ctcaacaagg                                              20

<210> SEQ ID NO 326
<211> LENGTH: 20
<212> TYPE: DNA
<213> ORGANISM: Human

<400> SEQUENCE: 326
ccaaaaggtc aagtacctgc                                              20

<210> SEQ ID NO 327
<211> LENGTH: 20
<212> TYPE: DNA
<213> ORGANISM: Human

<400> SEQUENCE: 327
acttaacctt cctctctgga                                              20
```

<210> SEQ ID NO 328
<211> LENGTH: 20
<212> TYPE: DNA
<213> ORGANISM: Human

<400> SEQUENCE: 328
gcagcttcgg aaggagaacg                                               20

<210> SEQ ID NO 329
<211> LENGTH: 20
<212> TYPE: DNA
<213> ORGANISM: Human

<400> SEQUENCE: 329
cacgcgcctc acctgcagaa                                               20

<210> SEQ ID NO 330
<211> LENGTH: 20
<212> TYPE: DNA
<213> ORGANISM: Human

<400> SEQUENCE: 330
gaaggcagag gagctagtga                                               20

<210> SEQ ID NO 331
<211> LENGTH: 20
<212> TYPE: DNA
<213> ORGANISM: Human

<400> SEQUENCE: 331
cctcacttaa ccttcctctc                                               20

<210> SEQ ID NO 332
<211> LENGTH: 20
<212> TYPE: DNA
<213> ORGANISM: Human

<400> SEQUENCE: 332
tgtgcacctt ggatgccagt                                               20

<210> SEQ ID NO 333
<211> LENGTH: 20
<212> TYPE: DNA
<213> ORGANISM: Human

<400> SEQUENCE: 333
ctcaggagag cgttaccatg                                               20

<210> SEQ ID NO 334
<211> LENGTH: 20
<212> TYPE: DNA
<213> ORGANISM: Human

<400> SEQUENCE: 334
cgagaagaag gtgaagatgc                                               20

<210> SEQ ID NO 335
<211> LENGTH: 20
<212> TYPE: DNA
<213> ORGANISM: Human

<400> SEQUENCE: 335
tatacctgtg agctcagcca                                          20

<210> SEQ ID NO 336
<211> LENGTH: 20
<212> TYPE: DNA
<213> ORGANISM: Human

<400> SEQUENCE: 336
ccaggtgaag atcttcgagg                                          20

<210> SEQ ID NO 337
<211> LENGTH: 20
<212> TYPE: DNA
<213> ORGANISM: Human

<400> SEQUENCE: 337
cttcacccac ctgggccgca                                          20

<210> SEQ ID NO 338
<211> LENGTH: 20
<212> TYPE: DNA
<213> ORGANISM: Human

<400> SEQUENCE: 338
gccgggaatt ctccttcact                                          20

<210> SEQ ID NO 339
<211> LENGTH: 20
<212> TYPE: DNA
<213> ORGANISM: Human

<400> SEQUENCE: 339
cccgcagaga tgttctgggt                                          20

<210> SEQ ID NO 340
<211> LENGTH: 20
<212> TYPE: DNA
<213> ORGANISM: Murine

<400> SEQUENCE: 340
aaaagagcaa gccttaccat                                          20

<210> SEQ ID NO 341
<211> LENGTH: 20
<212> TYPE: DNA
<213> ORGANISM: Murine

<400> SEQUENCE: 341
tgctgcagag ggccttcctc                                          20

<210> SEQ ID NO 342
<211> LENGTH: 20
<212> TYPE: DNA
<213> ORGANISM: Murine

<400> SEQUENCE: 342
ctccttctgt cctcaggtga                                          20

<210> SEQ ID NO 343
<211> LENGTH: 20
<212> TYPE: DNA
<213> ORGANISM: Murine

<400> SEQUENCE: 343

| tacagatatc ccatcgtcct | 20 |

<210> SEQ ID NO 344
<211> LENGTH: 20
<212> TYPE: DNA
<213> ORGANISM: Murine

<400> SEQUENCE: 344

| tgcagcttgt cagtacatgt | 20 |

<210> SEQ ID NO 345
<211> LENGTH: 20
<212> TYPE: DNA
<213> ORGANISM: Murine

<400> SEQUENCE: 345

| tctccttaag ggtgctgcag | 20 |

<210> SEQ ID NO 346
<211> LENGTH: 20
<212> TYPE: DNA
<213> ORGANISM: Murine

<400> SEQUENCE: 346

| agtgatcaca agcaggggcc | 20 |

<210> SEQ ID NO 347
<211> LENGTH: 20
<212> TYPE: DNA
<213> ORGANISM: Murine

<400> SEQUENCE: 347

| cactttcaaa ggagcaaaat | 20 |

<210> SEQ ID NO 348
<211> LENGTH: 20
<212> TYPE: DNA
<213> ORGANISM: Human

<400> SEQUENCE: 348

| ctcctcaggg ttccacgcca | 20 |

<210> SEQ ID NO 349
<211> LENGTH: 20
<212> TYPE: DNA
<213> ORGANISM: Human

<400> SEQUENCE: 349

| gccccacatg tactgagaag | 20 |

<210> SEQ ID NO 350
<211> LENGTH: 20
<212> TYPE: DNA
<213> ORGANISM: Human

<400> SEQUENCE: 350

| cttaccaaaa gaaatcaatc | 20 |

<210> SEQ ID NO 351
<211> LENGTH: 20
<212> TYPE: DNA
<213> ORGANISM: Human

```
<400> SEQUENCE: 351
acactgaatg tgcagcacaa                                              20

<210> SEQ ID NO 352
<211> LENGTH: 20
<212> TYPE: DNA
<213> ORGANISM: Human

<400> SEQUENCE: 352
aagtcagtcc cacagcgtcc                                              20

<210> SEQ ID NO 353
<211> LENGTH: 20
<212> TYPE: DNA
<213> ORGANISM: Human

<400> SEQUENCE: 353
actccaagcc gggccctgag                                              20

<210> SEQ ID NO 354
<211> LENGTH: 20
<212> TYPE: DNA
<213> ORGANISM: Human

<400> SEQUENCE: 354
gctcttaaaa gagtacttaa                                              20

<210> SEQ ID NO 355
<211> LENGTH: 20
<212> TYPE: DNA
<213> ORGANISM: Human

<400> SEQUENCE: 355
atggcaggaa aacagcgagc                                              20

<210> SEQ ID NO 356
<211> LENGTH: 20
<212> TYPE: DNA
<213> ORGANISM: Human

<400> SEQUENCE: 356
gaagtgccaa gcctgcctcc                                              20

<210> SEQ ID NO 357
<211> LENGTH: 20
<212> TYPE: DNA
<213> ORGANISM: Human

<400> SEQUENCE: 357
gacaccagtt gagtttcttc                                              20

<210> SEQ ID NO 358
<211> LENGTH: 20
<212> TYPE: DNA
<213> ORGANISM: Human

<400> SEQUENCE: 358
gaggcaggct tggcacttcc                                              20

<210> SEQ ID NO 359
<211> LENGTH: 20
<212> TYPE: DNA
<213> ORGANISM: Human
```

```
<400> SEQUENCE: 359
tcgggccatg ggtgtgtctg                                               20

<210> SEQ ID NO 360
<211> LENGTH: 20
<212> TYPE: DNA
<213> ORGANISM: Human

<400> SEQUENCE: 360
tcacctgaaa tgacaatgat                                               20

<210> SEQ ID NO 361
<211> LENGTH: 20
<212> TYPE: DNA
<213> ORGANISM: Human

<400> SEQUENCE: 361
ccgcattccc tccccaggca                                               20

<210> SEQ ID NO 362
<211> LENGTH: 20
<212> TYPE: DNA
<213> ORGANISM: Human

<400> SEQUENCE: 362 ggcccccag tggactcctc                                                20

<210> SEQ ID NO 363
<211> LENGTH: 20
<212> TYPE: DNA
<213> ORGANISM: Human

<400> SEQUENCE: 363
gtgatagaaa tccccgtcca                                               20

<210> SEQ ID NO 364
<211> LENGTH: 20
<212> TYPE: DNA
<213> ORGANISM: Human

<400> SEQUENCE: 364
ttctggaacc tggacgctgt                                               20

<210> SEQ ID NO 365
<211> LENGTH: 20
<212> TYPE: DNA
<213> ORGANISM: Human

<400> SEQUENCE: 365
agttgtactg aagtccactt                                               20

<210> SEQ ID NO 366
<211> LENGTH: 20
<212> TYPE: DNA
<213> ORGANISM: Human

<400> SEQUENCE: 366
cacacaaggc acttggatcc                                               20

<210> SEQ ID NO 367
<211> LENGTH: 20
<212> TYPE: DNA
```

```
<213> ORGANISM: Human

<400> SEQUENCE: 367
agaacaccat tccgtgcctg                                               20

<210> SEQ ID NO 368
<211> LENGTH: 20
<212> TYPE: DNA
<213> ORGANISM: Human

<400> SEQUENCE: 368
catggcgctc ggggcctctc                                               20

<210> SEQ ID NO 369
<211> LENGTH: 20
<212> TYPE: DNA
<213> ORGANISM: Human

<400> SEQUENCE: 369 gcccccagt ggactcctca                                                20

<210> SEQ ID NO 370
<211> LENGTH: 20
<212> TYPE: DNA
<213> ORGANISM: Human

<400> SEQUENCE: 370
gctgtcggtg gggccgaatg                                               20

<210> SEQ ID NO 371
<211> LENGTH: 20
<212> TYPE: DNA
<213> ORGANISM: Human

<400> SEQUENCE: 371
caagtgcctt gtgtggtctg                                               20

<210> SEQ ID NO 372
<211> LENGTH: 20
<212> TYPE: DNA
<213> ORGANISM: Human

<400> SEQUENCE: 372
gccacttctc agtacatgtg                                               20

<210> SEQ ID NO 373
<211> LENGTH: 20
<212> TYPE: DNA
<213> ORGANISM: Human

<400> SEQUENCE: 373
tacagatacc ccattgttct                                               20

<210> SEQ ID NO 374
<211> LENGTH: 20
<212> TYPE: DNA
<213> ORGANISM: Human

<400> SEQUENCE: 374
tagaaatccc cgtccaaggc                                               20

<210> SEQ ID NO 375
<211> LENGTH: 20
```

```
<212> TYPE: DNA
<213> ORGANISM: Human

<400> SEQUENCE: 375
aaagccggct gcgtgtattt                                              20

<210> SEQ ID NO 376
<211> LENGTH: 20
<212> TYPE: DNA
<213> ORGANISM: Human

<400> SEQUENCE: 376
tggtctcact gaacagaaaa                                              20

<210> SEQ ID NO 377
<211> LENGTH: 20
<212> TYPE: DNA
<213> ORGANISM: Human

<400> SEQUENCE: 377
tggtgaccct gaaggacagt                                              20

<210> SEQ ID NO 378
<211> LENGTH: 20
<212> TYPE: DNA
<213> ORGANISM: Human

<400> SEQUENCE: 378
agagaaagct ggggcacgga                                              20

<210> SEQ ID NO 379
<211> LENGTH: 20
<212> TYPE: DNA
<213> ORGANISM: Human

<400> SEQUENCE: 379
cgtgccccag ctttctctca                                              20

<210> SEQ ID NO 380
<211> LENGTH: 20
<212> TYPE: DNA
<213> ORGANISM: Human

<400> SEQUENCE: 380
tatgccatga gtgctcagag                                              20

<210> SEQ ID NO 381
<211> LENGTH: 20
<212> TYPE: DNA
<213> ORGANISM: Human

<400> SEQUENCE: 381
agggctgggt gctgtcggtg                                              20

<210> SEQ ID NO 382
<211> LENGTH: 20
<212> TYPE: DNA
<213> ORGANISM: Human

<400> SEQUENCE: 382
ccatgccagg gagcccctca                                              20

<210> SEQ ID NO 383
```

```
<211> LENGTH: 20
<212> TYPE: DNA
<213> ORGANISM: Human

<400> SEQUENCE: 383
gagtttcttc tggctttcca                                              20

<210> SEQ ID NO 384
<211> LENGTH: 20
<212> TYPE: DNA
<213> ORGANISM: Human

<400> SEQUENCE: 384
gctgtcatag ccgagaacaa                                              20

<210> SEQ ID NO 385
<211> LENGTH: 20
<212> TYPE: DNA
<213> ORGANISM: Human

<400> SEQUENCE: 385
gggagaagcc tatgagccct                                              20

<210> SEQ ID NO 386
<211> LENGTH: 20
<212> TYPE: DNA
<213> ORGANISM: Human

<400> SEQUENCE: 386
ggggtatctg tagcattcct                                              20

<210> SEQ ID NO 387
<211> LENGTH: 20
<212> TYPE: DNA
<213> ORGANISM: Human

<400> SEQUENCE: 387
tggatgatct cccgaaactg                                              20

<210> SEQ ID NO 388
<211> LENGTH: 20
<212> TYPE: DNA
<213> ORGANISM: Human

<400> SEQUENCE: 388
cttgtggcgc tgaaaacgaa                                              20

<210> SEQ ID NO 389
<211> LENGTH: 20
<212> TYPE: DNA
<213> ORGANISM: Human

<400> SEQUENCE: 389
actgagaagt ggcatgcatg                                              20

<210> SEQ ID NO 390
<211> LENGTH: 20
<212> TYPE: DNA
<213> ORGANISM: Human

<400> SEQUENCE: 390
tgaacatttc cagtgtgtat                                              20
```

```
<210> SEQ ID NO 391
<211> LENGTH: 20
<212> TYPE: DNA
<213> ORGANISM: Human

<400> SEQUENCE: 391
ttgctcaaat acaaagcctg                                          20

<210> SEQ ID NO 392
<211> LENGTH: 20
<212> TYPE: DNA
<213> ORGANISM: Human

<400> SEQUENCE: 392
tgagagactc cagttgccag                                          20

<210> SEQ ID NO 393
<211> LENGTH: 20
<212> TYPE: DNA
<213> ORGANISM: Human

<400> SEQUENCE: 393
gcatgagtac aagaaatggc                                          20

<210> SEQ ID NO 394
<211> LENGTH: 20
<212> TYPE: DNA
<213> ORGANISM: Human

<400> SEQUENCE: 394
gaggcaattg ccgtcacctg                                          20

<210> SEQ ID NO 395
<211> LENGTH: 20
<212> TYPE: DNA
<213> ORGANISM: Human

<400> SEQUENCE: 395
ctgtccttca gggtcaccaa                                          20

<210> SEQ ID NO 396
<211> LENGTH: 20
<212> TYPE: DNA
<213> ORGANISM: Human

<400> SEQUENCE: 396
cagaaacatc caggccaccc                                          20

<210> SEQ ID NO 397
<211> LENGTH: 20
<212> TYPE: DNA
<213> ORGANISM: Human

<400> SEQUENCE: 397
gtattcagct taaaaaattc                                          20

<210> SEQ ID NO 398
<211> LENGTH: 20
<212> TYPE: DNA
<213> ORGANISM: Human

<400> SEQUENCE: 398
atccatgcat gcctgccgga                                          20
```

```
<210> SEQ ID NO 399
<211> LENGTH: 20
<212> TYPE: DNA
<213> ORGANISM: Human

<400> SEQUENCE: 399
aatataccag acactgcaac                                              20

<210> SEQ ID NO 400
<211> LENGTH: 20
<212> TYPE: DNA
<213> ORGANISM: Human

<400> SEQUENCE: 400
tgtcttgcag ataacaatta                                              20

<210> SEQ ID NO 401
<211> LENGTH: 20
<212> TYPE: DNA
<213> ORGANISM: Human

<400> SEQUENCE: 401
ttgggtgtgt attccaaccg                                              20

<210> SEQ ID NO 402
<211> LENGTH: 20
<212> TYPE: DNA
<213> ORGANISM: Human

<400> SEQUENCE: 402
tttagaaagt gattcaaaag                                              20

<210> SEQ ID NO 403
<211> LENGTH: 20
<212> TYPE: DNA
<213> ORGANISM: Human

<400> SEQUENCE: 403
agtaaaagaa ttacagcaaa                                              20

<210> SEQ ID NO 404
<211> LENGTH: 20
<212> TYPE: DNA
<213> ORGANISM: Human

<400> SEQUENCE: 404
actacagcaa gggaaacagc                                              20

<210> SEQ ID NO 405
<211> LENGTH: 20
<212> TYPE: DNA
<213> ORGANISM: Human

<400> SEQUENCE: 405
ttgctttcta tactacagca                                              20

<210> SEQ ID NO 406
<211> LENGTH: 20
<212> TYPE: DNA
<213> ORGANISM: Human

<400> SEQUENCE: 406
gcagtccttt gctccatgaa                                              20
```

<210> SEQ ID NO 407
<211> LENGTH: 20
<212> TYPE: DNA
<213> ORGANISM: Human

<400> SEQUENCE: 407
gcagagaata cgtgaacaac                                                      20

<210> SEQ ID NO 408
<211> LENGTH: 20
<212> TYPE: DNA
<213> ORGANISM: Human

<400> SEQUENCE: 408
taacatgaac ataccttgag                                                      20

<210> SEQ ID NO 409
<211> LENGTH: 20
<212> TYPE: DNA
<213> ORGANISM: Human

<400> SEQUENCE: 409
cctgaaatca ctttatcttg                                                      20

<210> SEQ ID NO 410
<211> LENGTH: 20
<212> TYPE: DNA
<213> ORGANISM: Human

<400> SEQUENCE: 410
ataaagcgta tgaagccttc                                                      20

<210> SEQ ID NO 411
<211> LENGTH: 20
<212> TYPE: DNA
<213> ORGANISM: Human

<400> SEQUENCE: 411
gtattccaac cgcggtaaga                                                      20

<210> SEQ ID NO 412
<211> LENGTH: 20
<212> TYPE: DNA
<213> ORGANISM: Human

<400> SEQUENCE: 412
ccgggccccc agcaggtctg                                                      20

<210> SEQ ID NO 413
<211> LENGTH: 20
<212> TYPE: DNA
<213> ORGANISM: Human

<400> SEQUENCE: 413
cctacttagg cactgccagg                                                      20

<210> SEQ ID NO 414
<211> LENGTH: 20
<212> TYPE: DNA
<213> ORGANISM: Human

<400> SEQUENCE: 414

```
gcttacccag cggatgagcg                                              20

<210> SEQ ID NO 415
<211> LENGTH: 20
<212> TYPE: DNA
<213> ORGANISM: Human

<400> SEQUENCE: 415
cttctctgga gcctccagga                                              20

<210> SEQ ID NO 416
<211> LENGTH: 20
<212> TYPE: DNA
<213> ORGANISM: Human

<400> SEQUENCE: 416
tccactgacc tgtccttcct                                              20

<210> SEQ ID NO 417
<211> LENGTH: 20
<212> TYPE: DNA
<213> ORGANISM: Human

<400> SEQUENCE: 417
acccaggcat catccgacaa                                              20

<210> SEQ ID NO 418
<211> LENGTH: 20
<212> TYPE: DNA
<213> ORGANISM: Human

<400> SEQUENCE: 418
catggggttc aaggaagaag                                              20

<210> SEQ ID NO 419
<211> LENGTH: 20
<212> TYPE: DNA
<213> ORGANISM: Human

<400> SEQUENCE: 419
aaaccatcct gccacctgga                                              20

<210> SEQ ID NO 420
<211> LENGTH: 20
<212> TYPE: DNA
<213> ORGANISM: Human

<400> SEQUENCE: 420
tcatggctgg gctctccagg                                              20

<210> SEQ ID NO 421
<211> LENGTH: 20
<212> TYPE: DNA
<213> ORGANISM: Human

<400> SEQUENCE: 421
cagggccgag atcttcgagg                                              20

<210> SEQ ID NO 422
<211> LENGTH: 20
<212> TYPE: DNA
<213> ORGANISM: Human

<400> SEQUENCE: 422
```

```
agagtgatga agagtgtgac                                              20

<210> SEQ ID NO 423
<211> LENGTH: 20
<212> TYPE: DNA
<213> ORGANISM: Human

<400> SEQUENCE: 423
tcacatttca gtttaccatt                                              20

<210> SEQ ID NO 424
<211> LENGTH: 20
<212> TYPE: DNA
<213> ORGANISM: Human

<400> SEQUENCE: 424
gctgatgcag tctcatatga                                              20

<210> SEQ ID NO 425
<211> LENGTH: 20
<212> TYPE: DNA
<213> ORGANISM: Human

<400> SEQUENCE: 425
tgacattctg gagatagttg                                              20

<210> SEQ ID NO 426
<211> LENGTH: 20
<212> TYPE: DNA
<213> ORGANISM: Human

<400> SEQUENCE: 426
cactttgact atggaaacag                                              20

<210> SEQ ID NO 427
<211> LENGTH: 20
<212> TYPE: DNA
<213> ORGANISM: Human

<400> SEQUENCE: 427
aagctccaca ctggttacag                                              20

<210> SEQ ID NO 428
<211> LENGTH: 20
<212> TYPE: DNA
<213> ORGANISM: Human

<400> SEQUENCE: 428
tagctacgcc tgtagaagaa                                              20

<210> SEQ ID NO 429
<211> LENGTH: 20
<212> TYPE: DNA
<213> ORGANISM: Human

<400> SEQUENCE: 429
gctgtcatag agaagctcac                                              20

<210> SEQ ID NO 430
<211> LENGTH: 20
<212> TYPE: DNA
<213> ORGANISM: Human
```

```
<400> SEQUENCE: 430
ttactgcttg tcatgtgact                                              20

<210> SEQ ID NO 431
<211> LENGTH: 20
<212> TYPE: DNA
<213> ORGANISM: Human

<400> SEQUENCE: 431
aatcacctac cttggagctg                                              20

<210> SEQ ID NO 432
<211> LENGTH: 20
<212> TYPE: DNA
<213> ORGANISM: Human

<400> SEQUENCE: 432
gtaactttat gtgtctcaga                                              20

<210> SEQ ID NO 433
<211> LENGTH: 20
<212> TYPE: DNA
<213> ORGANISM: Human

<400> SEQUENCE: 433
cctcacaagt gcaactactg                                              20

<210> SEQ ID NO 434
<211> LENGTH: 20
<212> TYPE: DNA
<213> ORGANISM: Human

<400> SEQUENCE: 434
tccttacaat cttccatagg                                              20

<210> SEQ ID NO 435
<211> LENGTH: 20
<212> TYPE: DNA
<213> ORGANISM: Human

<400> SEQUENCE: 435
ggaggaatcc ggcttccgaa                                              20

<210> SEQ ID NO 436
<211> LENGTH: 20
<212> TYPE: DNA
<213> ORGANISM: Human

<400> SEQUENCE: 436
acaatgagct ttcacccgaa                                              20

<210> SEQ ID NO 437
<211> LENGTH: 20
<212> TYPE: DNA
<213> ORGANISM: Human

<400> SEQUENCE: 437
acttaccaga atgggtcctg                                              20

<210> SEQ ID NO 438
<211> LENGTH: 20
<212> TYPE: DNA
<213> ORGANISM: Human
```

```
<400> SEQUENCE: 438
gccatctcgc cgccacagtg                                              20

<210> SEQ ID NO 439
<211> LENGTH: 20
<212> TYPE: DNA
<213> ORGANISM: Human

<400> SEQUENCE: 439
gggctctatc acaaaatgaa                                              20

<210> SEQ ID NO 440
<211> LENGTH: 20
<212> TYPE: DNA
<213> ORGANISM: Human

<400> SEQUENCE: 440
cccctgacta tgaagaagga                                              20

<210> SEQ ID NO 441
<211> LENGTH: 20
<212> TYPE: DNA
<213> ORGANISM: Human

<400> SEQUENCE: 441
acctgtgctg gaccgggcct                                              20

<210> SEQ ID NO 442
<211> LENGTH: 20
<212> TYPE: DNA
<213> ORGANISM: Human

<400> SEQUENCE: 442
gtagacggag aggggccccg                                              20

<210> SEQ ID NO 443
<211> LENGTH: 20
<212> TYPE: DNA
<213> ORGANISM: Human

<400> SEQUENCE: 443
aagcttgtag tagagcccac                                              20

<210> SEQ ID NO 444
<211> LENGTH: 20
<212> TYPE: DNA
<213> ORGANISM: Human

<400> SEQUENCE: 444
ctggaggagg aatgccaatg                                              20

<210> SEQ ID NO 445
<211> LENGTH: 20
<212> TYPE: DNA
<213> ORGANISM: Human

<400> SEQUENCE: 445
cagccactcc tacatggacg                                              20

<210> SEQ ID NO 446
<211> LENGTH: 20
<212> TYPE: DNA
```

```
<213> ORGANISM: Human

<400> SEQUENCE: 446 gaagggctg agattccagg                                           20

<210> SEQ ID NO 447
<211> LENGTH: 20
<212> TYPE: DNA
<213> ORGANISM: Human

<400> SEQUENCE: 447
ggagctgtac tcgggcacgt                                          20

<210> SEQ ID NO 448
<211> LENGTH: 20
<212> TYPE: DNA
<213> ORGANISM: Human

<400> SEQUENCE: 448
gctttgccgc cgtccagcca                                          20

<210> SEQ ID NO 449
<211> LENGTH: 20
<212> TYPE: DNA
<213> ORGANISM: Human

<400> SEQUENCE: 449
aggcccggtc cagcacaggt                                          20

<210> SEQ ID NO 450
<211> LENGTH: 20
<212> TYPE: DNA
<213> ORGANISM: Murine

<400> SEQUENCE: 450
gaggtggcgc ttacctgtgc                                          20

<210> SEQ ID NO 451
<211> LENGTH: 20
<212> TYPE: DNA
<213> ORGANISM: Murine

<400> SEQUENCE: 451
gctagacatc ttccggtttc                                          20

<210> SEQ ID NO 452
<211> LENGTH: 20
<212> TYPE: DNA
<213> ORGANISM: Murine

<400> SEQUENCE: 452
ggaagctcag tatccgctga                                          20

<210> SEQ ID NO 453
<211> LENGTH: 20
<212> TYPE: DNA
<213> ORGANISM: Murine

<400> SEQUENCE: 453
tgtctgggtg ctgaccgttg                                          20

<210> SEQ ID NO 454
<211> LENGTH: 20
```

```
<212> TYPE: DNA
<213> ORGANISM: Murine

<400> SEQUENCE: 454
aaggcatcca gacccgaaac                                               20

<210> SEQ ID NO 455
<211> LENGTH: 20
<212> TYPE: DNA
<213> ORGANISM: Murine

<400> SEQUENCE: 455
caaggtggac tcaccgtggt                                               20

<210> SEQ ID NO 456
<211> LENGTH: 20
<212> TYPE: DNA
<213> ORGANISM: Murine

<400> SEQUENCE: 456
agcccacagg cattgcagac                                               20

<210> SEQ ID NO 457
<211> LENGTH: 20
<212> TYPE: DNA
<213> ORGANISM: Murine

<400> SEQUENCE: 457
cccctgacta tgaagaaaga                                               20

<210> SEQ ID NO 458
<211> LENGTH: 20
<212> TYPE: DNA
<213> ORGANISM: Human

<400> SEQUENCE: 458
agtccatatg gaacccacgg                                               20

<210> SEQ ID NO 459
<211> LENGTH: 20
<212> TYPE: DNA
<213> ORGANISM: Human

<400> SEQUENCE: 459
agtctgagtg caaattgggc                                               20

<210> SEQ ID NO 460
<211> LENGTH: 20
<212> TYPE: DNA
<213> ORGANISM: Human

<400> SEQUENCE: 460
tacgaattgc accggaccag                                               20

<210> SEQ ID NO 461
<211> LENGTH: 20
<212> TYPE: DNA
<213> ORGANISM: Human

<400> SEQUENCE: 461
ttagaggctt gaggaaaccg                                               20

<210> SEQ ID NO 462
```

-continued

```
<211> LENGTH: 20
<212> TYPE: DNA
<213> ORGANISM: Human

<400> SEQUENCE: 462
ttagaaccta tgaagctctg                                              20

<210> SEQ ID NO 463
<211> LENGTH: 20
<212> TYPE: DNA
<213> ORGANISM: Human

<400> SEQUENCE: 463
cctgaataaa ctccaccgca                                              20

<210> SEQ ID NO 464
<211> LENGTH: 20
<212> TYPE: DNA
<213> ORGANISM: Human

<400> SEQUENCE: 464
aattcgaaag cccatcagtt                                              20

<210> SEQ ID NO 465
<211> LENGTH: 20
<212> TYPE: DNA
<213> ORGANISM: Human

<400> SEQUENCE: 465
tggccacaac ccaaactgat                                              20

<210> SEQ ID NO 466
<211> LENGTH: 20
<212> TYPE: DNA
<213> ORGANISM: Human

<400> SEQUENCE: 466
cagcatactc tgaggtacga                                              20

<210> SEQ ID NO 467
<211> LENGTH: 20
<212> TYPE: DNA
<213> ORGANISM: Human

<400> SEQUENCE: 467
ttacctctag cactgctgag                                              20

<210> SEQ ID NO 468
<211> LENGTH: 20
<212> TYPE: DNA
<213> ORGANISM: Human

<400> SEQUENCE: 468
tatgcagtcc attattgaca                                              20

<210> SEQ ID NO 469
<211> LENGTH: 20
<212> TYPE: DNA
<213> ORGANISM: Human

<400> SEQUENCE: 469
gtaacacagc ttattccgcg                                              20
```

```
<210> SEQ ID NO 470
<211> LENGTH: 20
<212> TYPE: DNA
<213> ORGANISM: Human

<400> SEQUENCE: 470
actttcccta gcaatgcagg                                          20

<210> SEQ ID NO 471
<211> LENGTH: 20
<212> TYPE: DNA
<213> ORGANISM: Murine

<400> SEQUENCE: 471
caaatgggca agccttacgg                                          20

<210> SEQ ID NO 472
<211> LENGTH: 20
<212> TYPE: DNA
<213> ORGANISM: Murine

<400> SEQUENCE: 472
ctcaatgtcc gtattgatag                                          20

<210> SEQ ID NO 473
<211> LENGTH: 20
<212> TYPE: DNA
<213> ORGANISM: Murine

<400> SEQUENCE: 473
agtctgagtg caaattgggc                                          20

<210> SEQ ID NO 474
<211> LENGTH: 20
<212> TYPE: DNA
<213> ORGANISM: Murine

<400> SEQUENCE: 474
ccagatagtg caaattgcta                                          20

<210> SEQ ID NO 475
<211> LENGTH: 20
<212> TYPE: DNA
<213> ORGANISM: Murine

<400> SEQUENCE: 475
tgatagtggt ctggtcaaat                                          20

<210> SEQ ID NO 476
<211> LENGTH: 20
<212> TYPE: DNA
<213> ORGANISM: Murine

<400> SEQUENCE: 476
aattcgaaag cccatcagtt                                          20

<210> SEQ ID NO 477
<211> LENGTH: 20
<212> TYPE: DNA
<213> ORGANISM: Murine

<400> SEQUENCE: 477
gcccattact ttgtgtagtg                                          20
```

<210> SEQ ID NO 478
<211> LENGTH: 20
<212> TYPE: DNA
<213> ORGANISM: Murine

<400> SEQUENCE: 478
tggccacagc ccaaactgat                                          20

<210> SEQ ID NO 479
<211> LENGTH: 20
<212> TYPE: DNA
<213> ORGANISM: Human

<400> SEQUENCE: 479
gcattcatac ttgctttcca                                          20

<210> SEQ ID NO 480
<211> LENGTH: 20
<212> TYPE: DNA
<213> ORGANISM: Human

<400> SEQUENCE: 480
ttagatgcag aggaatcact                                          20

<210> SEQ ID NO 481
<211> LENGTH: 20
<212> TYPE: DNA
<213> ORGANISM: Human

<400> SEQUENCE: 481
atggtgaaat gtccaaatga                                          20

<210> SEQ ID NO 482
<211> LENGTH: 20
<212> TYPE: DNA
<213> ORGANISM: Human

<400> SEQUENCE: 482
ttggttgcca tgaaaaggta                                          20

<210> SEQ ID NO 483
<211> LENGTH: 20
<212> TYPE: DNA
<213> ORGANISM: Human

<400> SEQUENCE: 483
tcatttatgg aggagatcca                                          20

<210> SEQ ID NO 484
<211> LENGTH: 20
<212> TYPE: DNA
<213> ORGANISM: Human

<400> SEQUENCE: 484
tgttacagcg ctacaggagc                                          20

<210> SEQ ID NO 485
<211> LENGTH: 20
<212> TYPE: DNA
<213> ORGANISM: Human

<400> SEQUENCE: 485
ctaaactgtg aaaacagctg                                          20

<210> SEQ ID NO 486
<211> LENGTH: 20
<212> TYPE: DNA
<213> ORGANISM: Human

<400> SEQUENCE: 486
aggcgtattg taccctggaa                                              20

<210> SEQ ID NO 487
<211> LENGTH: 20
<212> TYPE: DNA
<213> ORGANISM: Human

<400> SEQUENCE: 487
acgtgagatt ctttctctga                                              20

<210> SEQ ID NO 488
<211> LENGTH: 20
<212> TYPE: DNA
<213> ORGANISM: Human

<400> SEQUENCE: 488
ccagtcacac atgagaatgt                                              20

<210> SEQ ID NO 489
<211> LENGTH: 20
<212> TYPE: DNA
<213> ORGANISM: Human

<400> SEQUENCE: 489
gaagcagtgc aaacgccatg                                              20

<210> SEQ ID NO 490
<211> LENGTH: 20
<212> TYPE: DNA
<213> ORGANISM: Human

<400> SEQUENCE: 490
acattctgaa ggattgtcca                                              20

<210> SEQ ID NO 491
<211> LENGTH: 20
<212> TYPE: DNA
<213> ORGANISM: Murine

<400> SEQUENCE: 491
agttgacaat gaaatactgc                                              20

<210> SEQ ID NO 492
<211> LENGTH: 20
<212> TYPE: DNA
<213> ORGANISM: Murine

<400> SEQUENCE: 492
aatatcatct gtgaatactg                                              20

<210> SEQ ID NO 493
<211> LENGTH: 20
<212> TYPE: DNA
<213> ORGANISM: Murine

<400> SEQUENCE: 493

-continued taaaggctgt ttgcaaaaga                                            20

<210> SEQ ID NO 494
<211> LENGTH: 20
<212> TYPE: DNA
<213> ORGANISM: Murine

<400> SEQUENCE: 494
tgcaaacacc atgtggccac                                            20

<210> SEQ ID NO 495
<211> LENGTH: 20
<212> TYPE: DNA
<213> ORGANISM: Murine

<400> SEQUENCE: 495
gcgagagatt ctttccctga                                            20

<210> SEQ ID NO 496
<211> LENGTH: 20
<212> TYPE: DNA
<213> ORGANISM: Murine

<400> SEQUENCE: 496
atcctcatca gagaacaggt                                            20

<210> SEQ ID NO 497
<211> LENGTH: 20
<212> TYPE: DNA
<213> ORGANISM: Murine

<400> SEQUENCE: 497
acggtaaagt gcccaaataa                                            20

<210> SEQ ID NO 498
<211> LENGTH: 20
<212> TYPE: DNA
<213> ORGANISM: Murine

<400> SEQUENCE: 498
ttaaactgtg agaacagctg                                            20

<210> SEQ ID NO 499
<211> LENGTH: 20
<212> TYPE: DNA
<213> ORGANISM: Murine

<400> SEQUENCE: 499
tctttgttgc aggagtctga                                            20

<210> SEQ ID NO 500
<211> LENGTH: 20
<212> TYPE: DNA
<213> ORGANISM: Murine

<400> SEQUENCE: 500 cagggggcttg ttatgaggta                                           20

<210> SEQ ID NO 501
<211> LENGTH: 20
<212> TYPE: DNA
<213> ORGANISM: Murine

<400> SEQUENCE: 501
ctgattgatg gtagcaggga                                              20

<210> SEQ ID NO 502
<211> LENGTH: 20
<212> TYPE: DNA
<213> ORGANISM: Murine

<400> SEQUENCE: 502
ccttatcttc agtcacatgc                                              20

<210> SEQ ID NO 503
<211> LENGTH: 20
<212> TYPE: DNA
<213> ORGANISM: Murine

<400> SEQUENCE: 503
tcacatgctg gcagaaatca                                              20

<210> SEQ ID NO 504
<211> LENGTH: 20
<212> TYPE: DNA
<213> ORGANISM: Murine

<400> SEQUENCE: 504
ttctgtcgct gtgagataaa                                              20

<210> SEQ ID NO 505
<211> LENGTH: 20
<212> TYPE: DNA
<213> ORGANISM: Murine

<400> SEQUENCE: 505
acaaggcagt acctgccacg                                              20

<210> SEQ ID NO 506
<211> LENGTH: 20
<212> TYPE: DNA
<213> ORGANISM: Murine

<400> SEQUENCE: 506
tgtgactcac ccgggataca                                              20

<210> SEQ ID NO 507
<211> LENGTH: 20
<212> TYPE: DNA
<213> ORGANISM: Murine

<400> SEQUENCE: 507
gaggtccatc agatcagctc                                              20

<210> SEQ ID NO 508
<211> LENGTH: 20
<212> TYPE: DNA
<213> ORGANISM: Murine

<400> SEQUENCE: 508
atctccctgg aactggccat                                              20

<210> SEQ ID NO 509
<211> LENGTH: 20
<212> TYPE: DNA
<213> ORGANISM: Murine

```
<400> SEQUENCE: 509
tgcaaaaatt gcaaaactca                                              20

<210> SEQ ID NO 510
<211> LENGTH: 20
<212> TYPE: DNA
<213> ORGANISM: Murine

<400> SEQUENCE: 510
tgcacagaac tattgtacca                                              20

<210> SEQ ID NO 511
<211> LENGTH: 20
<212> TYPE: DNA
<213> ORGANISM: Murine

<400> SEQUENCE: 511
cagattagtg cttaccttcc                                              20

<210> SEQ ID NO 512
<211> LENGTH: 20
<212> TYPE: DNA
<213> ORGANISM: Murine

<400> SEQUENCE: 512
attccgtaaa atagagcccc                                              20

<210> SEQ ID NO 513
<211> LENGTH: 20
<212> TYPE: DNA
<213> ORGANISM: Murine

<400> SEQUENCE: 513
ctgcactcgg ctgggacaat                                              20

<210> SEQ ID NO 514
<211> LENGTH: 20
<212> TYPE: DNA
<213> ORGANISM: Human

<400> SEQUENCE: 514
ccttatgaaa aagtcaaaac                                              20

<210> SEQ ID NO 515
<211> LENGTH: 20
<212> TYPE: DNA
<213> ORGANISM: Human

<400> SEQUENCE: 515
aaaatatcaa gtatatatgg                                              20

<210> SEQ ID NO 516
<211> LENGTH: 20
<212> TYPE: DNA
<213> ORGANISM: Human

<400> SEQUENCE: 516
tctagcatcg gcatgccaaa                                              20

<210> SEQ ID NO 517
<211> LENGTH: 20
<212> TYPE: DNA
<213> ORGANISM: Human
```

```
<400> SEQUENCE: 517
ttggaagctc atggacaaag                                               20

<210> SEQ ID NO 518
<211> LENGTH: 20
<212> TYPE: DNA
<213> ORGANISM: Human

<400> SEQUENCE: 518
gatttcctcc tcgaccacca                                               20

<210> SEQ ID NO 519
<211> LENGTH: 20
<212> TYPE: DNA
<213> ORGANISM: Human

<400> SEQUENCE: 519
cttcatctct tggatcaaag                                               20

<210> SEQ ID NO 520
<211> LENGTH: 20
<212> TYPE: DNA
<213> ORGANISM: Human

<400> SEQUENCE: 520
aatgtatgaa gaacagtcac                                               20

<210> SEQ ID NO 521
<211> LENGTH: 20
<212> TYPE: DNA
<213> ORGANISM: Human

<400> SEQUENCE: 521
taaacttacc tgaaacagcc                                               20

<210> SEQ ID NO 522
<211> LENGTH: 20
<212> TYPE: DNA
<213> ORGANISM: Human

<400> SEQUENCE: 522
aagaatatga tgttcctccc                                               20

<210> SEQ ID NO 523
<211> LENGTH: 20
<212> TYPE: DNA
<213> ORGANISM: Human

<400> SEQUENCE: 523
agcaagctgc cgcagatcgc                                               20

<210> SEQ ID NO 524
<211> LENGTH: 20
<212> TYPE: DNA
<213> ORGANISM: Human

<400> SEQUENCE: 524
agtactcatt ctcactgagt                                               20

<210> SEQ ID NO 525
<211> LENGTH: 20
<212> TYPE: DNA
```

-continued

<213> ORGANISM: Murine

<400> SEQUENCE: 525
gatgaccaga gactatctgt                                        20

<210> SEQ ID NO 526
<211> LENGTH: 20
<212> TYPE: DNA
<213> ORGANISM: Murine

<400> SEQUENCE: 526
cctaaacagt gccattatga                                        20

<210> SEQ ID NO 527
<211> LENGTH: 20
<212> TYPE: DNA
<213> ORGANISM: Murine

<400> SEQUENCE: 527
ctatctgtcg gtgaaggtct                                        20

<210> SEQ ID NO 528
<211> LENGTH: 20
<212> TYPE: DNA
<213> ORGANISM: Murine

<400> SEQUENCE: 528
gaatatatac aagttattgg                                        20

<210> SEQ ID NO 529
<211> LENGTH: 20
<212> TYPE: DNA
<213> ORGANISM: Murine

<400> SEQUENCE: 529
tggggtgcca ggctgtgtgg                                        20

<210> SEQ ID NO 530
<211> LENGTH: 20
<212> TYPE: DNA
<213> ORGANISM: Murine

<400> SEQUENCE: 530
catgtttcct tgcagaataa                                        20

<210> SEQ ID NO 531
<211> LENGTH: 20
<212> TYPE: DNA
<213> ORGANISM: Murine

<400> SEQUENCE: 531
aagttcgagt gctgctggaa                                        20

<210> SEQ ID NO 532
<211> LENGTH: 20
<212> TYPE: DNA
<213> ORGANISM: Murine

<400> SEQUENCE: 532
catcaagcca gctaatatgg                                        20

<210> SEQ ID NO 533
<211> LENGTH: 20

<212> TYPE: DNA
<213> ORGANISM: Human

<400> SEQUENCE: 533
aaatgagcag cattctgttg                                              20

<210> SEQ ID NO 534
<211> LENGTH: 20
<212> TYPE: DNA
<213> ORGANISM: Human

<400> SEQUENCE: 534
cttcttgcaa caggagacaa                                              20

<210> SEQ ID NO 535
<211> LENGTH: 20
<212> TYPE: DNA
<213> ORGANISM: Human

<400> SEQUENCE: 535
tggaacggtt cggataggta                                              20

<210> SEQ ID NO 536
<211> LENGTH: 20
<212> TYPE: DNA
<213> ORGANISM: Human

<400> SEQUENCE: 536
catcaagcct gctaacatgg                                              20

<210> SEQ ID NO 537
<211> LENGTH: 20
<212> TYPE: DNA
<213> ORGANISM: Human

<400> SEQUENCE: 537
ggcgtggaga ggagagctcg                                              20

<210> SEQ ID NO 538
<211> LENGTH: 20
<212> TYPE: DNA
<213> ORGANISM: Human

<400> SEQUENCE: 538
atgatcacta tttactgaaa                                              20

<210> SEQ ID NO 539
<211> LENGTH: 20
<212> TYPE: DNA
<213> ORGANISM: Human

<400> SEQUENCE: 539
tcgtctacag cagtagcaaa                                              20

<210> SEQ ID NO 540
<211> LENGTH: 20
<212> TYPE: DNA
<213> ORGANISM: Human

<400> SEQUENCE: 540
cagagactac ctgtcggtga                                              20

<210> SEQ ID NO 541

```
<211> LENGTH: 20
<212> TYPE: DNA
<213> ORGANISM: Human

<400> SEQUENCE: 541
gtgcttctcg caggtcaagg                                                      20

<210> SEQ ID NO 542
<211> LENGTH: 20
<212> TYPE: DNA
<213> ORGANISM: Human

<400> SEQUENCE: 542
tggcggctca gcatgatctg                                                      20

<210> SEQ ID NO 543
<211> LENGTH: 20
<212> TYPE: DNA
<213> ORGANISM: Murine

<400> SEQUENCE: 543
caacccacat ttcgatttgg                                                      20

<210> SEQ ID NO 544
<211> LENGTH: 20
<212> TYPE: DNA
<213> ORGANISM: Murine

<400> SEQUENCE: 544
agccattcac acttctcact                                                      20

<210> SEQ ID NO 545
<211> LENGTH: 20
<212> TYPE: DNA
<213> ORGANISM: Murine

<400> SEQUENCE: 545
ccggctgtca cttaccgctg                                                      20

<210> SEQ ID NO 546
<211> LENGTH: 20
<212> TYPE: DNA
<213> ORGANISM: Murine

<400> SEQUENCE: 546
tttgtttcac agtcgttcga                                                      20

<210> SEQ ID NO 547
<211> LENGTH: 20
<212> TYPE: DNA
<213> ORGANISM: Murine

<400> SEQUENCE: 547
tggtaagaat gagggtaacc                                                      20

<210> SEQ ID NO 548
<211> LENGTH: 20
<212> TYPE: DNA
<213> ORGANISM: Murine

<400> SEQUENCE: 548
gctgcggaaa gcgcccgcca                                                      20
```

```
<210> SEQ ID NO 549
<211> LENGTH: 20
<212> TYPE: DNA
<213> ORGANISM: Murine

<400> SEQUENCE: 549
gttgatcatg attctctggt                                               20

<210> SEQ ID NO 550
<211> LENGTH: 20
<212> TYPE: DNA
<213> ORGANISM: Murine

<400> SEQUENCE: 550
ttgttgcaga caaatgtggc                                               20

<210> SEQ ID NO 551
<211> LENGTH: 20
<212> TYPE: DNA
<213> ORGANISM: Murine

<400> SEQUENCE: 551
ctatgaccgg ctggagatct                                               20

<210> SEQ ID NO 552
<211> LENGTH: 20
<212> TYPE: DNA
<213> ORGANISM: Murine

<400> SEQUENCE: 552
cacatgtccg gctctcatgt                                               20

<210> SEQ ID NO 553
<211> LENGTH: 20
<212> TYPE: DNA
<213> ORGANISM: Murine

<400> SEQUENCE: 553
gaggtgtcat cattcagggt                                               20

<210> SEQ ID NO 554
<211> LENGTH: 20
<212> TYPE: DNA
<213> ORGANISM: Murine

<400> SEQUENCE: 554
ccagggtacc tcacatctcc                                               20

<210> SEQ ID NO 555
<211> LENGTH: 20
<212> TYPE: DNA
<213> ORGANISM: Murine

<400> SEQUENCE: 555
aaacctgtat cctgggaaac                                               20

<210> SEQ ID NO 556
<211> LENGTH: 20
<212> TYPE: DNA
<213> ORGANISM: Human

<400> SEQUENCE: 556
agaccagttg gtgctatact                                               20
```

```
<210> SEQ ID NO 557
<211> LENGTH: 20
<212> TYPE: DNA
<213> ORGANISM: Human

<400> SEQUENCE: 557
agtggagtga taaagtcccc                                                    20

<210> SEQ ID NO 558
<211> LENGTH: 20
<212> TYPE: DNA
<213> ORGANISM: Human

<400> SEQUENCE: 558
gaccggctag aaatctggga                                                    20

<210> SEQ ID NO 559
<211> LENGTH: 20
<212> TYPE: DNA
<213> ORGANISM: Human

<400> SEQUENCE: 559
cctcacattg ggcgttactg                                                    20

<210> SEQ ID NO 560
<211> LENGTH: 20
<212> TYPE: DNA
<213> ORGANISM: Human

<400> SEQUENCE: 560
ggatgttctg tcgctacgac                                                    20

<210> SEQ ID NO 561
<211> LENGTH: 20
<212> TYPE: DNA
<213> ORGANISM: Human

<400> SEQUENCE: 561
cctgactcaa atcctccagg                                                    20

<210> SEQ ID NO 562
<211> LENGTH: 20
<212> TYPE: DNA
<213> ORGANISM: Human

<400> SEQUENCE: 562
agagaatgcc cgatgaggat                                                    20

<210> SEQ ID NO 563
<211> LENGTH: 20
<212> TYPE: DNA
<213> ORGANISM: Human

<400> SEQUENCE: 563
tacctgtatc cactctcggt                                                    20

<210> SEQ ID NO 564
<211> LENGTH: 20
<212> TYPE: DNA
<213> ORGANISM: Human

<400> SEQUENCE: 564
tgtcctccaa atcgaagtga                                                    20
```

```
<210> SEQ ID NO 565
<211> LENGTH: 20
<212> TYPE: DNA
<213> ORGANISM: Human

<400> SEQUENCE: 565
cattctcagg gtagttcagg                                              20

<210> SEQ ID NO 566
<211> LENGTH: 20
<212> TYPE: DNA
<213> ORGANISM: Human

<400> SEQUENCE: 566
tactgtggac agaaaacacc                                              20

<210> SEQ ID NO 567
<211> LENGTH: 20
<212> TYPE: DNA
<213> ORGANISM: Murine

<400> SEQUENCE: 567
gccctttagc tggtatctgc                                              20

<210> SEQ ID NO 568
<211> LENGTH: 20
<212> TYPE: DNA
<213> ORGANISM: Murine

<400> SEQUENCE: 568
atcagaactg ctatccacat                                              20

<210> SEQ ID NO 569
<211> LENGTH: 20
<212> TYPE: DNA
<213> ORGANISM: Murine

<400> SEQUENCE: 569
catggcagag acacagacac                                              20

<210> SEQ ID NO 570
<211> LENGTH: 20
<212> TYPE: DNA
<213> ORGANISM: Murine

<400> SEQUENCE: 570
cgaggagaac gtatatgaag                                              20

<210> SEQ ID NO 571
<211> LENGTH: 20
<212> TYPE: DNA
<213> ORGANISM: Murine

<400> SEQUENCE: 571
aatgtgactc tggatgacca                                              20

<210> SEQ ID NO 572
<211> LENGTH: 20
<212> TYPE: DNA
<213> ORGANISM: Murine

<400> SEQUENCE: 572
```

| | |
|---|---|
| ggaaaatatc tacaccatcg | 20 |

<210> SEQ ID NO 573
<211> LENGTH: 20
<212> TYPE: DNA
<213> ORGANISM: Murine

<400> SEQUENCE: 573

| | |
|---|---|
| gtagtagttg cagcagcagc | 20 |

<210> SEQ ID NO 574
<211> LENGTH: 20
<212> TYPE: DNA
<213> ORGANISM: Murine

<400> SEQUENCE: 574

| | |
|---|---|
| ttggagtggg agtctctgct | 20 |

<210> SEQ ID NO 575
<211> LENGTH: 20
<212> TYPE: DNA
<213> ORGANISM: Murine

<400> SEQUENCE: 575

| | |
|---|---|
| tccttacttt atagggtcat | 20 |

<210> SEQ ID NO 576
<211> LENGTH: 20
<212> TYPE: DNA
<213> ORGANISM: Murine

<400> SEQUENCE: 576

| | |
|---|---|
| caacttgcct ccaggagggt | 20 |

<210> SEQ ID NO 577
<211> LENGTH: 20
<212> TYPE: DNA
<213> ORGANISM: Murine

<400> SEQUENCE: 577

| | |
|---|---|
| atgtgactct ggatgaccat | 20 |

<210> SEQ ID NO 578
<211> LENGTH: 20
<212> TYPE: DNA
<213> ORGANISM: Murine

<400> SEQUENCE: 578

| | |
|---|---|
| ggggcaaggg attctgtcct | 20 |

<210> SEQ ID NO 579
<211> LENGTH: 20
<212> TYPE: DNA
<213> ORGANISM: Murine

<400> SEQUENCE: 579

| | |
|---|---|
| actgctatcc acattggagt | 20 |

<210> SEQ ID NO 580
<211> LENGTH: 20
<212> TYPE: DNA
<213> ORGANISM: Murine

<400> SEQUENCE: 580
aaccatttct ctccgtggtt                                    20

<210> SEQ ID NO 581
<211> LENGTH: 20
<212> TYPE: DNA
<213> ORGANISM: Murine

<400> SEQUENCE: 581
agtgtaactg cagggcagat                                    20

<210> SEQ ID NO 582
<211> LENGTH: 20
<212> TYPE: DNA
<213> ORGANISM: Human

<400> SEQUENCE: 582
agaagtggaa tacagagcgg                                    20

<210> SEQ ID NO 583
<211> LENGTH: 20
<212> TYPE: DNA
<213> ORGANISM: Human

<400> SEQUENCE: 583
atcagaatag gcatctacat                                    20

<210> SEQ ID NO 584
<211> LENGTH: 20
<212> TYPE: DNA
<213> ORGANISM: Human

<400> SEQUENCE: 584
ggtgtagaag cagggcagat                                    20

<210> SEQ ID NO 585
<211> LENGTH: 20
<212> TYPE: DNA
<213> ORGANISM: Human

<400> SEQUENCE: 585
aacctcgtgc ccgtctgctg                                    20

<210> SEQ ID NO 586
<211> LENGTH: 20
<212> TYPE: DNA
<213> ORGANISM: Human

<400> SEQUENCE: 586
aagagaagat acagaattta                                    20

<210> SEQ ID NO 587
<211> LENGTH: 20
<212> TYPE: DNA
<213> ORGANISM: Human

<400> SEQUENCE: 587
atgtgactct agcagacagt                                    20

<210> SEQ ID NO 588
<211> LENGTH: 20
<212> TYPE: DNA
<213> ORGANISM: Human

```
<400> SEQUENCE: 588
tctacccccc agccgcccca                                                    20

<210> SEQ ID NO 589
<211> LENGTH: 20
<212> TYPE: DNA
<213> ORGANISM: Human

<400> SEQUENCE: 589
acatccagat actggctaaa                                                    20

<210> SEQ ID NO 590
<211> LENGTH: 20
<212> TYPE: DNA
<213> ORGANISM: Human

<400> SEQUENCE: 590
tgtgtttgaa tgtggcaacg                                                    20

<210> SEQ ID NO 591
<211> LENGTH: 20
<212> TYPE: DNA
<213> ORGANISM: Human

<400> SEQUENCE: 591
agtcacattc tctatggtca                                                    20

<210> SEQ ID NO 592
<211> LENGTH: 20
<212> TYPE: DNA
<213> ORGANISM: Human

<400> SEQUENCE: 592
agtcggtgca ggggtgacct                                                    20

<210> SEQ ID NO 593
<211> LENGTH: 20
<212> TYPE: DNA
<213> ORGANISM: Human

<400> SEQUENCE: 593
tggccaaaga gatgaggctg                                                    20

<210> SEQ ID NO 594
<211> LENGTH: 20
<212> TYPE: DNA
<213> ORGANISM: Murine

<400> SEQUENCE: 594
actcctgggg gcaaatgaca                                                    20

<210> SEQ ID NO 595
<211> LENGTH: 20
<212> TYPE: DNA
<213> ORGANISM: Murine

<400> SEQUENCE: 595
tgaagccatc tctgtaggtg                                                    20

<210> SEQ ID NO 596
<211> LENGTH: 20
<212> TYPE: DNA
<213> ORGANISM: Murine
```

```
<400> SEQUENCE: 596
ggctgaagga gcagttcaaa                                              20

<210> SEQ ID NO 597
<211> LENGTH: 20
<212> TYPE: DNA
<213> ORGANISM: Murine

<400> SEQUENCE: 597
tgccactctt tccagccacg                                              20

<210> SEQ ID NO 598
<211> LENGTH: 20
<212> TYPE: DNA
<213> ORGANISM: Murine

<400> SEQUENCE: 598
aagtcagccc cctggactct                                              20

<210> SEQ ID NO 599
<211> LENGTH: 20
<212> TYPE: DNA
<213> ORGANISM: Murine

<400> SEQUENCE: 599
acagtgattg ctagtccctc                                              20

<210> SEQ ID NO 600
<211> LENGTH: 20
<212> TYPE: DNA
<213> ORGANISM: Murine

<400> SEQUENCE: 600
agccccaggt cccagagtcc                                              20

<210> SEQ ID NO 601
<211> LENGTH: 20
<212> TYPE: DNA
<213> ORGANISM: Murine

<400> SEQUENCE: 601
ctgtgggtct ggcacaggct                                              20

<210> SEQ ID NO 602
<211> LENGTH: 20
<212> TYPE: DNA
<213> ORGANISM: Murine

<400> SEQUENCE: 602
gccaagtgga ctcctcctgg                                              20

<210> SEQ ID NO 603
<211> LENGTH: 20
<212> TYPE: DNA
<213> ORGANISM: Murine

<400> SEQUENCE: 603
gtaggtgagg acacagcccc                                              20

<210> SEQ ID NO 604
<211> LENGTH: 20
<212> TYPE: DNA
```

-continued

<213> ORGANISM: Murine

<400> SEQUENCE: 604
tgcacagaga ctgggcggtc                                                  20

<210> SEQ ID NO 605
<211> LENGTH: 20
<212> TYPE: DNA
<213> ORGANISM: Murine

<400> SEQUENCE: 605
acgtacaacc tcaaggttct                                                  20

<210> SEQ ID NO 606
<211> LENGTH: 20
<212> TYPE: DNA
<213> ORGANISM: Murine

<400> SEQUENCE: 606
gctcaatgcc actgtcacgt                                                  20

<210> SEQ ID NO 607
<211> LENGTH: 20
<212> TYPE: DNA
<213> ORGANISM: Murine

<400> SEQUENCE: 607
agtctctgtg cactggttcc                                                  20

<210> SEQ ID NO 608
<211> LENGTH: 20
<212> TYPE: DNA
<213> ORGANISM: Murine

<400> SEQUENCE: 608
tgggcggtca ggacggctga                                                  20

<210> SEQ ID NO 609
<211> LENGTH: 20
<212> TYPE: DNA
<213> ORGANISM: Human

<400> SEQUENCE: 609
gttccggaac caatgcacag                                                  20

<210> SEQ ID NO 610
<211> LENGTH: 20
<212> TYPE: DNA
<213> ORGANISM: Human

<400> SEQUENCE: 610
tgcgaagagc agggggtcact                                                 20

<210> SEQ ID NO 611
<211> LENGTH: 20
<212> TYPE: DNA
<213> ORGANISM: Human

<400> SEQUENCE: 611
gcggtccctg aggtgcaccg                                                  20

<210> SEQ ID NO 612
<211> LENGTH: 20

-continued

```
<212> TYPE: DNA
<213> ORGANISM: Human

<400> SEQUENCE: 612
tccccacacc agcaggcagg                                              20

<210> SEQ ID NO 613
<211> LENGTH: 20
<212> TYPE: DNA
<213> ORGANISM: Human

<400> SEQUENCE: 613
ccgctacacg gtgctgagcg                                              20

<210> SEQ ID NO 614
<211> LENGTH: 20
<212> TYPE: DNA
<213> ORGANISM: Human

<400> SEQUENCE: 614
ccggtggtgt gggcccagga                                              20

<210> SEQ ID NO 615
<211> LENGTH: 20
<212> TYPE: DNA
<213> ORGANISM: Human

<400> SEQUENCE: 615
gtttggggtg catacctgtc                                              20

<210> SEQ ID NO 616
<211> LENGTH: 20
<212> TYPE: DNA
<213> ORGANISM: Human

<400> SEQUENCE: 616
aggctctgag agatcctggg                                              20

<210> SEQ ID NO 617
<211> LENGTH: 20
<212> TYPE: DNA
<213> ORGANISM: Human

<400> SEQUENCE: 617
gctcaatgcc actgtcacat                                              20

<210> SEQ ID NO 618
<211> LENGTH: 20
<212> TYPE: DNA
<213> ORGANISM: Human

<400> SEQUENCE: 618
gtcccggagg cctgcgcagc                                              20

<210> SEQ ID NO 619
<211> LENGTH: 20
<212> TYPE: DNA
<213> ORGANISM: Human

<400> SEQUENCE: 619
gcagaaggct gagatcctgg                                              20

<210> SEQ ID NO 620
```

-continued

```
<211> LENGTH: 20
<212> TYPE: DNA
<213> ORGANISM: Human

<400> SEQUENCE: 620
taggtgagga tgcagcccca                                               20

<210> SEQ ID NO 621
<211> LENGTH: 20
<212> TYPE: DNA
<213> ORGANISM: Murine

<400> SEQUENCE: 621
ttcagtgatc gggtggtccc                                               20

<210> SEQ ID NO 622
<211> LENGTH: 20
<212> TYPE: DNA
<213> ORGANISM: Murine

<400> SEQUENCE: 622
gtctctgaca atgaatgaca                                               20

<210> SEQ ID NO 623
<211> LENGTH: 20
<212> TYPE: DNA
<213> ORGANISM: Murine

<400> SEQUENCE: 623
ctgagctttc ttggaccttc                                               20

<210> SEQ ID NO 624
<211> LENGTH: 20
<212> TYPE: DNA
<213> ORGANISM: Murine

<400> SEQUENCE: 624
aacatctctg cagaggaagg                                               20

<210> SEQ ID NO 625
<211> LENGTH: 20
<212> TYPE: DNA
<213> ORGANISM: Murine

<400> SEQUENCE: 625
caaggggaga atattcctga                                               20

<210> SEQ ID NO 626
<211> LENGTH: 20
<212> TYPE: DNA
<213> ORGANISM: Murine

<400> SEQUENCE: 626
cactataaat ggccagaagc                                               20

<210> SEQ ID NO 627
<211> LENGTH: 20
<212> TYPE: DNA
<213> ORGANISM: Murine

<400> SEQUENCE: 627
caggcacgat agatacaaag                                               20
```

```
<210> SEQ ID NO 628
<211> LENGTH: 20
<212> TYPE: DNA
<213> ORGANISM: Murine

<400> SEQUENCE: 628
gtatcctggt gggatttaca                                              20

<210> SEQ ID NO 629
<211> LENGTH: 20
<212> TYPE: DNA
<213> ORGANISM: Murine

<400> SEQUENCE: 629
aggcagcctg tatcagcccc                                              20

<210> SEQ ID NO 630
<211> LENGTH: 20
<212> TYPE: DNA
<213> ORGANISM: Murine

<400> SEQUENCE: 630
gctgctcctg gtctgggtcc                                              20

<210> SEQ ID NO 631
<211> LENGTH: 20
<212> TYPE: DNA
<213> ORGANISM: Murine

<400> SEQUENCE: 631
tctctaggct tctgtagctc                                              20

<210> SEQ ID NO 632
<211> LENGTH: 20
<212> TYPE: DNA
<213> ORGANISM: Murine

<400> SEQUENCE: 632
ctgaagcgac atgccacccc                                              20

<210> SEQ ID NO 633
<211> LENGTH: 20
<212> TYPE: DNA
<213> ORGANISM: Murine

<400> SEQUENCE: 633
tctctgacaa tgaatgacac                                              20

<210> SEQ ID NO 634
<211> LENGTH: 20
<212> TYPE: DNA
<213> ORGANISM: Murine

<400> SEQUENCE: 634
ccatttatag tgttgacctg                                              20

<210> SEQ ID NO 635
<211> LENGTH: 20
<212> TYPE: DNA
<213> ORGANISM: Murine

<400> SEQUENCE: 635
tgccttcctc gctacaggta                                              20
```

```
<210> SEQ ID NO 636
<211> LENGTH: 20
<212> TYPE: DNA
<213> ORGANISM: Human

<400> SEQUENCE: 636
ttccacagaa tggattctga                                              20

<210> SEQ ID NO 637
<211> LENGTH: 20
<212> TYPE: DNA
<213> ORGANISM: Human

<400> SEQUENCE: 637
gctgaccgtg aacgatacag                                              20

<210> SEQ ID NO 638
<211> LENGTH: 20
<212> TYPE: DNA
<213> ORGANISM: Human

<400> SEQUENCE: 638
cccatccttc aaggatcgag                                              20

<210> SEQ ID NO 639
<211> LENGTH: 20
<212> TYPE: DNA
<213> ORGANISM: Human

<400> SEQUENCE: 639
caccacggca caagtgaccc                                              20

<210> SEQ ID NO 640
<211> LENGTH: 20
<212> TYPE: DNA
<213> ORGANISM: Human

<400> SEQUENCE: 640
atgtcacctc tcctccacca                                              20

<210> SEQ ID NO 641
<211> LENGTH: 20
<212> TYPE: DNA
<213> ORGANISM: Human

<400> SEQUENCE: 641
agtgtacgtc ccatcagggt                                              20

<210> SEQ ID NO 642
<211> LENGTH: 20
<212> TYPE: DNA
<213> ORGANISM: Human

<400> SEQUENCE: 642
gttcacggtc agcgactgga                                              20

<210> SEQ ID NO 643
<211> LENGTH: 20
<212> TYPE: DNA
<213> ORGANISM: Human

<400> SEQUENCE: 643
gcagatgacc accagcgtcg                                              20
```

<210> SEQ ID NO 644
<211> LENGTH: 20
<212> TYPE: DNA
<213> ORGANISM: Human

<400> SEQUENCE: 644
aacatttctg cagagaaagg                                                   20

<210> SEQ ID NO 645
<211> LENGTH: 20
<212> TYPE: DNA
<213> ORGANISM: Human

<400> SEQUENCE: 645
ctgctgctcc cagttgacct                                                   20

<210> SEQ ID NO 646
<211> LENGTH: 20
<212> TYPE: DNA
<213> ORGANISM: Human

<400> SEQUENCE: 646
aggccacatc tgcttcctgt                                                   20

<210> SEQ ID NO 647
<211> LENGTH: 20
<212> TYPE: DNA
<213> ORGANISM: Human

<400> SEQUENCE: 647
ggtggtcgcg ttgactagaa                                                   20

<210> SEQ ID NO 648
<211> LENGTH: 20
<212> TYPE: DNA
<213> ORGANISM: Murine

<400> SEQUENCE: 648
aagaagtcct cttacaacag                                                   20

<210> SEQ ID NO 649
<211> LENGTH: 20
<212> TYPE: DNA
<213> ORGANISM: Murine

<400> SEQUENCE: 649
tccaagacaa gccatggctg                                                   20

<210> SEQ ID NO 650
<211> LENGTH: 20
<212> TYPE: DNA
<213> ORGANISM: Murine

<400> SEQUENCE: 650
tgctccttct tcttcataaa                                                   20

<210> SEQ ID NO 651
<211> LENGTH: 20
<212> TYPE: DNA
<213> ORGANISM: Murine

<400> SEQUENCE: 651
acaaaaggcc aagtcctaga                                                     20

<210> SEQ ID NO 652
<211> LENGTH: 20
<212> TYPE: DNA
<213> ORGANISM: Murine

<400> SEQUENCE: 652
tgaaattgct tttcacattc                                                     20

<210> SEQ ID NO 653
<211> LENGTH: 20
<212> TYPE: DNA
<213> ORGANISM: Murine

<400> SEQUENCE: 653
cacacaacac tgatgaggtc                                                     20

<210> SEQ ID NO 654
<211> LENGTH: 20
<212> TYPE: DNA
<213> ORGANISM: Murine

<400> SEQUENCE: 654
gtggtgttgg ctagcagcca                                                     20

<210> SEQ ID NO 655
<211> LENGTH: 20
<212> TYPE: DNA
<213> ORGANISM: Murine

<400> SEQUENCE: 655
cccatgccca caaagtatgg                                                     20

<210> SEQ ID NO 656
<211> LENGTH: 20
<212> TYPE: DNA
<213> ORGANISM: Murine

<400> SEQUENCE: 656
aggtccgggt gactgtgctg                                                     20

<210> SEQ ID NO 657
<211> LENGTH: 20
<212> TYPE: DNA
<213> ORGANISM: Murine

<400> SEQUENCE: 657
aggactgaga gctgttgaca                                                     20

<210> SEQ ID NO 658
<211> LENGTH: 20
<212> TYPE: DNA
<213> ORGANISM: Murine

<400> SEQUENCE: 658
tgaatattca catggaaagc                                                     20

<210> SEQ ID NO 659
<211> LENGTH: 20
<212> TYPE: DNA
<213> ORGANISM: Murine

<400> SEQUENCE: 659
attaaaggta ccactgcaga 20

<210> SEQ ID NO 660
<211> LENGTH: 20
<212> TYPE: DNA
<213> ORGANISM: Murine

<400> SEQUENCE: 660
cacgggactg tacctctgca 20

<210> SEQ ID NO 661
<211> LENGTH: 20
<212> TYPE: DNA
<213> ORGANISM: Murine

<400> SEQUENCE: 661
acatgagttc caccttgcag 20

<210> SEQ ID NO 662
<211> LENGTH: 20
<212> TYPE: DNA
<213> ORGANISM: Murine

<400> SEQUENCE: 662
ctagattacc ccttctgcag 20

<210> SEQ ID NO 663
<211> LENGTH: 20
<212> TYPE: DNA
<213> ORGANISM: Murine

<400> SEQUENCE: 663
gacccaacct tcagtggtgt 20

<210> SEQ ID NO 664
<211> LENGTH: 20
<212> TYPE: DNA
<213> ORGANISM: Murine

<400> SEQUENCE: 664
ctcaactgca gctgccttct 20

<210> SEQ ID NO 665
<211> LENGTH: 20
<212> TYPE: DNA
<213> ORGANISM: Murine

<400> SEQUENCE: 665
ccaagacaag ccatggctgg 20

<210> SEQ ID NO 666
<211> LENGTH: 20
<212> TYPE: DNA
<213> ORGANISM: Murine

<400> SEQUENCE: 666
aaaagaagtc ctcttacaac 20

<210> SEQ ID NO 667
<211> LENGTH: 20
<212> TYPE: DNA
<213> ORGANISM: Murine

<400> SEQUENCE: 667
gatgaaaaga agagtgagca                                              20

<210> SEQ ID NO 668
<211> LENGTH: 20
<212> TYPE: DNA
<213> ORGANISM: Human

<400> SEQUENCE: 668
atggactctc ttcttcataa                                              20

<210> SEQ ID NO 669
<211> LENGTH: 20
<212> TYPE: DNA
<213> ORGANISM: Human

<400> SEQUENCE: 669
tccttgcagc agttagttcg                                              20

<210> SEQ ID NO 670
<211> LENGTH: 20
<212> TYPE: DNA
<213> ORGANISM: Human

<400> SEQUENCE: 670
ccgccatact acctgggcat                                              20

<210> SEQ ID NO 671
<211> LENGTH: 20
<212> TYPE: DNA
<213> ORGANISM: Human

<400> SEQUENCE: 671
ctgaaatcca aggcaagcca                                              20

<210> SEQ ID NO 672
<211> LENGTH: 20
<212> TYPE: DNA
<213> ORGANISM: Human

<400> SEQUENCE: 672
accccgaact aactgctgca                                              20

<210> SEQ ID NO 673
<211> LENGTH: 20
<212> TYPE: DNA
<213> ORGANISM: Human

<400> SEQUENCE: 673
ttttcacatt ctggctctgt                                              20

<210> SEQ ID NO 674
<211> LENGTH: 20
<212> TYPE: DNA
<213> ORGANISM: Human

<400> SEQUENCE: 674
tggcttgcct tggatttcag                                              20

<210> SEQ ID NO 675
<211> LENGTH: 20
<212> TYPE: DNA
<213> ORGANISM: Human

```
<400> SEQUENCE: 675
tgcatactca cacacaaagc                                               20

<210> SEQ ID NO 676
<211> LENGTH: 20
<212> TYPE: DNA
<213> ORGANISM: Human

<400> SEQUENCE: 676
cctagatgat tccatctgca                                               20

<210> SEQ ID NO 677
<211> LENGTH: 20
<212> TYPE: DNA
<213> ORGANISM: Human

<400> SEQUENCE: 677
aaacaggaga gtgcagggcc                                               20

<210> SEQ ID NO 678
<211> LENGTH: 20
<212> TYPE: DNA
<213> ORGANISM: Human

<400> SEQUENCE: 678
ctgctggcca gtaccacagc                                               20

<210> SEQ ID NO 679
<211> LENGTH: 20
<212> TYPE: DNA
<213> ORGANISM: Human

<400> SEQUENCE: 679
aagaagccct cttacaacag                                               20

<210> SEQ ID NO 680
<211> LENGTH: 20
<212> TYPE: DNA
<213> ORGANISM: Murine

<400> SEQUENCE: 680
cgtcatgact accagagagg                                               20

<210> SEQ ID NO 681
<211> LENGTH: 20
<212> TYPE: DNA
<213> ORGANISM: Murine

<400> SEQUENCE: 681
atgatcaggt gactcatatt                                               20

<210> SEQ ID NO 682
<211> LENGTH: 20
<212> TYPE: DNA
<213> ORGANISM: Murine

<400> SEQUENCE: 682
gcctcgcagg gtggatgatc                                               20

<210> SEQ ID NO 683
<211> LENGTH: 20
<212> TYPE: DNA
```

-continued

<213> ORGANISM: Murine

<400> SEQUENCE: 683
ccggcctttc tccacctctc                                               20

<210> SEQ ID NO 684
<211> LENGTH: 20
<212> TYPE: DNA
<213> ORGANISM: Murine

<400> SEQUENCE: 684
ccagtacaag tttatttacg                                               20

<210> SEQ ID NO 685
<211> LENGTH: 20
<212> TYPE: DNA
<213> ORGANISM: Murine

<400> SEQUENCE: 685
gtgcccacct cgggccagta                                               20

<210> SEQ ID NO 686
<211> LENGTH: 20
<212> TYPE: DNA
<213> ORGANISM: Murine

<400> SEQUENCE: 686
cttctatgac ctgtacggag                                               20

<210> SEQ ID NO 687
<211> LENGTH: 20
<212> TYPE: DNA
<213> ORGANISM: Murine

<400> SEQUENCE: 687
tattcggatc cagaactcag                                               20

<210> SEQ ID NO 688
<211> LENGTH: 20
<212> TYPE: DNA
<213> ORGANISM: Murine

<400> SEQUENCE: 688
tgggtactta aggtggatga                                               20

<210> SEQ ID NO 689
<211> LENGTH: 20
<212> TYPE: DNA
<213> ORGANISM: Murine

<400> SEQUENCE: 689
atgtgtccca tactggcccg                                               20

<210> SEQ ID NO 690
<211> LENGTH: 20
<212> TYPE: DNA
<213> ORGANISM: Murine

<400> SEQUENCE: 690
tggtgccatc tcggtcctgc                                               20

<210> SEQ ID NO 691
<211> LENGTH: 20

```
<212> TYPE: DNA
<213> ORGANISM: Murine

<400> SEQUENCE: 691
gtggggtccg agcagttcag                                               20

<210> SEQ ID NO 692
<211> LENGTH: 20
<212> TYPE: DNA
<213> ORGANISM: Murine

<400> SEQUENCE: 692
catcgtcatg actaccagag                                               20

<210> SEQ ID NO 693
<211> LENGTH: 20
<212> TYPE: DNA
<213> ORGANISM: Murine

<400> SEQUENCE: 693
ggggacttct atgacctgta                                               20

<210> SEQ ID NO 694
<211> LENGTH: 20
<212> TYPE: DNA
<213> ORGANISM: Human

<400> SEQUENCE: 694
ccagggtgga cgctacacag                                               20

<210> SEQ ID NO 695
<211> LENGTH: 20
<212> TYPE: DNA
<213> ORGANISM: Human

<400> SEQUENCE: 695
cattgatgta gtcggacccg                                               20

<210> SEQ ID NO 696
<211> LENGTH: 20
<212> TYPE: DNA
<213> ORGANISM: Human

<400> SEQUENCE: 696
ggtgtcctgc aggaccgcga                                               20

<210> SEQ ID NO 697
<211> LENGTH: 20
<212> TYPE: DNA
<213> ORGANISM: Human

<400> SEQUENCE: 697
gcaggcagag acgctgctgc                                               20

<210> SEQ ID NO 698
<211> LENGTH: 20
<212> TYPE: DNA
<213> ORGANISM: Human

<400> SEQUENCE: 698
gcccccagga tggtgaggta                                               20

<210> SEQ ID NO 699
```

```
<211> LENGTH: 20
<212> TYPE: DNA
<213> ORGANISM: Human

<400> SEQUENCE: 699
gatgcagaga ccctgctcaa                                              20

<210> SEQ ID NO 700
<211> LENGTH: 20
<212> TYPE: DNA
<213> ORGANISM: Human

<400> SEQUENCE: 700
ctgagttctg gatccgaata                                              20

<210> SEQ ID NO 701
<211> LENGTH: 20
<212> TYPE: DNA
<213> ORGANISM: Human

<400> SEQUENCE: 701
gatgtgggtg accctgagcg                                              20

<210> SEQ ID NO 702
<211> LENGTH: 20
<212> TYPE: DNA
<213> ORGANISM: Human

<400> SEQUENCE: 702
aacttaagga cacctgcaag                                              20

<210> SEQ ID NO 703
<211> LENGTH: 20
<212> TYPE: DNA
<213> ORGANISM: Human

<400> SEQUENCE: 703
gctccgatcc cactagtgag                                              20

<210> SEQ ID NO 704
<211> LENGTH: 20
<212> TYPE: DNA
<213> ORGANISM: Human

<400> SEQUENCE: 704
cggcccagtc gcaagaacca                                              20

<210> SEQ ID NO 705
<211> LENGTH: 20
<212> TYPE: DNA
<213> ORGANISM: Human

<400> SEQUENCE: 705
gtttgcgact ctgacagagc                                              20

<210> SEQ ID NO 706
<211> LENGTH: 20
<212> TYPE: DNA
<213> ORGANISM: Human

<400> SEQUENCE: 706
tattcggatc cagaactcag                                              20
```

```
<210> SEQ ID NO 707
<211> LENGTH: 20
<212> TYPE: DNA
<213> ORGANISM: Human

<400> SEQUENCE: 707
tcacgcacaa gaaacgtcca                                              20

<210> SEQ ID NO 708
<211> LENGTH: 20
<212> TYPE: DNA
<213> ORGANISM: Human

<400> SEQUENCE: 708
agccagtgcc cgggcatgcc                                              20

<210> SEQ ID NO 709
<211> LENGTH: 20
<212> TYPE: DNA
<213> ORGANISM: Human

<400> SEQUENCE: 709
tcttcgttag gacttggccc                                              20

<210> SEQ ID NO 710
<211> LENGTH: 20
<212> TYPE: DNA
<213> ORGANISM: Human

<400> SEQUENCE: 710
cagctggatg aacagcgaga                                              20

<210> SEQ ID NO 711
<211> LENGTH: 20
<212> TYPE: DNA
<213> ORGANISM: Human

<400> SEQUENCE: 711
gaaaattgca gcgaaatatg                                              20

<210> SEQ ID NO 712
<211> LENGTH: 20
<212> TYPE: DNA
<213> ORGANISM: Human

<400> SEQUENCE: 712
actgggcgat accacagcag                                              20

<210> SEQ ID NO 713
<211> LENGTH: 20
<212> TYPE: DNA
<213> ORGANISM: Human

<400> SEQUENCE: 713
agtggcactt gggacttcta                                              20

<210> SEQ ID NO 714
<211> LENGTH: 20
<212> TYPE: DNA
<213> ORGANISM: Human

<400> SEQUENCE: 714
tcttggtagg tcacaaactc                                              20
```

<210> SEQ ID NO 715
<211> LENGTH: 20
<212> TYPE: DNA
<213> ORGANISM: Human

<400> SEQUENCE: 715
gtgcagactg gagaatacag                                             20

<210> SEQ ID NO 716
<211> LENGTH: 20
<212> TYPE: DNA
<213> ORGANISM: Human

<400> SEQUENCE: 716
tgatccctca ggagtccagg                                             20

<210> SEQ ID NO 717
<211> LENGTH: 20
<212> TYPE: DNA
<213> ORGANISM: Human

<400> SEQUENCE: 717
gatggccctg ctgtaacttt                                             20

<210> SEQ ID NO 718
<211> LENGTH: 20
<212> TYPE: DNA
<213> ORGANISM: Human

<400> SEQUENCE: 718
aacgttagtg atgacagcat                                             20

<210> SEQ ID NO 719
<211> LENGTH: 20
<212> TYPE: DNA
<213> ORGANISM: Human

<400> SEQUENCE: 719
ccatgagaga gcccgttacg                                             20

<210> SEQ ID NO 720
<211> LENGTH: 20
<212> TYPE: DNA
<213> ORGANISM: Human

<400> SEQUENCE: 720
ggataggcgt gggaatcaac                                             20

<210> SEQ ID NO 721
<211> LENGTH: 20
<212> TYPE: DNA
<213> ORGANISM: Human

<400> SEQUENCE: 721
tatcccaagg ctccggaagg                                             20

<210> SEQ ID NO 722
<211> LENGTH: 20
<212> TYPE: DNA
<213> ORGANISM: Human

<400> SEQUENCE: 722
tgggtaaggg aggtaactcc                                             20

```
<210> SEQ ID NO 723
<211> LENGTH: 20
<212> TYPE: DNA
<213> ORGANISM: Human

<400> SEQUENCE: 723
tttccaacac tatactcgcc                                                    20

<210> SEQ ID NO 724
<211> LENGTH: 20
<212> TYPE: DNA
<213> ORGANISM: Human

<400> SEQUENCE: 724
acgtagtatt cccctgtcag                                                    20

<210> SEQ ID NO 725
<211> LENGTH: 20
<212> TYPE: DNA
<213> ORGANISM: Human

<400> SEQUENCE: 725
actgcccaca caaaatggtt                                                    20

<210> SEQ ID NO 726
<211> LENGTH: 20
<212> TYPE: DNA
<213> ORGANISM: Human

<400> SEQUENCE: 726
gctttaggtt cttgtcggtg                                                    20

<210> SEQ ID NO 727
<211> LENGTH: 20
<212> TYPE: DNA
<213> ORGANISM: Human

<400> SEQUENCE: 727
tgcaaaggtg gatgcgagca                                                    20

<210> SEQ ID NO 728
<211> LENGTH: 20
<212> TYPE: DNA
<213> ORGANISM: Human

<400> SEQUENCE: 728
taactcctgg ggtagggaat                                                    20

<210> SEQ ID NO 729
<211> LENGTH: 20
<212> TYPE: DNA
<213> ORGANISM: Human

<400> SEQUENCE: 729
ggctttggcg cccttgctgc                                                    20

<210> SEQ ID NO 730
<211> LENGTH: 20
<212> TYPE: DNA
<213> ORGANISM: Human

<400> SEQUENCE: 730
```
ggtaccaaca aagagaacct                                                20

<210> SEQ ID NO 731
<211> LENGTH: 20
<212> TYPE: DNA
<213> ORGANISM: Human

<400> SEQUENCE: 731
gagttcatca tgcccgcgca                                                20

<210> SEQ ID NO 732
<211> LENGTH: 20
<212> TYPE: DNA
<213> ORGANISM: Human

<400> SEQUENCE: 732
tttgccagct tagatggctt                                                20

<210> SEQ ID NO 733
<211> LENGTH: 20
<212> TYPE: DNA
<213> ORGANISM: Human

<400> SEQUENCE: 733
tagatagcac aaccatttcc                                                20

<210> SEQ ID NO 734
<211> LENGTH: 20
<212> TYPE: DNA
<213> ORGANISM: Human

<400> SEQUENCE: 734
agtttcaaag caaacgagaa                                                20

<210> SEQ ID NO 735
<211> LENGTH: 20
<212> TYPE: DNA
<213> ORGANISM: Human

<400> SEQUENCE: 735
ctgccctatg ggcttcccac                                                20

<210> SEQ ID NO 736
<211> LENGTH: 20
<212> TYPE: DNA
<213> ORGANISM: Human

<400> SEQUENCE: 736
gtcaactgta gtgcccagga                                                20

<210> SEQ ID NO 737
<211> LENGTH: 20
<212> TYPE: DNA
<213> ORGANISM: Human

<400> SEQUENCE: 737
tcagtgatgt tagtcccctg                                                20

<210> SEQ ID NO 738
<211> LENGTH: 20
<212> TYPE: DNA
<213> ORGANISM: Human

<400> SEQUENCE: 738

| | |
|---|---|
| ctaaagagga gaaaccagag | 20 |

<210> SEQ ID NO 739
<211> LENGTH: 20
<212> TYPE: DNA
<213> ORGANISM: Human

<400> SEQUENCE: 739

| | |
|---|---|
| cagcagatgg caaacctggc | 20 |

<210> SEQ ID NO 740
<211> LENGTH: 20
<212> TYPE: DNA
<213> ORGANISM: Human

<400> SEQUENCE: 740

| | |
|---|---|
| cagggcaact gaaggagagg | 20 |

<210> SEQ ID NO 741
<211> LENGTH: 20
<212> TYPE: DNA
<213> ORGANISM: Human

<400> SEQUENCE: 741

| | |
|---|---|
| acgatgggag cagcaggtgt | 20 |

<210> SEQ ID NO 742
<211> LENGTH: 20
<212> TYPE: DNA
<213> ORGANISM: Human

<400> SEQUENCE: 742

| | |
|---|---|
| cccacgtgct gaataacgga | 20 |

<210> SEQ ID NO 743
<211> LENGTH: 20
<212> TYPE: DNA
<213> ORGANISM: Human

<400> SEQUENCE: 743

| | |
|---|---|
| taccaaagat ggagctgatg | 20 |

<210> SEQ ID NO 744
<211> LENGTH: 20
<212> TYPE: DNA
<213> ORGANISM: Human

<400> SEQUENCE: 744

| | |
|---|---|
| caggccactg gtgaccgcct | 20 |

<210> SEQ ID NO 745
<211> LENGTH: 20
<212> TYPE: DNA
<213> ORGANISM: Human

<400> SEQUENCE: 745

| | |
|---|---|
| ctgctgtttg gcaggcggcc | 20 |

<210> SEQ ID NO 746
<211> LENGTH: 20
<212> TYPE: DNA
<213> ORGANISM: Human

```
<400> SEQUENCE: 746
gccgactggg aaaggttgaa                                              20

<210> SEQ ID NO 747
<211> LENGTH: 20
<212> TYPE: DNA
<213> ORGANISM: Human

<400> SEQUENCE: 747
gctgtcatca ctaacgtttc                                              20

<210> SEQ ID NO 748
<211> LENGTH: 20
<212> TYPE: DNA
<213> ORGANISM: Human

<400> SEQUENCE: 748
tccatgtaag gattgaccca                                              20

<210> SEQ ID NO 749
<211> LENGTH: 20
<212> TYPE: DNA
<213> ORGANISM: Human

<400> SEQUENCE: 749
accgaataca cccgagacag                                              20

<210> SEQ ID NO 750
<211> LENGTH: 20
<212> TYPE: DNA
<213> ORGANISM: Human

<400> SEQUENCE: 750
acctggccgg caaagcagga                                              20

<210> SEQ ID NO 751
<211> LENGTH: 20
<212> TYPE: DNA
<213> ORGANISM: Human

<400> SEQUENCE: 751
tactacgtgg agaatgccga                                              20

<210> SEQ ID NO 752
<211> LENGTH: 20
<212> TYPE: DNA
<213> ORGANISM: Human

<400> SEQUENCE: 752
gaaaaccgat tccggagggt                                              20

<210> SEQ ID NO 753
<211> LENGTH: 20
<212> TYPE: DNA
<213> ORGANISM: Human

<400> SEQUENCE: 753
gcactgagca tggaccgcac                                              20

<210> SEQ ID NO 754
<211> LENGTH: 20
<212> TYPE: DNA
<213> ORGANISM: Human
```

```
<400> SEQUENCE: 754
gttctctaag gtgcagcaag                                              20

<210> SEQ ID NO 755
<211> LENGTH: 20
<212> TYPE: DNA
<213> ORGANISM: Human

<400> SEQUENCE: 755
agttagcagc gagttccccg                                              20

<210> SEQ ID NO 756
<211> LENGTH: 20
<212> TYPE: DNA
<213> ORGANISM: Human

<400> SEQUENCE: 756
cagaagcgct gggcttggac                                              20

<210> SEQ ID NO 757
<211> LENGTH: 20
<212> TYPE: DNA
<213> ORGANISM: Human

<400> SEQUENCE: 757
cagcggctgg gccaagctgt                                              20

<210> SEQ ID NO 758
<211> LENGTH: 20
<212> TYPE: DNA
<213> ORGANISM: Human

<400> SEQUENCE: 758
actttcgttc tgttctgcaa                                              20

<210> SEQ ID NO 759
<211> LENGTH: 20
<212> TYPE: DNA
<213> ORGANISM: Human

<400> SEQUENCE: 759
cgccttggca gagggaaccc                                              20

<210> SEQ ID NO 760
<211> LENGTH: 20
<212> TYPE: DNA
<213> ORGANISM: Human

<400> SEQUENCE: 760
gatgaggctg aatcaaatga                                              20

<210> SEQ ID NO 761
<211> LENGTH: 20
<212> TYPE: DNA
<213> ORGANISM: Human

<400> SEQUENCE: 761
gcggttcaag acagaaaaga                                              20

<210> SEQ ID NO 762
<211> LENGTH: 20
<212> TYPE: DNA
```

```
<213> ORGANISM: Human

<400> SEQUENCE: 762
tcttgttctc taagcagtac                                          20

<210> SEQ ID NO 763
<211> LENGTH: 20
<212> TYPE: DNA
<213> ORGANISM: Human

<400> SEQUENCE: 763
ggtgccatct gcattggcat                                          20

<210> SEQ ID NO 764
<211> LENGTH: 20
<212> TYPE: DNA
<213> ORGANISM: Human

<400> SEQUENCE: 764
tggcaagtat cccaaggctc                                          20

<210> SEQ ID NO 765
<211> LENGTH: 20
<212> TYPE: DNA
<213> ORGANISM: Human

<400> SEQUENCE: 765
gctgccacaa gcactctagg                                          20

<210> SEQ ID NO 766
<211> LENGTH: 20
<212> TYPE: DNA
<213> ORGANISM: Human

<400> SEQUENCE: 766
atagcactga agccatttgg                                          20

<210> SEQ ID NO 767
<211> LENGTH: 20
<212> TYPE: DNA
<213> ORGANISM: Human

<400> SEQUENCE: 767
gaatacaccc gagacagtgg                                          20

<210> SEQ ID NO 768
<211> LENGTH: 20
<212> TYPE: DNA
<213> ORGANISM: Human

<400> SEQUENCE: 768
tccaagtatc tgtggctcag                                          20

<210> SEQ ID NO 769
<211> LENGTH: 20
<212> TYPE: DNA
<213> ORGANISM: Human

<400> SEQUENCE: 769
tcaatggtgc tagttatctg                                          20

<210> SEQ ID NO 770
<211> LENGTH: 20
```

```
<212> TYPE: DNA
<213> ORGANISM: Human

<400> SEQUENCE: 770
gtgaacgttc ccatacaggg                                               20

<210> SEQ ID NO 771
<211> LENGTH: 20
<212> TYPE: DNA
<213> ORGANISM: Human

<400> SEQUENCE: 771
gaatcccttg aaccacaacg                                               20

<210> SEQ ID NO 772
<211> LENGTH: 20
<212> TYPE: DNA
<213> ORGANISM: Human

<400> SEQUENCE: 772
gctgtgtgca gacgaagaag                                               20

<210> SEQ ID NO 773
<211> LENGTH: 20
<212> TYPE: DNA
<213> ORGANISM: Murine

<400> SEQUENCE: 773
gacacacggc gcaatgacag                                               20

<210> SEQ ID NO 774
<211> LENGTH: 20
<212> TYPE: DNA
<213> ORGANISM: Murine

<400> SEQUENCE: 774
cagctgtatg atctggaagc                                               20

<210> SEQ ID NO 775
<211> LENGTH: 20
<212> TYPE: DNA
<213> ORGANISM: Murine

<400> SEQUENCE: 775
cagcaaccag actgaaaaac                                               20

<210> SEQ ID NO 776
<211> LENGTH: 20
<212> TYPE: DNA
<213> ORGANISM: Murine

<400> SEQUENCE: 776
gcagggagat ggccccacag                                               20

<210> SEQ ID NO 777
<211> LENGTH: 20
<212> TYPE: DNA
<213> ORGANISM: Murine

<400> SEQUENCE: 777
acagtggcat ctacctctgt                                               20

<210> SEQ ID NO 778
```

```
<211> LENGTH: 20
<212> TYPE: DNA
<213> ORGANISM: Murine

<400> SEQUENCE: 778
cggaggatct tatgctgaac                                        20

<210> SEQ ID NO 779
<211> LENGTH: 20
<212> TYPE: DNA
<213> ORGANISM: Murine

<400> SEQUENCE: 779
gagccctgga gcagagctcg                                        20

<210> SEQ ID NO 780
<211> LENGTH: 20
<212> TYPE: DNA
<213> ORGANISM: Murine

<400> SEQUENCE: 780
gcaaaaatcg aggagagccc                                        20

<210> SEQ ID NO 781
<211> LENGTH: 20
<212> TYPE: DNA
<213> ORGANISM: Murine

<400> SEQUENCE: 781
gccaggctgg gtagaaggtg                                        20

<210> SEQ ID NO 782
<211> LENGTH: 20
<212> TYPE: DNA
<213> ORGANISM: Murine

<400> SEQUENCE: 782
gctcaaacca ttacagaagg                                        20

<210> SEQ ID NO 783
<211> LENGTH: 20
<212> TYPE: DNA
<213> ORGANISM: Murine

<400> SEQUENCE: 783
ggacaagctg caggtgaagg                                        20

<210> SEQ ID NO 784
<211> LENGTH: 20
<212> TYPE: DNA
<213> ORGANISM: Murine

<400> SEQUENCE: 784
gagccctgga gcagagctcg                                        20

<210> SEQ ID NO 785
<211> LENGTH: 20
<212> TYPE: DNA
<213> ORGANISM: Murine

<400> SEQUENCE: 785
ggacaagctg caggtgaagg                                        20
```

-continued

```
<210> SEQ ID NO 786
<211> LENGTH: 20
<212> TYPE: DNA
<213> ORGANISM: Murine

<400> SEQUENCE: 786
gctcaaacca ttacagaagg                                              20

<210> SEQ ID NO 787
<211> LENGTH: 20
<212> TYPE: DNA
<213> ORGANISM: Murine

<400> SEQUENCE: 787
gccaggctgg gtagaaggtg                                              20

<210> SEQ ID NO 788
<211> LENGTH: 20
<212> TYPE: DNA
<213> ORGANISM: Murine

<400> SEQUENCE: 788
gacacacggc gcaatgacag                                              20

<210> SEQ ID NO 789
<211> LENGTH: 20
<212> TYPE: DNA
<213> ORGANISM: Murine

<400> SEQUENCE: 789
cagctgtatg atctggaagc                                              20

<210> SEQ ID NO 790
<211> LENGTH: 20
<212> TYPE: DNA
<213> ORGANISM: Murine

<400> SEQUENCE: 790
cagcaaccag actgaaaaac                                              20

<210> SEQ ID NO 791
<211> LENGTH: 20
<212> TYPE: DNA
<213> ORGANISM: Murine

<400> SEQUENCE: 791
gcagggagat ggccccacag                                              20

<210> SEQ ID NO 792
<211> LENGTH: 20
<212> TYPE: DNA
<213> ORGANISM: Murine

<400> SEQUENCE: 792
acagtggcat ctacctctgt                                              20

<210> SEQ ID NO 793
<211> LENGTH: 20
<212> TYPE: DNA
<213> ORGANISM: Murine

<400> SEQUENCE: 793
cggaggatct tatgctgaac                                              20
```

```
<210> SEQ ID NO 794
<211> LENGTH: 20
<212> TYPE: DNA
<213> ORGANISM: Murine

<400> SEQUENCE: 794
gcaaaaatcg aggagagccc                                               20

<210> SEQ ID NO 795
<211> LENGTH: 20
<212> TYPE: DNA
<213> ORGANISM: Murine

<400> SEQUENCE: 795
cgaccagttg gacaagctgc                                               20

<210> SEQ ID NO 796
<211> LENGTH: 20
<212> TYPE: DNA
<213> ORGANISM: Murine

<400> SEQUENCE: 796
catgtggaag tcatgcctgt                                               20

<210> SEQ ID NO 797
<211> LENGTH: 20
<212> TYPE: DNA
<213> ORGANISM: Murine

<400> SEQUENCE: 797
agcgggcatc ctggacgggt                                               20

<210> SEQ ID NO 798
<211> LENGTH: 20
<212> TYPE: DNA
<213> ORGANISM: Murine

<400> SEQUENCE: 798
ccaggctggg tagaaggtga                                               20

<210> SEQ ID NO 799
<211> LENGTH: 20
<212> TYPE: DNA
<213> ORGANISM: Murine

<400> SEQUENCE: 799
gcaccccaag gcaaaaatcg                                               20

<210> SEQ ID NO 800
<211> LENGTH: 20
<212> TYPE: DNA
<213> ORGANISM: Murine

<400> SEQUENCE: 800
gctcaaacca ttacagaagg                                               20

<210> SEQ ID NO 801
<211> LENGTH: 20
<212> TYPE: DNA
<213> ORGANISM: Murine

<400> SEQUENCE: 801
gacacacggc gcaatgacag                                               20
```

<210> SEQ ID NO 802
<211> LENGTH: 20
<212> TYPE: DNA
<213> ORGANISM: Murine

<400> SEQUENCE: 802
cagctgtatg atctggaagc                                          20

<210> SEQ ID NO 803
<211> LENGTH: 20
<212> TYPE: DNA
<213> ORGANISM: Human

<400> SEQUENCE: 803
cggccagttc caaaccctgg                                          20

<210> SEQ ID NO 804
<211> LENGTH: 20
<212> TYPE: DNA
<213> ORGANISM: Human

<400> SEQUENCE: 804
cagttccaaa ccctggtggt                                          20

<210> SEQ ID NO 805
<211> LENGTH: 20
<212> TYPE: DNA
<213> ORGANISM: Human

<400> SEQUENCE: 805
ctgcagcttc tccaacacat                                          20

<210> SEQ ID NO 806
<211> LENGTH: 20
<212> TYPE: DNA
<213> ORGANISM: Human

<400> SEQUENCE: 806
cgtgtcacac aactgcccaa                                          20

<210> SEQ ID NO 807
<211> LENGTH: 20
<212> TYPE: DNA
<213> ORGANISM: Human

<400> SEQUENCE: 807
agagctcagg gtgacaggtg                                          20

<210> SEQ ID NO 808
<211> LENGTH: 20
<212> TYPE: DNA
<213> ORGANISM: Human

<400> SEQUENCE: 808
gcgtgacttc cacatgagcg                                          20

<210> SEQ ID NO 809
<211> LENGTH: 20
<212> TYPE: DNA
<213> ORGANISM: Human

<400> SEQUENCE: 809
cagcggcacc tacctctgtg                                           20

<210> SEQ ID NO 810
<211> LENGTH: 20
<212> TYPE: DNA
<213> ORGANISM: Human

<400> SEQUENCE: 810
gctgcggtcc tcgggaagg                                            20

<210> SEQ ID NO 811
<211> LENGTH: 20
<212> TYPE: DNA
<213> ORGANISM: Human

<400> SEQUENCE: 811
gcagggctgg ggagaaggtg                                           20

<210> SEQ ID NO 812
<211> LENGTH: 20
<212> TYPE: DNA
<213> ORGANISM: Human

<400> SEQUENCE: 812
catgagcccc agcaaccaga                                           20

<210> SEQ ID NO 813
<211> LENGTH: 20
<212> TYPE: DNA
<213> ORGANISM: Human

<400> SEQUENCE: 813
gccctgtgtc cctgagcaga                                           20

<210> SEQ ID NO 814
<211> LENGTH: 20
<212> TYPE: DNA
<213> ORGANISM: Murine

<400> SEQUENCE: 814
tagggccccc aggcctgagc                                           20

<210> SEQ ID NO 815
<211> LENGTH: 20
<212> TYPE: DNA
<213> ORGANISM: Murine

<400> SEQUENCE: 815
aagatctgcg cccggagata                                           20

<210> SEQ ID NO 816
<211> LENGTH: 20
<212> TYPE: DNA
<213> ORGANISM: Murine

<400> SEQUENCE: 816
gttctgtctg tagggaggta                                           20

<210> SEQ ID NO 817
<211> LENGTH: 20
<212> TYPE: DNA
<213> ORGANISM: Murine

<400> SEQUENCE: 817
caacgaaact tacacaagga    20

<210> SEQ ID NO 818
<211> LENGTH: 20
<212> TYPE: DNA
<213> ORGANISM: Murine

<400> SEQUENCE: 818
cactcagaac ttacatcaga    20

<210> SEQ ID NO 819
<211> LENGTH: 20
<212> TYPE: DNA
<213> ORGANISM: Murine

<400> SEQUENCE: 819
tctgagtgtg acagagaagg    20

<210> SEQ ID NO 820
<211> LENGTH: 20
<212> TYPE: DNA
<213> ORGANISM: Murine

<400> SEQUENCE: 820
ttcctcctga gactgtcgta    20

<210> SEQ ID NO 821
<211> LENGTH: 20
<212> TYPE: DNA
<213> ORGANISM: Murine

<400> SEQUENCE: 821
gacaattgca gcctgctgag    20

<210> SEQ ID NO 822
<211> LENGTH: 20
<212> TYPE: DNA
<213> ORGANISM: Murine

<400> SEQUENCE: 822
acttacatca gaaggttgct    20

<210> SEQ ID NO 823
<211> LENGTH: 20
<212> TYPE: DNA
<213> ORGANISM: Murine

<400> SEQUENCE: 823
gcacaggagc tgcggcggat    20

<210> SEQ ID NO 824
<211> LENGTH: 20
<212> TYPE: DNA
<213> ORGANISM: Murine

<400> SEQUENCE: 824
gttgtaagat aaccatttga    20

<210> SEQ ID NO 825
<211> LENGTH: 20
<212> TYPE: DNA
<213> ORGANISM: Murine

```
<400> SEQUENCE: 825
gtttgcaaat gattaccgcg                                              20

<210> SEQ ID NO 826
<211> LENGTH: 20
<212> TYPE: DNA
<213> ORGANISM: Murine

<400> SEQUENCE: 826
tcctgtgcaa tccgtatctc                                              20

<210> SEQ ID NO 827
<211> LENGTH: 20
<212> TYPE: DNA
<213> ORGANISM: Murine

<400> SEQUENCE: 827
tcgccgtcgg gattaccttg                                              20

<210> SEQ ID NO 828
<211> LENGTH: 20
<212> TYPE: DNA
<213> ORGANISM: Murine

<400> SEQUENCE: 828
tcttccgtct ggtatggaga                                              20

<210> SEQ ID NO 829
<211> LENGTH: 20
<212> TYPE: DNA
<213> ORGANISM: Murine

<400> SEQUENCE: 829
ttccatacga cagtctcagg                                              20

<210> SEQ ID NO 830
<211> LENGTH: 20
<212> TYPE: DNA
<213> ORGANISM: Murine

<400> SEQUENCE: 830
ttctgtctgt agggaggtag                                              20

<210> SEQ ID NO 831
<211> LENGTH: 20
<212> TYPE: DNA
<213> ORGANISM: Murine

<400> SEQUENCE: 831
caaccactat ctcagtgcaa                                              20

<210> SEQ ID NO 832
<211> LENGTH: 20
<212> TYPE: DNA
<213> ORGANISM: Human

<400> SEQUENCE: 832
agctggggag gcctctccgc                                              20

<210> SEQ ID NO 833
<211> LENGTH: 20
<212> TYPE: DNA
<213> ORGANISM: Human
```

```
<400> SEQUENCE: 833
ccactgaact tccctatgaa                                               20

<210> SEQ ID NO 834
<211> LENGTH: 20
<212> TYPE: DNA
<213> ORGANISM: Human

<400> SEQUENCE: 834
ttaacgctta ctatgcaagg                                               20

<210> SEQ ID NO 835
<211> LENGTH: 20
<212> TYPE: DNA
<213> ORGANISM: Human

<400> SEQUENCE: 835
aaccattcgt gggtggtctt                                               20

<210> SEQ ID NO 836
<211> LENGTH: 20
<212> TYPE: DNA
<213> ORGANISM: Human

<400> SEQUENCE: 836
aggcaatcac ggaggtgaag                                               20

<210> SEQ ID NO 837
<211> LENGTH: 20
<212> TYPE: DNA
<213> ORGANISM: Human

<400> SEQUENCE: 837
tggcttgcag atgactccgc                                               20

<210> SEQ ID NO 838
<211> LENGTH: 20
<212> TYPE: DNA
<213> ORGANISM: Human

<400> SEQUENCE: 838
aaagatcacc tatatcctct                                               20

<210> SEQ ID NO 839
<211> LENGTH: 20
<212> TYPE: DNA
<213> ORGANISM: Human

<400> SEQUENCE: 839
gttgatttgt cacaactcat                                               20

<210> SEQ ID NO 840
<211> LENGTH: 20
<212> TYPE: DNA
<213> ORGANISM: Human

<400> SEQUENCE: 840
gttctgatgc agcttccatg                                               20

<210> SEQ ID NO 841
<211> LENGTH: 20
<212> TYPE: DNA
```

```
<213> ORGANISM: Human

<400> SEQUENCE: 841
ttttccagtt agagaaatag                                              20

<210> SEQ ID NO 842
<211> LENGTH: 20
<212> TYPE: DNA
<213> ORGANISM: Human

<400> SEQUENCE: 842
tagtggttga aggcctggca                                              20

<210> SEQ ID NO 843
<211> LENGTH: 20
<212> TYPE: DNA
<213> ORGANISM: Human

<400> SEQUENCE: 843
ttgccttcag gattaccttg                                              20

<210> SEQ ID NO 844
<211> LENGTH: 20
<212> TYPE: DNA
<213> ORGANISM: Human

<400> SEQUENCE: 844
acagtctcac tctgtcaccc                                              20

<210> SEQ ID NO 845
<211> LENGTH: 20
<212> TYPE: DNA
<213> ORGANISM: Human

<400> SEQUENCE: 845
cactcagaac ttacatcaga                                              20

<210> SEQ ID NO 846
<211> LENGTH: 20
<212> TYPE: DNA
<213> ORGANISM: Human

<400> SEQUENCE: 846
cttgggcgat ccatatctct                                              20

<210> SEQ ID NO 847
<211> LENGTH: 20
<212> TYPE: DNA
<213> ORGANISM: Human

<400> SEQUENCE: 847
aggtagacaa ttgcagcctg                                              20

<210> SEQ ID NO 848
<211> LENGTH: 20
<212> TYPE: DNA
<213> ORGANISM: Human

<400> SEQUENCE: 848
acttcctcta tttctctaac                                              20

<210> SEQ ID NO 849
<211> LENGTH: 20
```

-continued

```
<212> TYPE: DNA
<213> ORGANISM: Human

<400> SEQUENCE: 849
actggaggat cgagacagca                                            20

<210> SEQ ID NO 850
<211> LENGTH: 20
<212> TYPE: DNA
<213> ORGANISM: Human

<400> SEQUENCE: 850
tccctacaga cagagccaca                                            20

<210> SEQ ID NO 851
<211> LENGTH: 20
<212> TYPE: DNA
<213> ORGANISM: Human

<400> SEQUENCE: 851
ttgtggctct gtctgtaggg                                            20

<210> SEQ ID NO 852
<211> LENGTH: 20
<212> TYPE: DNA
<213> ORGANISM: Murine

<400> SEQUENCE: 852
gctgttaact ctgttgatgc                                            20

<210> SEQ ID NO 853
<211> LENGTH: 20
<212> TYPE: DNA
<213> ORGANISM: Murine

<400> SEQUENCE: 853
ggctcgccgg ctcgggatgg                                            20

<210> SEQ ID NO 854
<211> LENGTH: 20
<212> TYPE: DNA
<213> ORGANISM: Murine

<400> SEQUENCE: 854
ccggagccgc ggaccaccac                                            20

<210> SEQ ID NO 855
<211> LENGTH: 20
<212> TYPE: DNA
<213> ORGANISM: Murine

<400> SEQUENCE: 855
cgattgagaa gttattagaa                                            20

<210> SEQ ID NO 856
<211> LENGTH: 20
<212> TYPE: DNA
<213> ORGANISM: Murine

<400> SEQUENCE: 856
gctcaagtac tcgcccgacc                                            20

<210> SEQ ID NO 857
```

```
<210> SEQ ID NO 857
<211> LENGTH: 20
<212> TYPE: DNA
<213> ORGANISM: Murine

<400> SEQUENCE: 857
tccccgcagg actcaccttg                                               20

<210> SEQ ID NO 858
<211> LENGTH: 20
<212> TYPE: DNA
<213> ORGANISM: Murine

<400> SEQUENCE: 858
ctgtgctgct gctgcacgtt                                               20

<210> SEQ ID NO 859
<211> LENGTH: 20
<212> TYPE: DNA
<213> ORGANISM: Murine

<400> SEQUENCE: 859
ggacgaggag cgggccctgg                                               20

<210> SEQ ID NO 860
<211> LENGTH: 20
<212> TYPE: DNA
<213> ORGANISM: Human

<400> SEQUENCE: 860
cgaaatctat gaggaagagg                                               20

<210> SEQ ID NO 861
<211> LENGTH: 20
<212> TYPE: DNA
<213> ORGANISM: Human

<400> SEQUENCE: 861
actgttaact ctgttgatgc                                               20

<210> SEQ ID NO 862
<211> LENGTH: 20
<212> TYPE: DNA
<213> ORGANISM: Human

<400> SEQUENCE: 862
gcacattagg ttgcagtatg                                               20

<210> SEQ ID NO 863
<211> LENGTH: 20
<212> TYPE: DNA
<213> ORGANISM: Human

<400> SEQUENCE: 863
ggatttcgac gaaatctatg                                               20

<210> SEQ ID NO 864
<211> LENGTH: 20
<212> TYPE: DNA
<213> ORGANISM: Human

<400> SEQUENCE: 864
tctcaatcga tcttcgtgtc                                               20
```

-continued

```
<210> SEQ ID NO 865
<211> LENGTH: 20
<212> TYPE: DNA
<213> ORGANISM: Human

<400> SEQUENCE: 865
tgcattggag actgagcaaa                                               20

<210> SEQ ID NO 866
<211> LENGTH: 20
<212> TYPE: DNA
<213> ORGANISM: Human

<400> SEQUENCE: 866
gccaacgtac attaacagga                                               20

<210> SEQ ID NO 867
<211> LENGTH: 20
<212> TYPE: DNA
<213> ORGANISM: Human

<400> SEQUENCE: 867
gaattccctt cttcattaac                                               20

<210> SEQ ID NO 868
<211> LENGTH: 20
<212> TYPE: DNA
<213> ORGANISM: Human

<400> SEQUENCE: 868
ccggacccgg tggtcgtccg                                               20

<210> SEQ ID NO 869
<211> LENGTH: 20
<212> TYPE: DNA
<213> ORGANISM: Human

<400> SEQUENCE: 869
gcagctgctc aagtactcgc                                               20

<210> SEQ ID NO 870
<211> LENGTH: 20
<212> TYPE: DNA
<213> ORGANISM: Human

<400> SEQUENCE: 870
aaacaatagg ttataccaca                                               20

<210> SEQ ID NO 871
<211> LENGTH: 20
<212> TYPE: DNA
<213> ORGANISM: Human

<400> SEQUENCE: 871
cggtgacgtg accggagccg                                               20

<210> SEQ ID NO 872
<211> LENGTH: 20
<212> TYPE: DNA
<213> ORGANISM: Murine

<400> SEQUENCE: 872
ccactgcaga ccccacactg                                               20
```

```
<210> SEQ ID NO 873
<211> LENGTH: 20
<212> TYPE: DNA
<213> ORGANISM: Murine

<400> SEQUENCE: 873
tataaaggaa tacggattga                                               20

<210> SEQ ID NO 874
<211> LENGTH: 20
<212> TYPE: DNA
<213> ORGANISM: Murine

<400> SEQUENCE: 874
gtggctggag tgggctataa                                               20

<210> SEQ ID NO 875
<211> LENGTH: 20
<212> TYPE: DNA
<213> ORGANISM: Murine

<400> SEQUENCE: 875
cggagagtca ttgtgcctgc                                               20

<210> SEQ ID NO 876
<211> LENGTH: 20
<212> TYPE: DNA
<213> ORGANISM: Murine

<400> SEQUENCE: 876
cacaggagca cgttcgacag                                               20

<210> SEQ ID NO 877
<211> LENGTH: 20
<212> TYPE: DNA
<213> ORGANISM: Murine

<400> SEQUENCE: 877
aatgacggac cctgatgagg                                               20

<210> SEQ ID NO 878
<211> LENGTH: 20
<212> TYPE: DNA
<213> ORGANISM: Murine

<400> SEQUENCE: 878
catggtactt actttccctg                                               20

<210> SEQ ID NO 879
<211> LENGTH: 20
<212> TYPE: DNA
<213> ORGANISM: Murine

<400> SEQUENCE: 879
ccaacgccag ctgtatcacc                                               20

<210> SEQ ID NO 880
<211> LENGTH: 20
<212> TYPE: DNA
<213> ORGANISM: Human

<400> SEQUENCE: 880
cagcacttcc gtgttgtaga                                               20
```

<210> SEQ ID NO 881
<211> LENGTH: 20
<212> TYPE: DNA
<213> ORGANISM: Human

<400> SEQUENCE: 881
caaaatgacg gaccccgatg                                                   20

<210> SEQ ID NO 882
<211> LENGTH: 20
<212> TYPE: DNA
<213> ORGANISM: Human

<400> SEQUENCE: 882
tggttctcga attacctgcg                                                   20

<210> SEQ ID NO 883
<211> LENGTH: 20
<212> TYPE: DNA
<213> ORGANISM: Human

<400> SEQUENCE: 883
tgtgaggcaa tggctggagt                                                   20

<210> SEQ ID NO 884
<211> LENGTH: 20
<212> TYPE: DNA
<213> ORGANISM: Human

<400> SEQUENCE: 884
gatcgtttgt gccctccaa                                                    20

<210> SEQ ID NO 885
<211> LENGTH: 20
<212> TYPE: DNA
<213> ORGANISM: Human

<400> SEQUENCE: 885
tcgttggtgg tcatgttggg                                                   20

<210> SEQ ID NO 886
<211> LENGTH: 20
<212> TYPE: DNA
<213> ORGANISM: Human

<400> SEQUENCE: 886
tcagtaagaa tacagagcaa                                                   20

<210> SEQ ID NO 887
<211> LENGTH: 20
<212> TYPE: DNA
<213> ORGANISM: Human

<400> SEQUENCE: 887
ccagctgtat cacctgggag                                                   20

<210> SEQ ID NO 888
<211> LENGTH: 20
<212> TYPE: DNA
<213> ORGANISM: Human

<400> SEQUENCE: 888

```
tgtcggagag cagctccagg                                               20

<210> SEQ ID NO 889
<211> LENGTH: 20
<212> TYPE: DNA
<213> ORGANISM: Human

<400> SEQUENCE: 889
aacattatga ccaaagtgca                                               20

<210> SEQ ID NO 890
<211> LENGTH: 20
<212> TYPE: DNA
<213> ORGANISM: Human

<400> SEQUENCE: 890
ggcggcactt actttccctg                                               20

<210> SEQ ID NO 891
<211> LENGTH: 20
<212> TYPE: DNA
<213> ORGANISM: Human

<400> SEQUENCE: 891
actgtgtaaa atgaacaagg                                               20

<210> SEQ ID NO 892
<211> LENGTH: 20
<212> TYPE: DNA
<213> ORGANISM: Murine

<400> SEQUENCE: 892
atcccccgcc acctggacct                                               20

<210> SEQ ID NO 893
<211> LENGTH: 20
<212> TYPE: DNA
<213> ORGANISM: Murine

<400> SEQUENCE: 893
ggaaggcagg tcactattac                                               20

<210> SEQ ID NO 894
<211> LENGTH: 20
<212> TYPE: DNA
<213> ORGANISM: Murine

<400> SEQUENCE: 894
ctgatgcacg gaaaggaagt                                               20

<210> SEQ ID NO 895
<211> LENGTH: 20
<212> TYPE: DNA
<213> ORGANISM: Murine

<400> SEQUENCE: 895
cctgggcccc ggtgctctcg                                               20

<210> SEQ ID NO 896
<211> LENGTH: 20
<212> TYPE: DNA
<213> ORGANISM: Murine

<400> SEQUENCE: 896
```
accagccgaa gtgtgaccgg 20

<210> SEQ ID NO 897
<211> LENGTH: 20
<212> TYPE: DNA
<213> ORGANISM: Murine

<400> SEQUENCE: 897
gtcagcgtga tgatcctctc 20

<210> SEQ ID NO 898
<211> LENGTH: 20
<212> TYPE: DNA
<213> ORGANISM: Murine

<400> SEQUENCE: 898
ctccagcttg tcgatgatca 20

<210> SEQ ID NO 899
<211> LENGTH: 20
<212> TYPE: DNA
<213> ORGANISM: Murine

<400> SEQUENCE: 899
tcccgtcccg ccgtgcatca 20

<210> SEQ ID NO 900
<211> LENGTH: 20
<212> TYPE: DNA
<213> ORGANISM: Human

<400> SEQUENCE: 900
tggcgcgcgg atcaacatct 20

<210> SEQ ID NO 901
<211> LENGTH: 20
<212> TYPE: DNA
<213> ORGANISM: Human

<400> SEQUENCE: 901
gagagaatca tcactctgac 20

<210> SEQ ID NO 902
<211> LENGTH: 20
<212> TYPE: DNA
<213> ORGANISM: Human

<400> SEQUENCE: 902
tccgtgcata agaagccgaa 20

<210> SEQ ID NO 903
<211> LENGTH: 20
<212> TYPE: DNA
<213> ORGANISM: Human

<400> SEQUENCE: 903
aagcatcatt gggaagaaag 20

<210> SEQ ID NO 904
<211> LENGTH: 20
<212> TYPE: DNA
<213> ORGANISM: Human

```
<400> SEQUENCE: 904
ctccatgacc aacagtaccg                                          20

<210> SEQ ID NO 905
<211> LENGTH: 20
<212> TYPE: DNA
<213> ORGANISM: Human

<400> SEQUENCE: 905
atttggaatg gtgagttcat                                          20

<210> SEQ ID NO 906
<211> LENGTH: 20
<212> TYPE: DNA
<213> ORGANISM: Human

<400> SEQUENCE: 906
agagatccgc gagagtacgg                                          20

<210> SEQ ID NO 907
<211> LENGTH: 20
<212> TYPE: DNA
<213> ORGANISM: Human

<400> SEQUENCE: 907
gaaagcctta aagatggcat                                          20

<210> SEQ ID NO 908
<211> LENGTH: 20
<212> TYPE: DNA
<213> ORGANISM: Human

<400> SEQUENCE: 908
cagctcccca gtcatctgcg                                          20

<210> SEQ ID NO 909
<211> LENGTH: 20
<212> TYPE: DNA
<213> ORGANISM: Human

<400> SEQUENCE: 909
acacactcgg tgacagactg                                          20

<210> SEQ ID NO 910
<211> LENGTH: 20
<212> TYPE: DNA
<213> ORGANISM: Human

<400> SEQUENCE: 910
aatcagggag ccgcactggg                                          20

<210> SEQ ID NO 911
<211> LENGTH: 20
<212> TYPE: DNA
<213> ORGANISM: Human

<400> SEQUENCE: 911
gtcggttaag aggatccgcg                                          20

<210> SEQ ID NO 912
<211> LENGTH: 20
<212> TYPE: DNA
<213> ORGANISM: Murine
```

```
<400> SEQUENCE: 912
ccaaaacata caatgagcct                                               20

<210> SEQ ID NO 913
<211> LENGTH: 20
<212> TYPE: DNA
<213> ORGANISM: Murine

<400> SEQUENCE: 913
agactattat gcaataatta                                               20

<210> SEQ ID NO 914
<211> LENGTH: 20
<212> TYPE: DNA
<213> ORGANISM: Murine

<400> SEQUENCE: 914
aagactttgc gatctattta                                               20

<210> SEQ ID NO 915
<211> LENGTH: 20
<212> TYPE: DNA
<213> ORGANISM: Murine

<400> SEQUENCE: 915
gagcacatca cttaccactt                                               20

<210> SEQ ID NO 916
<211> LENGTH: 20
<212> TYPE: DNA
<213> ORGANISM: Murine

<400> SEQUENCE: 916
gtaccaagac atagattcta                                               20

<210> SEQ ID NO 917
<211> LENGTH: 20
<212> TYPE: DNA
<213> ORGANISM: Murine

<400> SEQUENCE: 917
cctctgtgag ctgttcatta                                               20

<210> SEQ ID NO 918
<211> LENGTH: 20
<212> TYPE: DNA
<213> ORGANISM: Murine

<400> SEQUENCE: 918
aacgggcaag aaggatgaac                                               20

<210> SEQ ID NO 919
<211> LENGTH: 20
<212> TYPE: DNA
<213> ORGANISM: Murine

<400> SEQUENCE: 919
gaaaccactt cataatagtc                                               20

<210> SEQ ID NO 920
<211> LENGTH: 20
<212> TYPE: DNA
```

```
<213> ORGANISM: Human

<400> SEQUENCE: 920
cacacctggc ggaagatggt                                               20

<210> SEQ ID NO 921
<211> LENGTH: 20
<212> TYPE: DNA
<213> ORGANISM: Human

<400> SEQUENCE: 921
tggagagatt cttctttcac                                               20

<210> SEQ ID NO 922
<211> LENGTH: 20
<212> TYPE: DNA
<213> ORGANISM: Human

<400> SEQUENCE: 922
ggagttgtcg gaataaccaa                                               20

<210> SEQ ID NO 923
<211> LENGTH: 20
<212> TYPE: DNA
<213> ORGANISM: Human

<400> SEQUENCE: 923
caaatcccag agtttgcaag                                               20

<210> SEQ ID NO 924
<211> LENGTH: 20
<212> TYPE: DNA
<213> ORGANISM: Human

<400> SEQUENCE: 924
tcaggcaact cagatctaga                                               20

<210> SEQ ID NO 925
<211> LENGTH: 20
<212> TYPE: DNA
<213> ORGANISM: Human

<400> SEQUENCE: 925
ttacccggtg gtgggatgcc                                               20

<210> SEQ ID NO 926
<211> LENGTH: 20
<212> TYPE: DNA
<213> ORGANISM: Human

<400> SEQUENCE: 926
tcaaccagac tattatgaag                                               20

<210> SEQ ID NO 927
<211> LENGTH: 20
<212> TYPE: DNA
<213> ORGANISM: Human

<400> SEQUENCE: 927
cccttccagc agtgtcagcg                                               20

<210> SEQ ID NO 928
<211> LENGTH: 20
```

```
<212> TYPE: DNA
<213> ORGANISM: Human

<400> SEQUENCE: 928
gccaggcact ataatgagga                                           20

<210> SEQ ID NO 929
<211> LENGTH: 20
<212> TYPE: DNA
<213> ORGANISM: Human

<400> SEQUENCE: 929
tcattagggc accaaagcga                                           20

<210> SEQ ID NO 930
<211> LENGTH: 20
<212> TYPE: DNA
<213> ORGANISM: Human

<400> SEQUENCE: 930
ttgagcatcc ccattggtgt                                           20

<210> SEQ ID NO 931
<211> LENGTH: 20
<212> TYPE: DNA
<213> ORGANISM: Human

<400> SEQUENCE: 931
ttgcattgtt aaaaagaagc                                           20

<210> SEQ ID NO 932
<211> LENGTH: 20
<212> TYPE: DNA
<213> ORGANISM: Human

<400> SEQUENCE: 932
aggctgcctt tactgtgtga                                           20

<210> SEQ ID NO 933
<211> LENGTH: 20
<212> TYPE: DNA
<213> ORGANISM: Human

<400> SEQUENCE: 933
tgctgattga gcatccccat                                           20

<210> SEQ ID NO 934
<211> LENGTH: 20
<212> TYPE: DNA
<213> ORGANISM: Human

<400> SEQUENCE: 934
ccagctgcac gctatgaaga                                           20

<210> SEQ ID NO 935
<211> LENGTH: 20
<212> TYPE: DNA
<213> ORGANISM: Human

<400> SEQUENCE: 935
aaaacatttg cataatgatg                                           20

<210> SEQ ID NO 936
```

```
<211> LENGTH: 20
<212> TYPE: DNA
<213> ORGANISM: Human

<400> SEQUENCE: 936
ggataggact ccatccaact                                          20

<210> SEQ ID NO 937
<211> LENGTH: 20
<212> TYPE: DNA
<213> ORGANISM: Human

<400> SEQUENCE: 937
atctcaagac cattgcccag                                          20

<210> SEQ ID NO 938
<211> LENGTH: 20
<212> TYPE: DNA
<213> ORGANISM: Murine

<400> SEQUENCE: 938
gctcatactc ctcccggtta                                          20

<210> SEQ ID NO 939
<211> LENGTH: 20
<212> TYPE: DNA
<213> ORGANISM: Murine

<400> SEQUENCE: 939
aggcgagggg cctgatttac                                          20

<210> SEQ ID NO 940
<211> LENGTH: 20
<212> TYPE: DNA
<213> ORGANISM: Murine

<400> SEQUENCE: 940
gttacgggtc tggagtgtgt                                          20

<210> SEQ ID NO 941
<211> LENGTH: 20
<212> TYPE: DNA
<213> ORGANISM: Murine

<400> SEQUENCE: 941
tgttggggac aggctgctgg                                          20

<210> SEQ ID NO 942
<211> LENGTH: 20
<212> TYPE: DNA
<213> ORGANISM: Murine

<400> SEQUENCE: 942
tctggactct cttcaccatt                                          20

<210> SEQ ID NO 943
<211> LENGTH: 20
<212> TYPE: DNA
<213> ORGANISM: Human

<400> SEQUENCE: 943
gagaatcact tgaacctggg                                          20
```

```
<210> SEQ ID NO 944
<211> LENGTH: 20
<212> TYPE: DNA
<213> ORGANISM: Human

<400> SEQUENCE: 944
gcaggatgca ccctactaca                                              20

<210> SEQ ID NO 945
<211> LENGTH: 20
<212> TYPE: DNA
<213> ORGANISM: Human

<400> SEQUENCE: 945
cattaggctc tggccgtacc                                              20

<210> SEQ ID NO 946
<211> LENGTH: 20
<212> TYPE: DNA
<213> ORGANISM: Human

<400> SEQUENCE: 946
ccgtgagggc caccatctcg                                              20

<210> SEQ ID NO 947
<211> LENGTH: 20
<212> TYPE: DNA
<213> ORGANISM: Human

<400> SEQUENCE: 947
agcgttcgta tctggaaggt                                              20

<210> SEQ ID NO 948
<211> LENGTH: 20
<212> TYPE: DNA
<213> ORGANISM: Human

<400> SEQUENCE: 948
ataagctccg aggttgcccg                                              20

<210> SEQ ID NO 949
<211> LENGTH: 20
<212> TYPE: DNA
<213> ORGANISM: Human

<400> SEQUENCE: 949
gctggcagtg actgatacag                                              20

<210> SEQ ID NO 950
<211> LENGTH: 20
<212> TYPE: DNA
<213> ORGANISM: Human

<400> SEQUENCE: 950
acaaagatgg ccttgccaga                                              20

<210> SEQ ID NO 951
<211> LENGTH: 20
<212> TYPE: DNA
<213> ORGANISM: Human

<400> SEQUENCE: 951
aagaagtaaa ctacctcaca                                              20
```

```
<210> SEQ ID NO 952
<211> LENGTH: 20
<212> TYPE: DNA
<213> ORGANISM: Human

<400> SEQUENCE: 952
gctacgttct tcatggccgt                                              20

<210> SEQ ID NO 953
<211> LENGTH: 20
<212> TYPE: DNA
<213> ORGANISM: Human

<400> SEQUENCE: 953
aagaattcga ccaagggatt                                              20

<210> SEQ ID NO 954
<211> LENGTH: 20
<212> TYPE: DNA
<213> ORGANISM: Human

<400> SEQUENCE: 954
ttaatggcaa gacttgcaga                                              20

<210> SEQ ID NO 955
<211> LENGTH: 20
<212> TYPE: DNA
<213> ORGANISM: Human

<400> SEQUENCE: 955
tgaaagtatc cagctgatga                                              20

<210> SEQ ID NO 956
<211> LENGTH: 20
<212> TYPE: DNA
<213> ORGANISM: Human

<400> SEQUENCE: 956
ggcgagatgt gtgacagagg                                              20

<210> SEQ ID NO 957
<211> LENGTH: 20
<212> TYPE: DNA
<213> ORGANISM: Human

<400> SEQUENCE: 957
agatgtagag ctttccaagg                                              20

<210> SEQ ID NO 958
<211> LENGTH: 20
<212> TYPE: DNA
<213> ORGANISM: Human

<400> SEQUENCE: 958
tagatcttct tacatggaag                                              20

<210> SEQ ID NO 959
<211> LENGTH: 20
<212> TYPE: DNA
<213> ORGANISM: Human

<400> SEQUENCE: 959
ctttctaggt tcgagatgtg                                              20
```

```
<210> SEQ ID NO 960
<211> LENGTH: 20
<212> TYPE: DNA
<213> ORGANISM: Human

<400> SEQUENCE: 960
caacccaatc tttcctcgga                                               20

<210> SEQ ID NO 961
<211> LENGTH: 20
<212> TYPE: DNA
<213> ORGANISM: Human

<400> SEQUENCE: 961
gtagaagcaa agagaggcga                                               20

<210> SEQ ID NO 962
<211> LENGTH: 20
<212> TYPE: DNA
<213> ORGANISM: Human

<400> SEQUENCE: 962
ttcgatctcg acttcttgag                                               20

<210> SEQ ID NO 963
<211> LENGTH: 20
<212> TYPE: DNA
<213> ORGANISM: Human

<400> SEQUENCE: 963
gcttgaggct ccttacaaga                                               20

<210> SEQ ID NO 964
<211> LENGTH: 20
<212> TYPE: DNA
<213> ORGANISM: Human

<400> SEQUENCE: 964
ctgatgatgg acagtgaaac                                               20

<210> SEQ ID NO 965
<211> LENGTH: 20
<212> TYPE: DNA
<213> ORGANISM: Human

<400> SEQUENCE: 965
cataataaca aacaaagcta                                               20

<210> SEQ ID NO 966
<211> LENGTH: 20
<212> TYPE: DNA
<213> ORGANISM: Human

<400> SEQUENCE: 966
aggagatgta gagctttcca                                               20

<210> SEQ ID NO 967
<211> LENGTH: 20
<212> TYPE: DNA
<213> ORGANISM: Human

<400> SEQUENCE: 967
```
ttggtcagat aatatgatta                                              20

<210> SEQ ID NO 968
<211> LENGTH: 20
<212> TYPE: DNA
<213> ORGANISM: Human

<400> SEQUENCE: 968
gaggcaaccc aatctttcct                                              20

<210> SEQ ID NO 969
<211> LENGTH: 20
<212> TYPE: DNA
<213> ORGANISM: Human

<400> SEQUENCE: 969
aggtgaattc atgggagtag                                              20

<210> SEQ ID NO 970
<211> LENGTH: 20
<212> TYPE: DNA
<213> ORGANISM: Human

<400> SEQUENCE: 970
tacttactat gaagcattta                                              20

<210> SEQ ID NO 971
<211> LENGTH: 20
<212> TYPE: DNA
<213> ORGANISM: Human

<400> SEQUENCE: 971
cagggcgaga tgtgtgacag                                              20

<210> SEQ ID NO 972
<211> LENGTH: 20
<212> TYPE: DNA
<213> ORGANISM: Human

<400> SEQUENCE: 972
agcgaagtag aagcaaagag                                              20

<210> SEQ ID NO 973
<211> LENGTH: 20
<212> TYPE: DNA
<213> ORGANISM: Human

<400> SEQUENCE: 973
agtgatgaac tggaaaggac                                              20

<210> SEQ ID NO 974
<211> LENGTH: 20
<212> TYPE: DNA
<213> ORGANISM: Human

<400> SEQUENCE: 974
atgaagcatt tagggatctt                                              20

<210> SEQ ID NO 975
<211> LENGTH: 20
<212> TYPE: DNA
<213> ORGANISM: Human

<400> SEQUENCE: 975
cttggcacct tgaagagcat 20

<210> SEQ ID NO 976
<211> LENGTH: 20
<212> TYPE: DNA
<213> ORGANISM: Human

<400> SEQUENCE: 976
tttaattggg gaggaccatg 20

<210> SEQ ID NO 977
<211> LENGTH: 20
<212> TYPE: DNA
<213> ORGANISM: Human

<400> SEQUENCE: 977
gtcattattc acagcagggt 20

<210> SEQ ID NO 978
<211> LENGTH: 20
<212> TYPE: DNA
<213> ORGANISM: Human

<400> SEQUENCE: 978
cgtcctagag agtttacata 20

<210> SEQ ID NO 979
<211> LENGTH: 20
<212> TYPE: DNA
<213> ORGANISM: Human

<400> SEQUENCE: 979
ctgcagggtg aagtttacaa 20

<210> SEQ ID NO 980
<211> LENGTH: 20
<212> TYPE: DNA
<213> ORGANISM: Human

<400> SEQUENCE: 980
tgacatctgc cttgacgaag 20

<210> SEQ ID NO 981
<211> LENGTH: 20
<212> TYPE: DNA
<213> ORGANISM: Human

<400> SEQUENCE: 981
aaaacaggta cacttggcac 20

<210> SEQ ID NO 982
<211> LENGTH: 20
<212> TYPE: DNA
<213> ORGANISM: Human

<400> SEQUENCE: 982
acttctaggc ttactatctg 20

<210> SEQ ID NO 983
<211> LENGTH: 20
<212> TYPE: DNA
<213> ORGANISM: Human

```
<400> SEQUENCE: 983
cgcaacagag atcagaaaag                                         20

<210> SEQ ID NO 984
<211> LENGTH: 20
<212> TYPE: DNA
<213> ORGANISM: Human

<400> SEQUENCE: 984
aaggctctca gggagagccg                                         20

<210> SEQ ID NO 985
<211> LENGTH: 20
<212> TYPE: DNA
<213> ORGANISM: Human

<400> SEQUENCE: 985
gttcatgtta cagaggaaag                                         20

<210> SEQ ID NO 986
<211> LENGTH: 20
<212> TYPE: DNA
<213> ORGANISM: Human

<400> SEQUENCE: 986
gcaagcatgc tcgaggacag                                         20

<210> SEQ ID NO 987
<211> LENGTH: 20
<212> TYPE: DNA
<213> ORGANISM: Human

<400> SEQUENCE: 987
tgcttgaagt tggacagcaa                                         20

<210> SEQ ID NO 988
<211> LENGTH: 20
<212> TYPE: DNA
<213> ORGANISM: Human

<400> SEQUENCE: 988
cactaaacca tttcaggtaa                                         20

<210> SEQ ID NO 989
<211> LENGTH: 20
<212> TYPE: DNA
<213> ORGANISM: Human

<400> SEQUENCE: 989
ctatttgaca aagatggtga                                         20

<210> SEQ ID NO 990
<211> LENGTH: 20
<212> TYPE: DNA
<213> ORGANISM: Human

<400> SEQUENCE: 990
aagaagttga tgaaatgatc                                         20

<210> SEQ ID NO 991
<211> LENGTH: 20
<212> TYPE: DNA
<213> ORGANISM: Human
```

```
<400> SEQUENCE: 991
cgccatgtga tgacaaacct                                        20

<210> SEQ ID NO 992
<211> LENGTH: 20
<212> TYPE: DNA
<213> ORGANISM: Human

<400> SEQUENCE: 992
gtcctgtaac tctgcttctg                                        20

<210> SEQ ID NO 993
<211> LENGTH: 20
<212> TYPE: DNA
<213> ORGANISM: Human

<400> SEQUENCE: 993
tcagcagttc aagaccagcc                                        20

<210> SEQ ID NO 994
<211> LENGTH: 20
<212> TYPE: DNA
<213> ORGANISM: Human

<400> SEQUENCE: 994
tgatggaact ataacaacaa                                        20

<210> SEQ ID NO 995
<211> LENGTH: 20
<212> TYPE: DNA
<213> ORGANISM: Human

<400> SEQUENCE: 995
ccatcattgt cagaaattca                                        20

<210> SEQ ID NO 996
<211> LENGTH: 20
<212> TYPE: DNA
<213> ORGANISM: Human

<400> SEQUENCE: 996
gacgtacctt atcaaacaca                                        20

<210> SEQ ID NO 997
<211> LENGTH: 20
<212> TYPE: DNA
<213> ORGANISM: Human

<400> SEQUENCE: 997
ctttgcacaa caaccctgca                                        20

<210> SEQ ID NO 998
<211> LENGTH: 20
<212> TYPE: DNA
<213> ORGANISM: Human

<400> SEQUENCE: 998
aaggcggtgg agatgctcag                                        20

<210> SEQ ID NO 999
<211> LENGTH: 20
<212> TYPE: DNA
```

```
<213> ORGANISM: Human

<400> SEQUENCE: 999
aggtgatgca aactcatcat                                              20

<210> SEQ ID NO 1000
<211> LENGTH: 20
<212> TYPE: DNA
<213> ORGANISM: Human

<400> SEQUENCE: 1000
cggattagcc tccgccaacg                                              20

<210> SEQ ID NO 1001
<211> LENGTH: 20
<212> TYPE: DNA
<213> ORGANISM: Human

<400> SEQUENCE: 1001
tgctcccaga gaccctgaag                                              20

<210> SEQ ID NO 1002
<211> LENGTH: 20
<212> TYPE: DNA
<213> ORGANISM: Human

<400> SEQUENCE: 1002
tgacgaggag aatctgaccc                                              20

<210> SEQ ID NO 1003
<211> LENGTH: 20
<212> TYPE: DNA
<213> ORGANISM: Human

<400> SEQUENCE: 1003
gctgaaagcg aagtccacgt                                              20

<210> SEQ ID NO 1004
<211> LENGTH: 20
<212> TYPE: DNA
<213> ORGANISM: Human

<400> SEQUENCE: 1004
aggcctcaag ttcaacctca                                              20

<210> SEQ ID NO 1005
<211> LENGTH: 20
<212> TYPE: DNA
<213> ORGANISM: Human

<400> SEQUENCE: 1005
agctgagtcc tgaaagtcag                                              20

<210> SEQ ID NO 1006
<211> LENGTH: 20
<212> TYPE: DNA
<213> ORGANISM: Human

<400> SEQUENCE: 1006
tctgctggac aggttcacgg                                              20

<210> SEQ ID NO 1007
<211> LENGTH: 20
```

<212> TYPE: DNA
<213> ORGANISM: Human

<400> SEQUENCE: 1007
ccccagagac aggaaggcca                                          20

<210> SEQ ID NO 1008
<211> LENGTH: 20
<212> TYPE: DNA
<213> ORGANISM: Human

<400> SEQUENCE: 1008
cctaccttca aacagaacca                                          20

<210> SEQ ID NO 1009
<211> LENGTH: 20
<212> TYPE: DNA
<213> ORGANISM: Human

<400> SEQUENCE: 1009
atggtggctt tgatgaactg                                          20

<210> SEQ ID NO 1010
<211> LENGTH: 20
<212> TYPE: DNA
<213> ORGANISM: Human

<400> SEQUENCE: 1010
attgtattcc tgcttccgga                                          20

<210> SEQ ID NO 1011
<211> LENGTH: 20
<212> TYPE: DNA
<213> ORGANISM: Human

<400> SEQUENCE: 1011
gatctactac ttcttccgag                                          20

<210> SEQ ID NO 1012
<211> LENGTH: 20
<212> TYPE: DNA
<213> ORGANISM: Human

<400> SEQUENCE: 1012
gttcactgtc agtctccaag                                          20

<210> SEQ ID NO 1013
<211> LENGTH: 20
<212> TYPE: DNA
<213> ORGANISM: Human

<400> SEQUENCE: 1013
tagacctcac acaggtccag                                          20

<210> SEQ ID NO 1014
<211> LENGTH: 20
<212> TYPE: DNA
<213> ORGANISM: Human

<400> SEQUENCE: 1014
ggaatacacc tcgtcccctg                                          20

<210> SEQ ID NO 1015

```
<211> LENGTH: 20
<212> TYPE: DNA
<213> ORGANISM: Human

<400> SEQUENCE: 1015
actcaagcct tcccaacccg                                              20

<210> SEQ ID NO 1016
<211> LENGTH: 20
<212> TYPE: DNA
<213> ORGANISM: Human

<400> SEQUENCE: 1016
aatacaatgg gaagatccct                                              20

<210> SEQ ID NO 1017
<211> LENGTH: 20
<212> TYPE: DNA
<213> ORGANISM: Murine

<400> SEQUENCE: 1017
gtgtccagtc ccaacactgc                                              20

<210> SEQ ID NO 1018
<211> LENGTH: 20
<212> TYPE: DNA
<213> ORGANISM: Murine

<400> SEQUENCE: 1018
agcggtggaa cacaggctac                                              20

<210> SEQ ID NO 1019
<211> LENGTH: 20
<212> TYPE: DNA
<213> ORGANISM: Murine

<400> SEQUENCE: 1019
aatccagtag ggattgctgc                                              20

<210> SEQ ID NO 1020
<211> LENGTH: 20
<212> TYPE: DNA
<213> ORGANISM: Murine

<400> SEQUENCE: 1020
ttaataacag cttggtcctc                                              20

<210> SEQ ID NO 1021
<211> LENGTH: 20
<212> TYPE: DNA
<213> ORGANISM: Murine

<400> SEQUENCE: 1021
aagtgtgact ccccagcctc                                              20

<210> SEQ ID NO 1022
<211> LENGTH: 20
<212> TYPE: DNA
<213> ORGANISM: Murine

<400> SEQUENCE: 1022
gggtttcctt cctgaggctg                                              20
```

```
<210> SEQ ID NO 1023
<211> LENGTH: 20
<212> TYPE: DNA
<213> ORGANISM: Murine

<400> SEQUENCE: 1023
ggggaagaat aagacttcgg                                               20

<210> SEQ ID NO 1024
<211> LENGTH: 20
<212> TYPE: DNA
<213> ORGANISM: Murine

<400> SEQUENCE: 1024
gggtttatgt gcaccaggta                                               20

<210> SEQ ID NO 1025
<211> LENGTH: 20
<212> TYPE: DNA
<213> ORGANISM: Human

<400> SEQUENCE: 1025
ttcccaggaa gtgagagttc                                               20

<210> SEQ ID NO 1026
<211> LENGTH: 20
<212> TYPE: DNA
<213> ORGANISM: Human

<400> SEQUENCE: 1026
cactcgcggg actcactttc                                               20

<210> SEQ ID NO 1027
<211> LENGTH: 20
<212> TYPE: DNA
<213> ORGANISM: Human

<400> SEQUENCE: 1027
atagaaacgc tcatctcccg                                               20

<210> SEQ ID NO 1028
<211> LENGTH: 20
<212> TYPE: DNA
<213> ORGANISM: Human

<400> SEQUENCE: 1028
ggatgctgtg atcatcctgg                                               20

<210> SEQ ID NO 1029
<211> LENGTH: 20
<212> TYPE: DNA
<213> ORGANISM: Human

<400> SEQUENCE: 1029
cctcaccagc caggataagg                                               20

<210> SEQ ID NO 1030
<211> LENGTH: 20
<212> TYPE: DNA
<213> ORGANISM: Human

<400> SEQUENCE: 1030
aatccagtag gaattgctgc                                               20
```

<210> SEQ ID NO 1031
<211> LENGTH: 20
<212> TYPE: DNA
<213> ORGANISM: Human

<400> SEQUENCE: 1031
tgacaagcat ggggaagccg                                              20

<210> SEQ ID NO 1032
<211> LENGTH: 20
<212> TYPE: DNA
<213> ORGANISM: Human

<400> SEQUENCE: 1032
tctcttcgcc tcctacctga                                              20

<210> SEQ ID NO 1033
<211> LENGTH: 20
<212> TYPE: DNA
<213> ORGANISM: Human

<400> SEQUENCE: 1033
acctgatgcc gactctgcag                                              20

<210> SEQ ID NO 1034
<211> LENGTH: 20
<212> TYPE: DNA
<213> ORGANISM: Human

<400> SEQUENCE: 1034
cagtcacggg ctttcagtgg                                              20

<210> SEQ ID NO 1035
<211> LENGTH: 20
<212> TYPE: DNA
<213> ORGANISM: Human

<400> SEQUENCE: 1035
cactcgcggg actcacttgc                                              20

<210> SEQ ID NO 1036
<211> LENGTH: 20
<212> TYPE: DNA
<213> ORGANISM: Human

<400> SEQUENCE: 1036
ccgtggaagg agccccaggg                                              20

<210> SEQ ID NO 1037
<211> LENGTH: 20
<212> TYPE: DNA
<213> ORGANISM: Human

<400> SEQUENCE: 1037
cataaattcc gaaatccagt                                              20

<210> SEQ ID NO 1038
<211> LENGTH: 20
<212> TYPE: DNA
<213> ORGANISM: Human

<400> SEQUENCE: 1038
cactcgcggg actcactttc                                              20

```
<210> SEQ ID NO 1039
<211> LENGTH: 20
<212> TYPE: DNA
<213> ORGANISM: Human

<400> SEQUENCE: 1039
gtggacggac tttataagat                                               20

<210> SEQ ID NO 1040
<211> LENGTH: 20
<212> TYPE: DNA
<213> ORGANISM: Human

<400> SEQUENCE: 1040
gatgaaggag ttgataactc                                               20

<210> SEQ ID NO 1041
<211> LENGTH: 20
<212> TYPE: DNA
<213> ORGANISM: Human

<400> SEQUENCE: 1041
cccatctaca tcgatctgcg                                               20

<210> SEQ ID NO 1042
<211> LENGTH: 20
<212> TYPE: DNA
<213> ORGANISM: Human

<400> SEQUENCE: 1042
gttgaggttc ttcagaagga                                               20

<210> SEQ ID NO 1043
<211> LENGTH: 20
<212> TYPE: DNA
<213> ORGANISM: Human

<400> SEQUENCE: 1043
gcacccaaag aactcagctt                                               20

<210> SEQ ID NO 1044
<211> LENGTH: 20
<212> TYPE: DNA
<213> ORGANISM: Human

<400> SEQUENCE: 1044
gaacagataa ctgtagccaa                                               20

<210> SEQ ID NO 1045
<211> LENGTH: 20
<212> TYPE: DNA
<213> ORGANISM: Murine

<400> SEQUENCE: 1045
cactttcctt tctcaggtgc                                               20

<210> SEQ ID NO 1046
<211> LENGTH: 20
<212> TYPE: DNA
<213> ORGANISM: Murine

<400> SEQUENCE: 1046
```
cagctacaac atggtcattc                                               20

<210> SEQ ID NO 1047
<211> LENGTH: 20
<212> TYPE: DNA
<213> ORGANISM: Murine

<400> SEQUENCE: 1047
cccgggccaa gtacttcatt                                               20

<210> SEQ ID NO 1048
<211> LENGTH: 20
<212> TYPE: DNA
<213> ORGANISM: Murine

<400> SEQUENCE: 1048
gaatgtagtc cactctgaac                                               20

<210> SEQ ID NO 1049
<211> LENGTH: 20
<212> TYPE: DNA
<213> ORGANISM: Murine

<400> SEQUENCE: 1049
gaccgtacca tcctcaggag                                               20

<210> SEQ ID NO 1050
<211> LENGTH: 20
<212> TYPE: DNA
<213> ORGANISM: Murine

<400> SEQUENCE: 1050
gtggtgtagc gagcgaactc                                               20

<210> SEQ ID NO 1051
<211> LENGTH: 20
<212> TYPE: DNA
<213> ORGANISM: Murine

<400> SEQUENCE: 1051
tgaagcactg gatccacttg                                               20

<210> SEQ ID NO 1052
<211> LENGTH: 20
<212> TYPE: DNA
<213> ORGANISM: Murine

<400> SEQUENCE: 1052
tgaggatcct gcatgttaat                                               20

<210> SEQ ID NO 1053
<211> LENGTH: 20
<212> TYPE: DNA
<213> ORGANISM: Human

<400> SEQUENCE: 1053
cattaaaccc attaacatgc                                               20

<210> SEQ ID NO 1054
<211> LENGTH: 20
<212> TYPE: DNA
<213> ORGANISM: Human

<400> SEQUENCE: 1054
gggcaccagg ttgctcatgg 20

<210> SEQ ID NO 1055
<211> LENGTH: 20
<212> TYPE: DNA
<213> ORGANISM: Human

<400> SEQUENCE: 1055
actgggcaca gtcaatcagc 20

<210> SEQ ID NO 1056
<211> LENGTH: 20
<212> TYPE: DNA
<213> ORGANISM: Human

<400> SEQUENCE: 1056
ggaatctgac cacgagcacg 20

<210> SEQ ID NO 1057
<211> LENGTH: 20
<212> TYPE: DNA
<213> ORGANISM: Human

<400> SEQUENCE: 1057
tgcctaagag gatggatcgg 20

<210> SEQ ID NO 1058
<211> LENGTH: 20
<212> TYPE: DNA
<213> ORGANISM: Human

<400> SEQUENCE: 1058
cgcccgtgcc cagcagcgcg 20

<210> SEQ ID NO 1059
<211> LENGTH: 20
<212> TYPE: DNA
<213> ORGANISM: Human

<400> SEQUENCE: 1059
gaaggacaag caggtctacc 20

<210> SEQ ID NO 1060
<211> LENGTH: 20
<212> TYPE: DNA
<213> ORGANISM: Human

<400> SEQUENCE: 1060
ggaccagcgc aacgaggaga 20

<210> SEQ ID NO 1061
<211> LENGTH: 20
<212> TYPE: DNA
<213> ORGANISM: Human

<400> SEQUENCE: 1061
cgaggagaag gcgcagcgtg 20

<210> SEQ ID NO 1062
<211> LENGTH: 20
<212> TYPE: DNA
<213> ORGANISM: Human

<400> SEQUENCE: 1062
ggagagccag aggagcgcgg                                           20

<210> SEQ ID NO 1063
<211> LENGTH: 20
<212> TYPE: DNA
<213> ORGANISM: Human

<400> SEQUENCE: 1063
actgttcccg aggcagccca                                           20

<210> SEQ ID NO 1064
<211> LENGTH: 20
<212> TYPE: DNA
<213> ORGANISM: Human

<400> SEQUENCE: 1064
gcaggagagc cagaggagcg                                           20

<210> SEQ ID NO 1065
<211> LENGTH: 20
<212> TYPE: DNA
<213> ORGANISM: Human

<400> SEQUENCE: 1065
gtcctctccc tcccagccat                                           20

<210> SEQ ID NO 1066
<211> LENGTH: 20
<212> TYPE: DNA
<213> ORGANISM: Human

<400> SEQUENCE: 1066
tccccagggt cccgccaaga                                           20

<210> SEQ ID NO 1067
<211> LENGTH: 20
<212> TYPE: DNA
<213> ORGANISM: Human

<400> SEQUENCE: 1067
agtgagcagt gcagcctgga                                           20

<210> SEQ ID NO 1068
<211> LENGTH: 20
<212> TYPE: DNA
<213> ORGANISM: Human

<400> SEQUENCE: 1068
tgtcctctcc ctcccagcca                                           20

<210> SEQ ID NO 1069
<211> LENGTH: 20
<212> TYPE: DNA
<213> ORGANISM: Human

<400> SEQUENCE: 1069
ctggactggg atgaaggtga                                           20

<210> SEQ ID NO 1070
<211> LENGTH: 20
<212> TYPE: DNA
<213> ORGANISM: Human

```
<400> SEQUENCE: 1070
ggggtgggcc cggctcacca                                              20

<210> SEQ ID NO 1071
<211> LENGTH: 20
<212> TYPE: DNA
<213> ORGANISM: Human

<400> SEQUENCE: 1071
caccaccccg cgggactaga                                              20

<210> SEQ ID NO 1072
<211> LENGTH: 20
<212> TYPE: DNA
<213> ORGANISM: Human

<400> SEQUENCE: 1072
ctgctgccac tgccccgct                                               20

<210> SEQ ID NO 1073
<211> LENGTH: 20
<212> TYPE: DNA
<213> ORGANISM: Human

<400> SEQUENCE: 1073
cggcccgacg tgcccatcac                                              20

<210> SEQ ID NO 1074
<211> LENGTH: 20
<212> TYPE: DNA
<213> ORGANISM: Human

<400> SEQUENCE: 1074
cactgccccc gctaggtgcg                                              20

<210> SEQ ID NO 1075
<211> LENGTH: 20
<212> TYPE: DNA
<213> ORGANISM: Human

<400> SEQUENCE: 1075
atacacgctg gcctgctcct                                              20

<210> SEQ ID NO 1076
<211> LENGTH: 20
<212> TYPE: DNA
<213> ORGANISM: Human

<400> SEQUENCE: 1076
caaacactgt gatgtctgtg                                              20

<210> SEQ ID NO 1077
<211> LENGTH: 20
<212> TYPE: DNA
<213> ORGANISM: Human

<400> SEQUENCE: 1077
gcgggaccct ggggatgcct                                              20

<210> SEQ ID NO 1078
<211> LENGTH: 20
<212> TYPE: DNA
```

```
<213> ORGANISM: Human

<400> SEQUENCE: 1078
gcgggagcgc cagacctcac                                           20

<210> SEQ ID NO 1079
<211> LENGTH: 20
<212> TYPE: DNA
<213> ORGANISM: Human

<400> SEQUENCE: 1079
aggacaggct tctctccaca                                           20

<210> SEQ ID NO 1080
<211> LENGTH: 20
<212> TYPE: DNA
<213> ORGANISM: Human

<400> SEQUENCE: 1080
gcagacacca acacggtgct                                           20

<210> SEQ ID NO 1081
<211> LENGTH: 20
<212> TYPE: DNA
<213> ORGANISM: Human

<400> SEQUENCE: 1081
ccaccacccc gcgggactag                                           20

<210> SEQ ID NO 1082
<211> LENGTH: 20
<212> TYPE: DNA
<213> ORGANISM: Human

<400> SEQUENCE: 1082
atccccaggg tcccgccaag                                           20

<210> SEQ ID NO 1083
<211> LENGTH: 20
<212> TYPE: DNA
<213> ORGANISM: Human

<400> SEQUENCE: 1083
cctggaggaa ggagcagcct                                           20

<210> SEQ ID NO 1084
<211> LENGTH: 20
<212> TYPE: DNA
<213> ORGANISM: Human

<400> SEQUENCE: 1084
agagccagat gtcggaactt                                           20

<210> SEQ ID NO 1085
<211> LENGTH: 20
<212> TYPE: DNA
<213> ORGANISM: Human

<400> SEQUENCE: 1085
atgacccact gggccggcac                                           20

<210> SEQ ID NO 1086
<211> LENGTH: 20
```

```
<212> TYPE: DNA
<213> ORGANISM: Human

<400> SEQUENCE: 1086
gcagctttgg gcccacagac                                          20

<210> SEQ ID NO 1087
<211> LENGTH: 20
<212> TYPE: DNA
<213> ORGANISM: Human

<400> SEQUENCE: 1087
actctctgtt agcagagagc                                          20

<210> SEQ ID NO 1088
<211> LENGTH: 20
<212> TYPE: DNA
<213> ORGANISM: Human

<400> SEQUENCE: 1088
ccaggaagga aatgcaccta                                          20

<210> SEQ ID NO 1089
<211> LENGTH: 20
<212> TYPE: DNA
<213> ORGANISM: Human

<400> SEQUENCE: 1089
aggcaccact cacctgtgat                                          20

<210> SEQ ID NO 1090
<211> LENGTH: 20
<212> TYPE: DNA
<213> ORGANISM: Human

<400> SEQUENCE: 1090
ctgggcccgt gccggcccag                                          20

<210> SEQ ID NO 1091
<211> LENGTH: 20
<212> TYPE: DNA
<213> ORGANISM: Human

<400> SEQUENCE: 1091
cagccagctg ctggggtcc                                           20

<210> SEQ ID NO 1092
<211> LENGTH: 20
<212> TYPE: DNA
<213> ORGANISM: Human

<400> SEQUENCE: 1092
tccactcctg ccgctcgcct                                          20

<210> SEQ ID NO 1093
<211> LENGTH: 20
<212> TYPE: DNA
<213> ORGANISM: Human

<400> SEQUENCE: 1093
cgtccaggca gacaccaaca                                          20

<210> SEQ ID NO 1094
```

```
<211> LENGTH: 20
<212> TYPE: DNA
<213> ORGANISM: Human

<400> SEQUENCE: 1094
cccacccaca tcagtccttc                                              20

<210> SEQ ID NO 1095
<211> LENGTH: 20
<212> TYPE: DNA
<213> ORGANISM: Human

<400> SEQUENCE: 1095
gccagctctt gacccggcct                                              20

<210> SEQ ID NO 1096
<211> LENGTH: 20
<212> TYPE: DNA
<213> ORGANISM: Human

<400> SEQUENCE: 1096
ctgccctcct tttcctcttc                                              20

<210> SEQ ID NO 1097
<211> LENGTH: 20
<212> TYPE: DNA
<213> ORGANISM: Human

<400> SEQUENCE: 1097
ccagccccac catgagtctg                                              20

<210> SEQ ID NO 1098
<211> LENGTH: 20
<212> TYPE: DNA
<213> ORGANISM: Human

<400> SEQUENCE: 1098
gccgattctt ccacccagag                                              20

<210> SEQ ID NO 1099
<211> LENGTH: 20
<212> TYPE: DNA
<213> ORGANISM: Human

<400> SEQUENCE: 1099
ctcccagaag aggaaaagga                                              20

<210> SEQ ID NO 1100
<211> LENGTH: 20
<212> TYPE: DNA
<213> ORGANISM: Human

<400> SEQUENCE: 1100
gtggggcagg gcaggcagcc                                              20

<210> SEQ ID NO 1101
<211> LENGTH: 20
<212> TYPE: DNA
<213> ORGANISM: Human

<400> SEQUENCE: 1101
gggtcaagag ctggccgctg                                              20
```

```
<210> SEQ ID NO 1102
<211> LENGTH: 20
<212> TYPE: DNA
<213> ORGANISM: Human

<400> SEQUENCE: 1102 atgcccctg atgacccact                                                  20

<210> SEQ ID NO 1103
<211> LENGTH: 20
<212> TYPE: DNA
<213> ORGANISM: Human

<400> SEQUENCE: 1103
agccttctct gcctttggcc                                                 20

<210> SEQ ID NO 1104
<211> LENGTH: 20
<212> TYPE: DNA
<213> ORGANISM: Human

<400> SEQUENCE: 1104
ctctgccttt ggccgggcca                                                 20

<210> SEQ ID NO 1105
<211> LENGTH: 20
<212> TYPE: DNA
<213> ORGANISM: Human

<400> SEQUENCE: 1105
ggaacccagc ctgccctccc                                                 20

<210> SEQ ID NO 1106
<211> LENGTH: 20
<212> TYPE: DNA
<213> ORGANISM: Human

<400> SEQUENCE: 1106
ggcaggagcc tcgcacctag                                                 20

<210> SEQ ID NO 1107
<211> LENGTH: 20
<212> TYPE: DNA
<213> ORGANISM: Human

<400> SEQUENCE: 1107
tcccagacca gcacatcctg                                                 20

<210> SEQ ID NO 1108
<211> LENGTH: 20
<212> TYPE: DNA
<213> ORGANISM: Human

<400> SEQUENCE: 1108
gtgagcagtg cagcctggat                                                 20

<210> SEQ ID NO 1109
<211> LENGTH: 20
<212> TYPE: DNA
<213> ORGANISM: Human

<400> SEQUENCE: 1109
gagccagatg tcggaacttt                                                 20
```

```
<210> SEQ ID NO 1110
<211> LENGTH: 20
<212> TYPE: DNA
<213> ORGANISM: Human

<400> SEQUENCE: 1110
ggccgatggc aagccttgct                                               20

<210> SEQ ID NO 1111
<211> LENGTH: 20
<212> TYPE: DNA
<213> ORGANISM: Human

<400> SEQUENCE: 1111
aggagcctcg cacctagcgg                                               20

<210> SEQ ID NO 1112
<211> LENGTH: 20
<212> TYPE: DNA
<213> ORGANISM: Human

<400> SEQUENCE: 1112
aggtccccaa gaggaaaaca                                               20

<210> SEQ ID NO 1113
<211> LENGTH: 20
<212> TYPE: DNA
<213> ORGANISM: Human

<400> SEQUENCE: 1113
cgctgaggag gcctcggccc                                               20

<210> SEQ ID NO 1114
<211> LENGTH: 20
<212> TYPE: DNA
<213> ORGANISM: Human

<400> SEQUENCE: 1114
gaggacagcc acagccgtca                                               20

<210> SEQ ID NO 1115
<211> LENGTH: 20
<212> TYPE: DNA
<213> ORGANISM: Human

<400> SEQUENCE: 1115
cagccccacc atgagtctgt                                               20

<210> SEQ ID NO 1116
<211> LENGTH: 20
<212> TYPE: DNA
<213> ORGANISM: Human

<400> SEQUENCE: 1116 acccccccaga gccccaagca                                              20

<210> SEQ ID NO 1117
<211> LENGTH: 20
<212> TYPE: DNA
<213> ORGANISM: Human

<400> SEQUENCE: 1117
gaggcaccac tcacctgtga                                               20
```

<210> SEQ ID NO 1118
<211> LENGTH: 20
<212> TYPE: DNA
<213> ORGANISM: Human

<400> SEQUENCE: 1118
ccaagaggaa aacagggcac                                           20

<210> SEQ ID NO 1119
<211> LENGTH: 20
<212> TYPE: DNA
<213> ORGANISM: Human

<400> SEQUENCE: 1119
gtacgtctcc caggattgcc                                           20

<210> SEQ ID NO 1120
<211> LENGTH: 20
<212> TYPE: DNA
<213> ORGANISM: Human

<400> SEQUENCE: 1120
cacagcctcc accaggtgcg                                           20

<210> SEQ ID NO 1121
<211> LENGTH: 20
<212> TYPE: DNA
<213> ORGANISM: Human

<400> SEQUENCE: 1121
gatctcggca gccagctgct                                           20

<210> SEQ ID NO 1122
<211> LENGTH: 20
<212> TYPE: DNA
<213> ORGANISM: Human

<400> SEQUENCE: 1122
cagccttctc tgcctttggc                                           20

<210> SEQ ID NO 1123
<211> LENGTH: 20
<212> TYPE: DNA
<213> ORGANISM: Human

<400> SEQUENCE: 1123
cagaagtgac acttacctca                                           20

<210> SEQ ID NO 1124
<211> LENGTH: 20
<212> TYPE: DNA
<213> ORGANISM: Human

<400> SEQUENCE: 1124
gctggccgct gaggaggcct                                           20

<210> SEQ ID NO 1125
<211> LENGTH: 20
<212> TYPE: DNA
<213> ORGANISM: Human

<400> SEQUENCE: 1125

```
cagctccctc tagtcccgcg                                          20

<210> SEQ ID NO 1126
<211> LENGTH: 20
<212> TYPE: DNA
<213> ORGANISM: Human

<400> SEQUENCE: 1126
cggggtgggc ccggctcacc                                          20

<210> SEQ ID NO 1127
<211> LENGTH: 20
<212> TYPE: DNA
<213> ORGANISM: Human

<400> SEQUENCE: 1127
gacacatacc gtgacctcca                                          20

<210> SEQ ID NO 1128
<211> LENGTH: 20
<212> TYPE: DNA
<213> ORGANISM: Human

<400> SEQUENCE: 1128
caggaaggaa atgcacctat                                          20

<210> SEQ ID NO 1129
<211> LENGTH: 20
<212> TYPE: DNA
<213> ORGANISM: Human

<400> SEQUENCE: 1129
agtggccagc acccatggcc                                          20

<210> SEQ ID NO 1130
<211> LENGTH: 20
<212> TYPE: DNA
<213> ORGANISM: Human

<400> SEQUENCE: 1130
ctctcctatt cttcccagca                                          20

<210> SEQ ID NO 1131
<211> LENGTH: 20
<212> TYPE: DNA
<213> ORGANISM: Human

<400> SEQUENCE: 1131
gcccgagtcc aggcaatcct                                          20

<210> SEQ ID NO 1132
<211> LENGTH: 20
<212> TYPE: DNA
<213> ORGANISM: Human

<400> SEQUENCE: 1132
caccttcatc tgcagttcca                                          20

<210> SEQ ID NO 1133
<211> LENGTH: 20
<212> TYPE: DNA
<213> ORGANISM: Human

<400> SEQUENCE: 1133
```
ggcacaggca gacaggtgag 20

<210> SEQ ID NO 1134
<211> LENGTH: 20
<212> TYPE: DNA
<213> ORGANISM: Human

<400> SEQUENCE: 1134
agcacccatg gcccggccaa 20

<210> SEQ ID NO 1135
<211> LENGTH: 20
<212> TYPE: DNA
<213> ORGANISM: Human

<400> SEQUENCE: 1135
ccacaggcag cttactcact 20

<210> SEQ ID NO 1136
<211> LENGTH: 20
<212> TYPE: DNA
<213> ORGANISM: Human

<400> SEQUENCE: 1136
ttcctgtgct ccaaagtgag 20

<210> SEQ ID NO 1137
<211> LENGTH: 20
<212> TYPE: DNA
<213> ORGANISM: Human

<400> SEQUENCE: 1137
accgcagcct tctctgcctt 20

<210> SEQ ID NO 1138
<211> LENGTH: 20
<212> TYPE: DNA
<213> ORGANISM: Human

<400> SEQUENCE: 1138
gggagccaat gcccgagtcc 20

<210> SEQ ID NO 1139
<211> LENGTH: 20
<212> TYPE: DNA
<213> ORGANISM: Human

<400> SEQUENCE: 1139
ttcccagcaa ggcttgccat 20

<210> SEQ ID NO 1140
<211> LENGTH: 20
<212> TYPE: DNA
<213> ORGANISM: Human

<400> SEQUENCE: 1140
agccagatgt cggaactttg 20

<210> SEQ ID NO 1141
<211> LENGTH: 20
<212> TYPE: DNA
<213> ORGANISM: Human

```
<400> SEQUENCE: 1141
tacacgggct acagtccta                                                    20

<210> SEQ ID NO 1142
<211> LENGTH: 20
<212> TYPE: DNA
<213> ORGANISM: Human

<400> SEQUENCE: 1142
tctgtgttag accctcttgg                                                   20

<210> SEQ ID NO 1143
<211> LENGTH: 20
<212> TYPE: DNA
<213> ORGANISM: Human

<400> SEQUENCE: 1143
aagctgcccc cagcgctctg                                                   20

<210> SEQ ID NO 1144
<211> LENGTH: 20
<212> TYPE: DNA
<213> ORGANISM: Human

<400> SEQUENCE: 1144
ctttgggggg ttcgaggagg                                                   20

<210> SEQ ID NO 1145
<211> LENGTH: 20
<212> TYPE: DNA
<213> ORGANISM: Human

<400> SEQUENCE: 1145
gggccgatgg caagccttgc                                                   20

<210> SEQ ID NO 1146
<211> LENGTH: 20
<212> TYPE: DNA
<213> ORGANISM: Human

<400> SEQUENCE: 1146
cacaggcagc ttactcactg                                                   20

<210> SEQ ID NO 1147
<211> LENGTH: 20
<212> TYPE: DNA
<213> ORGANISM: Human

<400> SEQUENCE: 1147
cccagaccag cacatcctgc                                                   20

<210> SEQ ID NO 1148
<211> LENGTH: 20
<212> TYPE: DNA
<213> ORGANISM: Human

<400> SEQUENCE: 1148
aggctgggtt ccataccata                                                   20

<210> SEQ ID NO 1149
<211> LENGTH: 20
<212> TYPE: DNA
<213> ORGANISM: Human
```

```
<400> SEQUENCE: 1149
ggacttctaa ttgctgagaa                                        20

<210> SEQ ID NO 1150
<211> LENGTH: 20
<212> TYPE: DNA
<213> ORGANISM: Human

<400> SEQUENCE: 1150
ctcaaattcc cacagactca                                        20

<210> SEQ ID NO 1151
<211> LENGTH: 20
<212> TYPE: DNA
<213> ORGANISM: Human

<400> SEQUENCE: 1151
aaaacagggc acaggcagac                                        20

<210> SEQ ID NO 1152
<211> LENGTH: 20
<212> TYPE: DNA
<213> ORGANISM: Human

<400> SEQUENCE: 1152
ccagatgtcg gaactttggg                                        20

<210> SEQ ID NO 1153
<211> LENGTH: 20
<212> TYPE: DNA
<213> ORGANISM: Human

<400> SEQUENCE: 1153
ctccctctag tcccgcgggg                                        20

<210> SEQ ID NO 1154
<211> LENGTH: 20
<212> TYPE: DNA
<213> ORGANISM: Human

<400> SEQUENCE: 1154
agcccccagt gcagagccca                                        20

<210> SEQ ID NO 1155
<211> LENGTH: 20
<212> TYPE: DNA
<213> ORGANISM: Human

<400> SEQUENCE: 1155
cctggacgcc cagcttctgc                                        20

<210> SEQ ID NO 1156
<211> LENGTH: 20
<212> TYPE: DNA
<213> ORGANISM: Human

<400> SEQUENCE: 1156 cagggggctgg caggagcccg                                       20

<210> SEQ ID NO 1157
<211> LENGTH: 20
<212> TYPE: DNA
```

```
<213> ORGANISM: Human

<400> SEQUENCE: 1157
ccttgttccc atggctggga                                                  20

<210> SEQ ID NO 1158
<211> LENGTH: 20
<212> TYPE: DNA
<213> ORGANISM: Human

<400> SEQUENCE: 1158
ctcatctgcc acagagcgct                                                  20

<210> SEQ ID NO 1159
<211> LENGTH: 20
<212> TYPE: DNA
<213> ORGANISM: Human

<400> SEQUENCE: 1159
ggcagacacc aacacggtgc                                                  20

<210> SEQ ID NO 1160
<211> LENGTH: 20
<212> TYPE: DNA
<213> ORGANISM: Human

<400> SEQUENCE: 1160
tccctcttga ttcctcttcc                                                  20

<210> SEQ ID NO 1161
<211> LENGTH: 20
<212> TYPE: DNA
<213> ORGANISM: Human

<400> SEQUENCE: 1161
ccctcccagc catgggaaca                                                  20

<210> SEQ ID NO 1162
<211> LENGTH: 20
<212> TYPE: DNA
<213> ORGANISM: Human

<400> SEQUENCE: 1162
gcgtaagaag ccactcactt                                                  20

<210> SEQ ID NO 1163
<211> LENGTH: 20
<212> TYPE: DNA
<213> ORGANISM: Human

<400> SEQUENCE: 1163
tgtgtttccc ccgcacctgg                                                  20

<210> SEQ ID NO 1164
<211> LENGTH: 20
<212> TYPE: DNA
<213> ORGANISM: Human

<400> SEQUENCE: 1164
ctgagaccag tggtcatcga                                                  20

<210> SEQ ID NO 1165
<211> LENGTH: 20
```

```
<212> TYPE: DNA
<213> ORGANISM: Human

<400> SEQUENCE: 1165
gggcagcgac ctgagaccag                                          20

<210> SEQ ID NO 1166
<211> LENGTH: 20
<212> TYPE: DNA
<213> ORGANISM: Human

<400> SEQUENCE: 1166
agcaattaga agtccctgca                                          20

<210> SEQ ID NO 1167
<211> LENGTH: 20
<212> TYPE: DNA
<213> ORGANISM: Human

<400> SEQUENCE: 1167
tgggtgagct ggtgaaacac                                          20

<210> SEQ ID NO 1168
<211> LENGTH: 20
<212> TYPE: DNA
<213> ORGANISM: Human

<400> SEQUENCE: 1168
ctgttagcag agagctggac                                          20

<210> SEQ ID NO 1169
<211> LENGTH: 20
<212> TYPE: DNA
<213> ORGANISM: Human

<400> SEQUENCE: 1169
cccctgatga cccactgggc                                          20

<210> SEQ ID NO 1170
<211> LENGTH: 20
<212> TYPE: DNA
<213> ORGANISM: Human

<400> SEQUENCE: 1170
gttcacacca tcacgacgcg                                          20

<210> SEQ ID NO 1171
<211> LENGTH: 20
<212> TYPE: DNA
<213> ORGANISM: Human

<400> SEQUENCE: 1171
tgtccaggct gggcccgtgc                                          20

<210> SEQ ID NO 1172
<211> LENGTH: 20
<212> TYPE: DNA
<213> ORGANISM: Human

<400> SEQUENCE: 1172
acacagacct atgccccatc                                          20

<210> SEQ ID NO 1173
```

-continued

```
<211> LENGTH: 20
<212> TYPE: DNA
<213> ORGANISM: Human

<400> SEQUENCE: 1173
ggctgcctgc cctgccccac                                              20

<210> SEQ ID NO 1174
<211> LENGTH: 20
<212> TYPE: DNA
<213> ORGANISM: Human

<400> SEQUENCE: 1174
ccataggtgc atttccttcc                                              20

<210> SEQ ID NO 1175
<211> LENGTH: 20
<212> TYPE: DNA
<213> ORGANISM: Human

<400> SEQUENCE: 1175
caggctgggt tccataccat                                              20

<210> SEQ ID NO 1176
<211> LENGTH: 20
<212> TYPE: DNA
<213> ORGANISM: Human

<400> SEQUENCE: 1176
gccccatcac agcctccacc                                              20

<210> SEQ ID NO 1177
<211> LENGTH: 20
<212> TYPE: DNA
<213> ORGANISM: Human

<400> SEQUENCE: 1177
tgccctcctt ttcctcttct                                              20

<210> SEQ ID NO 1178
<211> LENGTH: 20
<212> TYPE: DNA
<213> ORGANISM: Human

<400> SEQUENCE: 1178
gccagatgtc ggaactttgg                                              20

<210> SEQ ID NO 1179
<211> LENGTH: 20
<212> TYPE: DNA
<213> ORGANISM: Human

<400> SEQUENCE: 1179
caggcagaca ggtgagagga                                              20

<210> SEQ ID NO 1180
<211> LENGTH: 20
<212> TYPE: DNA
<213> ORGANISM: Human

<400> SEQUENCE: 1180
ccaggagtct gagctatgag                                              20
```

```
<210> SEQ ID NO 1181
<211> LENGTH: 20
<212> TYPE: DNA
<213> ORGANISM: Human

<400> SEQUENCE: 1181
gctccaggtt gggagcctta                                              20

<210> SEQ ID NO 1182
<211> LENGTH: 20
<212> TYPE: DNA
<213> ORGANISM: Human

<400> SEQUENCE: 1182
ctcacctgtg atgggcacgt                                              20

<210> SEQ ID NO 1183
<211> LENGTH: 20
<212> TYPE: DNA
<213> ORGANISM: Human

<400> SEQUENCE: 1183
agctggccta cgagtctgac                                              20

<210> SEQ ID NO 1184
<211> LENGTH: 20
<212> TYPE: DNA
<213> ORGANISM: Human

<400> SEQUENCE: 1184
gtgggtgggg gcagtgggta                                              20

<210> SEQ ID NO 1185
<211> LENGTH: 20
<212> TYPE: DNA
<213> ORGANISM: Human

<400> SEQUENCE: 1185
catctgcagt tccagggccg                                              20

<210> SEQ ID NO 1186
<211> LENGTH: 20
<212> TYPE: DNA
<213> ORGANISM: Human

<400> SEQUENCE: 1186
gatgacccac tgggccggca                                              20

<210> SEQ ID NO 1187
<211> LENGTH: 20
<212> TYPE: DNA
<213> ORGANISM: Human

<400> SEQUENCE: 1187
tgacctccaa ggcgagcggc                                              20

<210> SEQ ID NO 1188
<211> LENGTH: 20
<212> TYPE: DNA
<213> ORGANISM: Human

<400> SEQUENCE: 1188
ggatctcggc agccagctgc                                              20
```

```
<210> SEQ ID NO 1189
<211> LENGTH: 20
<212> TYPE: DNA
<213> ORGANISM: Human

<400> SEQUENCE: 1189
tccttttcct cttctgggag                                               20

<210> SEQ ID NO 1190
<211> LENGTH: 20
<212> TYPE: DNA
<213> ORGANISM: Human

<400> SEQUENCE: 1190
cacgacgcgt gggtggcaag                                               20

<210> SEQ ID NO 1191
<211> LENGTH: 20
<212> TYPE: DNA
<213> ORGANISM: Human

<400> SEQUENCE: 1191
ttcacaccat cacgacgcgt                                               20

<210> SEQ ID NO 1192
<211> LENGTH: 20
<212> TYPE: DNA
<213> ORGANISM: Human

<400> SEQUENCE: 1192
gcaggagcct cgcacctagc                                               20

<210> SEQ ID NO 1193
<211> LENGTH: 20
<212> TYPE: DNA
<213> ORGANISM: Human

<400> SEQUENCE: 1193 caccccctaag gctcccaacc                                              20

<210> SEQ ID NO 1194
<211> LENGTH: 20
<212> TYPE: DNA
<213> ORGANISM: Human

<400> SEQUENCE: 1194
ttgtccttgc ttggggctct                                               20

<210> SEQ ID NO 1195
<211> LENGTH: 20
<212> TYPE: DNA
<213> ORGANISM: Human

<400> SEQUENCE: 1195
caggacaggc ttctctccac                                               20

<210> SEQ ID NO 1196
<211> LENGTH: 20
<212> TYPE: DNA
<213> ORGANISM: Human

<400> SEQUENCE: 1196
cacctggtgg aggctgtgat                                               20
```

<210> SEQ ID NO 1197
<211> LENGTH: 20
<212> TYPE: DNA
<213> ORGANISM: Human

<400> SEQUENCE: 1197
cgtctgtggg agccagtctg                                                  20

<210> SEQ ID NO 1198
<211> LENGTH: 20
<212> TYPE: DNA
<213> ORGANISM: Human

<400> SEQUENCE: 1198 cccccccaaag ttccgacatc                                                 20

<210> SEQ ID NO 1199
<211> LENGTH: 20
<212> TYPE: DNA
<213> ORGANISM: Human

<400> SEQUENCE: 1199
aggcagcctg gccaaggagc                                                  20

<210> SEQ ID NO 1200
<211> LENGTH: 20
<212> TYPE: DNA
<213> ORGANISM: Human

<400> SEQUENCE: 1200
tctgcctttg gccgggccat                                                  20

<210> SEQ ID NO 1201
<211> LENGTH: 20
<212> TYPE: DNA
<213> ORGANISM: Human

<400> SEQUENCE: 1201
ggacaggctt ctctccacag                                                  20

<210> SEQ ID NO 1202
<211> LENGTH: 20
<212> TYPE: DNA
<213> ORGANISM: Human

<400> SEQUENCE: 1202
acgtgcccat cacaggtgag                                                  20

<210> SEQ ID NO 1203
<211> LENGTH: 20
<212> TYPE: DNA
<213> ORGANISM: Human

<400> SEQUENCE: 1203
agagagtgag cagtgcagcc                                                  20

<210> SEQ ID NO 1204
<211> LENGTH: 20
<212> TYPE: DNA
<213> ORGANISM: Human

<400> SEQUENCE: 1204

| | |
|---|---|
| cgcaggaagt tgtccaggct | 20 |

<210> SEQ ID NO 1205
<211> LENGTH: 20
<212> TYPE: DNA
<213> ORGANISM: Human

<400> SEQUENCE: 1205

| | |
|---|---|
| ggctgggagc tcagatccat | 20 |

<210> SEQ ID NO 1206
<211> LENGTH: 20
<212> TYPE: DNA
<213> ORGANISM: Human

<400> SEQUENCE: 1206

| | |
|---|---|
| cagctcaccc agcaccgtgt | 20 |

<210> SEQ ID NO 1207
<211> LENGTH: 20
<212> TYPE: DNA
<213> ORGANISM: Human

<400> SEQUENCE: 1207

| | |
|---|---|
| ccagcacatc ctgcgggaac | 20 |

<210> SEQ ID NO 1208
<211> LENGTH: 20
<212> TYPE: DNA
<213> ORGANISM: Human

<400> SEQUENCE: 1208

| | |
|---|---|
| gacctccttg ttcccatggc | 20 |

<210> SEQ ID NO 1209
<211> LENGTH: 20
<212> TYPE: DNA
<213> ORGANISM: Human

<400> SEQUENCE: 1209

| | |
|---|---|
| ggggttcgag gaggaggccc | 20 |

<210> SEQ ID NO 1210
<211> LENGTH: 20
<212> TYPE: DNA
<213> ORGANISM: Human

<400> SEQUENCE: 1210

| | |
|---|---|
| cagagaaggc tgcggtggct | 20 |

<210> SEQ ID NO 1211
<211> LENGTH: 20
<212> TYPE: DNA
<213> ORGANISM: Human

<400> SEQUENCE: 1211

| | |
|---|---|
| gggagtgagt ccagcgtctg | 20 |

<210> SEQ ID NO 1212
<211> LENGTH: 20
<212> TYPE: DNA
<213> ORGANISM: Human

<400> SEQUENCE: 1212
caggagcctc gcacctagcg 20

<210> SEQ ID NO 1213
<211> LENGTH: 20
<212> TYPE: DNA
<213> ORGANISM: Human

<400> SEQUENCE: 1213
ggaggaggcc ctggtgagcc 20

<210> SEQ ID NO 1214
<211> LENGTH: 20
<212> TYPE: DNA
<213> ORGANISM: Human

<400> SEQUENCE: 1214
caagcaagga caaaaatggc 20

<210> SEQ ID NO 1215
<211> LENGTH: 20
<212> TYPE: DNA
<213> ORGANISM: Human

<400> SEQUENCE: 1215
cgtcagggca ccccaaggcc 20

<210> SEQ ID NO 1216
<211> LENGTH: 20
<212> TYPE: DNA
<213> ORGANISM: Human

<400> SEQUENCE: 1216
gctggcagtg aactggtttc 20

<210> SEQ ID NO 1217
<211> LENGTH: 20
<212> TYPE: DNA
<213> ORGANISM: Human

<400> SEQUENCE: 1217
acctccttgt tcccatggct 20

<210> SEQ ID NO 1218
<211> LENGTH: 20
<212> TYPE: DNA
<213> ORGANISM: Human

<400> SEQUENCE: 1218
tcccgcagga tgtgctggtc 20

<210> SEQ ID NO 1219
<211> LENGTH: 20
<212> TYPE: DNA
<213> ORGANISM: Human

<400> SEQUENCE: 1219
agggactgta gcccgtgtaa 20

<210> SEQ ID NO 1220
<211> LENGTH: 20
<212> TYPE: DNA
<213> ORGANISM: Human

-continued

<400> SEQUENCE: 1220
ccagtactct cgaggtggaa                                          20

<210> SEQ ID NO 1221
<211> LENGTH: 20
<212> TYPE: DNA
<213> ORGANISM: Human

<400> SEQUENCE: 1221
aattcccaca gactcatggt                                          20

<210> SEQ ID NO 1222
<211> LENGTH: 20
<212> TYPE: DNA
<213> ORGANISM: Human

<400> SEQUENCE: 1222
cccaccccga gccccttaca                                          20

<210> SEQ ID NO 1223
<211> LENGTH: 20
<212> TYPE: DNA
<213> ORGANISM: Human

<400> SEQUENCE: 1223
gtgcatttcc ttcctggaag                                          20

<210> SEQ ID NO 1224
<211> LENGTH: 20
<212> TYPE: DNA
<213> ORGANISM: Human

<400> SEQUENCE: 1224
tcagcggcca gctcttgacc                                          20

<210> SEQ ID NO 1225
<211> LENGTH: 20
<212> TYPE: DNA
<213> ORGANISM: Human

<400> SEQUENCE: 1225
ggcccggcca aaggcagaga                                          20

<210> SEQ ID NO 1226
<211> LENGTH: 20
<212> TYPE: DNA
<213> ORGANISM: Human

<400> SEQUENCE: 1226
acagagcgct gggggcagct                                          20

<210> SEQ ID NO 1227
<211> LENGTH: 20
<212> TYPE: DNA
<213> ORGANISM: Human

<400> SEQUENCE: 1227
tcttgattcc tcttccagga                                          20

<210> SEQ ID NO 1228
<211> LENGTH: 20
<212> TYPE: DNA
<213> ORGANISM: Human

<400> SEQUENCE: 1228
gcaaggacaa aaatggccgg                                            20

<210> SEQ ID NO 1229
<211> LENGTH: 20
<212> TYPE: DNA
<213> ORGANISM: Human

<400> SEQUENCE: 1229
cagggcaggc agcctggcca                                            20

<210> SEQ ID NO 1230
<211> LENGTH: 20
<212> TYPE: DNA
<213> ORGANISM: Human

<400> SEQUENCE: 1230
atctcggcag ccagctgctg                                            20

<210> SEQ ID NO 1231
<211> LENGTH: 20
<212> TYPE: DNA
<213> ORGANISM: Human

<400> SEQUENCE: 1231
cccgcaggat gtgctggtct                                            20

<210> SEQ ID NO 1232
<211> LENGTH: 20
<212> TYPE: DNA
<213> ORGANISM: Human

<400> SEQUENCE: 1232
ggctccaggt tgggagcctt                                            20

<210> SEQ ID NO 1233
<211> LENGTH: 20
<212> TYPE: DNA
<213> ORGANISM: Human

<400> SEQUENCE: 1233
caacacggtg ctgggtgagc                                            20

<210> SEQ ID NO 1234
<211> LENGTH: 20
<212> TYPE: DNA
<213> ORGANISM: Human

<400> SEQUENCE: 1234
gcagccgtgt ccctatggta                                            20

<210> SEQ ID NO 1235
<211> LENGTH: 20
<212> TYPE: DNA
<213> ORGANISM: Human

<400> SEQUENCE: 1235
tgtccttgct tggggctctg                                            20

<210> SEQ ID NO 1236
<211> LENGTH: 20
<212> TYPE: DNA

```
<213> ORGANISM: Human

<400> SEQUENCE: 1236
tcatggtggg gctggcttcc                                              20

<210> SEQ ID NO 1237
<211> LENGTH: 20
<212> TYPE: DNA
<213> ORGANISM: Human

<400> SEQUENCE: 1237
gaagctgggc tattcatcca                                              20

<210> SEQ ID NO 1238
<211> LENGTH: 20
<212> TYPE: DNA
<213> ORGANISM: Human

<400> SEQUENCE: 1238
gaccctcttg gcgggaccct                                              20

<210> SEQ ID NO 1239
<211> LENGTH: 20
<212> TYPE: DNA
<213> ORGANISM: Human

<400> SEQUENCE: 1239
ggaaaggcag ggggcgcggg                                              20

<210> SEQ ID NO 1240
<211> LENGTH: 20
<212> TYPE: DNA
<213> ORGANISM: Human

<400> SEQUENCE: 1240
aggtctgtgt tagaccctct                                              20

<210> SEQ ID NO 1241
<211> LENGTH: 20
<212> TYPE: DNA
<213> ORGANISM: Human

<400> SEQUENCE: 1241
ctcagctccc tctagtcccg                                              20

<210> SEQ ID NO 1242
<211> LENGTH: 20
<212> TYPE: DNA
<213> ORGANISM: Human

<400> SEQUENCE: 1242
tagggactgt agcccgtgta                                              20

<210> SEQ ID NO 1243
<211> LENGTH: 20
<212> TYPE: DNA
<213> ORGANISM: Human

<400> SEQUENCE: 1243 aggggggcata aacctgcaga                                             20

<210> SEQ ID NO 1244
<211> LENGTH: 20
```

```
<212> TYPE: DNA
<213> ORGANISM: Human

<400> SEQUENCE: 1244
ctcccaggat tgcctggact                                               20

<210> SEQ ID NO 1245
<211> LENGTH: 20
<212> TYPE: DNA
<213> ORGANISM: Human

<400> SEQUENCE: 1245
gggatgaagg tgaaggccgc                                               20

<210> SEQ ID NO 1246
<211> LENGTH: 20
<212> TYPE: DNA
<213> ORGANISM: Human

<400> SEQUENCE: 1246
tgcagagccc aggggctggc                                               20

<210> SEQ ID NO 1247
<211> LENGTH: 20
<212> TYPE: DNA
<213> ORGANISM: Human

<400> SEQUENCE: 1247
gaatcggcac ttgatcccat                                               20

<210> SEQ ID NO 1248
<211> LENGTH: 20
<212> TYPE: DNA
<213> ORGANISM: Human

<400> SEQUENCE: 1248
ccgaggctgc tccttcctcc                                               20

<210> SEQ ID NO 1249
<211> LENGTH: 20
<212> TYPE: DNA
<213> ORGANISM: Human

<400> SEQUENCE: 1249
ccagcttctg caggacgctg                                               20

<210> SEQ ID NO 1250
<211> LENGTH: 20
<212> TYPE: DNA
<213> ORGANISM: Human

<400> SEQUENCE: 1250
gggccggcac gggcccagcc                                               20

<210> SEQ ID NO 1251
<211> LENGTH: 20
<212> TYPE: DNA
<213> ORGANISM: Human

<400> SEQUENCE: 1251
tgaggtctgg cgctcccgct                                               20

<210> SEQ ID NO 1252
```

-continued

```
<211> LENGTH: 20
<212> TYPE: DNA
<213> ORGANISM: Human

<400> SEQUENCE: 1252
ttggggtgcc ctgacggctg                                                 20

<210> SEQ ID NO 1253
<211> LENGTH: 20
<212> TYPE: DNA
<213> ORGANISM: Human

<400> SEQUENCE: 1253
actagaggga gctgagggca                                                 20

<210> SEQ ID NO 1254
<211> LENGTH: 20
<212> TYPE: DNA
<213> ORGANISM: Human

<400> SEQUENCE: 1254
ccagttcccg caggatgtgc                                                 20

<210> SEQ ID NO 1255
<211> LENGTH: 20
<212> TYPE: DNA
<213> ORGANISM: Human

<400> SEQUENCE: 1255
tatgccccct gatgacccac                                                 20

<210> SEQ ID NO 1256
<211> LENGTH: 20
<212> TYPE: DNA
<213> ORGANISM: Human

<400> SEQUENCE: 1256
gtgagaggag agcattggca                                                 20

<210> SEQ ID NO 1257
<211> LENGTH: 20
<212> TYPE: DNA
<213> ORGANISM: Human

<400> SEQUENCE: 1257
agcttactca ctggggtgct                                                 20

<210> SEQ ID NO 1258
<211> LENGTH: 20
<212> TYPE: DNA
<213> ORGANISM: Human

<400> SEQUENCE: 1258
atcacagcct ccaccaggtg                                                 20

<210> SEQ ID NO 1259
<211> LENGTH: 20
<212> TYPE: DNA
<213> ORGANISM: Human

<400> SEQUENCE: 1259
actgaagtgg ccagcaccca                                                 20
```

```
<210> SEQ ID NO 1260
<211> LENGTH: 20
<212> TYPE: DNA
<213> ORGANISM: Human

<400> SEQUENCE: 1260
gccggcccag tgggtcatca                                                    20

<210> SEQ ID NO 1261
<211> LENGTH: 20
<212> TYPE: DNA
<213> ORGANISM: Human

<400> SEQUENCE: 1261
cctgcagaag ctgggcgtcc                                                    20

<210> SEQ ID NO 1262
<211> LENGTH: 20
<212> TYPE: DNA
<213> ORGANISM: Human

<400> SEQUENCE: 1262
gcaccgtgtt ggtgtctgcc                                                    20

<210> SEQ ID NO 1263
<211> LENGTH: 20
<212> TYPE: DNA
<213> ORGANISM: Human

<400> SEQUENCE: 1263
ggccctggaa ctgcagatga                                                    20

<210> SEQ ID NO 1264
<211> LENGTH: 20
<212> TYPE: DNA
<213> ORGANISM: Human

<400> SEQUENCE: 1264
gtccttgctt ggggctctgg                                                    20

<210> SEQ ID NO 1265
<211> LENGTH: 20
<212> TYPE: DNA
<213> ORGANISM: Human

<400> SEQUENCE: 1265
ctccctggag agccagatgt                                                    20

<210> SEQ ID NO 1266
<211> LENGTH: 20
<212> TYPE: DNA
<213> ORGANISM: Human

<400> SEQUENCE: 1266
aaattcccac agactcatgg                                                    20

<210> SEQ ID NO 1267
<211> LENGTH: 20
<212> TYPE: DNA
<213> ORGANISM: Human

<400> SEQUENCE: 1267
tcatctgcca cagagcgctg                                                    20
```

<210> SEQ ID NO 1268
<211> LENGTH: 20
<212> TYPE: DNA
<213> ORGANISM: Human

<400> SEQUENCE: 1268
agtcggcagg gacactgaag                                          20

<210> SEQ ID NO 1269
<211> LENGTH: 20
<212> TYPE: DNA
<213> ORGANISM: Human

<400> SEQUENCE: 1269
actctcgagg tggaaaggca                                          20

<210> SEQ ID NO 1270
<211> LENGTH: 20
<212> TYPE: DNA
<213> ORGANISM: Human

<400> SEQUENCE: 1270
cccagtgagt aagctgcctg                                          20

<210> SEQ ID NO 1271
<211> LENGTH: 20
<212> TYPE: DNA
<213> ORGANISM: Human

<400> SEQUENCE: 1271
agagggtgca aagaactctc                                          20

<210> SEQ ID NO 1272
<211> LENGTH: 20
<212> TYPE: DNA
<213> ORGANISM: Human

<400> SEQUENCE: 1272
cacgatcccg tcagactcgt                                          20

<210> SEQ ID NO 1273
<211> LENGTH: 20
<212> TYPE: DNA
<213> ORGANISM: Human

<400> SEQUENCE: 1273
tctgcactgg gggctcctga                                          20

<210> SEQ ID NO 1274
<211> LENGTH: 20
<212> TYPE: DNA
<213> ORGANISM: Human

<400> SEQUENCE: 1274 caggggcat aaacctgcag                                           20

<210> SEQ ID NO 1275
<211> LENGTH: 20
<212> TYPE: DNA
<213> ORGANISM: Human

<400> SEQUENCE: 1275
tgaggacagc cacagccgtc                                          20

-continued

<210> SEQ ID NO 1276
<211> LENGTH: 20
<212> TYPE: DNA
<213> ORGANISM: Human

<400> SEQUENCE: 1276
gtttcccccg cacctggtgg                                                    20

<210> SEQ ID NO 1277
<211> LENGTH: 20
<212> TYPE: DNA
<213> ORGANISM: Human

<400> SEQUENCE: 1277 ttagggtgc caccaccccg                                                     20

<210> SEQ ID NO 1278
<211> LENGTH: 20
<212> TYPE: DNA
<213> ORGANISM: Human

<400> SEQUENCE: 1278
actggggtgc tgggacttgt                                                    20

<210> SEQ ID NO 1279
<211> LENGTH: 20
<212> TYPE: DNA
<213> ORGANISM: Human

<400> SEQUENCE: 1279
ctcactcccg tacgtctccc                                                    20

<210> SEQ ID NO 1280
<211> LENGTH: 20
<212> TYPE: DNA
<213> ORGANISM: Human

<400> SEQUENCE: 1280
aggggctggc aggagcccgt                                                    20

<210> SEQ ID NO 1281
<211> LENGTH: 20
<212> TYPE: DNA
<213> ORGANISM: Human

<400> SEQUENCE: 1281
tccttgttcc catggctggg                                                    20

<210> SEQ ID NO 1282
<211> LENGTH: 20
<212> TYPE: DNA
<213> ORGANISM: Human

<400> SEQUENCE: 1282
gccaaaggca gagaaggctg                                                    20

<210> SEQ ID NO 1283
<211> LENGTH: 20
<212> TYPE: DNA
<213> ORGANISM: Human

<400> SEQUENCE: 1283
cacgggctcc tgccagcccc                                        20

<210> SEQ ID NO 1284
<211> LENGTH: 20
<212> TYPE: DNA
<213> ORGANISM: Human

<400> SEQUENCE: 1284
ccacagcgtc ctgcagaagc                                        20

<210> SEQ ID NO 1285
<211> LENGTH: 20
<212> TYPE: DNA
<213> ORGANISM: Human

<400> SEQUENCE: 1285
acgggctcct gccagcccct                                        20

<210> SEQ ID NO 1286
<211> LENGTH: 20
<212> TYPE: DNA
<213> ORGANISM: Human

<400> SEQUENCE: 1286
atgggagcaa cgtggccatg                                        20

<210> SEQ ID NO 1287
<211> LENGTH: 20
<212> TYPE: DNA
<213> ORGANISM: Human

<400> SEQUENCE: 1287
cccaaggccg ggtcaagagc                                        20

<210> SEQ ID NO 1288
<211> LENGTH: 20
<212> TYPE: DNA
<213> ORGANISM: Human

<400> SEQUENCE: 1288
aattgctgag aaggggccga                                        20

<210> SEQ ID NO 1289
<211> LENGTH: 20
<212> TYPE: DNA
<213> ORGANISM: Human

<400> SEQUENCE: 1289
gggcaggagt gaggagggcc                                        20

<210> SEQ ID NO 1290
<211> LENGTH: 20
<212> TYPE: DNA
<213> ORGANISM: Human

<400> SEQUENCE: 1290
ggcgggaccc tgggatgcc                                         20

<210> SEQ ID NO 1291
<211> LENGTH: 20
<212> TYPE: DNA
<213> ORGANISM: Human

<400> SEQUENCE: 1291

```
ggggctggca ggagcccgtg                                         20

<210> SEQ ID NO 1292
<211> LENGTH: 20
<212> TYPE: DNA
<213> ORGANISM: Human

<400> SEQUENCE: 1292
ttccgacatc tggctctcca                                         20

<210> SEQ ID NO 1293
<211> LENGTH: 20
<212> TYPE: DNA
<213> ORGANISM: Human

<400> SEQUENCE: 1293
gtgctgccct tgccagccac                                         20

<210> SEQ ID NO 1294
<211> LENGTH: 20
<212> TYPE: DNA
<213> ORGANISM: Human

<400> SEQUENCE: 1294
actcctgccg ctcgccttgg                                         20

<210> SEQ ID NO 1295
<211> LENGTH: 20
<212> TYPE: DNA
<213> ORGANISM: Human

<400> SEQUENCE: 1295
gtggacttct tccggaagct                                         20

<210> SEQ ID NO 1296
<211> LENGTH: 20
<212> TYPE: DNA
<213> ORGANISM: Human

<400> SEQUENCE: 1296
ccagtgcaga gcccaggggc                                         20

<210> SEQ ID NO 1297
<211> LENGTH: 20
<212> TYPE: DNA
<213> ORGANISM: Human

<400> SEQUENCE: 1297
ggggcagtgg cagcagcttt                                         20

<210> SEQ ID NO 1298
<211> LENGTH: 20
<212> TYPE: DNA
<213> ORGANISM: Human

<400> SEQUENCE: 1298
gggactgtag cccgtgtaag                                         20

<210> SEQ ID NO 1299
<211> LENGTH: 20
<212> TYPE: DNA
<213> ORGANISM: Human
```

-continued

```
<400> SEQUENCE: 1299
ccacagactc atggtggggc                                              20

<210> SEQ ID NO 1300
<211> LENGTH: 20
<212> TYPE: DNA
<213> ORGANISM: Human

<400> SEQUENCE: 1300
aacacgggac agccaccgag                                              20

<210> SEQ ID NO 1301
<211> LENGTH: 20
<212> TYPE: DNA
<213> ORGANISM: Human

<400> SEQUENCE: 1301
gcaaagaact ctctggaggt                                              20

<210> SEQ ID NO 1302
<211> LENGTH: 20
<212> TYPE: DNA
<213> ORGANISM: Human

<400> SEQUENCE: 1302
tgggcccgtg ccggcccagt                                              20

<210> SEQ ID NO 1303
<211> LENGTH: 20
<212> TYPE: DNA
<213> ORGANISM: Human

<400> SEQUENCE: 1303
ctcctgccgg ggcatcctgc                                              20

<210> SEQ ID NO 1304
<211> LENGTH: 20
<212> TYPE: DNA
<213> ORGANISM: Human

<400> SEQUENCE: 1304
aggcagacag gtgagaggaa                                              20

<210> SEQ ID NO 1305
<211> LENGTH: 20
<212> TYPE: DNA
<213> ORGANISM: Human

<400> SEQUENCE: 1305
aggcaatcct gggagacgta                                              20

<210> SEQ ID NO 1306
<211> LENGTH: 20
<212> TYPE: DNA
<213> ORGANISM: Human

<400> SEQUENCE: 1306
tcagaccagt actctcgagg                                              20

<210> SEQ ID NO 1307
<211> LENGTH: 20
<212> TYPE: DNA
<213> ORGANISM: Human
```

```
<400> SEQUENCE: 1307
aacatacttg tcattgacga                                              20

<210> SEQ ID NO 1308
<211> LENGTH: 20
<212> TYPE: DNA
<213> ORGANISM: Human

<400> SEQUENCE: 1308
ggcagcttgg ccgctctggg                                              20

<210> SEQ ID NO 1309
<211> LENGTH: 20
<212> TYPE: DNA
<213> ORGANISM: Human

<400> SEQUENCE: 1309
gagttctttg caccctctgc                                              20

<210> SEQ ID NO 1310
<211> LENGTH: 20
<212> TYPE: DNA
<213> ORGANISM: Human

<400> SEQUENCE: 1310
gccacaggca gcttactcac                                              20

<210> SEQ ID NO 1311
<211> LENGTH: 20
<212> TYPE: DNA
<213> ORGANISM: Human

<400> SEQUENCE: 1311
aggctgcctg ccctgcccca                                              20

<210> SEQ ID NO 1312
<211> LENGTH: 20
<212> TYPE: DNA
<213> ORGANISM: Human

<400> SEQUENCE: 1312
ccggcccagt gggtcatcag                                              20

<210> SEQ ID NO 1313
<211> LENGTH: 20
<212> TYPE: DNA
<213> ORGANISM: Human

<400> SEQUENCE: 1313
ctctcgaggt ggaaaggcag                                              20

<210> SEQ ID NO 1314
<211> LENGTH: 20
<212> TYPE: DNA
<213> ORGANISM: Human

<400> SEQUENCE: 1314
gattgcctgg actcgggcat                                              20

<210> SEQ ID NO 1315
<211> LENGTH: 20
<212> TYPE: DNA
```

```
<213> ORGANISM: Human

<400> SEQUENCE: 1315
tccttgcttg gggctctggg                                        20

<210> SEQ ID NO 1316
<211> LENGTH: 20
<212> TYPE: DNA
<213> ORGANISM: Human

<400> SEQUENCE: 1316
gcagagaagg ctgcggtggc                                        20

<210> SEQ ID NO 1317
<211> LENGTH: 20
<212> TYPE: DNA
<213> ORGANISM: Human

<400> SEQUENCE: 1317
accgtgacct ccaaggcgag                                        20

<210> SEQ ID NO 1318
<211> LENGTH: 20
<212> TYPE: DNA
<213> ORGANISM: Human

<400> SEQUENCE: 1318
caggacgctg tggatctccg                                        20

<210> SEQ ID NO 1319
<211> LENGTH: 20
<212> TYPE: DNA
<213> ORGANISM: Human

<400> SEQUENCE: 1319
aggaagcagc cgtgtcccta                                        20

<210> SEQ ID NO 1320
<211> LENGTH: 20
<212> TYPE: DNA
<213> ORGANISM: Human

<400> SEQUENCE: 1320
acgcaggaag ttgtccaggc                                        20

<210> SEQ ID NO 1321
<211> LENGTH: 20
<212> TYPE: DNA
<213> ORGANISM: Human

<400> SEQUENCE: 1321
gaggtcccca agaggaaaac                                        20

<210> SEQ ID NO 1322
<211> LENGTH: 20
<212> TYPE: DNA
<213> ORGANISM: Human

<400> SEQUENCE: 1322
cccccagctt cttcccatcc                                        20

<210> SEQ ID NO 1323
<211> LENGTH: 20
```

```
<212> TYPE: DNA
<213> ORGANISM: Human

<400> SEQUENCE: 1323
attcccacag actcatggtg                                              20

<210> SEQ ID NO 1324
<211> LENGTH: 20
<212> TYPE: DNA
<213> ORGANISM: Human

<400> SEQUENCE: 1324
tccaaggcga gcggcaggag                                              20

<210> SEQ ID NO 1325
<211> LENGTH: 20
<212> TYPE: DNA
<213> ORGANISM: Human

<400> SEQUENCE: 1325
gctgggagct cagatccata                                              20

<210> SEQ ID NO 1326
<211> LENGTH: 20
<212> TYPE: DNA
<213> ORGANISM: Human

<400> SEQUENCE: 1326
tgggggccca ggcatcccca                                              20

<210> SEQ ID NO 1327
<211> LENGTH: 20
<212> TYPE: DNA
<213> ORGANISM: Human

<400> SEQUENCE: 1327
gggtgcaaag aactctctgg                                              20

<210> SEQ ID NO 1328
<211> LENGTH: 20
<212> TYPE: DNA
<213> ORGANISM: Human

<400> SEQUENCE: 1328
gcgggactag agggagctga                                              20

<210> SEQ ID NO 1329
<211> LENGTH: 20
<212> TYPE: DNA
<213> ORGANISM: Human

<400> SEQUENCE: 1329
actggagaag aagaagatcc                                              20

<210> SEQ ID NO 1330
<211> LENGTH: 20
<212> TYPE: DNA
<213> ORGANISM: Human

<400> SEQUENCE: 1330
ccagctcttg acccggcctt                                              20

<210> SEQ ID NO 1331
```

```
<211> LENGTH: 20
<212> TYPE: DNA
<213> ORGANISM: Human

<400> SEQUENCE: 1331
gaactttggg gggttcgagg                                              20

<210> SEQ ID NO 1332
<211> LENGTH: 20
<212> TYPE: DNA
<213> ORGANISM: Human

<400> SEQUENCE: 1332
gaaaccagtt cactgccagc                                              20

<210> SEQ ID NO 1333
<211> LENGTH: 20
<212> TYPE: DNA
<213> ORGANISM: Human

<400> SEQUENCE: 1333
acagccgtca gggcaccccca                                             20

<210> SEQ ID NO 1334
<211> LENGTH: 20
<212> TYPE: DNA
<213> ORGANISM: Human

<400> SEQUENCE: 1334
ccaccccgag cccccttacac                                             20

<210> SEQ ID NO 1335
<211> LENGTH: 20
<212> TYPE: DNA
<213> ORGANISM: Human

<400> SEQUENCE: 1335
tctcggcagc cagctgctgg                                              20

<210> SEQ ID NO 1336
<211> LENGTH: 20
<212> TYPE: DNA
<213> ORGANISM: Human

<400> SEQUENCE: 1336
agagagctgg actgggatga                                              20

<210> SEQ ID NO 1337
<211> LENGTH: 20
<212> TYPE: DNA
<213> ORGANISM: Human

<400> SEQUENCE: 1337
cctttccacc tcgagagtac                                              20

<210> SEQ ID NO 1338
<211> LENGTH: 20
<212> TYPE: DNA
<213> ORGANISM: Human

<400> SEQUENCE: 1338
aagctggcct acgagtctga                                              20
```

```
<210> SEQ ID NO 1339
<211> LENGTH: 20
<212> TYPE: DNA
<213> ORGANISM: Human

<400> SEQUENCE: 1339
gtctgtggga gccagtctgt                                               20

<210> SEQ ID NO 1340
<211> LENGTH: 20
<212> TYPE: DNA
<213> ORGANISM: Human

<400> SEQUENCE: 1340
agacctatgc cccatcaggc                                               20

<210> SEQ ID NO 1341
<211> LENGTH: 20
<212> TYPE: DNA
<213> ORGANISM: Human

<400> SEQUENCE: 1341
tgggaagaag ctgggggccc                                               20

<210> SEQ ID NO 1342
<211> LENGTH: 20
<212> TYPE: DNA
<213> ORGANISM: Human

<400> SEQUENCE: 1342
ctgtggagag aagcctgtcc                                               20

<210> SEQ ID NO 1343
<211> LENGTH: 20
<212> TYPE: DNA
<213> ORGANISM: Human

<400> SEQUENCE: 1343
gggacttcta attgctgaga                                               20

<210> SEQ ID NO 1344
<211> LENGTH: 20
<212> TYPE: DNA
<213> ORGANISM: Human

<400> SEQUENCE: 1344
ggactcgggc attggctccc                                               20

<210> SEQ ID NO 1345
<211> LENGTH: 20
<212> TYPE: DNA
<213> ORGANISM: Human

<400> SEQUENCE: 1345
catctgccac agagcgctgg                                               20

<210> SEQ ID NO 1346
<211> LENGTH: 20
<212> TYPE: DNA
<213> ORGANISM: Human

<400> SEQUENCE: 1346
cttctgggag tggaggctcc                                               20
```

```
<210> SEQ ID NO 1347
<211> LENGTH: 20
<212> TYPE: DNA
<213> ORGANISM: Human

<400> SEQUENCE: 1347
gcccccagtg cagagcccag                                                  20

<210> SEQ ID NO 1348
<211> LENGTH: 20
<212> TYPE: DNA
<213> ORGANISM: Human

<400> SEQUENCE: 1348
tttgtccttg cttggggctc                                                  20

<210> SEQ ID NO 1349
<211> LENGTH: 20
<212> TYPE: DNA
<213> ORGANISM: Human

<400> SEQUENCE: 1349
gtggggctgg cttccaggac                                                  20

<210> SEQ ID NO 1350
<211> LENGTH: 20
<212> TYPE: DNA
<213> ORGANISM: Human

<400> SEQUENCE: 1350
tcaagagctg gccgctgagg                                                  20

<210> SEQ ID NO 1351
<211> LENGTH: 20
<212> TYPE: DNA
<213> ORGANISM: Human

<400> SEQUENCE: 1351
cctctagtcc cgcggggtgg                                                  20

<210> SEQ ID NO 1352
<211> LENGTH: 20
<212> TYPE: DNA
<213> ORGANISM: Human

<400> SEQUENCE: 1352
gctcatctgc cacagagcgc                                                  20

<210> SEQ ID NO 1353
<211> LENGTH: 20
<212> TYPE: DNA
<213> ORGANISM: Human

<400> SEQUENCE: 1353
catgagtctg tgggaatttg                                                  20

<210> SEQ ID NO 1354
<211> LENGTH: 20
<212> TYPE: DNA
<213> ORGANISM: Human

<400> SEQUENCE: 1354
tgcgaggctc ctgcctgatg                                                  20
```

<210> SEQ ID NO 1355
<211> LENGTH: 20
<212> TYPE: DNA
<213> ORGANISM: Human

<400> SEQUENCE: 1355
ggagtgagtc cagcgtctgt                                              20

<210> SEQ ID NO 1356
<211> LENGTH: 20
<212> TYPE: DNA
<213> ORGANISM: Human

<400> SEQUENCE: 1356
tgcaaagaac tctctggagg                                              20

<210> SEQ ID NO 1357
<211> LENGTH: 20
<212> TYPE: DNA
<213> ORGANISM: Human

<400> SEQUENCE: 1357
cacagcgtcc tgcagaagct                                              20

<210> SEQ ID NO 1358
<211> LENGTH: 20
<212> TYPE: DNA
<213> ORGANISM: Human

<400> SEQUENCE: 1358
cagcttactc actggggtgc                                              20

<210> SEQ ID NO 1359
<211> LENGTH: 20
<212> TYPE: DNA
<213> ORGANISM: Human

<400> SEQUENCE: 1359
actgatgtgg gtgggggcag                                              20

<210> SEQ ID NO 1360
<211> LENGTH: 20
<212> TYPE: DNA
<213> ORGANISM: Human

<400> SEQUENCE: 1360
gcaggatgtg ctggtctggg                                              20

<210> SEQ ID NO 1361
<211> LENGTH: 20
<212> TYPE: DNA
<213> ORGANISM: Human

<400> SEQUENCE: 1361
tcacagtgtt tgtgccatcc                                              20

<210> SEQ ID NO 1362
<211> LENGTH: 20
<212> TYPE: DNA
<213> ORGANISM: Human

<400> SEQUENCE: 1362
gtttgtgcca tcctggagga                    20

<210> SEQ ID NO 1363
<211> LENGTH: 20
<212> TYPE: DNA
<213> ORGANISM: Human

<400> SEQUENCE: 1363
tcctgaagga ctgatgtggg                    20

<210> SEQ ID NO 1364
<211> LENGTH: 20
<212> TYPE: DNA
<213> ORGANISM: Human

<400> SEQUENCE: 1364
tgttagcaga gagctggact                    20

<210> SEQ ID NO 1365
<211> LENGTH: 20
<212> TYPE: DNA
<213> ORGANISM: Human

<400> SEQUENCE: 1365
cagtgtttgt gccatcctgg                    20

<210> SEQ ID NO 1366
<211> LENGTH: 20
<212> TYPE: DNA
<213> ORGANISM: Human

<400> SEQUENCE: 1366
agtctgtcag ggcctctggg                    20

<210> SEQ ID NO 1367
<211> LENGTH: 20
<212> TYPE: DNA
<213> ORGANISM: Human

<400> SEQUENCE: 1367
tctcgaggtg gaaaggcagg                    20

<210> SEQ ID NO 1368
<211> LENGTH: 20
<212> TYPE: DNA
<213> ORGANISM: Human

<400> SEQUENCE: 1368
agactggctc ccacagacgc                    20

<210> SEQ ID NO 1369
<211> LENGTH: 20
<212> TYPE: DNA
<213> ORGANISM: Human

<400> SEQUENCE: 1369
agccactcac tttggagcac                    20

<210> SEQ ID NO 1370
<211> LENGTH: 20
<212> TYPE: DNA
<213> ORGANISM: Human

<400> SEQUENCE: 1370
tcccaggatt gcctggactc                                                20

<210> SEQ ID NO 1371
<211> LENGTH: 20
<212> TYPE: DNA
<213> ORGANISM: Human

<400> SEQUENCE: 1371
cctggaactg cagatgaagg                                                20

<210> SEQ ID NO 1372
<211> LENGTH: 20
<212> TYPE: DNA
<213> ORGANISM: Human

<400> SEQUENCE: 1372
ggggcgcttc ccacagctcc                                                20

<210> SEQ ID NO 1373
<211> LENGTH: 20
<212> TYPE: DNA
<213> ORGANISM: Human

<400> SEQUENCE: 1373
cagcccctgg gctctgcact                                                20

<210> SEQ ID NO 1374
<211> LENGTH: 20
<212> TYPE: DNA
<213> ORGANISM: Human

<400> SEQUENCE: 1374
gcgcgggtgg gtagtcggca                                                20

<210> SEQ ID NO 1375
<211> LENGTH: 20
<212> TYPE: DNA
<213> ORGANISM: Human

<400> SEQUENCE: 1375
gccccaagca aggacaaaaa                                                20

<210> SEQ ID NO 1376
<211> LENGTH: 20
<212> TYPE: DNA
<213> ORGANISM: Human

<400> SEQUENCE: 1376
agcctggatg ggaagaagct                                                20

<210> SEQ ID NO 1377
<211> LENGTH: 20
<212> TYPE: DNA
<213> ORGANISM: Human

<400> SEQUENCE: 1377
cagctcttga cccggccttg                                                20

<210> SEQ ID NO 1378
<211> LENGTH: 20
<212> TYPE: DNA
<213> ORGANISM: Human

-continued

<400> SEQUENCE: 1378 tagggtgcc accaccccgc					20

<210> SEQ ID NO 1379
<211> LENGTH: 20
<212> TYPE: DNA
<213> ORGANISM: Human

<400> SEQUENCE: 1379
tccactccca gaagaggaaa					20

<210> SEQ ID NO 1380
<211> LENGTH: 20
<212> TYPE: DNA
<213> ORGANISM: Human

<400> SEQUENCE: 1380
ggaagcgctt catcgaggag					20

<210> SEQ ID NO 1381
<211> LENGTH: 20
<212> TYPE: DNA
<213> ORGANISM: Human

<400> SEQUENCE: 1381
gcatcctgct ggcagtgaac					20

<210> SEQ ID NO 1382
<211> LENGTH: 20
<212> TYPE: DNA
<213> ORGANISM: Human

<400> SEQUENCE: 1382
tggatgaata gcccagcttc					20

<210> SEQ ID NO 1383
<211> LENGTH: 20
<212> TYPE: DNA
<213> ORGANISM: Human

<400> SEQUENCE: 1383
acacgggaca gccaccgagc					20

<210> SEQ ID NO 1384
<211> LENGTH: 20
<212> TYPE: DNA
<213> ORGANISM: Human

<400> SEQUENCE: 1384
gggctcctga aggactgatg					20

<210> SEQ ID NO 1385
<211> LENGTH: 20
<212> TYPE: DNA
<213> ORGANISM: Human

<400> SEQUENCE: 1385
cagcctggat gggaagaagc					20

<210> SEQ ID NO 1386
<211> LENGTH: 20
<212> TYPE: DNA
<213> ORGANISM: Human

```
<400> SEQUENCE: 1386
ttttcctctt ctgggagtgg                                              20

<210> SEQ ID NO 1387
<211> LENGTH: 20
<212> TYPE: DNA
<213> ORGANISM: Human

<400> SEQUENCE: 1387
ctccaggttg ggagccttag                                              20

<210> SEQ ID NO 1388
<211> LENGTH: 20
<212> TYPE: DNA
<213> ORGANISM: Human

<400> SEQUENCE: 1388
gggagctgag ggcaggggtc                                              20

<210> SEQ ID NO 1389
<211> LENGTH: 20
<212> TYPE: DNA
<213> ORGANISM: Human

<400> SEQUENCE: 1389
agatgaaggt ggacttcttc                                              20

<210> SEQ ID NO 1390
<211> LENGTH: 20
<212> TYPE: DNA
<213> ORGANISM: Human

<400> SEQUENCE: 1390
tttggccggg ccatgggtgc                                              20

<210> SEQ ID NO 1391
<211> LENGTH: 20
<212> TYPE: DNA
<213> ORGANISM: Human

<400> SEQUENCE: 1391
ctcgcaccta gcgggggcag                                              20

<210> SEQ ID NO 1392
<211> LENGTH: 20
<212> TYPE: DNA
<213> ORGANISM: Human

<400> SEQUENCE: 1392
cccgtgtaag gggctcgggg                                              20

<210> SEQ ID NO 1393
<211> LENGTH: 20
<212> TYPE: DNA
<213> ORGANISM: Human

<400> SEQUENCE: 1393
tgccggccca gtgggtcatc                                              20

<210> SEQ ID NO 1394
<211> LENGTH: 20
<212> TYPE: DNA
```

```
<213> ORGANISM: Human

<400> SEQUENCE: 1394
aaaggcagag aaggctgcgg                                               20

<210> SEQ ID NO 1395
<211> LENGTH: 20
<212> TYPE: DNA
<213> ORGANISM: Human

<400> SEQUENCE: 1395
aggagcccgt ggggcagggc                                               20

<210> SEQ ID NO 1396
<211> LENGTH: 20
<212> TYPE: DNA
<213> ORGANISM: Human

<400> SEQUENCE: 1396
taaggggctc ggggtgggcc                                               20

<210> SEQ ID NO 1397
<211> LENGTH: 20
<212> TYPE: DNA
<213> ORGANISM: Human

<400> SEQUENCE: 1397
acaccatcac gacgcgtggg                                               20

<210> SEQ ID NO 1398
<211> LENGTH: 20
<212> TYPE: DNA
<213> ORGANISM: Human

<400> SEQUENCE: 1398
ctggcaggag cccgtggggc                                               20

<210> SEQ ID NO 1399
<211> LENGTH: 20
<212> TYPE: DNA
<213> ORGANISM: Human

<400> SEQUENCE: 1399
ccggccttgg ggtgccctga                                               20

<210> SEQ ID NO 1400
<211> LENGTH: 20
<212> TYPE: DNA
<213> ORGANISM: Human

<400> SEQUENCE: 1400
ctgtgttaga ccctcttggc                                               20

<210> SEQ ID NO 1401
<211> LENGTH: 20
<212> TYPE: DNA
<213> ORGANISM: Human

<400> SEQUENCE: 1401
gtgatgggca cgtcgggccg                                               20

<210> SEQ ID NO 1402
<211> LENGTH: 20
```

```
<212> TYPE: DNA
<213> ORGANISM: Human

<400> SEQUENCE: 1402
gcccctgggc tctgcactgg                                              20

<210> SEQ ID NO 1403
<211> LENGTH: 20
<212> TYPE: DNA
<213> ORGANISM: Human

<400> SEQUENCE: 1403
ctgggtgagc tggtgaaaca                                              20

<210> SEQ ID NO 1404
<211> LENGTH: 20
<212> TYPE: DNA
<213> ORGANISM: Human

<400> SEQUENCE: 1404
ggctgctcct tcctccagga                                              20

<210> SEQ ID NO 1405
<211> LENGTH: 20
<212> TYPE: DNA
<213> ORGANISM: Human

<400> SEQUENCE: 1405
acagcctcca ccaggtgcgg                                              20

<210> SEQ ID NO 1406
<211> LENGTH: 20
<212> TYPE: DNA
<213> ORGANISM: Human

<400> SEQUENCE: 1406
tgcccgagtc caggcaatcc                                              20

<210> SEQ ID NO 1407
<211> LENGTH: 20
<212> TYPE: DNA
<213> ORGANISM: Human

<400> SEQUENCE: 1407
aggtggaaag gcagggggcg                                              20

<210> SEQ ID NO 1408
<211> LENGTH: 20
<212> TYPE: DNA
<213> ORGANISM: Human

<400> SEQUENCE: 1408
cgacagattc attgtgaagc                                              20

<210> SEQ ID NO 1409
<211> LENGTH: 20
<212> TYPE: DNA
<213> ORGANISM: Human

<400> SEQUENCE: 1409
gcggggtggt ggcaccccta                                              20

<210> SEQ ID NO 1410
```

```
<211> LENGTH: 20
<212> TYPE: DNA
<213> ORGANISM: Human

<400> SEQUENCE: 1410
ggcaatcctg ggagacgtac                                               20

<210> SEQ ID NO 1411
<211> LENGTH: 20
<212> TYPE: DNA
<213> ORGANISM: Human

<400> SEQUENCE: 1411
gccgctcgcc ttggaggtca                                               20

<210> SEQ ID NO 1412
<211> LENGTH: 20
<212> TYPE: DNA
<213> ORGANISM: Human

<400> SEQUENCE: 1412
tcactgccag caggatgccc                                               20

<210> SEQ ID NO 1413
<211> LENGTH: 20
<212> TYPE: DNA
<213> ORGANISM: Human

<400> SEQUENCE: 1413
cctgaaggac tgatgtgggt                                               20

<210> SEQ ID NO 1414
<211> LENGTH: 20
<212> TYPE: DNA
<213> ORGANISM: Human

<400> SEQUENCE: 1414
gtgcgaggct cctgcctgat                                               20

<210> SEQ ID NO 1415
<211> LENGTH: 20
<212> TYPE: DNA
<213> ORGANISM: Human

<400> SEQUENCE: 1415
gcacctggtg gaggctgtga                                               20

<210> SEQ ID NO 1416
<211> LENGTH: 20
<212> TYPE: DNA
<213> ORGANISM: Human

<400> SEQUENCE: 1416
tcacagcctc caccaggtgc                                               20

<210> SEQ ID NO 1417
<211> LENGTH: 20
<212> TYPE: DNA
<213> ORGANISM: Human

<400> SEQUENCE: 1417
gccgctctgg gtggaagaat                                               20
```

-continued

```
<210> SEQ ID NO 1418
<211> LENGTH: 20
<212> TYPE: DNA
<213> ORGANISM: Human

<400> SEQUENCE: 1418
gactagaggg agctgagggc                                              20

<210> SEQ ID NO 1419
<211> LENGTH: 20
<212> TYPE: DNA
<213> ORGANISM: Human

<400> SEQUENCE: 1419
tcagctccct ctagtcccgc                                              20

<210> SEQ ID NO 1420
<211> LENGTH: 20
<212> TYPE: DNA
<213> ORGANISM: Human

<400> SEQUENCE: 1420
ggagcctcca ctcccagaag                                              20

<210> SEQ ID NO 1421
<211> LENGTH: 20
<212> TYPE: DNA
<213> ORGANISM: Human

<400> SEQUENCE: 1421
agaccctctt ggcgggaccc                                              20

<210> SEQ ID NO 1422
<211> LENGTH: 20
<212> TYPE: DNA
<213> ORGANISM: Human

<400> SEQUENCE: 1422
ccaccttcat ctgcagttcc                                              20

<210> SEQ ID NO 1423
<211> LENGTH: 20
<212> TYPE: DNA
<213> ORGANISM: Human

<400> SEQUENCE: 1423
gggagtggag gctccaggtt                                              20

<210> SEQ ID NO 1424
<211> LENGTH: 20
<212> TYPE: DNA
<213> ORGANISM: Human

<400> SEQUENCE: 1424
cagtgaactg gtttctggag                                              20

<210> SEQ ID NO 1425
<211> LENGTH: 20
<212> TYPE: DNA
<213> ORGANISM: Human

<400> SEQUENCE: 1425
tcacctgtga tgggcacgtc                                              20
```

```
<210> SEQ ID NO 1426
<211> LENGTH: 20
<212> TYPE: DNA
<213> ORGANISM: Human

<400> SEQUENCE: 1426
tgccagcagg atgccccggc                                               20

<210> SEQ ID NO 1427
<211> LENGTH: 20
<212> TYPE: DNA
<213> ORGANISM: Human

<400> SEQUENCE: 1427
accctcttgg cgggaccctg                                               20

<210> SEQ ID NO 1428
<211> LENGTH: 20
<212> TYPE: DNA
<213> ORGANISM: Human

<400> SEQUENCE: 1428
tgggggcagc ttggccgctc                                               20

<210> SEQ ID NO 1429
<211> LENGTH: 20
<212> TYPE: DNA
<213> ORGANISM: Human

<400> SEQUENCE: 1429
aggaggaggc cctggtgagc                                               20

<210> SEQ ID NO 1430
<211> LENGTH: 20
<212> TYPE: DNA
<213> ORGANISM: Human

<400> SEQUENCE: 1430
ctggaggtgg gagccatgca                                               20

<210> SEQ ID NO 1431
<211> LENGTH: 20
<212> TYPE: DNA
<213> ORGANISM: Human

<400> SEQUENCE: 1431
tctggaggtg ggagccatgc                                               20

<210> SEQ ID NO 1432
<211> LENGTH: 20
<212> TYPE: DNA
<213> ORGANISM: Human

<400> SEQUENCE: 1432
cctggatggg aagaagctgg                                               20

<210> SEQ ID NO 1433
<211> LENGTH: 20
<212> TYPE: DNA
<213> ORGANISM: Human

<400> SEQUENCE: 1433
ccagcccctg ggctctgcac                                               20
```

<210> SEQ ID NO 1434
<211> LENGTH: 20
<212> TYPE: DNA
<213> ORGANISM: Human

<400> SEQUENCE: 1434
ggagtggaag cgcttcatcg                                          20

<210> SEQ ID NO 1435
<211> LENGTH: 20
<212> TYPE: DNA
<213> ORGANISM: Human

<400> SEQUENCE: 1435
tgtagcccgt gtaagggct                                           20

<210> SEQ ID NO 1436
<211> LENGTH: 20
<212> TYPE: DNA
<213> ORGANISM: Human

<400> SEQUENCE: 1436
ggagtgagga gggccgggga                                          20

<210> SEQ ID NO 1437
<211> LENGTH: 20
<212> TYPE: DNA
<213> ORGANISM: Human

<400> SEQUENCE: 1437
gaggtcacgg tatgtgtcgt                                          20

<210> SEQ ID NO 1438
<211> LENGTH: 20
<212> TYPE: DNA
<213> ORGANISM: Human

<400> SEQUENCE: 1438
ctagagggag ctgagggcag                                          20

<210> SEQ ID NO 1439
<211> LENGTH: 20
<212> TYPE: DNA
<213> ORGANISM: Human

<400> SEQUENCE: 1439
tggtgtgttt cccccgcacc                                          20

<210> SEQ ID NO 1440
<211> LENGTH: 20
<212> TYPE: DNA
<213> ORGANISM: Human

<400> SEQUENCE: 1440
ctgatgtggg tggggcagt                                           20

<210> SEQ ID NO 1441
<211> LENGTH: 20
<212> TYPE: DNA
<213> ORGANISM: Human

<400> SEQUENCE: 1441

| | |
|---|---|
| agggccgggg agggcaggct | 20 |

<210> SEQ ID NO 1442
<211> LENGTH: 20
<212> TYPE: DNA
<213> ORGANISM: Human

<400> SEQUENCE: 1442

| | |
|---|---|
| tgagctatga gtggcccctg | 20 |

<210> SEQ ID NO 1443
<211> LENGTH: 20
<212> TYPE: DNA
<213> ORGANISM: Human

<400> SEQUENCE: 1443

| | |
|---|---|
| tcttacgcag gaagttgtcc | 20 |

<210> SEQ ID NO 1444
<211> LENGTH: 20
<212> TYPE: DNA
<213> ORGANISM: Human

<400> SEQUENCE: 1444

| | |
|---|---|
| gttccgacat ctggctctcc | 20 |

<210> SEQ ID NO 1445
<211> LENGTH: 20
<212> TYPE: DNA
<213> ORGANISM: Human

<400> SEQUENCE: 1445

| | |
|---|---|
| aggggggcgcg ggtgggtagt | 20 |

<210> SEQ ID NO 1446
<211> LENGTH: 20
<212> TYPE: DNA
<213> ORGANISM: Human

<400> SEQUENCE: 1446

| | |
|---|---|
| cgctggcctg ctccttggcc | 20 |

<210> SEQ ID NO 1447
<211> LENGTH: 20
<212> TYPE: DNA
<213> ORGANISM: Human

<400> SEQUENCE: 1447

| | |
|---|---|
| gaaaggcagg gggcgcgggt | 20 |

<210> SEQ ID NO 1448
<211> LENGTH: 20
<212> TYPE: DNA
<213> ORGANISM: Human

<400> SEQUENCE: 1448

| | |
|---|---|
| tagcccgtgt aaggggctcg | 20 |

<210> SEQ ID NO 1449
<211> LENGTH: 20
<212> TYPE: DNA
<213> ORGANISM: Human

<400> SEQUENCE: 1449
ctgagggcag gggtccggtg 20

<210> SEQ ID NO 1450
<211> LENGTH: 20
<212> TYPE: DNA
<213> ORGANISM: Human

<400> SEQUENCE: 1450
acacagctta gtatacacgc 20

<210> SEQ ID NO 1451
<211> LENGTH: 20
<212> TYPE: DNA
<213> ORGANISM: Human

<400> SEQUENCE: 1451
ccgtcagggc accccaaggc 20

<210> SEQ ID NO 1452
<211> LENGTH: 20
<212> TYPE: DNA
<213> ORGANISM: Human

<400> SEQUENCE: 1452
ggcaggggtc cggtgaggtc 20

<210> SEQ ID NO 1453
<211> LENGTH: 20
<212> TYPE: DNA
<213> ORGANISM: Human

<400> SEQUENCE: 1453
ggacttgtag gagaggatct 20

<210> SEQ ID NO 1454
<211> LENGTH: 20
<212> TYPE: DNA
<213> ORGANISM: Human

<400> SEQUENCE: 1454
tcccagccat gggaacaagg 20

<210> SEQ ID NO 1455
<211> LENGTH: 20
<212> TYPE: DNA
<213> ORGANISM: Human

<400> SEQUENCE: 1455
gacttctaat tgctgagaag 20

<210> SEQ ID NO 1456
<211> LENGTH: 20
<212> TYPE: DNA
<213> ORGANISM: Human

<400> SEQUENCE: 1456
ggctcctgaa ggactgatgt 20

<210> SEQ ID NO 1457
<211> LENGTH: 20
<212> TYPE: DNA
<213> ORGANISM: Human

```
<400> SEQUENCE: 1457
tggcaggagc ccgtggggca                                              20

<210> SEQ ID NO 1458
<211> LENGTH: 20
<212> TYPE: DNA
<213> ORGANISM: Human

<400> SEQUENCE: 1458
agacaggtga gaggaagggc                                              20

<210> SEQ ID NO 1459
<211> LENGTH: 20
<212> TYPE: DNA
<213> ORGANISM: Human

<400> SEQUENCE: 1459
tcggaacttt gggggttcg                                               20

<210> SEQ ID NO 1460
<211> LENGTH: 20
<212> TYPE: DNA
<213> ORGANISM: Human

<400> SEQUENCE: 1460
gcctggatgg gaagaagctg                                              20

<210> SEQ ID NO 1461
<211> LENGTH: 20
<212> TYPE: DNA
<213> ORGANISM: Human

<400> SEQUENCE: 1461
tgaaggactg atgtgggtgg                                              20

<210> SEQ ID NO 1462
<211> LENGTH: 20
<212> TYPE: DNA
<213> ORGANISM: Human

<400> SEQUENCE: 1462
ctgggggccc aggcatcccc                                              20

<210> SEQ ID NO 1463
<211> LENGTH: 20
<212> TYPE: DNA
<213> ORGANISM: Human

<400> SEQUENCE: 1463
gagcccccag tgcagagccc                                              20

<210> SEQ ID NO 1464
<211> LENGTH: 20
<212> TYPE: DNA
<213> ORGANISM: Human

<400> SEQUENCE: 1464
ggcgcgggtg ggtagtcggc                                              20

<210> SEQ ID NO 1465
<211> LENGTH: 20
<212> TYPE: DNA
<213> ORGANISM: Human
```

<400> SEQUENCE: 1465
ccgtgtaagg ggctcggggt                                               20

<210> SEQ ID NO 1466
<211> LENGTH: 20
<212> TYPE: DNA
<213> ORGANISM: Human

<400> SEQUENCE: 1466
gtcgtgatgg tgtgaacacc                                               20

<210> SEQ ID NO 1467
<211> LENGTH: 20
<212> TYPE: DNA
<213> ORGANISM: Human

<400> SEQUENCE: 1467
acgacgcgtg ggtggcaagc                                               20

<210> SEQ ID NO 1468
<211> LENGTH: 20
<212> TYPE: DNA
<213> ORGANISM: Human

<400> SEQUENCE: 1468
gggggcagtg gcagcagctt                                               20

<210> SEQ ID NO 1469
<211> LENGTH: 20
<212> TYPE: DNA
<213> ORGANISM: Human

<400> SEQUENCE: 1469
agcgtgtata ctaagctgtg                                               20

<210> SEQ ID NO 1470
<211> LENGTH: 20
<212> TYPE: DNA
<213> ORGANISM: Human

<400> SEQUENCE: 1470
gctcctgcct gatggggcat                                               20

<210> SEQ ID NO 1471
<211> LENGTH: 20
<212> TYPE: DNA
<213> ORGANISM: Human

<400> SEQUENCE: 1471
gtctgtcagg gcctctggga                                               20

<210> SEQ ID NO 1472
<211> LENGTH: 20
<212> TYPE: DNA
<213> ORGANISM: Human

<400> SEQUENCE: 1472
gtagcccgtg taaggggctc                                               20

<210> SEQ ID NO 1473
<211> LENGTH: 20
<212> TYPE: DNA

```
<213> ORGANISM: Human

<400> SEQUENCE: 1473
agcccctggg ctctgcactg                                               20

<210> SEQ ID NO 1474
<211> LENGTH: 20
<212> TYPE: DNA
<213> ORGANISM: Human

<400> SEQUENCE: 1474
gtgaactggt ttctggagcg                                               20

<210> SEQ ID NO 1475
<211> LENGTH: 20
<212> TYPE: DNA
<213> ORGANISM: Human

<400> SEQUENCE: 1475
ctacgagtct gacgggatcg                                               20

<210> SEQ ID NO 1476
<211> LENGTH: 20
<212> TYPE: DNA
<213> ORGANISM: Human

<400> SEQUENCE: 1476
agtgaactgg tttctggagc                                               20

<210> SEQ ID NO 1477
<211> LENGTH: 20
<212> TYPE: DNA
<213> ORGANISM: Human

<400> SEQUENCE: 1477
acgcgtgggt ggcaagcggg                                               20

<210> SEQ ID NO 1478
<211> LENGTH: 20
<212> TYPE: DNA
<213> ORGANISM: Human

<400> SEQUENCE: 1478
cgcgggacta gagggagctg                                               20

<210> SEQ ID NO 1479
<211> LENGTH: 20
<212> TYPE: DNA
<213> ORGANISM: Human

<400> SEQUENCE: 1479
ggcaggagtg aggagggccg                                               20

<210> SEQ ID NO 1480
<211> LENGTH: 20
<212> TYPE: DNA
<213> ORGANISM: Human

<400> SEQUENCE: 1480
aagtgagtgg cttcttacgc                                               20

<210> SEQ ID NO 1481
<211> LENGTH: 20
```

```
<212> TYPE: DNA
<213> ORGANISM: Human

<400> SEQUENCE: 1481
ctgaaggact gatgtgggtg                                      20

<210> SEQ ID NO 1482
<211> LENGTH: 20
<212> TYPE: DNA
<213> ORGANISM: Human

<400> SEQUENCE: 1482
ttgccaccca cgcgtcgtga                                      20

<210> SEQ ID NO 1483
<211> LENGTH: 20
<212> TYPE: DNA
<213> ORGANISM: Human

<400> SEQUENCE: 1483
agggcaggag tgaggagggc                                      20

<210> SEQ ID NO 1484
<211> LENGTH: 20
<212> TYPE: DNA
<213> ORGANISM: Human

<400> SEQUENCE: 1484
tcttcttctc cagttcccgc                                      20

<210> SEQ ID NO 1485
<211> LENGTH: 20
<212> TYPE: DNA
<213> ORGANISM: Human

<400> SEQUENCE: 1485
aggagtgagg agggccgggg                                      20

<210> SEQ ID NO 1486
<211> LENGTH: 20
<212> TYPE: DNA
<213> ORGANISM: Human

<400> SEQUENCE: 1486
actcccagaa gaggaaaagg                                      20

<210> SEQ ID NO 1487
<211> LENGTH: 20
<212> TYPE: DNA
<213> ORGANISM: Human

<400> SEQUENCE: 1487
tgaggagggc cggggagggc                                      20

<210> SEQ ID NO 1488
<211> LENGTH: 20
<212> TYPE: DNA
<213> ORGANISM: Human

<400> SEQUENCE: 1488
acctggtgga ggctgtgatg                                      20

<210> SEQ ID NO 1489
```

-continued

```
<211> LENGTH: 20
<212> TYPE: DNA
<213> ORGANISM: Human

<400> SEQUENCE: 1489
cagggccgag gcctcctcag                                                 20

<210> SEQ ID NO 1490
<211> LENGTH: 20
<212> TYPE: DNA
<213> ORGANISM: Human

<400> SEQUENCE: 1490
tactctcgag gtggaaaggc                                                 20

<210> SEQ ID NO 1491
<211> LENGTH: 20
<212> TYPE: DNA
<213> ORGANISM: Human

<400> SEQUENCE: 1491
ttggggctct gggggtgag                                                  20

<210> SEQ ID NO 1492
<211> LENGTH: 20
<212> TYPE: DNA
<213> ORGANISM: Human

<400> SEQUENCE: 1492
gctcctggac ccccagcagc                                                 20

<210> SEQ ID NO 1493
<211> LENGTH: 20
<212> TYPE: DNA
<213> ORGANISM: Human

<400> SEQUENCE: 1493 gggggtgag aggagagcat                                                  20

<210> SEQ ID NO 1494
<211> LENGTH: 20
<212> TYPE: DNA
<213> ORGANISM: Human

<400> SEQUENCE: 1494
cggcccagtg ggtcatcagg                                                 20

<210> SEQ ID NO 1495
<211> LENGTH: 20
<212> TYPE: DNA
<213> ORGANISM: Human

<400> SEQUENCE: 1495
aggaagggca ggagtgagga                                                 20

<210> SEQ ID NO 1496
<211> LENGTH: 20
<212> TYPE: DNA
<213> ORGANISM: Human

<400> SEQUENCE: 1496
gagggccggg gagggcaggc                                                 20
```

```
<210> SEQ ID NO 1497
<211> LENGTH: 20
<212> TYPE: DNA
<213> ORGANISM: Human

<400> SEQUENCE: 1497
tgctgggggt ccaggagctg                                           20

<210> SEQ ID NO 1498
<211> LENGTH: 20
<212> TYPE: DNA
<213> ORGANISM: Human

<400> SEQUENCE: 1498 gctggggtc caggagctgt                                            20

<210> SEQ ID NO 1499
<211> LENGTH: 20
<212> TYPE: DNA
<213> ORGANISM: Human

<400> SEQUENCE: 1499
tgagaggaag ggcaggagtg                                           20

<210> SEQ ID NO 1500
<211> LENGTH: 20
<212> TYPE: DNA
<213> ORGANISM: Human

<400> SEQUENCE: 1500
tgggagtgga ggctccaggt                                           20

<210> SEQ ID NO 1501
<211> LENGTH: 20
<212> TYPE: DNA
<213> ORGANISM: Human

<400> SEQUENCE: 1501
gaggaagggc aggagtgagg                                           20

<210> SEQ ID NO 1502
<211> LENGTH: 20
<212> TYPE: DNA
<213> ORGANISM: Murine

<400> SEQUENCE: 1502
gctggctgtg aactggtttc                                           20

<210> SEQ ID NO 1503
<211> LENGTH: 20
<212> TYPE: DNA
<213> ORGANISM: Murine

<400> SEQUENCE: 1503
ctagttcccg aaggatgtgc                                           20

<210> SEQ ID NO 1504
<211> LENGTH: 20
<212> TYPE: DNA
<213> ORGANISM: Murine

<400> SEQUENCE: 1504
attggagacc accactccgt                                           20
```

```
<210> SEQ ID NO 1505
<211> LENGTH: 20
<212> TYPE: DNA
<213> ORGANISM: Murine

<400> SEQUENCE: 1505
ttccctcctc tgccagccat                                                   20

<210> SEQ ID NO 1506
<211> LENGTH: 20
<212> TYPE: DNA
<213> ORGANISM: Murine

<400> SEQUENCE: 1506
cgaaggaagt tgtccaggct                                                   20

<210> SEQ ID NO 1507
<211> LENGTH: 20
<212> TYPE: DNA
<213> ORGANISM: Murine

<400> SEQUENCE: 1507
atacctgtga taggcacatc                                                   20

<210> SEQ ID NO 1508
<211> LENGTH: 20
<212> TYPE: DNA
<213> ORGANISM: Murine

<400> SEQUENCE: 1508
gacttccttg ttcccatggc                                                   20

<210> SEQ ID NO 1509
<211> LENGTH: 20
<212> TYPE: DNA
<213> ORGANISM: Murine

<400> SEQUENCE: 1509
ggccttcgaa tccgacggag                                                   20

<210> SEQ ID NO 1510
<211> LENGTH: 20
<212> TYPE: DNA
<213> ORGANISM: Murine

<400> SEQUENCE: 1510
atcaccagag gtaactgcca                                                   20

<210> SEQ ID NO 1511
<211> LENGTH: 20
<212> TYPE: DNA
<213> ORGANISM: Murine

<400> SEQUENCE: 1511
ggctttgaag atggtgaaga                                                   20

<210> SEQ ID NO 1512
<211> LENGTH: 20
<212> TYPE: DNA
<213> ORGANISM: Murine

<400> SEQUENCE: 1512
atgggctaag acatcaccag                                                   20
```

<210> SEQ ID NO 1513
<211> LENGTH: 20
<212> TYPE: DNA
<213> ORGANISM: Murine

<400> SEQUENCE: 1513
ctatgatcta ctgcaacgac                                               20

<210> SEQ ID NO 1514
<211> LENGTH: 20
<212> TYPE: DNA
<213> ORGANISM: Murine

<400> SEQUENCE: 1514
ttctcatgct gaaaacttgc                                               20

<210> SEQ ID NO 1515
<211> LENGTH: 20
<212> TYPE: DNA
<213> ORGANISM: Murine

<400> SEQUENCE: 1515
ttgccggcac gccaacatcg                                               20

<210> SEQ ID NO 1516
<211> LENGTH: 20
<212> TYPE: DNA
<213> ORGANISM: Murine

<400> SEQUENCE: 1516
gagaatctcc ttctgaaggg                                               20

<210> SEQ ID NO 1517
<211> LENGTH: 20
<212> TYPE: DNA
<213> ORGANISM: Murine

<400> SEQUENCE: 1517
ggctcgcgac aaggtgtcta                                               20

<210> SEQ ID NO 1518
<211> LENGTH: 20
<212> TYPE: DNA
<213> ORGANISM: Murine

<400> SEQUENCE: 1518
ctgtggagct ggttctctcc                                               20

<210> SEQ ID NO 1519
<211> LENGTH: 20
<212> TYPE: DNA
<213> ORGANISM: Murine

<400> SEQUENCE: 1519
tctaaccttg gtagatgtcc                                               20

<210> SEQ ID NO 1520
<211> LENGTH: 20
<212> TYPE: DNA
<213> ORGANISM: Murine

<400> SEQUENCE: 1520

-continued

| | |
|---|---|
| cgactgggtg gtggaactta | 20 |

<210> SEQ ID NO 1521
<211> LENGTH: 20
<212> TYPE: DNA
<213> ORGANISM: Murine

<400> SEQUENCE: 1521

| | |
|---|---|
| cttcttctct gaatgcaggt | 20 |

<210> SEQ ID NO 1522
<211> LENGTH: 20
<212> TYPE: DNA
<213> ORGANISM: Murine

<400> SEQUENCE: 1522

| | |
|---|---|
| gccaacatcg tggcttacca | 20 |

<210> SEQ ID NO 1523
<211> LENGTH: 20
<212> TYPE: DNA
<213> ORGANISM: Murine

<400> SEQUENCE: 1523

| | |
|---|---|
| cgacaaggtg tctaaggacc | 20 |

<210> SEQ ID NO 1524
<211> LENGTH: 20
<212> TYPE: DNA
<213> ORGANISM: Murine

<400> SEQUENCE: 1524

| | |
|---|---|
| atcaccagag gtaactgcca | 20 |

<210> SEQ ID NO 1525
<211> LENGTH: 20
<212> TYPE: DNA
<213> ORGANISM: Murine

<400> SEQUENCE: 1525

| | |
|---|---|
| atgggctaag acatcaccag | 20 |

<210> SEQ ID NO 1526
<211> LENGTH: 20
<212> TYPE: DNA
<213> ORGANISM: Human

<400> SEQUENCE: 1526

| | |
|---|---|
| atggggaagt ctttaaggtg | 20 |

<210> SEQ ID NO 1527
<211> LENGTH: 20
<212> TYPE: DNA
<213> ORGANISM: Human

<400> SEQUENCE: 1527

| | |
|---|---|
| gggtgcacat caaagagcgg | 20 |

<210> SEQ ID NO 1528
<211> LENGTH: 20
<212> TYPE: DNA
<213> ORGANISM: Human

<400> SEQUENCE: 1528

-continued tacacccacg tagtccggct                                               20

<210> SEQ ID NO 1529
<211> LENGTH: 20
<212> TYPE: DNA
<213> ORGANISM: Human

<400> SEQUENCE: 1529
cctttgcaag gctcgagaca                                               20

<210> SEQ ID NO 1530
<211> LENGTH: 20
<212> TYPE: DNA
<213> ORGANISM: Human

<400> SEQUENCE: 1530
gttgcttcct gaagggtgac                                               20

<210> SEQ ID NO 1531
<211> LENGTH: 20
<212> TYPE: DNA
<213> ORGANISM: Human

<400> SEQUENCE: 1531
ctgggcgcca ctcaccagta                                               20

<210> SEQ ID NO 1532
<211> LENGTH: 20
<212> TYPE: DNA
<213> ORGANISM: Human

<400> SEQUENCE: 1532
agggtgacag gtatgagcct                                               20

<210> SEQ ID NO 1533
<211> LENGTH: 20
<212> TYPE: DNA
<213> ORGANISM: Human

<400> SEQUENCE: 1533
tatgacctgc tacagcggct                                               20

<210> SEQ ID NO 1534
<211> LENGTH: 20
<212> TYPE: DNA
<213> ORGANISM: Human

<400> SEQUENCE: 1534
gatctgcatg gaattctgtg                                               20

<210> SEQ ID NO 1535
<211> LENGTH: 20
<212> TYPE: DNA
<213> ORGANISM: Human

<400> SEQUENCE: 1535
gctgggatac cagttgatgc                                               20

<210> SEQ ID NO 1536
<211> LENGTH: 20
<212> TYPE: DNA
<213> ORGANISM: Human

-continued

<400> SEQUENCE: 1536
ctttcctagc cggactacgt                                       20

<210> SEQ ID NO 1537
<211> LENGTH: 20
<212> TYPE: DNA
<213> ORGANISM: Human

<400> SEQUENCE: 1537
agagggtgca catcaaagag                                       20

<210> SEQ ID NO 1538
<211> LENGTH: 20
<212> TYPE: DNA
<213> ORGANISM: Human

<400> SEQUENCE: 1538
cccatggtag gccacgatgt                                       20

<210> SEQ ID NO 1539
<211> LENGTH: 20
<212> TYPE: DNA
<213> ORGANISM: Murine

<400> SEQUENCE: 1539
tggacggctg ctgttgctgg                                       20

<210> SEQ ID NO 1540
<211> LENGTH: 20
<212> TYPE: DNA
<213> ORGANISM: Murine

<400> SEQUENCE: 1540
ccttgcagcc ctcgcaggtg                                       20

<210> SEQ ID NO 1541
<211> LENGTH: 20
<212> TYPE: DNA
<213> ORGANISM: Murine

<400> SEQUENCE: 1541
aaatgcaaaa tatgtttgcc                                       20

<210> SEQ ID NO 1542
<211> LENGTH: 20
<212> TYPE: DNA
<213> ORGANISM: Murine

<400> SEQUENCE: 1542
gaagtgtctc agtgtcggga                                       20

<210> SEQ ID NO 1543
<211> LENGTH: 20
<212> TYPE: DNA
<213> ORGANISM: Murine

<400> SEQUENCE: 1543
atggaagagg gtcgcgagca                                       20

<210> SEQ ID NO 1544
<211> LENGTH: 20
<212> TYPE: DNA
<213> ORGANISM: Murine

```
<400> SEQUENCE: 1544
ggcagcgttg tcgccgcaca                                              20

<210> SEQ ID NO 1545
<211> LENGTH: 20
<212> TYPE: DNA
<213> ORGANISM: Murine

<400> SEQUENCE: 1545
ttccgagcca taagtctgcg                                              20

<210> SEQ ID NO 1546
<211> LENGTH: 20
<212> TYPE: DNA
<213> ORGANISM: Murine

<400> SEQUENCE: 1546
gaaggcacat gtgccgtgtg                                              20

<210> SEQ ID NO 1547
<211> LENGTH: 20
<212> TYPE: DNA
<213> ORGANISM: Murine

<400> SEQUENCE: 1547
tgcgtggcgt aagtggaccc                                              20

<210> SEQ ID NO 1548
<211> LENGTH: 20
<212> TYPE: DNA
<213> ORGANISM: Murine

<400> SEQUENCE: 1548
tggacggctg ctgttgctgg                                              20

<210> SEQ ID NO 1549
<211> LENGTH: 20
<212> TYPE: DNA
<213> ORGANISM: Murine

<400> SEQUENCE: 1549
ccttgcagcc ctcgcaggtg                                              20

<210> SEQ ID NO 1550
<211> LENGTH: 20
<212> TYPE: DNA
<213> ORGANISM: Murine

<400> SEQUENCE: 1550
catggtcagc ttggtgtagt                                              20

<210> SEQ ID NO 1551
<211> LENGTH: 20
<212> TYPE: DNA
<213> ORGANISM: Murine

<400> SEQUENCE: 1551
gctatactgg gcttgcacgc                                              20

<210> SEQ ID NO 1552
<211> LENGTH: 20
<212> TYPE: DNA
```

-continued

<213> ORGANISM: Murine

<400> SEQUENCE: 1552
ccccgtgcta ccgaggtcca                                               20

<210> SEQ ID NO 1553
<211> LENGTH: 20
<212> TYPE: DNA
<213> ORGANISM: Murine

<400> SEQUENCE: 1553
ttcagaagtg tctcagtgtc                                               20

<210> SEQ ID NO 1554
<211> LENGTH: 20
<212> TYPE: DNA
<213> ORGANISM: Murine

<400> SEQUENCE: 1554
ttcggcgtct cttgtccact                                               20

<210> SEQ ID NO 1555
<211> LENGTH: 20
<212> TYPE: DNA
<213> ORGANISM: Human

<400> SEQUENCE: 1555
tcaatcagat ttggaaatgt                                               20

<210> SEQ ID NO 1556
<211> LENGTH: 20
<212> TYPE: DNA
<213> ORGANISM: Human

<400> SEQUENCE: 1556
ctacggcgtg cgaacctgcg                                               20

<210> SEQ ID NO 1557
<211> LENGTH: 20
<212> TYPE: DNA
<213> ORGANISM: Human

<400> SEQUENCE: 1557
atacagctcg gaatacacca                                               20

<210> SEQ ID NO 1558
<211> LENGTH: 20
<212> TYPE: DNA
<213> ORGANISM: Human

<400> SEQUENCE: 1558
ctgattgagt catgcatgta                                               20

<210> SEQ ID NO 1559
<211> LENGTH: 20
<212> TYPE: DNA
<213> ORGANISM: Human

<400> SEQUENCE: 1559
tggtgatggt gatggtagct                                               20

<210> SEQ ID NO 1560
<211> LENGTH: 20

<212> TYPE: DNA
<213> ORGANISM: Human

<400> SEQUENCE: 1560
gaaatcgaca gtactgacat                                               20

<210> SEQ ID NO 1561
<211> LENGTH: 20
<212> TYPE: DNA
<213> ORGANISM: Human

<400> SEQUENCE: 1561
cctgcgtgta ccaaatgcag                                               20

<210> SEQ ID NO 1562
<211> LENGTH: 20
<212> TYPE: DNA
<213> ORGANISM: Human

<400> SEQUENCE: 1562
gggcacgtgt gccgtgtgcg                                               20

<210> SEQ ID NO 1563
<211> LENGTH: 20
<212> TYPE: DNA
<213> ORGANISM: Human

<400> SEQUENCE: 1563
ataacgcccc cgcctgcggg                                               20

<210> SEQ ID NO 1564
<211> LENGTH: 20
<212> TYPE: DNA
<213> ORGANISM: Human

<400> SEQUENCE: 1564
ggactgcttg aagtacatgg                                               20

<210> SEQ ID NO 1565
<211> LENGTH: 20
<212> TYPE: DNA
<213> ORGANISM: Human

<400> SEQUENCE: 1565
ccacctcggc tacgacccga                                               20

<210> SEQ ID NO 1566
<211> LENGTH: 20
<212> TYPE: DNA
<213> ORGANISM: Human

<400> SEQUENCE: 1566
aaatgcaaaa tatgtttgcc                                               20

<210> SEQ ID NO 1567
<211> LENGTH: 25
<212> TYPE: RNA
<213> ORGANISM: Artificial Sequence
<220> FEATURE:
<223> OTHER INFORMATION: Zc3h12a siRNA

<400> SEQUENCE: 1567
ccuggacaac uuccuucgua agaaa                                         25

<210> SEQ ID NO 1568
<211> LENGTH: 19
<212> TYPE: RNA
<213> ORGANISM: Artificial Sequence
<220> FEATURE:
<223> OTHER INFORMATION: Zc3h12a siRNA

<400> SEQUENCE: 1568
gugucccuau ggaaggaaa                                                    19

<210> SEQ ID NO 1569
<211> LENGTH: 19
<212> TYPE: RNA
<213> ORGANISM: Artificial Sequence
<220> FEATURE:
<223> OTHER INFORMATION: Zc3h12a siRNA

<400> SEQUENCE: 1569
caacuuccuu cguaagaaa                                                    19

<210> SEQ ID NO 1570
<211> LENGTH: 21
<212> TYPE: DNA
<213> ORGANISM: Artificial Sequence
<220> FEATURE:
<223> OTHER INFORMATION: Zc3h12a shRNA

<400> SEQUENCE: 1570
agcgaggcca cacagatatt a                                                 21

<210> SEQ ID NO 1571
<211> LENGTH: 21
<212> TYPE: DNA
<213> ORGANISM: Artificial Sequence
<220> FEATURE:
<223> OTHER INFORMATION: Zc3h12a shRNA

<400> SEQUENCE: 1571
gctatgatga ccgcttcatt g                                                 21

<210> SEQ ID NO 1572
<211> LENGTH: 21
<212> TYPE: DNA
<213> ORGANISM: Artificial Sequence
<220> FEATURE:
<223> OTHER INFORMATION: Zc3h12a shRNA

<400> SEQUENCE: 1572
tggtctgagc cgtacccatt a                                                 21

<210> SEQ ID NO 1573
<211> LENGTH: 21
<212> TYPE: DNA
<213> ORGANISM: Artificial Sequence
<220> FEATURE:
<223> OTHER INFORMATION: Zc3h12a shRNA

<400> SEQUENCE: 1573
ctgtgtacag aggcgagatt t                                                 21

<210> SEQ ID NO 1574
<211> LENGTH: 20
<212> TYPE: DNA
<213> ORGANISM: Homo sapiens

<400> SEQUENCE: 1574

```
agatgatgtc aaccaaggag                                          20

<210> SEQ ID NO 1575
<211> LENGTH: 20
<212> TYPE: DNA
<213> ORGANISM: Mus musculus

<400> SEQUENCE: 1575
ggaagaagta catctgcaag                                          20
```

GENE-REGULATING COMPOSITIONS AND METHODS FOR IMPROVED IMMUNOTHERAPY

CROSS-REFERENCE TO RELATED APPLICATIONS

This application is a continuation of U.S. application Ser. No. 16/791,273, filed Feb. 14, 2020, which is a continuation of U.S. application Ser. No. 16/354,102, filed Mar. 14, 2019, which claims priority to U.S. Provisional Application No. 62/804,265, filed Feb. 12, 2019, U.S. Provisional Application No. 62/768,428, filed Nov. 16, 2018, U.S. Provisional Application No. 62/768,443, filed Nov. 16, 2018, U.S. Provisional Application No. 62/768,448, filed Nov. 16, 2018, U.S. Provisional Application No. 62/768,458, filed Nov. 16, 2018, U.S. Provisional Application No. 62/692,010, filed Jun. 29, 2018, U.S. Provisional Application No. 62/692,019, filed Jun. 29, 2018, U.S. Provisional Application No. 62/692,100, filed Jun. 29, 2018, U.S. Provisional Application No. 62/692,110, filed Jun. 29, 2018, U.S. Provisional Application No. 62/643,578, filed Mar. 15, 2018, U.S. Provisional Application No. 62/643,587, filed Mar. 15, 2018, U.S. Provisional Application No. 62/643,597, filed Mar. 15, 2018, and U.S. Provisional Application No. 62/643,598, filed Mar. 15, 2018, each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: K071370003US06-SEQ-HJD.txt; date recorded: Jun. 24, 2021; file size 308 kilobytes).

FIELD

The disclosure relates to methods, compositions, and components for editing a target nucleic acid sequence, or modulating expression of a target nucleic acid sequence, and applications thereof in connection with immunotherapy, including use with receptor-engineered immune effector cells, in the treatment of cell proliferative diseases, inflammatory diseases, and/or infectious diseases.

BACKGROUND

Adoptive cell transfer utilizing genetically modified T cells, in particular CAR-T cells has entered clinical testing as a therapeutic for solid and hematologic malignancies. Results to date have been mixed. In hematologic malignancies (especially lymphoma, CLL and ALL), the majority of patients in several Phase 1 and 2 trials exhibited at least a partial response, with some exhibiting complete responses (Kochenderfer et al., 2012 Blood 1 19, 2709-2720). In 2017, the FDA approved two CAR-T therapies, Kymriah™ and Yescarta™, both for the treatment of hematological cancers. However, in most tumor types (including melanoma, renal cell carcinoma and colorectal cancer), fewer responses have been observed (Johnson et al., 2009 Blood 1 14, 535-546; Lamers et al., 2013 Mol. Ther. 21, 904-912; Warren et al., 1998 Cancer Gene Ther. 5, S1-S2). As such, there is considerable room for improvement with adoptive T cell therapies, as success has largely been limited to CAR-T cells approaches targeting hematological malignancies of the B cell lineage.

SUMMARY

There exists a need to improve the efficacy of adoptive transfer of modified immune cells in cancer treatment, in particular increasing the efficacy of adoptive cell therapies against solid malignancies, as reduced responses have been observed in these tumor types (melanoma, renal cell carcinoma and colorectal cancer; Yong, 2017, Imm Cell Biol., 95:356-363). In addition, even in hematological malignancies where a benefit of adoptive transfer has been observed, not all patients respond and relapses occur with a greater than desired frequency, likely as a result of diminished function of the adoptively transferred T cells.

Factors limiting the efficacy of genetically modified immune cells as cancer therapeutics include (1) cell proliferation, e.g., limited proliferation of T cells following adoptive transfer; (2) cell survival, e.g., induction of T cell apoptosis by factors in the tumor environment; and (3) cell function, e.g., inhibition of cytotoxic T cell function by inhibitory factors secreted by host immune cells and cancer cells and exhaustion of immune cells during manufacturing processes and/or after transfer.

Particular features thought to increase the anti-tumor effects of an immune cell include a cell's ability to 1) proliferate in the host following adoptive transfer; 2) infiltrate a tumor; 3) persist in the host and/or exhibit resistance to immune cell exhaustion; and 4) function in a manner capable of killing tumor cells. The present disclosure provides immune cells comprising decreased expression and/or function of one or more endogenous target genes wherein the modified immune cells demonstrate an enhancement of one or more effector functions including increased proliferation, increased infiltration into tumors, persistence of the immune cells in a subject, and/or increased resistance to immune cell exhaustion. The present disclosure also provides methods and compositions for modification of immune effector cells to elicit enhanced immune cell activity towards a tumor cell, as well as methods and compositions suitable for use in the context of adoptive immune cell transfer therapy.

In some embodiments, the present disclosure provides a modified immune effector cell comprising reduced expression and/or function of ZC3H12A nucleic acid or protein (also known as Regnase-1). The present disclosure describes and demonstrates inhibition of ZC3H12A by multiple modalities, including CRISPR/Cas systems, zinc-finger systems, and siRNA/shRNA systems. In some embodiments, the reduced expression/function of ZC3H12A is mediated by an antibody, a small molecule, or a peptide. In some embodiments, the present disclosure provides a method of killing a cancerous cell comprising exposing the cancerous cell to a ZC3H12A protein inhibitor, wherein said inhibitor is an antibody, small molecule or peptide that binds to ZC3H12A and reduces ZC3H12A function and wherein said inhibitor is in an amount effective to kill said cancerous cell. In some embodiments, the exposure is in vitro, in vivo, or ex vivo In some embodiments, the present disclosure provides a modified immune effector cell comprising a gene-regulating system capable of reducing expression and/or function of one or more endogenous target genes selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c)

MAP4K1; or (d) NR4A3. In some embodiments, the reduced expression and/or function of the one or more endogenous genes enhances an effector function of the immune effector cell.

In some embodiments, the present disclosure provides a modified immune effector cell comprising a gene-regulating system capable of reducing the expression and/or function of one or more endogenous target genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the reduced expression and/or function of the one or more endogenous genes enhances an effector function of the immune effector cell. In some embodiments, the gene-regulating system is capable of reducing the expression and/or function of two or more of endogenous target genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and at least one of the endogenous target genes is selected from the group consisting of CBLB, PPP2R2D, NRP1, HAVCR2, LAG3, TIGIT, CTLA4, PTPN6, PDCD1, and BCOR.

In some embodiments, the gene-regulating system is capable of reducing the expression and/or function of at least one endogenous target gene selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR.

In some embodiments, the gene-regulating system is capable of reducing the expression and/or function of ZC3H12A and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the gene-regulating system is capable of reducing the expression and/or function of ZC3H12A and CBLB. In some embodiments, the gene-regulating system is capable of reducing the expression and/or function of ZC3H12A and BCOR. In some embodiments, the gene-regulating system is capable of reducing the expression and/or function of ZC3H12A and TNFAIP3.

In some embodiments, the gene-regulating system is capable of reducing the expression and/or function of MAP4K1 and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the gene-regulating system is capable of reducing the expression and/or function of MAP4K1 and CBLB. In some embodiments, the gene-regulating system is capable of reducing the expression and/or function of MAP4K1 and BCOR. In some embodiments, the gene-regulating system is capable of reducing the expression and/or function of MAP4K1 and TNFAPI3.

In some embodiments, the gene-regulating system is capable of reducing the expression and/or function of NR4A3 and at least one endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the gene-regulating system is capable of reducing the expression and/or function of NR4A3 and CBLB. In some embodiments, the gene-regulating system is capable of reducing the expression and/or function of NR4A3 and BCOR. In some embodiments, the gene-regulating system is capable of reducing the expression and/or function of NR4A3 and TNFAPI3.

In some embodiments, the present disclosure provides a modified immune effector cell comprising a gene-regulating system, wherein the gene-regulating system comprises (i) one or more nucleic acid molecules; (ii) one or more enzymatic proteins; or (iii) one or more guide nucleic acid molecules and an enzymatic protein. In some embodiments, the one or more nucleic acid molecules are selected from an siRNA, an shRNA, a microRNA (miR), an antagomiR, or an antisense RNA. In some embodiments, the gene-regulating system comprises an siRNA or an shRNA nucleic acid molecule.

In some embodiments, the present disclosure provides a modified immune effector cell comprising a gene-regulating system, wherein the gene-regulating system comprises an siRNA or an shRNA nucleic acid molecule, wherein the siRNA or shRNA molecule comprises about 19-30 nucleotides that bind to an RNA sequence encoded by a DNA sequence defined by a set of genome coordinates shown in Table 5A and Table 5B. In some embodiments, the siRNA or shRNA comprises about 19-30 nucleotides that bind to an RNA sequence encoded by a DNA sequence selected from the group consisting of SEQ ID NOs: 154-813. In some embodiments, the gene-regulating system comprises an siRNA or an shRNA nucleic acid molecule, wherein the siRNA or shRNA molecule comprises about 19-30 nucleotides that bind to an RNA sequence encoded by a DNA sequence defined by a set of genome coordinates shown in Table 6A and Table 6B. In some embodiments, the siRNA or shRNA comprises about 19-30 nucleotides that bind to an RNA sequence encoded by a DNA sequence selected from the group consisting of SEQ ID NOs: 814-1064.

In some embodiments, the gene-regulating system comprises an siRNA or an shRNA nucleic acid molecule, wherein the siRNA or shRNA molecule comprises about 19-30 nucleotides that bind to an RNA sequence encoded by a DNA sequence defined by a set of genome coordinates shown in Table 6C and Table 6D. In some embodiments, the siRNA or shRNA comprises about 19-30 nucleotides that bind to an RNA sequence encoded by a DNA sequence selected from the group consisting of SEQ ID NOs: 1065-1509. In some embodiments, the gene-regulating system comprises an siRNA or an shRNA nucleic acid molecule, wherein the siRNA or shRNA molecule comprises about 19-30 nucleotides that bind to an RNA sequence encoded by a DNA sequence defined by a set of genome coordinates shown in Table 6E and Table 6F. In some embodiments, the siRNA or shRNA comprises about 19-30 nucleotides that bind to an RNA sequence encoded by a DNA sequence selected from the group consisting of SEQ ID NOs: 510-1538. In some embodiments, the gene-regulating system comprises an siRNA or an shRNA nucleic acid molecule, wherein the siRNA or shRNA molecule comprises about 19-30 nucleotides that bind to an RNA sequence encoded by a DNA sequence defined by a set of genome coordinates shown in Table 6G and Table 6H. In some embodiments, the siRNA or shRNA comprises about 19-30 nucleotides that bind to an RNA sequence encoded by a DNA sequence selected from the group consisting of SEQ ID NOs: 1539-1566.

In some embodiments, the gene-regulating system comprises a plurality of siRNA or shRNA molecules and is capable of reducing the expression and/or function of two or more endogenous target genes. In some embodiments, at least one of the endogenous target genes is selected from the group consisting of BCL2L11, FLI1, CALM2, DHODH, UMPS, RBM39, SEMA7A, CHIC2, PCBP 1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to to an RNA sequence encoded by a DNA sequence defined by a set of genome coordinates shown in Table 6A and Table 6B and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and at least one of the plurality of siRNA or shRNA molecules comprises about 19-30 nucleotides that bind to an RNA sequence encoded by a DNA sequence selected from the group consisting of SEQ ID NOs: 154-813. In some embodiments, at least one of the endogenous target genes is selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of TNFAIP3, CBLB, and BCOR.

In some embodiments, the gene-regulating system comprises a plurality of siRNA or shRNA molecules and is capable of reducing the expression and/or function of two or more endogenous target genes. In some embodiments, at least one of the endogenous target genes is ZC3H12A and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1065-1509 and at least one of the plurality of siRNA or shRNA molecules comprises about 19-30 nucleotides that bind to an RNA sequence encoded by a DNA sequence selected from the group consisting of SEQ ID NOs: 154-813. In some embodiments, at least one of the endogenous target genes is selected from the group consisting of ZC3H12A and at least one of the endogenous target genes is selected from the group consisting of TNFAIP3, CBLB, and BCOR.

In some embodiments, the gene-regulating system comprises a plurality of siRNA or shRNA molecules and is capable of reducing the expression and/or function of two or more endogenous target genes. In some embodiments, at least one of the endogenous target genes is MAP4K1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6E and Table 6F and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 510-1538 and at least one of the plurality of siRNA or shRNA molecules comprises about 19-30 nucleotides that bind to an RNA sequence encoded by a DNA sequence selected from the group consisting of SEQ ID NOs: 154-813. In some embodiments, at least one of the endogenous target genes is MAP4K1 and at least one of the endogenous target genes is selected from the group consisting of TNFAIP3, CBLB, and BCOR.

In some embodiments, the gene-regulating system comprises a plurality of siRNA or shRNA molecules and is capable of reducing the expression and/or function of two or more endogenous target genes. In some embodiments, at least one of the endogenous target genes is NR4A3 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6G and Table 6H and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1539-1566 and at least one of the plurality of siRNA or shRNA molecules comprises about 19-30 nucleotides that bind to an RNA sequence encoded by a DNA sequence selected from the group consisting of SEQ ID NOs: 154-813. In some embodiments, at least one of the endogenous target genes is NR4A3 and at least one of the endogenous target genes is selected from the group consisting of TNFAIP3, CBLB, and BCOR.

In some embodiments, the present disclosure provides a modified immune effector cell comprising a gene-regulating system, wherein the gene-regulating system comprises an enzymatic protein, and wherein the enzymatic protein has been engineered to specifically bind to a target sequence in one or more of the endogenous genes. In some embodiments, the protein is a Transcription activator-like effector nuclease (TALEN), a zinc-finger nuclease, or a meganuclease.

In some embodiments, the present disclosure provides a modified immune effector cell comprising a gene-regulating system, wherein the gene-regulating system comprises a guide nucleic acid molecule and an enzymatic protein, wherein the nucleic acid molecule is a guide RNA (gRNA) molecule and the enzymatic protein is a Cas protein or Cas ortholog.

In some embodiments, the present disclosure provides a modified immune effector cell comprising a gene-regulating system capable of reducing the expression and/or function of at least one endogenous target gene, wherein the gene-regulating system comprises a guide RNA (gRNA) molecule and a Cas protein or Cas ortholog, and wherein the one or more endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, and wherein the gRNA molecule comprises a targeting domain sequence that binds to a nucleic acid sequence defined by a set of genome coordinates shown in Table 5A and Table 5B. In some embodiments, the gRNA molecule comprises a targeting domain sequence that binds to a target DNA sequence selected from the group consisting of SEQ ID NOs: 154-813. In some embodiments, the gRNA molecule comprises a targeting domain sequence encoded by a nucleic acid sequence selected from the group consisting of SEQ ID NOs: 154-813.

In some embodiments, the present disclosure provides a modified immune effector cell comprising a gene-regulating system capable of reducing the expression and/or function of at least one endogenous target gene, wherein the gene-regulating system comprises a guide RNA (gRNA) molecule and a Cas protein or Cas ortholog, and wherein the one or more endogenous target genes is selected from the group consisting of BCL2L11, FLI1, CALM2, DHODH, UMPS, RBM39, SEMA7A, CHIC2, PCBP1, PBRM1, WDR6, E2F8, SERPINA3, and GNAS, and wherein the gRNA molecule comprises a targeting domain sequence that binds to a nucleic acid sequence defined by a set of genome coordinates shown in Table 6A and Table 6B. In some embodiments, the gRNA molecule comprises a targeting domain sequence that binds to a target DNA sequence selected from the group consisting of SEQ ID NOs: 814-1064. In some embodiments, the gRNA molecule comprises a targeting domain sequence encoded by a nucleic acid sequence selected from the group consisting of SEQ ID NOs: 814-1064.

In some embodiments, the present disclosure provides a modified immune effector cell comprising a gene-regulating system capable of reducing the expression and/or function of at least one endogenous target gene, wherein the gene-regulating system comprises a guide RNA (gRNA) molecule and a Cas protein or Cas ortholog, and wherein the one or more endogenous target genes is ZC3H12A, and wherein the gRNA molecule comprises a targeting domain sequence that binds to a nucleic acid sequence defined by a set of genome coordinates shown in Table 6C and Table 6D. In some embodiments, the gRNA molecule comprises a targeting domain sequence that binds to a nucleic acid sequence selected from the group consisting of SEQ ID NOs: 1065-1509. In some embodiments, the gRNA molecule comprises a targeting domain sequence encoded by a nucleic acid sequence selected from the group consisting of SEQ ID NOs: 1065-1509.

In some embodiments, the present disclosure provides a modified immune effector cell comprising a gene-regulating system capable of reducing the expression and/or function of at least one endogenous target gene, wherein the gene-regulating system comprises a guide RNA (gRNA) molecule and a Cas protein or Cas ortholog, and wherein the one or more endogenous target genes is MAP4K1, and wherein the gRNA molecule comprises a targeting domain sequence that binds to a nucleic acid sequence defined by a set of genome coordinates shown in Tables 6E and 6F. In some embodiments, the gRNA molecule comprises a targeting domain sequence that binds to a target DNA sequence selected from the group consisting of SEQ ID NOs: 510-1538. In some embodiments, the gRNA molecule comprises a targeting domain sequence encoded by a nucleic acid sequence selected from the group consisting of SEQ ID NOs: 510-1538.

In some embodiments, the present disclosure provides a modified immune effector cell comprising a gene-regulating system capable of reducing the expression and/or function of at least one endogenous target gene, wherein the gene-regulating system comprises a guide RNA (gRNA) molecule and a Cas protein or Cas ortholog, and wherein the one or more endogenous target genes is NR4A3, and wherein the gRNA molecule comprises a targeting domain sequence that binds to a nucleic acid sequence defined by a set of genome coordinates shown in Tables 6G and 6H. In some embodiments, the gRNA molecule comprises a targeting domain sequence that binds to a target DNA sequence selected from the group consisting of SEQ ID NOs: 1539-1566. In some embodiments, the gRNA molecule comprises a targeting domain sequence encoded by a nucleic acid sequence selected from the group consisting of SEQ ID NOs: 1539-1566.

In some embodiments, the present disclosure provides a modified immune effector cell comprising a gene-regulating system capable of reducing the expression and/or function of at least two endogenous target genes, wherein the gene-regulating system comprises a plurality of gRNAs and a Cas protein or Cas ortholog. In some embodiments, the present disclosure provides a modified immune effector cell comprising a gene-regulating system capable of reducing the expression and/or function of at least two endogenous target genes, wherein the gene-regulating system comprises a plurality of gRNAs and a Cas protein or Cas ortholog, wherein at least one of the endogenous target genes selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6A and Table 6B and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 814-1064 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 814-1064 and at least one of the plurality of gRNA molecules comprises a targeting domain sequence encoded by a nucleic acid sequence selected from the group consisting of SEQ ID NOs: 154-813. In some embodiments, at least one of the endogenous target genes selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of TNFAIP3, CBLB, and BCOR.

In some embodiments, the present disclosure provides a modified immune effector cell comprising a gene-regulating system capable of reducing the expression and/or function of at least two endogenous target genes, wherein the gene-regulating system comprises a plurality of gRNAs and a Cas protein or Cas ortholog, wherein at least one of the endogenous target genes is ZC3H12A and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6C and Table 6D and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 1065-1509 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a DNA sequence selected from the group consisting of SEQ ID NOs: 1065-1509 and at least one of the plurality of gRNA molecules comprises a targeting domain sequence encoded by a DNA sequence selected from the group consisting of SEQ ID NOs: 154-813. In some embodiments, at least one of the endogenous target genes is ZC3H12A and at least one of the endogenous target genes is selected from the group consisting of TNFAIP3, CBLB, and BCOR.

In some embodiments, the present disclosure provides a modified immune effector cell comprising a gene-regulating system capable of reducing the expression and/or function of at least two endogenous target genes, wherein the gene-regulating system comprises a plurality of gRNAs and a Cas protein or Cas ortholog, wherein at least one of the endogenous target genes is MAP4K1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6E and Table 6F and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 510-1538 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 510-1538 and at least one of the plurality of gRNA molecules comprises a targeting domain sequence encoded by a DNA sequence selected from the group consisting of SEQ ID NOs: 154-813. In some embodiments, at least one of the endogenous target genes is MAP4K1 and at least one of the endogenous target genes is selected from the group consisting of TNFAIP3, CBLB, and BCOR.

In some embodiments, the present disclosure provides a modified immune effector cell comprising a gene-regulating system capable of reducing the expression and/or function of at least two endogenous target genes, wherein the gene-regulating system comprises a plurality of gRNAs and a Cas protein or Cas ortholog, wherein at least one of the endogenous target genes is NR4A3 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNA molecules comprises a targeting domain sequence that binds to a nucleic acid sequence defined by a set of genome coordinates shown in Table 6G and Table 6H and at least one of the plurality of gRNA molecule comprises a targeting domain sequence that binds to a nucleic acid sequence defined by a set of genome coordinates shown in Table 5A and Table 5B. In some embodiments, at least one of the plurality of gRNA molecules comprises a targeting domain sequence that binds to a target DNA sequence selected from the group consisting of SEQ ID NOs: 1539-1566 and at least one of the plurality of gRNA molecules comprises a targeting domain sequence that binds to a target DNA sequence selected from the group consisting of SEQ ID NOs: 154-813. In some embodiments, at least one of the plurality of gRNA molecules comprises a targeting domain sequence encoded by a nucleic acid sequence selected from the group consisting of SEQ ID NOs: 1539-1566 and at least one of the plurality of gRNA molecules comprises a targeting domain sequence encoded by a nucleic acid sequence selected from the group consisting of SEQ ID NOs: 154-813. In some embodiments, at least one of the endogenous target genes is NR4A3 and at least one of the endogenous target genes is selected from the group consisting of TNFAIP3, CBLB, and BCOR.

In some embodiments, the present disclosure provides a modified immune effector cell comprising a Cas protein or Cas ortholog, wherein: (a) the Cas protein is a wild-type Cas protein comprising two enzymatically active domains, and capable of inducing double stranded DNA breaks; (b) the Cas protein is a Cas nickase mutant comprising one enzymatically active domain and capable of inducing single stranded DNA breaks; or (c) the Cas protein is a deactivated Cas protein (dCas) and is associated with a heterologous protein capable of modulating the expression of the one or more endogenous target genes. In some embodiments, the Cas protein is a Cas9 protein. In some embodiments, the heterologous protein is selected from the group consisting of MAX-interacting protein 1 (MXI1), Krüppel-associated box (KRAB) domain, methyl-CpG binding protein 2 (MECP2), and four concatenated mSin3 domains (SID4X).

In some embodiments, the gene regulating system introduces an inactivating mutation into the one or more endogenous target genes. In some embodiments, the inactivating mutation comprises a deletion, substitution, or insertion of one or more nucleotides in the genomic sequences of the two or more endogenous genes. In some embodiments, the deletion is a partial or complete deletion of the two or more endogenous target genes. In some embodiments, the inactivating mutation is a frame shift mutation. In some embodiments, the inactivating mutation reduces the expression and/or function of the two or more endogenous target genes.

In some embodiments, the gene-regulating system is introduced to the immune effector cell by transfection, transduction, electroporation, or physical disruption of the cell membrane by a microfluidics device. In some embodiments, the gene-regulating system is introduced as a polynucleotide encoding one or more components of the system, a protein, or a ribonucleoprotein (RNP) complex.

In some embodiments, the present disclosure provides a modified immune effector cell comprising reduced expression and/or function of one or more endogenous genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the one or more endogenous genes enhances an effector function of the immune effector cell. In some embodiments, the present disclosure provides a modified immune effector cell comprising reduced expression and/or function of one or more endogenous genes selected from: (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR, wherein the reduced expression and/or function of the one or more endogenous genes enhances an effector function of the immune effector cell.

In some embodiments, the present disclosure provides a modified immune effector cell comprising reduced expression and/or function of one or more endogenous genes selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c) MAP4K1; or (d) NR4A3, wherein the reduced expression and/or function of the one or more endogenous genes enhances an effector function of the modified immune effector cell.

In some embodiments, the present disclosure provides a modified immune effector cell comprising reduced expression and/or function of two or more target genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector comprises reduced expression and/or function of CBLB and BCOR.

In some embodiments, the present disclosure provides a modified immune effector cell comprising reduced expression and/or function of two or more target genes, wherein at least one target gene is selected from the group consisting of BCL2L11, FLI1, CALM2, DHODH, UMPS, RBM39, SEMA7A, CHIC2, PCBP1, PBRM1, WDR6, E2F8, SERPINA3, and GNAS, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell.

In some embodiments, the present disclosure provides a modified immune effector cell comprising reduced expression and/or function of two or more target genes, wherein at least one target gene is ZC3H12A, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector comprises reduced expression and/or function of ZC3H12A and CBLB. In some embodiments, the modified immune effector comprises reduced expression and/or function of ZC3H12A and BCOR. In some embodiments, the modified immune effector comprises reduced expression and/or function of ZC3H12A and TNFAIP3.

In some embodiments, the present disclosure provides a modified immune effector cell comprising reduced expression and/or function of two or more target genes, wherein at least one target gene is MAP4K1, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector comprises reduced expression and/or function of MAP4K1 and CBLB. In some embodiments, the modified immune effector comprises reduced expression and/or function of MAP4K1 and BCOR. In some embodiments, the modified immune effector comprises reduced expression and/or function of MAP4K1 and TNFAIP3.

In some embodiments, the present disclosure provides a modified immune effector cell comprising reduced expression and/or function of two or more target genes, wherein at least one target gene is NR4A3, and wherein at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR, wherein the reduced expression and/or function of the two or more endogenous genes enhances an effector function of the modified immune effector cell. In some embodiments, the modified immune effector comprises reduced expression and/or function of NR4A3 and CBLB. In some embodiments, the modified immune effector comprises reduced expression and/or function of NR4A3 and BCOR. In some embodiments, the modified immune effector comprises reduced expression and/or function of NR4A3 and TNFAIP3.

In some embodiments, the present disclosure provides a modified immune effector cell comprising an inactivating mutation in one or more endogenous genes selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the present disclosure provides a modified immune effector cell comprising an inactivating mutation in one or more endogenous genes selected from: (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR.

In some embodiments, the present disclosure provides a modified immune effector cell comprising an inactivating mutation in one or more endogenous genes selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c) MAP4K1; or (d) NR4A3.

In some embodiments, the present disclosure provides a modified immune effector cell comprising an inactivating mutation in two or more target genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector comprises an inactivating mutation in the CBLB and BCOR genes.

In some embodiments, the present disclosure provides a modified immune effector cell comprising an inactivating mutation in two or more target genes, wherein at least one target gene is selected from the group consisting of BCL2L11, FLI1, CALM2, DHODH, UMPS, RBM39, SEMA7A, CHIC2, PCBP1, PBRM1, WDR6, E2F8, SERPINA3, and GNAS, and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR.

In some embodiments, the present disclosure provides a modified immune effector cell comprising an inactivating mutation in two or more target genes, wherein at least one target gene is ZC3H12A and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector comprises an inactivating mutation in the ZC3H12A and CBLB genes. In some embodiments, the modified immune effector comprises an inactivating mutation in the ZC3H12A and BCOR genes. In some embodiments, the modified immune effector comprises an inactivating mutation in the ZC3H12A and TNFAIP3 genes.

In some embodiments, the present disclosure provides a modified immune effector cell comprising an inactivating mutation in two or more target genes, wherein at least one target gene is MAP4K1 and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector comprises an inactivating mutation in the MAP4K1 and CBLB genes. In some embodiments, the modified immune effector comprises an inactivating mutation in the MAP4K1 and BCOR genes. In some embodiments, the modified immune effector comprises an inactivating mutation in the MAP4K1 and TNFAIP3 genes.

In some embodiments, the present disclosure provides a modified immune effector cell comprising an inactivating mutation in two or more target genes, wherein at least one target gene is NR4A3 and at least one target gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, the modified immune effector comprises an inactivating mutation in the NR4A3 and CBLB genes. In some embodiments, the modified immune effector comprises an inactivating mutation in the NR4A3 and BCOR genes. In some embodiments, the modified immune effector comprises an inactivating mutation in the NR4A3 and TNFAIP3 genes.

In some embodiments, the inactivating mutation comprises a deletion, substitution, or insertion of one or more nucleotides in the genomic sequences of the two or more endogenous genes. In some embodiments, the deletion is a partial or complete deletion of the two or more endogenous target genes. In some embodiments, the inactivating mutation is a frame shift mutation. In some embodiments, the inactivating mutation reduces the expression and/or function of the two or more endogenous target genes.

In some embodiments, the expression of the one or more endogenous target genes is reduced by at least 50%, at least 60%, at least 70%, at least 80%, or at least 90% compared to an un-modified or control immune effector cell. In some embodiments, the function of the one or more endogenous target genes is reduced by at least 50%, at least 60%, at least 70%, at least 80%, or at least 90% compared to an un-modified or control immune effector cell.

In some embodiments, the modified immune effector cell further comprises an engineered immune receptor displayed on the cell surface. In some embodiments, the engineered immune receptor is a CAR comprising an antigen-binding domain, a transmembrane domain, and an intracellular signaling domain. In some embodiments, the engineered immune receptor is an engineered TCR. In some embodiments, the engineered immune receptor specifically binds to an antigen expressed on a target cell, wherein the antigen is a tumor-associated antigen.

In some embodiments, the modified immune effector cell further comprises an exogenous transgene expressing an immune activating molecule. In some embodiments, the immune activating molecule is selected from the group consisting of a cytokine, a chemokine, a co-stimulatory molecule, an activating peptide, an antibody, or an antigen-binding fragment thereof. In some embodiments, the antibody or binding fragment thereof specifically binds to and inhibits the function of the protein encoded by NRP1, HAVCR2, LAG3, TIGIT, CTLA4, or PDCD1.

In some embodiments, the immune effector cell is a wherein the immune effector cell is a lymphocyte selected from a T cell, a natural killer (NK) cell, an NKT cell. In some embodiments, the lymphocyte is a tumor infiltrating lymphocyte (TIL).

In some embodiments, the effector function is selected from cell proliferation, cell viability, tumor infiltration, cytotoxicity, anti-tumor immune responses, and/or resistance to exhaustion.

In some embodiments, the present disclosure provides a composition comprising the modified immune effector cells described herein. In some embodiments, the composition further comprises a pharmaceutically acceptable carrier or diluent. In some embodiments, the composition comprises at least $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ modified immune effector cells. In some embodiments, the composition is suitable for administration to a subject in need thereof. In some embodiments, the composition comprises autologous immune effector cells derived from the subject in need thereof. In some embodiments, the composition comprises allogeneic immune effector cells derived from a donor subject.

In some embodiments, the present disclosure provides a gene-regulating system capable of reducing expression and/or function of one or more endogenous target genes in a cell selected from: (a) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (b) the group consisting of CBLB, PPP2R2D, NRP1, HAVCR2, LAG3, TIGIT, CTLA4, PTPN6, PDCD1, and BCOR, wherein the system comprises (i) a nucleic acid molecule; (ii) an enzymatic; or (iii) a guide nucleic acid molecule and an enzymatic protein.

In some embodiments, the present disclosure provides a gene-regulating system capable of reducing expression of one or more endogenous target genes in a cell selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c) MAP4K1; or (d) NR4A3, wherein the system comprises (i) a nucleic acid molecule; (ii) an enzymatic; or (iii) a guide nucleic acid molecule and an enzymatic protein.

In some embodiments, the present disclosure provides a gene-regulating system capable of reducing expression of one or more endogenous target genes in a cell comprising a guide RNA (gRNA) nucleic acid molecule and a Cas endonuclease.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 or is selected from CBLB, PPP2R2D, NRP1, HAVCR2, LAG3, TIGIT, CTLA4, PTPN6, PDCD1, and BCOR and wherein the gRNA molecule comprises a targeting domain sequence that binds to a target DNA sequence defined by a set of genomic coordinates shown in Table 5A and Table 5B. In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and wherein the gRNA molecule comprises a targeting domain sequence that binds to a target DNA sequence selected from the group consisting of SEQ ID NOs: 154-498. In some embodiments, the gRNA molecule comprises a targeting domain sequence encoded by a nucleic acid sequence selected from the group consisting of SEQ ID NOs: 154-498.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target genes are selected from CBLB, PPP2R2D, NRP1, HAVCR2, LAG3, TIGIT, CTLA4, PTPN6, PDCD1, and BCOR and wherein the gRNA molecule comprises a targeting domain sequence that binds to a target DNA sequence selected from the group consisting of SEQ ID NOs: 499-813. In some embodiments, the gRNA molecule comprises a targeting domain sequence encoded by a nucleic acid sequence selected from the group consisting of SEQ ID NOs: 499-813.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target genes are selected from BCL2L11, FLI1, CALM2, DHODH, UMPS, RBM39, SEMA7A, CHIC2, PCBP1, PBRM1, WDR6, E2F8, SERPINA3, and GNAS and wherein the gRNA molecule comprises a targeting domain sequence that binds to a target DNA sequence defined by a set of genomic coordinates shown in Table 6A and Table 6B. In some embodiments, the gRNA molecule comprises a targeting domain sequence that binds to a target DNA sequence selected from the group consisting of SEQ ID NOs: 814-1064. In some embodiments, the gRNA molecule comprises a targeting domain sequence encoded by a nucleic acid sequence selected from the group consisting of SEQ ID NOs: 814-1064.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target gene is ZC3H12A and wherein the gRNA molecule comprises a targeting domain sequence that binds to a target DNA sequence defined by a set of genomic coordinates shown in Table 6C and Table 6D. In some embodiments, the gRNA molecule comprises a targeting domain sequence that binds to a target DNA sequence selected from the group consisting of SEQ ID NOs: 1065-1509. In some embodiments, the gRNA molecule comprises a targeting domain sequence encoded by a nucleic acid sequence selected from the group consisting of SEQ ID NOs: 1065-1509. In some embodiments, the gRNA molecule comprises a targeting domain sequence encoded by a nucleic acid sequence selected from the group consisting of SEQ ID NOs: 1065-1509.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target genes comprises MAP4K1 and wherein the gRNA molecule comprises a targeting domain sequence that binds to a target DNA sequence defined by a set of genomic coordinates shown in Table 6E and Table 6F. In some embodiments, the gRNA molecule comprises a targeting domain sequence that binds to a target DNA sequence selected from the group consisting of SEQ ID NOs: 510-1538. In some embodiments, the gRNA molecule comprises a targeting domain sequence encoded by a nucleic acid sequence selected from the group consisting of SEQ ID NOs: 510-1538.

In some embodiments, the present disclosure provides a gene-regulating system capable of reducing expression of one or more endogenous target genes in a cell comprising a guide RNA (gRNA) nucleic acid molecule and a Cas endonuclease, wherein the one or more endogenous target genes comprises NR4A3 and wherein the gRNA molecule comprises a targeting domain sequence that binds to a target DNA sequence defined by a set of genomic coordinates shown in Table 6G and Table 6H. In some embodiments, the gRNA molecule comprises a targeting domain sequence that binds to a target DNA sequence selected from the group consisting of SEQ ID NOs: 1539-1566. In some embodiments, the gRNA molecule comprises a targeting domain sequence encoded by a nucleic acid sequence selected from the group consisting of SEQ ID NOs: 1539-1566.

In some embodiments, the gene-regulating system comprises an siRNA or an shRNA nucleic acid molecule.

In some embodiments, the present disclosure provides a gene-regulating system capable of reducing expression of one or more endogenous target genes in a cell, wherein the gene-regulating system comprises an siRNA or an shRNA nucleic acid molecule and wherein the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 or is selected from CBLB, PPP2R2D, NRP1, HAVCR2, LAG3, TIGIT, CTLA4, PTPN6, PDCD1, and BCOR and wherein the siRNA or shRNA molecule comprises about 19-30 nucleotides that bind to an RNA sequence encoded by a DNA sequence defined by a set of genome coordinates shown in Table 5A and Table 5B. In some embodiments, the one or more endogenous target genes are selected from IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and wherein the siRNA or shRNA molecule comprises about 19-30 nucleotides that bind to an RNA sequence encoded by a DNA sequence selected from SEQ ID NOs: 154-498. In some embodiments, the one or more endogenous target genes are selected from CBLB, PPP2R2D, NRP1, HAVCR2, LAG3, TIGIT, CTLA4, PTPN6, PDCD1, and BCOR and wherein the siRNA or shRNA molecule comprises about 19-30 nucleotides that bind to an RNA sequence encoded by a DNA sequence selected from SEQ ID NOs: 499-813.

In some embodiments, the present disclosure provides a gene-regulating system capable of reducing expression of one or more endogenous target genes in a cell, wherein the gene-regulating system comprises an siRNA or an shRNA nucleic acid molecule, wherein the one or more endogenous target genes are selected from BCL2L11, FLI1, CALM2, DHODH, UMPS, RBM39, SEMA7A, CHIC2, PCBP1, PBRM1, WDR6, E2F8, SERPINA3, and GNAS and wherein the siRNA or shRNA molecule comprises about 19-30 nucleotides that bind to an RNA sequence encoded by a DNA sequence defined by a set of genome coordinates shown in Table 6A and Table 6B. In some embodiments, the siRNA or shRNA molecule comprises about 19-30 nucleotides that bind to an RNA sequence encoded by a DNA sequence selected from SEQ ID NOs: 814-1064.

In some embodiments, the present disclosure provides a gene-regulating system capable of reducing expression of one or more endogenous target genes in a cell, wherein the gene-regulating system comprises an siRNA or an shRNA nucleic acid molecule, wherein the one or more endogenous target gene is ZC3H12A and wherein the siRNA or shRNA molecule comprises about 19-30 nucleotides that bind to an RNA sequence encoded by a DNA sequence defined by a set of genome coordinates shown in Table 6C and Table 6D. In some embodiments, the siRNA or shRNA molecule comprises about 19-30 nucleotides that bind to an RNA sequence encoded by a DNA sequence selected from SEQ ID NOs: 1065-1509.

In some embodiments, the present disclosure provides a gene-regulating system capable of reducing expression of one or more endogenous target genes in a cell, wherein the gene-regulating system comprises an siRNA or an shRNA nucleic acid molecule, wherein the one or more endogenous target genes comprises MAP4K1 and wherein the siRNA or shRNA molecule comprises about 19-30 nucleotides that bind to an RNA sequence encoded by a DNA sequence defined by a set of genome coordinates shown in Table 6E and Table 6F. In some embodiments, the siRNA or shRNA molecule comprises about 19-30 nucleotides that bind to an RNA sequence encoded by a DNA sequence selected from SEQ ID NOs: 510-1538.

In some embodiments, the present disclosure provides a gene-regulating system capable of reducing expression of one or more endogenous target genes in a cell, wherein the gene-regulating system comprises an siRNA or an shRNA nucleic acid molecule, wherein the one or more endogenous target genes comprises NR4A3 and wherein the siRNA or shRNA molecule comprises about 19-30 nucleotides that bind to an RNA sequence encoded by a DNA sequence defined by a set of genome coordinates shown in Table 6G and Table 6H. In some embodiments, the siRNA or shRNA molecule comprises about 19-30 nucleotides that bind to an RNA sequence encoded by a DNA sequence selected from SEQ ID NOs: 1539-1566.

In some embodiments, the present disclosure provides a gene-regulating system capable of reducing the expression and/or function of two or more endogenous target genes in a cell, wherein at least one of the endogenous target genes is selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c) MAP4K1; or (d) NR4A3, and wherein at least one of the endogenous target genes is selected from: (e) the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (f) the group consisting of CBLB, PPP2R2D, NRP1, HAVCR2, LAG3, TIGIT, CTLA4, PTPN6, PDCD1, and BCOR, wherein the system comprises (i) a nucleic acid molecule; (ii) an enzymatic; or (iii) a guide nucleic acid molecule and an enzymatic protein In some embodiments, the present disclosure provides a gene-regulating system capable of reducing the expression and/or function of two or more endogenous target genes in a cell, wherein the system comprises a plurality of guide RNA (gRNA) nucleic acid molecules and a Cas endonuclease.

In some embodiments, the present disclosure provides a gene-regulating system capable of reducing the expression and/or function of two or more endogenous target genes in a cell, wherein the system comprises a plurality of guide RNA (gRNA) nucleic acid molecules and a Cas endonuclease, wherein at least one of the endogenous target genes is selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6A and Table 6B, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 814-1064 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence encoded by a nucleic acid sequence selected from the group consisting of SEQ ID NOs: 814-1064 and wherein at least one of the plurality of gRNA molecules comprises a targeting domain sequence encoded by a nucleic acid sequence selected from SEQ ID NOs: 154-498 or SEQ ID NOs: 499-813.

In some embodiments, the present disclosure provides a gene-regulating system capable of reducing the expression and/or function of two or more endogenous target genes in a cell, wherein the system comprises a plurality of guide RNA (gRNA) nucleic acid molecules and a Cas endonuclease, wherein at least one of the endogenous target genes is ZC3H12A and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6C and Table 6D, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 1065-1509 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence that binds to a target DNA sequence selected from the group consisting of SEQ ID NOs: 1065-1509 and wherein at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 1065-1509 and wherein at least one of the plurality of gRNA molecules comprises a targeting domain sequence encoded by a nucleic acid sequence selected from the group consisting of SEQ ID NOs: 154-498 or SEQ ID NOs: 499-813. In some embodiments, at least one of the plurality of gRNA molecules comprises a targeting domain sequence encoded by a nucleic acid sequence selected from the group consisting of SEQ ID NOs: 1065-1509 and wherein at least one of the plurality of gRNA molecules comprises a targeting domain sequence encoded by a nucleic acid sequence selected from SEQ ID NOs: 499-524.

In some embodiments, the present disclosure provides a gene-regulating system capable of reducing the expression and/or function of two or more endogenous target genes in a cell, wherein the system comprises a plurality of guide RNA (gRNA) nucleic acid molecules and a Cas endonuclease, wherein at least one of the endogenous target genes is MAP4K1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6E and Table 6F, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 510-1538 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence that binds to a target DNA sequence selected from the group consisting of SEQ ID NOs: 510-1538 and wherein at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 510-1538 and wherein at least one of the plurality of gRNA molecules comprises a targeting domain sequence encoded by a nucleic acid sequence selected from SEQ ID NOs: 154-498 or SEQ ID NOs: 499-813. In some embodiments, at least one of the plurality of gRNA molecules comprises a targeting domain sequence encoded by a nucleic acid sequence selected from the group consisting of SEQ ID NOs: 510-1538 and wherein at least one of the plurality of gRNA molecules comprises a targeting domain sequence encoded by a nucleic acid sequence selected from the group consisting of SEQ ID NOs: 499-524.

In some embodiments, the present disclosure provides a gene-regulating system capable of reducing the expression and/or function of two or more endogenous target genes in a cell, wherein the system comprises a plurality of guide RNA (gRNA) nucleic acid molecules and a Cas endonuclease, wherein at least one of the endogenous target genes is NR4A3 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of gRNAs binds to a target DNA sequence defined by a set of genomic coordinates shown in Table 6G and Table 6H, and wherein at least one of the plurality of gRNAs binds to a target DNA sequence defined by a set of genomic coordinates shown in Table 5A and Table 5B. In some embodiments, at least one of the plurality of gRNA molecules comprises a targeting domain sequence that binds to a target DNA sequence selected from the group consisting of SEQ ID NOs: 1539-1566 and wherein at least one of the plurality of gRNA molecules comprises a targeting domain sequence that binds to a target DNA sequence selected from the group consisting of SEQ ID NOs: 154-498 or SEQ ID NOs: 499-813. In some embodiments, at least one of the plurality of gRNA molecules comprises a targeting domain sequence that binds to a target DNA sequence selected from the group consisting of SEQ ID NOs: 1539-1566 and wherein at least one of the plurality of gRNA molecules comprises a targeting domain sequence that binds to a target DNA sequence selected from the group consisting of SEQ ID NOs: 499-524. In some embodiments, at least one of the plurality of gRNA molecules comprises a targeting domain sequence encoded by a nucleic acid sequence selected from the group consisting of SEQ ID NOs: 1539-1566 and wherein at least one of the plurality of gRNA molecules comprises a targeting domain sequence encoded by a nucleic acid sequence selected from SEQ ID NOs: 154-498 or SEQ ID NOs: 499-813. In some embodiments, at least one of the plurality of gRNA molecules comprises a targeting domain sequence encoded by a nucleic acid sequence selected from the group consisting of SEQ ID NOs: 1539-1566 and wherein at least one of the plurality of gRNA molecules comprises a targeting domain sequence encoded by a nucleic acid sequence selected from the group consisting of SEQ ID NOs: 499-524.

In some embodiments, the gene-regulating system comprises a Cas protein, wherein the Cas protein is: (a) a wild-type Cas protein comprising two enzymatically active domains, and capable of inducing double stranded DNA breaks; (b) a Cas nickase mutant comprising one enzymatically active domain and capable of inducing single stranded DNA breaks; (c) a deactivated Cas protein (dCas) and is associated with a heterologous protein capable of modulating the expression of the one or more endogenous target genes. In some embodiments, the heterologous protein is selected from the group consisting of MAX-interacting protein 1 (MXI1), Krüppel-associated box (KRAB) domain, and four concatenated mSin3 domains (SID4X). In some embodiments, the Cas protein is a Cas9 protein.

In some embodiments, the gene-regulating system comprises a nucleic acid molecule and wherein the nucleic acid molecule is an siRNA, an shRNA, a microRNA (miR), an antagomiR, or an antisense RNA. In some embodiments, the gene-regulating system comprises a plurality of shRNA or siRNA molecules.

In some embodiments, the present disclosure provides a gene-regulating system capable of reducing the expression and/or function of two or more endogenous target genes in a cell, wherein the gene-regulating system comprises a plurality of shRNA or siRNA molecules, wherein at least one of the endogenous target genes is selected from the group consisting of BCL2L11, FLI1, CALM2, DHODH, UMPS, RBM39, SEMA7A, CHIC2, PCBP1, PBRM1, WDR6, E2F8, SERPINA3, and GNAS and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6A and Table 6B and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 814-1064 and wherein at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813.

In some embodiments, the present disclosure provides a gene-regulating system capable of reducing the expression and/or function of two or more endogenous target genes in a cell, wherein the gene-regulating system comprises a plurality of shRNA or siRNA molecules, wherein at least one of the endogenous target genes is ZC3H12A and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6C and Table 6D and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1065-1509 and at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813. In some embodiments, at least one of the plurality of siRNA or shRNA molecules comprises about 19-30 nucleotides that bind to an RNA sequence encoded by a DNA sequence selected from the group consisting of SEQ ID NOs: 1065-1509 and at least one of the plurality of siRNA or shRNA molecules comprises about 19-30 nucleotides that bind to an RNA sequence encoded by a DNA sequence selected from the group consisting of SEQ ID NOs: 499-524.

In some embodiments, the present disclosure provides a gene-regulating system capable of reducing the expression and/or function of two or more endogenous target genes in a cell, wherein the gene-regulating system comprises a plurality of shRNA or siRNA molecules, wherein at least one of the endogenous target genes is MAP4K1 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6E and Table 6F and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 510-1538 and at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813. In some embodiments, at least one of the plurality of siRNA or shRNA molecules comprises about 19-30 nucleotides that bind to an RNA sequence encoded by a DNA sequence selected from the group consisting of SEQ ID NOs: 510-1538 and at least one of the plurality of siRNA or shRNA molecules comprises about 19-30 nucleotides that bind to an RNA sequence encoded by a DNA sequence selected from the group consisting of SEQ ID NOs: 499-524.

In some embodiments, the present disclosure provides a gene-regulating system capable of reducing the expression and/or function of two or more endogenous target genes in a cell, wherein the gene-regulating system comprises a plurality of shRNA or siRNA molecules, wherein at least one of the endogenous target genes is NR4A3 and at least one of the endogenous target genes is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR. In some embodiments, at least one of the plurality of siRNA or shRNA molecules comprises about 19-30 nucleotides that bind to an RNA sequence encoded by a DNA sequence defined by a set of genome coordinates shown in Table 6G and Table 6H and at least one of the plurality of siRNA or shRNA molecules comprises about 19-30 nucleotides that bind to an RNA sequence encoded by a DNA sequence defined by a set of genome coordinates shown in Table 5A and Table 5B. In some embodiments, at least one of the plurality of siRNA or shRNA molecules comprises about 19-30 nucleotides that bind to an RNA sequence encoded by a DNA sequence selected from the group consisting of SEQ ID NOs: 1539-1566 and at least one of the plurality of siRNA or shRNA molecules comprises about 19-30 nucleotides that bind to an RNA sequence encoded by a DNA sequence selected from the group consisting of SEQ ID NOs: 154-498 or SEQ ID NOs: 499-813. In some embodiments, at least one of the plurality of siRNA or shRNA molecules comprises about 19-30 nucleotides that bind to an RNA sequence selected from the group consisting of SEQ ID NOs: 1539-1566 and at least one of the plurality of siRNA or shRNA molecules comprises about 19-30 nucleotides that bind to an RNA sequence encoded by a DNA sequence selected from the group consisting of SEQ ID NOs: 499-524.

In some embodiments, the gene-regulating system comprises a protein comprising a DNA binding domain and an enzymatic domain and is selected from a zinc finger nuclease and a transcription-activator-like effector nuclease (TALEN).

In some embodiments, the present disclosure provides a gene-regulating system comprising a vector encoding one or more gRNAs and a vector encoding a Cas endonuclease protein, wherein the one or more gRNAs comprise a targeting domain sequence encoded by a nucleic acid sequence selected from: SEQ ID NOs: 814-1064, SEQ ID NOs: 1065-1509, SEQ ID NOs: 510-1538, SEQ ID NOs: 1539-1566, SEQ ID NOs: 154-498, or SEQ ID NOs: 499-813.

In some embodiments, the present disclosure provides a gene-regulating system comprising a vector encoding a plurality of gRNAs and a vector encoding a Cas endonuclease protein, wherein at least one of the plurality of gRNA comprises a targeting domain sequence encoded by a nucleic acid sequence selected from: SEQ ID NOs: 814-1064, SEQ ID NOs: 1065-1509, SEQ ID NOs: 510-1538, or SEQ ID NOs: 1539-1566, and wherein at least one of the plurality of gRNA comprises a targeting domain sequence encoded by a nucleic acid sequence selected from: SEQ ID NOs: 154-498 or SEQ ID NOs: 499-813.

In some embodiments, the present disclosure provides a gene-regulating system comprising a vector encoding one or more gRNAs and an mRNA molecule encoding a Cas endonuclease protein, wherein the one or more gRNAs comprise a targeting domain sequence encoded by a nucleic acid sequence selected from SEQ ID NOs: 814-1064, SEQ ID NOs: 1065-1509, SEQ ID NOs: 510-1538, SEQ ID NOs: 1539-1566, SEQ ID NOs: 154-498, or SEQ ID NOs: 499-813.

In some embodiments, the present disclosure provides a gene-regulating system comprising a vector encoding a plurality of gRNAs and an mRNA molecule encoding a Cas endonuclease protein, wherein at least one of the plurality of gRNA comprises a targeting domain sequence encoded by a nucleic acid sequence selected from: SEQ ID NOs: 814-1064, SEQ ID NOs: 1065-1509, SEQ ID NOs: 510-1538, or SEQ ID NOs: 1539-1566, and wherein at least one of the plurality of gRNA comprises a targeting domain sequence encoded by a nucleic acid sequence selected from: SEQ ID NOs: 154-498 or SEQ ID NOs: 499-813.

In some embodiments, the present disclosure provides a gene-regulating system comprising one or more gRNAs and a Cas endonuclease protein, wherein the one or more gRNAs comprise a targeting domain sequence encoded by a nucleic acid sequence selected from: SEQ ID NOs: 814-1064, SEQ ID NOs: 1065-1509, SEQ ID NOs: 510-1538, SEQ ID NOs: 1539-1566, SEQ ID NOs: 154-498, or SEQ ID NOs: 499-813, and wherein the one or more gRNAs and the Cas endonuclease protein are complexed to form a ribonucleoprotein (RNP) complex.

In some embodiments, the present disclosure provides a gene-regulating system comprising a plurality of gRNAs and a Cas endonuclease protein: wherein at least one of the plurality of gRNA comprises a targeting domain sequence encoded by a nucleic acid sequence selected from: SEQ ID NOs: 814-1064, SEQ ID NOs: 1065-1509, SEQ ID NOs: 510-1538, or SEQ ID NOs: 1539-1566, wherein at least one of the plurality of gRNA comprises a targeting domain sequence encoded by a nucleic acid sequence selected from: SEQ ID NOs: 154-498 or SEQ ID NOs: 499-813, and wherein the one or more gRNAs and the Cas endonuclease protein are complexed to form a ribonucleoprotein (RNP) complex.

In some embodiments, the present disclosure provides a kit comprising a gene-regulating system described herein.

In some embodiments, the present disclosure provides a gRNA nucleic acid molecule comprising a targeting domain nucleic acid sequence that binds to a target sequence in an endogenous target gene selected from: (a) the group consisting of BCL2L11, FLI1, CALM2, DHODH, UMPS, RBM39, SEMA7A, CHIC2, PCBP1, PBRM1, WDR6, E2F8, SERPINA3, and GNAS; (b) ZC3H12A; (c) MAP4K1; (d) NR4A3; (e) IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2; or (f) CBLB, PPP2R2D, NRP1, HAVCR2, LAG3, TIGIT, CTLA4, PTPN6, PDCD1, and BCOR. In some embodiments, (a) the endogenous gene is selected from the group consisting of BCL2L11, FLI1, CALM2, DHODH, UMPS, RBM39, SEMA7A, CHIC2, PCBP1, PBRM1, WDR6, E2F8, SERPINA3, and GNAS and the gRNA comprises a targeting domain sequence that binds to a target DNA sequence located at genomic coordinates selected from those shown in Tables 6A and 6B; (b) the endogenous gene is ZC3H12A and the gRNA comprises a targeting domain sequence that binds to a target DNA sequence located at genomic coordinates selected from those shown in Table 6C and Table 6D; (c) the endogenous gene is MAP4K1 and the gRNA comprises a targeting domain sequence that binds to a target DNA sequence located at genomic coordinates selected from those shown in Table 6E and Table 6F; (d) the endogenous gene is NR4A3 and the gRNA comprises a targeting domain sequence that binds to a target DNA sequence located at genomic coordinates selected from those shown in Table 6G and Table 6H; (e) the endogenous gene is selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, and IKZF2 and the gRNA comprises a targeting domain sequence that binds to a target DNA sequence located at genomic coordinates selected from those shown in Table 5A and Table 5B; or (f) the endogenous gene is selected from the group consisting of CBLB, PPP2R2D, NRP1, HAVCR2, LAG3, TIGIT, CTLA4, PTPN6, PDCD1, and BCOR and the gRNA comprises a targeting domain sequence that binds to a target DNA sequence located at genomic coordinates selected from those shown in Table 5A and Table 5B.

In some embodiments, the gRNA comprises a targeting domain sequence that binds to a target DNA sequence selected from SEQ ID NOs: 814-1064, SEQ ID NOs: 1065-1509, SEQ ID NOs: 510-1538, SEQ ID NOs: 1539-1566, SEQ ID NOs: 154-498, or SEQ ID NOs: 499-813. In some embodiments, the gRNA comprises a targeting domain sequence encoded by a sequence selected from SEQ ID NOs: 814-1064, SEQ ID NOs: 1065-1509, SEQ ID NOs: 510-1538, SEQ ID NOs: 1539-1566, SEQ ID NOs: 154-498, or SEQ ID NOs: 499-813. In some embodiments, the target sequence comprises a PAM sequence.

In some embodiments, the gRNA is a modular gRNA molecule. In some embodiments, the gRNA is a dual gRNA molecule. In some embodiments, the targeting domain is 16, 17, 18, 19, 20, 21, 22, 23, 24, 25, 26 or more nucleotides in length. In some embodiments, the gRNA molecule comprises a modification at or near its 5' end (e.g., within 1-10, 1-5, or 1-2 nucleotides of its 5' end) and/or a modification at or near its 3' end (e.g., within 1-10, 1-5, or 1-2 nucleotides of its 3' end). In some embodiments, the modified gRNA exhibits increased stability towards nucleases when introduced into a T cell. In some embodiments, the modified gRNA exhibits a reduced innate immune response when introduced into a T cell.

In some embodiments, the present disclosure provides a polynucleotide molecule encoding a gRNA molecule described herein. In some embodiments, the present disclosure provides a composition comprising one or more gRNA molecules described herein or polynucleotides encoding the same. In some embodiments, the present disclosure provides a kit comprising one or more gRNA molecules described herein or polynucleotides encoding the same.

In some embodiments, the present disclosure provides a method of producing a modified immune effector cell comprising: (a) obtaining an immune effector cell from a subject; (b) introducing the gene-regulating system described herein into the immune effector cell; and (c) culturing the immune effector cell such that the expression and/or function of one or more endogenous target genes is reduced compared to an immune effector cell that has not been modified.

In some embodiments, the present disclosure provides a method of producing a modified immune effector cell comprising introducing a gene-regulating system described herein into the immune effector cell. In some embodiments, the methods further comprise introducing a polynucleotide sequence encoding an engineered immune receptor selected from a CAR and a TCR. In some embodiments, the gene-regulating system and/or the polynucleotide encoding the engineered immune receptor are introduced to the immune effector cell by transfection, transduction, electroporation, or physical disruption of the cell membrane by a microfluidics device. In some embodiments, the gene-regulating system is introduced as a polynucleotide sequence encoding one or more components of the system, as a protein, or as an ribonucleoprotein (RNP) complex.

In some embodiments, the present disclosure provides a method of producing a modified immune effector cell comprising: (a) expanding a population of immune effector cells in culture; and (b) introducing a gene-regulating system described herein into the population of immune effector cells. In some embodiments, the methods further comprise obtaining the population of immune effector cells from a subject. In some embodiments, the gene-regulating system is introduced to the population of immune effector cells before, during, or after expansion. In some embodiments, the expansion of the population of immune effector cells comprises a first round expansion and a second round of expansion. In some embodiments, the gene-regulating system is introduced to the population of immune effector cells before, during, or after the first round of expansion. In some embodiments, the gene-regulating system is introduced to the population of immune effector cells before, during, or after the second round of expansion. In some embodiments, the gene-regulating system is introduced to the population of immune effector cells before the first and second rounds of expansion. In some embodiments, the gene-regulating system is introduced to the population of immune effector cells after the first and second rounds of expansion. In some embodiments, the gene-regulating system is introduced to the population of immune effector cells after the first round of expansion and before the second round of expansion.

In some embodiments, the present disclosure provides a method of treating a disease or disorder in a subject in need thereof comprising administering an effective amount of a modified immune effector described herein, or composition thereof. In some embodiments, the disease or disorder is a cell proliferative disorder, an inflammatory disorder, or an infectious disease. In some embodiments, the disease or disorder is a cancer or a viral infection. In some embodiments, the cancer is selected from a leukemia, a lymphoma, or a solid tumor. In some embodiments, the solid tumor is a melanoma, a pancreatic tumor, a bladder tumor, a lung tumor or metastasis, a colorectal cancer, or a head and neck cancer. In some embodiments, the cancer is a PD1 resistant or insensitive cancer. In some embodiments, the subject has previously been treated with a PD1 inhibitor or a PDL1 inhibitor. In some embodiments, the methods further comprise administering to the subject an antibody or binding fragment thereof that specifically binds to and inhibits the function of the protein encoded by NRP1, HAVCR2, LAG3, TIGIT, CTLA4, or PDCD1. In some embodiments, the modified immune effector cells are autologous to the subject. In some embodiments, the modified immune effector cells are allogenic to the subject. In some embodiments, the subject has not undergone lymphodepletion prior to administration of the modified immune effector cells or compositions thereof. In some embodiments, the subject does not receive high-dose IL-2 treatment with or after the administration of the modified immune effector cells or compositions thereof. In some embodiments, the subject receives low-dose IL-2 treatment with or after the administration of the modified immune effector cells or compositions thereof. In some embodiments, the subject does not receive IL-2 treatment with or after the administration of the modified immune effector cells or compositions thereof.

In some embodiments, the present disclosure provides a method of killing a cancerous cell comprising exposing the cancerous cell to a modified immune effector cell described herein or a composition thereof. In some embodiments, the exposure is in vitro, in vivo, or ex vivo.

In some embodiments, the present disclosure provides a method of enhancing one or more effector functions of an immune effector cell comprising introducing a gene-regulating system described herein into the immune effector cell. In some embodiments, the present disclosure provides a method of enhancing one or more effector functions of an immune effector cell comprising introducing a gene-regulating system described herein into the immune effector cell, wherein the modified immune effector cell demonstrates one or more enhanced effector functions compared to the immune effector cell that has not been modified. In some embodiments, the one or more effector functions are selected from cell proliferation, cell viability, cytotoxicity, tumor infiltration, increased cytokine production, anti-tumor immune responses, and/or resistance to exhaustion.

BRIEF DESCRIPTION OF THE FIGURES

FIG. 1A-FIG. 1B illustrate combinations of endogenous target genes that can be modified by the methods described herein.

FIG. 2A-FIG. 2B illustrate combinations of endogenous target genes that can be modified by the methods described herein.

FIG. 3A-FIG. 3B illustrate combinations of endogenous target genes that can be modified by the methods described herein.

FIG. 4A-FIG. 4D illustrates editing of the TRAC and B2M genes using methods described herein.

FIG. 7A shows tumor growth in mice treated with CBLB-edited OT1 T cells compared to unedited OT1 T cells. FIG. 7B-FIG. 7C shows tumor growth in mice treated with ZC3H12A-edited OT1 T cells compared to unedited OT1 T cells. FIG. 7D shows tumor growth in mice treated with MAP4K1-edited OT1 T cells compared to unedited OT1 T cells. FIG. 7E shows tumor growth in mice treated with NR4A3-edited OT1 T cells compared to unedited OT1 T cells.

FIG. 8A-FIG. 8B show tumor growth over time in a murine B16/Ova syngeneic tumor model in mice treated with single-edited T cells and/or in combination with anti-PD1 therapy. FIG. 8A shows tumor growth in mice treated with a combination of MAP4K1-edited OT1 T cells and anti-PD1 therapy compared to control and MAP4K1-edited OT1 cells alone. FIG. 8B shows tumor growth in mice treated with a combination of NR4A3-edited OT1 T cells and anti-PD1 therapy compared to control and NR4A3-edited OT1 cells alone.

FIG. 12A shows tumor growth over time in a murine A375 xenograft model for mice treated with CBLB-edited NY-ESO-1-specific TCR transgenic T cells compared to unedited NY-ESO-1-specific TCR transgenic T cells. FIG. 12B shows tumor growth over time in a murine A375 xenograft model for mice treated with ZC3H12A-edited NY-ESO-1-specific TCR transgenic T cells compared to control edited T cells.

FIG. 13A shows tumor growth after treatment with MAP4K1-edited CD19 CAR T cells compared to unedited CD19 CAR T cells. FIG. 13B shows tumor growth after treatment with NR4A3-edited CD19 CAR T cells compared to unedited CD19 CAR T cells.

FIG. 25A shows IL-6 protein production from ZC3H12A-edited PBMCs derived from donors. FIG. 25B shows IL6 mRNA expression in ZC3H12A-edited PBMCs.

DETAILED DESCRIPTION

Figures 4C, 4D:
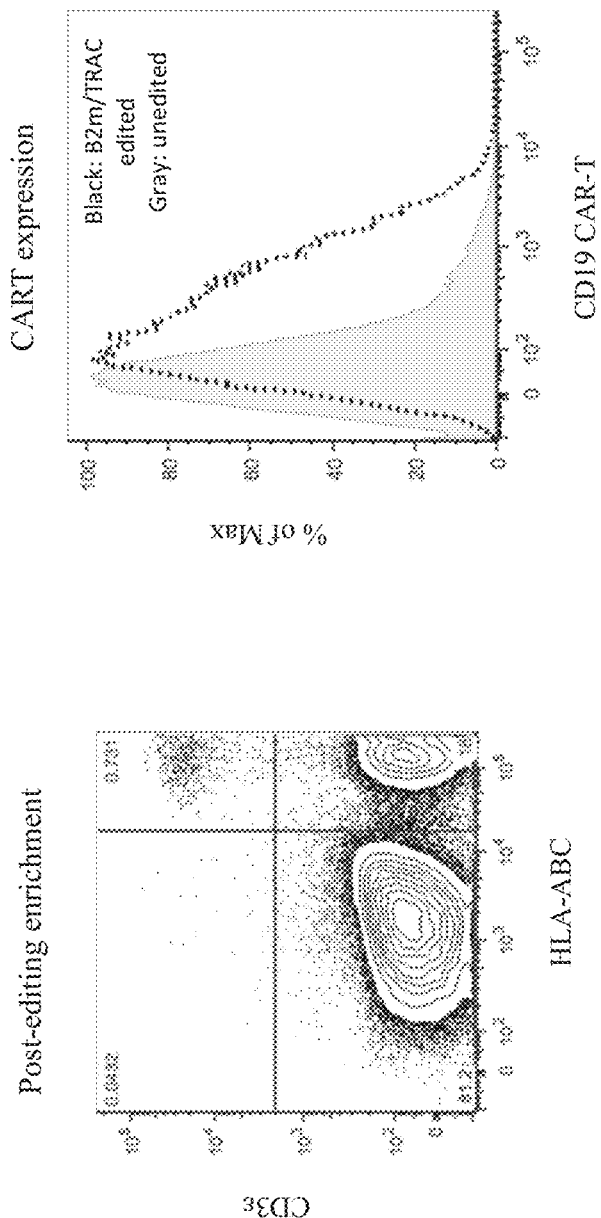

The present disclosure provides methods and compositions related to the modification of immune effector cells to increase their therapeutic efficacy in the context of immunotherapy. In some embodiments, immune effector cells are modified by the methods of the present disclosure to reduce expression of one or more endogenous target genes, or to reduce one or more functions of an endogenous protein such that one or more effector functions of the immune cells are enhanced. In some embodiments, the immune effector cells are further modified by introduction of transgenes conferring antigen specificity, such as introduction of T cell receptor (TCR) or chimeric antigen receptor (CAR) expression constructs. In some embodiments, the present disclosure provides compositions and methods for modifying immune effector cells, such as compositions of gene-regulating systems. In some embodiments, the present disclosure provides methods of treating a cell proliferative disorder, such as a cancer, comprising administration of the modified immune effector cells described herein to a subject in need thereof.

I. Definitions

As used in this specification and the appended claims, the singular forms "a," "an" and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% decrease as compared to a reference value. A decrease or reduction in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, 500%, or more increase as compared to a reference value. An increase in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, increase as compared to the level of a reference value.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Fragment" refers to a portion of a polypeptide or polynucleotide molecule containing less than the entire polypeptide or polynucleotide sequence. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, or more nucleotides or amino acids.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

The term "naturally-occurring" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

"Isolated" refers to a material that is free to varying degrees from components which normally accompany it as found in its native state.

An "expression cassette" or "expression construct" refers to a DNA polynucleotide sequence operably linked to a promoter. "Operably linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

The term "recombinant vector" as used herein refers to a polynucleotide molecule capable transferring or transporting another polynucleotide inserted into the vector. The inserted polynucleotide may be an expression cassette. In some embodiments, a recombinant vector may be viral vector or a non-viral vector (e.g., a plasmid).

The term "sample" refers to a biological composition (e.g., a cell or a portion of a tissue) that is subjected to analysis and/or genetic modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

"Treating" as used herein refers to delivering an agent or composition to a subject to affect a physiologic outcome.

As used herein, the term "effective amount" refers to the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1\times10^3$ cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ or more cells. A population of cells may refer to an in vitro population (e.g., a population of cells in culture) or an in vivo population (e.g., a population of cells residing in a particular tissue).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

II. Modified Immune Effector Cells

In some embodiments, the present disclosure provides modified immune effector cells. Herein, the term "modified immune effector cells" encompasses immune effector cells comprising one or more genomic modifications resulting in the reduced expression and/or function of one or more endogenous target genes as well as immune effector cells comprising a gene-regulating system capable of reducing the expression and/or function of one or more endogenous target genes. Herein, an "un-modified immune effector cell" or "control immune effector cell" refers to a cell or population of cells wherein the genomes have not been modified and that does not comprise a gene-regulating system or comprises a control gene-regulating system (e.g., an empty vector control, a non-targeting gRNA, a scrambled siRNA, etc.).

The term "immune effector cell" refers to cells involved in mounting innate and adaptive immune responses, including but not limited to lymphocytes (such as T-cells (including thymocytes) and B-cells), natural killer (NK) cells, NKT cells, macrophages, monocytes, eosinophils, basophils, neutrophils, dendritic cells, and mast cells. In some embodiments, the modified immune effector cell is a T cell, such as a CD4+ T cell, a CD8+ T cell (also referred to as a cytotoxic T cell or CTL), a regulatory T cell (Treg), a Th1 cell, a Th2 cell, or a Th17 cell.

In some embodiments, the immune effector cell is a T cell that has been isolated from a tumor sample (referred to herein as "tumor infiltrating lymphocytes" or "TILs"). Without wishing to be bound by theory, it is thought that TILs possess increased specificity to tumor antigens (Radvanyi et al., 2012 Clin Canc Res 18:6758-6770) and can therefore mediate tumor antigen-specific immune response (e.g., activation, proliferation, and cytotoxic activity against the cancer cell) leading to cancer cell destruction (Brudno et al., 2018 Nat Rev Clin Onc 15:31-46)) without the introduction of an exogenous engineered receptor. Therefore, in some embodiments, TILs are isolated from a tumor in a subject, expanded ex vivo, and re-infused into a subject. In some embodiments, TILs are modified to express one or more exogenous receptors specific for an autologous tumor antigen, expanded ex vivo, and re-infused into the subject. Such embodiments can be modeled using in vivo mouse models wherein mice have been transplanted with a cancer cell line expressing a cancer antigen (e.g., CD19) and are treated with modified T cells that express an exogenous receptor that is specific for the cancer antigen (See e.g., Examples 10 and 11).

In some embodiments, the immune effector cell is an animal cell or is derived from an animal cell, including invertebrate animals and vertebrate animals (e.g., fish, amphibian, reptile, bird, or mammal). In some embodiments, the immune effector cell is a mammalian cell or is derived from a mammalian cell (e.g., a pig, a cow, a goat, a sheep, a rodent, a non-human primate, a human, etc.). In some embodiments, the immune effector cell is a rodent cell or is derived from a rodent cell (e.g., a rat or a mouse). In some embodiments, the modified immune effector cell is a human cell or is derived from a human cell.

In some embodiments, the modified immune effector cells comprise one or more modifications (e.g., insertions, deletions, or mutations of one or more nucleic acids) in the genomic DNA sequence of an endogenous target gene resulting in the reduced expression and/or function the endogenous gene. Such modifications are referred to herein as "inactivating mutations" and endogenous genes comprising an inactivating mutation are referred to as "modified endogenous target genes." In some embodiments, the inactivating mutations reduce or inhibit mRNA transcription, thereby reducing the expression level of the encoded mRNA transcript and protein. In some embodiments, the inactivating mutations reduce or inhibit mRNA translation, thereby reducing the expression level of the encoded protein. In some embodiments, the inactivating mutations encode a modified endogenous protein with reduced or altered function compared to the unmodified (i.e., wild-type) version of the endogenous protein (e.g., a dominant-negative mutant, described infra).

In some embodiments, the modified immune effector cells comprise one or more genomic modifications at a genomic location other than an endogenous target gene that result in the reduced expression and/or function of the endogenous target gene or that result in the expression of a modified version of an endogenous protein. For example, in some embodiments, a polynucleotide sequence encoding a gene regulating system is inserted into one or more locations in the genome, thereby reducing the expression and/or function of an endogenous target gene upon the expression of the gene-regulating system. In some embodiments, a polynucleotide sequence encoding a modified version of an endogenous protein is inserted at one or more locations in the genome, wherein the function of the modified version of the protein is reduced compared to the un-modified or wild-type version of the protein (e.g., a dominant-negative mutant, described infra).

In some embodiments, the modified immune effector cells described herein comprise one or more modified endogenous target genes, wherein the one or more modifications result in a reduced expression and/or function of a gene product (i.e., an mRNA transcript or a protein) encoded by the endogenous target gene compared to an unmodified immune effector cell. For example, in some embodiments, a modified immune effector cell demonstrates reduced expression of an mRNA transcript and/or reduced expression of a protein. In some embodiments, the expression of the gene product in a modified immune effector cell is reduced by at least 5% compared to the expression of the gene product in an unmodified immune effector cell. In some embodiments, the expression of the gene product in a modified immune effector cell is reduced by at least 10%, 20%, 30%, 40%, 50%, 60%, 70%, 80%, 90%, or more compared to the expression of the gene product in an unmodified immune effector cell. In some embodiments, the modified immune effector cells described herein demonstrate reduced expression and/or function of gene products encoded by a plurality (e.g., two or more) of endogenous target genes compared to the expression of the gene products in an unmodified immune effector cell. For example, in some embodiments, a modified immune effector cell demonstrates reduced expression and/or function of gene products from 2, 3, 4, 5, 6, 7, 8, 9, 10, or more endogenous target genes compared to the expression of the gene products in an unmodified immune effector cell.

In some embodiments, the present disclosure provides a modified immune effector cell wherein one or more endogenous target genes, or a portion thereof, are deleted (i.e., "knocked-out") such that the modified immune effector cell does not express the mRNA transcript or protein. In some embodiments, a modified immune effector cell comprises deletion of a plurality of endogenous target genes, or portions thereof. In some embodiments, a modified immune effector cell comprises deletion of 2, 3, 4, 5, 6, 7, 8, 9, 10, or more endogenous target genes.

In some embodiments, the modified immune effector cells described herein comprise one or more modified endogenous target genes, wherein the one or more modifications to the target DNA sequence result in expression of a protein with reduced or altered function (e.g., a "modified endogenous protein") compared to the function of the corresponding protein expressed in an unmodified immune effector cell (e.g., a "unmodified endogenous protein"). In some embodiments, the modified immune effector cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates reduced or altered binding affinity for another protein expressed by the modified immune effector cell or expressed by another cell; reduced or altered signaling capacity; reduced or altered enzymatic activity; reduced or altered DNA-binding activity; or reduced or altered ability to function as a scaffolding protein.

In some embodiments, the modified endogenous target gene comprises one or more dominant negative mutations. As used herein, a "dominant-negative mutation" refers to a substitution, deletion, or insertion of one or more nucleotides of a target gene such that the encoded protein acts antagonistically to the protein encoded by the unmodified target gene. The mutation is dominant-negative because the negative phenotype confers genic dominance over the positive phenotype of the corresponding unmodified gene. A gene comprising one or more dominant-negative mutations and the protein encoded thereby are referred to as a "dominant-negative mutants", e.g. dominant-negative genes and dominant-negative proteins. In some embodiments, the dominant negative mutant protein is encoded by an exogenous transgene inserted at one or more locations in the genome of the immune effector cell.

Various mechanisms for dominant negativity are known. Typically, the gene product of a dominant negative mutant retains some functions of the unmodified gene product but lacks one or more crucial other functions of the unmodified gene product. This causes the dominant-negative mutant to antagonize the unmodified gene product. For example, as an illustrative embodiment, a dominant-negative mutant of a transcription factor may lack a functional activation domain but retain a functional DNA binding domain. In this example, the dominant-negative transcription factor cannot activate transcription of the DNA as the unmodified transcription factor does, but the dominant-negative transcription factor can indirectly inhibit gene expression by preventing the unmodified transcription factor from binding to the transcription-factor binding site. As another illustrative embodiment, dominant-negative mutations of proteins that function as dimers are known. Dominant-negative mutants of such dimeric proteins may retain the ability to dimerize with unmodified protein but be unable to function otherwise. The dominant-negative monomers, by dimerizing with unmodified monomers to form heterodimers, prevent formation of functional homodimers of the unmodified monomers.

In some embodiments, the modified immune effector cells comprise a gene-regulating system capable of reducing the expression or function of one or more endogenous target genes. The gene-regulating system can reduce the expression and/or function of the endogenous target genes modifications by a variety of mechanisms including by modifying the genomic DNA sequence of the endogenous target gene (e.g., by insertion, deletion, or mutation of one or more nucleic acids in the genomic DNA sequence); by regulating transcription of the endogenous target gene (e.g., inhibition or repression of mRNA transcription); and/or by regulating translation of the endogenous target gene (e.g., by mRNA degradation).

In some embodiments, the modified immune effector cells described herein comprise a gene-regulating system (e.g., a nucleic acid-based gene-regulating system, a protein-based gene-regulating system, or a combination protein/nucleic acid-based gene-regulating system). In such embodiments, the gene-regulating system comprised in the modified immune effector cell is capable of modifying one or more endogenous target genes. In some embodiments, the modified immune effector cells described herein comprise a gene-regulating system comprising:

(a) one or more nucleic acid molecules capable of reducing the expression or modifying the function of a gene product encoded by one or more endogenous target genes;

(b) one or more polynucleotides encoding a nucleic acid molecule that is capable of reducing the expression or modifying the function of a gene product encoded by one or more endogenous target genes;

(c) one or more proteins capable of reducing the expression or modifying the function of a gene product encoded by one or more endogenous target genes;

(d) one or more polynucleotides encoding a protein that is capable of reducing the expression or modifying the function of a gene product encoded by one or more endogenous target genes;

(e) one or more guide RNAs (gRNAs) capable of binding to a target DNA sequence in an endogenous gene;

(f) one or more polynucleotides encoding one or more gRNAs capable of binding to a target DNA sequence in an endogenous gene;

(g) one or more site-directed modifying polypeptides capable of interacting with a gRNA and modifying a target DNA sequence in an endogenous gene;

(h) one or more polynucleotides encoding a site-directed modifying polypeptide capable of interacting with a gRNA and modifying a target DNA sequence in an endogenous gene;

(i) one or more guide DNAs (gDNAs) capable of binding to a target DNA sequence in an endogenous gene;

(j) one or more polynucleotides encoding one or more gDNAs capable of binding to a target DNA sequence in an endogenous gene;

(k) one or more site-directed modifying polypeptides capable of interacting with a gDNA and modifying a target DNA sequence in an endogenous gene;

(l) one or more polynucleotides encoding a site-directed modifying polypeptide capable of interacting with a gDNA and modifying a target DNA sequence in an endogenous gene;

(m) one or more gRNAs capable of binding to a target mRNA sequence encoded by an endogenous gene;

(n) one or more polynucleotides encoding one or more gRNAs capable of binding to a target mRNA sequence encoded by an endogenous gene;

(o) one or more site-directed modifying polypeptides capable of interacting with a gRNA and modifying a target mRNA sequence encoded by an endogenous gene;

(p) one or more polynucleotides encoding a site-directed modifying polypeptide capable of interacting with a gRNA and modifying a target mRNA sequence encoded by an endogenous gene; or (q) any combination of the above.

In some embodiments, one or more polynucleotides encoding the gene-regulating system are inserted into the genome of the immune effector cell. In some embodiments, one or more polynucleotides encoding the gene-regulating system are expressed episomally and are not inserted into the genome of the immune effector cell.

In some embodiments, the modified immune effector cells described herein comprise reduced expression and/or function of one or more endogenous target genes and further comprise one or more exogenous transgenes inserted at one or more genomic loci (e.g., a genetic "knock-in"). In some embodiments, the one or more exogenous transgenes encode detectable tags, safety-switch systems, chimeric switch receptors, and/or engineered antigen-specific receptors.

In some embodiments, the modified immune effector cells described herein further comprise an exogenous transgene encoding a detectable tag. Examples of detectable tags include but are not limited to, FLAG tags, poly-histidine tags (e.g. 6× His), SNAP tags, Halo tags, cMyc tags, glutathione-S-transferase tags, avidin, enzymes, fluorescent proteins, luminescent proteins, chemiluminescent proteins, bioluminescent proteins, and phosphorescent proteins. In some embodiments the fluorescent protein is selected from the group consisting of blue/UV proteins (such as BFP, TagBFP, mTagBFP2, Azurite, EBFP2, mKalama1, Sirius, Sapphire, and T-Sapphire); cyan proteins (such as CFP, eCFP, Cerulean, SCFP3A, mTurquoise, mTurquoise2, monomeric Midoriishi-Cyan, TagCFP, and mTFP1); green proteins (such as: GFP, eGFP, meGFP (A208K mutation), Emerald, Superfolder GFP, Monomeric Azami Green, TagGFP2, mUKG, mWasabi, Clover, and mNeonGreen); yellow proteins (such as YFP, eYFP, Citrine, Venus, SYFP2, and TagYFP); orange proteins (such as Monomeric Kusabira-Orange, mKOK, mKO2, mOrange, and mOrange2); red proteins (such as RFP, mRaspberry, mCherry, mStrawberry, mTangerine, tdTomato, TagRFP, TagRFP-T, mApple, mRuby, and mRuby2); far-red proteins (such as mPlum, HcRed-Tandem, mKate2, mNeptune, and NirFP); near-infrared proteins (such as TagRFP657, IFP1.4, and iRFP); long stokes shift proteins (such as mKeima Red, LSS-mKate1, LSS-mKate2, and mBeRFP); photoactivatible proteins (such as PA-GFP, PAmCherry1, and PATagRFP); photoconvertible proteins (such as Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, and PSmOrange); and photoswitchable proteins (such as Dronpa). In some embodiments, the detectable tag can be selected from AmCyan, AsRed, DsRed2, DsRed Express, E2-Crimson, HcRed, ZsGreen, ZsYellow, mCherry, mStrawberry, mOrange, mBanana, mPlum, mRasberry, tdTomato, DsRed Monomer, and/or AcGFP, all of which are available from Clontech.

In some embodiments, the modified immune effector cells described herein further comprise an exogenous transgene encoding a safety-switch system. Safety-switch systems (also referred to in the art as suicide gene systems) comprise exogenous transgenes encoding for one or more proteins that enable the elimination of a modified immune effector cell after the cell has been administered to a subject. Examples of safety-switch systems are known in the art. For example, safety-switch systems include genes encoding for proteins that convert non-toxic pro-drugs into toxic compounds such as the Herpes simplex thymidine kinase (Hsv-tk) and ganciclovir (GCV) system (Hsv-tk/GCV). Hsv-tk converts non-toxic GCV into a cytotoxic compound that leads to cellular apoptosis. As such, administration of GCV to a subject that has been treated with modified immune effector cells comprising a transgene encoding the Hsv-tk protein can selectively eliminate the modified immune effector cells while sparing endogenous immune effector cells. (See e.g., Bonini et al., Science, 1997, 276(5319):1719-1724; Ciceri et al., Blood, 2007, 109(11):1828-1836; Bondanza et al., Blood 2006, 107(5):1828-1836).

Additional safety-switch systems include genes encoding for cell-surface markers, enabling elimination of modified immune effector cells by administration of a monoclonal antibody specific for the cell-surface marker via ADCC. In some embodiments, the cell-surface marker is CD20 and the modified immune effector cells can be eliminated by administration of an anti-CD20 monoclonal antibody such as Rituximab (See e.g., Introna et al., Hum Gene Ther, 2000, 11(4):611-620; Serafini et al., Hum Gene Ther, 2004, 14, 63-76; van Meerten et al., Gene Ther, 2006, 13, 789-797). Similar systems using EGF-R and Cetuximab or Panitumumab are described in International PCT Publication No. WO 2018006880. Additional safety-switch systems include transgenes encoding pro-apoptotic molecules comprising one or more binding sites for a chemical inducer of dimerization (CID), enabling elimination of modified immune effector cells by administration of a CID which induces oligomerization of the pro-apoptotic molecules and activation of the apoptosis pathway. In some embodiments, the pro-apoptotic molecule is Fas (also known as CD95) (Thomis et al., Blood, 2001, 97(5), 1249-1257). In some embodiments, the pro-apoptotic molecule is caspase-9 (Straathof et al., Blood, 2005, 105(11), 4247-4254).

In some embodiments, the modified immune effector cells described herein further comprise an exogenous transgene encoding a chimeric switch receptor. Chimeric switch receptors are engineered cell-surface receptors comprising an extracellular domain from an endogenous cell-surface receptor and a heterologous intracellular signaling domain, such that ligand recognition by the extracellular domain results in activation of a different signaling cascade than that activated by the wild type form of the cell-surface receptor.

In some embodiments, the chimeric switch receptor comprises the extracellular domain of an inhibitory cell-surface receptor fused to an intracellular domain that leads to the transmission of an activating signal rather than the inhibitory signal normally transduced by the inhibitory cell-surface receptor. In particular embodiments, extracellular domains derived from cell-surface receptors known to inhibit immune effector cell activation can be fused to activating intracellular domains. Engagement of the corresponding ligand will then activate signaling cascades that increase, rather than inhibit, the activation of the immune effector cell. For example, in some embodiments, the modified immune effector cells described herein comprise a transgene encoding a PD1-CD28 switch receptor, wherein the extracellular domain of PD1 is fused to the intracellular signaling domain of CD28 (See e.g., Liu et al., Cancer Res 76:6 (2016), 1578-1590 and Moon et al., Molecular Therapy 22 (2014), S201). In some embodiments, the modified immune effector cells described herein comprise a transgene encoding the extracellular domain of CD200R and the intracellular signaling domain of CD28 (See Oda et al., Blood 130:22 (2017), 2410-2419).

In some embodiments, the modified immune effector cells described herein further comprise an engineered antigen-specific receptor recognizing a protein target expressed by a target cell, such as a tumor cell or an antigen presenting cell (APC), referred to herein as "modified receptor-engineered cells" or "modified RE-cells". The term "engineered antigen receptor" refers to a non-naturally occurring antigen-specific receptor such as a chimeric antigen receptor (CAR) or a recombinant T cell receptor (TCR). In some embodiments, the engineered antigen receptor is a CAR comprising an extracellular antigen binding domain fused via hinge and transmembrane domains to a cytoplasmic domain comprising a signaling domain. In some embodiments, the CAR extracellular domain binds to an antigen expressed by a target cell in an MHC-independent manner leading to activation and proliferation of the RE cell. In some embodiments, the extracellular domain of a CAR recognizes a tag fused to an antibody or antigen-binding fragment thereof. In such embodiments, the antigen-specificity of the CAR is dependent on the antigen-specificity of the labeled antibody, such that a single CAR construct can be used to target multiple different antigens by substituting one antibody for another (See e.g., U.S. Pat. Nos. 9,233,125 and 9,624,279; US Patent Application Publication Nos. 20150238631 and 20180104354). In some embodiments, the extracellular domain of a CAR may comprise an antigen binding fragment derived from an antibody. Antigen binding domains that are useful in the present disclosure include, for example, scFvs; antibodies; antigen binding regions of antibodies; variable regions of the heavy/light chains; and single chain antibodies.

In some embodiments, the intracellular signaling domain of a CAR may be derived from the TCR complex zeta chain (such as CD3 signaling domains), FcγRIII, FcεRI, or the T-lymphocyte activation domain. In some embodiments, the intracellular signaling domain of a CAR further comprises a costimulatory domain, for example a 4-1BB, CD28, CD40, MyD88, or CD70 domain. In some embodiments, the intracellular signaling domain of a CAR comprises two costimulatory domains, for example any two of 4-1BB, CD28, CD40, MyD88, or CD70 domains. Exemplary CAR structures and intracellular signaling domains are known in the art (See e.g., WO 2009/091826; US 20130287748; WO 2015/142675; WO 2014/055657; and WO 2015/090229, incorporated herein by reference).

CARs specific for a variety of tumor antigens are known in the art, for example CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-α-specific CARs (Kershaw et al., Clin Cancer Res (2006) 12(20):6106-6015), HER2-specific CARs (Ahmed et al., J Clin Oncol (2015) 33(15)1688-1696; Nakazawa et al., Mol Ther (2011) 19(12):2133-2143; Ahmed et al., Mol Ther (2009) 17(10):1779-1787; Luo et al., Cell Res (2016) 26(7): 850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13Rα2-specific CARs (Brown et al., Clin Cacner Res (2015) 21(18):4062-4072), GD2-specific CARs (Louis et al., Blood (2011) 118(23):6050-6056; Caruana et al., Nat Med (2015) 21(5):524-529), ErbB2-specific CARs (Wilkie et al., J Clin Immunol (2012) 32(5): 1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta®) and Tisagenlecleucel (Kymriah®). See also, Li et al., J Hematol and Oncol (2018) 11(22), reviewing clinical trials of tumor-specific CARs.

In some embodiments, the engineered antigen receptor is an engineered TCR. Engineered TCRs comprise TCRα and/or TCRβ chains that have been isolated and cloned from T cell populations recognizing a particular target antigen. For example, TCRα and/or TCRβ genes (i.e., TRAC and TRBC) can be cloned from T cell populations isolated from individuals with particular malignancies or T cell populations that have been isolated from humanized mice immunized with specific tumor antigens or tumor cells. Engineered TCRs recognize antigen through the same mechanisms as their endogenous counterparts (e.g., by recognition of their cognate antigen presented in the context of major histocompatibility complex (MHC) proteins expressed on the surface of a target cell). This antigen engagement stimulates endogenous signal transduction pathways leading to activation and proliferation of the TCR-engineered cells.

Engineered TCRs specific for tumor antigens are known in the art, for example WT1-specific TCRs (JTCR016, Juno Therapeutics; WT1-TCRc4, described in US Patent Application Publication No. 20160083449), MART-1 specific TCRs (including the DMF4T clone, described in Morgan et al., Science 314 (2006) 126-129); the DMF5T clone, described in Johnson et al., Blood 114 (2009) 535-546); and the ID3T clone, described in van den Berg et al., Mol. Ther. 23 (2015) 1541-1550), gp100-specific TCRs (Johnson et al., Blood 114 (2009) 535-546), CEA-specific TCRs (Parkhurst et al., Mol Ther. 19 (2011) 620-626), NY-ESO and LAGE-1 specific TCRs (1G4T clone, described in Robbins et al., J Clin Oncol 26 (2011) 917-924; Robbins et al., Clin Cancer Res 21 (2015) 1019-1027; and Rapoport et al., Nature Medicine 21 (2015) 914-921), and MAGE-A3-specific TCRs (Morgan et al., J Immunother 36 (2013) 133-151) and Linette et al., Blood 122 (2013) 227-242). (See also, Debets et al., Seminars in Immunology 23 (2016) 10-21).

In some embodiments, the engineered antigen receptor is directed against a target antigen selected from a cluster of differentiation molecule, such as CD3, CD4, CD8, CD16, CD24, CD25, CD33, CD34, CD45, CD64, CD71, CD78, CD80 (also known as B7-1), CD86 (also known as B7-2), CD96, CD116, CD117, CD123, CD133, and CD138, CD371 (also known as CLL1); a tumor-associated surface antigen, such as 5T4, BCMA (also known as CD269 and TNFRSF17, UniProt #Q02223), carcinoembryonic antigen (CEA), carbonic anhydrase 9 (CAIX or MN/CALX), CD19, CD20, CD22, CD30, CD40, disialogangliosides such as GD2, ELF2M, ductal-epithelial mucin, ephrin B2, epithelial cell adhesion molecule (EpCAM), ErbB2 (HER2/neu), FCRL5 (UniProt #Q68SN8), FKBP11 (UniProt #Q9NYL4), glioma-associated antigen, glycosphingolipids, gp36, GPRC5D (UniProt #Q9NZD1), mut hsp70-2, intestinal carboxyl esterase, IGF-I receptor, ITGA8 (UniProt #P53708), KAMP3, LAGE-1a, MAGE, mesothelin, neutrophil elastase, NKG2D, Nkp30, NY-ESO-1, PAP, prostase, prostate-carcinoma tumor antigen-1 (PCTA-1), prostate specific antigen (PSA), PSMA, prostein, RAGE-1, ROR1, RU1 (SFMBT1), RU2 (DCDC2), SLAMF7 (UniProt #Q9NQ25), survivin, TAG-72, and telomerase; a major histocompatibility complex (MHC) molecule presenting a tumor-specific peptide epitope; tumor stromal antigens, such as the extra domain A (EDA) and extra domain B (EDB) of fibronectin; the A1 domain of tenascin-C (TnC A1) and fibroblast associated protein (FAP); cytokine receptors, such as epidermal growth factor receptor (EGFR), EGFR variant III (EGFRvIII), TFGβ-R or components thereof such as endoglin; a major histocompatibility complex (MHC) molecule; a virus-specific surface antigen such as an HIV-specific antigen (such as HIV gp120); an EBV-specific antigen, a CMV-specific antigen, a HPV-specific antigen, a Lassa virus-specific antigen, an Influenza virus-specific antigen as well as any derivate or variant of these surface antigens.

A. Effector Functions

In some embodiments, the modified immune effector cells described herein demonstrate an increase in one or more immune cell effector functions. Herein, the term "effector function" refers to functions of an immune cell related to the generation, maintenance, and/or enhancement of an immune response against a target cell or target antigen. In some embodiments, the modified immune effector cells described herein demonstrate one or more of the following characteristics compared to an unmodified immune effector cell: increased infiltration or migration in to a tumor, increased proliferation, increased or prolonged cell viability, increased resistance to inhibitory factors in the surrounding microenvironment such that the activation state of the cell is prolonged or increased, increased production of pro-inflammatory immune factors (e.g., pro-inflammatory cytokines, chemokines, and/or enzymes), increased cytotoxicity, and/or increased resistance to exhaustion.

In some embodiments, the modified immune effector cells described herein demonstrate increased infiltration into a tumor compared to an unmodified immune effector cell. In some embodiments, increased tumor infiltration by modified immune effector cells refers to an increase the number of modified immune effector cells infiltrating into a tumor during a given period of time compared to the number of unmodified immune effector cells that infiltrate into a tumor during the same period of time. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in tumor filtration compared to an unmodified immune cell. Tumor infiltration can be measured by isolating one or more tumors from a subject and assessing the number of modified immune cells in the sample by flow cytometry, immunohistochemistry, and/or immunofluorescence.

In some embodiments, the modified immune effector cells described herein demonstrate an increase in cell proliferation compared to an unmodified immune effector cell. In these embodiments, the result is an increase in the number of modified immune effector cells present compared to unmodified immune effector cells after a given period of time. For example, in some embodiments, modified immune effector cells demonstrate increased rates of proliferation compared to unmodified immune effector cells, wherein the modified immune effector cells divide at a more rapid rate than unmodified immune effector cells. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in the rate of proliferation compared to an unmodified immune cell. In some embodiments, modified immune effector cells demonstrate prolonged periods of proliferation compared to unmodified immune effector cells, wherein the modified immune effector cells and unmodified immune effector cells divide at similar rates, but wherein the modified immune effector cells maintain the proliferative state for a longer period of time. In some embodiments, the modified immune effector cells maintain a proliferative state for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased or prolonged cell viability compared to an unmodified immune effector cell. In such embodiments, the result is an increase in the number of modified immune effector cells or present compared to unmodified immune effector cells after a given period of time. For example, in some embodiments, modified immune effector cells described herein remain viable and persist for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased resistance to inhibitory factors compared to an unmodified immune effector cell. Exemplary inhibitory factors include signaling by immune checkpoint molecules (e.g., PD1, PDL1, CTLA4, LAG3, IDO) and/or inhibitory cytokines (e.g., IL-10, TGFβ).

In some embodiments, the modified T cells described herein demonstrate increased resistance to T cell exhaustion compared to an unmodified T cell. T cell exhaustion is a state of antigen-specific T cell dysfunction characterized by decreased effector function and leading to subsequent deletion of the antigen-specific T cells. In some embodiments, exhausted T cells lack the ability to proliferate in response to antigen, demonstrate decreased cytokine production, and/or demonstrate decreased cytotoxicity against target cells such as tumor cells. In some embodiments, exhausted T cells are identified by altered expression of cell surface markers and transcription factors, such as decreased cell surface expression of CD122 and CD127; increased expression of inhibitory cell surface markers such as PD1, LAG3, CD244, CD160, TIM3, and/or CTLA4; and/or increased expression of transcription factors such as Blimp1, NFAT, and/or BATF. In some embodiments, exhausted T cells demonstrate altered sensitivity to cytokine signaling, such as increased sensitivity to TGFβ signaling and/or decreased sensitivity to IL-7 and IL-15 signaling. T cell exhaustion can be determined, for example, by co-culturing the T cells with a population of target cells and measuring T cell proliferation, cytokine production, and/or lysis of the target cells. In some embodiments, the modified immune effector cells described herein are co-cultured with a population of target cells (e.g., autologous tumor cells or cell lines that have been engineered to express a target tumor antigen) and effector cell proliferation, cytokine production, and/or target cell lysis is measured. These results are then compared to the results obtained from co-culture of target cells with a control population of immune cells (such as unmodified immune effector cells or immune effector cells that have a control modification).

In some embodiments, resistance to T cell exhaustion is demonstrated by increased production of one or more cytokines (e.g., IFNγ, TNFα, or IL-2) from the modified immune effector cells compared to the cytokine production observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in cytokine production from the modified immune effector cells compared to the cytokine production from the control population of immune cells is indicative of an increased resistance to T cell exhaustion. In some embodiments, resistance to T cell exhaustion is demonstrated by increased proliferation of the modified immune effector cells compared to the proliferation observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in proliferation of the modified immune effector cells compared to the proliferation of the control population of immune cells is indicative of an increased resistance to T cell exhaustion. In some embodiments, resistance to T cell exhaustion is demonstrated by increased target cell lysis by the modified immune effector cells compared to the target cell lysis observed by the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in target cell lysis by the modified immune effector cells compared to the target cell lysis by the control population of immune cells is indicative of an increased resistance to T cell exhaustion.

In some embodiments, exhaustion of the modified immune effector cells compared to control populations of immune cells is measured during the in vitro or ex vivo manufacturing process. For example, in some embodiments, TILs isolated from tumor fragments are modified according to the methods described herein and then expanded in one or more rounds of expansion to produce a population of modified TILs. In such embodiments, the exhaustion of the modified TILs can be determined immediately after harvest and prior to a first round of expansion, after the first round of expansion but prior to a second round of expansion, and/or after the first and the second round of expansion. In some embodiments, exhaustion of the modified immune effector cells compared to control populations of immune cells is measured at one or more time points after transfer of the modified immune effector cells into a subject. For example, in some embodiments, the modified cells are produced according to the methods described herein and administered to a subject. Samples can then be taken from the subject at various time points after the transfer to determine exhaustion of the modified immune effector cells in vivo over time.

In some embodiments, the modified immune effector cells described herein demonstrate increased expression or production of pro-inflammatory immune factors compared to an unmodified immune effector cell. Examples of pro-inflammatory immune factors include cytolytic factors, such as granzyme B, perforin, and granulysin; and pro-inflammatory cytokines such as interferons (IFNα, IFNβ, IFNγ), TNFα, IL-1β, IL-12, IL-2, IL-17, CXCL8, and/or IL-6.

In some embodiments, the modified immune effector cells described herein demonstrate increased cytotoxicity against a target cell compared to an unmodified immune effector cell. In some embodiments, the modified immune effector cells demonstrate a 1, 2, 3, 4, 5, 6, 7, 8, 9, 10, 20, 30, 40, 50, 60, 70, 80, 90, 100, or more fold increase in cytotoxicity against a target cell compared to an unmodified immune cell.

Assays for measuring immune effector function are known in the art. For example, tumor infiltration can be measured by isolating tumors from a subject and determining the total number and/or phenotype of the lymphocytes present in the tumor by flow cytometry, immunohistochemistry, and/or immunofluorescence. Cell-surface receptor expression can be determined by flow cytometry, immunohistochemistry, immunofluorescence, Western blot, and/or qPCR. Cytokine and chemokine expression and production can be measured by flow cytometry, immunohistochemistry, immunofluorescence, Western blot, ELISA, and/or qPCR. Responsiveness or sensitivity to extracellular stimuli (e.g., cytokines, inhibitory ligands, or antigen) can be measured by assaying cellular proliferation and/or activation of downstream signaling pathways (e.g., phosphorylation of downstream signaling intermediates) in response to the stimuli. Cytotoxicity can be measured by target-cell lysis assays known in the art, including in vitro or ex vivo co-culture of the modified immune effector cells with target cells and in vivo murine tumor models, such as those described throughout the Examples.

B. Regulation of Endogenous Pathways and Genes

In some embodiments, the modified immune effector cells described herein demonstrate a reduced expression or function of one or more endogenous target genes and/or comprise a gene-regulating system capable of reducing the expression and/or function of one or more endogenous target genes (described infra). In some embodiments, the one or more endogenous target genes are present in pathways related to the activation and regulation of effector cell responses. In such embodiments, the reduced expression or function of the one or more endogenous target genes enhances one or more effector functions of the immune cell.

Exemplary pathways suitable for regulation by the methods described herein are shown in Table 1. In some embodiments, the expression of an endogenous target gene in a particular pathway is reduced in the modified immune effector cells. In some embodiments, the expression of a plurality (e.g., two or more) of endogenous target genes in a particular pathway are reduced in the modified immune effector cells. For example, the expression of 2, 3, 4, 5, 6, 7, 8, 9, 10, or more endogenous target genes in a particular pathway may be reduced. In some embodiments, the expression of an endogenous target gene in one pathway and the expression of an endogenous target genes in another pathway is reduced in the modified immune effector cells. In some embodiments, the expression of a plurality of endogenous target genes in one pathway and the expression of a plurality of endogenous target genes in another pathway are reduced in the modified immune effector cells. For example, the expression of 2, 3, 4, 5, 6, 7, 8, 9, 10, or more endogenous target genes in one pathway may be reduced and the expression of 2, 3, 4, 5, 6, 7, 8, 9, 10, or more endogenous target genes in another particular pathway may be reduced.

In some embodiments, the expression of a plurality of endogenous target genes in a plurality of pathways is reduced. For example, one endogenous gene from each of a plurality of pathways (e.g., 2, 3, 4, 5, 6, 7, 8, 9, 10, or more pathways) may be reduced. In additional aspects, a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be reduced.

TABLE 1

Exemplary Endogenous Pathways

| Pathway | Description |
| --- | --- |
| Lymphocyte differentiation | Signaling pathway which controls stem cell differentiation from a common lymphoid progenitor to the distinctive lymphocyte type (T cell, B cell or NK cell) |
| NFκβ signaling | Signaling pathway that controls transcription of DNA, cytokine production and cell survival generally in response to harmful cell stimuli. |
| TGF-β signaling | Signaling pathway that regulates cell growth, cell differentiation, apoptosis, cellular homeostasis and other cellular functions. |
| T cell activation | Pathway that is initiated by binding of the T cell receptor (TCR) complex to a major histocompatibility complex molecule carrying a peptide antigen and by binding of the co-stimulatory receptor CD28 to proteins in the surface of the antigen presenting cell. Activation of a TCR initiates a signaling pathway which triggers antibody production, activation of phagocytic cells and direct cell killing. |
| T cell growth | Signaling pathway that controls programmed cell death in response to either extrinsic signals or intrinsic cellular stresses |
| Pyrimidine biosynthesis | A de novo nucleotide biosynthesis pathway for components of RNA and DNA |
| Cytokine Signaling | Signaling pathways down stream of cytokine receptors, typically involve positive JAK/STAT signaling |
| Apoptosis initiation | Genes that initiate either the intrinsic or extrinsic apoptotic pathway, which drives programed cell death of the cell |
| Transcription initiation | Genes that directly bind the promoters of target genes and act as repressors or transcriptional activators of target gene transcription |
| Ca2++ binding | Ca2++ serves as a second messenger in response to stimuli and drives intracellular signaling in a number of processes, including inflammation and the immune response. In T cells, Ca2++ signaling is required for the activation of T cells in response to antigen |

Exemplary endogenous target genes are shown below in Tables 2 and 3.

In some embodiments, the modified effector cells comprise reduced expression and/or function of one or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more endogenous target genes selected from Table 2). In some embodiments, the modified effector cells comprise reduced expression and/or function of one or more of TNFAIP3, CBLB, or BCOR.

In some embodiments, the modified immune effector cells comprise reduced expression and/or function of at least two genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR (e.g., at least two genes selected from Table 2). For example, in some embodiments, the modified immune effector cells comprise reduced expression and/or function of at least two genes selected from Combination Nos. 1-600, as illustrated in FIG. 1A-FIG. 1B. In some embodiments, the modified immune effector cells comprise reduced expression and/or function of BCOR and reduced expression and/or function of CBLB. While exemplary methods for modifying the expression of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and/or BCOR are described herein, the expression of these endogenous target genes may also be modified by methods known in the art. For example, inhibitory antibodies against PD1 (encoded by PDCD1), NRP1, HACR2, LAG3, TIGIT, and CTLA4 are known in the art and some are FDA approved for oncologic indications (e.g., nivolumab and pembrolizumab for PD1).

In some embodiments, the modified immune effector cells comprise reduced expression and/or function of one or more of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., one or more endogenous target genes selected from Table 3).

In some embodiments, the modified effector cells described herein comprise reduced expression and/or function of the Semaphorin 7A, (SEMA7A) gene, also known as CD108. In some embodiments, the modified effector cells described herein comprise an inactivating mutation in the SEMA7A gene.

In some embodiments, the modified effector cells described herein comprise reduced expression and/or function of the RNA-binding protein 39 (RBM39) gene. The RBM39 protein is found in the nucleus, where it colocalizes with core spliceosomal proteins. Studies of a mouse protein with high sequence similarity to this protein suggest that this protein may act as a transcriptional coactivator for JUN/AP-1 and estrogen receptors. In some embodiments, the modified effector cells described herein comprise an inactivating mutation in the RBM39 gene.

In some embodiments, the modified effector cells described herein comprise reduced expression and/or function of the Bcl-2-like protein 11 (BCL2L11) gene, also commonly called BIM. In some embodiments, the modified effector cells described herein comprise an inactivating mutation in the BCL2L11 gene In some embodiments, the modified effector cells described herein comprise reduced expression and/or function of the Friend leukemia integration 1 transcription factor (FLI1) gene, also known as transcription factor ERGB. In some embodiments, the modified effector cells described herein comprise an inactivating mutation in the FLI1 gene.

In some embodiments, the modified effector cells described herein comprise reduced expression and/or function of the Calmodulin 2 (CALM2) gene. In some embodiments, the modified effector cells described herein comprise an inactivating mutation in the CALM2 gene.

In some embodiments, the modified effector cells described herein comprise reduced expression and/or function of the Dihydroorotate dehydrogenase gene (DHODH) gene. The DHODH protein is a mitochondrial protein located on the outer surface of the inner mitochondrial membrane and catalyzes the ubiquinone-mediated oxidation of dihydroorotate to orotate in de novo pyrimidine biosynthesis. In some embodiments, the modified effector cells described herein comprise an inactivating mutation in the DHODH gene.

In some embodiments, the modified effector cells described herein comprise reduced expression and/or function of the uridine monophosphate synthase (UMPS) gene, also referred to as orotate phosphoribosyl transferase or orotidine-5'-decarboxylase. The UMPS protein catalyses the formation of uridine monophosphate (UMP), an energy-carrying molecule in many important biosynthetic pathways. In some embodiments, the modified effector cells described herein comprise an inactivating mutation in the UMPS gene.

In some embodiments, the modified effector cells described herein comprise reduced expression and/or function of the cysteine rich hydrophobic domain 2 (CHIC2) gene. The encoded CHIC2 protein contains a cysteine-rich hydrophobic (CHIC) motif, and is localized to vesicular structures and the plasma membrane and is associated with some cases of acute myeloid leukemia. In some embodiments, the modified effector cells described herein comprise an inactivating mutation in the CHIC2 gene.

In some embodiments, the modified effector cells described herein comprise reduced expression and/or function of the Poly(rC)-binding protein 1(PCBP1) gene. In some embodiments, the modified effector cells described herein comprise an inactivating mutation in the PCBP1 gene.

In some embodiments, the modified effector cells described herein comprise reduced expression and/or function of the Protein polybromo-1 (PBRM1) gene, also known as BRG1-associated factor 180 (BAF180). PBRM1 is a component of the SWI/SNF-B chromatin-remodeling complex, and is a tumor suppressor gene in many cancer subtypes. Mutations are especially prevalent in clear cell renal cell carcinoma. In some embodiments, the modified effector cells described herein comprise an inactivating mutation in the PBRM1 gene.

In some embodiments, the modified effector cells described herein comprise reduced expression and/or function of the WD repeat-containing protein 6 (WDR6) gene, a member of the WD repeat protein family ubiquitously expressed in adult and fetal tissues. WD repeats are minimally conserved regions of approximately 40 amino acids typically bracketed by gly-his and trp-asp (GH-WD), which may facilitate formation of heterotrimeric or multiprotein complexes. Members of this family are involved in a variety of cellular processes, including cell cycle progression, signal transduction, apoptosis, and gene regulation. In some embodiments, the modified effector cells described herein comprise an inactivating mutation in the WDR6 gene.

In some embodiments, the modified effector cells described herein comprise reduced expression and/or function of the E2F transcription factor 8 (E2F8) gene. The encoded E2F8 protein regulates progression from G1 to S phase by ensuring the nucleus divides at the proper time. In some embodiments, the modified effector cells described herein comprise an inactivating mutation in the E2F8 gene.

In some embodiments, the modified effector cells described herein comprise reduced expression and/or function of the serpin family A member 3 (SERPINA3) gene. SERPINA3 encodes the Alpha 1-antichymotrypsin (α1AC, A1AC, or a1ACT) protein, which inhibits the activity of certain proteases, such as cathepsin G and chymases. In some embodiments, the modified effector cells described herein comprise an inactivating mutation in the SERPINA3 gene.

In some embodiments, the modified effector cells described herein comprise reduced expression and/or function of the GNAS complex locus (GNAS) gene. It is the stimulatory G-protein alpha subunit (Gs-α), a key component of many signal transduction pathways. In some embodiments, the modified effector cells described herein comprise an inactivating mutation in the GNAS gene.

In some embodiments, the modified effector cells described herein comprise reduced expression and/or function of the ZC3H12A gene. Zc3h12a, also referred to as MCPIP1 and Regnase-1, is a RNase that possesses a RNase domain just upstream of a CCCH-type zinc-finger motif. Through its nuclease activity, Zc3h12a targets and destabilizes the mRNAs of transcripts, such as IL-6, by binding a conserved stem loop structure within the 3' UTR of these genes. In T cells, Zc3h12a controls the transcript levels of a number of pro-inflammatory genes, including c-Rel, Ox40, and IL-2. In monocytes, Zc3h12a downregulates IL-6 and IL-12B mRNAs, thus mitigating inflammation. In cancer cells, Zc3h12a promotes apoptosis by inhibiting anti-apoptotic genes including Bcl2L1, Bcl2A1, RelB and Bcl3. Zc3h12a activation is transient and is subject to negative feedback mechanisms including proteasome-mediated degradation or mucosa-associated lymphoid tissue 1 (MALT1) mediated cleavage. In some embodiments, the modified effector cells described herein comprise an inactivating mutation in the ZC3H12A gene.

In some embodiments, the modified effector cells described herein comprise reduced expression and/or function of the MAP4K1 gene. MAP4K1, also referred to as HPK1, is a member of the MAP4K family of mammalian Ste20-related protein kinases and is a protein serine-threonine kinase predominantly expressed in hematopoietic organs. The MAP4K1 protein comprises an N-terminal kinase domain followed by four proline-rich motifs capable of binding to proteins containing Src homology 3 domains. Upon phosphorylation by kinases such as Lck and Zap70 and in the presence of ATP, MAP4K1 possesses catalytic activity and mediates autophosphorylation as well as phosphorylation of downstream substrate proteins such as SLP-76 and MAP3K proteins. Phosphorylation of SLP-76 at Ser-376 leads to both the ubiquitination and proteosomal degradation of SLP-76 as well as increased interactions between SLP-76 and 14-3-3τ, which negatively regulates TCR signaling. In some embodiments, the modified effector cells described herein comprise an inactivating mutation in the MAP4K1 gene.

In some embodiments, the modified effector cells described herein comprise reduced expression and/or function of the NR4A3 gene. NR4A3 is an inducible orphan receptor and member of the steroid-thyroid hormone-retinoid receptor superfamily, and is a transcriptional activator. When expression is induced by various stimuli, NR4A3 drives gene expression in a ligand-independent way by translocating from the cytoplasm to the nucleus and binding to NR4A1 response elements (NBRE) as monomers and Nur response elements (NurRE) as homodimers. NR4A3 then drives the transcription of discrete sets of genes controlling cellular survival and differentiation both within and outside the immune system. In some embodiments, the modified effector cells described herein comprise an inactivating mutation in the NR4A3 gene.

In some embodiments, the modified immune effector cells comprise reduced expression and/or function of at least two genes selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., two or more genes selected from Table 3). For example, in some embodiments, the modified immune effector cells comprise reduced expression and/or function of at least two genes selected from Combination Nos. 1176-1681, as illustrated in FIG. 3A-FIG. 3B. In some embodiments, the modified immune effector cells comprise reduced expression and/or function of at least two genes selected from Combination Nos. 1176-1483, as illustrated in FIG. 3A. In some embodiments, the modified immune effector cells comprise reduced expression and/or function of at least two genes selected from Combination Nos. 1250-1265, as illustrated in FIG. 3B. In some embodiments, the modified immune effector cells comprise reduced expression and/or function of at least two genes selected from Combination Nos. 1266-1281, as illustrated in FIG. 3B. In some embodiments, the modified immune effector cells comprise reduced expression and/or function of at least two genes selected from Combination Nos. 1282-1297, as illustrated in FIG. 3B.

In some embodiments, the modified effector cells comprise reduced expression and/or function of one or more of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., one or more gene selected from Table 3) and one or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2). For example, the modified immune effector cells may comprise reduced expression and/or function of a combination of an endogenous target genes selected from Combination Nos. 601-1025. In some embodiments, the modified immune effector cells may comprise reduced expression and/or function of a combination of two endogenous target genes selected from Combination Nos. 601-950 (as illustrated in FIG. 2A). In some embodiments, the modified immune effector cells may comprise reduced expression and/or function of a combination of two endogenous target genes selected from Combination Nos. 951-975 (as illustrated in FIG. 2B). In some embodiments, the modified immune effector cells may comprise reduced expression and/or function of a combination of two endogenous target genes selected from Combination Nos. 976-1000 (as illustrated in FIG. 2B). In some embodiments, the modified immune effector cells may comprise reduced expression and/or function of a combination of two endogenous target genes selected from Combination Nos. 1001-1025 (as illustrated in FIG. 2B).

In some embodiments, the modified effector cells comprise reduced expression and/or function of at least one gene selected from BCL2L11, FLI1, CALM2, DHODH, UMPS, RBM39, SEMA7A, CHIC2, PCBP1, PBRM1, WDR6, E2F8, SERPINA3, and GNAS and reduced expression and/or function of at least one gene selected from TNFAIP3, CBLB, or BCOR. In some embodiments, the modified effector cells comprise reduced expression and/or function of ZC3H12A and at least one gene selected from TNFAIP3, CBLB, or BCOR. In some embodiments, the modified effector cells comprise inactivating mutations in ZC3H12A and at least one gene selected from TNFAIP3, CBLB, or BCOR. In some embodiments, the modified effector cells comprise reduced expression and/or function of MAP4K1 and at least one gene selected from TNFAIP3, CBLB, or BCOR. In some embodiments, the modified effector cells comprise inactivating mutations in MAP4K1 and at least one gene selected from TNFAIP3, CBLB, or BCOR. In some embodiments, the modified effector cells comprise reduced expression and/or function of NR4A3 and at least one gene selected from TNFAIP3, CBLB, or BCOR. In some embodiments, the modified effector cells comprise inactivating mutations in NR4A3 and at least one gene selected from TNFAIP3, CBLB, or BCOR.

In some embodiments, the modified effector cells comprise reduced expression and/or function of at least one gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 and reduced expression and/or function of CBLB. In some embodiments, the modified effector cells comprise reduced expression and/or function of at least one gene selected from BCL2L11, FLI1, CALM2, DHODH, UMPS, RBM39, SEMA7A, CHIC2, PCBP1, PBRM1, WDR6, E2F8, SERPINA3, and GNAS and reduced expression and/or function of CBLB. In some embodiments, the modified effector cells comprise reduced expression and/or function of ZC3H12A and CBLB. In some embodiments, the modified effector cells comprise inactivating mutations in ZC3H12A and CBLB. In some embodiments, the modified effector cells comprise reduced expression and/or function of MAP4K1 and CBLB. In some embodiments, the modified effector cells comprise inactivating mutations in MAP4K1 and CBLB. In some embodiments, the modified effector cells comprise reduced expression and/or function of NR4A3 and CBLB. In some embodiments, the modified effector cells comprise inactivating mutations in NR4A3 and CBLB.

In some embodiments, the modified immune effector cells comprise reduced expression and/or function of a gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2) and reduced expression and/or function of two genes selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., one or more gene selected from Table 3). For example, in some embodiments, the modified immune effector cells comprises reduced expression and/or function of a gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, and BCOR in addition to reduced expression and/or function of two endogenous target gene combinations selected from Combination Nos. 1026-1297 (as illustrated in FIG. 3A-FIG. 3B).

In some embodiments, the modified immune effector cells comprise reduced expression and/or function of a gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3) and reduced expression and/or function of two genes selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., one or more gene selected from Table 2). For example, in some embodiments, the modified immune effector cells comprise reduced expression and/or function of any one of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 in addition to reduced expression and/or function of two endogenous target gene combinations selected from Combination Nos. 1-600 illustrated in FIG. 1A-FIG. 1B. In some embodiments, the modified immune effector cells comprise reduced expression and/or function of a gene selected from BCL2L11, FLI1, CALM2, DHODH, UMPS, RBM39, SEMA7A, CHIC2, PCBP1, PBRM1, WDR6, E2F8, SERPINA3, and GNAS in addition to reduced expression and/or function of two endogenous target gene combinations selected from Combination Nos. 1-600 illustrated in FIG. 1A-FIG. 1B. In some embodiments, the modified immune effector cells comprise reduced expression and/or function of ZC3H12A in addition to reduced expression and/or function of two endogenous target gene combinations selected from Combination Nos. 1-600 illustrated in FIG. 1A-FIG. 1B. In some embodiments, the modified immune effector cells comprise reduced expression and/or function of MAP4K1 in addition to reduced expression and/or function of two endogenous target gene combinations selected from Combination Nos. 1-600 illustrated in FIG. 1A-FIG. 1B. In some embodiments, the modified immune effector cells comprise reduced expression and/or function of NR4A3 in addition to reduced expression and/or function of two endogenous target gene combinations selected from Combination Nos. 1-600 illustrated in FIG. 1A-FIG. 1B.

In some embodiments, the modified immune effector cells comprise reduced expression and/or function of a plurality of genes selected from Table 2 and reduced expression and/or function of a plurality of genes selected from Table 3. In some embodiments, the modified immune effector cells comprise reduced expression and/or function of two genes selected from Table 2 and reduced expression and/or function of two genes selected from Table 3. For example, in some embodiments, the modified immune effector cells comprise reduced expression and/or function of a combination of two genes selected from Combination Nos. 1026-1297 as shown in FIG. 3A-FIG. 3B and a combination of two genes selected from Combination Nos. 1-600 as shown in FIG. 1A-FIG. 1B. In some embodiments, the modified immune effector cells may comprise reduced expression and/or function of three or more of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and reduced expression and/or function of three or more of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3.

TABLE 2

Exemplary Endogenous Genes

| Gene Symbol | Gene Name | Human UniProt Ref. | Human NCBI ID | Murine UniProt Ref. | Murine NCBI ID |
| --- | --- | --- | --- | --- | --- |
| IKZF1 | IKAROS family zinc finger 1 | Q13422 | 10320 | Q03267 | 22778 |
| IKZF2 | IKAROS family zinc finger 2 | Q9UKS7 | 22807 | P81183 | 22779 |
| IKZF3 | IKAROS family zinc finger 3 | Q9UKT9 | 22806 | O08900 | 22780 |
| NFKBIA | NFKB inhibitor alpha | P25963 | 4792 | Q9Z1E3 | 18035 |
| BCL3 | B cell CLL/lymphoma 3 | P20749 | 602 | Q9Z2F6 | 12051 |
| TNIP1 | TNFAIP3 interacting protein 1 | Q15025 | 10318 | Q9WUU8 | 57783 |
| TNFAIP3 | TNF alpha induced protein 3 | P21580 | 7128 | Q60769 | 21929 |
| SMAD2 | SMAD family member 2 | Q15796 | 4087 | Q919P9 | 17126 |
| TGFBR1 | transforming growth factor beta receptor 1 | P36897 | 7046 | Q64729 | 21812 |
| TGFBR2 | transforming growth factor beta receptor 2 | P37173 | 7048 | Q623212 | 21813 |
| TANK | TRAF family member associated NFKB activator | Q92844 | 10010 | P70347 | 21353 |
| FOXP3 | forkhead box P3 | Q9BZS1 | 50943 | Q99JB6 | 20371 |
| CBLB | Cbl proto-oncogene B | Q13191 | 868 | Q3TTA7 | 208650 |
| PPP2R2D | protein phosphatase 2 regulatory subunit Bdelta | Q66LE6 | 55844 | Q7ZX64 | 52432 |
| NRP1 | neuropilin 1 | Q14786 | 8829 | P97333 | 18186 |
| HAVCR2 | hepatitis A virus cellular receptor 2 | Q8TDQ0 | 84868 | Q8VIM0 | 171285 |
| LAG3 | lymphocyte activating 3 | P18627 | 3902 | Q61790 | 16768 |
| TIGIT | T cell immunoreceptor with Ig and ITIM domains | Q495A1 | 201633 | P86176 | 100043314 |
| CTLA4 | cytotoxic T-lymphocyte associated protein 4 | P16410 | 1493 | P09793 | 12477 |

TABLE 2-continued

Exemplary Endogenous Genes

| Gene Symbol | Gene Name | Human UniProt Ref. | Human NCBI ID | Murine UniProt Ref. | Murine NCBI ID |
|---|---|---|---|---|---|
| PTPN6 | protein tyrosine phosphatase, non-receptor type 6 | P29350 | 5777 | P29351 | 15170 |
| BCOR | BCL6 corepressor | Q6W2J9 | 54880 | Q8CGN4 | 71458 |
| GATA3 | GATA binding protein 3 | P23771 | 2625 | P23772 | 14462 |
| PDCD1 | Programmed cell death 1 protein | Q15116 | 5133 | Q02242 | 18566 |
| RC3H1 | Ring finger and CCCH-type domains 1 | Q5TC82 | 149041 | Q4VGL6 | 381305 |
| TRAF6 | TNF receptor associated factor 6 | Q9Y4K3 | 7186 | P70196 | 22034 |

TABLE 3

Exemplary Genes for Novel Regulation

| Gene Symbol | Gene Name | Human UniProt Ref. | Human NCBI ID | Murine UniProt Ref. | Murine NCBI ID |
|---|---|---|---|---|---|
| SEMA7A | semaphorin 7A | O75326 | 8482 | Q9QUR8 | 20361 |
| RBM39 | RNA binding motif protein 39 | Q14498 | 9584 | Q8VH51 | 170791 |
| BCL2L11 | BCL2 like 11 | O43521 | 10018 | O54918 | 12125 |
| FLI1 | Fli-1 proto-oncogene, ETS transcription factor | Q01543 | 2313 | P26323 | 14247 |
| CALM2 | calmodulin 2 | P0DP24 | 805 | P0DP30 | 12314 |
| DHODH | dihydroorotate dehydrogenase (quinone) | Q02127 | 1723 | O35435 | 56749 |
| UMPS | uridine monophosphate synthetase | P11172 | 7372 | P13439 | 22247 |
| CHIC2 | cysteine rich hydrophobic domain 2 | Q9UKJ5 | 26511 | Q9D9G3 | 74277 |
| PCBP1 | poly(rC) binding protein 1 | Q15365 | 5093 | P60335 | 23983 |
| PBRM1 | polybromo 1 | Q86U86 | 55193 | Q8BSQ9 | 66923 |
| WDR6 | WD repeat domain 6 | Q9NNW5 | 11180 | Q99ME2 | 83669 |
| E2F8 | E2F transcription factor 8 | A0AVK6 | 79733 | Q58FA4 | 108961 |
| SERPINA3 | serpin family A member 3 | P01011 | 12 | | |
| GNAS | guanine nucleotide binding protein, alpha stimulating | Q5JWF2 | 2778 | Q6R0H7 | 14683 |
| ZC3H12A | Endoribonuclease ZC3H12A | Q5D1E8 | 80149 | Q5D1E7 | 230738 |
| MAP4K1 | mitogen-activated protein kinase kinase kinase kinase 1 | Q92918 | 11184 | P70218 | 26411 |
| NR4A3 | Nuclear receptor subfamily 4 group A member 3 | Q92570 | 8013 | Q9QZB6 | 18124 |

III. Gene-Regulating Systems

Herein, the term "gene-regulating system" refers to a protein, nucleic acid, or combination thereof that is capable of modifying an endogenous target DNA sequence when introduced into a cell, thereby regulating the expression or function of the encoded gene product. Numerous gene editing systems suitable for use in the methods of the present disclosure are known in the art including, but not limited to, shRNAs, siRNAs, zinc-finger nuclease systems, TALEN systems, and CRISPR/Cas systems.

As used herein, "regulate," when used in reference to the effect of a gene-regulating system on an endogenous target gene encompasses any change in the sequence of the endogenous target gene, any change in the epigenetic state of the endogenous target gene, and/or any change in the expression or function of the protein encoded by the endogenous target gene.

In some embodiments, the gene-regulating system may mediate a change in the sequence of the endogenous target gene, for example, by introducing one or more mutations into the endogenous target sequence, such as by insertion or deletion of one or more nucleic acids in the endogenous target sequence. Exemplary mechanisms that can mediate alterations of the endogenous target sequence include, but are not limited to, non-homologous end joining (NHEJ) (e.g., classical or alternative), microhomology-mediated end joining (MMEJ), homology-directed repair (e.g., endogenous donor template mediated), SDSA (synthesis dependent strand annealing), single strand annealing or single strand invasion.

In some embodiments, the gene-regulating system may mediate a change in the epigenetic state of the endogenous target sequence. For example, in some embodiments, the gene-regulating system may mediate covalent modifications of the endogenous target gene DNA (e.g., cytosine methylation and hydroxymethylation) or of associated histone proteins (e.g. lysine acetylation, lysine and arginine methylation, serine and threonine phosphorylation, and lysine ubiquitination and sumoylation).

In some embodiments, the gene-regulating system may mediate a change in the expression of the protein encoded by the endogenous target gene. In such embodiments, the gene-regulating system may regulate the expression of the encoded protein by modifications of the endogenous target DNA sequence, or by acting on the mRNA product encoded by the DNA sequence. In some embodiments, the gene-regulating system may result in the expression of a modified endogenous protein. In such embodiments, the modifications to the endogenous DNA sequence mediated by the gene-regulating system result in the expression of an endogenous protein demonstrating a reduced function as compared to the corresponding endogenous protein in an unmodified immune effector cell. In such embodiments, the expression level of the modified endogenous protein may be increased, decreased or may be the same, or substantially similar to, the expression level of the corresponding endogenous protein in an unmodified immune cell.

A. Nucleic Acid-Based Gene-Regulating Systems

As used herein, a nucleic acid-based gene-regulating system is a system comprising one or more nucleic acid molecules that is capable of regulating the expression of an endogenous target gene without the requirement for an exogenous protein. In some embodiments, the nucleic acid-based gene-regulating system comprises an RNA interference molecule or antisense RNA molecule that is complementary to a target nucleic acid sequence.

An "antisense RNA molecule" refers to an RNA molecule, regardless of length, that is complementary to an mRNA transcript. Antisense RNA molecules refer to single stranded RNA molecules that can be introduced to a cell, tissue, or subject and result in decreased expression of an endogenous target gene product through mechanisms that do not rely on endogenous gene silencing pathways, but rather rely on RNaseH-mediated degradation of the target mRNA transcript. In some embodiments, an antisense nucleic acid comprises a modified backbone, for example, phosphorothioate, phosphorodithioate, or others known in the art, or may comprise non-natural internucleoside linkages. In some embodiments, an antisense nucleic acid can comprise locked nucleic acids (LNA).

"RNA interference molecule" as used herein refers to an RNA polynucleotide that mediates the decreased the expression of an endogenous target gene product by degradation of a target mRNA through endogenous gene silencing pathways (e.g., Dicer and RNA-induced silencing complex (RISC)). Exemplary RNA interference agents include micro RNAs (also referred to herein as "miRNAs"), short hair-pin RNAs (shRNAs), small interfering RNAs (siRNAs), RNA aptamers, and morpholinos.

In some embodiments, the nucleic acid-based gene-regulating system comprises one or more miRNAs. miRNAs refers to naturally occurring, small non-coding RNA molecules of about 21-25 nucleotides in length. miRNAs are at least partially complementary to one or more target mRNA molecules. miRNAs can downregulate (e.g., decrease) expression of an endogenous target gene product through translational repression, cleavage of the mRNA, and/or deadenylation.

In some embodiments, the nucleic acid-based gene-regulating system comprises one or more shRNAs. shRNAs are single stranded RNA molecules of about 50-70 nucleotides in length that form stem-loop structures and result in degradation of complementary mRNA sequences. shRNAs can be cloned in plasmids or in non-replicating recombinant viral vectors to be introduced intracellularly and result in the integration of the shRNA-encoding sequence into the genome. As such, an shRNA can provide stable and consistent repression of endogenous target gene translation and expression.

In some embodiments, nucleic acid-based gene-regulating system comprises one or more siRNAs. siRNAs refer to double stranded RNA molecules typically about 21-23 nucleotides in length. The siRNA associates with a multi protein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA, resulting in specific gene silencing. Optimally, an siRNA is 18, 19, 20, 21, 22, 23 or 24 nucleotides in length and has a 2 base overhang at its 3' end. siRNAs can be introduced to an individual cell and/or culture system and result in the degradation of target mRNA sequences. siRNAs and shRNAs are further described in Fire et al., Nature, 391:19, 1998 and U.S. Pat. Nos. 7,732,417; 8,202,846; and 8,383,599.

In some embodiments, the nucleic acid-based gene-regulating system comprises one or more morpholinos. "Morpholino" as used herein refers to a modified nucleic acid oligomer wherein standard nucleic acid bases are bound to morpholine rings and are linked through phosphorodiamidate linkages. Similar to siRNA and shRNA, morpholinos bind to complementary mRNA sequences. However, morpholinos function through steric-inhibition of mRNA translation and alteration of mRNA splicing rather than targeting complementary mRNA sequences for degradation.

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (i.e., those listed in Table 2). In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to a RNA sequence encoded by a DNA sequence defined by a set of genomic coordinates shown in Table 5A or Table 5B. Throughout this application, the referenced genomic coordinates are based on genomic annotations in the GRCh38 (also referred to as hg38) assembly of the human genome from the Genome Reference Consortium, available at the National Center for Biotechnology Information website. Tools and methods for converting genomic coordinates between one assembly and another are known in the art and can be used to convert the genomic coordinates provided herein to the corresponding coordinates in another assembly of the human genome, including conversion to an earlier assembly generated by the same institution or using the same algorithm (e.g., from GRCh38 to GRCh37), and conversion an assembly generated by a different institution or algorithm (e.g., from GRCh38 to NCBI33, generated by the International Human Genome Sequencing Consortium). Available methods and tools known in the art include, but are not limited to, NCBI Genome Remapping Service, available at the National Center for Biotechnology Information website, UCSC LiftOver, available at the UCSC Genome Brower website, and Assembly Converter, available at the Ensembl.org website.

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813. In some embodiments, the nucleic acid-based gene-regulating system is capable of reducing the expression and/or function of CBLB, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 499-524. In some embodiments, the nucleic acid-based gene-regulating system is capable of reducing the expression and/or function of BCOR, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 708-772 or SEQ ID NOs: 708-764. In some embodiments, the nucleic acid-based gene-regulating system is capable of reducing the expression and/or function of TNFAIP3, and comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by one of SEQ ID NOs: 348-396 or SEQ ID NOs: 348-386. In some embodiments, the nucleic acid-based gene-regulating system comprises an siRNA molecule or an shRNA molecule selected from those known in the art, such as the siRNA and shRNA constructs available from commercial suppliers such as Sigma Aldrich, Dharmacon, ThermoFisher, and the like.

In some embodiments, the endogenous target gene is CBLB and the nucleic acid molecule is an shRNA encoded by a nucleic acid sequence selected from SEQ ID NOs: 41-44 (See International PCT Publication No. 2018156886) or selected from SEQ ID NOs: 45-53 (See International PCT Publication No. WO 2017120998). In some embodiments, the endogenous target gene is CBLB and the nucleic acid molecule is an siRNA comprising a nucleic acid sequence selected from SEQ ID NOs: 54-63 (See International PCT Publication No. WO 2018006880) or SEQ ID NOs: 64-73 (See International PCT Publication Nos. WO 2018120998 and WO 2018137293).

In some embodiments, the endogenous target gene is TNFAIP3 and the nucleic acid molecule is an shRNA encoded by a nucleic acid sequence selected from SEQ ID NOs: 74-95 (See U.S. Pat. No. 8,324,369). In some embodiments, the endogenous target gene is TNFAIP3 and the nucleic acid molecule is an siRNA comprising a nucleic acid sequence selected from SEQ ID NOs: 96-105 (See International PCT Publication No. WO 2018006880).

In some embodiments, the endogenous target gene is CTLA4 and the nucleic acid molecule is an shRNA encoded by a nucleic acid sequence selected from SEQ ID NOs: 128-133 (See International PCT Publication No. Nos. WO 2017120996). In some embodiments, the endogenous target gene is CTLA4 and the nucleic acid molecule is an siRNA comprising a nucleic acid sequence selected from SEQ ID NOs: 134-143 (See International PCT Publication Nos. WO2017120996, WO 2017120998, WO 2018137295, and WO 2018137293) or SEQ ID NOs: 144-153 (See International PCT Publication No. WO 2018006880).

In some embodiments, the endogenous target gene is PDCD1 and the nucleic acid molecule is an shRNA encoded by a nucleic acid sequence selected from SEQ ID NOs: 106-107 (See International PCT Publication Nos. WO 2017120996). In some embodiments, the endogenous target gene is PDCD1 and the nucleic acid molecule is an siRNA comprising a nucleic acid sequence selected from SEQ ID NOs: 108-117 (See International PCT Publication Nos. WO2017120996, WO 201712998, WO 2018137295, and WO 2018137293) or SEQ ID NOs: 118-127 (See International PCT Publication No. WO 2018006880).

In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99% identical, or is 100% identical to an RNA sequence encoded by a DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (i.e., those listed in Table 3). In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in Table 6A-Table 6H. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 814-1566.

In some embodiments, the nucleic acid-based gene-regulating system is capable of reducing the expression and/or function of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in one of Table 6A or Table 6B. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 814-1064.

In some embodiments, the nucleic acid-based gene-regulating system is capable of reducing the expression and/or function of ZC3H12A. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in one of Table 6C or Table 6D. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 1065-1509. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 1065-1264.

In some embodiments, the nucleic acid-based gene-regulating system is capable of reducing the expression and/or function of MAP4K1. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in one of Table 6E or Table 6F. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 510-1538.

In some embodiments, the nucleic acid-based gene-regulating system is capable of reducing the expression and/or function of NR4A3. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by a DNA sequence defined by a set of genomic coordinates shown in one of Table 6G or Table 6H. In some embodiments, the nucleic acid-based gene-regulating system comprises a nucleic acid molecule (e.g., an siRNA, an shRNA, an RNA aptamer, or a morpholino) that binds to a target RNA sequence that is at least 90%, 95%, 96%, 97%, 98%, or 99%, or is 100% identical to an RNA sequence encoded by one of SEQ ID NOs: 1539-1566.

In some embodiments, the nucleic acid-based gene-regulating system comprises an siRNA molecule or an shRNA molecule selected from those known in the art, such as those available from commercial suppliers such as Sigma Aldrich, Dharmacon, ThermoFisher, and the like. Exemplary siRNA and shRNA constructs are described in Table 4A and Table 4B below. In some embodiments, the nucleic acid-based gene-regulating system comprises two or more siRNA molecules selected from those known in the art, such as the siRNA constructs described in Table 4A. In some embodiments, the nucleic acid-based gene-regulating system comprises two or more shRNA molecules selected from those known in the art, such as the shRNA constructs described in Table 4B.

TABLE 4A

Exemplary siRNA constructs

| Target Gene | siRNA construct |
|---|---|
| SEMA7A | MISSION ® esiRNA human SEMA7A (esiRNA1) (SigmaAldrich Product# EHU143161) |
| | MISSION ® esiRNA targeting mouse Sema7a (esiRNA1) (SigmaAldrich Product# EMU010311) |
| | human Rosetta Predictions (SigmaAldrich Product# NM_003612) |
| | murine Rosetta Predictions (SigmaAldrich Product# NM_011352) |
| RBM39 | MISSION ® esiRNA human RBM39 (esiRNA1) (SigmaAldrich Product# EHU070351) |
| | human Rosetta Predictions (SigmaAldrich Product# NM_004902) |
| | human Rosetta Predictions (SigmaAldrich Product# NM_184234) |
| | human Rosetta Predictions (SigmaAldrich Product# NM_184237) |
| | human Rosetta Predictions (SigmaAldrich Product# NM_184241) |
| | human Rosetta Predictions (SigmaAldrich Product# NM_184244) |
| BCL2L11 | MISSION ® esiRNA targeting mouse Bcl2l11 (esiRNA1) (SigmaAldrich Product# |
| | human Rosetta Predictions (SigmaAldrich Product# NM_006538) |
| | human Rosetta Predictions (SigmaAldrich Product# NM_138621) |
| | human Rosetta Predictions (SigmaAldrich Product# NM_138622) |
| | human Rosetta Predictions (SigmaAldrich Product# NM_138623) |
| | human Rosetta Predictions (SigmaAldrich Product# NM_138624) |
| FLI1 | MISSION ® esiRNA human FLI1 (esiRNA1) (SigmaAldrich Product# EHU091961) |
| | MISSION ® esiRNA targeting mouse Fli1 (esiRNA1) (SigmaAldrich Product# EMU090601) |
| | human Rosetta Predictions (SigmaAldrich Product# NM_002017) |
| | murine Rosetta Predictions (SigmaAldrich Product# NM_008026) |
| CALM2 | MISSION ® esiRNA human CALM2 (esiRNA1) (SigmaAldrich Product# EHU110161) |
| | MISSION ® esiRNA targeting mouse Calm2 (SigmaAldrich Product# EMU176331) |
| | human Rosetta Predictions (SigmaAldrich Product# NM_001743) |
| | murine Rosetta Predictions (SigmaAldrich Product# NM_007589) |

TABLE 4A-continued

Exemplary siRNA constructs

| Target Gene | siRNA construct |
|---|---|
| DHODH | MISSION ® esiRNA human DHODH (esiRNA1) (SigmaAldrich Product# EHU138421)<br>MISSION ® esiRNA targeting mouse Dhodh (esiRNA1) (SigmaAldrich Product# EMU072221)<br>human Rosetta Predictions (SigmaAldrich Product# NM_001025193)<br>human Rosetta Predictions (SigmaAldrich Product# NM_001361) |
| DHODH | murine Rosetta Predictions (SigmaAldrich Product# NM_020046) |
| UMPS | MISSION ® esiRNA human UMPS (esiRNA1) (SigmaAldrich Product# EHU093891)<br>MISSION ® esiRNA targeting mouse Umps (esiRNA1) (SigmaAldrich Product# EMU023181)<br>human Rosetta Predictions (SigmaAldrich Product# NM_000373)<br>murine Rosetta Predictions (SigmaAldrich Product# NM_009471) |
| CHIC2 | MISSION ® esiRNA human CHIC2 (esiRNA1) (SigmaAldrich Product# EHU137501)<br>MISSION ® esiRNA targeting mouse Chic2 (esiRNA1) (SigmaAldrich Product# EMU019221)<br>human Rosetta Predictions (SigmaAldrich Product# NM_012110)<br>murine Rosetta Predictions (SigmaAldrich Product# NM_028850) |
| PCBP1 | MISSION ® esiRNA targeting mouse Pcbp1 (esiRNA1) (SigmaAldrich Product# EMU011551)<br>human Rosetta Predictions (SigmaAldrich Product# NM_006196)<br>murine Rosetta Predictions (SigmaAldrich Product# NM_011865) |
| PBRM1 | MISSION ® esiRNA human PBRM1 (esiRNA1) (SigmaAldrich Product# EHU075001)<br>human Rosetta Predictions (SigmaAldrich Product# NM_018165)<br>human Rosetta Predictions (SigmaAldrich Product# NM_018313)<br>human Rosetta Predictions (SigmaAldrich Product# NM_181042) |
| WDR6 | MISSION ® esiRNA human WDR6 (esiRNA1) (SigmaAldrich Product# EHU065441)<br>MISSION ® esiRNA targeting mouse Wdr6 (esiRNA1) (SigmaAldrich Product# EMU038981)<br>human Rosetta Predictions (SigmaAldrich Product# NM_018031)<br>murine Rosetta Predictions (SigmaAldrich Product# NM_031392) |
| E2F8 | MISSION ® esiRNA human E2F8 (esiRNA1) (SigmaAldrich Product# EHU025641)<br>MISSION ® esiRNA targeting mouse E2f8 (SigmaAldrich Product# EMU206861)<br>human Rosetta Predictions (SigmaAldrich Product# NM_024680)<br>murine Rosetta Predictions (SigmaAldrich Product# NM_001013368) |
| SERPINA3 | MISSION ® esiRNA human SERPINA3 (esiRNA1) (SigmaAldrich Product# EHU150301)<br>human Rosetta Predictions (SigmaAldrich Product# NM_001085) |
| GNAS | MISSION ® esiRNA human GNAS (esiRNA1) (SigmaAldrich Product# EHU117321)<br>MISSION ® esiRNA targeting mouse Gnas (esiRNA1) (SigmaAldrich Product# EMU074141)<br>human Rosetta Predictions (SigmaAldrich Product# NM_000516)<br>human Rosetta Predictions (SigmaAldrich Product# NM_001077488)<br>human Rosetta Predictions (SigmaAldrich Product# NM_001077489) |
| GNAS | human Rosetta Predictions (SigmaAldrich Product# NM_001077490)<br>human Rosetta Predictions (SigmaAldrich Product# NM_016592) |
| ZC3H12A | MISSION ® esiRNA targeting human ZC3H12A (esiRNA1) (SigmaAldrich# EHU009491)<br>MISSION ® esiRNA targeting mouse Zc3h12a (esiRNA1) (SigmaAldrich# EMU048551)<br>Rosetta Predictions human (SigmaAldrich# NM_025079)<br>Rosetta Predictions mouse (SigmaAldrich# NM_153159) |
| ZC3H12A | Accell Mouse Zc3h12a (230738) siRNA - SMARTpool (Dharmacon# E-052076-00-0005) |
| MAP4K1 | MISSION ® esiRNA targeting human MAP4K1 (esiRNA1) (SigmaAldrich# EHU005191)<br>MISSION ® esiRNA targeting mouse Map4kl (esiRNA1) (SigmaAldrich# EMU086771)<br>Rosetta Predictions human (SigmaAldrich# NM_001042600)<br>Rosetta Predictions human (SigmaAldrich# NM_007181)<br>Rosetta Predictions mouse (SigmaAldrich# NM_008279) |
| NR4A3 | MISSION ® esiRNA targeting human NR4A3 (esiRNA1) (SigmaAldrich# EHU014951)<br>Rosetta Predictions human (SigmaAldrich# NM_006981)<br>Rosetta Predictions human (SigmaAldrich# NM_173198)<br>Rosetta Predictions human (SigmaAldrich# NM_173199)<br>Rosetta Predictions human (SigmaAldrich# NM_173200) |

TABLE 4B

Exemplary shRNA constructs

| Target Gene | shRNA construct |
|---|---|
| SEMA7A | MISSION ® shRNA murine Plasmid DNA (SigmaAldrich Product# SHCLND-NM_011352) |
| | MISSION ® shRNA human Plasmid DNA (SigmaAldrich Product# SHCLND-NM_003612) |
| RBM39 | MISSION ® shRNA murine Plasmid DNA (SigmaAldrich Product# SHCLND-NM_133242) |
| | MISSION ® shRNA human Plasmid DNA (SigmaAldrich Product# SHCLND-NM_004902) |
| BCL2L11 | MISSION ® shRNA murine Plasmid DNA (SigmaAldrich Product# SHCLND-NM_009754) |
| | MISSION ® shRNA human Plasmid DNA (SigmaAldrich Product# SHCLND-NM_138621) |
| FLI1 | MISSION ® shRNA murine Plasmid DNA (SigmaAldrich Product# SHCLND-NM_002017) |
| | MISSION ® shRNA murine Plasmid DNA (SigmaAldrich Product# SHCLND-NM_008026) |
| CALM2 | MISSION ® shRNA murine Plasmid DNA (SigmaAldrich Product# SHCLND-NM_007589) |
| | MISSION ® shRNA human Plasmid DNA (SigmaAldrich Product# SHCLND-NM_001743) |
| DHODH | MISSION ® shRNA murine Plasmid DNA (SigmaAldrich Product# SHCLND-NM_020046) |
| | MISSION ® shRNA human Plasmid DNA (SigmaAldrich Product# SHCLND-NM_001361) |
| UMPS | MISSION ® shRNA murine Plasmid DNA (SigmaAldrich Product# SHCLND-NM_009471) |
| | MISSION ® shRNA human Plasmid DNA (SigmaAldrich Product# SHCLND-NM_000373) |
| CHIC2 | MISSION ® shRNA murine Plasmid DNA (SigmaAldrich Product# SHCLND-NM_028850) |
| | MISSION ® shRNA human Plasmid DNA (SigmaAldrich Product# SHCLND-NM_012110) |
| PCBP1 | MISSION ® shRNA murine Plasmid DNA (SigmaAldrich Product# SHCLND-NM_011865) |
| | MISSION ® shRNA human Plasmid DNA (SigmaAldrich Product# SHCLND-NM_006196) |
| PBRM1 | MISSION ® shRNA murine Plasmid DNA (SigmaAldrich Product# SHCLND-NM_001081251) |
| PBRM1 | MISSION ® shRNA human Plasmid DNA (SigmaAldrich Product# SHCLND-NM_018165) |
| WDR6 | MISSION ® shRNA murine Plasmid DNA (SigmaAldrich Product# SHCLND-NM_031392) |
| | MISSION ® shRNA human Plasmid DNA (SigmaAldrich Product# SHCLND-NM_018031) |
| E2F8 | MISSION ® shRNA murine Plasmid DNA (SigmaAldrich Product# SHCLND-NM_001013368) |
| | MISSION ® shRNA human Plasmid DNA (SigmaAldrich Product# SHCLND-NM_024680) |
| SERPINA3 | MISSION ® shRNA human Plasmid DNA (SigmaAldrich Product# SHCLND-NM_001085) |
| GNAS | MISSION ® shRNA murine Plasmid DNA (SigmaAldrich Product# SHCLND-NM_010309) |
| | MISSION ® shRNA human Plasmid DNA (SigmaAldrich Product# SHCLND-NM_000516) |
| ZC3H12A | MISSION ® shRNA Plasmid DNA human (SigmaAldrich# SHCLND-NM_025079) |
| | MISSION ® shRNA Plasmid DNA mouse (SigmaAldrich# SHCLND-NM_153159) |
| MAP4K1 | MISSION ® shRNA Plasmid DNA human (SigmaAldrich# SHCLND-NM_007181) |
| | MISSION ® shRNA Plasmid DNA mouse (SigmaAldrich# SHCLND-NM_008279) |
| NR4A3 | MISSION ® shRNA Plasmid DNA human (SigmaAldrich# SHCLND-NM_006981) |
| | MISSION ® shRNA Plasmid DNA mouse (SigmaAldrich# SHCLND-NM_015743) |

In some embodiments, the gene-regulating system comprises two or more nucleic acid molecules (e.g., two or more siRNAs, two or more shRNAs, two or more RNA aptamers, or two or more morpholinos), wherein at least one of the nucleic acid molecules binds to a target RNA sequence that is at least 90%, 95%, 96%, 97%, 98%, or 99% identical, or is 100% identical to an RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2) and wherein at least one of the nucleic acid molecules binds to a target RNA sequence that is at least 90%, 95%, 96%, 97%, 98%, or 99% identical, or is 100% identical to an RNA sequence encoded by a DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3).

In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6A-Table 6H. In some embodiments, at least one of the two or more nucleic acid molecules binds to a target RNA sequence that is at least 90%, 95%, 96%, 97%, 98%, or 99% identical, or is 100% identical an RNA sequence encoded by one of SEQ ID NOs: 814-1566 and at least one of the two or more nucleic acid molecules binds to a target RNA sequence that is at least 90%, 95%, 96%, 97%, 98%, or 99% identical, or is 100% identical an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6A or Table 6B. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 814-1064 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of CBLB and wherein at least one of the nucleic acid molecules binds to a target RNA sequence encoded by a DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 814-1064 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of ZC3H12A. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6C or Table 6D. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1509 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813 In some embodiments, the gene-regulating system comprises two or more nucleic acid molecules, wherein at least one of the nucleic acid molecules binds to a target RNA sequence encoded by a DNA sequence of the CBLB gene and wherein at least one of the nucleic acid molecules binds to a target RNA sequence encoded by a DNA sequence of the ZC3H12A gene. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1509 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1065-1264 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of MAP4K1. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6E or Table 6F. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 510-1538 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of the CBLB gene and wherein at least one of the nucleic acid molecules binds to a target RNA sequence encoded by a DNA sequence of MAP4K1. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 510-1538 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524.

In some embodiments, the gene-regulating system comprises two or more nucleic acid molecules, wherein at least one of the nucleic acid molecules binds to a target RNA sequence encoded by a DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the nucleic acid molecules binds to a target RNA sequence encoded by a DNA sequence of NR4A3. In some embodiments, at least one of the two or more nucleic acid molecules to a target RNA sequence that is at least 90%, 95%, 96%, 97%, 98%, or 99% identical, or is 100% identical to an RNA sequence encoded by a DNA sequence defined by a set of genomic coordinates shown in Table 5A or Table 5B and at least one of the two or more nucleic acid molecules binds to a target RNA sequence that is at least 90%, 95%, 96%, 97%, 98%, or 99% identical, or is 100% identical to an RNA sequence encoded by a DNA sequence defined by a set of genomic coordinates shown in Table 6G or Table 6H. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1539-1566 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 154-498 or SEQ ID NOs: 499-813.

In some embodiments, the gene-regulating system comprises two or more nucleic acid molecules, wherein at least one of the nucleic acid molecules binds to a target RNA sequence encoded by a DNA sequence of the CBLB gene and wherein at least one of the nucleic acid molecules binds to a target RNA sequence encoded by a DNA sequence of NR4A3. In some embodiments, at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 1539-1566 and at least one of the two or more nucleic acid molecules binds to a target RNA sequence that is at least 90%, 95%, 96%, 97%, 98%, or 99% identical, or is 100% identical to an RNA sequence encoded by one of SEQ ID NOs: 499-524.

B. Protein-Based Gene-Regulating Systems

In some embodiments, a protein-based gene-regulating system is a system comprising one or more proteins capable of regulating the expression of an endogenous target gene in a sequence specific manner without the requirement for a nucleic acid guide molecule. In some embodiments, the protein-based gene-regulating system comprises a protein comprising one or more zinc-finger binding domains and an enzymatic domain. In some embodiments, the protein-based gene-regulating system comprises a protein comprising a Transcription activator-like effector nuclease (TALEN) domain and an enzymatic domain. Such embodiments are referred to herein as "TALENs".

1. Zinc Finger Systems

Zinc finger-based systems comprise a fusion protein comprising two protein domains: a zinc finger DNA binding domain and an enzymatic domain. A "zinc finger DNA binding domain", "zinc finger protein", or "ZFP" is a protein, or a domain within a larger protein, that binds DNA in a sequence-specific manner through one or more zinc fingers, which are regions of amino acid sequence within the binding domain whose structure is stabilized through coordination of a zinc ion. The zinc finger domain, by binding to a target DNA sequence, directs the activity of the enzymatic domain to the vicinity of the sequence and, hence, induces modification of the endogenous target gene in the vicinity of the target sequence. A zinc finger domain can be engineered to bind to virtually any desired sequence. Accordingly, after identifying a target genetic locus containing a target DNA sequence at which cleavage or recombination is desired (e.g., a target locus in a target gene referenced in Tables 2 or 3), one or more zinc finger binding domains can be engineered to bind to one or more target DNA sequences in the target genetic locus. Expression of a fusion protein comprising a zinc finger binding domain and an enzymatic domain in a cell, effects modification in the target genetic locus.

In some embodiments, a zinc finger binding domain comprises one or more zinc fingers. Miller et al. (1985) EMBO J. 4:1609-1614; Rhodes (1993) Scientific American February: 56-65; U.S. Pat. No. 6,453,242. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. In some embodiments, the DNA-binding domains of individual ZFNs comprise between three and six individual zinc finger repeats and can each recognize between 9 and 18 basepairs.

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection.

Selection of a target DNA sequence for binding by a zinc finger domain can be accomplished, for example, according to the methods disclosed in U.S. Pat. No. 6,453,242. It will be clear to those skilled in the art that simple visual inspection of a nucleotide sequence can also be used for selection of a target DNA sequence. Accordingly, any means for target DNA sequence selection can be used in the methods described herein. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

In some embodiments, the zinc finger binding domains bind to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the zinc finger binding domains bind to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the zinc finger binding domains bind to a target DNA sequence that is at least 90%, 95%, 96%, 97%, 98%, or 99% identical, or is 100% identical to a target DNA sequence of CBLB. In some embodiments, the zinc finger binding domains bind to a target DNA sequence that is at least 90%, 95%, 96%, 97%, 98%, or 99% identical, or is 100% identical to one of SEQ ID NOs: 499-524. In some embodiments, the zinc finger binding domains bind to a target DNA sequence that is at least 90%, 95%, 96%, 97%, 98%, or 99% identical, or is 100% identical to a target DNA sequence of BCOR. In some embodiments, the zinc finger binding domains bind to a target DNA sequence that is at least 90%, 95%, 96%, 97%, 98%, or 99% identical, or is 100% identical to one of SEQ ID NOs: 708-772 or SEQ ID NOs: 708-764. In some embodiments, the zinc finger binding domains bind to a target DNA sequence that is at least 90%, 95%, 96%, 97%, 98%, or 99% identical, or is 100% identical to a target DNA sequence of TNFAIP3. In some embodiments, the zinc finger binding domains bind to a target DNA sequence that is at least 90%, 95%, 96%, 97%, 98%, or 99% identical, or is 100% identical to one of SEQ ID NOs: 348-396 or SEQ ID NOs: 348-386.

In some embodiments, the zinc finger binding domains bind to a target DNA sequence that is at least 90%, 95%, 96%, 97%, 98%, or 99% identical, or is 100% identical to a target DNA sequence of a target gene selected BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3). In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in one of Table 6A-Table 6H. In some embodiments, the zinc finger binding domains bind to a target DNA sequence that is at least 90%, 95%, 96%, 97%, 98%, or 99% identical, or is 100% identical to one of SEQ ID NOs: 814-1566.

In some embodiments, the zinc finger binding domains bind to a target DNA sequence that is at least 90%, 95%, 96%, 97%, 98%, or 99% identical, or is 100% identical to a target DNA sequence of a target gene selected BCL2L11, FLI1, CALM2, DHODH, UMPS, RBM39, SEMA7A, CHIC2, PCBP1, PBRM1, WDR6, E2F8, SERPINA3, and GNAS. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the zinc finger binding domains bind to a target DNA sequence that is at least 90%, 95%, 96%, 97%, 98%, or 99% identical, or is 100% identical to one of SEQ ID NOs: 814-1064. In some embodiments, the zinc finger binding domains bind to a target DNA sequence that is at least 90%, 95%, 96%, 97%, 98%, or 99% identical, or is 100% identical to a target DNA sequence of ZC3H12A. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the zinc finger binding domains bind to a target DNA sequence that is at least 90%, 95%, 96%, 97%, 98%, or 99% identical, or is 100% identical to one of SEQ ID NOs: 1065-1509. In some embodiments, the zinc finger binding domains bind to a target DNA sequence that is at least 90%, 95%, 96%, 97%, 98%, or 99% identical, or is 100% identical to one of SEQ ID NOs: 1065-1264.

In some embodiments, the zinc finger binding domains bind to a target DNA sequence that is at least 90%, 95%, 96%, 97%, 98%, or 99% identical, or is 100% identical to a target DNA sequence of the MAP4K1 gene. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, the zinc finger binding domains bind to a target DNA sequence that is at least 90%, 95%, 96%, 97%, 98%, or 99% identical, or is 100% identical to one of SEQ ID NOs: 510-1538. In some embodiments, the zinc finger binding domains bind to a target DNA sequence that is at least 90%, 95%, 96%, 97%, 98%, or 99% identical, or is 100% identical to a target DNA sequence of the NR4A3 gene. In some embodiments, the zinc finger binding domains bind to a target DNA sequence that is at least 90%, 95%, 96%, 97%, 98%, or 99% identical, or is 100% identical to a target DNA sequence defined by a set of genomic coordinates shown in Table 6G or Table 6H. In some embodiments, the zinc finger binding domains bind to a target DNA sequence that is at least 90%, 95%, 96%, 97%, 98%, or 99% identical, or is 100% identical to one of SEQ ID NOs: 1539-1566.

In some embodiments, the zinc finger system is selected from those known in the art, such as those available from commercial suppliers such as Sigma Aldrich. For example, in some embodiments, the zinc finger system is selected from those known in the art, such as those described in Table 7 below.

TABLE 7

Exemplary Zinc Finger Systems

| Target Gene | Zinc Finger System |
| --- | --- |
| SEMA7A | CompoZr ® Knockout ZFN plasmid human SEMA7A NM_003612 (SigmaAldrich Product # CKOZFND19082) |
| | CompoZr ® Knockout ZFN plasmid murine Sema7a NM_011352.2 (SigmaAldrich Product # CKOZFND 19082) |
| RBM39 | CompoZr ® Knockout ZFN plasmid Human RBM39 (NM_004902) (SigmaAldrich Product # CKOZFND 18044) |
| | CompoZr ® Knockout ZFN plasmid Mouse Rbm39 (NM_133242.2) (SigmaAldrich Product # CKOZFND39983) |
| BCL2L11 | CompoZr ® Knockout ZFN plasmid Human BCL2L11 (NM_006538) (SigmaAldrich Product # CKOZFND3909) |
| | CompoZr ® Knockout ZFN plasmid Mouse Bcl2l11 (NM_207680.2) (SigmaAldrich Product # CKOZFND27562) |
| FLI1 | CompoZr ® Knockout ZFN Kit Human FLI1 (NM_002017) (SigmaAldrich Product # CKOZFN8731) |

TABLE 7-continued

Exemplary Zinc Finger Systems

| Target Gene | Zinc Finger System |
|---|---|
| FLI1 | CompoZr ® Knockout ZFN plasmid Mouse Fli1 (NM_008026.4) (SigmaAldrich Product # CKOZFND31430) |
| CALM2 | CompoZr ® Knockout ZFN Kit Human CALM2 (NM_001743) (SigmaAldrich Product # CKOZFN5301)<br>CompoZr ® Knockout ZFN plasmid Mouse Calm2 (NM_007589.5) (SigmaAldrich Product # CKOZFND27915) |
| DHODH | CompoZr ® Knockout ZFN plasmid Human DHODH (NM_001361) (SigmaAldrich Product # CKOZFND 1982)<br>CompoZr ® Knockout ZFN plasmid Mouse Dhodh (NM_020046.3) (SigmaAldrich Product # CKOZFND29960) |
| UMPS | CompoZr ® Knockout ZFN plasmid Human UMPS (NM_000373) (SigmaAldrich Product # CKOZFND1693)<br>CompoZr ® Knockout ZFN plasmid Mouse Umps (NM_009471.2) (SigmaAldrich Product # CKOZFND43931) |
| CHIC2 | CompoZr ® Knockout ZFN Kit Human CHIC2 (NM_012110) (SigmaAldrich Product # CKOZFN6059)<br>CompoZr ® Knockout ZFN plasmid Mouse Chic2 (NM_028850.4) (SigmaAldrich Product # CKOZFND28691) |
| PCBP1 | CompoZr ® Knockout ZFN plasmid Human PCBP1 (NM_006196) (SigmaAldrich Product # CKOZFND16392)<br>CompoZr ® Knockout ZFN plasmid Mouse Pcbp1 (NM_011865.3) (SigmaAldrich Product # CKOZFND38313) |
| PBRM1 | CompoZr ® Knockout ZFN plasmid Human PBRM1 (NM_018165) (SigmaAldrich Product # CKOZFND2434)<br>CompoZr ® Knockout ZFN plasmid Mouse Pbrm1 (NM_001081251.1) (SigmaAldrich Product # CKOZFND38304) |
| WDR6 | CompoZr ® Knockout ZFN plasmid Human WDR6 (NM_018031) (SigmaAldrich Product # CKOZFND22841)<br>CompoZr ® Knockout ZFN plasmid Mouse Wdr6 (NM_031392.2) (SigmaAldrich Product # CKOZFND44594) |
| E2F8 | CompoZr ® Knockout ZFN plasmid Human E2F8 (NM_024680) (SigmaAldrich Product # CKOZFND7610)<br>CompoZr ® Knockout ZFN plasmid Mouse E2f8 (NM_001013368.5) (SigmaAldrich Product # CKOZFND30371) |
| SERPINA3 | CompoZr ® Knockout ZFN plasmid Human SERPINA3 (NM_001085) (SigmaAldrich Product # CKOZFND1900) |
| GNAS | CompoZr ® Knockout ZFN plasmid Human GNAS (NM_000516) (SigmaAldrich Product # CKOZFND1354)<br>CompoZr ® Knockout ZFN plasmid Mouse Gnas (NM_001077510.2) (SigmaAldrich Product # CKOZFND32583) |
| ZC3H12A | CompoZr ® Knockout ZFN Kit, ZFN plasmid Human ZC3H12A (NM_025079) (SigmaAldrich# CKOZFND23094)<br>CompoZr ® Knockout ZFN Kit, ZFN plasmid mouse Zc3h12a (NM_153159.2) (SigmaAldrich# CKOZFND44851) |
| MAP4K1 | CompoZr ® Knockout ZFN plasmid Human MAP4K1 (NM_001042600) (SigmaAldrich# CKOZFND12999)<br>CompoZr ® Knockout ZFN plasmid Mouse Map4k1 (NM_008279.2) (SigmaAldrich# CKOZFND35246) |
| NR4A3 | CompoZr ® Knockout ZFN plasmid Human NR4A3 (NM_006981) (SigmaAldrich# CKOZFND2362)<br>CompoZr ® Knockout ZFN plasmid Mouse Nr4a3 (NM_015743.2) (SigmaAldrich# CKOZFND36667) |

In some embodiments, the gene-regulating system comprises two or more ZFP-fusion proteins each comprising a zinc finger binding domain, wherein at least one of the zinc finger binding domains binds to a target DNA sequence that is at least 90%, 95%, 96%, 97%, 98%, or 99% identical, or 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the zinc finger binding domains binds to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3. In some embodiments, at least one of the zinc finger binding domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the zinc finger binding domains binds to a target DNA sequence that is at least 90%, 95%, 96%, 97%, 98%, or 99% identical, or is 100% identical to a target DNA sequence defined by a set of genomic coordinates shown in one of Tables 6A-Table 6H. In some embodiments, at least one of the zinc finger binding domains bind to a target DNA sequence that is at least 90%, 95%, 96%, 97%, 98%, or 99% identical, or is 100% identical to one of SEQ ID NOs: 154-498 or SEQ ID NOs: 499-813 and at least one of the zinc finger binding domains bind to a target DNA sequence that is at least 90%, 95%, 96%, 97%, 98%, or 99% identical, or is 100% identical to one of SEQ ID NOs: 814-1566.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the two or more zinc finger binding domains binds to a target DNA sequence that is at least 90% 95%, 96%, 97%, 98%, or 99% identical, or 100% identical to a target DNA sequence defined by a set of genomic coordinates shown in Table 5A or Table 5B and at least one of the two or more zinc finger binding domains binds to a target DNA sequence that is at least 90% 95%, 96%, 97%, 98%, or 99% identical, or is 100% identical to a target DNA sequence defined by a set of genomic coordinates shown in Table 6A or Table 6B. In some embodiments, at least one of the two or more zinc finger binding domains binds to a target DNA sequence that is at least 90%, 95%, 96%, 97%, 98%, or 99% identical, or is 100% identical to one of SEQ ID NOs: 814-1064 and at least one of the two or more zinc finger binding domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, at least one of the two or more zinc finger binding domains binds to a target DNA sequence that is at least 90%, 95%, 96%, 97%, 98%, or 99% identical, or is 100% identical to one of SEQ ID NOs: 814-1064 and at least one of the two or more zinc finger binding domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of ZC3H12A. In some embodiments, at least one of the two or more zinc finger binding domains binds to a target DNA sequence that is at least 90% 95%, 96%, 97%, 98%, or 99% identical, or is 100% identical to a target DNA sequence defined by a set of genomic coordinates shown in Table 5A or Table 5B and at least one of the two or more zinc finger binding domains binds to a target DNA sequence that is at least 90% 95%, 96%, 97%, 98%, or 99% identical, or is 100% identical to a target DNA sequence defined by a set of genomic coordinates shown in Table 6C or Table 6D. In some embodiments, at least one of the two or more zinc finger binding domains binds to a target DNA sequence that is at least 90%, 95%, 96%, 97%, 98%, or 99% identical, or is 100% identical to one of SEQ ID NOs: 1065-1509 and at least one of the two or more zinc finger binding domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more ZFP-fusion proteins each comprising a zinc finger binding domain, wherein at least one of the zinc finger binding domains binds to a target DNA sequence the CBLB gene and at least one of the zinc finger binding domains binds to a target DNA sequence of the ZC3H12A gene. In some embodiments, at least one of the two or more zinc finger binding domains binds to a target DNA sequence that is at least 90%, 95%, 96%, 97%, 98%, or 99% identical, or is 100% identical to one of SEQ ID NOs: 1065-1509 and at least one of the two or more zinc finger binding domains binds to a target DNA sequence that is at least 90%, 95%, 96%, 97%, 98%, or 99% identical, or is 100% identical to one of SEQ ID NOs: 499-524. In some embodiments, at least one of the two or more zinc finger binding domains binds to a target DNA sequence that is at least 90%, 95%, 96%, 97%, 98%, or 99% identical, or is 100% identical to one of SEQ ID NOs: 1065-1264 and at least one of the two or more zinc finger binding domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of the MAP4K1 gene. In some embodiments, at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6D or Table 6E. In some embodiments, at least one of the two or more zinc finger binding domains binds to a target DNA sequence that is at least 90%, 95%, 96%, 97%, 98%, or 99% identical, or is 100% identical to one of SEQ ID NOs: 510-1538 and at least one of the two or more zinc finger binding domains binds to a target DNA sequence that is at least at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more ZFP-fusion proteins each comprising a zinc finger binding domain, wherein at least one of the zinc finger binding domains binds to a target DNA sequence the CBLB gene selected and at least one of the zinc finger binding domains binds to a target DNA sequence of the MAP4K1 gene. In some embodiments, at least one of the two or more zinc finger binding domains binds to a target DNA sequence that is at least 90%, 95%, 96%, 97%, 98%, or 99% identical, or is 100% identical to one of SEQ ID NOs: 510-1538 and at least one of the two or more zinc finger binding domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more ZFP-fusion proteins each comprising a zinc finger binding domain, wherein at least one of the zinc finger binding domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the zinc finger binding domains binds to a target DNA sequence of the NR4A3 gene. In some embodiments, at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more zinc finger binding domains binds to a target DNA sequence that is at least 90%, 95%, 96%, 97%, 98%, or 99% identical, or is 100% identical to a target DNA sequence defined by a set of genomic coordinates shown in Table 6F or Table 6G. In some embodiments, at least one of the two or more zinc finger binding domains binds to a target DNA sequence that is at least 90%, 95%, 96%, 97%, 98%, or 99% identical, or is 100% identical to one of SEQ ID NOs: 1539-1566 and at least one of the two or more zinc finger binding domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more ZFP-fusion proteins each comprising a zinc finger binding domain, wherein at least one of the zinc finger binding domains binds to a target DNA sequence the CBLB gene selected and at least one of the zinc finger binding domains binds to a target DNA sequence of the NR4A3 gene. In some embodiments, at least one of the two or more zinc finger binding domains binds to a target DNA sequence that is at least 90%, 95%, 96%, 97%, 98%, or 99% identical, or is 100% identical to one of SEQ ID NOs: 1539-1566 and at least one of the two or more zinc finger binding domains binds to a target DNA sequence that is at least 90%, 95%, 96%, 97%, 98%, or 99% identical, or is 100% identical to one of SEQ ID NOs: 499-524.

The enzymatic domain portion of the zinc finger fusion proteins can be obtained from any endo- or exonuclease. Exemplary endonucleases from which an enzymatic domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNaseI; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

Exemplary restriction endonucleases (restriction enzymes) suitable for use as an enzymatic domain of the ZFPs described herein are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 31,978-31,982. Thus, in one embodiment, fusion proteins comprise the enzymatic domain from at least one Type IIS restriction enzyme and one or more zinc finger binding domains.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Thus, for targeted double-stranded DNA cleavage using zinc finger-FokI fusions, two fusion proteins, each comprising a FokI enzymatic domain, can be used to reconstitute a catalytically active cleavage domain. Alternatively, a single polypeptide molecule containing a zinc finger binding domain and two FokI enzymatic domains can also be used. Exemplary ZFPs comprising FokI enzymatic domains are described in U.S. Pat. No. 9,782,437.

2. TALEN Systems

TALEN-based systems comprise a protein comprising a TAL effector DNA binding domain and an enzymatic domain. They are made by fusing a TAL effector DNA-binding domain to a DNA cleavage domain (a nuclease which cuts DNA strands). The FokI restriction enzyme described above is an exemplary enzymatic domain suitable for use in TALEN-based gene-regulating systems.

TAL effectors are proteins that are secreted by *Xanthomonas* bacteria via their type III secretion system when they infect plants. The DNA binding domain contains a repeated, highly conserved, 33-34 amino acid sequence with divergent 12th and 13th amino acids. These two positions, referred to as the Repeat Variable Diresidue (RVD), are highly variable and strongly correlated with specific nucleotide recognition. Therefore, the TAL effector domains can be engineered to bind specific target DNA sequences by selecting a combination of repeat segments containing the appropriate RVDs. The nucleic acid specificity for RVD combinations is as follows: HD targets cytosine, NI targets adenenine, NG targets thymine, and NN targets guanine (though, in some embodiments, NN can also bind adenenine with lower specificity).

In some embodiments, the TAL effector domains bind to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the TAL effector domains bind to a target DNA sequence that is at least 90%, 95%, 96%, 97%, 98%, or 99% identical, or is 100% identical to one of SEQ ID NOs: 154-498 or SEQ ID NOs: 499-813. In some embodiments, the TAL effector domains bind to a target DNA sequence that is at least 90%, 95%, 96%, 97%, 98%, or 99% identical, or is 100% identical to a target DNA sequence of the CBLB gene. In some embodiments, the TAL effector domains bind to a target DNA sequence that is at least 90%, 95%, 96%, 97%, 98%, or 99% identical, or is 100% identical to one of SEQ ID NOs: 499-524. In some embodiments, the TAL effector domains bind to a target DNA sequence that is at least 90%, 95%, 96%, 97%, 98%, or 99% identical, or is 100% identical to a target DNA sequence of the BCOR gene, and bind to a target DNA sequence that is at least 90%, 95%, 96%, 97%, 98%, or 99% identical, or is 100% identical to one of SEQ ID NOs: 708-772 or SEQ ID NOs: 708-764. In some embodiments, the TAL effector domains bind to a target DNA sequence that is at least 90%, 95%, 96%, 97%, 98%, or 99% identical, or is 100% identical to a target DNA sequence of the TNFAIP3, bind to a target DNA sequence that is at least 90%, 95%, 96%, 97%, 98%, or 99% identical, or is 100% identical to one of SEQ ID NOs: 348-396 or SEQ ID NOs: 348-386.

In some embodiments, the TAL effector domains bind to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3). In some embodiments, the TAL effector domains bind to a target DNA sequence that is at least 90%, 95%, 96%, 97%, 98%, or 99% identical, or is 100% identical to a target DNA sequence defined by a set of genomic coordinates shown in one of Tables 6A-Table 6H. In some embodiments, the TAL effector domains bind to a target DNA sequence that is at least 90%, 95%, 96%, 97%, 98%, or 99% identical, or is 100% identical to one of SEQ ID NOs: 814-1566.

In some embodiments, the TAL effector domains bind to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the TAL effector domains bind to a target DNA sequence that is at least 90%, 95%, 96%, 97%, 98%, or 99% identical, or is 100% identical to one of SEQ ID NOs: 814-1064. In some embodiments, the TAL effector domains bind to a target DNA sequence that is at least 90%, 95%, 96%, 97%, 98%, or 99% identical, or is 100% identical to a target DNA sequence of ZC3H12A. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the TAL effector domains bind to a target DNA sequence that is at least 90%, 95%, 96%, 97%, 98%, or 99% identical, or is 100% identical to one of SEQ ID NOs: 1065-1509. In some embodiments, the TAL effector domains bind to a target DNA sequence that is at least 90%, 95%, 96%, 97%, 98%, or 99% identical, or is 100% identical to one of SEQ ID NOs: 1065-1264.

In some embodiments, the TAL effector domains bind to a target DNA sequence that is at least 90%, 95%, 96%, 97%, 98%, or 99% identical, or is 100% identical to a target DNA sequence of the MAP4K1 gene. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, the TAL effector domains bind to a target DNA sequence that is at least 90%, 95%, 96%, 97%, 98%, or 99% identical, or is 100% identical to one of SEQ ID NOs: 510-1538. In some embodiments, the TAL effector domains bind to a target DNA sequence that is at least 90%, 95%, 96%, 97%, 98%, or 99% identical, or is 100% identical to a target DNA sequence of the NR4A3 gene. In some embodiments, the TAL effector domains bind to a target DNA sequence that is at least 90%, 95%, 96%, 97%, 98%, or 99% identical, or is 100% identical to a target DNA sequence defined by a set of genomic coordinates shown in Table 6G or Table 6H. In some embodiments, the TAL effector domains bind to a target DNA sequence that is at least 90%, 95%, 96%, 97%, 98%, or 99% identical, or is 100% identical to one of SEQ ID NOs: 1539-1566.

In some embodiments, the gene-regulating system comprises two or more TAL effector-fusion proteins each comprising a TAL effector domain, wherein at least one of the TAL effector domains binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3. In some embodiments, at least one of the TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the TAL effector domains binds to a target DNA sequence that is at least 90%, 95%, 96%, 97%, 98%, or 99% identical, or is 100% identical to a target DNA sequence defined by a set of genomic coordinates shown in one of Tables 6A-Table 6H. In some embodiments, at least one of the TAL effector domains binds to a target DNA sequence that is at least 90%, 95%, 96%, 97%, 98%, or 99% identical, or is 100% identical to one of SEQ ID NOs: 154-498 or SEQ ID NOs: 499-813 and at least one of the TAL effector domains binds to a target DNA sequence that is at least 90%, 95%, 96%, 97%, 98%, or 99% identical, or is 100% identical to one of SEQ ID NOs: 814-1566.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, at least one of the two or more TAL effector domains binds to a target DNA sequence that is at least 90%, 95%, 96%, 97%, 98%, or 99% identical, or is 100% identical to one of SEQ ID NOs: 814-1064 and at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more TAL effector-fusion proteins each comprising a TAL effector domain, wherein at least one of the TAL effector domains binds to a target DNA sequence of CBLB and at least one of the TAL effector domains binds to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the two or more TAL effector domains binds to a target DNA sequence that is at least 90%, 95%, 96%, 97%, 98%, or 99% identical, or is 100% identical to one of SEQ ID NOs: 814-1064 and at least one of the two or more TAL effector domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of ZC3H12A. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds binds to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, at least one of the two or more TAL effector domains binds binds to a target DNA sequence that is at least 90%, 95%, 96%, 97%, 98%, or 99% identical, or is 100% identical to one of SEQ ID NOs: 1065-1509 and at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more TAL effector-fusion proteins each comprising a TAL effector domain, wherein at least one of the TAL effector domains binds to a target DNA sequence the CBLB gene and at least one of the TAL effector domains binds to a target DNA sequence of the ZC3H12A gene. In some embodiments, at least one of the two or more TAL effector domains binds to a target DNA sequence that is at least 90%, 95%, 96%, 97%, 98%, or 99% identical, or is 100% identical to one of SEQ ID NOs: 1065-1509 and at least one of the two or more TAL effector domains binds to a target DNA sequence that is at least 90%, 95%, 96%, 97%, 98%, or 99% identical, or is 100% identical to one of SEQ ID NOs: 499-524. In some embodiments, at least one of the two or more TAL effector domains binds to a target DNA sequence that is at least 90%, 95%, 96%, 97%, 98%, or 99% identical, or is 100% identical to one of SEQ ID NOs: 1065-1264 and at least one of the two or more TAL effector domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of the MAP4K1 gene. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6D or Table 6E. In some embodiments, at least one of the two or more TAL effector domains binds to a target DNA sequence that is at least 90%, 95%, 96%, 97%, 98%, or 99% identical, or is 100% identical to one of SEQ ID NOs: 510-1538 and at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more TAL effector-fusion proteins each comprising a TAL effector domain, wherein at least one of the TAL effector domains binds to a target DNA sequence of the CBLB gene selected and at least one of the TAL effector domains binds to a target DNA sequence of the MAP4K1 gene. In some embodiments, at least one of the two or more TAL effector domains binds to a target DNA sequence that is at least 90%, 95%, 96%, 97%, 98%, or 99% identical, or is 100% identical to one of SEQ ID NOs: 510-1538 and at least one of the two or more TAL effector domains binds to a target DNA sequence that is at least 90%, 95%, 96%, 97%, 98%, or 99% identical, or is 100% identical to one of SEQ ID NOs: 499-524.

In some embodiments, the gene-regulating system comprises two or more TAL effector-fusion proteins each comprising a TAL effector domain, wherein at least one of the TAL effector domains binds to a target DNA sequence a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and at least one of the TAL effector domains binds to a target DNA sequence of the NR4A3 gene. In some embodiments, at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the two or more TAL effector domains binds to a target DNA sequence that is at least 90%, 95%, 96%, 97%, 98%, or 99% identical, or is 100% identical to a target DNA sequence defined by a set of genomic coordinates shown in Table 6F or Table 6G. In some embodiments, at least one of the two or more TAL effector domains binds to a target DNA sequence that is at least 90%, 95%, 96%, 97%, 98%, or 99% identical, or is 100% identical to one of SEQ ID NOs: 1539-1566 and at least one of the two or more TAL effector domains binds to a target DNA sequence that is at least 90%, 95%, 96%, 97%, 98%, or 99% identical, or is 100% identical to one of SEQ ID NOs: 154-498 or SEQ ID NOs: 499-813.

In some embodiments, the gene-regulating system comprises two or more TAL effector-fusion proteins each comprising a TAL effector domain, wherein at least one of the TAL effector domains binds to a target DNA sequence of the CBLB gene selected and at least one of the TAL effector domains binds to a target DNA sequence of the NR4A3 gene. In some embodiments, at least one of the two or more TAL effector domains binds to a target DNA sequence that is at least 90%, 95%, 96%, 97%, 98%, or 99% identical, or is 100% identical to one of SEQ ID NOs: 1539-1566 and at least one of the two or more TAL effector domains binds to a target DNA sequence that is at least 90%, 95%, 96%, 97%, 98%, or 99% identical, or is 100% identical to one of SEQ ID NOs: 499-524.

Methods and compositions for assembling the TAL-effector repeats are known in the art. See e.g., Cermak et al, Nucleic Acids Research, 39:12, 2011, e82. Plasmids for constructions of the TAL-effector repeats are commercially available from Addgene.

C. Combination Nucleic Acid/Protein-Based Gene-Regulating Systems

Combination gene-regulating systems comprise a site-directed modifying polypeptide and a nucleic acid guide molecule. Herein, a "site-directed modifying polypeptide" refers to a polypeptide that binds to a nucleic acid guide molecule, is targeted to a target nucleic acid sequence, (for example, an endogenous target DNA or RNA sequence) by the nucleic acid guide molecule to which it is bound, and modifies the target nucleic acid sequence (e.g., by cleavage, mutation, or methylation of the target nucleic acid sequence).

A site-directed modifying polypeptide comprises two portions, a portion that binds the nucleic acid guide and an activity portion. In some embodiments, a site-directed modifying polypeptide comprises an activity portion that exhibits site-directed enzymatic activity (e.g., DNA methylation, DNA or RNA cleavage, histone acetylation, histone methylation, etc.), wherein the site of enzymatic activity is determined by the guide nucleic acid. In some cases, a site-directed modifying polypeptide comprises an activity portion that has enzymatic activity that modifies the endogenous target nucleic acid sequence (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). In other cases, a site-directed modifying polypeptide comprises an activity portion that has enzymatic activity that modifies a polypeptide (e.g., a histone) associated with the endogenous target nucleic acid sequence (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity). In some embodiments, a site-directed modifying polypeptide comprises an activity portion that modulates transcription of a target DNA sequence (e.g., to increase or decrease transcription). In some embodiments, a site-directed modifying polypeptide comprises an activity portion that modulates expression or translation of a target RNA sequence (e.g., to increase or decrease transcription).

The nucleic acid guide comprises two portions: a first portion that is complementary to, and capable of binding with, an endogenous target nucleic sequence (referred to herein as a "nucleic acid-binding segment"), and a second portion that is capable of interacting with the site-directed modifying polypeptide (referred to herein as a "protein-binding segment"). In some embodiments, the nucleic acid-binding segment and protein-binding segment of a nucleic acid guide are comprised within a single polynucleotide molecule. In some embodiments, the nucleic acid-binding segment and protein-binding segment of a nucleic acid guide are each comprised within separate polynucleotide molecules, such that the nucleic acid guide comprises two polynucleotide molecules that associate with each other to form the functional guide.

The nucleic acid guide mediates the target specificity of the combined protein/nucleic acid gene-regulating systems by specifically hybridizing with a target nucleic acid sequence. In some embodiments, the target nucleic acid sequence is an RNA sequence, such as an RNA sequence comprised within an mRNA transcript of a target gene. In some embodiments, the target nucleic acid sequence is a DNA sequence comprised within the DNA sequence of a target gene. Reference herein to a target gene encompasses the full-length DNA sequence for that particular gene which comprises a plurality of target genetic loci (i.e., portions of a particular target gene sequence (e.g., an exon or an intron)). Within each target genetic loci are shorter stretches of DNA sequences referred to herein as "target DNA sequences" that can be modified by the gene-regulating systems described herein. Further, each target genetic loci comprises a "target modification site," which refers to the precise location of the modification induced by the gene-regulating system (e.g., the location of an insertion, a deletion, or mutation, the location of a DNA break, or the location of an epigenetic modification).

The gene-regulating systems described herein may comprise a single nucleic acid guide, or may comprise a plurality of nucleic acid guides (e.g., 2, 3, 4, 5, 6, 7, 8, 9, 10, or more nucleic acid guides).

In some embodiments, the combined protein/nucleic acid gene-regulating systems comprise site-directed modifying polypeptides derived from Argonaute (Ago) proteins (e.g., *T. thermophiles* Ago or TtAgo). In such embodiments, the site-directed modifying polypeptide is a *T. thermophiles* Ago DNA endonuclease and the nucleic acid guide is a guide DNA (gDNA) (See, Swarts et al., Nature 507 (2014), 258-261). In some embodiments, the present disclosure provides a polynucleotide encoding a gDNA. In some embodiments, a gDNA-encoding nucleic acid is comprised in an expression vector, e.g., a recombinant expression vector. In some embodiments, the present disclosure provides a polynucleotide encoding a TtAgo site-directed modifying polypeptide or variant thereof. In some embodiments, the polynucleotide encoding a TtAgo site-directed modifying polypeptide is comprised in an expression vector, e.g., a recombinant expression vector.

In some embodiments, the gene editing systems described herein are CRISPR (Clustered Regularly Interspaced Short Palindromic Repeats)/Cas (CRISPR Associated) nuclease systems. In some embodiments, the CRISPR/Cas system is a Class 2 system. Class 2 CRISPR/Cas systems are divided into three types: Type II, Type V, and Type VI systems. In some embodiments, the CRISPR/Cas system is a Class 2 Type II system, utilizing the Cas9 protein. In such embodiments, the site-directed modifying polypeptide is a Cas9 DNA endonuclease (or variant thereof) and the nucleic acid guide molecule is a guide RNA (gRNA). In some embodiments, the CRISPR/Cas system is a Class 2 Type V system, utilizing the Cas12 proteins (e.g., Cas12a (also known as Cpf1), Cas12b (also known as C2c1), Cas12c (also known as C2c3), Cas12d (also known as CasY), and Cas12e (also known as CasX)). In such embodiments, the site-directed modifying polypeptide is a Cas12 DNA endonuclease (or variant thereof) and the nucleic acid guide molecule is a gRNA. In some embodiments, the CRISPR/Cas system is a Class 2 and Type VI system, utilizing the Cas13 proteins (e.g., Cas13a (also known as C2c2), Cas13b, and Cas13c). (See, Pyzocha et al., ACS Chemical Biology, 13(2), 347-356). In such embodiments, the site-directed modifying polypeptide is a Cas13 RNA riboendonuclease and the nucleic acid guide molecule is a gRNA.

A Cas polypeptide refers to a polypeptide that can interact with a gRNA molecule and, in concert with the gRNA molecule, home or localize to a target DNA or target RNA sequence. Cas polypeptides include naturally occurring Cas proteins and engineered, altered, or otherwise modified Cas proteins that differ by one or more amino acid residues from a naturally-occurring Cas sequence.

A guide RNA (gRNA) comprises two segments, a DNA-binding segment and a protein-binding segment. In some embodiments, the protein-binding segment of a gRNA is comprised in one RNA molecule and the DNA-binding segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The protein-binding segment of a gRNA comprises, in part, two complementary stretches of nucleotides that hybridize to one another to form a double stranded RNA duplex (dsRNA duplex), which facilitates binding to the Cas protein. The nucleic acid-binding segment (or "nucleic acid-binding sequence") of a gRNA comprises a nucleotide sequence that is complementary to and capable of binding to a specific target nucleic acid sequence. The protein-binding segment of the gRNA interacts with a Cas polypeptide and the interaction of the gRNA molecule and site-directed modifying polypeptide results in Cas binding to the endogenous nucleic acid sequence and produces one or more modifications within or around the target nucleic acid sequence. The precise location of the target modification site is determined by both (i) base-pairing complementarity between the gRNA and the target nucleic acid sequence; and (ii) the location of a short motif, referred to as the protospacer adjacent motif (PAM), in the target DNA sequence (referred to as a protospacer flanking sequence (PFS) in target RNA sequences). The PAM/PFS sequence is required for Cas binding to the target nucleic acid sequence. A variety of PAM/PFS sequences are known in the art and are suitable for use with a particular Cas endonuclease (e.g., a Cas9 endonuclease)(See e.g., Nat Methods. 2013 November; 10(11): 1116-1121 and Sci Rep. 2014; 4: 5405). In some embodiments, the PAM sequence is located within 50 base pairs of the target modification site in a target DNA sequence. In some embodiments, the PAM sequence is located within 10 base pairs of the target modification site in a target DNA sequence. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the PFS sequence is located at the 3' end of the target RNA sequence. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

1. Cas Proteins

In some embodiments, the site-directed modifying polypeptide is a Cas protein. Cas molecules of a variety of species can be used in the methods and compositions described herein, including Cas molecules derived from *S. pyogenes, S. aureus, N. meningitidis, S. thermophiles, Acidovorax avenae, Actinobacillus pleuropneumoniae, Actinobacillus succinogenes, Actinobacillus suis, Actinomyces* sp., *Cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae.*

In some embodiments, the Cas protein is a naturally-occurring Cas protein. In some embodiments, the Cas endonuclease is selected from the group consisting of C2C1, C2C3, Cpf1 (also referred to as Cas12a), Cas12b, Cas12c, Cas12d, Cas12e, Cas13a, Cas13b, Cas13c, Cas13d, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In some embodiments, the Cas protein is an endoribonuclease such as a Cas13 protein. In some embodiments, the Cas13 protein is a Cas13a (Abudayyeh et al., Nature 550 (2017), 280-284), Cas13b (Cox et al., Science (2017) 358: 6336, 1019-1027), Cas13c (Cox et al., Science (2017) 358:6336, 1019-1027), or Cas13d (Zhang et al., Cell 175 (2018), 212-223) protein.

In some embodiments, the Cas protein is a wild-type or naturally occurring Cas9 protein or a Cas9 ortholog. Wild-type Cas9 is a multi-domain enzyme that uses an HNH nuclease domain to cleave the target strand of DNA and a RuvC-like domain to cleave the non-target strand. Binding of WT Cas9 to DNA based on gRNA specificity results in double-stranded DNA breaks that can be repaired by non-homologous end joining (NHEJ) or homology-directed repair (HDR). Exemplary naturally occurring Cas9 molecules are described in Chylinski et al., RNA Biology 2013 10:5, 727-737 and additional Cas9 orthologs are described in International PCT Publication No. WO 2015/071474. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 1 1 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

In some embodiments, the naturally occurring Cas9 polypeptide is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, the Cas polypeptide comprises one or more of the following activities:

(a) a nickase activity, i.e., the ability to cleave a single strand, e.g., the non-complementary strand or the complementary strand, of a nucleic acid molecule;

(b) a double stranded nuclease activity, i.e., the ability to cleave both strands of a double stranded nucleic acid and create a double stranded break, which in an embodiment is the presence of two nickase activities;

(c) an endonuclease activity;

(d) an exonuclease activity; and/or (e) a helicase activity, i.e., the ability to unwind the helical structure of a double stranded nucleic acid.

In some embodiments, the Cas polypeptide is fused to heterologous proteins that recruit DNA-damage signaling proteins, exonucleases, or phosphatases to further increase the likelihood or the rate of repair of the target sequence by one repair mechanism or another. In some embodiments, a WT Cas polypeptide is co-expressed with a nucleic acid repair template to facilitate the incorporation of an exogenous nucleic acid sequence by homology-directed repair.

In some embodiments, different Cas proteins (i.e., Cas9 proteins from various species) may be advantageous to use in the various provided methods in order to capitalize on various enzymatic characteristics of the different Cas proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from *S. pyogenes* and recognizes the PAM sequence motif NGG, NAG, NGA (Mali et al, Science 2013; 339 (6121): 823-826). In some embodiments, the Cas protein is a Cas9 protein derived from *S. thermophiles* and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190(4): 1390-1400). In some embodiments, the Cas protein is a Cas9 protein derived from *S. mutans* and recognizes the PAM sequence motif NGG and/or NAAR (R=A or G) (See, e.g., Deveau et al, J BACTERIOL 2008; 190(4): 1390-1400). In some embodiments, the Cas protein is a Cas9 protein derived from *S. aureus* and recognizes the PAM sequence motif NNGRR (R=A or G). In some embodiments, the Cas protein is a Cas9 protein derived from *S. aureus* and recognizes the PAM sequence motif N GRRT (R=A or G). In some embodiments, the Cas protein is a Cas9 protein derived from *S. aureus* and recognizes the PAM sequence motif N GRRV (R=A or G). In some embodiments, the Cas protein is a Cas9 protein derived from *N. meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the Cas protein is a Cas13a protein derived from *Leptotrichia shahii* and recognizes the PFS sequence motif of a single 3' A, U, or C.

In some embodiments, a polynucleotide encoding a Cas protein is provided. In some embodiments, the polynucleotide encodes a Cas protein that is at least 90% identical to a Cas protein described in International PCT Publication No. WO 2015/071474 or Chylinski et al., RNA Biology 2013 10:5, 727-737. In some embodiments, the polynucleotide encodes a Cas protein that is at least 95%, 96%, 97%, 98%, or 99% identical to a Cas protein described in International PCT Publication No. WO 2015/071474 or Chylinski et al., RNA Biology 2013 10:5, 727-737. In some embodiments, the polynucleotide encodes a Cas protein that is 100% identical to a Cas protein described in International PCT Publication No. WO 2015/071474 or Chylinski et al., RNA Biology 2013 10:5, 727-737.

2. Cas Mutants

In some embodiments, the Cas polypeptides are engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild-type Cas protein.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a deactivated Cas (dCas) mutant. In such embodiments, the Cas polypeptide does not comprise any intrinsic enzymatic activity and is unable to mediate target nucleic acid cleavage. In such embodiments, the dCas may be fused with a heterologous protein that is capable of modifying the target nucleic acid in a non-cleavage based manner. For example, in some embodiments, a dCas protein is fused to transcription activator or transcription repressor domains (e.g., the Kruppel associated box (KRAB or SKD); the Mad mSIN3 interaction domain (SID or SID4X); the ERF repressor domain (ERD); the MAX-interacting protein 1 (MXI1); methyl-CpG binding protein 2 (MECP2); etc.). In some such cases, the dCas fusion protein is targeted by the ggRNA to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, the dCas is a dCas13 mutant (Konermann et al., Cell 173 (2018), 665-676). These dCas13 mutants can then be fused to enzymes that modify RNA, including adenosine deaminases (e.g., ADAR1 and ADAR2). Adenosine deaminases convert adenine to inosine, which the translational machinery treats like guanine, thereby creating a functional A→G change in the RNA sequence. In some embodiments, the dCas is a dCas9 mutant.

In some embodiments, the mutant Cas9 is a Cas9 nickase mutant. Cas9 nickase mutants comprise only one catalytically active domain (either the HNH domain or the RuvC domain). The Cas9 nickase mutants retain DNA binding based on gRNA specificity, but are capable of cutting only one strand of DNA resulting in a single-strand break (e.g. a "nick"). In some embodiments, two complementary Cas9 nickase mutants (e.g., one Cas9 nickase mutant with an inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

In some embodiments, the Cas polypeptides described herein can be engineered to alter the PAM/PFS specificity of the Cas polypeptide. In some embodiments, a mutant Cas polypeptide has a PAM/PFS specificity that is different from the PAM/PFS specificity of the parental Cas polypeptide. For example, a naturally occurring Cas protein can be modified to alter the PAM/PFS sequence that the mutant Cas polypeptide recognizes to decrease off target sites, improve specificity, or eliminate a PAM/PFS recognition requirement. In some embodiments, a Cas protein can be modified to increase the length of the PAM/PFS recognition sequence. In some embodiments, the length of the PAM recognition sequence is at least 4, 5, 6, 7, 8, 9, 10 or 15 amino acids in length. Cas polypeptides that recognize different PAM/PFS sequences and/or have reduced off-target activity can be generated using directed evolution. Exemplary methods and systems that can be used for directed evolution of Cas polypeptides are described, e.g., in Esvelt et al. Nature 2011, 472(7344): 499-503.

Exemplary Cas mutants are described in International PCT Publication No. WO 2015/161276 and Konermann et al., Cell 173 (2018), 665-676which are incorporated herein by reference in their entireties.

3. gRNAs

The present disclosure provides guide RNAs (gRNAs) that direct a site-directed modifying polypeptide to a specific target nucleic acid sequence. A gRNA comprises a "nucleic acid-targeting domain" or "targeting domain" and protein-binding segment. The targeting domain may also be referred to as a "spacer" sequence and comprises a nucleotide sequence that is complementary to a target nucleic acid sequence. As such, the targeting domain segment of a gRNA interacts with a target nucleic acid in a sequence-specific manner via hybridization (i.e., base pairing) and determines the location within the target nucleic acid that the gRNA will bind. The targeting domain segment of a gRNA can be modified (e.g., by genetic engineering) to hybridize to a desired sequence within a target nucleic acid sequence. In some embodiments, the targeting domain sequence is between about 13 and about 22 nucleotides in length. In some embodiments, the targeting domain sequence is about 13, 14, 15, 16, 17, 18, 19, 20, 21, or 22 nucleotides in length.

In some embodiments, the targeting domain sequence is about 20 nucleotides in length.

The protein-binding segment of a gRNA interacts with a site-directed modifying polypeptide (e.g. a Cas protein) to form a ribonucleoprotein (RNP) complex comprising the gRNA and the site-directed modifying polypeptide. The targeting domain segment of the gRNA then guides the bound site-directed modifying polypeptide to a specific nucleotide sequence within target nucleic acid via the above-described spacer sequence. The protein-binding segment of a gRNA comprises at least two stretches of nucleotides that are complementary to one another and which form a double stranded RNA duplex. The protein-binding segment of a gRNA may also be referred to as a "scaffold" segment or a "tracr RNA". In some embodiments, the tracr RNA sequence is between about 30 and about 180 nucleotides in length. In some embodiments, the tracr RNA sequence is between about 40 and about 90 nucleotides, about 50 and about 90 nucleotides, about 60 and about 90 nucleotides, about 65 and about 85 nucleotides, about 70 and about 80 nucleotides, about 65 and about 75 nucleotides, or about 75 and about 85 nucleotides in length. In some embodiments, the tracr RNA sequence is about 70, 71, 72, 73, 74, 75, 76, 77, 78, 79, 80, 81, 82, 83, 84, 85, 86, 87, 88, or about 90 nucleotides in length. In some embodiments, the tracr RNA comprises a nucleic acid sequence encoded by the DNA sequence of SEQ ID NO: 34 (See Mali et al., Science (2013) 339(6121):823-826), SEQ ID NOs: 35-36 (See PCT Publication No. WO 2016/106236), SEQ ID NOs: 37-39 (See Deltcheva et al., Nature. 2011 Mar. 31; 471(7340): 602-607), or SEQ ID NO: 40 (See Chen et al., Cell. 2013; 155(7); 1479-1491). Any of the foregoing tracr sequences are suitable for use in combination with any of the gRNA targeting domain embodiments described herein.

In some embodiments, a gRNA comprises two separate RNA molecules (i.e., a "dual gRNA"). In some embodiments, a gRNA comprises a single RNA molecule (i.e. a "single guide RNA" or "sgRNA"). Herein, use of the term "guide RNA" or "gRNA" is inclusive of both dual gRNAs and sgRNAs. A dual gRNA comprises two separate RNA molecules: a "crispr RNA" (or "crRNA") and a "tracr RNA". A crRNA molecule comprises a spacer sequence covalently linked to a "tracr mate" sequence. The tracer mate sequence comprises a stretch of nucleotides that are complementary to a corresponding sequence in the tracr RNA molecule. The crRNA molecule and tracr RNA molecule hybridize to one another via the complementarity of the tracr and tracer mate sequences.

In some embodiments, the gRNA is an sgRNA. In such embodiments, the nucleic acid-targeting sequence and the protein-binding sequence are present in a single RNA molecule by fusion of the spacer sequence to the tracr RNA sequence. In some embodiments, the sgRNA is about 50 to about 200 nucleotides in length. In some embodiments, the sgRNA is about 75 to about 150 or about 100 to about 125 nucleotides in length. In some embodiments, the sgRNA is about 100 nucleotides in length.

In some embodiments, the gRNAs of the present disclosure comprise a targeting domain sequence that is least 90%, 95%, 96%, 97%, 98%, or 99% complementary, or is 100% complementary to a target nucleic acid sequence within a target locus. In some embodiments, the target nucleic acid sequence is an RNA target sequence. In some embodiments, the target nucleic acid sequence is a DNA target sequence.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2). In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 5A or Table 5B. In some embodiments, the targeting domain sequence binds to a target DNA sequence that is at least 90%, 95%, 96%, 97%, 98%, or 99% identical, or is 100% identical to one of SEQ ID NOs: 154-498 or SEQ ID NOs: 499-813. In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the CBLB gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 499-524. Additional gRNAs suitable for targeting CBLB are described in US Patent Application Publication No. 2017/0175128.

In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the TNFAIP3 gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 348-396 or SEQ ID NOs: 348-3486. In some embodiments, the gRNAs provided herein comprise a targeting domain sequence that binds to a target DNA sequence that is at least 90%, 95%, 96%, 97%, 98%, or 99% identical, or is 100% identical to a target DNA sequence of the BCOR gene. In some embodiments, the nucleic acid-binding segments of the gRNA sequences bind to a target DNA sequence that is at least 90%, 95%, 96%, 97%, 98%, or 99% identical, or is 100% identical to one of SEQ ID NOs: 708-772 or SEQ ID NOs: 708-764.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3). In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Tables 6A-Table 6H. In some embodiments, the targeting domain sequence binds to a target DNA sequence that is at least 90%, 95%, 96%, 97%, 98%, or 99% identical, or is 100% identical to one of SEQ ID NOs: 814-1566.

In some embodiments, the gRNAs provided herein comprise a targeting domain sequence that binds to a target DNA sequence that is at least 90%, 95%, 96%, 97%, 98%, or 99% identical, or is 100% identical to a sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6A or Table 6B. In some embodiments, the targeting domain sequence binds to a target DNA sequence that is at least 90%, 95%, 96%, 97%, 98%, or 99% identical, or is 100% identical to one of SEQ ID NOs: 814-1064. In some embodiments, the gRNAs provided herein comprise a targeting domain sequence that binds to a target DNA sequence that is at least 90%, 95%, 96%, 97%, 98%, or 99% identical, or is 100% identical to a sequence of ZC3H12A. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6C or Table 6D. In some embodiments, the targeting domain sequence binds to a target DNA sequence that is at least 90%, 95%, 96%, 97%, 98%, or 99% identical, or is 100% identical to one of SEQ ID NOs: 1065-1509. In some embodiments, the targeting domain sequence binds to a target DNA sequence that is at least 90%, 95%, 96%, 97%, 98%, or 99% identical, or is 100% identical to one of SEQ ID NOs: 1065-1264.

In some embodiments, the gRNAs provided herein comprise a targeting domain sequence that binds to a target DNA sequence that is at least 90%, 95%, 96%, 97%, 98%, or 99% identical, or is 100% identical to a sequence of the MAP4K1 gene. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6E or Table 6F. In some embodiments, the targeting domain sequence binds to a target DNA sequence that is at least 90%, 95%, 96%, 97%, 98%, or 99% identical, or is 100% identical to one of SEQ ID NOs: 510-1538. In some embodiments, the gRNAs provided herein comprise a targeting domain sequence that binds to a target DNA sequence that is at least 90%, 95%, 96%, 97%, 98%, or 99% identical, or is 100% identical to a sequence of the NR4A3 gene. In some embodiments, the targeting domain sequence binds to a target DNA sequence that is at least 90%, 95%, 96%, 97%, 98%, or 99% identical, or is 100% identical to a target DNA sequence defined by a set of genomic coordinates shown in Table 6G or Table 6H. In some embodiments, the targeting domain sequence binds to a target DNA sequence that is at least 90%, 95%, 96%, 97%, 98%, or 99% identical, or is 100% identical to one of SEQ ID NOs: 1539-1566.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR (e.g., a gene selected from Table 2) and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and NR4A3 (e.g., a gene selected from Table 3). In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Tables 6A-6H. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 814-1566. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1566.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6A or Table 6B. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 814-1064. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1064.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB and wherein at least one of the gRNAs comprises a targeting domain that binds to a target DNA sequence that is at least 90%, 95%, 96%, 97%, 98%, or 99% identical, or is 100% identical to a target DNA sequence of a target gene selected from BCL2L11, FLI1, CALM2, DHODH, UMPS, RBM39, SEMA7A, CHIC2, PCBP1, PBRM1, WDR6, E2F8, SERPINA3, and GNAS. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 814-1064. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 814-1064.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of ZC3H12A. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6C or Table 6D. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 1065-1509. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 1065-1509.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB gene and wherein at least one of the gRNAs comprises a targeting domain that binds to a target DNA sequence that is at least 90%, 95%, 96%, 97%, 98%, or 99% identical, or is 100% identical to a target DNA sequence of the ZC3H12A gene. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1065-1509. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1065-1509. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1065-1264. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1065-1264.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of the MAP4K1 gene. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6E or Table 6F. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 1510-1538. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 1510-1538.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB gene and wherein at least one of the gRNAs comprises a targeting domain that binds to a target DNA sequence that is at least 90%, 95%, 96%, 97%, 98%, or 99% identical, or is 100% identical to a target DNA sequence of the MAP4K1 gene. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1510-1538. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1510-1538.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of a target gene selected from IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, or BCOR and wherein at least one of the gRNAs comprises a targeting domain that binds to a target DNA sequence that is at least 90%, 95%, 96%, 97%, 98%, or 99% identical, or is 100% identical to a target DNA sequence of the NR4A3 gene. In some embodiments, at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in Table 5A or Table 5B and at least one of the gRNAs comprises a targeting domain that binds to a target DNA sequence that is at least 90%, 95%, 96%, 97%, 98%, or 99% identical, or is 100% identical to a target DNA sequence defined by a set of genomic coordinates shown in one of Table 6G or Table 6H. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain that binds to a target DNA sequence that is at least 90%, 95%, 96%, 97%, 98%, or 99% identical, or is 100% identical to one of SEQ ID NOs: 1539-1566. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 154-498 or SEQ ID NOs: 499-813 and at least one of the gRNAs comprises a targeting domain encoded by a nucleic acid sequence that is at least 90%, 95%, 96%, 97%, 98%, or 99% identical, or is 100% identical to one of SEQ ID NOs: 1539-1566.

In some embodiments, the gene-regulating system comprises two or more gRNA molecules, wherein at least one of the gRNAs comprises a targeting domain that binds to a target DNA sequence that is at least 90%, 95%, 96%, 97%, 98%, or 99% identical, or is 100% identical to a target DNA sequence of the CBLB gene and wherein at least one of the gRNAs comprises a targeting domain that binds to a target DNA sequence that is at least 90%, 95%, 96%, 97%, 98%, or 99% identical, or is 100% identical to a target DNA sequence of the NR4A3 gene. In some embodiments, at least one of the gRNAs comprises a targeting domain that binds to a target DNA sequence that is at least 90%, 95%, 96%, 97%, 98%, or 99% identical, or is 100% identical to one of SEQ ID NOs: 499-524 and at least one of the gRNAs comprises a targeting domain that binds to a target DNA sequence that is at least 90%, 95%, 96%, 97%, 98%, or 99% identical, or is 100% identical to one of SEQ ID NOs: 1539-1566. In some embodiments, at least one of the gRNAs comprises a targeting domain encoded by a nucleic acid sequence that is at least 90%, 95%, 96%, 97%, 98%, or 99% identical, or is 100% identical to one of SEQ ID NOs: 499-524 and at least one of the gRNAs comprises a targeting domain encoded by a nucleic acid sequence that is at least 90%, 95%, 96%, 97%, 98%, or 99% identical, or is 100% identical to one of SEQ ID NOs: 1539-1566.

In some embodiments, the nucleic acid-binding segments of the gRNA sequences described herein are designed to minimize off-target binding using algorithms known in the art (e.g., Cas-OFF finder) to identify target sequences that are unique to a particular target locus or target gene.

In some embodiments, the gRNAs described herein can comprise one or more modified nucleosides or nucleotides which introduce stability toward nucleases. In such embodiments, these modified gRNAs may elicit a reduced innate immune as compared to a non-modified gRNA. The term "innate immune response" includes a cellular response to exogenous nucleic acids, including single stranded nucleic acids, generally of viral or bacterial origin, which involves the induction of cytokine expression and release, particularly the interferons, and cell death.

In some embodiments, the gRNAs described herein are modified at or near the 5' end (e.g., within 1-10, 1-5, or 1-2 nucleotides of their 5' end). In some embodiments, the 5' end of a gRNA is modified by the inclusion of a eukaryotic mRNA cap structure or cap analog (e.g., a G(5')ppp(5')G cap analog, a m7G(5')ppp(5')G cap analog, or a 3'-0-Me-m7G (5')ppp(5')G anti reverse cap analog (ARCA)). In some embodiments, an in vitro transcribed gRNA is modified by treatment with a phosphatase (e.g., calf intestinal alkaline phosphatase) to remove the 5' triphosphate group. In some embodiments, a gRNA comprises a modification at or near its 3' end (e.g., within 1-10, 1-5, or 1-2 nucleotides of its 3' end). For example, in some embodiments, the 3' end of a gRNA is modified by the addition of one or more (e.g., 25-200) adenine (A) residues.

In some embodiments, modified nucleosides and modified nucleotides can be present in a gRNA, but also may be present in other gene-regulating systems, e.g., mRNA, RNAi, or siRNA-based systems. In some embodiments, modified nucleosides and nucleotides can include one or more of:

(a) alteration, e.g., replacement, of one or both of the non-linking phosphate oxygens and/or of one or more of the linking phosphate oxygens in the phosphodiester backbone linkage;

(b) alteration, e.g., replacement, of a constituent of the ribose sugar, e.g., of the 2' hydroxyl on the ribose sugar;

(c) wholesale replacement of the phosphate moiety with "dephospho" linkers;

(d) modification or replacement of a naturally occurring nucleobase;

(e) replacement or modification of the ribose-phosphate backbone;

(f) modification of the 3' end or 5' end of the oligonucleotide, e.g., removal, modification or replacement of a terminal phosphate group or conjugation of a moiety; and (g) modification of the sugar.

In some embodiments, the modifications listed above can be combined to provide modified nucleosides and nucleotides that can have two, three, four, or more modifications. For example, in some embodiments, a modified nucleoside or nucleotide can have a modified sugar and a modified nucleobase. In some embodiments, every base of a gRNA is modified. In some embodiments, each of the phosphate groups of a gRNA molecule are replaced with phosphorothioate groups.

In some embodiments, a software tool can be used to optimize the choice of gRNA within a user's target sequence, e.g., to minimize total off-target activity across the genome. Off target activity may be other than cleavage. For example, for each possible gRNA choice using S. pyogenes Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool.

IV. Polynucleotides

In some embodiments, the present disclosure provides polynucleotides or nucleic acid molecules encoding a gene-regulating system described herein. As used herein, the terms "nucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, (xi) isolated removal of spurious translation initiation sites and/or (xii) elimination of fortuitous polyadenylation sites otherwise leading to truncated RNA transcripts.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed in particular embodiments, with the total length preferably being limited by the ease of preparation and use in the intended recombinant DNA protocol.

Polynucleotides can be prepared, manipulated and/or expressed using any of a variety of well-established techniques known and available in the art.

Vectors

In order to express a gene-regulating system described herein in a cell, an expression cassette encoding the gene-regulating system can be inserted into appropriate vector. The term "nucleic acid vector" is used herein to refer to a nucleic acid molecule capable transferring or transporting another nucleic acid molecule. The transferred nucleic acid is generally linked to, e.g., inserted into, the vector nucleic acid molecule. A nucleic acid vector may include sequences that direct autonomous replication in a cell, or may include sequences sufficient to allow integration into host cell DNA.

The term "expression cassette" as used herein refers to genetic sequences within a vector which can express an RNA, and subsequently a protein. The nucleic acid cassette contains the gene of interest, e.g., a gene-regulating system. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. The cassette can be removed and inserted into a plasmid or viral vector as a single unit.

In particular embodiments, vectors include, without limitation, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and animal viruses. In particular embodiments, the coding sequences of the gene-regulating systems disclosed herein can be ligated into such vectors for the expression of the gene-regulating systems in mammalian cells.

In some embodiments, non-viral vectors are used to deliver one or more polynucleotides contemplated herein to an immune effector cell, e.g., a T cell. In some embodiments, the recombinant vector comprising a polynucleotide encoding one or more components of a gene-regulating system described herein is a plasmid. Numerous suitable plasmid expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the host cell. Depending on the cell type and gene-regulating system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, the recombinant vector comprising a polynucleotide encoding one or more components of a gene-regulating system described herein is a viral vector. Suitable viral vectors include, but are not limited to, viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al, PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al, Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Examples of vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells.

In some embodiments, the vector is a non-integrating vector, including but not limited to, an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus.

In some embodiments, a polynucleotide is introduced into a target or host cell using a transposon vector system. In certain embodiments, the transposon vector system comprises a vector comprising transposable elements and a polynucleotide contemplated herein; and a transposase. In one embodiment, the transposon vector system is a single transposase vector system, see, e.g., WO 2008/027384. Exemplary transposases include, but are not limited to: piggyBac, Sleeping Beauty, Mos1, Tc1/mariner, Tol2, mini-Tol2, Tc3, MuA, Himar I, Frog Prince, and derivatives thereof. The piggyBac transposon and transposase are described, for example, in U.S. Pat. No. 6,962,810, which is incorporated herein by reference in its entirety. The Sleeping Beauty transposon and transposase are described, for example, in Izsvak et al., *J. Mol. Biol.* 302: 93-102 (2000), which is incorporated herein by reference in its entirety. The Tol2 transposon which was first isolated from the medaka fish *Oryzias latipes* and belongs to the hAT family of transposons is described in Kawakami et al. (2000). Mini-Tol2 is a variant of Tol2 and is described in Balciunas et al. (2006). The Tol2 and Mini-Tol2 transposons facilitate integration of a transgene into the genome of an organism when co-acting with the Tol2 transposase. The Frog Prince transposon and transposase are described, for example, in Miskey et al., *Nucleic Acids Res.* 31:6873-6881 (2003).

In some embodiments, a polynucleotide sequence encoding one or more components of a gene-regulating system described herein is operably linked to a control element, e.g., a transcriptional control element, such as a promoter. "Control elements" refer those non-translated regions of the vector (e.g., origin of replication, selection cassettes, promoters, enhancers, translation initiation signals (Shine Dalgarno sequence or Kozak sequence) introns, a polyadenylation sequence, 5' and 3' untranslated regions) which interact with host cellular proteins to carry out transcription and translation. Such elements may vary in their strength and specificity. The transcriptional control element may be functional in either a eukaryotic cell (e.g., a mammalian cell) or a prokaryotic cell (e.g., bacterial or archaeal cell). In some embodiments, a polynucleotide sequence encoding one or more components of a gene-regulating system described herein is operably linked to multiple control elements that allow expression of the polynucleotide in both prokaryotic and eukaryotic cells.

Depending on the cell type and gene-regulating system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544). The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

In some embodiments, polynucleotides encoding one or more components of a gene-regulating system described herein are operably linked to a promoter. The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide encoding one or more components of a gene-regulating system, wherein the expression control sequence directs transcription of the nucleic acid corresponding to the second sequence.

Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a a Rous sarcoma virus (RSV) LTR), a herpes simplex virus (HSV) (thymidine kinase) promoter, H5, P7.5, and P11 promoters from vaccinia virus, an elongation factor 1-alpha (EF1α) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, the human ROSA 26 locus (Irions et al., *Nature Biotechnology* 25, 1477-1482 (2007)), a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6× His tag, hemagglutinin tag, green fluorescent protein, etc.) that are fused to the site-directed modifying polypeptide, thus resulting in a chimeric polypeptide.

In some embodiments, a polynucleotide sequence encoding one or more components of a gene-regulating system described herein is operably linked to a constitutive promoter. In such embodiments, the polynucleotides encoding one or more components of a gene-regulating system described herein are constitutively and/or ubiquitously expressed in a cell.

In some embodiments, a polynucleotide sequence encoding one or more components of a gene-regulating system described herein is operably linked to an inducible promoter. In such embodiments, polynucleotides encoding one or more components of a gene-regulating system described herein are conditionally expressed. As used herein, "conditional expression" may refer to any type of conditional expression including, but not limited to, inducible expression; repressible expression; expression in cells or tissues having a particular physiological, biological, or disease state (e.g., cell type or tissue specific expression) etc. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

In some embodiments, the vectors described herein further comprise a transcription termination signal. Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

In some embodiments, a vector may also comprise a sequence encoding a signal peptide (e.g., for nuclear localization, nucleolar localization, mitochondrial localization), fused to the polynucleotide encoding the one or more components of the system. For example, a vector may comprise a nuclear localization sequence (e.g., from SV40) fused to the polynucleotide encoding the one or more components of the system.

Methods of introducing polynucleotides and recombinant vectors into a host cell are known in the art, and any known method can be used to introduce components of a gene-regulating system into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pii: 50169-409X (12)00283-9), microfluidics delivery methods (See e.g., International PCT Publication No. WO 2013/059343), and the like. In some embodiments, delivery via electroporation comprises mixing the cells with the components of a gene-regulating system in a cartridge, chamber, or cuvette and applying one or more electrical impulses of defined duration and amplitude. In some embodiments, cells are mixed with components of a gene-regulating system in a vessel connected to a device (e.g., a pump) which feeds the mixture into a cartridge, chamber, or cuvette wherein one or more electrical impulses of defined duration and amplitude are applied, after which the cells are delivered to a second vessel. Illustrative examples of polynucleotide delivery systems suitable for use in particular embodiments contemplated in particular embodiments include, but are not limited to, those provided by Amaxa Biosystems, Maxcyte, Inc., BTX Molecular Delivery Systems, Neon™ Transfection Systems, and Copernicus Therapeutics Inc. Lipofection reagents are sold commercially (e.g., Transfectam™ and Lipofectin™). Cationic and neutral lipids that are suitable for efficient lipofection of polynucleotides have been described in the literature. See e.g., Liu et al. (2003) *Gene Therapy.* 10:180-187; and Balazs et al. (2011) *Journal of Drug Delivery.* 2011:1-12.

In some embodiments, vectors comprising polynucleotides encoding one or more components of a gene-regulating system described herein are introduced to cells by viral delivery methods, e.g., by viral transduction. In some embodiments, vectors comprising polynucleotides encoding one or more components of a gene-regulating system described herein are introduced to cells by non-viral delivery methods. Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

In some embodiments, one or more components of a gene-regulating system, or polynucleotide sequence encoding one or more components of a gene-regulating system described herein are introduced to a cell in a non-viral delivery vehicle, such as a transposon, a nanoparticle (e.g., a lipid nanoparticle), a liposome, an exosome, an attenuated bacterium, or a virus-like particle. In some embodiments, the vehicle is an attenuated bacterium (e.g., naturally or artificially engineered to be invasive but attenuated to prevent pathogenesis including *Listeria monocytogenes*, certain *Salmonella* strains, *Bifidobacterium longum*, and modified *Escherichia coli*), bacteria having nutritional and tissue-specific tropism to target specific cells, and bacteria having modified surface proteins to alter target cell specificity. In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In some embodiments, the vehicle is a biological liposome. For example, the biological liposome is a phospholipid-based particle derived from human cells (e.g., erythrocyte ghosts, which are red blood cells broken down into spherical structures derived from the subject and wherein tissue targeting can be achieved by attachment of various tissue or cell-specific ligands), secretory exosomes, or subjectiderived membrane-bound nanovescicles (30-100 nm) of endocytic origin (e.g., can be produced from various cell types and can therefore be taken up by cells without the need for targeting ligands).

V. Methods of Producing Modified Immune Effector Cells

In some embodiments, the present disclosure provides methods for producing modified immune effector cells. In some embodiments, the methods comprise introducing a gene-regulating system into a population of immune effector cells wherein the gene-regulating system is capable of reducing expression and/or function of one or more endogenous target genes.

The components of the gene-regulating systems described herein, e.g., a nucleic acid-, protein-, or nucleic acid/protein-based system can be introduced into target cells in a variety of forms using a variety of delivery methods and formulations. In some embodiments, a polynucleotide encoding one or more components of the system is delivered by a recombinant vector (e.g., a viral vector or plasmid, described supra). In some embodiments, where the system comprises more than a single component, a vector may comprise a plurality of polynucleotides, each encoding a component of the system. In some embodiments, where the system comprises more than a single component, a plurality of vectors may be used, wherein each vector comprises a polynucleotide encoding a particular component of the system. In some embodiments, the introduction of the gene-regulating system to the cell occurs in vitro. In some embodiments, the introduction of the gene-regulating system to the cell occurs in vivo. In some embodiments, the introduction of the gene-regulating system to the cell occurs ex vivo.

In particular embodiments, the introduction of the gene-regulating system to the cell occurs in vitro or ex vivo. In some embodiments, the immune effector cells are modified in vitro or ex vivo without further manipulation in culture. For example, in some embodiments, the methods of producing a modified immune effector cell described herein comprise introduction of a gene-regulating system in vitro or ex vivo without additional activation and/or expansion steps. In some embodiments, the immune effector cells are modified and are further manipulated in vitro or ex vivo. For example, in some embodiments, the immune effector cells are activated and/or expanded in vitro or ex vivo prior to introduction of a gene-regulating system. In some embodiments, a gene-regulating system is introduced to the immune effector cells and are then activated and/or expanded in vitro or ex vivo. In some embodiments, successfully modified cells can be sorted and/or isolated (e.g., by flow cytometry) from unsuccessfully modified cells to produce a purified population of modified immune effector cells. These successfully modified cells can then be further propagated to increase the number of the modified cells and/or cryopreserved for future use.

In some embodiments, the present disclosure provides methods for producing modified immune effector cells comprising obtaining a population of immune effector cells. The population of immune effector cells may be cultured in vitro under various culture conditions necessary to support growth, for example, at an appropriate temperature (e.g., 37° C.) and atmosphere (e.g., air plus 5% $CO_2$) and in an appropriate culture medium. Culture medium may be liquid or semi-solid, e.g. containing agar, methylcellulose, etc. Illustrative examples of cell culture media include Minimal Essential Media (MEM), Iscove's modified DMEM, RPMI 1640Clicks, AIM-V, F-12, X-Vivo 15, X-Vivo 20, and Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of the immune effector cells.

Culture media may be supplemented with one or more factors necessary for proliferation and viability including, but not limited to, growth factors such as serum (e.g., fetal bovine or human serum at about 5%-10%), interleukin-2 (IL-2), insulin, IFN-γ, IL-4, IL-7, IL-21, GM-CSF, IL-10, IL-12, IL-15, TGFβ, and TNF-α. Illustrative examples of other additives for T cell expansion include, but are not limited to, surfactant, piasmanate, pH buffers such as HEPES, and reducing agents such as N-acetyl-cysteine and 2-mercaptoethanol, or any other additives suitable for the growth of cells known to the skilled artisan such as L-glutamine, a thiol, particularly 2-mercaptoethanol, and/or antibiotics, e.g. penicillin and streptomycin. Typically, antibiotics are included only in experimental cultures, not in cultures of cells that are to be infused into a subject.

In some embodiments, the population of immune effector cells is obtained from a sample derived from a subject. In some embodiments, a population of immune effector cells is obtained is obtained from a first subject and the population of modified immune effector cells produced by the methods described herein is administered to a second, different subject. In some embodiments, a population of immune effector cells is obtained from a subject and the population of modified immune effector cells produced by the methods described herein is administered to the same subject. In some embodiments, the sample is a tissue sample, a fluid sample, a cell sample, a protein sample, or a DNA or RNA sample. In some embodiments, a tissue sample may be derived from any tissue type including, but not limited to skin, hair (including roots), bone marrow, bone, muscle, salivary gland, esophagus, stomach, small intestine (e.g., tissue from the duodenum, jejunum, or ileum), large intestine, liver, gallbladder, pancreas, lung, kidney, bladder, uterus, ovary, vagina, placenta, testes, thyroid, adrenal gland, cardiac tissue, thymus, spleen, lymph node, spinal cord, brain, eye, ear, tongue, cartilage, white adipose tissue, or brown adipose tissue. In some embodiments, a tissue sample may be derived from a cancerous, pre-cancerous, or non-cancerous tumor. In some embodiments, a fluid sample comprises buccal swabs, blood, plasma, oral mucous, vaginal mucous, peripheral blood, cord blood, saliva, semen, urine, ascites fluid, pleural fluid, spinal fluid, pulmonary lavage, tears, sweat, semen, seminal fluid, seminal plasma, prostatic fluid, pre-ejaculatory fluid (Cowper's fluid), excreta, cerebrospinal fluid, lymph, cell culture media comprising one or more populations of cells, buffered solutions comprising one or more populations of cells, and the like.

In some embodiments, the sample is processed to enrich or isolate a population of immune effector cells from the remainder of the sample. In certain embodiments, the sample is a peripheral blood sample which is then subject to leukapheresis to separate the red blood cells and platelets and to isolate lymphocytes. In some embodiments, the sample is a leukopak from which immune effector cells can be isolated or enriched. In some embodiments, the sample is a tumor sample that is further processed to isolate lymphocytes present in the tumor (i.e., by fragmentation and enzymatic digestion of the tumor to obtain a cell suspension of tumor infiltrating lymphocytes).

In some embodiments, a method for manufacturing modified immune effector cells contemplated herein comprises activation and/or expansion of a population of immune effector cells, as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In various embodiments, a method for manufacturing modified immune effector cells contemplated herein comprises activating a population of cells comprising immune effector cells. In particular embodiments, the immune effector cells are T cells. T cell activation can be accomplished by providing a primary stimulation signal (e.g., through the T cell TCR/CD3 complex or via stimulation of the CD2 surface protein) and by providing a secondary co-stimulation signal through an accessory molecule.

In some embodiments, the TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, CRIS-7 and 64.1. In some embodiments, a CD2 binding agent may be used to provide a primary stimulation signal to the T cells. Illustrative examples of CD2 binding agents include, but are not limited to, CD2 ligands and anti-CD2 antibodies, e.g., the T11.3 antibody in combination with the T11.1 or T11.2 antibody (Meuer, S. C. et al. (1984) *Cell* 36:897-906) and the 9.6 antibody (which recognizes the same epitope as TI 1.1) in combination with the 9-1 antibody (Yang, S. Y. et al. (1986) *J. Immunol.* 137:1097-1100).

In addition to the stimulatory signal provided through the TCR/CD3 complex or CD2, induction of T cell responses typically requires a second, costimulatory signal provided by a ligand that specifically binds a costimulatory molecule on a T cell, thereby providing a costimulatory signal which, in addition to the primary signal provided by, for instance, binding of a TCR/CD3 complex, mediates a desired T cell response. Suitable costimulatory ligands include, but are not limited to, CD7, B7-1 (CD80), B7-2 (CD86), 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

In some embodiments, a costimulatory ligand comprises an antibody or antigen binding fragment thereof that specifically binds to a costimulatory molecule present on a T cell, including but not limited to, CD27, CD28, 4-1BB, OX40, CD30, CD40, ICOS, lymphocyte function-associated antigen-1 (LFA-1), CD7, LIGHT, NKG2C, B7-H3, and a ligand that specifically binds with CD83. In particular embodiments, a CD28 binding agent can be used to provide a costimulatory signal. Illustrative examples of CD28 binding agents include but are not limited to: natural CD28 ligands, e.g., a natural ligand for CD28 (e.g., a member of the B7 family of proteins, such as B7-1 (CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface. In some embodiments, the costimulatory signal is provided by a costimulatory ligand presented on an antigen presenting cell, such as an artificial APC (aAPC). Artificial APCs can be made by engineering K562, U937, 721.221, T2, or C1R cells to stably express and/or secrete of a variety of costimulatory molecules and cytokines to support ex vivo growth and long-term expansion of genetically modified T cells. In a particular embodiment, K32 or U32 aAPCs are used to direct the display of one or more antibody-based stimulatory molecules on the aAPC cell surface. Populations of T cells can be expanded by aAPCs expressing a variety of costimulatory molecules including, but not limited to, CD137L (4-1BBL), CD134L (OX40L), and/or CD80 or CD86. Exemplary aAPCs are provided in WO 03/057171 and US2003/0147869, incorporated by reference in their entireties.

In some embodiments, binding agents that provide activating and costimulatory signals are localized a solid surface (e.g., a bead or a plate). In some embodiments, the binding agents that provide activating and costimulatory signals are both provided in a soluble form (provided in solution).

In some embodiments, the population of immune effector cells is expanded in culture in one or more expansion phases. "Expansion" refers to culturing the population of immune effector cells for a pre-determined period of time in order to increase the number of immune effector cells. Expansion of immune effector cells may comprise addition of one or more of the activating factors described above and/or addition of one or more growth factors such as a cytokine (e.g., IL-2, IL-15, IL-21, and/or IL-7) to enhance or promote cell proliferation and/or survival. In some embodiments, combinations of IL-2, IL-15, and/or IL-21 can be added to the cultures during the one or more expansion phases. In some embodiments, the amount of IL-2 added during the one or more expansion phases is less than 6000 U/mL. In some embodiments, the amount of IL-2 added during the one or more expansion phases is about 5500 U/mL, about 5000 U/mL, about 4500 U/mL, about 4000 U/mL, about 3500 U/mL, about 3000 U/mL, about 2500 U/mL, about 2000 U/mL, about 1500 U/mL, about 1000 U/mL, or about 500 U/mL. In some embodiments, the amount of IL-2 added during the one or more expansion phases is between about 500 U/mL and about 5500 U/mL. In some embodiments, the population of immune effector cells may be co-cultured with feeder cells during the expansion process.

In some embodiments, the population of immune effector cells is expanded for a pre-determined period of time, wherein the pre-determined period of time is less than about 30 days. In some embodiments, the pre-determined period of time is less than 30 days, less than 25 days, less than 20 days, less than 18 days, less than 15 days, or less than 10 days. In some embodiments, the pre-determined period of time is less than 4 weeks, less than 3 weeks, less than 2 weeks, or less than 1 week. In some embodiments, the pre-determined period of time is about 7 days, 8 days, 9 days, 10 days, 11 days, 12 days, 13 days, 14 days, 15 days, 16 days, 17 days, 18 days, 19 days, 20 days, or 21 days. In some embodiments, the pre-determined period of time is about 5 days to about 25 days, about 10 to about 28 days, about 10 to about 25 days, about 10 to about 21 days, about 10 to about 20 days, about 10 to about 19 days, about 11 to about 28 days, about 11 to about 25 days, about 11 to about 21 days, about 11 to about 20 days, about 11 to about 19 days, about 12 to about 28 days, about 12 to about 25 days, about 12 to about 21 days, about 12 to about 20 days, about 12 to about 19 days, about 15 to about 28 days, about 15 to about 25 days, about 15 to about 21 days, about 15 to about 20 days, or about 15 to about 19 days. In some embodiments, the pre-determined period of time is about 5 days to about 10 days, about 10 days to about 15 days, about 15 days to about 20 days, or about 20 days to about 25 days.

In some embodiments, the population of immune effector cells is expanded until the number of cells reaches a pre-determined threshold. For example, in some embodiments, the population of immune effector cells is expanded until the culture comprises at least $5\times10^6$, $1\times10^7$, $5\times10^7$, $1\times10^8$, $5\times10^8$, $1\times10^9$, $5\times10^9$, $1\times10^{10}$, $5\times10^{11}$, $1\times10^{11}$, $5\times10^{11}$, $1\times10^{12}$, $5\times10^{12}$, $1\times10^{13}$, or at least $5\times10^{13}$ total cells. In some embodiments, the population of immune effector cells is expanded until the culture comprises between about $1\times10^9$ total cells and about $1\times10^{11}$ total cells.

In some embodiments, the methods provided herein comprise at least two expansion phases. For example, in some embodiments, the population of immune effector cells can be expanded after isolation from a sample, allowed to rest, and then expanded again. In some embodiments, the immune effector cells can be expanded in one set of expansion conditions followed by a second round of expansion in a second, different, set of expansion conditions. Methods for ex vivo expansion of immune cells are known in the art, for example, as described in US Patent Application Publication Nos. 2018-0207201, 20180282694 and 20170152478 and U.S. Pat. Nos. 8,383,099 and 8,034,334, herein incorporated by reference.

At any point during the activation and/or expansion processes, the gene-regulating systems described herein can be introduced to the immune effector cells to produce a population of modified immune effector cells. In some embodiments, the gene-regulating system is introduced to the population of immune effector cells immediately after enrichment from a sample. In some embodiments, the gene-regulating system is introduced to the population of immune effector cells before, during, or after the one or more expansion process. In some embodiments, the gene-regulating system is introduced to the population of immune effector cells immediately after enrichment from a sample or harvest from a subject, and prior to any expansion rounds. In some embodiments, the gene-regulating system is introduced to the population of immune effector cells after a first round of expansion and prior to a second round of expansion. In some embodiments, the gene-regulating system is introduced to the population of immune effector cells after a first and a second round of expansion.

In some embodiments, the present disclosure provides methods of manufacturing populations of modified immune effector cells comprising obtaining a population of immune effector cells, introducing a gene-regulating system described herein to the population of immune effector cells, and expanding the population of immune effector cells in one or more round of expansion. In some aspects of this embodiment, the population of immune effector cells is expanded in a first round of expansion prior to the introduction of the gene-regulating system and is expanded in a second round of expansion after the introduction of the gene-regulating system. In some aspects of this embodiment, the population of immune effector cells is expanded in a first round of expansion and a second round of expansion prior to the introduction of the gene-regulating system. In some aspects of this embodiment, the gene-regulating system is introduced to the population of immune effector cells prior to the first and second rounds of expansion.

In some embodiments, the methods described herein comprise removal of a tumor from a subject and processing of the tumor sample to obtain a population of tumor infiltrating lymphocytes (e.g., by fragmentation and enzymatic digestion of the tumor to obtain a cell suspension) introducing a gene-regulating system described herein to the population of immune effector cells, and expanding the population of immune effector cells in one or more round of expansion. In some aspects of this embodiment, the population of tumor infiltrating lymphocytes is expanded in a first round of expansion prior to the introduction of the gene-regulating system and is expanded in a second round of expansion after the introduction of the gene-regulating system. In some aspects of this embodiment, the population of tumor infiltrating lymphocytes is expanded in a first round of expansion and a second round of expansion prior to the introduction of the gene-regulating system. In some aspects of this embodiment, the gene-regulating system is introduced to the population of tumor infiltrating lymphocytes prior to the first and second rounds of expansion.

In some embodiments, the modified immune effector cells produced by the methods described herein may be used immediately. In some embodiments, the manufacturing methods contemplated herein may further comprise cryopreservation of modified immune cells for storage and/or preparation for use in a subject. As used herein, "cryopreserving," refers to the preservation of cells by cooling to sub-zero temperatures, such as (typically) 77 K or −196° C. (the boiling point of liquid nitrogen). In some embodiments, a method of storing modified immune effector cells comprises cryopreserving the immune effector cells such that the cells remain viable upon thawing. When needed, the cryopreserved modified immune effector cells can be thawed, grown and expanded for more such cells. Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used include but are not limited to dimethyl sulfoxide (DMSO) (Lovelock and Bishop, *Nature*, 1959; 183: 1394-1395; Ashwood-Smith, *Nature*, 1961; 190: 1204-1205), glycerol, polyvinylpyrrolidine (Rinfret, *Ann. N.Y. Acad. Sci.*, 1960; 85: 576), and polyethylene glycol (Sloviter and Ravdin, *Nature*, 1962; 196: 48). In some embodiments, the cells are frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

A. Producing Modified Immune Effector Cells Using CRISPR/Cas Systems

In some embodiments, a method of producing a modified immune effector cell involves contacting a target DNA sequence with a complex comprising a gRNA and a Cas polypeptide. As discussed above, a gRNA and Cas polypeptide form a complex, wherein the DNA-binding domain of the gRNA targets the complex to a target DNA sequence and wherein the Cas protein (or heterologous protein fused to an enzymatically inactive Cas protein) modifies target DNA sequence. In some embodiments, this complex is formed intracellularly after introduction of the gRNA and Cas protein (or polynucleotides encoding the gRNA and Cas proteins) to a cell. In some embodiments, the nucleic acid encoding the Cas protein is a DNA nucleic acid and is introduced to the cell by transduction. In some embodiments, the Cas9 and gRNA components of a CRISPR/Cas gene editing system are encoded by a single polynucleotide molecule. In some embodiments, the polynucleotide encoding the Cas protein and gRNA component are comprised in a viral vector and introduced to the cell by viral transduction. In some embodiments, the Cas9 and gRNA components of a CRISPR/Cas gene editing system are encoded by different polynucleotide molecules. In some embodiments, the polynucleotide encoding the Cas protein is comprised in a first viral vector and the polynucleotide encoding the gRNA is comprised in a second viral vector. In some aspects of this embodiment, the first viral vector is introduced to a cell prior to the second viral vector. In some aspects of this embodiment, the second viral vector is introduced to a cell prior to the first viral vector. In such embodiments, integration of the vectors results in sustained expression of the Cas9 and gRNA components. However, sustained expression of Cas9 may lead to increased off-target mutations and cutting in some cell types. Therefore, in some embodiments, an mRNA nucleic acid sequence encoding the Cas protein may be introduced to the population of cells by transfection. In such embodiments, the expression of Cas9 will decrease over time, and may reduce the number of off target mutations or cutting sites. In some embodiments, the gRNA and Cas protein are introduced separately by electroporation.

In some embodiments, this complex is formed in a cell-free system by mixing the gRNA molecules and Cas proteins together and incubating for a period of time sufficient to allow complex formation. This pre-formed complex, comprising the gRNA and Cas protein and referred to herein as a CRISPR-ribonucleoprotein (CRISPR-RNP) can then be introduced to a cell in order to modify a target DNA sequence. In some embodiments, the CRISPR-RNP is introduced to the cell by electroporation.

In any of the above described embodiments for producing a modified immune effector cell using the CRISPR/Cas system, the system may comprise one or more gRNAs targeting a single endogenous target gene, for example to produce a single-edited modified immune effector cell. Alternatively, in any of the above described embodiments for producing a modified immune effect cell using the CRISPR/Cas system, the system may comprise two or more gRNAs targeting two or more endogenous target genes, for example to produce a dual-edited modified immune effector cell.

B. Producing Modified Immune Effector Cells Using shRNA Systems

In some embodiments, a method of producing a modified immune effector cell introducing into the cell one or more DNA polynucleotides encoding one or more shRNA molecules with sequence complementary to the mRNA transcript of a target gene. The immune effector cell can be modified to produce the shRNA by introducing specific DNA sequences into the cell nucleus via a small gene cassette. Both retroviruses and lentiviruses can be used to introduce shRNA-encoding DNAs into immune effector cells. The introduced DNA can either become part of the cell's own DNA or persist in the nucleus, and instructs the cell machinery to produce shRNAs. shRNAs may be processed by Dicer or AGO2-mediated slicer activity inside the cell to induce RNAi mediated gene knockdown.

VI. Compositions and Kits

The term "composition" as used herein refers to a formulation of a gene-regulating system or a modified immune effector cell described herein that is capable of being administered or delivered to a subject or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of a gene-regulating system or a modified immune effector cell capable of being administered to a subject for the treatment of a particular disease or disorder or contacted with a cell for modification of one or more endogenous target genes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

"Pharmaceutically acceptable salt" includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

In some embodiments, the present disclosure provides kits for carrying out a method described herein. In some embodiments, a kit can include:

(a) one or more nucleic acid molecules capable of reducing the expression or modifying the function of a gene product encoded by one or more endogenous target genes;

(b) one or more polynucleotides encoding a nucleic acid molecule that is capable of reducing the expression or modifying the function of a gene product encoded by one or more endogenous target genes;

(c) one or more proteins capable of reducing the expression or modifying the function of a gene product encoded by one or more endogenous target genes;

(d) one or more polynucleotides encoding a modifying protein that is capable of reducing the expression or modifying the function of a gene product encoded by one or more endogenous target genes;

(e) one or more gRNAs capable of binding to a target DNA sequence in an endogenous gene;

(f) one or more polynucleotides encoding one or more gRNAs capable of binding to a target DNA sequence in an endogenous gene;

(g) one or more site-directed modifying polypeptides capable of interacting with a gRNA and modifying a target DNA sequence in an endogenous gene;

(h) one or more polynucleotides encoding a site-directed modifying polypeptide capable of interacting with a gRNA and modifying a target DNA sequence in an endogenous gene;

(i) one or more guide DNAs (gDNAs) capable of binding to a target DNA sequence in an endogenous gene;

(j) one or more polynucleotides encoding one or more gDNAs capable of binding to a target DNA sequence in an endogenous gene;

(k) one or more site-directed modifying polypeptides capable of interacting with a gDNA and modifying a target DNA sequence in an endogenous gene;

(l) one or more polynucleotides encoding a site-directed modifying polypeptide capable of interacting with a gDNA and modifying a target DNA sequence in an endogenous gene;

(m) one or more gRNAs capable of binding to a target mRNA sequence encoded by an endogenous gene;

(n) one or more polynucleotides encoding one or more gRNAs capable of binding to a target mRNA sequence encoded by an endogenous gene;

(o) one or more site-directed modifying polypeptides capable of interacting with a gRNA and modifying a target mRNA sequence encoded by an endogenous gene;

(p) one or more polynucleotides encoding a site-directed modifying polypeptide capable of interacting with a gRNA and modifying a target mRNA sequence encoded by an endogenous gene;

(q) a modified immune effector cell described herein; or (r) any combination of the above.

In some embodiments, the kits described herein further comprise one or more immune checkpoint inhibitors. Several immune checkpoint inhibitors are known in the art and have received FDA approval for the treatment of one or more cancers. For example, FDA-approved PD-L1 inhibitors include Atezolizumab (Tecentriq®, Genentech), Avelumab (Bavencio®, Pfizer), and Durvalumab (Imfinzi®, AstraZeneca); FDA-approved PD-1 inhibitors include Pembrolizumab (Keytruda®, Merck) and Nivolumab (Opdivo®, Bristol-Myers Squibb); and FDA-approved CTLA4 inhibitors include Ipilimumab (Yervoy®, Bristol-Myers Squibb). Additional inhibitory immune checkpoint molecules that may be the target of future therapeutics include A2AR, B7-H3, B7-H4, BTLA, IDO, LAG3 (e.g., BMS-986016, under development by BSM), KIR (e.g., Lirilumab, under development by BSM), TIM3, TIGIT, and VISTA.

In some embodiments, the kits described herein comprise one or more components of a gene-regulating system (or one or more polynucleotides encoding the one or more components) and one or more immune checkpoint inhibitors known in the art (e.g., a PD1 inhibitor, a CTLA4 inhibitor, a PDL1 inhibitor, etc.). In some embodiments, the kits described herein comprise one or more components of a gene-regulating system (or one or more polynucleotides encoding the one or more components) and an anti-PD1 antibody (e.g., Pembrolizumab or Nivolumab). In some embodiments, the kits described herein comprise a modified immune effector cell described herein (or population thereof) and one or more immune checkpoint inhibitors known in the art (e.g., a PD1 inhibitor, a CTLA4 inhibitor, a PDL1 inhibitor, etc.). In some embodiments, the kits described herein comprise a modified immune effector cell described herein (or population thereof) and an anti-PD1 antibody (e.g., Pembrolizumab or Nivolumab).

In some embodiments, the kit comprises one or more components of a gene-regulating system (or one or more polynucleotides encoding the one or more components) and a reagent for reconstituting and/or diluting the components. In some embodiments, a kit comprising one or more components of a gene-regulating system (or one or more polynucleotides encoding the one or more components) and further comprises one or more additional reagents, where such additional reagents can be selected from: a buffer for introducing the gene-regulating system into a cell; a wash buffer; a control reagent; a control expression vector or RNA polynucleotide; a reagent for in vitro production of the gene-regulating system from DNA, and the like. Components of a kit can be in separate containers or can be combined in a single container.

In addition to above-mentioned components, in some embodiments a kit further comprises instructions for using the components of the kit to practice the methods of the present disclosure. The instructions for practicing the methods are generally recorded on a suitable recording medium. For example, the instructions may be printed on a substrate, such as paper or plastic, etc. As such, the instructions may be present in the kits as a package insert or in the labeling of the container of the kit or components thereof (i.e., associated with the packaging or sub-packaging). In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

VII. Therapeutic Methods and Applications

In some embodiments, the modified immune effector cells and gene-regulating systems described herein may be used in a variety of therapeutic applications. For example, in some embodiments the modified immune effector cells and/or gene-regulating systems described herein may be administered to a subject for purposes such as gene therapy, e.g. to treat a disease, for use as an antiviral, for use as an anti-pathogenic, for use as an anti-cancer therapeutic, or for biological research.

In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

Administration of the modified immune effector cells described herein, populations thereof, and compositions thereof can occur by injection, irrigation, inhalation, consumption, electro-osmosis, hemodialysis, iontophoresis, and other methods known in the art. In some embodiments, administration route is local or systemic. In some embodiments administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, or intrauterine.

In some embodiments, the administration route is by infusion (e.g., continuous or bolus). Examples of methods for local administration, that is, delivery to the site of injury or disease, include through an Ommaya reservoir, e.g. for intrathecal delivery (See e.g., U.S. Pat. Nos. 5,222,982 and 5,385,582, incorporated herein by reference); by bolus injection, e.g. by a syringe, e.g. into a joint; by continuous infusion, e.g. by cannulation, such as with convection (See e.g., US Patent Application Publication No. 2007-0254842, incorporated herein by reference); or by implanting a device upon which the cells have been reversibly affixed (see e.g. US Patent Application Publication Nos. 2008-0081064 and 2009-0196903, incorporated herein by reference). In some embodiments, the administration route is by topical administration or direct injection. In some embodiments, the modified immune effector cells described herein may be provided to the subject alone or with a suitable substrate or matrix, e.g. to support their growth and/or organization in the tissue to which they are being transplanted.

In some embodiments, at least $1 \times 10^3$ cells are administered to a subject. In some embodiments, at least $5 \times 10^3$ cells, $1 \times 10^4$ cells, $5 \times 10^4$ cells, $1 \times 10^5$ cells, $5 \times 10^5$ cells, $1 \times 10^6$, $2 \times 10^6$, $3 \times 10^6$, $4 \times 10^6$, $5 \times 10^6$, $1 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more cells are administered to a subject. In some embodiments, between about $1 \times 10^7$ and about $1 \times 10^{12}$ cells are administered to a subject. In some embodiments, between about $1 \times 10^8$ and about $1 \times 10^{12}$ cells are administered to a subject. In some embodiments, between about $1 \times 10^9$ and about $1 \times 10^{12}$ cells are administered to a subject. In some embodiments, between about $1 \times 10^{10}$ and about $1 \times 10^{12}$ cells are administered to a subject. In some embodiments, between about $1 \times 10^{11}$ and about $1 \times 10^{12}$ cells are administered to a subject. In some embodiments, between about $1 \times 10^7$ and about $1 \times 10^{11}$ cells are administered to a subject. In some embodiments, between about $1 \times 10^7$ and about $1 \times 10^{10}$ cells are administered to a subject. In some embodiments, between about $1 \times 10^7$ and about $1 \times 10^9$ cells are administered to a subject. In some embodiments, between about $1 \times 10^7$ and about $1 \times 10^8$ cells are administered to a subject. The number of administrations of treatment to a subject may vary. In some embodiments, introducing the modified immune effector cells into the subject may be a one-time event. In some embodiments, such treatment may require an on-going series of repeated treatments. In some embodiments, multiple administrations of the modified immune effector cells may be required before an effect is observed. The exact protocols depend upon the disease or condition, the stage of the disease and parameters of the individual subject being treated.

In some embodiments, the gene-regulating systems described herein are employed to modify cellular DNA or RNA in vivo, such as for gene therapy or for biological research. In such embodiments, a gene-regulating system may be administered directly to the subject, such as by the methods described supra. In some embodiments, the gene-regulating systems described herein are employed for the ex vivo or in vitro modification of a population of immune effector cells. In such embodiments, the gene-regulating systems described herein are administered to a sample comprising immune effector cells.

In some embodiments, the modified immune effector cells described herein are administered to a subject. In some embodiments, the modified immune effector cells described herein administered to a subject are autologous immune effector cells. The term "autologous" in this context refers to cells that have been derived from the same subject to which they are administered. For example, immune effector cells may be obtained from a subject, modified ex vivo according to the methods described herein, and then administered to the same subject in order to treat a disease. In such embodiments, the cells administered to the subject are autologous immune effector cells. In some embodiments, the modified immune effector cells, or compositions thereof, administered to a subject are allogenic immune effector cells. The term "allogenic" in this context refers to cells that have been derived from one subject and are administered to another subject. For example, immune effector cells may be obtained from a first subject, modified ex vivo according to the methods described herein and then administered to a second subject in order to treat a disease. In such embodiments, the cells administered to the subject are allogenic immune effector cells.

In some embodiments, the modified immune effector cells described herein are administered to a subject in order to treat a disease. In some embodiments, treatment comprises delivering an effective amount of a population of cells (e.g., a population of modified immune effector cells) or composition thereof to a subject in need thereof. In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment may refer to a short-term (e.g., temporary and/or acute) and/or a long-term (e.g., sustained) reduction in one or more disease symptoms. In some embodiments, treatment results in an improvement or remediation of the symptoms of the disease. The improvement is an observable or measurable improvement, or may be an improvement in the general feeling of well-being of the subject.

The effective amount of a modified immune effector cell administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

In some embodiments, the effective amount of a modified immune effector cell may be the number of cells required to result in at least 1, 2, 3, 4, 5, 6, 7, 8, 9, 10, 20, 30, 40, 50, 60, 70, 80, 90, 100, or more fold decrease in tumor mass or volume, decrease in the number of tumor cells, or decrease in the number of metastases. In some embodiments, the effective amount of a modified immune effector cell may be the number of cells required to achieve an increase in life expectancy, an increase in progression-free or disease-free survival, or amelioration of various physiological symptoms associated with the disease being treated. In some embodiments, an effective amount of modified immune effector cells will be at least $1 \times 10^3$ cells, for example $5 \times 10^3$ cells, $1 \times 10^4$ cells, $5 \times 10^4$ cells, $1 \times 10^5$ cells, $5 \times 10^5$ cells, $1 \times 10^6$, $2 \times 10^6$, $3 \times 10^6$, $4 \times 10^6$, $5 \times 10^6$, $1 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more cells.

In some embodiments, the modified immune effector cells and gene-regulating systems described herein may be used in the treatment of a cell-proliferative disorder, such as a cancer. Cancers that may be treated using the compositions and methods disclosed herein include cancers of the blood and solid tumors. For example, cancers that may be treated using the compositions and methods disclosed herein include, but are not limited to, adenoma, carcinoma, sarcoma, leukemia or lymphoma. In some embodiments, the cancer is chronic lymphocytic leukemia (CLL), B cell acute lymphocytic leukemia (B-ALL), acute lymphoblastic leukemia (ALL), acute myeloid leukemia (AML), non-Hodgkin's lymphoma (NHL), diffuse large cell lymphoma (DLCL), diffuse large B cell lymphoma (DLBCL), Hodgkin's lymphoma, multiple myeloma, renal cell carcinoma (RCC), neuroblastoma, colorectal cancer, bladder cancer, breast cancer, colorectal cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma, and liver cancer. In some embodiments, the cancer is selected from a melanoma, head and neck cancer, bladder cancer, lung cancer, cervical cancer, pancreatic cancer, breast cancer, and colorectal cancer. In some embodiments, the cancer is insensitive, or resistant, to treatment with a PD1 inhibitor. In some embodiments, the cancer is insensitive, or resistant to treatment with a PD1 inhibitor and is selected from a melanoma, head and neck cancer, bladder cancer, lung cancer, cervical cancer, pancreatic cancer, breast cancer, and colorectal cancer.

As described above, several immune checkpoint inhibitors are currently approved for use in a variety of oncologic indications (e.g., CTLA4 inhibitors, PD1 inhibitors, PDL1 inhibitors, etc.). In some embodiments, administration of a modified immune effector cell comprising reduced expression and/or function of an endogenous target gene described herein results in an enhanced therapeutic effect (e.g., a more significant reduction in tumor growth, an increase in tumor infiltration by lymphocytes, an increase in the length of progression free survival, etc.) than is observed after treatment with an immune checkpoint inhibitor.

Further, some oncologic indications are non-responsive (i.e., are insensitive) to treatment with immune checkpoint inhibitors. Further still, some oncologic indications that are initially responsive (i.e., sensitive) to treatment with immune checkpoint inhibitors develop an inhibitor-resistant phenotype during the course of treatment. Therefore, in some embodiments, the modified immune effector cells described herein, or compositions thereof, are administered to treat a cancer that is resistant (or partially resistant) or insensitive (or partially insensitive) to treatment with one or more immune checkpoint inhibitors. In some embodiments, administration of the modified immune effector cells or compositions thereof to a subject suffering from a cancer that is resistant (or partially resistant) or insensitive (or partially insensitive) to treatment with one or more immune checkpoint inhibitors results in treatment of the cancer (e.g., reduction in tumor growth, an increase in the length of progression free survival, etc.). In some embodiments, the cancer is resistant (or partially resistant) or insensitive (or partially insensitive) to treatment with a PD1 inhibitor.

In some embodiments, the modified immune effector cells or compositions thereof are administered in combination with an immune checkpoint inhibitor. In some embodiments, administration of the modified immune effector cells in combination with the immune checkpoint inhibitor results in an enhanced therapeutic effect in a cancer that is resistant, refractory, or insensitive to treatment by an immune checkpoint inhibitor than is observed by treatment with either the modified immune effector cells or the immune checkpoint inhibitor alone. In some embodiments, administration of the modified immune effector cells in combination with the immune checkpoint inhibitor results in an enhanced therapeutic effect in a cancer that is partially resistant, partially refractory, or partially insensitive to treatment by an immune checkpoint inhibitor than is observed by treatment with either the modified immune effector cells or the immune checkpoint inhibitor alone. In some embodiments, the cancer is resistant (or partially resistant), refractory (or partially refractory), or insensitive (or partially insensitive) to treatment with a PD1 inhibitor.

In some embodiments, administration of a modified immune effector cell described herein or composition thereof in combination with an anti-PD1 antibody results in an enhanced therapeutic effect in a cancer that is resistant or insensitive to treatment by the anti-PD1 antibody alone. In some embodiments, administration of a modified immune effector cell described herein or composition thereof in combination with an anti-PD1 antibody results in an enhanced therapeutic effect in a cancer that is partially resistant or partially insensitive to treatment by the anti-PD1 antibody alone.

Cancers that demonstrate resistance or sensitivity to immune checkpoint inhibition are known in the art and can be tested in a variety of in vivo and in vitro models. For example, some melanomas are sensitive to treatment with an immune checkpoint inhibitor such as an anti-PD1 antibody and can be modeled in an in vivo B16-Ova tumor model (See Examples 6, 7, 16, and 19). Further, some colorectal cancers are known to be resistant to treatment with an immune checkpoint inhibitor such as an anti-PD1 antibody and can be modeled in a PMEL/MC38-gp100 model (See Examples 8 and 17). Further still, some lymphomas are known to be insensitive to treatment with an immune checkpoint inhibitor such as an anti-PD1 antibody and can be modeled in a various models by adoptive transfer or subcutaneous administration of lymphoma cell lines, such as Raji cells (See Examples 12, 14, 15, 21, and 22).

In some embodiments, the modified immune effector cells and gene-regulating systems described herein may be used in the treatment of a viral infection. In some embodiments, the virus is selected from one of adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus, or retroviruses.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1

Materials and Methods

The experiments described herein utilize the CRISPR/Cas9 system to modulate expression of one or more endogenous target genes in different T cell populations.

I. Materials gRNAs: Unless otherwise indicated, all experiments use single-molecule gRNAs (sgRNAs). Dual gRNA molecules were used as indicated and were formed by duplexing 200 µM tracrRNA (IDT Cat #1072534) with 200 µM of target-specific crRNA (IDT) in nuclease free duplex buffer (IDT Cat #11-01-03-01) for 5 min at 95° C., to form 100 µM of tracrRNA:crRNA duplex, where the tracrRNA and crRNA are present at a 1:1 ratio. Targeting sequences of the gRNAs used in the following experiments are provided in Table 10 below.

TABLE 10

Experiment gRNA targeting-domain encoding sequences

| Target Gene | Guide ID | Sequence | SEQ ID |
|---|---|---|---|
| Pdcd1-murine | Nm.Pdcd1 | CGGAGGATCTTATGCTGAAC | 778 |
| Lag3-murine | Nm.Lag3 | GCCAAGTGGACTCCTCCTGG | 602 |
| Cblb-murine | Nm.Cblb | CCTTATCTTCAGTCACATGC | 502 |
| CBLBhuman | Nm.CBLB | TAAACTTACCTGAAACAGCC | 521 |
| BCOR-human | Nm.BCOR | GTGCAGACTGGAGAATACAG | 715 |
| Zc3h12a-murine | Nm.Zc3h12a | TTCCCTCCTCTGCCAGCCAT | 1505 |
| ZC3H12A-human | Nh.ZC3H12A_1 | GGAGTGGAAGCGCTTCATCG | 1434 |
| Nr4a3-murine | Nm.Nr4a3 | GGCAGCGTTGTCGCCGCACA | 1544 |
| Map4k1-murine | Nm.Map4k1 | TTGCCGGCACGCCAACATCG | 1515 |

TABLE 10-continued

Experiment gRNA targeting-domain encoding sequences

| Target Gene | Guide ID | Sequence | SEQ ID |
|---|---|---|---|
| OR1A2-human | Nh.OR1A2_1 | AGATGATGTCAACCAAGGAG | 1574 |
| Olfr421-mouse | Nm.Olfr421_1 | GGAAGAAGTACATCTGCAAG | 1574 | scFv domain specifically binding to one of CD19, Her2/Erbb2, or EGFR. The human CD8α stalk was used as a transmembrane domain. The intracellular signaling domains of the CD3ξ chain were fused to the cytoplasmic end of the CD8α stalk. For anti-CD19 CARs, the scFv was derived from the anti-human CD19 clone FMC63. To create a CAR specific for human HER2/ERBB2, the anti-human HER2 scFv derived from trastuzumab was used. Similarly, to generate a CAR specific for EGFR, the anti-EGFR scFv derived from cetuximab was used. A summary of exemplary CAR constructs is shown below and amino acid sequences of the full length CAR constructs are provided in SEQ ID NOs: 26, 28, and 30, and nucleic acid sequences of the full length CAR constructs are provided in SEQ ID NOs: 27, 29, and 31.

TABLE 11

Exemplary CAR constructs

| CAR Ref ID | Target | Ag-binding domain | Intracellular Domain | Transmembrane Domain | AA SEQ ID | NA SEQ ID |
|---|---|---|---|---|---|---|
| KSQCAR017 | human EGFR | Cetuximab H225 scFv | CD3 zeta | CD8a hinge | 26 | 27 |
| KSQCAR1909 | human CD19 | FMC63 scFv | CD3 zeta | CD8a hinge | 28 | 28 |
| KSQCAR010 | human HER2 | Herceptin scFv | CD3 zeta | CD8a hinge | 30 | 31 |

Cas9: Cas9 was expressed in target cells by introduction of either Cas9 mRNA or a Cas9 protein. Unless otherwise indicated, Cas9-encoding mRNA comprising a nuclear localization sequence (Cas9-NLS mRNA) derived from *S. pyogenes* (Trilink L-7206) or Cas9 protein derived from *S. pyogenes* (IDT Cat #1074182) was used in the following experiments.

RNPs: Human gRNA-Cas9 ribonucleoproteins (RNPs) were formed by combining 1.2 μL of 100 μM tracrRNA:crRNA duplex with 1 μL of 20 μM Cas9 protein and 0.8 μL of PBS. Mixtures were incubated at RT for 20 minutes to form the RNP complexes. Murine RNPs were formed by combining 1 Volume of 44 μM tracrRNA:crRNA duplex with 1 Volume of 36 μM Cas9. Mixtures were incubated at RT for 20 minutes to form the RNP complexes.

Mice: Wild type CD8+ T cells were derived from C57BL/6J mice (The Jackson Laboratory, Bar Harbor Me.). Ovalbumin (Ova)-specific CD8+ T cells were derived from OT1 mice (C57BL/6-Tg(TcraTcrb) 1100Mjb/J; Jackson Laboratory). OT1 mice comprise a transgenic TCR that recognizes residues 257-264 of the ovalbumin (Ova) protein. gp100-specific CD8+ T cells were derived from PMEL mice (B6.Cg-Thy1<a>/CyTg(TcraTcrb) 8Rest/J; The Jackson Laboratory, Bar Harbor Me. Cat #005023). Mice constitutively expressing the Cas9 protein were obtain from Jackson labs (B6J.129(Cg)-Gt(ROSA)26Sortm1.1(CAG-cas9*,-EGFP)Fezh/J; The Jackson Laboratory, Bar Harbor Me. Strain #026179), TCR-transgenic mice constitutively expressing Cas9 were obtained by breeding of OT1 and PMEL mice with Cas9 mice.

CAR Expression Constructs: CARs specific for human CD19, Her2/Erbb2, and EGFR proteins were generated. Briefly, the 22 amino acid signal peptide of the human granulocyte-macrophage colony stimulating factor receptor subunit alpha (GMSCF-Rα) was fused to an antigen-specific Engineered TCRs Expression Constructs: Recombinant TCRs specific for NY-ESO1, MART-1, and WT-1 were generated. Paired TCR-α:TCR-β variable region protein sequences encoding the 1G4 TCR specific for the NY-ESO-1 peptide SLLMWITQC (SEQ ID NO: 2), the DMF4 and DMFS TCRs specific for the MART-1 peptide AAGIGILTV (SEQ ID NO: 3), and the DLT and high-affinity DLT TCRs specific for the WT-1 peptide, each presented by HLA-A*02:01, were identified from the literature (Robbins et al, Journal of Immunology 2008 180:6116-6131). TCRα chains were composed of V and J gene segments and CDR3α sequences and TCRβ chains were composed of V, D, and J gene segment and CDR3-β sequences. The native TRAC (SEQ ID NO: 22) and TRBC (SEQ ID NOs: 24) protein sequences were fused to the C-terminal ends of the α and β chain variable regions, respectively, to produce 1G4-TCR α/βchains (SEQ ID NOs: 11 and 12, respectively), 95:LY 1G4-TCR α/βchains (SEQ ID NOs: 14 and 13, respectively), DLT-TCR α/βchains (SEQ ID NOs: 5 and 4, respectively), high-affinity DLT-TCR α/βchains (SEQ ID NOs: 8 and 7, respectively), DMF4-TCR α/βchains (SEQ ID NOs: 17 and 16, respectively), and DMFS-TCR α/βchains (SEQ ID NOs: 20 and 19, respectively).

Codon-optimized DNA sequences encoding the engineered TCRα and TCRβ chain proteins were generated where the P2A sequence (SEQ ID NO: 1) was inserted between the DNA sequences encoding the TCRβ and the TCRα chain, such that expression of both TCR chains was driven off of a single promoter in a stoichiometric fashion. The expression cassettes encoding the engineered TCR chains therefore comprised the following format: TCRβ-P2A-TCRα. Final protein sequences for each TCR construct are provided in SEQ ID NO: 12 (1G4), SEQ ID NO: 15 (95:LY 1G4), SEQ ID NO: 6 (DLT), SEQ ID NO: 9 (high-affinity DLT), SEQ ID NO: 18 (DMF4), and SEQ ID NO: 21 (DMF5).

Lentiviral Expression of CAR and TCR Constructs: The CAR and engineered TCR expression constructs described above were then inserted into a plasmid comprising an SFFV promoter driving expression of the engineered receptor, a T2A sequence, and a puromycin resistance cassette. Unless otherwise indicated, these plasmids further comprised a human or a murine (depending on the species the T cells were derived from) U6 promoter driving expression of one or more sgRNAs. Lentivirus constructs comprising an engineered TCR expression construct may further comprise an sgRNA targeting the endogenous TRAC gene, which encodes the constant region of the α chain of the T cell receptor. Lentiviruses encoding the engineered receptors described above were generated as follows. Briefly, $289 \times 10^6$ of LentiX-293T cells were plated out in a 5-layer Cell-STACK 24 hours prior to transfection. Serum-free OptiMEM and TransIT-293 were combined and incubated for 5 minutes before combining helper plasmids (58 µg VSVG and 115 µg PAX2-Gag-Pol) with 231 µg of an engineered receptor- and sgRNA-expressing plasmid described above. After 20 minutes, this mixture was added to the LentiX-293T cells with fresh media. Media was replaced 18 hours after transfection and viral supernatants were collected 48 hours post-transfection. Supernatants were treated with Benzonase® nuclease and passed through a 0.45 µm filter to isolate the viral particles. Virus particles were then concentrated by Tangential Flow Filtration (TFF), aliquoted, tittered, and stored at −80° C.

Retroviral sgRNA expression constructs and production: sgRNA sequences were inserted into a plasmid downstream of a murine U6 promoter. Human CD2 was inserted under the UbiC promoter downstream of the sgRNA as a selectable marker. When rescue experiments were conducted, plasmids included the above elements as well as a codon optimized, gRNA-resistant cDNA encoding wild-type murine Zc3h12a. Retroviruses were generated as follows. Phoenix-GP cells (ATCC® CRL-3215™) were used as producer cells. When 80% confluent, producer cells were transfected with pCL-Eco Retrovirus Packaging Vector and the plasmid encoding the sgRNA and surface selection marker described above using TransIT®-293 Transfection Reagent (Mirusbio, Catalog #2706). 18 hours after transfection, media was changed for complete T cell media (RPMI+10% heat inactivated FBS, 20 mM HEPES, 100 U/mL Penicillin, 100 µg/mL Streptomycin, 50 µM Beta-Mercaptoethanol). Viral supernatants were harvested every 12 hours for a total of 3 harvests, spun and frozen at −80° C.

II. Methods

Human T cell Isolation and Activation: Total human PBMCs were isolated from fresh leukopacks by Ficoll gradient centrifugation. CD8+ T-cells were then purified from total PBMCs using a CD8+ T-cell isolation kit (Stemcell Technologies Cat #17953). For T cell activation, CD8+ T cells were plated at $2 \times 10^6$ cells/mL in X-VIVO 15 T Cell Expansion Medium (Lonza, Cat #04-418Q) in a T175 flask, with 6.25 µL/mL of ImmunoCult T-cell activators (anti-CD3/CD28/CD2, StemCell Technologies, Vancouver BC, Canada) and 10 ng/mL human IL2. T-cells were activated for 18 hours prior to transduction with lentiviral constructs.

Human TIL Isolation and Activation: Tumor infiltrating lymphocytes can also be modified by the methods described herein. In such cases, tumors are surgically resected from human patients and diced with scalpel blades into 1 mm3 pieces, with a single piece of tumor placed into each well of a 24 plate. 2 mL of complete TIL media (RPMI+10% heat inactivated human male AB serum, 1 mM pyruvate, 20 µg/mL gentamycin, 1× glutamax) supplemented with 6000 U/mL of recombinant human IL-2 is added to each well of isolated TILs. 1 mL of media is removed from the well and replaced with fresh media and IL-2 up to 3 times a week as needed. As wells reach confluence, they are split 1:1 in new media+IL-2. After 4-5 weeks of culture, the cells are harvested for rapid expansion.

TIL Rapid Expansion: TILs are rapidly expanded by activating 500,000 TILs with $26 \times 106$ allogeneic, irradiated (5000cGy) PBMC feeder cells in 20 mL TIL media+20 mL of Aim-V media (Invitrogen)+30 ng/mL OKT3 mAb. 48 hours later (Day 2), 6000 U/mL IL-2 is added to the cultures. On day 5, 20 mL of media is removed, and 20 mL fresh media (+30 ng/ml OKT3) is added. On Day 7, cells are counted, and reseeded at $60 \times 106$ cells/L in G-Rex6M well plates (Wilson Wolf, Cat #80660M) or G-Rex100M (Wilson Wolf, Cat #81100S), depending on the number of cells available. 6000 U/mL fresh IL-2 is added on Day 9 and 3000 U/mL fresh IL-2 is added on Day 12. TILs are harvested on Day 14. Expanded cells are then slow-frozen in Cryostor CS-10 (Stemcell Technologies Cat #07930) using Coolcell Freezing containers (Corning) and stored long term in liquid nitrogen.

Murine T cell Isolation and Activation: Spleens from WT or transgenic mice were harvested and reduced to a single cell suspension using the GentleMACS system, according to the manufacturer's recommendations. Purified CD8$^+$ T cells were obtained using the EasySep Mouse CD8$^+$ T Cell Isolation Kit (StemCell Catalog #19853). CD8 T-cells were cultured at $1 \times 106$ cells/mL in complete T cell media (RPMI+10% heat inactivated FBS, 20 mM HEPES, 100 U/mL Penicillin, 100 µg/mL Streptomycin, 50 µM Beta-Mercaptoethanol) supplemented with 2 ng/mL of Recombinant Mouse IL-2 (Biolegend Catalog #575406) and activated with anti-CD3/anti-CD28 beads (Dynabeads™ Mouse T-Activator CD3/CD28 for T-Cell Expansion and Activation Cat #11456D).

Lentiviral transduction of human T cells: T-cells activated 18 hours prior were seeded at $5 \times 10^6$ cells per well in a 6 well plate, in 1.5 mL volume of X-VIVO 15 media, 10 ng/mL human IL-2 and 12.5 µL Immunocult Human CD3/CD28/CD2 T-cell Activator. Lentivirus expressing the engineered receptors was added at an MOI capable of infecting 80% of all cells. 25 µL of Retronectin (1 mg/mL) was added to each well. XVIVO-15 media was added to a final volume of 2.0 mL per well. Unless otherwise indicated, lentiviruses also expressed the sgRNAs. Plates were spun at 600×g for 1.5 hours at room temperature. After 18 hours (Day 2), cells were washed and seeded at $1 \times 10^6$ cells/mL in X-VIVO 15, 10 ng/mL IL2+ T-cell activators.

Retroviral transduction of murine T cells: Where indicated, gRNAs were introduced into Cas9 transgenic T cells by Retroviral transduction. Murine T-cells activated 24 hours prior were seeded at $3 \times 10^6$ cells per well in a 6 well plate coated with 5 µg/mL RetroNectin (Takara Clontech Catalog #T100B), in 2 mL Retrovirus supernatant with 5 µg/mL protamine sulfate and 2 ng/mL of Recombinant Mouse IL-2. Retroviruses express the gRNAs and a surface selection marker (hCD2 or CD90.1). Plates were spun at 600×g for 1.5 hours at room temperature. After 18 hours (Day 2), cells were washed and seeded at $1 \times 10^6$ cells/mL in complete T cell media supplemented with 2 ng/mL of Recombinant Mouse IL-2. 24 hours after infection, cells were washed and cultured in complete T cell media supplemented with IL-2. After 24 hours, activation beads were removed and infected cells were purified using EasySep Human CD2 Positive Selection Kit (StemCell Catalog #18657) or EasySep Mouse CD90.1 Positive Selection Kit (StemCell Catalog #18958). Edited murine CD8 T were cultured at $1\times10^6$ cells/mL in complete T cell media supplemented with IL-2 for an additional 1-4 days.

Electroporation of human T cells: 3 days after T cell activation, T cells were harvested and resuspended in nucleofection buffer (18% supplement 1, 82% P3 buffer from the Amaxa P3 primary cell 4D-Nuclefector X kit S) at a concentration of $100\times10^6$ cells/mL. 1.5 µL of sgRNA/Cas9 RNP complexes (containing 120 pmol of crRNA:tracrRNA duplex and 20 pmol of Cas9 nuclease) and 2.1 µL (100 pmol) of electroporation enhancer were added per 20 µL of cell solution. 25 µL of the cell/RNP/enhancer mixture was then added to each electroporation well. Cells were electroporated using the Lonza electroporator with the "EO-115" program. After electroporation, 80 µL of warm X-VIVO 15 media was added to each well and cells were pooled into a culture flask at a density of $2\times10^6$ cells/mL in X-VIVO 15 media containing IL-2 (10 ng/mL). On Day 4, cells were washed, counted, and seeded at densities of $50\text{-}100\times10^6$ cells/L in X-VIVO 15 media containing IL-2 (10 ng/mL) in G-Rex6M well plates or G-Rex100M, depending on the number of cells available. On Days 6 and 8, 10 ng/mL of fresh recombinant human IL-2 was added to the cultures.

Electroporation of mouse T cells: Murine T-cells activated 48 hours prior were harvested, activation beads were removed and cells were washed and resuspended in Neon nucleofection buffer T. Up to $2\times10^6$ cells resuspended in 9 uL Buffer T and $20\times10^6$ cells resuspended in 90 uL Buffer T can be electroporated using Neon™ 10-µL tip and Neon™ 100-µL tip respectively. gRNA/Cas9 RNP complexes or ZFN mRNAs (1 µL per 10 µL tip or 10 µL per 100 µL Tip) and 10.8 µM electroporation enhancer (2 µL per 10 µL Tip or 20 µL per 100 µL Tip) were added to the cells. T-cells mixed with gRNA/Cas9 RNP complexes or ZFN mRNAs were pipeted into the Neon™ tips and electroporated using the Neon Transfection System (1700 V/20 ms/1 pulses). Immediately after electroporation, cells were transferred into a culture flask at a density of $1.6\times10^6$ cells/mL in warm complete T cell media supplemented with 2 ng/mL of Recombinant Mouse IL-2. Edited murine CD8 T cells were further cultured at $1\times10^6$ cells/mL in complete T cell media supplemented with IL-2 for an additional 1-4 days.

Purification and characterization of engineered T cells: 10 days after T cell activation, cells were removed from the culture flasks, and edited, engineered receptor-expressing CD8+ T cells were purified. Expression of the engineered receptor can be determined by antibody staining, e.g., antibodies for Vβ12 for DMF4 TCR or Vβ13/13.1 for NY-ESO-1 or 1G4). Further determination of editing of target genes can be assessed by FACS analysis of surface proteins (e.g., CD3), western blot of the target protein, and/or TIDE/NGS analysis of the genomic cut-site. Purified cells can then be slow-frozen in Cryostor CS-10 (Stemcell Technologies Cat #07930) using Coolcell Freezing containers (Corning), and stored long term in liquid nitrogen for future use.

Example 2

Characterization of Edited, Receptor-Engineered T Cells

Experiments were performed in which edited receptor-expressing cells were purified based on cell surface expression of CD3. Prior to engineering, CD8+ T cells express CD3 molecules on the cell surface as part of a complex that includes the TCR α/β chains (FIG. 4A). The T cells were transduced with a lentivirus expressing a CAR, a guide RNA targeting the TRAC gene, and a guide RNA targeting the B2M gene, which was used to assess the editing of non-TCR genes as a proxy for target gene editing. Following lentiviral transduction and Cas9 mRNA electroporation, successfully transduced and edited T cells demonstrate a loss of surface CD3 expression due to editing of the TRAC gene and a loss of HLA-ABC expression due to the editing of the B2M gene (FIG. 4B). CD3-expressing cells were removed from the bulk population (FIG. 4B) using the EasySep human CD3-positive selection kit (StemCell Tech Cat #18051). Cells were then subjected to two rounds of negative magnetic selection for CD3. This process yielded highly purified CD3-negative T cells expressing (FIG. 4C). Staining with a recombinant CD19-Fc reagent (which binds CD19 CAR) demonstrated that edited cells show surface expression of the CD19 CAR, whereas unedited cells do not (FIG. 4D). Similar experiments were performed with CD45 and B2M targeting sgRNAs. Cas9 editing activity in T cells was confirmed by assessing CD45 and B2M expression by flow cytometry was assessed 96 hours later, and efficient Cas9 function is indicated by a loss of CD45 expression on the surface of the T cells as determined by FACS. Co-electroporation with Cas9 mRNA and Cas9 RNPs led to substantial editing at the CD45 and B2M loci, with 66.3% of the cells exhibiting dual editing.

Target editing was performed as described in the above examples and the editing of a single exemplary gene, CBLB, was confirmed using both the Tracking of Indels by Decomposition (TIDE) analysis method and western blot analysis. TIDE quantifies editing efficacy and identifies the predominant types of insertions and deletions (indels) in the DNA of a targeted cell pool.

Figure 5A:
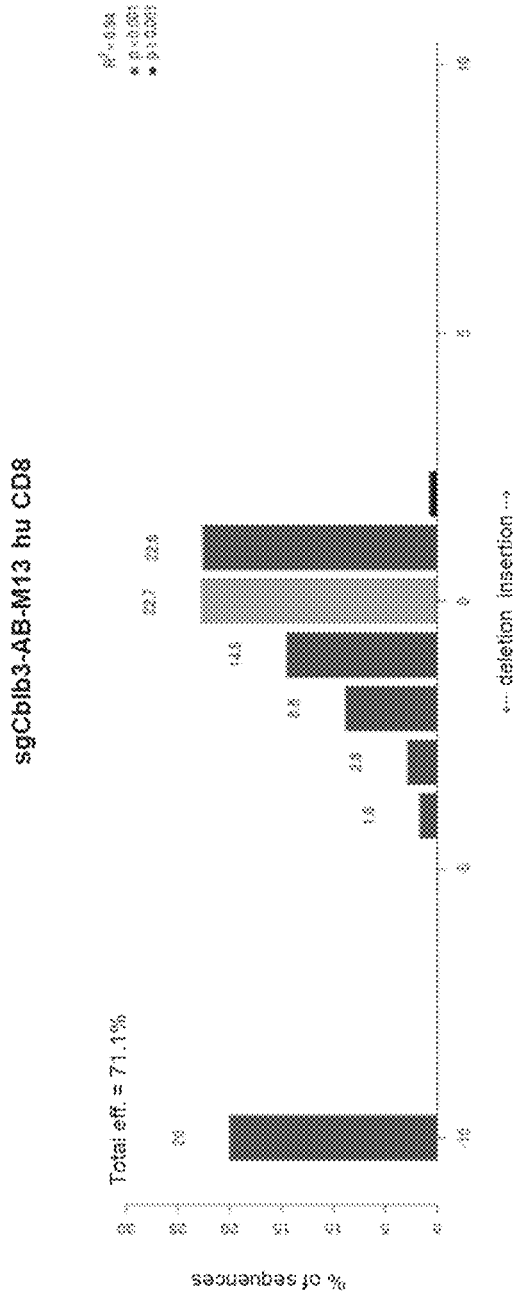
FIG. 5A-FIG. 5B illustrate TIDE analysis data for editing of CBLB in primary human T cells.
Figure 5B:
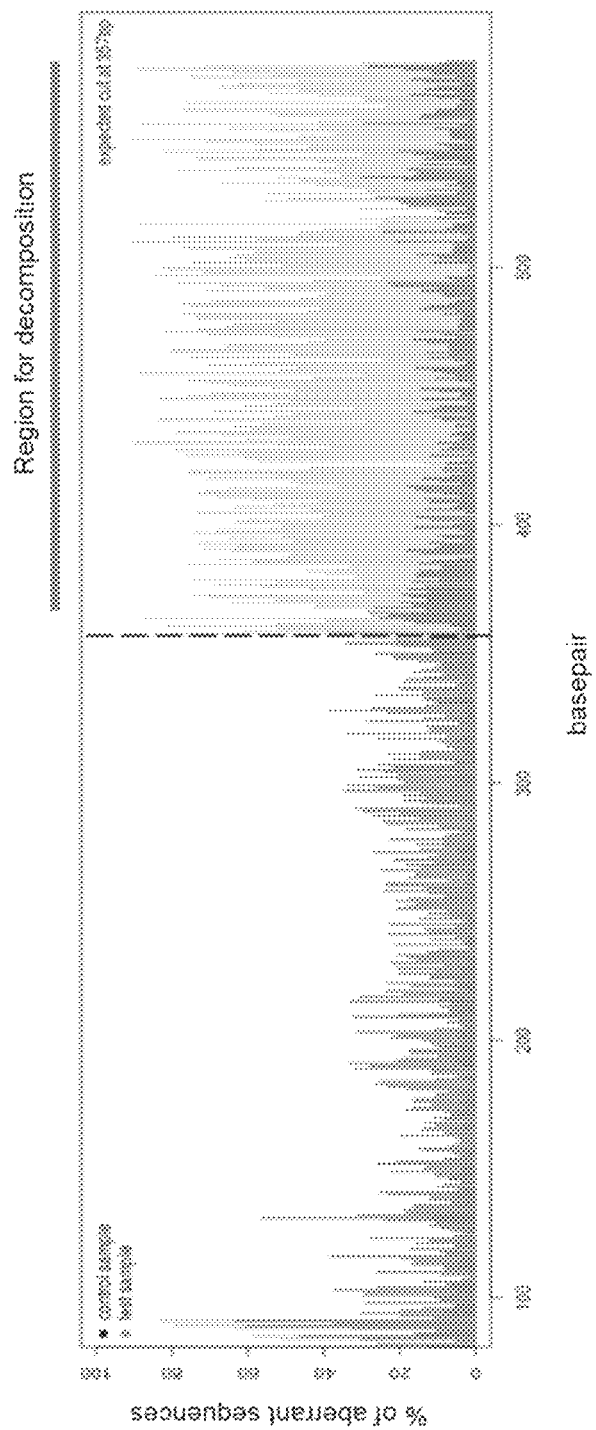
Figure 6:
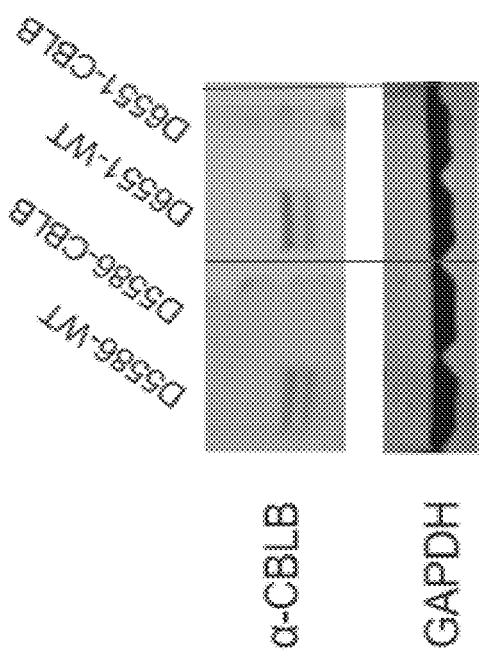
FIG. 6 illustrates a western blot for CBLB protein in primary human T cells edited with a CBLB gRNA (D6551-CBLB) compared to unedited controls (D6551-WT).

Genomic DNA (gDNA) was isolated from edited T cells using the Qiagen Blood and Cell Culture DNA Mini Kit (Cat #: 13323) following the vendor recommended protocol and quantified. Following gDNA isolation, PCR was performed to amplify the region of edited DNA using locus-specific PCR primers (F: 5'-CCACCTCCAGTTGTTGCATT-3' (SEQ ID NO: 32); R: 5'-TGCTGCTTCAAAGGGAGGTA-3' (SEQ ID NO: 33). The resulting PCR products were run on a 1% agarose gel, extracted, and purified using the QIAquick Gel Extraction Kit (Cat #: 28706). Extracted products were sequenced by Sanger sequencing and Sanger sequencing chromatogram sequence files were analyzed by TIDE. In CBLB-edited T cells edited by methods using either gRNA/Cas9 RNP complexes or Cas9 mRNA introduced with gRNA expressing lentivirus (in each case, the CBLB gRNA used is SEQ ID NO: 288), the resulting TIDE analysis confirmed editing of the CBLB target gene. In addition to TIDE, depletion of CBLB protein levels were confirmed by western blot using an anti-CBLB antibody (SCT Cat #9498). The data is provided in FIGS. 5A and 5B and FIG. 6.

Another method by which editing of a gene is assessed is by next generation sequencing. For this method, genomic DNA (gDNA) was isolated from edited T cells using the Qiagen Blood and Cell Culture DNA Mini Kit (Cat #: 13323) following the vendor recommended protocol and quantified. Following gDNA isolation, PCR was performed to amplify the region of edited genomic DNA using locus-specific PCR primers containing overhangs required for the addition of Illumina Next Generation sequencing adapters. The resulting PCR product was run on a 1% agarose gel to ensure specific and adequate amplification of the genomic locus occurred before PCR cleanup was conducted according to the vendor recommended protocol using the Monarch PCR & DNA Cleanup Kit (Cat #: T1030S). Purified PCR product was then quantified, and a second PCR was performed to anneal the Illumina sequencing adapters and sample specific indexing sequences required for multiplexing. Following this, the PCR product was run on a 1% agarose gel to assess size before being purified using AMPure XP beads (produced internally). Purified PCR product was then quantified via qPCR using the Kapa Illumina Library Quantification Kit (Cat #: KK4923) and Kapa Illumina Library Quantification DNA Standards (Cat #: KK4903). Quantified product was then loaded on the Illumina NextSeq 500 system using the Illumina NextSeq 500/550 Mid Output Reagent Cartridge v2 (Cat #: FC-404-2003). Analysis of produced sequencing data was performed to assess insertions and deletions (indels) at the anticipated cut site in the DNA of the edited T cell pool.

Example 3

Identification of Adoptive T Cell Transfer Therapy Targets Through an OT1/B16-Ova CRISPR/Cas9 Functional Genomic Screen Experiments were performed to identify targets that regulate accumulation of T cells in tumors. A pooled CRISPR screen was performed in which a pool of sgRNAs, each of which target a single gene, were introduced into a population of tumor-specific T cells such that each cell in the population comprised a single sgRNA targeting a single gene. To determine the effect of a particular gene on the accumulation of T cells in tumor samples, the frequency of each sgRNA in the population of T cells was determined at the beginning of the experiment and compared to the frequency of the same sgRNA at a later time-point in the experiment. The frequency of sgRNAs targeting genes that positively regulate T cell accumulation in tumor samples (e.g., genes that positively-regulate T cell proliferation, viability, and/or tumor infiltration) is expected to increase over time, while the frequency of sgRNAs targeting genes that negatively regulate T cell accumulation in tumor samples (e.g., genes that negatively-regulate T cell proliferation, viability, and/or tumor infiltration) is expected to decrease over time.

Pooled CRISPR screens were performed with CD8$^+$ T cells derived from Cas9 expressing OT1 mice according to methods described in Example 1. The pooled sgRNA library was introduced to purified OTI CD8$^+$ T cells cultured in vitro to generate a population of edited CD8$^+$ T cells. After in vitro engineering, the edited OT1 CD8$^+$ T cells were intravenously (iv) administered to B16/Ova tumor-bearing, C56BL/6 mice. After in vivo expansion, organs were harvested and CD45+ cells were enriched. Genomic DNA from the isolated CD45+ cells was isolated using Qiagen DNA extraction kits. The sgRNA library was then amplified by PCR and sequenced using Illumina next-generation sequencing (NGS).

The distribution and/or frequency of each sgRNA in samples harvested from tumor-bearing mice was analyzed and compared to the distribution and/or frequency of each sgRNA in the initial T cell population. Statistical analyses were performed for each individual sgRNA to identify guides that were significantly enriched in T cell populations harvested from tumor bearing mice and to assign an enrichment score to each of the guides. Enrichment scores for individual sgRNA targeting the same gene were aggregated to identify target genes that had a consistent and reproducible effect on T cell accumulation across multiple sgRNAs and across multiple OT1 donor mice. The results of these experiments are shown below in Table 12. Percentiles in Table 12 were calculated using the following equation: percentile score=1−(gene enrichment rank/total number of genes screened).

TABLE 12

Target Gene Percentile Scores

| Target Name | Percentile Score |
| --- | --- |
| IKZF1 | 0.995 |
| NFKBIA | 0.986 |
| GATA3 | 0.993 |
| BCL3 | 0.698 |
| IKZF3 | 0.995 |
| SMAD2 | 0.978 |
| TGFBR1 | 0.991 |
| TGFBR2 | 0.987 |
| TNIP1 | 0.991 |
| TNFAIP3 | 0.998 |
| IKZF2 | 0.622 |
| TANK | 0.83 |
| PTPN6 | 0.782 |
| BCOR | 0.720 |
| CBLB | 0.999 |
| NRP1 | 0.826 |
| HAVCR2 | 0.86 |
| LAG3 | 0.82 |
| BCL2L11 | 0.9928 |
| CHIC2 | 0.997 |
| FLI1 | 0.999 |
| PCBP1 | 0.997 |
| PBRM1 | 0.944 |
| WDR6 | 0.953 |
| E2F8 | 0.867 |
| SERPINA3 | 0.822 |
| SEMA7A | 0.78 |
| DHODH | 0.990 |
| UMPS | 0.989 |
| ZC3H12A | 0.999 |
| MAP4K1 | 0.842 |
| NR4A3 | 0.997 |

Example 4

Identification of Adoptive T Cell Transfer Therapy Targets Through In Vitro CAR-T and CRISPR/Cas9 Functional Genomic Screens Experiments were performed to identify targets that regulate accumulation of CAR-T cells tumor samples. A pooled, genome-wide CRISPR screen was performed in which a pool of sgRNAs, each of which target a single gene, was introduced into a population of tumor-specific human CAR-T cells, such that each cell in the population comprised a single sgRNA targeting a single gene. To determine the effect of a particular gene in CAR-T cell accumulation in tumor samples, the frequency of each sgRNA in the population of CAR-T cells was determined at the beginning of the experiment and compared to the frequency of the same sgRNA at a later time-point in the experiment. The frequency of sgRNAs targeting genes that positively regulate CAR-T cell accumulation in tumor samples (e.g., genes that positively-regulate T cell proliferation, viability, and/or tumor infiltration) is expected to increase over time, while the frequency of sgRNAs targeting genes that negatively regulate CAR-T cell accumulation in tumor samples (e.g., genes that negatively-regulate T cell proliferation, viability, and/or tumor infiltration) is expected to decrease over time.

In vitro screens were performed using CAR-T cells specific for human CD19. Pooled sgRNA libraries were introduced to the CD19 CARTs as described above and cells were electroporated with Cas9 mRNA as described in Example 1 to generate a population of Cas9-edited CD19 CARTs. The edited CD19 CARTs were then co-cultured with an adherent colorectal carcinoma (CRC) cell line engineered to express CD19 or a Burkitt's lymphoma cell line expressing endogenous CD19. CARTs were harvested at various time points throughout the co-culture period and cell pellets were frozen down. Genomic DNA (gDNA) was isolated from these cell pellets using Qiagen DNA extraction kits and sequenced using Illumina next-generation sequencing.

The distribution and/or frequency of each sgRNA in the aliquots taken from the CART/tumor cell co-culture was analyzed and compared to the distribution and/or frequency of each sgRNA in the initial edited CAR-T cell population. Statistical analyses were performed for each individual sgRNA to identify sgRNAs that were significantly enriched in CAR-T cell populations after tumor cell co-culture and to assign an enrichment score to each of the guides. Enrichment scores for individual sgRNA that target the same gene were aggregated to identify target genes that have a consistent and reproducible effect on CAR-T cell accumulation in tumor samples across multiple sgRNAs and CAR-T cell population. Targets were ranked and called for further investigation based on percentile. The results of these experiments are shown below in Table 13. Percentiles in Table 13 were calculated using the following equation: percentile score=1−(gene enrichment rank/total number of genes screened).

TABLE 13

Target Gene Percentile Scores

| Target Name | Percentile Score |
|---|---|
| IKZF1 | 0.999 |
| IKZF3 | 0.962 |
| TGFBR1 | 0.778 |
| TNIP1 | 0.64 |
| TNFAIP3 | 0.791 |
| FOXP3 | 0.866 |
| IKZF2 | 0.907 |
| TANK | 0.93 |
| PTPN6 | 0.707 |
| BCOR | 0.999 |
| CBLB | 0.989 |
| BCL2L11 | 0.93 |
| CHIC2 | 0.71 |
| WDR6 | 0.962 |
| E2F8 | 0.971 |
| DHODH | 0.763 |

Example 5

Identification of Adoptive T Cell Transfer Therapy Targets Through an In Vivo CAR-T/Tumor CRISPR/Cas9 Functional Genomic Screen Experiments were performed to identify targets that regulate CAR-T cell accumulation in the presence of tumors. A pooled CRISPR screen was performed in which a pool of sgRNAs, each of which target a single gene, was introduced into a population of tumor-specific human CAR-T cells such that each cell in the population comprised a single sgRNA targeting a single gene. To determine the effect of a particular gene in CAR-T cell accumulation in tumor samples, the frequency of each sgRNA in the population of CAR-T cells was determined at the beginning of the experiment and compared to the frequency of the same sgRNA at a later time-point in the experiment. The frequency of sgRNAs targeting genes that positively regulate CAR-T cell accumulation in tumor samples (e.g., genes that positively-regulate T cell proliferation, viability, and/or tumor infiltration) is expected to increase over time, while the frequency of sgRNAs targeting genes that negatively regulate CAR-T cell accumulation in tumor samples (e.g., genes that negatively regulate T cell proliferation, viability, and/or tumor infiltration) is expected to decrease over time.

In vivo screens performed in two separate subcutaneous xenograft models: a Burkitt lymphoma model and a colorectal cancer (CRC) model. For the Burkitt model, $1 \times 10^6$ Burkitt lymphoma tumor cells in Matrigel were subcutaneously injected into the right flank of 6-8 week old NOD/SCID gamma (NSG) mice. Mice were monitored, randomized, and enrolled into the study 13 days post-inoculation, when tumors reached approximately 200 mm$^3$ in volume. For the CRC model, CRC cells were engineered to express CD19, and $5 \times 10^6$ tumor cells in Matrigel were subcutaneously injected into the right flank of 6-8 week old NSG mice. Mice were monitored, randomized, and enrolled into the study 12 days post-inoculation when tumors reached approximately 200 mm$^3$ in volume. Cas9-engineered CD19 CAR-T cells were administered iv via the tail vein at $3 \times 10^6$ and $10 \times 10^6$/mouse (3M and 10M). Tumors were collected 8 to 10 days post-CAR-T injection and frozen in liquid nitrogen. These tissues were later dissociated and processed for genomic DNA extraction.

The distribution and/or frequency of each sgRNA in the genomic DNA samples taken at study end was analyzed and compared to the distribution and/or frequency of each sgRNA in the initial edited-CAR-T cell population. Statistical analyses were performed for each individual sgRNA to identify sgRNAs were are significantly enriched in genomic DNA samples taken at study end and to assign an enrichment score to each of the guides. Enrichment scores for individual sgRNA that target the same gene were aggregated to identify target genes that have a consistent and reproducible effect on CAR-T cell abundance across multiple sgRNAs and CAR-T cell populations. Targets were ranked and called for further investigation based on percentile. The results of these experiments are shown below in Table 14. Percentiles in Table 14 were calculated using the following equation: percentile score=1−(gene enrichment rank/total number of genes screened).

TABLE 14

Target Gene Percentile Scores

| Target Name | Percentile Score |
|---|---|
| NFKBIA | 0.95 |
| SMAD2 | 0.816 |
| FOXP3 | 0.92 |
| IKZF2 | 0.895 |
| TANK | 0.923 |
| PTPN6 | 0.979 |
| CBLB | 0.958 |
| PPP2R2D | 0.926 |
| NRP1 | 0.795 |
| HAVCR2 | 0.992 |
| LAG3 | 0.97 |
| TIGIT | 0.916 |
| CTLA4 | 0.884 |
| BCL2L11 | 0.776 |

TABLE 14-continued

Target Gene Percentile Scores

| Target Name | Percentile Score |
|---|---|
| RBM39 | 0.94 |
| E2F8 | 0.968 |
| CALM2 | 0.902 |
| SERPINA3 | 0.907 |
| SEMA7A | 0.918 |

Example 6

Validation of Single-Edited Adoptively Transferred T Cells in a Murine OT1/B16-Ova Syngeneic Tumor Model Targets with percentile scores of 0.6 or greater in Examples 3-5 were selected for further evaluation in a single-guide format to determine whether editing a target gene in tumor-specific T cells conferred an increase in anti-tumor efficacy in a murine OT1/B16-Ova subcutaneous tumor model. Evaluation of exemplary targets is described herein, however these methods can be used to evaluate any of the potential targets described above.

Anti-tumor efficacy of single-edited T cells was evaluated in mice using the B16-Ova subcutaneous syngeneic tumor model, which is sensitive to treatment with anti-PD1 antibodies. Briefly, 6-8 week old female C57BL/6J mice from Jackson labs were injected subcutaneously with $0.5 \times 10^6$ B16-Ova tumor cells. When tumors reached a volume of approximately 100 mm$^3$ mice were randomized into groups of 10 and injected intravenously with edited mouse OT1 CD8+ T cells via tail vein. Prior to injection, the OT1 T cells were edited by electroporation with gRNA/Cas9 RNP complexes comprising (i) a control gRNA; (ii) a single Map4k1-targeting gRNA, (iii) a single Zc3h12a-targeting gRNA; (iv) a single Cblb-targeting gRNA; (v) a single Nr4a3-targeting gRNA or; (vi) a single PD1-targeting gRNA. To generate a population of tumor-specific CD8+ T cells with edited target genes, spleens from female OT1 mice were harvested and CD8 T cells were isolated and edited as described in Example 1. The edited OT1 CD8+ T cells were then administered intravenously to B16-Ova tumor-bearing C56BL/6 mice. Body weight and tumor volume were measured at least twice per week. Tumor volume was calculated as mean and standard error of the mean for each treatment group. The percentage tumor growth inhibition (TGI) was calculated using mean tumor volumes (TV) according to the following formulas:

$$\% \text{ TGI} = (\text{TV-Target}_{final} - \text{TV-Target}_{Initial})/(\text{TV-Control}_{final} - \text{TV-Control}_{Initial}),$$

where TV=mean tumor volume, final for Cblb TGI=Day 18 post-T cell transfer, final for Zc3h12a, Nr4a3, and Map4k1=Day 14 post-T cell transfer, and initial=Day 0 (i.e., day of T cell transfer).

Figure 7A:
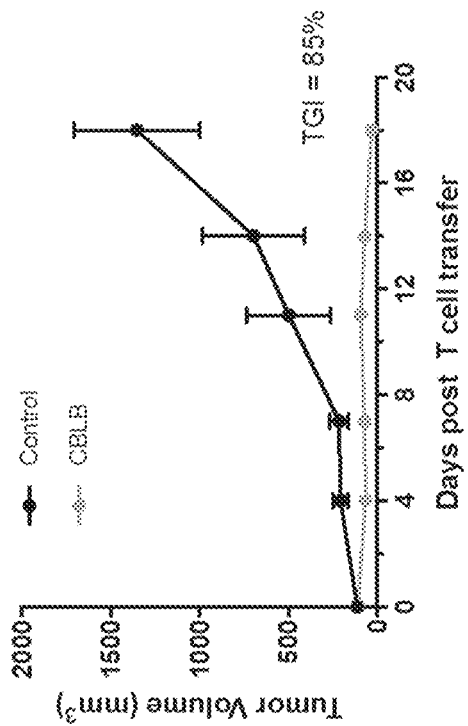
FIG. 7A-FIG. 7E show tumor growth over time in a murine B16/Ova syngeneic tumor model.
Figure 7C:
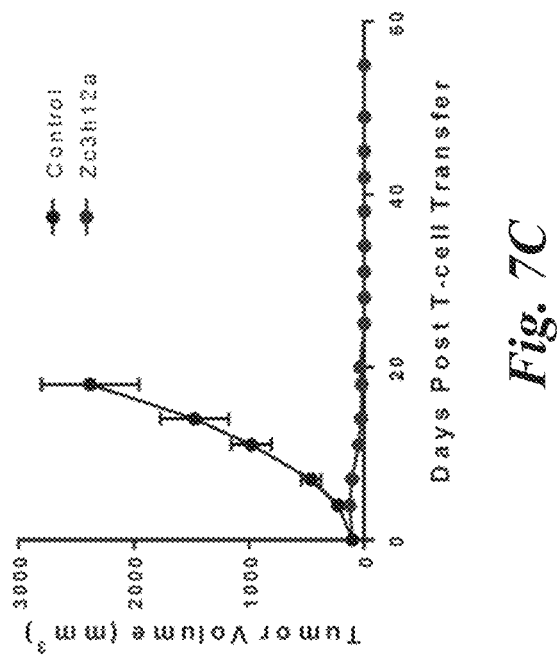
Figure 7B:
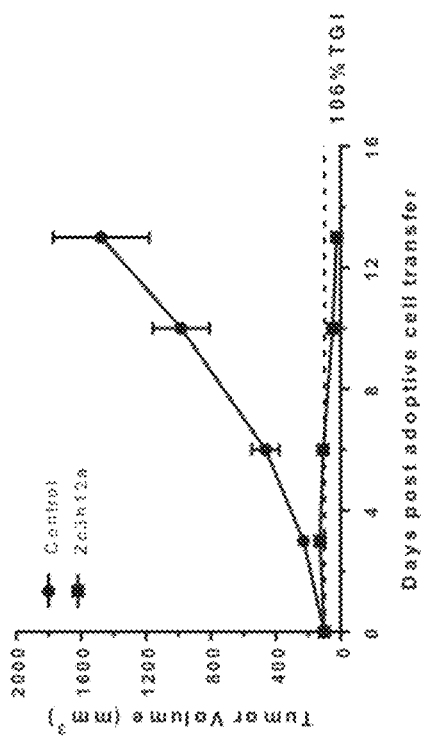
Figure 7E:
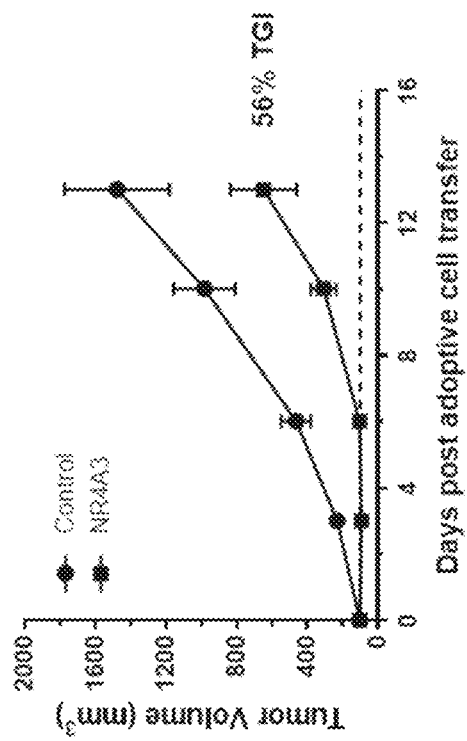
Figure 7D:
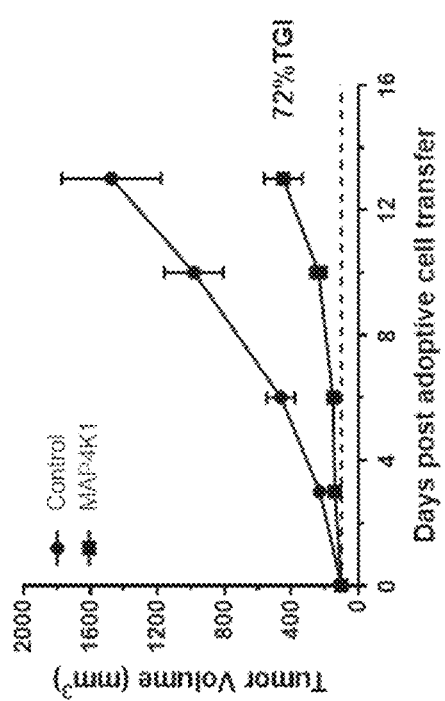

Results of Cblb-edited T cells are shown in FIG. 7A. These data demonstrate that editing of the Cblb gene in T cells leads to anti-tumor efficacy with a TGI of 85% at day 18. Results of Zc3h12a-edited T cells are shown in FIG. 7B. These data demonstrate that editing of the Zc3h12a gene in T cells enhances anti-tumor efficacy of the T cells with a TGI of 106% at day 14. Data from an additional experiment with Zc3h12a-edited cells are shown in FIG. 7C. Results of Map4k1-edited T cells are shown in FIG. 7D. These data demonstrate that editing of the Map4k1 gene in T cells enhances anti-tumor efficacy of the T cells with a TGI of 72% at day 14. Results of Nr4a3-edited T cells are shown in FIG. 7E. These data demonstrate that editing of the Nr4a3 gene in T cells enhances anti-tumor efficacy of the T cells with a TGI of 56% at day 14.

Example 7

Validation of Single-Edited Adoptively Transferred T Cells in a Murine OT1/B16-Ova Syngeneic Tumor Model in Combination with Anti-PD1 Therapy Further experiments were performed to assess the effect of Map4k1-edited cells in combination with anti-PD1 therapy. 6-8 week old female C57BL/6J mice from Jackson labs were injected subcutaneously with $0.5 \times 10^6$ B16-Ova tumor cells. When tumors reached a volume of approximately 100 mm$^3$ mice were randomized into groups of 10 and injected intravenously with edited mouse OT1 CD8+ T cells via tail vein. Prior to injection these cells were edited with either a control guide or a single guide editing for the Map4k1 gene. The editing efficiency of the gRNA/Cas9 complex targeting Map4k1 gene was determined to be 82% using the NGS method. At the time of T cell transfer, designated cohorts were also initiated treatment with 2.5 mg/kg of anti-mouse PD1 antibody (clone RMP1-14, BioX-cell), injected 3× week for the duration of the study. Body weight and tumor volume was measured at least twice per week. Tumor volume was calculated as mean and standard error of the mean for each treatment group. The percentage tumor growth inhibition (TGI) was calculated using the mean tumor volume from the Map4k1 group on day 14-day 1/mean tumor volume from control treated group on day 14-day 1 where day 1 is the day of edited mouse OT1 CD8+ T cell transfer. Results of this experiment are shown in FIG. 8A.

A similar experiment was conducted using Nr4a3-edited cells. The editing efficiency of the gRNA/Cas9 complex targeting the Nr4a3 gene was determined to be 28% using the NGS method. The percentage tumor growth inhibition (TGI) was calculated using the mean tumor volume from the Nr4a3 group on day 14-day 1/mean tumor volume from control treated group on day 14-day 1 where day 1 is the day of edited mouse OT1 CD8+ T cell transfer. Results of this experiment are shown in FIG. 8B.

Similar experiments are performed to assess the effect of Zc3h12a-edited cells in combination with anti-PD1 therapy on anti-tumor efficacy.

Example 8

Validation of Single-Edited Adoptively Transferred T Cells in a Murine PMEL and MC38/gp100 Syngeneic Tumor Model Targets with percentile scores of 0.6 or greater in Examples 3-5 were selected for further evaluation in a single-guide format to determine whether editing a target gene in tumor-specific T cells conferred an increase in anti-tumor efficacy in a murine MC38gp100 subcutaneous syngeneic tumor model of colorectal cancer (which is insensitive to treatment with anti-PD1 antibodies). Evaluation of exemplary targets is described herein, however these methods can be used to evaluate any of the potential targets described above.

Briefly, 6-8 week old female C57BL/6J mice from Jackson labs were injected subcutaneously with 1×10⁶ MC38gp100 tumor cells. Prior to injection, the T cells were edited by electroporation with gRNA/Cas9 RNP complexes comprising (i) a control gRNA or (ii) a single Zc3h12a-targeting gRNA. When tumors reached a volume of approximately 100 mm³ mice were randomized into groups of 10 and injected intravenously with Zc3h12a-edited mouse PMEL CD8⁺ T cells via tail vein. Body weight and tumor volume was measured at least twice per week. Tumor volume was calculated as mean and standard error of the mean for each treatment group.

Figure 9:
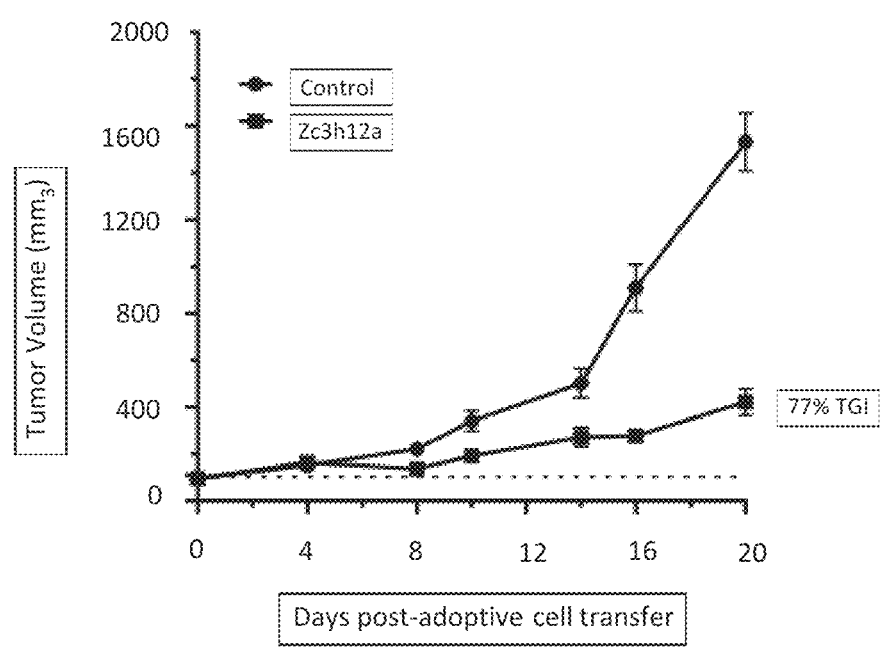
FIG. 9 shows tumor growth over time in a murine MC38/gp100 syngeneic tumor model in mice treated with Zc3h12a-edited PMEL T cells.

Results of Zc3h12a-edited T cells are shown in FIG. 9. These data demonstrate that editing of the Zc3h12a gene in T cells enhances anti-tumor efficacy of the T cells with a TGI of 77% at day 20. Similar experiments are performed to assess the effect of Nr4a3-edited cells and Map4k1-edited cells on anti-tumor efficacy in a PMEL/MC38 syngeneic tumor model.

Example 9

Validation of Single-Edited Adoptively Transferred T Cells in a Murine B16-F10 Syngeneic Tumor Model Additional experiments are performed to assess the effect of editing Zc3h12a in the aggressive metastatic B16-F10 syngeneic tumor model with disease manifesting as lung metastasis.

Briefly, 6-8 week old female C57BL/6J mice from Jackson labs are injected intravenously with 0.5×10⁶ B16-F10 tumor cells. Mice are weighed and assigned to treatment groups using a randomization procedure prior to inoculation. At D3 post tumor inoculation, mice are injected intravenously with murine PMEL CD8+ T cells via tail vein. Prior to injection, these cells were edited by electroporation with gRNA/Cas9 RNP complexes comprising (i) a control gRNA; (ii) a single gRNA targeting the PD-1 gene; or (iii) a single gRNA targeting the Zc3h12a gene. Body weight is monitored at least twice per week. At Day 15 post tumor inoculation (Day 12 post edited PMEL transfer), mice lungs are perfused and fixed with 10% para-formaldehyde. After overnight fixation, lungs are transferred to 70% EtOH for further preservation. Anti-tumor efficacy can be evaluated by visually assessing the B16-F10 tumor burden which can be seen as black colonies of cancer cells on the lungs.

Figure 10:
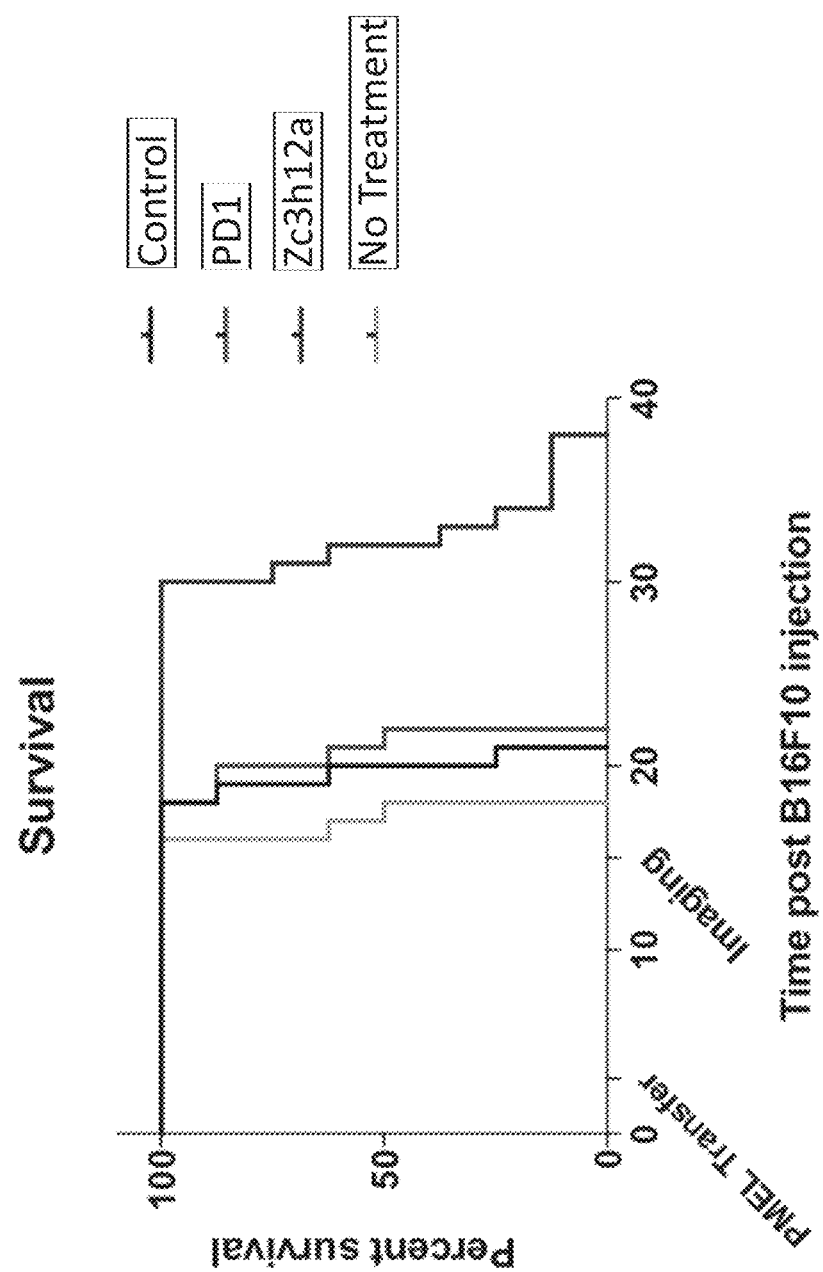
FIG. 10 shows a survival curve of mice treated with Zc3h12a-edited PMEL T cells and PD1-edited PMEL T cells in a B16F10 lung met model.

Survival is graphed as percent (FIG. 10). As shown in FIG. 10A, Zc3h12a-edited PMEL T cells were able to convey increased survival in comparison to control and PD1-edited PMEL T cells in a B16F10 lung met model. Similar experiments are performed to assess the effects of Nr4a3-edited and Map4k1-edited cells in a B16-F10 syngeneic tumor model.

Example 10

Validation of Single-Edited Adoptively Transferred T Cells in a Murine OT1/EG7-Ova Subcutaneous Syngeneic Tumor Model Anti-tumor efficacy of Zc3h12a was further evaluated in mice using the Eg7-Ova subcutaneous syngeneic tumor model. 6-8 week old female C57BL/6J mice from Jackson labs were injected subcutaneously with 1×10⁶ Eg7-Ova tumor cells. When tumors reached a volume of approximately 100 mm³ mice were randomized into groups of 10 and injected intravenously with edited mouse OT1 CD8+ T cells via tail vein. Prior to injection these cells were edited with either a control guide or a single guide editing for the Zc3h12a gene. Body weight and tumor volume was measured at least twice per week. Tumor volume was calculated as mean and standard error of the mean for each treatment group.

The percentage tumor growth inhibition (TGI) was calculated using mean tumor volumes (TV) according to the following formulas:

$$TGI=(TV\text{-}Target_{final}-TV\text{-}Target_{Initial})/(TV\text{-}Control_{final}-TV\text{-}Control_{Initial}),$$

where TV=mean tumor volume, final TGI=Day 14 post-T cell transfer, and initial=Day 0 (i.e., day of T cell transfer).

Figure 11:
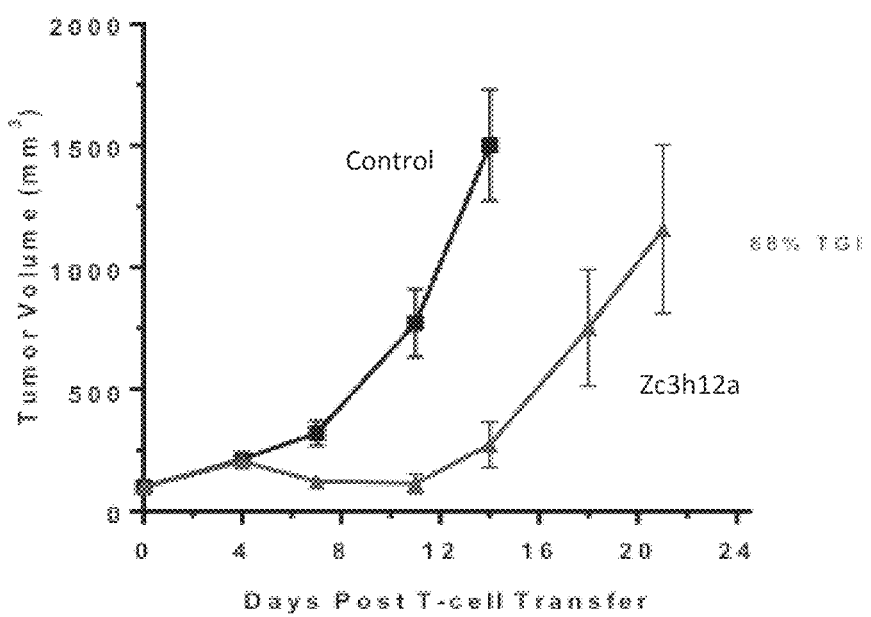
FIG. 11 shows tumor growth over time in a murine Eg7 Ova syngeneic tumor model in mice treated with Zc3h12a-edited T cells.

These data demonstrate that editing of the Zc3h12a in T cells enhances anti-tumor efficacy of the T cells with a TGI of 88% as shown in in FIG. 11. Similar experiments are performed to assess the effect of Nr4a3-edited cells and Map4k1-edited cells on anti-tumor efficacy in a OT1/EG7OVA subcutaneous syngeneic tumor model.

Example 11

Validation of Single-Edited Adoptively Transferred T Cells in the A375 Xenograft Tumor Model Targets with percentile scores of 0.6 or greater in Examples 3-5 were selected for further evaluation in a single-guide format to determine whether editing a target gene in tumor-specific T cells conferred an increase in anti-tumor efficacy in the A375 xenograft tumor model. Evaluation of exemplary targets is described herein, however these methods can be used to evaluate any of the potential targets described above.

Briefly, 6-12 week old NSG mice from Jackson labs were injected subcutaneously with 5×10⁶ A375 cells. When tumors reached a volume of approximately 200 mm³, mice were randomized into groups of 8 and injected intravenously with 18.87×10⁶ for CBLB-edited NY-ESO-1-specific TCR transgenic T cells or 5.77×10⁶ ZC3H12A-edited NY-ESO-1-specific TCR transgenic T cells via tail vein. Body weight and tumor volume was measured at least twice per week. Tumor volume was calculated as mean and standard error of the mean for each treatment group and efficacy was evaluated as a decrease in mean tumor volume and an increase in survival compared to control edited cells. The percentage tumor growth inhibition (TGI) was calculated using the mean tumor volume from the ZC3H12A group on day 19-day 0/mean tumor volume from control treated group on day 19-day 0 where day 0 is the day of human TCR transgenic T cell transfer.

Figure 12B:
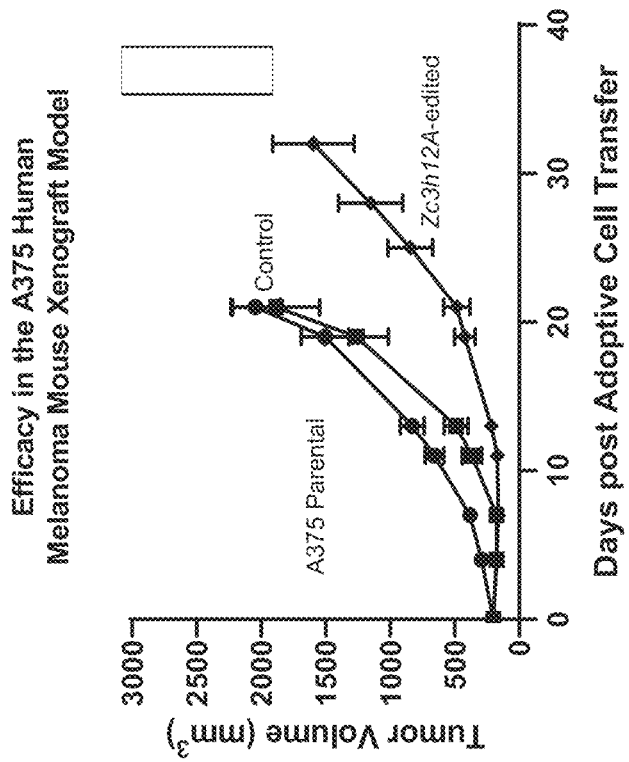
FIG. 12A-FIG. 12B shows tumor growth over time in a murine A375 xenograft model for mice.
Figure 12A:
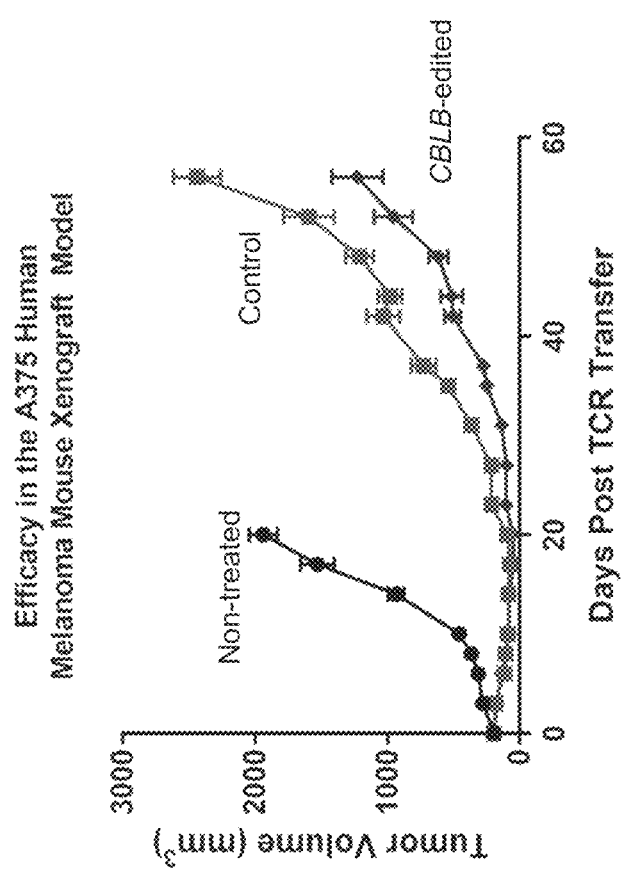

Results of these experiments are shown in FIG. 12. These data demonstrate that editing of the CBLB (FIG. 12A) and ZC3H12A (FIG. 12B) gene in T cells leads to anti-tumor efficacy in an A375 xenograft model. Similar experiments are performed to assess the efficacy of MAP4K1-edited T cells and NR4A3-edited T cells in the A375 xenograft model.

Example 12

Validation of Single-Edited Adoptively Transferred CD19 CAR-T Cells in a Raji Xenograft Model The anti-tumor efficacy of editing MAP4K1 and NR4A3 in 1ˢᵗ generation CD19 CAR-T cells was evaluated in mice using the Raji subcutaneous cell derived xenograft tumor model. Raji cells are a human lymphoma cell line that are known to be insensitive to treatment with anti-PD1 antibodies.

Figure 13B:
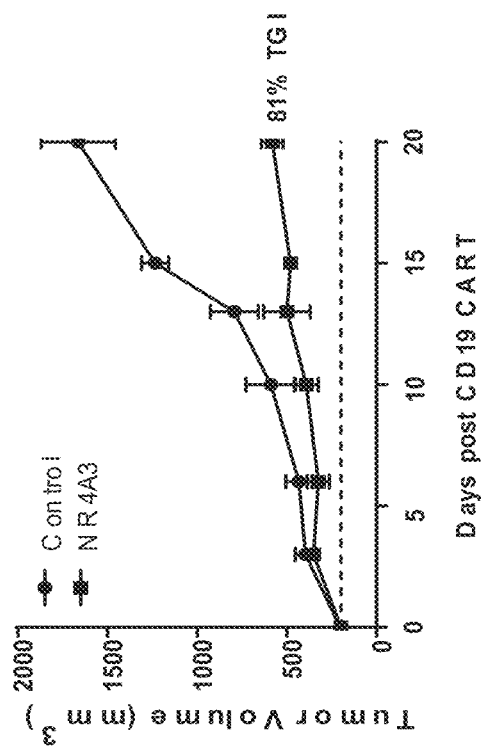
FIG. 13A-FIG. 13B shows tumor growth after treatment with single-edited CD19 CAR T cells in a subcutaneous model of Burkitt's lymphoma using Raji cells.
Figure 13A:
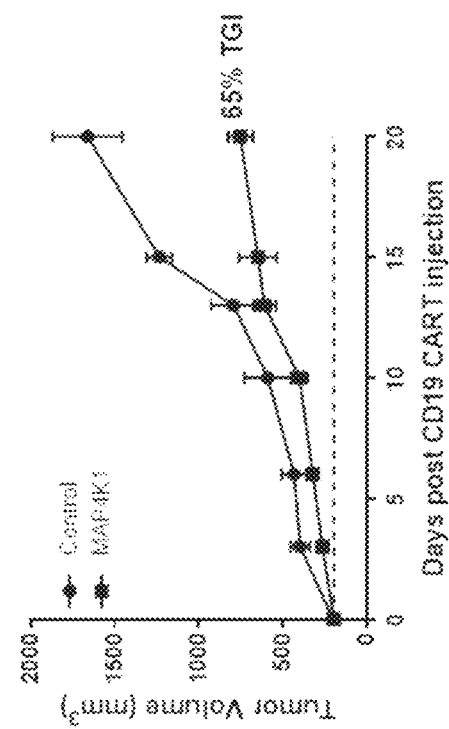

Briefly, 6-8 week old female NSG mice from Jackson labs were injected subcutaneously with 3×10⁶ Raji tumor cells. When tumors reached a volume of approximately 200 mm³ mice were randomized into groups of 5 and injected intravenously with edited human CD19 CART cells via tail vein. Prior to injection the adoptively transferred cells were edited with either a control guide or a guide editing for MAP4K1 or NR4A3. Using the NGS method, the editing efficiency of the gRNA/Cas9 complex targeting the MAP4K1 gene and NR4A3 were determined to be 83% and 71%, respectively. Body weight and tumor volume was measured at least twice per week. Tumor volume was calculated as mean and standard error of the mean for each treatment group. The results demonstrate that editing of MAP4K1 and NR4A3 in an adoptive T cell transfer model leads to increased efficacy, with a 65% TGI for MAP4K1 (FIG. 13A) and 81% TGI for NR4A3 (FIG. 13B). Similar experiments will be performed to assess the anti-tumor efficacy of ZC3H12A-edited 1$^{st}$ generation CD19 CAR-T cells (human) in the Raji cell-derived xenograft subcutaneous tumor model.

Example 13

Screen for Dual-Edit Combinations

A double sgRNA library was constructed in a retroviral backbone. The library consisted of two U6 promoters (one human and one mouse), each driving expression of a single guide RNA (guide+tracr, sgRNA). The guides were cloned as pools to provide random pairings between guides, such that every sgRNA would be paired with every other sgRNA. The final double guide library was transfected into Phoenix-Eco 293T cells to generate murine ecotropic retrovirus. TCR transgenic OT1 cells expressing Cas9 were infected with the sgRNA-expressing virus to edit the two loci targeted by each of the sgRNAs. The edited transgenic T-cells were then transferred into mice bearing>400 mm³ B16-Ova tumors allografts. After two weeks, the tumors were excised and the tumor-infiltrating T-cells were purified by digesting the tumors and enriching for CD45+ cells present in the tumors. Genomic DNA was extracted from CD45+ cells using a Qiagen QUIAamp DNA blood kit and the retroviral inserts were recovered by PCR using primers corresponding to the retroviral backbone sequences. The resulting PCR product were then sequenced to identify the sgRNAs present in the tumors two weeks after transfer. The representation of guide pairs in the final isolated cell populations was compared to the initial plasmid population and the population of infected transgenic T-cells before injection into the mouse. The frequency of sgRNA pairs that improved T-cells fitness and/or tumor infiltration were expected to increase over time, while combinations that impaired fitness were expected to decrease over time. Table 15 below shows the median fold change of sgRNA frequency in the final cell population compared to the sgRNA frequency in the initial cell population transferred in vivo.

TABLE 15 sgRNA frequency in Combination Screen

| GeneA | GeneB | Avg(Tmedian.Ifoldch.all) |
|---|---|---|
| CBLB | CBLB | 0.17 |
| CBLB | CTLA4 | 0.21 |
| CBLB | LAG3 | 0.08 |
| CBLB | Olfr1389 | 0.03 |
| CBLB | Olfr453 | 0.04 |
| CBLB | TGFBR1 | 0.15 |
| CBLB | TGFBR2 | 0.75 |
| CBLB | TIGIT | 0.31 |
| CBLB | ZAP70 | 0 |
| Havcr2 | Havcr2 | 0.02 |
| Havcr2 | LAG3 | 0.01 |
| Havcr2 | Olfr1389 | 0 |
| Havcr2 | Olfr453 | 0.01 |
| Havcr2 | PDCD1 | 0.02 |
| LAG3 | Olfr1389 | 0 |
| LAG3 | Olfr453 | 0.02 |
| LAG3 | PDCD1 | 0.02 |
| Olfr1389 | Olfr1389 | 0.01 |
| Olfr1389 | Olfr453 | 0 |
| Olfr1389 | PDCD1 | 0.02 |
| Olfr453 | Olfr453 | 0.01 |
| Olfr453 | PDCD1 | 0.01 |
| PDCD1 | CTLA4 | 0.59 |
| PDCD1 | LAG3 | 0.02 |
| PDCD1 | PDCD1 | 0.02 |
| PDCD1 | TGFBR1 | 0.02 |
| PDCD1 | TGFBR2 | 0.07 |
| PDCD1 | TIGIT | 0.02 |
| PDCD1 | ZAP70 | 0 |
| TGFBR1 | CTLA4 | 0.01 |
| TGFBR1 | LAG3 | 0 |
| TGFBR1 | TGFBR1 | 0.06 |
| TGFBR1 | TGFBR2 | 0.07 |
| TGFBR1 | TIGIT | 0.03 |
| TGFBR1 | ZAP70 | 0 |
| CBLB | ZC3H12A | 8.9 |
| Havcr2 | ZC3H12A | 2.1 |
| Olfr1389 | ZC3H12A | 0.78 |
| Olfr453 | ZC3H12A | 1.58 |
| PDCD1 | ZC3H12A | 1.33 |
| TGFBR1 | ZC3H12A | 3.33 |
| Tigit | ZC3H12A | 2.53 |
| ZAP70 | ZC3H12A | 0.01 |
| ZC3H12A | CTLA4 | 0.61 |
| ZC3H12A | LAG3 | 0.73 |
| ZC3H12A | ZAP70 | 0.01 |
| ZC3H12A | ZC3H12A | 1.14 |

Example 14

Validation of Dual-Edited CD19 CAR-T Cells in Raji Xenograft Model

Figure 14:
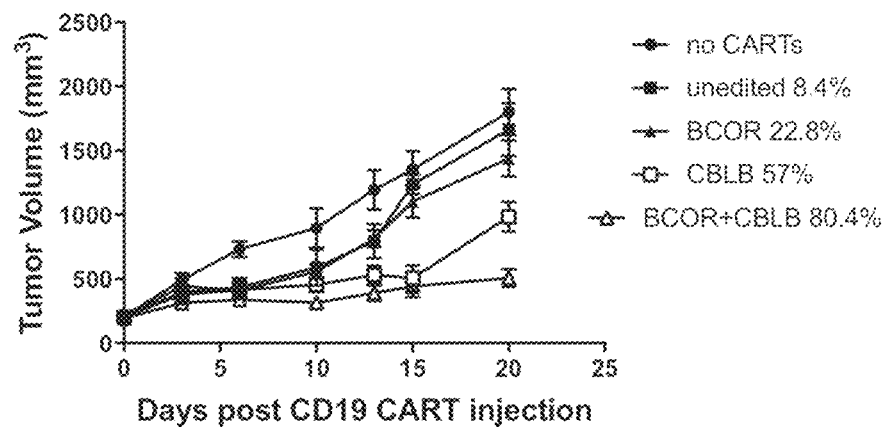
FIG. 14 shows tumor growth over time in mice treated with BCOR-edited, CBLB-edited, or BCOR/CBLB dual-edited anti-CD19 CAR T cells. Tumor growth is compared to mice treated with no CAR T cells or unedited anti-CD19 CAR T cells.

Targets were further evaluated in combination studies to determine combinations of edited genes that increased anti-tumor efficacy of T cells in xenograft tumor models. Evaluation of exemplary targets is described herein, however these methods can be used to evaluate any of the potential targets described above As an example of a combination effect for anti-tumor efficacy of editing, CBLB and BCOR were edited, either independently or together, in 1$^{st}$ generation CD19 CAR-T cells and evaluated in mice using the Raji subcutaneous cell derived xenograft tumor model. Raji cells are a lymphoma cell line that are known to be insensitive to treatment with anti-PD1 antibodies. 6-8 week old female NSG mice from Jackson labs were injected subcutaneously with 3×10⁶ Raji tumor cells. When tumors reached a volume of approximately 200 mm³ mice were randomized into groups of 5 and injected intravenously with edited human CD19 CART cells via tail vein. Prior to injection, the adoptively transferred cells were edited by electroporation with gRNA/Cas9 RNP complexes comprising (i) a control gRNA; (ii) single gRNA targeting CBLB; (iii) a single gRNA targeting BCOR; or (iv) 2 gRNAs targeting CBLB and BCOR. Body weight and tumor volume were measured at least twice per week. Tumor volume was calculated as mean and standard error of the mean for each treatment group. As shown in FIG. 14, when compared to a control guide, adoptive transfer of BCOR/CBLB dual-edited human CD19 CART cells, with target genes edited either alone or together as indicated, resulted in an anti-tumor response in the subcutaneous Burkitt's Lymphoma Raji mouse model. The anti-tumor efficacy was greater when both targets were edited in combination as compared to either target alone or as compared to a control guide. Similar experiments are performed to assess the efficacy of ZC3H12A/CBLB dual-edited T cells, MAP4K1/CBLB dual-edited T cells, and NR4A3/CBLB dual-edited T cells in the CD19 CAR-T Raji cell xenograft model.

Example 15

Figure 15:
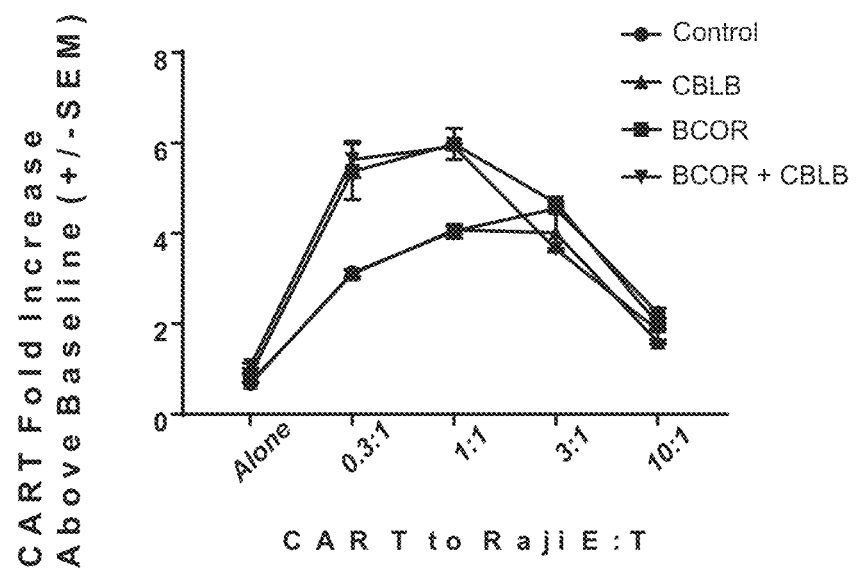
FIG. 15 shows accumulation of BCOR-edited or BCOR/CBLB-edited CD19 CAR T cells in an in vitro culture system.
Figures 16, 17:
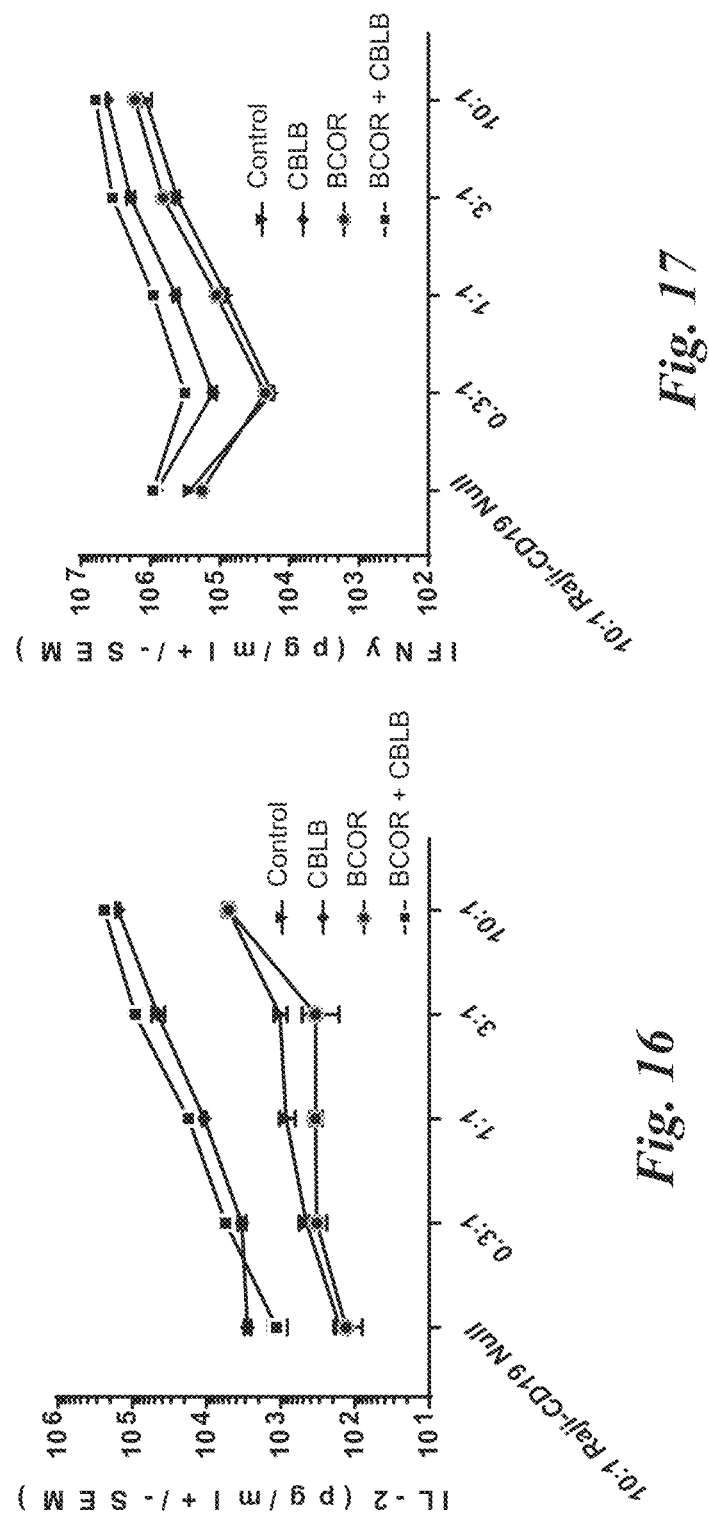
FIG. 16 shows IL-2 production by BCOR-edited or BCOR/CBLB-edited CD19 CAR T cells in an in vitro culture system.
FIG. 17 shows IFNγ production by BCOR-edited or BCOR/CBLB-edited CD19 CAR T cells in an in vitro culture system.

Double-Editing of BCPR and CBLB in CAR-Ts Leads to Enhanced Accumulation and Cytokine Production in the Presence of Tumor $1^{st}$ generation CD19 CAR-Ts were generated from human CD8 T cells, and a negative control gene, BCOR, CBLB, or both BCOR and CBLB were edited by electroporation using guide RNAs complexed to Cas9 in an RNP format. CD19 CAR-Ts were co-cultured with Raji Burkitt's Lymphoma cells in vitro at a 1:0, 0.3:1, 1:1, 3:1 and 10:1 ratio. After 24 hours, total cell counts of CAR-T cells were determined, and supernatants saved for cytokine analyses. As shown in FIG. 15, BCOR and BCOR+CBLB-edited CARTs demonstrated 30% greater accumulation compared to either control or CBLB-edited CARTs, demonstrating that editing of the BCOR confers an enhanced ability of the CAR-T cells to accumulate in the presence of a tumor. Further, CBLB and CBLB+BCOR-edited CARTs produced 10-fold or more IL-2 (FIG. 16) and IFNγ (FIG. 17) compared to either control-edited CARTs, demonstrating that editing of CBLB resulted in enhanced CAR-T cell production of cytokines known to increase overall T cell fitness and functional ability. The increased production of IL-2 by CD8 T cells is surprising as these cells typically do not produce IL-2. These data demonstrate that, in some instances, production of CAR-T cells with enhanced effector functions requires editing of multiple genes. For example, in this example, the production of CAR-T cells that demonstrated both enhanced accumulation in the presence of a tumor and enhanced production of IL-2 and IFNγ cytokines required editing of both BCOR and CBLB genes.

Example 16

Validation of Dual-Edited, Adoptively Transferred T Cells in a Murine OT1/B16-Ova Syngeneic Tumor Model Targets were further evaluated in combination studies to determine combinations of edited genes that increased anti-tumor efficacy of T cells in a murine OT1/B16-Ova subcutaneous syngeneic tumor model. Evaluation of exemplary targets is described herein, however these methods can be used to evaluate any of the potential targets described above.

Anti-tumor efficacy of Zc3h12a/Cblb dual-edited T cells was evaluated in mice using the B16Ova subcutaneous syngeneic tumor model. Briefly, 6-8 week old female C57BL/6J mice from Jackson labs were injected subcutaneously with $0.5 \times 10^6$ B16Ova tumor cells. When tumors in the entire cohort of mice reached an average volume of approximately 378.3 mm$^3$, the mice were randomized into groups and injected intravenously with edited murine OT1 CD8+ T cells via tail vein. Prior to injection, these cells were edited by electroporation with gRNA/Cas9 RNP complexes comprising (i) a control gRNA; (ii) a single gRNA targeting the Cblb gene; (iii) a single gRNA targeting the Zc3h12a gene; or (iv) 2 gRNAs targeting the Cblb and Zc3h12a genes. Editing efficiency of the gRNA/Cas9 complex targeting the Cblb and Zc3h12a genes was determined to be 82% and 80% respectively, assessed using the NGS method. Body weight and tumor volume were measured at least twice per week. Tumor volume was calculated as mean and standard error of the mean for each treatment group. The percentage tumor growth inhibition (TGI) was calculated using the mean tumor volume according to the following formula:

% TGI=(TV-Target$_{final}$-TV-Target$_{Initial}$)/(TV-Control$_{final}$-TV-Control$_{Initial}$)*100, where TV=mean tumor volume, final=Day 7 post-T cell transfer, and initial=Day 0 (i.e., day of T cell transfer).

Figure 18:
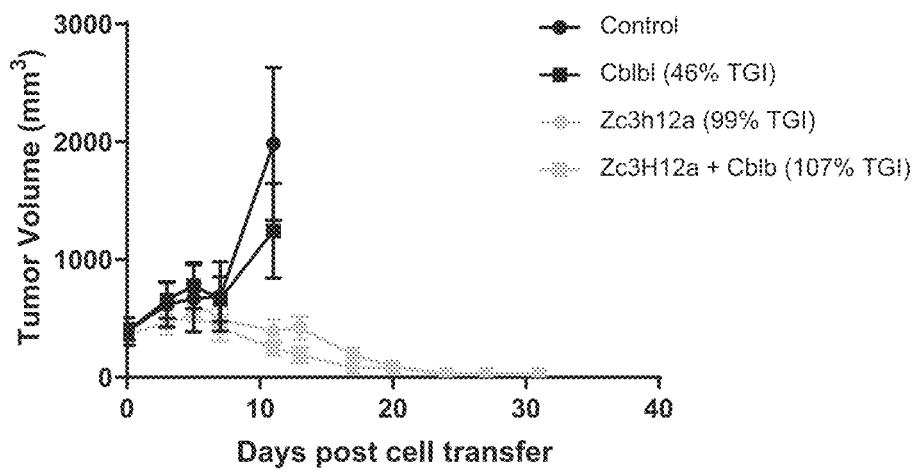
FIG. 18 shows tumor growth over time in a murine B16/Ova syngeneic tumor model in mice treated with dual-edited Zc3h12a/Cblb OT1 T cells.

As shown in FIG. 18, transfer of Zc3h12a/Cblb dual-edited T cells resulted in an enhanced TGI compared to transfer of Cblb single-edited T cells or Zc3h12a single-edited T cells or Cblb single-edited T cells (Zc3h12a/Cblb TGI=107% compared to 46% and 99% for Cblb and Zc3h12a single edits, respectively).

Similar experiments are performed to assess the efficacy of Map4k1/Cblb dual-edited T cells and Nr4a3/Cblb dual-edited T cells in the OT1/B16 Ova syngeneic tumor model.

Example 17

Validation of Dual-Edited, Adoptively Transferred T Cells in a Murine PMEL/MC38-gp100 Tumor Model Anti-tumor efficacy of Zc3h12a/Cblb dual-edited T cells, Map4k1/Cblb dual-edited T cells, and Nr4a3/Cblb dual-edited T cells is evaluated in mice using the MC38gp100 subcutaneous syngeneic tumor model. Briefly, 6-8 week old female C57BL/6J mice from Jackson labs are injected subcutaneously with $1 \times 10^6$ MC38gp100 tumor cells. When tumors reach a volume of approximately 100 mm$^3$, mice are randomized into groups of 10 and injected intravenously with edited murine PMEL CD8+ T cells via tail vein. Prior to injection, T cells are edited by electroporation with gRNA/Cas9 RNP complexes comprising (i) a control gRNA; (ii) a single gRNA targeting the PD1 gene; (iii) a single gRNA targeting the Zc3h12a gene; (iv) a single gRNA targeting the Cblb gene; (v) a single gRNA targeting the Map4k1 gene; (vi) a single gRNA targeting the Nr4a3 gene; (vii) 2 gRNAs targeting both the Zc3h12a and Cblb genes; (viii) 2 gRNAs targeting both the Nr4a3 and Cblb genes; or (ix) 2 gRNAs targeting both the Map4k1 and Cblb genes. Body weight and tumor volume are measured at least twice per week. Tumor volume is calculated as mean and standard error of the mean for each treatment group. The percentage TGI is calculated using the mean tumor volume according to the following formula:

$(TV\text{-}Target_{final} - TV\text{-}Target_{initial}) / (TV\text{-}Control_{final} - TV\text{-}Control_{initial})$, where TV=mean tumor volume, final=Day 21 post-T cell transfer, and initial=Day 0 (i.e., day of T cell transfer)

These experiments are expected to show enhanced TGI after transfer of Zc3h12a/Cblb, Map4k1/Cblb, or Nr4a3/Cblb dual-edited T cells compared to transfer of PD1 single-edited T cells, Zc3h12a single-edited T cells, Map4k1 single-edited T cells, or Nr4a3 single-edited T cells.

Example 18

Validation of Dual-Edited, Adoptively Transferred T Cells in a Murine B16-F10 Syngeneic Tumor Model Anti-tumor efficacy of Zc3h12a/Cblb dual-edited T cells is evaluated in mice using the aggressive metastatic B16-F10 syngeneic tumor model with disease manifesting as lung metastasis. Briefly, 6-8 week old female C57BL/6J mice from Jackson labs are injected intravenously with $0.5 \times 10^6$ B16-F10 tumor cells. Mice are weighed and assigned to treatment groups using a randomization procedure prior to inoculation. At Day 3 post tumor inoculation, mice are injected intravenously with edited murine PMEL CD8+ T cells via tail vein. Prior to injection these cells are edited by electroporation with gRNA/Cas9 RNP complexes comprising (i) a control gRNA; (ii) a single gRNA targeting the Zc3h12a gene; (iii) a single gRNA targeting the Cblb gene; (iv) a single gRNA targeting the Map4k1 gene; (v) a single gRNA targeting the Nr4a3 gene; (vi) 2 gRNAs targeting each of the Map4k1 and Cblb genes; (vii) 2 gRNAs targeting each of the Nr4a3 and Cblb genes or; (viii) 2 gRNAs targeting each of the Zc3h12a and Cblb genes. Editing efficiency of the gRNA/Cas9 complex targeting the aforementioned genes is assessed using the NGS method. Body weight will be monitored at least twice per week. At Day 15 post tumor inoculation (Day 12 post edited PMEL transfer), mice lungs are perfused and fixed with 10% para-formaldehyde. After overnight fixation, lungs are transferred to 70% EtOH for further preservation. Tumor efficacy is evaluated by visually assessing the B16-F10 tumor burden which will be seen as black colonies of cancer cells on the lungs.

These experiments are expected to show increased anti-tumor efficacy of dual-edited cells compared to controls and single-edited cells.

Example 19

Efficacy of PD1/Lag3 Dual-Edited Transgenic T Cells in a B16-Ova Murine Tumor Model Anti-tumor efficacy of PD-1/Lag3 dual-edited T cells was evaluated in mice using the B16Ova subcutaneous syngeneic tumor model. 6-8 week old female C57BL/6J mice from Jackson labs were injected subcutaneously with $0.5 \times 10^6$ B16Ova tumor cells. When tumors in the entire cohort of mice reached an average volume of approximately 485 mm³, the mice were randomized into groups of 10 and injected intravenously with edited mouse OT1 CD8+ T cells via tail vein. Prior to injection these cells were edited by electroporation with gRNA/Cas9 RNP complexes comprising (1) a non-targeting control gRNA; (2) a single gRNA targeting the PD1 gene; (3) a single gRNA targeting the Lag3 gene; (4) 2 gRNAs, one targeting each of the PD1 and Lag3 genes. Body weight and tumor volume were measured at least twice per week. Tumor volume was calculated as mean and standard error of the mean for each treatment group. The percentage tumor growth inhibition (TGI) was calculated using the following formula:

% TGI=(PD1/Lag3 $TV_{final}$–PD1/Lag3 $TV_{initial}$)/ (Control $TV_{final}$–Control $TV_{initial}$), where TV=mean tumor volume, final=Day 10 and initial=day of edited mouse OT1 CD8+ T cell transfer.

Figure 19:
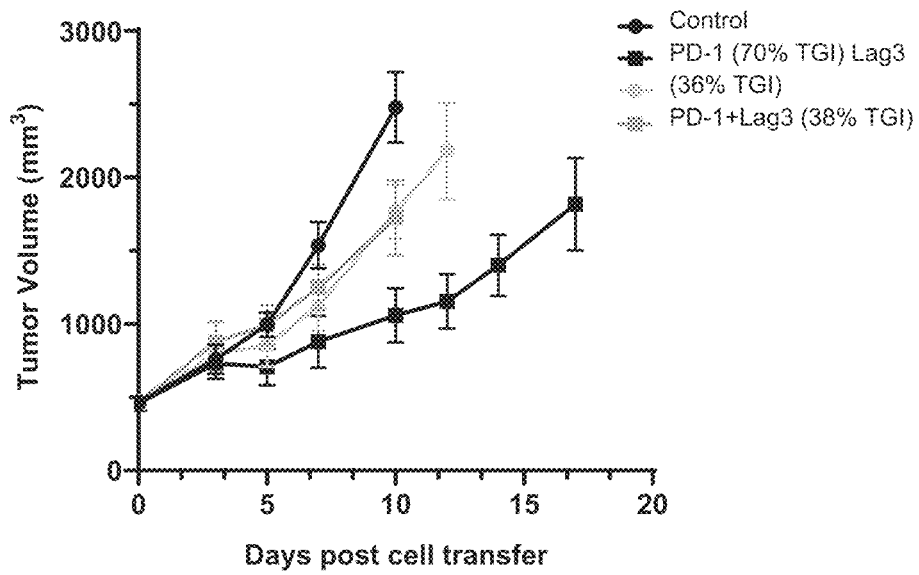
FIG. 19 shows tumor growth over time in a murine B16/Ova syngeneic tumor model in mice treated with Pd1/Lag3 dual-edited OT1 T cells.

The data in FIG. 19 show adoptive transfer of PD1 single-edited T cells resulted in a TGI of 70% and adoptive transfer of Lag3 single-edited T cells resulted in a TGI of 36%. Surprisingly, combination edits of PD1 and Lag3 did not result in enhanced tumor growth inhibition and demonstrated a TGI of 38%.

Example 20

Validation of Targets for Adoptive T Cell Transfer of Tumor Infiltrating Lymphocytes Anti-tumor efficacy of Zc3h12, Map4k1, and Nr4a3/Cblb single and dual-edited tumor infiltrating lymphocytes (TILs) are evaluated in mice using the B16Ova subcutaneous syngeneic tumor model. Two mice cohorts are used in this experiment: a donor cohort of CD45.1 Pep Boy mice (B6.SJL-Ptprc$^a$ Pepc$^b$/BoyJ) and a recipient cohort of CD45.2 C57BL/6J mice (Jackson labs), each comprised of 6-8 week old female mice.

To generate TILs, donor CD45.1 Pep Boy mice (B6.SJL-Ptprc$^a$ Pepc$^b$/BoyJ) are injected subcutaneously with $0.5 \times 10^6$ B16-Ova cells. On Day 14 post-tumor cell inoculation, tumors are harvested to generate edited CD45.1 Tumor Infiltrating Lymphocytes (TILs) to infuse into the second cohort of mice. B16-OVA tumors (200-600 mm³) are harvested, diced, and reduced to a single cell suspension using the GentleMACS system and mouse Tumor Dissociation Kit (Miltenyi Biotech Catalog #130-096-730), according to the manufacturer's recommendations. Tumor suspension are filtered over 70 μm cell strainers and TILs are enriched using CD4/CD8 (TIL) Microbeads (Miltenyi Biotech Catalog #130-116-480). Isolated TILs are cultured in 6 well plates at $1.5 \times 10^6$ cells/mL in complete mTIL media (RPMI+10% heat inactivated FBS, 20 mM HEPES, 100 U/mL Penicillin, 100 μg/mL Streptomycin, 50 μM Beta-Mercaptoethanol, 1× Glutamx) supplemented with 3000 U/mL of recombinant human IL-2 (Peprotech Catalog #200-02). On Day 3 cells are harvested, washed and resuspended in nucleofection buffer T and electroporated with gRNA/Cas9 RNPs using the Neon Transfection System as described in Example 1. After electroporation, TILs are cultured in 6 well plates at $1.5 \times 10^6$ cells/mL in complete mTIL media supplemented with 3000 U/mL of recombinant human IL-2. On Day 5 and 7, cells are resuspended in fresh complete mTIL media supplemented with 3000 U/mL of recombinant human IL-2 and plated in flasks at a density of $1 \times 10^6$ cells/mL. On Day 8, cells are harvested counted and resuspended in PBS for injection in vivo and pellets were prepared for gene expression analysis by qRT-PCR.

These TIL cells are edited by electroporation of gRNA/Cas9 complexes comprising (1) a non-targeting control gRNA; (2) a single gRNA targeting the Zc3h12a gene; (3) a single gRNA targeting the Map4k1 gene; (4) a single gRNA targeting the Nr4a3 gene; (5) a single gRNA targeting Cblb; (6) 2 gRNAs targeting the Zc3h12a gene and Cblb gene; (7) 2 gRNAs targeting the Map4k1 gene and Cblb gene; or (8) 2 gRNAs targeting the Nr4a3 gene and Cblb gene.

Recipient CD45.2 C57BL/6J mice are injected subcutaneously with $0.5 \times 10^6$ B16-Ova tumor cells. When tumors reached a volume of approximately 100 mm³, mice are randomized into groups of 10 and injected intravenously with edited CD45.1 TILs via tail vein. Optionally, mice can be injected intraperitoneal with cyclophosphamide (200 mg/kg) to induce lymphodepletion prior to T cell transfer and the edited-TILs can be administered intravenously in combination with intraperitoneal treatment with recombinant human IL-2 (720,000 IU/Kg) twice daily for up to a maximum of 4 days.

Body weight and tumor volume are measured at least twice per week. Tumor volume is calculated as mean and standard error of the mean for each treatment group and the % TGI is calculated according to the following formula:

$$\% \; TGI = (TV\text{-}target_{final}) - TV\text{-}target_{initial} / (TV\text{-}Control_{final} - TV\text{-}Control_{initial}),$$

where TV=mean tumor volume, final=Day 17 and initial=day of edited TIL transfer.

These results are expected to show that compared to a control guide, adoptive transfer of single-edited or dual-edited mouse TILs results in an enhanced anti-tumor response in the B16Ova subcutaneous mouse model compared to treatment with control-edited cells.

Example 21

Validation of Targets for Engineered T Cell Therapy

Experiments will be performed to validate the effects of editing BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3 on the anti-tumor efficacy of CAR T cells and T cells engineered to express an artificial TCR. The engineered T cells described in Table 17 are edited as described in Example 1 to reduce expression of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3. These edited T cells are then evaluated in subcutaneous murine xenograft models using the indicated cell type. For example, T cells engineered with a CD19-specific CAR or artificial TCR can be evaluated as described above in Example 12 in a Raji cell model or any of the other cell lines shown in Table 16, T cells engineered with a MART1-specific CAR or artificial TCR can be evaluated in a SKMEL5, WM2664, or IGR1 cell model, etc.

TABLE 16

Engineered Receptor Specificity and Target Cell Lines

| Receptor Specificity | Target Cell Line |
|---|---|
| CD19 | Raji, Daudi, Jeko, NALM-6, NALM-16, RAMOS, JeKo1 |
| BCMA | Multiple Myeloma cell lines NCI-H929, U266-B1, and RPMI-8226 |

TABLE 16-continued

Engineered Receptor Specificity and Target Cell Lines

| Receptor Specificity | Target Cell Line |
|---|---|
| NYESO | A375 |
| MART1 | SKMEL5, WM2664, IGR1 |
| HER2+ | BT474 |

Briefly, 6-8 week old female NSG mice from Jackson labs are injected subcutaneously with $3 \times 10^6$ target cells. When tumors reached a volume of approximately 200 mm³, mice are randomized into groups of 5 and injected intravenously with the edited engineered T cells via tail vein. Prior to injection the adoptively transferred cells are edited with either a control guide or a guide editing for BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3. Body weight and tumor volume are measured at least twice per week. Tumor volume is calculated as mean and standard error of the mean for each treatment group. The results of these experiments are expected to show enhanced anti-tumor efficacy of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3-edited engineered T cells or as compared to a control guide, measured by survival and or reduction in tumor size.

Example 22

Validation of Target Editing on Receptor-Engineered T Function

Experiments will be performed to validate the effects of editing BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3 on engineered T cell cytokine production. Briefly, the engineered T cells described in Table 16 above are generated from human CD8 T cells, and one or more of BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3 are edited by electroporation using guide RNAs complexed to Cas9 in an RNP format. CAR-Ts are co-cultured with the corresponding cell line indicated in Table 18 in vitro at a 1:0, 0.3:1, 1:1, 3:1 and 10:1 ratio. After 24 hours, total cell counts of engineered T cells are determined, and supernatants saved for cytokine analyses. The results of these experiments are expected to show enhanced accumulation of and increased levels of cytokine production from edited CAR T cells compared to control edited cells.

Example 23

Manufacturing of Dual-Edited Tumor Infiltrating Lymphocytes

Edited TILs are manufactured following established protocols used previously in FDA-approved clinical trials for the isolation and expansion of TIL's. Following removal of tumor tissue, the tumor is both fragmented into 2 mm³ pieces and mechanically/enzymatically homogenized and cultured in 6,000 IU/mL recombinant human IL-2 for up to 6 weeks or until the cell numbers reach or exceed $1 \times 10^8$; this is defined as the pre-rapid expansion phase (pre-REP) of TIL manufacturing. Upon completion of the pre-REP stage TILs are electroporated with gRNA/Cas9 RNP complexes targeting BCL2L11, FLI1, CALM2, DHODH, UMPS, RBM39, SEMA7A, CHIC2, PCBP1, PBRM1, WDR6, E2F8, SERPINA3, GNAS, ZC3H12A, MAP4K1, and/or NR4A3 genes under cGMP conditions. Cells may be also electroporated prior to or during the pre-REP process. Following electroporation, $50 \times 10^6$ cells are transferred into a 1 L G-Rex™ culture flask with a 1:100 ratio of TIL:irradiated feeder cells for approximately 2 weeks. This portion of manufacturing is defined as the rapid expansion phase (REP). After the REP phase, TIL's are harvested, washed, and suspended in a solution for immediate infusion into the patient.

Example 24

Phase I Studies of Edited Immune Effector Cells

Phase 1, open-label, single-center studies will be performed, in which metastatic melanoma patients who are relapsed or refractory to anti PD-1 therapy will be treated with the modified cells described herein. Patients will receive a single infusion of cells and will remain on study until they experience progressive disease or therapy intolerance. Radiological PD will be determined by a local radiologist before discontinuation of study participation.

Study Objectives: The primary objectives of the study are (1) to determine the maximum tolerated dose (MTD), dose limiting toxicities (DLTs), and dose of cell compositions (and the associated concomitant medications required) recommended for future studies for patients with advanced solid tumors; and (2) to observe patients for any evidence of anti-cancer activity of the transferred edited cells. The secondary objectives of the study are: (1) to determine the pharmacokinetics of the cellular compositions; (2) to assess of on-target activity of the cellular compositions, as determined by changes in pharmacodynamic biomarkers in biologic samples; and (3) to assess of proliferation of the modified cells, as determined by engineered TIL persistence post treatment. The exploratory objectives of the study are (1) to correlate any underlying genetic mutation(s) with clinical response.

Study End-Points: The primary endpoints of this study are: Incidence and severity of adverse events (AEs), graded according the National Cancer Institute Common Terminology Criteria for Adverse Events (NCI CTCAE), version 4.3; Clinical laboratory abnormalities; Changes in 12-lead electrocardiogram (ECG) parameters; Objective response rate (ORR), per RECIST v1.1; CNS response (ORR and progression free survival [PFS], per RECIST v1.1, in patients who have active brain metastases). The secondary endpoints of this study are: Patient-reported symptoms and health-related quality of life (HRQoL) scores; Time to response; Duration of response; Disease control rate (the percentage of patients with best response of complete response [CR], PR, or SD), per RECIST v1.1; Time on treatment; Immunophenotyping; Persistence, trafficking and function of genetically engineered TIL; Pharmacodynamic biomarker in pre and post-dose samples. The exploratory endpoints of this study are: Assessment of cancer-associated mutations and/or genetic alterations utilizing FoundationOne® Cancer Gene Panel, or comparable alternative, in pre-dose tumor biopsy and/or peripheral blood.

Treatment Regimen: A summary of the treatment regimen is as follows:
(a) Day −7 & −6: cyclophosphamide 60 mg/kg, i.v.
(b) Days −5 to −1: fludarabine 25 mg/m², i.v.
(c) Day 1: Cell infusion
(d) Day 1-Day 15: IL-2 (125,000 IU/kg/day) up to a maximum of 14 administrations The first dose of cells administered will not exceed a total dose of $1 \times 10^9$ cells. Should the patient experience dose limiting toxicity (DLT), two additional patients will be treated at this dose level. If the first patient completes the DLT monitoring period (21 days) without experiencing a DLT, subsequent patients will be treated at doses not to exceed $1 \times 10^{11}$ TILs.

Concomitant Treatment: Palliation and supportive care are permitted during the study for management of symptoms and underlying medical conditions that may develop during the study.

Efficacy Evaluation: Tumor response will be determined per RECIST v1.1 by the local radiologist and/or investigator. Tumor assessment will be performed every 6 weeks until disease progression and will continue for patients who have discontinued due to reasons other than disease progression, until disease progression, or to the start of another anticancer therapy. Survival will also be followed for up to 3 years after the last patient enrolled into the study.

Safety Evaluation: Safety assessments will include physical and laboratory examinations, vital signs, and ECGs. Adverse events will be graded according to the NCI CTCAE v4.03. Adverse event incidence rates, as well as the frequency of occurrence of overall toxicity, categorized by toxicity grades (severity), will be described for each cohort of the study. Listings of laboratory test results will also be generated, and descriptive statistics summarizing the changes in laboratory tests over time will be presented.

Molecular Genetic Evaluations: The mutation status of genes implicated in tumor biology will be determined through molecular analysis of tumor tissue and plasma samples. Results of these tests will be provided to the investigator and the sponsor immediately after analysis, per the testing procedure. Molecular analysis methods include, but are not limited to, direct sequencing and/or digital polymerase chain reaction (PCR).

Patient-Reported Symptoms and Quality of Life Evaluations: Patient-reported symptoms and HRQoL will be collected by administering the validated European Organisation for Research and Treatment of Cancer (EORTC) Quality of Life Questionnaire (QLQ)-C30 (v.3.0), which has been studied extensively in global clinical studies. The EORTC QLQ-C30 will be scored for 5 functional scales (physical, role, cognitive, emotional, and social functioning); 3 symptom scales (fatigue, pain, and nausea/vomiting); and a global health status/QoL scale. Six single-item scales also are included (dyspnea, insomnia, appetite loss, constipation, diarrhea, and financial difficulties).

Study Assessments: Assessment parameters for these studies include radiological imaging of the tumor prior to dose administration and on Day 1 of every odd number cycle thereafter, blood sample collection for PK analysis (Day 1, 2, 3, weekly×4, monthly×6) and pharmacodynamics analysis, and cytokine panel analysis (Day 1, 2, 3, weekly×4, monthly×6).

Example 25

Validation of Zc3h12a as Target Conferring Anti-Tumor Memory and Epitope Spreading Anti-tumor memory and epitope spreading driven by Zc3h12a inhibition or deletion in T cells was evaluated in mice using the B16-Ova subcutaneous syngeneic tumor model. 6-8 week old female C57BL/6J mice from Jackson labs were injected subcutaneously with $0.5\times10^6$ B16-Ova tumor cells. When tumors reached a volume of approximately 100 mm$^3$, mice were randomized into groups of 10 and injected intravenously with edited mouse OT1 CD8+ T cells via tail vein. Prior to injection, these cells were edited by electroporation with gRNA/Cas9 RNP complexes comprising (i) a control gRNA; or (ii) a single gRNA targeting the Zc3h12a gene. Body weight and tumor volume were measured at least twice per week. Tumor volume was calculated as mean and standard error of the mean for each treatment group.

Figure 20:
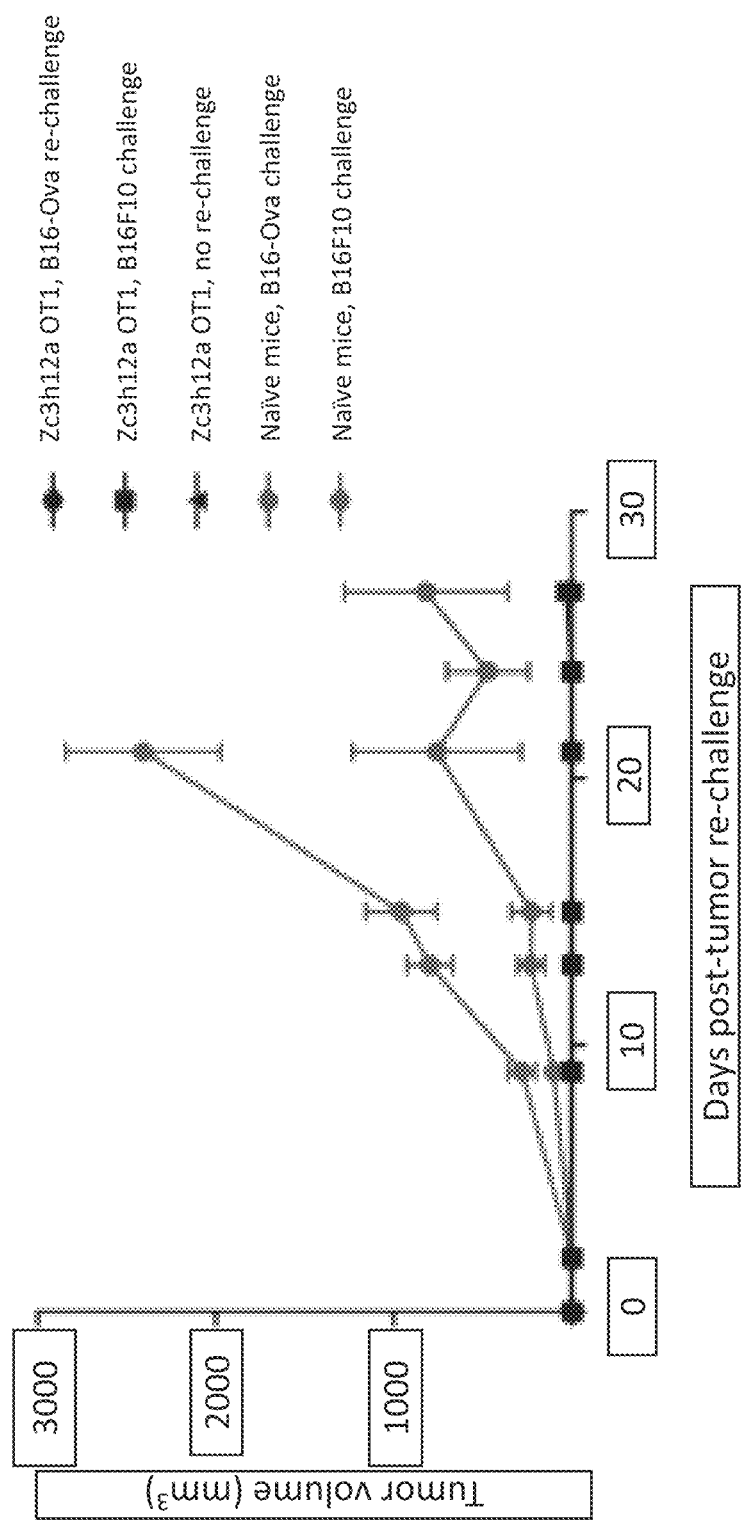
FIG. 20 shows validation of Zc3h12a as target conferring anti-tumor memory and epitope spreading.

As shown in FIG. 20, 9 of the 10 mice receiving Zc3h12a-edited T cells were evaluable and rejected the tumors completely by 55 days after the transfer of OT1 CD8+ T cells (or 65 days after the initial B16-Ova tumor inoculation). These mice were deemed to be Complete Responders (CRs). Four of the CR mice were re-challenged with a second B16-Ova inoculation, with another four CR mice challenged with a B16F10 inoculation. B16-Ova is a derivative of B16F10 engineered to contain the Ova antigen against which OT1 cells are specific for. In addition, ten naïve mice were inoculated with B16-Ova, and another ten naïve mice were inoculated with B16F10 tumor cells. Following these inoculations, B16-Ova CR mice were found to also reject both B16-Ova re-challenge and B16F10 challenge. The B16-Ova rejection demonstrates a Zc3h12a-driven anti-tumor memory response. The B16F10 rejection demonstrates that Zc3h12a-edited T cells instruct other T cells within the host to mount a productive anti-tumor response against non-Ova tumor antigens through a phenomenon known as "epitope spreading." Epitope spreading, which is also known as determinant spreading, is when T cells not involved in the initial immune response are activated against epitopes linked in a tissue-specific manner to the initial response progressively contribute to an immune response.

Example 26

Editing of MAP4K1 in Naive Human T Cells Enhances Cytokine Production

Figure 21:
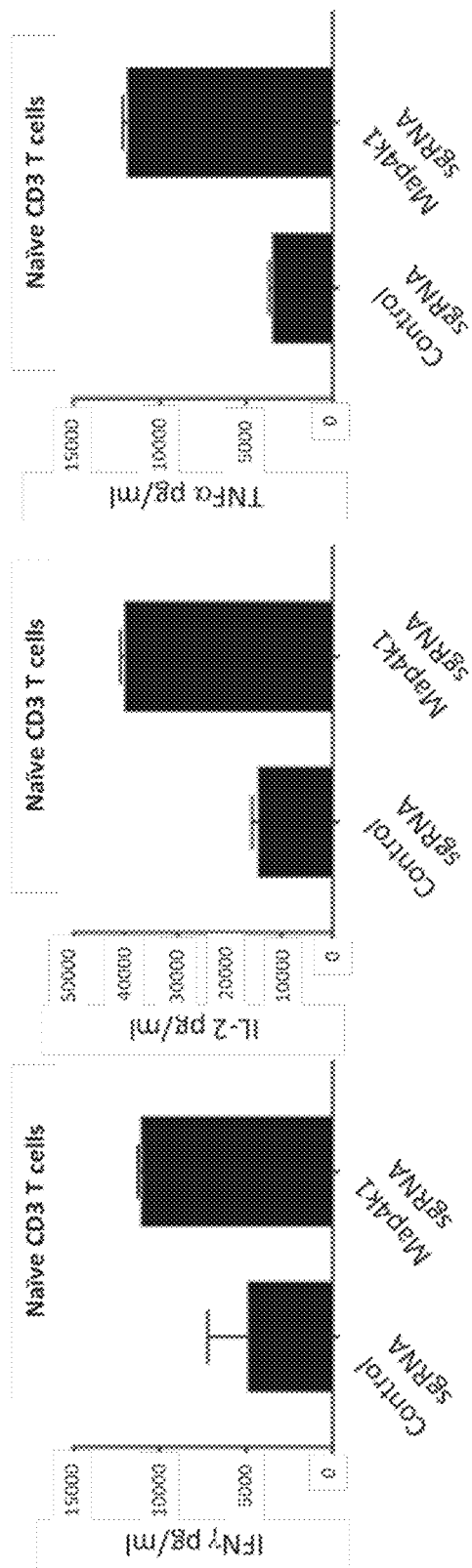
FIG. 21 shows production of IFNγ, IL-2, and TNFα in MAP4K1-edited PBMCs.

Primary human T cells were isolated from thawed donor PBMCs and cultured overnight in Immunocult+10 ng/mL IL-2. The next day, T cells were electroporated with an RNP for a single guide control gene or MAP4K1. After four days in culture (Immunocult+10 ng/mL IL-2) to ensure gene editing, cells were cultured for 24 hr in Immunocult+CD3/28/2 activation. Supernatants were collected 24 hrs after activation and secreted cytokine levels were measured by the mesoscale discovery (MSD) platform. As shown in FIG. 21, MAP4K1-edited T cells demonstrated increased production of IFNγ, IL-2, and TNFα. Similar experiments can be performed to assess cytokine production of ZC3H/2a-edited and NR4A3-edited PBMCs.

Example 27

Expression of T Cell Activation Markers in Zc3h12a-Edited Murine CD8 T Cells

Spleens from female OT1 or pMEL mice were harvested and CD8 T cells were isolated as described in Example 1. CD8 T cells were electroporated with RNPs comprising a Cas9 protein and sgRNAs targeting either Zc3h12a or a control gene were according to methods described in Example 1. Across multiple guides, Zc3h12a-editing efficiency was measured to be 36-69%.

Expression of Ifng, Gzma, and Icos was measured by RNA-seq. RNA extraction and sequencing (RNA-seq) from pellets of 3 million edited cells was performed by Wuxi NextCode. Gene expression levels are quantified as TPMs (Li et al., in Bioinformatics: The Impact of Accurate Quantification on Proteomic and Genetic Analysis and Research (2014)) using Salmon (version 0.11.2, Patro et al., Nat. Methods (2017) and Gencode mouse gene annotation (version M15). R package limma[3] (version 3.38.0, Ritchie et al., Nucleic Acids Res. (2015)) was used to analyze the differentially expressed genes (DEGs). When multiple guides were used to inhibit a target, the analysis incorporated the impact of each guide and only genes affected by all guides were considered significantly differentially expressed.

These experiments revealed that Zc3h12a-edited mouse OT-1 or PMEL cells demonstrated significantly increased expression of Ifng (144.5-fold in OT-1; 119.2-fold in PMEL relative to control sgRNA) and Gzma mRNA (7.2-fold in OT-1 and 3.1 fold in pMEL compared to control sgRNA). In Zc3h12a -edited cells, mRNA expression of Icos, a known ZC3H12A substrate, was also upregulated 11-fold and 9.1 fold in OT-1 and PMEL cells, respectively. Together these data demonstrate that Zc3h12a-edited mouse OT-1 or PMEL cells demonstrate increased expression of the T cell activation markers Ifng, Gzma, and Icos as measured by mRNA expression.

Example 28

ICOS Expression by Zc3h12a siRNA Modified Murine T Cells

Zc3h12a mRNA targeting siRNAs were used to demonstrate the effects of modifying expression of the Zc3h12a by additional mechanisms of inhibition. Control (catalog #: K-005000-G1-02) or Zc3h12a -targeting (catalog #: E-052076-00-0005) Self-delivering Accell siRNAs were prepared according to the manufacturer's instructions. Purified murine CD8 T-cells were activated with anti-CD3/anti-CD28 beads (Dynabeads™ Mouse T-Activator CD3/CD28 for T-Cell Expansion and Activation Cat #11456D) in siRNA delivery media (Dharmacon Catalog #B-005000-500) containing 2.5% heat inactivated FBS supplemented with 10 ng/mL of recombinant murine IL-2 (Biolegend Catalog #575406) and Self-delivering Accell siRNAs at a final concentration of 1 µM. After 72 hours, activation beads were removed and cells were assessed for surface ICOS expression by flow cytometry or gene expression analysis by qRT-PCR.

For qRT-PCR analysis, RNA was purified from T-cells using a Qiagen RNeasy miniprep kit (catalog #: 74104) and cDNA was prepared using SuperScript IV VILO (catalog #: 11755-050, Life Technologies)) according to the manufacturer's instructions. Listed below are the taqman probes (Life Technologies) used for detection of mouse or human transcripts. GAPDH was used as the control gene and relative expression was quantified using the delta-delta Ct method. Treatment of cells with Zc3h12a-specific siRNAs resulted in a 30% reduction in Zc3h12a mRNA levels compared to controls.

| Gene | Mouse Assay ID | Human Assay ID |
| --- | --- | --- |
| GAPDH | Mm99999915_g1 | Hs02786624_g1 |
| IL6 | Mm00446190-m1 | Hs00174131_m1 |
| ICOS | Mm00497600_m1 | N/A |
| GZMA | Mm013044562-m1 | N/A |
| IFNG | Mm01168134_m1 | Hs00989291_m1 |

For ICOS surface expression, murine CD8 cells were stained with fluorescently labeled anti-ICOS antibodies (Biolegend cat #: 313524) at a 1:100 dilution according to the manufacturer's instructions. The relative amount of cell surface ICOS expression was measured by calculating the mean fluorescence intensity of the cells stained with the fluorescent anti-ICOS antibody, using FlowJo v10.1 software (Treestar). Consistent with sgRNA-mediated inhibition of Zc3h12a, ICOS levels were 1.8-fold higher in cells treated with Zc3h12a-targeting siRNA.

Example 29

Expression of T Cell Activation Markers in Murine T Cells Edited with Zc3h12a Zinc Fingers ZFN-mediated editing of the Zc3h12a gene was performed to demonstrate the effects of modifying expression of the Zc3h12a by additional mechanisms of inhibition.

Engineered zinc finger nuclease (ZFN) domains were generated by Sigma Aldrich in plasmid pairs (CSTZFN-1KT COMPOZR® Custom Zinc Finger Nuclease (ZFN) R-3257609). The domains were customized to recognize positions Chr4:125122398-125122394 and Chr4:125121087-125121084 of mouse Zc3h12a gene and positions Chr6:42538446-42538447 of the control mouse gene Olfr455. Plasmids were prepared using the commercial NEB Monarch Miniprep system (Cat #T1010) following manufacturer's protocol. The DNA template was linearized using 10 µg total input and purified using the NEB Monarch PCR and DNA Cleanup kit (Cat #T1030). An in vitro transcription reaction to generate 5'-capped RNA transcripts was performed using 6 µg of purified DNA template and the Promega T7 RiboMAX Large Scale RNA Production System (P1300 and P1712) following the manufacturer's conditions. Transcripts were purified using Qiagen RNeasy Mini purification kit (Cat #74104). The integrity and concentration of each ZFN domain transcript were confirmed using the Agilent 4200 TapeStation system. Purified transcripts were polyadenylated using the NEB E. coli Poly(A) Polymerase (M0276) using 10 units per reaction. The addition of polyadenylated tails were confirmed by a size shift using the Agilent 4200 TapeStation system. Each mature ZFN domain mRNA transcript was combined with its corresponding pair and 10 µg of each pair mixed with 5 million mouse CD8 T cells and electroporated according to the methods described above for murine T cell electroporation.

Two loci in Zc3h12a were targeted by 3 ZFN each and editing efficiency was measured by NGS. To follow the effects of ZFN-mediated ZC3H12A inactivation, mRNA levels of the ZC3H12A substrates Il6 and Icos, as well as the T-cell activation marker Ifng, were assessed by by qRT-PCR. All 3 ZFNs targeting locus Chr4:125121088-125121085 resulted in increased expression of Icos (range 1.2-2-fold), Il6 (range 2.3-62.8-fold) and Ifng (2.9-12.8) mRNA compared to a control ZFN target Olfr455, confirming that ZFN-mediated editing of Zc3h12a induces similar effects on T-cells as CRISPR-mediated inhibition.

Example 30

Expression of T Cell Activation Markers in Zc3h12a-Edited Murine TILs

Mouse CD8 TILs were isolated and edited with Zc3h12a-targeting gRNA/Cas9 RNPs as described in Example 1. Zc3h12a-specific sgRNAs lead to 86% inhibition of Zc3h12a. FACS analysis confirmed that inhibition of Zc3h12a with sgRNA led to a 2.7-fold increase in ICOS expression on the cell surface. RNA-seq analysis confirmed a significant 2.7-fold increase in Icos mRNA ($p=1.6\times10^{-71}$) as well as significant increases in the mRNA of Ifng (9.3-fold relative to control sgRNA, p=0) and Gzma (1.2 fold relative to control sgRNA, $p=6.3\times10^{-6}$), confirming Zc3h12a editing in mouse TILs activates T-cells.

Example 31

Inactivation of Zc3h12a Activity by CRISPR-Mediated Editing of Zc3h12a in Mouse CD8 T Cells The effect of genetic inactivation of Zc3h12a on the function and inflammatory phenotype of mouse CD8 T cells was assessed. Mouse OT-I CD8 T cells were activated and infected with one of 3 different retroviral supernatants using the methods described in Example 30. Retroviruses encoded either 1) an sgRNA targeting an olfactory receptor gene (negative control), 2) an sgRNA targeting Zc3h12a (Zc3h12a-edited condition), or 3) an sgRNA targeting Zc3h12a along with gene encoding the protein product of Zc3h12a (Zc3h12a edited, WT ZC3H12A rescue condition). Post selection transduction rates were greater than 91% in all cases, and next generation sequencing confirmed that genome editing rates were greater than 80% in all cases.

Figure 22:
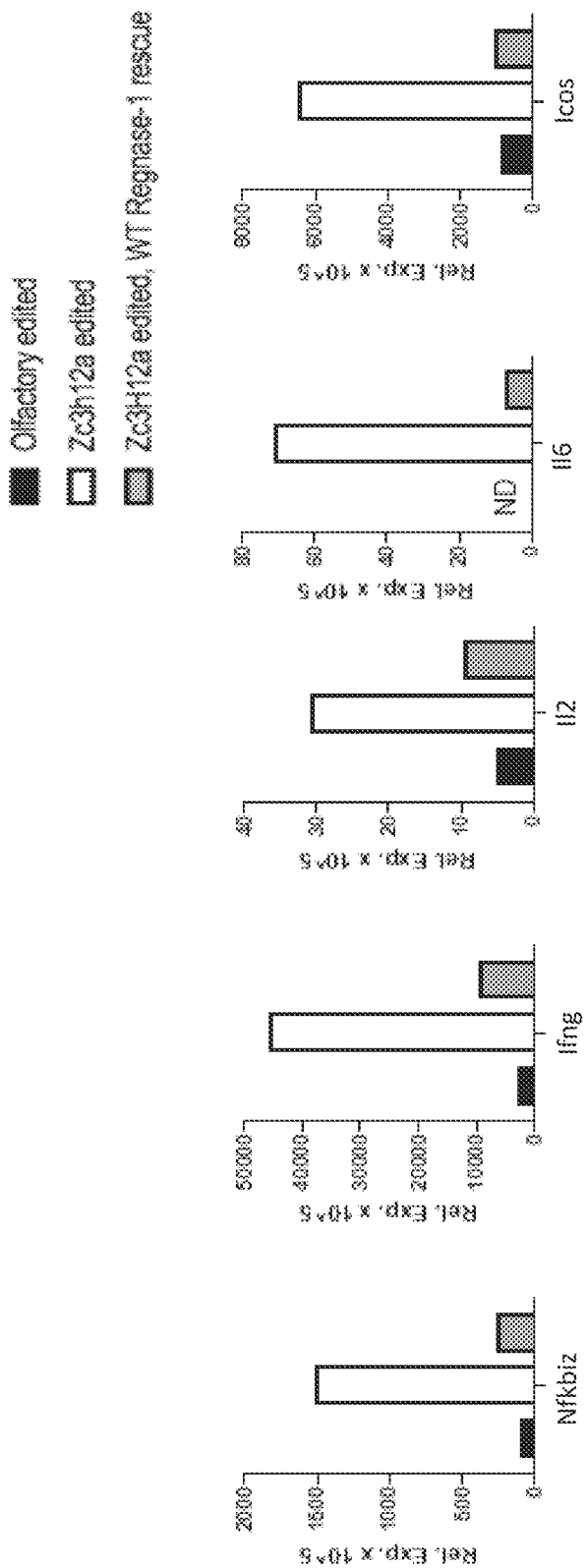
FIG. 22 shows mRNA expression of Icos, Il6, Il2, Ifng, and Nfkbiz in Zc3h12a-edited murine CD8 T cells.

CD8 T cells were then stimulated for 6 hours stimulation with PMA and Ionomycin to induce inflammatory transcript expression, and quantitative RT-PCR was performed to assess mRNA levels. Transcript expression levels were evaluated relative to expression of the housekeeping gene Gapdh. Editing of the Zc3h12a locus led to a dramatic increase in the levels of Icos, Il6, Il2, Ifng, and Nfkbiz transcripts when compared to negative control cells edited at the Olf421 locus (FIG. 22). Expression of ZC3H12A protein by lentiviral co-delivery of a codon optimized Zc3h12a gene into endogenous Zc3h12a edited cells led to a reduction of inflammatory mRNA levels (FIG. 22), demonstrating dependence of the observed phenotype on the absence of functional ZC3H12A protein.

Figure 23:
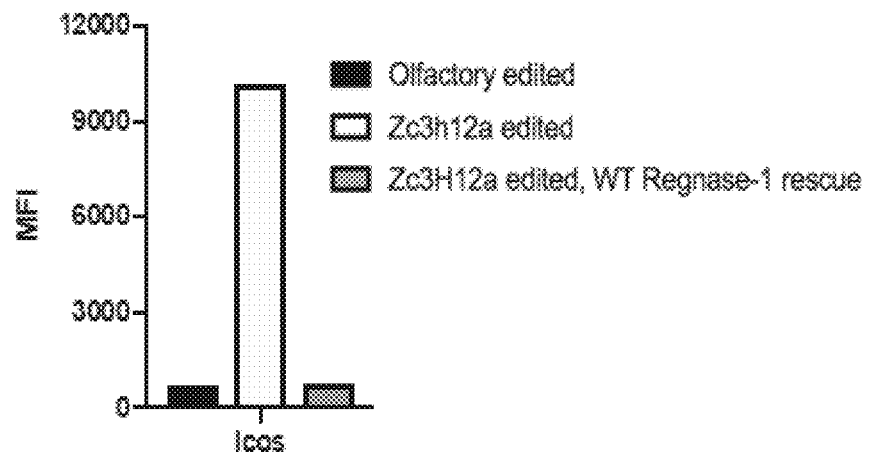
FIG. 23 shows cell surface expression of ICOS in Zc3h12a-edited murine CD8 T cells.

To determine if the ZC3H12A-dependent transcriptional changes observed translated to changes on the cell surface, cells were stained with fluorescent anti-ICOS antibodies and cell surface ICOS levels were determined using flow cytometry. Editing of the Zc3h12a locus led to an increase in cell surface Icos expression that was reversed by overexpression of retrovirally derived ZC3H12A (FIG. 23).

Figure 24:
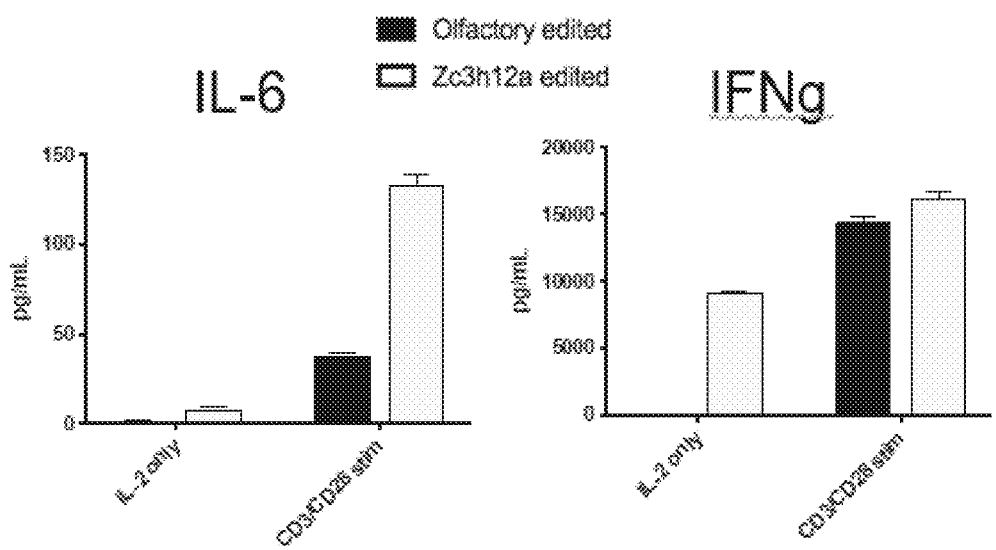
FIG. 24 shows production of IL-2 and IFNγ by Zc3h12a-edited murine CD8 T cells after anti-CD3/CD28 stimulation.

The effects of genetic inactivation of the Zc3h12a gene on cytokine secretion by CD8 T cells were also measured. Cells were seeded into wells containing media containing either IL-2 alone, or IL-2 and anti-CD3/CD28 dynabeads, for 48 hours. Cell supernatants were harvested and the levels of secreted IFNγ and IL-6 were measured using the mesoscale discovery MSD platform. Upon stimulation, Zc3h12a edited CD8 T cells produced greater quantities of IL-6 and IFNγ than Olf421-edited cells. Furthermore, Zc3h12a-edited cells also produced significant quantities of IFNγ in the absence of exogenous anti-CD3/CD28 stimulation compared to Olf421 edited cells (FIG. 24).

Example 32

Inactivation of ZC3H12A by CRISPR-Mediated Editing of the ZC3H12A Gene in Primary Human T Cells To determine the effects of inactivation of ZC3H12A on primary human T cells, the production of IL6 mRNA transcript and IL-6 protein by genome-edited human T cells was evaluated. Briefly, primary human T cells were isolated from peripheral blood mononuclear cells (PBMC) and genome-edited using RNPs targeting either the ZC3H12A or OR1A2 loci, following the methods as outline in Example 1. Editing efficiencies ranged from 30-72%, as determined by next generation sequencing.

Figure 25A:
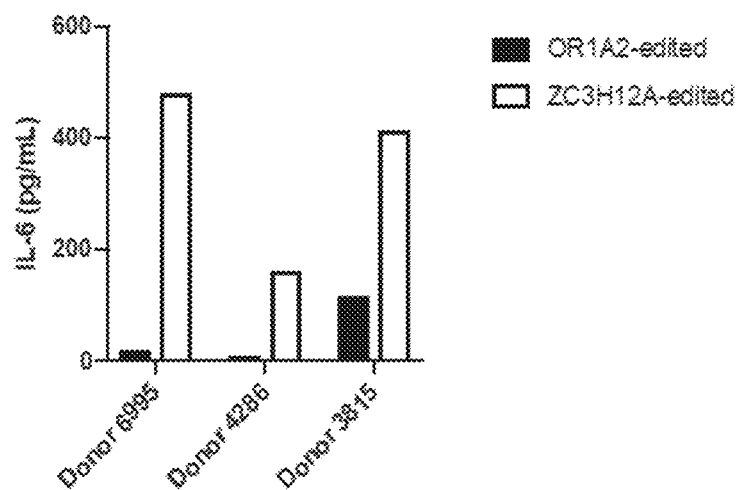
FIG. 25A-FIG. 25B show increased expression of IL6 in ZC3H12A-edited primary human T cells.
Figure 25B:
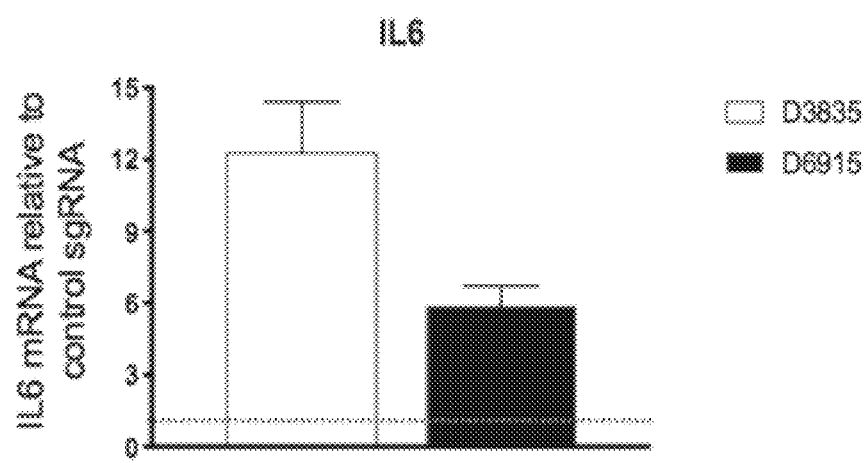

Cells were seeded at equal concentrations and cultured in culture medium containing anti-CD3/CD2/CD28 tetramer reagent (Stemcell Technologies). After 24 hours, cell supernatants was harvested and IL-6 levels were determined using the Mesoscale discovery V-plex human proinflammatory panel 1. Across multiple donors, T cells edited at the ZC3H12A locus secreted more IL-6 into the culture medium than those edited at the OR1A2 locus over the 24 hour period (FIG. 25A). Significantly increased production of IL-6 mRNA (12.3-fold and 5.9-fold in donors 3835 and 6915, respectively) was also observed after 24 hour anti-CD3/CD28 stimulation (FIG. 25B).

Example 33

ZC3H12A-Tiling Screen and Validation Assays

A CRISPR-Cas9 tiling screen was performed to determine candidate inhibitor target locations within a target locus spanning the ZC3H12A gene. Primary human CD8+ T cells were isolated as described in Example 1 and transduced with a lentiviral library expressing sgRNAs designed to target genomic positions across the full length of the ZC3H12A gene. Two days after transduction with the lentiviral library, the transduced CD8+ T cells were electroporated with Cas9 mRNA and cultured for an additional 10 days. After 10 days of culture subsequent to electroporation with Cas9 mRNA, the screen performed as described below. Additional assays were performed to validate gRNAs identified in the tiling screen. 437 distinct ZC3H12A-targeting gRNAs were assayed according to the following parameters.

Tiling Screen

Proliferation Read-out: Cells in the first arm were harvested on Day 10 after Cas9 mRNA electroporation. DNA was extracted and amplicons spanning the recognition sites for the various sgRNAs in the library were amplified by PCR and sequenced by next-generation sequencing (NGS). Enrichment or depletion of each of the sgRNAs was determined by the log ratio of final counts divided by reference counts.

Additional Assays for Guide Validation

Additional assays were developed to further characterize the efficacy and on-target activity of gRNAs identified in the tiling screen described above. Cells were isolated and electroporated with Cas9:gRNA RNPs containing ZC3H12A-specific gRNAs identified in tiling screens. Cells were cultured for approximately 10 days at which point the following assays were performed.

DNA Editing Assay: A DNA editing assay was developed to compare the ability of individual guides to direct editing of their respective target at the DNA level. After electroporation with Cas9:gRNA RNPs, cells were cultured for approximately 10 days, at which point pellets were harvested and DNA was extracted. Amplicons spanning the genomic target loci for the various sgRNAs were amplified by PCR using guide-specific primer sets and sequenced by NGS. Sequencing reads were aligned to the predicted guide cut site, and the percentage of reads displaying an edited DNA sequence was determined. Outcomes were evaluated based on two criteria: 1) the overall percentage of off target editing and 2) the identity of the off-target edited genes. Optimal guides were identified those having the lowest level percent off-target editing and/or most benign off target edited genes profile. For example, gene editing in intragenic regions was viewed as a benign effect while editing in known oncogenes or tumor suppressors was viewed as an undesirable off target profile Western Blot Assay: A Western Blot assay was used to compare the ability of individual guides to reduce protein expression of their respective targets. P After electroporation with Cas9:gRNA RNPs, cells were cultured for approximately 10 days, cell pellets were then harvested, and lysed in RIPA buffer with protease and phosphatase inhibitors. Extracted protein was quantified by Bradford assay, and 1 µg was loaded onto an automated Western Blotting instrument (Wes Separation Module by Protein Simple) using the machine's standard 12-230 kD Wes Separation Module protocol. Commercially available target specific primary antibodies were employed, followed by incubation with HRP-conjugated secondary antibodies. The signal detected per target guide was normalized to the respective signal seen in the negative control guide sample.

Tiling and Validation Results: 200 ZC3H12A-targeting gRNAs (SEQ ID NOs: 1065-1264) were identified as optimal guides based on the assays described above. Similar experiments were performed for BCOR and TNFAIP3, with 57 BCOR gRNAs (SEQ ID NOs: 708-764) and 39 TNFAIP3 gRNAs (SEQ ID NOs: 348-386) identified as potential optimal guides.

TABLE 5A

| | Human Genome Coordinates | | | | |
|---|---|---|---|---|---|
| Target | Coordinates | Target | Coordinates | Target | Coordinates |
| IKZF1 | chr7: 50387344-50387363 | TNFAIP3 | chr6: 137879270-137879289 | HAVCR2 | chr5: 157106863-157106882 |
| IKZF1 | chr7: 50400471-50400490 | TNFAIP3 | chr6: 137878846-137878865 | HAVCR2 | chr5: 157088943-157088962 |
| IKZF1 | chr7: 50327652-50327671 | TNFAIP3 | chr6: 137876140-137876159 | HAVCR2 | chr5: 157106706-157106725 |
| IKZF1 | chr7: 50400507-50400526 | TNFAIP3 | chr6: 137878571-137878590 | HAVCR2 | chr5: 157106886-157106905 |

TABLE 5A-continued

| | Human Genome Coordinates | | | | |
|---|---|---|---|---|---|
| Target | Coordinates | Target | Coordinates | Target | Coordinates |
| IKZF1 | chr7: 50376576-50376595 | TNFAIP3 | chr6: 137878573-137878592 | HAVCR2 | chr5: 157106767-157106786 |
| IKZF1 | chr7: 50400314-50400333 | TNFAIP3 | chr6: 137878653-137878672 | HAVCR2 | chr5: 157106825-157106844 |
| IKZF1 | chr7: 50327681-50327700 | TNFAIP3 | chr6: 137878827-137878846 | HAVCR2 | chr5: 157106718-157106737 |
| IKZF1 | chr7: 50391851-50391870 | TNFAIP3 | chr6: 137878726-137878745 | HAVCR2 | chr5: 157104727-157104746 |
| IKZF1 | chr7: 50368009-50368028 | TNFAIP3 | chr6: 137871457-137871476 | HAVCR2 | chr5: 157087278-157087297 |
| IKZF1 | chr7: 50382569-50382588 | TNFAIP3 | chr6: 137876104-137876123 | LAG3 | chr12: 6774679-6774698 |
| IKZF1 | chr7: 50376631-50376650 | TNFAIP3 | chr6: 137878762-137878781 | LAG3 | chr12: 6773300-6773319 |
| IKZF1 | chr7: 50400366-50400385 | TNFAIP3 | chr6: 137876083-137876102 | LAG3 | chr12: 6773939-6773958 |
| IKZF1 | chr7: 50391772-50391791 | TNFAIP3 | chr6: 137871402-137871421 | LAG3 | chr12: 6775340-6775359 |
| IKZF1 | chr7: 50399915-50399934 | TNFAIP3 | chr6: 137871501-137871520 | LAG3 | chr12: 6773781-6773800 |
| IKZF1 | chr7: 50400414-50400433 | TNFAIP3 | chr6: 137874861-137874880 | LAG3 | chr12: 6773221-6773240 |
| IKZF1 | chr7: 50368040-50368059 | TNFAIP3 | chr6: 137871362-137871381 | LAG3 | chr12: 6773335-6773354 |
| IKZF1 | chr7: 50382550-50382569 | TNFAIP3 | chr6: 137871249-137871268 | LAG3 | chr12: 6774608-6774627 |
| IKZF1 | chr7: 50387353-50387372 | TNFAIP3 | chr6: 137874972-137874991 | LAG3 | chr12: 6775514-6775533 |
| NFKBIA | chr14: 35404635-35404654 | TNFAIP3 | chr6: 137878495-137878514 | LAG3 | chr12: 6773804-6773823 |
| NFKBIA | chr14: 35402653-35402672 | TNFAIP3 | chr6: 137874842-137874861 | LAG3 | chr12: 6773283-6773302 |
| NFKBIA | chr14: 35402494-35402513 | TNFAIP3 | chr6: 137876139-137876158 | LAG3 | chr12: 6774798-6774817 |
| NFKBIA | chr14: 35404445-35404464 | TNFAIP3 | chr6: 137871437-137871456 | TIGIT | chr3: 114307905-114307924 |
| NFKBIA | chr14: 35403152-35403171 | TANK | chr2: 161232836-161232855 | TIGIT | chr3: 114295774-114295793 |
| NFKBIA | chr14: 35403258-35403277 | TANK | chr2: 161179709-161179728 | TIGIT | chr3: 114295717-114295736 |
| NFKBIA | chr14: 35404463-35404482 | TANK | chr2: 161224725-161224744 | TIGIT | chr3: 114295630-114295649 |
| NFKBIA | chr14: 35403202-35403221 | TANK | chr2: 161204665-161204684 | TIGIT | chr3: 114295615-114295634 |
| NFKBIA | chr14: 35404411-35404430 | TANK | chr2: 161161386-161161405 | TIGIT | chr3: 114295821-114295840 |
| NFKBIA | chr14: 35402666-35402685 | TANK | chr2: 161231124-161231143 | TIGIT | chr3: 114295767-114295786 |
| NFKBIA | chr14: 35403330-35403349 | TANK | chr2: 161179740-161179759 | TIGIT | chr3: 114299648-114299667 |
| NFKBIA | chr14: 35403695-35403714 | TANK | chr2: 161232788-161232807 | TIGIT | chr3: 114295577-114295596 |
| BCL3 | chr19: 44757097-44757116 | TANK | chr2: 161232777-161232796 | TIGIT | chr3: 114295650-114295669 |
| BCL3 | chr19: 44757336-44757355 | TANK | chr2: 161223970-161223989 | TIGIT | chr3: 114294023-114294042 |
| BCL3 | chr19: 44756280-44756299 | TANK | chr2: 161203501-161203520 | TIGIT | chr3: 114299682-114299701 |
| BCL3 | chr19: 44748932-44748951 | TANK | chr2: 161203590-161203609 | CTLA4 | chr2: 203872820-203872839 |
| BCL3 | chr19: 44756229-44756248 | TANK | chr2: 161204749-161204768 | CTLA4 | chr2: 203871417-203871436 |
| BCL3 | chr19: 44751352-44751371 | TANK | chr2: 161179691-161179710 | CTLA4 | chr2: 203870885-203870904 |
| BCL3 | chr19: 44756315-44756334 | TANK | chr2: 161161378-161161397 | CTLA4 | chr2: 203867944-203867963 |
| BCL3 | chr19: 44757028-44757047 | FOXP3 | chrX: 49258389-49258408 | CTLA4 | chr2: 203871421-203871440 |
| BCL3 | chr19: 44748876-44748895 | FOXP3 | chrX: 49255792-49255811 | CTLA4 | chr2: 203872759-203872778 |
| BCL3 | chr19: 44758720-44758739 | FOXP3 | chrX: 49253120-49253139 | CTLA4 | chr2: 203867944-203867963 |
| BCL3 | chr19: 44756334-44756353 | FOXP3 | chrX: 49251742-49251761 | CTLA4 | chr2: 203870640-203870659 |
| BCL3 | chr19: 44751300-44751319 | FOXP3 | chrX: 49256916-49256935 | CTLA4 | chr2: 203870767-203870786 |

TABLE 5A-continued

Human Genome Coordinates

| Target | Coordinates | Target | Coordinates | Target | Coordinates |
|---|---|---|---|---|---|
| BCL3 | chr19: 44758258-44758277 | FOXP3 | chrX: 49254054-49254073 | CTLA4 | chr2: 203868001-203868020 |
| IKZF3 | chr17: 39765927-39765946 | FOXP3 | chrX: 49258314-49258333 | CTLA4 | chr2: 203870606-203870625 |
| IKZF3 | chr17: 39766306-39766325 | FOXP3 | chrX: 49251666-49251685 | CTLA4 | chr2: 203872716-203872735 |
| IKZF3 | chr17: 39788315-39788334 | FOXP3 | chrX: 49257496-49257515 | PTPN6 | chr12: 6955147-6955166 |
| IKZF3 | chr17: 39832082-39832101 | FOXP3 | chrX: 49258351-49258370 | PTPN6 | chr12: 6956188-6956207 |
| IKZF3 | chr17: 39766366-39766385 | IKZF2 | chr2: 213057056-213057075 | PTPN6 | chr12: 6952101-6952120 |
| IKZF3 | chr17: 39766410-39766429 | IKZF2 | chr2: 213056895-213056914 | PTPN6 | chr12: 6954832-6954851 |
| IKZF3 | chr17: 39765981-39766000 | IKZF2 | chr2: 213007992-213008011 | PTPN6 | chr12: 6951504-6951523 |
| IKZF3 | chr17: 39766262-39766281 | IKZF2 | chr2: 213022029-213022048 | PTPN6 | chr12: 6951637-6951656 |
| IKZF3 | chr17: 39766122-39766141 | IKZF2 | chr2: 213148620-213148639 | PTPN6 | chr12: 6952004-6952023 |
| IKZF3 | chr17: 39777926-39777945 | IKZF2 | chr2: 213049845-213049864 | PTPN6 | chr12: 6954960-6954979 |
| IKZF3 | chr17: 39777960-39777979 | IKZF2 | chr2: 213049749-213049768 | PTPN6 | chr12: 6945764-6945783 |
| IKZF3 | chr17: 39791548-39791567 | IKZF2 | chr2: 213013838-213013857 | PTPN6 | chr12: 6952156-6952175 |
| IKZF3 | chr17: 39791554-39791573 | IKZF2 | chr2: 213147704-213147723 | PTPN6 | chr12: 6951688-6951707 |
| IKZF3 | chr17: 39788306-39788325 | IKZF2 | chr2: 213007950-213007969 | PTPN6 | chr12: 6952055-6952074 |
| IKZF3 | chr17: 39777690-39777709 | IKZF2 | chr2: 213049803-213049822 | PTPN6 | chr12: 6952004-6952023 |
| SMAD2 | chr18: 47869428-47869447 | IKZF2 | chr2: 213022103-213022122 | PTPN6 | chr12: 6954869-6954888 |
| SMAD2 | chr18: 47896710-47896729 | IKZF2 | chr2: 213013910-213013929 | BCOR | chrX: 40074116-40074135 |
| SMAD2 | chr18: 47869333-47869352 | IKZF2 | chr2: 213056913-213056932 | BCOR | chrX: 40073790-40073809 |
| SMAD2 | chr18: 47869252-47869271 | IKZF2 | chr2: 213147790-213147809 | BCOR | chrX: 40077875-40077894 |
| SMAD2 | chr18: 47869371-47869390 | IKZF2 | chr2: 213049707-213049726 | BCOR | chrX: 40052324-40052343 |
| SMAD2 | chr18: 47870547-47870566 | GATA3 | chr10: 8064032-8064051 | BCOR | chrX: 40073729-40073748 |
| SMAD2 | chr18: 47896523-47896542 | GATA3 | chr10: 8064079-8064098 | BCOR | chrX: 40054273-40054292 |
| SMAD2 | chr18: 47845647-47845666 | GATA3 | chr10: 8073748-8073767 | BCOR | chrX: 40073193-40073212 |
| SMAD2 | chr18: 47896640-47896659 | GATA3 | chr10: 8058824-8058843 | BCOR | chrX: 40074630-40074649 |
| TGFBR1 | chr9: 99128854-99128873 | GATA3 | chr10: 8058443-8058462 | BCOR | chrX: 40062797-40062816 |
| TGFBR1 | chr9: 99137867-99137886 | GATA3 | chr10: 8069573-8069592 | BCOR | chrX: 40072605-40072624 |
| TGFBR1 | chr9: 99128995-99129014 | GATA3 | chr10: 8069532-8069551 | BCOR | chrX: 40073675-40073694 |
| TGFBR1 | chr9: 99132565-99132584 | GATA3 | chr10: 8055748-8055767 | BCOR | chrX: 40073080-40073099 |
| TGFBR1 | chr9: 99137897-99137916 | GATA3 | chr10: 8058395-8058414 | BCOR | chrX: 40074432-40074451 |
| TGFBR1 | chr9: 99137998-99138017 | GATA3 | chr10: 8058737-8058756 | BCOR | chrX: 40074150-40074169 |
| TGFBR1 | chr9: 99137939-99137958 | GATA3 | chr10: 8058349-8058368 | BCOR | chrX: 40073363-40073382 |
| TGFBR1 | chr9: 99132706-99132725 | GATA3 | chr10: 8058824-8058843 | BCOR | chrX: 40064581-40064600 |
| TGFBR1 | chr9: 99128942-99128961 | RC3H1 | chr1: 173946812-173946831 | BCOR | chrX: 40062765-40062784 |
| TGFBR1 | chr9: 99129014-99129033 | RC3H1 | chr1: 173992926-173992945 | BCOR | chrX: 40072562-40072581 |
| TGFBR2 | chr3: 30650327-30650346 | RC3H1 | chr1: 173980872-173980891 | BCOR | chrX: 40072987-40073006 |
| TGFBR2 | chr3: 30650394-30650413 | RC3H1 | chr1: 173982779-173982798 | BCOR | chrX: 40075168-40075187 |
| TGFBR2 | chr3: 30671914-30671933 | RC3H1 | chr1: 173980941-173980960 | BCOR | chrX: 40073376-40073395 |

TABLE 5A-continued

| Target | Coordinates | Target | Coordinates | Target | Coordinates |
|---|---|---|---|---|---|
| TGFBR2 | chr3: 30671753-30671772 | RC3H1 | chr1: 173992844-173992863 | BCOR | chrX: 40073489-40073508 |
| TGFBR2 | chr3: 30672089-30672108 | RC3H1 | chr1: 173992895-173992914 | BCOR | chrX: 40072671-40072690 |
| TGFBR2 | chr3: 30623239-30623258 | RC3H1 | chr1: 173992882-173992901 | BCOR | chrX: 40073707-40073726 |
| TGFBR2 | chr3: 30650357-30650376 | RC3H1 | chr1: 173961717-173961736 | BCOR | chrX: 40072455-40072474 |
| TGFBR2 | chr3: 30672412-30672431 | RC3H1 | chr1: 173984495-173984514 | BCOR | chrX: 40073856-40073875 |
| TGFBR2 | chr3: 30671782-30671801 | RC3H1 | chr1: 173980811-173980830 | BCOR | chrX: 40073454-40073473 |
| TGFBR2 | chr3: 30644886-30644905 | RC3H1 | chr1: 173964926-173964945 | BCOR | chrX: 40073223-40073242 |
| TGFBR2 | chr3: 30671709-30671728 | RC3H1 | chr1: 173982894-173982913 | BCOR | chrX: 40057164-40057183 |
| TGFBR2 | chr3: 30671765-30671784 | TRAF6 | chr11: 36501306-36501325 | BCOR | chrX: 40063694-40063713 |
| TGFBR2 | chr3: 30623229-30623248 | TRAF6 | chr11: 36490635-36490654 | BCOR | chrX: 40073114-40073133 |
| TGFBR2 | chr3: 30671933-30671952 | TRAF6 | chr11: 36498527-36498546 | BCOR | chrX: 40063765-40063784 |
| TGFBR2 | chr3: 30644834-30644853 | TRAF6 | chr11: 36492548-36492567 | BCOR | chrX: 40074230-40074249 |
| TNIP1 | chr5: 151039096-151039115 | TRAF6 | chr11: 36501355-36501374 | BCOR | chrX: 40063788-40063807 |
| TNIP1 | chr5: 151039165-151039184 | TRAF6 | chr11: 36501423-36501442 | BCOR | chrX: 40073550-40073569 |
| TNIP1 | chr5: 151033531-151033550 | TRAF6 | chr11: 36501487-36501506 | BCOR | chrX: 40072510-40072529 |
| TNIP1 | chr5: 151052229-151052248 | TRAF6 | chr11: 36490112-36490131 | BCOR | chrX: 40074371-40074390 |
| TNIP1 | chr5: 151056754-151056773 | TRAF6 | chr11: 36498546-36498565 | BCOR | chrX: 40062953-40062972 |
| TNIP1 | chr5: 151063682-151063701 | TRAF6 | chr11: 36490590-36490609 | BCOR | chrX: 40071047-40071066 |
| TNIP1 | chr5: 151033527-151033546 | TRAF6 | chr11: 36501262-36501281 | BCOR | chrX: 40073673-40073692 |
| TNIP1 | chr5: 151056795-151056814 | TRAF6 | chr11: 36497165-36497184 | BCOR | chrX: 40074756-40074775 |
| TNIP1 | chr5: 151033778-151033797 | CBLB | chr3: 105853475-105853494 | BCOR | chrX: 40074952-40074971 |
| TNIP1 | chr5: 151045881-151045900 | CBLB | chr3: 105853600-105853619 | BCOR | chrX: 40063752-40063771 |
| TNIP1 | chr5: 151063608-151063627 | CBLB | chr3: 105720111-105720130 | BCOR | chrX: 40062753-40062772 |
| TNIP1 | chr5: 151035692-151035711 | CBLB | chr3: 105867412-105867431 | BCOR | chrX: 40073052-40073071 |
| TNIP1 | chr5: 151056834-151056853 | CBLB | chr3: 105867529-105867548 | BCOR | chrX: 40075122-40075141 |
| TNIP1 | chr5: 151064993-151065012 | CBLB | chr3: 105720160-105720179 | BCOR | chrX: 40063806-40063825 |
| TNIP1 | chr5: 151033749-151033768 | CBLB | chr3: 105853421-105853440 | BCOR | chrX: 40074193-40074212 |
| TNFAIP3 | chr6: 137878782-137878801 | CBLB | chr3: 105751453-105751472 | BCOR | chrX: 40074839-40074858 |
| TNFAIP3 | chr6: 137874872-137874891 | CBLB | chr3: 105693541-105693560 | BCOR | chrX: 40074647-40074666 |
| TNFAIP3 | chr6: 137878447-137878466 | CBLB | chr3: 105867449-105867468 | BCOR | chrX: 40070980-40070999 |
| TNFAIP3 | chr6: 137878901-137878920 | CBLB | chr3: 105853514-105853533 | BCOR | chrX: 40074386-40074405 |
| TNFAIP3 | chr6: 137880092-137880111 | PPP2R2D | chr10: 131940160-131940179 | BCOR | chrX: 40072494-40072513 |
| TNFAIP3 | chr6: 137878710-137878729 | PPP2R2D | chr10: 131934499-131934518 | BCOR | chrX: 40074087-40074106 |
| TNFAIP3 | chr6: 137877173-137877192 | PPP2R2D | chr10: 131947775-131947794 | BCOR | chrX: 40057291-40057310 |
| TNFAIP3 | chr6: 137878510-137878529 | PPP2R2D | chr10: 131945305-131945324 | BCOR | chrX: 40073603-40073622 |
| TNFAIP3 | chr6: 137879002-137879021 | PPP2R2D | chr10: 131911562-131911581 | BCOR | chrX: 40074157-40074176 |
| TNFAIP3 | chr6: 137871467-137871486 | PPP2R2D | chr10: 131944056-131944075 | BCOR | chrX: 40075017-40075036 |
| TNFAIP3 | chr6: 137879001-137879020 | PPP2R2D | chr10: 131945382-131945401 | BCOR | chrX: 40074903-40074922 |

TABLE 5A-continued

Human Genome Coordinates

| Target | Coordinates | Target | Coordinates | Target | Coordinates |
|---|---|---|---|---|---|
| TNFAIP3 | chr6: 137875731-137875750 | PPP2R2D | chr10: 131947633-131947652 | BCOR | chrX: 40074949-40074968 |
| TNFAIP3 | chr6: 137875820-137875839 | PPP2R2D | chr10: 131901284-131901303 | BCOR | chrX: 40053888-40053907 |
| TNFAIP3 | chr6: 137880133-137880152 | PPP2R2D | chr10: 131911594-131911613 | BCOR | chrX: 40074785-40074804 |
| TNFAIP3 | chr6: 137878796-137878815 | NRP1 | chr10: 33254103-33254122 | BCOR | chrX: 40077894-40077913 |
| TNFAIP3 | chr6: 137877195-137877214 | NRP1 | chr10: 33263822-33263841 | BCOR | chrX: 40076456-40076475 |
| TNFAIP3 | chr6: 137880103-137880122 | NRP1 | chr10: 33263660-33263679 | BCOR | chrX: 40062904-40062923 |
| TNFAIP3 | chr6: 137875750-137875769 | NRP1 | chr 10: 33256447-33256466 | PDCD1 | chr2: 241852282-241852301 |
| TNFAIP3 | chr6: 137878979-137878998 | NRP1 | chr10: 33263677-33263696 | PDCD1 | chr2: 241852278-241852297 |
| TNFAIP3 | chr6: 137880119-137880138 | NRP1 | chr10: 33263699-33263718 | PDCD1 | chr2: 241852879-241852898 |
| TNFAIP3 | chr6: 137878741-137878760 | NRP1 | chr10: 33256400-33256419 | PDCD1 | chr2: 241852752-241852771 |
| TNFAIP3 | chr6: 137878795-137878814 | NRP1 | chr10: 33254025-33254044 | PDCD1 | chr2: 241852618-241852637 |
| TNFAIP3 | chr6: 137878817-137878836 | NRP1 | chr10: 33330718-33330737 | PDCD1 | chr2: 241852729-241852748 |
| TNFAIP3 | chr6: 137878974-137878993 | NRP1 | chr10: 33254069-33254088 | PDCD1 | chr2: 241852687-241852706 |
| TNFAIP3 | chr6: 137874868-137874887 | NRP1 | chr10: 33256432-33256451 | PDCD1 | chr2: 241852796-241852815 |
| TNFAIP3 | chr6: 17876091-137876110 | HAVCR2 | chr5: 157106936-157106955 | PDCD1 | chr2: 241852933-241852952 |
| TNFAIP3 | chr6: 137877199-137877218 | HAVCR2 | chr5: 157095368-157095387 | PDCD1 | chr2: 241852831-241852850 |
|  |  | HAVCR2 | chr5: 157106898-157106917 | PDCD1 | chr2: 241851189-241851208 |

TABLE 5B

Murine Genome Coordinates

| Target | Coordinates | Target | Coordinates | Target | Coordinates |
|---|---|---|---|---|---|
| Ikzf1 | chr11: 11754053-11754072 | Gata3 | chr2: 9874375-9874394 | Lag3 | chr6: 124908392-124908411 |
| Ikzf1 | chr11: 11707883-11707902 | Gata3 | chr2: 9858592-9858611 | Lag3 | chr6: 124909391-124909410 |
| Ikzf1 | chr11: 11754068-11754087 | Gata3 | chr2: 9877463-9877482 | Lag3 | chr6: 124909410-124909429 |
| Ikzf1 | chr11: 11754134-11754153 | Gata3 | chr2: 9877514-9877533 | Tigit | chr16: 43662107-43662126 |
| Ikzf1 | chr11: 11754153-11754172 | Gata3 | chr2: 9858607-9858626 | Tigit | chr16: 43662060-43662079 |
| Ikzf1 | chr11: 11754103-11754122 | Gata3 | chr2: 9877338-9877357 | Tigit | chr16: 43661976-43661995 |
| Ikzf1 | chr11: 11754015-11754034 | Gata3 | chr2: 9863114-9863133 | Tigit | chr16: 43662254-43662273 |
| Ikzf1 | chr11: 11754119-11754138 | Gata3 | chr2: 9858626-9858645 | Tigit | chr16: 43661994-43662013 |
| Nfkbia | chr12: 55491236-55491255 | Rc3h1 | chr1: 160930251-160930270 | Tigit | chr16: 43662156-43662175 |
| Nfkbia | chr12: 55491172-55491191 | Rc3h1 | chr1: 160930280-160930299 | Tigit | chr16: 43662277-43662296 |
| Nfkbia | chr12: 55491206-55491225 | Rc3h1 | chr1: 160930154-160930173 | Tigit | chr16: 43662012-43662031 |
| Nfkbia | chr12: 55490633-55490652 | Rc3h1 | chr1: 160942614-160942633 | Tigit | chr16: 43664036-43664055 |
| Nfkbia | chr12: 55491112-55491131 | Rc3h1 | chr1: 160930266-160930285 | Tigit | chr16: 43664057-43664076 |
| Nfkbia | chr12: 55490800-55490819 | Rc3h1 | chr1: 160930185-160930204 | Tigit | chr16: 43649030-43649049 |
| Nfkbia | chr12: 55490821-55490840 | Rc3h1 | chr1: 160938126-160938145 | Tigit | chr16: 43662129-43662148 |
| Nfkbia | chr12: 55490526-55490545 | Rc3h1 | chr1: 160930198-160930217 | Tigit | chr16: 43662059-43662078 |

TABLE 5B-continued

| Murine Genome Coordinates | | | | | |
|---|---|---|---|---|---|
| Target | Coordinates | Target | Coordinates | Target | Coordinates |
| Nfkbia | chr12: 55491657-55491676 | Traf6 | chr2: 101688485-101688504 | Tigit | chr16: 43662148-43662167 |
| Nfkbia | chr12: 55491177-55491196 | Traf6 | chr2: 101691455-101691474 | Tigit | chr16: 43664021-43664040 |
| Nfkbia | chr12: 55491675-55491694 | Traf6 | chr2: 101688575-101688594 | Ctla4 | chr1: 60914621-60914640 |
| Nfkbia | chr12: 55490773-55490792 | Traf6 | chr2: 101684742-101684761 | Ctla4 | chr1: 60909166-60909185 |
| Nfkbia | chr12: 55490809-55490828 | Traf6 | chr2: 101688539-101688558 | Ctla4 | chr1: 60914725-60914744 |
| Nfkbia | chr12: 55491735-55491754 | Traf6 | chr2: 101691482-101691501 | Ctla4 | chr1: 60909219-60909238 |
| Nfkbia | chr12: 55490571-55490590 | Traf6 | chr2: 101688558-101688577 | Ctla4 | chr1: 60914673-60914692 |
| Nfkbia | chr12: 55490588-55490607 | Traf6 | chr2: 101684510-101684529 | Ctla4 | chr1: 60912501-60912520 |
| Nfkbia | chr12: 55491715-55491734 | Cblb | chr16: 52152499-52152518 | Ctla4 | chr1: 60912446-60912465 |
| Nfkbia | chr12: 55492316-55492335 | Cblb | chr16: 52139574-52139593 | Ctla4 | chr1: 60912725-60912744 |
| Nfkbia | chr12: 55491207-55491226 | Cblb | chr16: 52139603-52139622 | Ctla4 | chr1: 60912516-60912535 |
| Bcl3 | chr3: 19809245-19809264 | Cblb | chr16: 52112122-52112141 | Ctla4 | chr1: 60912664-60912683 |
| Bcl3 | chr3: 19811059-19811078 | Cblb | chr16: 52112134-52112153 | Ctla4 | chr1: 60912477-60912496 |
| Bcl3 | chr3: 19809632-19809651 | Cblb | chr16: 52152535-52152554 | Ctla4 | chr1: 60912618-60912637 |
| Bcl3 | chr3: 19809634-19809653 | Cblb | chr16: 52142891-52142910 | Ctla4 | chr1: 60912682-60912701 |
| Bcl3 | chr3: 19809551-19809570 | Cblb | chr16: 52135797-52135816 | Ctla4 | chr1: 60912697-60912716 |
| Bcl3 | chr3: 19809516-19809535 | Cblb | chr16: 52131105-52131124 | Ctla4 | chr1: 60912605-60912624 |
| Bcl3 | chr3: 19812411-19812430 | Cblb | chr16: 52112169-52112188 | Ctla4 | chr1: 60912433-60912452 |
| Bcl3 | chr3: 19811610-19811629 | Cblb | chr16: 52204542-52204561 | Ctla4 | chr1: 60909202-60909221 |
| Ikzf3 | chr11: 98516898-98516917 | Cblb | chr16: 52131058-52131077 | Ctla4 | chr1: 60909165-60909184 |
| Ikzf3 | chr11: 98467268-98467287 | Cblb | chr16: 52135876-52135895 | Ctla4 | chr1: 60914619-60914638 |
| Ikzf3 | chr11: 98467464-98467483 | Cblb | chr16: 52135763-52135782 | Ctla4 | chr1: 60909244-60909263 |
| Ikzf3 | chr11: 98467325-98467344 | Cblb | chr16: 52139509-52139528 | Ptpn6 | chr6: 124727399-124727418 |
| Ikzf3 | chr11: 98467181-98467200 | Ppp2r2d | chr7: 138876553-138876572 | Ptpn6 | chr6: 124732470-124732489 |
| Ikzf3 | chr11: 98477038-98477057 | Ppp2r2d | chr7: 138882200-138882219 | Ptpn6 | chr6: 124732484-124732503 |
| Ikzf3 | chr11: 98466977-98466996 | Ppp2r2d | chr7: 138876565-138876584 | Ptpn6 | chr6: 124727385-124727404 |
| Ikzf3 | chr11: 98467103-98467122 | Ppp2r2d | chr7: 138882451-138882470 | Ptpn6 | chr6: 124721816-124721835 |
| Tgfbr1 | chr4: 47396418-47396437 | Ppp2r2d | chr7: 138882404-138882423 | Ptpn6 | chr6: 124725324-124725343 |
| Tgfbr1 | chr4: 47396363-47396382 | Ppp2r2d | chr7: 138869675-138869694 | Ptpn6 | chr6: 124732430-124732449 |
| Tgfbr1 | chr4: 47393272-47393291 | Ppp2r2d | chr7: 138876686-138876705 | Ptpn6 | chr6: 124732454-124732473 |
| Tgfbr1 | chr4: 47393468-47393487 | Ppp2r2d | chr7: 138874130-138874149 | Ptpn6 | chr6: 124732329-124732348 |
| Tgfbr1 | chr4: 47393456-47393475 | Nrp1 | chr8: 128363358-128363377 | Ptpn6 | chr6: 124725334-124725353 |
| Tgfbr1 | chr4: 47396564-47396583 | Nrp1 | chr8: 128363296-128363315 | Ptpn6 | chr6: 124732349-124732368 |
| Tgfbr1 | chr4: 47393315-47393334 | Nrp1 | chr8: 128359628-128359647 | Ptpn6 | chr6: 124732309-124732328 |
| Tgfbr1 | chr4: 47396434-47396453 | Nrp1 | chr8: 128476138-128476157 | Ptpn6 | chr6: 124727402-124727421 |
| Tgfbr1 | chr4: 47393288-47393307 | Nrp1 | chr8: 128363272-128363291 | Ptpn6 | chr6: 124732435-124732454 |
| Tgfbr1 | chr4: 47396512-47396531 | Nrp1 | chr8: 128359612-128359631 | Pdcd1 | chr1: 94041239-94041258 |
| Tgfbr1 | chr4: 47402873-47402892 | Nrp1 | chr8: 128363336-128363355 | Pdcd1 | chr1: 94041292-94041311 |

TABLE 5B-continued

| Murine Genome Coordinates | | | | | |
|---|---|---|---|---|---|
| Target | Coordinates | Target | Coordinates | Target | Coordinates |
| Tgfbr1 | chr4: 47396539-47396558 | Nrp1 | chr8: 128363210-128363229 | Pdcd1 | chr1: 94041357-94041376 |
| Tgfbr1 | chr4: 47393266-47393285 | Nrp1 | chr8: 128425932-128425951 | Pdcd1 | chr1: 94041207-94041226 |
| Tgfbr1 | chr4: 47396394-47396413 | Nrp1 | chr8: 128497936-128497955 | Pdcd1 | chr1: 94041223-94041242 |
| Tgfbr1 | chr4: 47393462-47393481 | Nrp1 | chr8: 128468551-128468570 | Pdcd1 | chr1: 94041394-94041413 |
| Tgfbr2 | chr9: 116129944-116129963 | Nrp1 | chr8: 128363251-128363270 | Pdcd1 | chr1: 94041165-94041184 |
| Tgfbr2 | chr9: 116129900-116129919 | Nrp1 | chr8: 128460693-128460712 | Pdcd1 | chr1: 94041179-94041198 |
| Tgfbr2 | chr9: 116129928-116129947 | Havcr2 | chr11: 46456439-46456458 | Pdcd1 | chr1: 94041468-94041487 |
| Tgfbr2 | chr9: 116131548-116131567 | Havcr2 | chr11: 46469515-46469534 | Pdcd1 | chr1: 94041331-94041350 |
| Tgfbr2 | chr9: 116131562-116131581 | Havcr2 | chr11: 46466864-46466883 | Pdcd1 | chr1: 94041421-94041440 |
| Tgfbr2 | chr9: 116131610-116131629 | Havcr2 | chr11: 46479374-46479393 | Pdcd1 | chr1: 94041165-94041184 |
| Tgfbr2 | chr9: 116131588-116131607 | Havcr2 | chr11: 46456495-46456514 | Pdcd1 | chr1: 94041421-94041440 |
| Tgfbr2 | chr9: 116131529-116131548 | Havcr2 | chr11: 46479356-46479375 | Pdcd1 | chr1: 94041331-94041350 |
| Tgfbr2 | chr9: 116110272-116110291 | Havcr2 | chr11: 46455033-46455052 | Pdcd1 | chr1: 94041468-94041487 |
| Tgfbr2 | chr9: 116109969-116109988 | Havcr2 | chr11: 46469534-46469553 | Pdcd1 | chr1: 94041239-94041258 |
| Tgfbr2 | chr9: 116129901-116129920 | Havcr2 | chr11: 46456242-46456261 | Pdcd1 | chr1: 94041292-94041311 |
| Tgfbr2 | chr9: 116129988-116130007 | Havcr2 | chr11: 46479302-46479321 | Pdcd1 | chr1: 94041357-94041376 |
| Tgfbr2 | chr9: 116110004-116110023 | Havcr2 | chr11: 46456496-46456515 | Pdcd1 | chr1: 94041207-94041226 |
| Tnip1 | chr11: 54939673-54939692 | Havcr2 | chr11: 46456355-46456374 | Pdcd1 | chr1: 94041223-94041242 |
| Tnip1 | chr11: 54930778-54930797 | Havcr2 | chr11: 46469521-46469540 | Pdcd1 | chr1: 94041394-94041413 |
| Tnip1 | chr11: 54934036-54934055 | Havcr2 | chr11: 46459111-46459130 | Pdcd1 | chr1: 94041179-94041198 |
| Tnip1 | chr11: 54934071-54934090 | Havcr2 | chr11: 46456301-46456320 | Pdcd1 | chr1: 94041412-94041431 |
| Tnip1 | chr11: 54930799-54930818 | Lag3 | chr6: 124908571-124908590 | Pdcd1 | chr1: 94041268-94041287 |
| Tnip1 | chr11: 54930820-54930839 | Lag3 | chr6: 124909259-124909278 | Pdcd1 | chr1: 94041309-94041328 |
| Tnip1 | chr11: 54933977-54933996 | Lag3 | chr6: 124909424-124909443 | Pdcd1 | chr1: 94041469-94041488 |
| Tnip1 | chr11: 54929117-54929136 | Lag3 | chr6: 124908491-124908510 | Pdcd1 | chr1: 94041189-94041208 |
| Tnfaip3 | chr10: 19011464-19011483 | Lag3 | chr6: 124909299-124909318 | Pdcd1 | chr1: 94041331-94041350 |
| Tnfaip3 | chr10: 19008246-19008265 | Lag3 | chr6: 124909474-124909493 | Pdcd1 | chr1: 94041239-94041258 |
| Tnfaip3 | chr10: 19008332-19008351 | Lag3 | chr6: 124909286-124909305 | Pdcd1 | chr1: 94041292-94041311 |
| Tnfaip3 | chr10: 19006919-19006938 | Lag3 | chr6: 124908450-124908469 | | |
| Tnfaip3 | chr10: 19008294-19008313 | Lag3 | chr6: 124908529-124908548 | | |
| Tnfaip3 | chr10: 19008234-19008253 | Lag3 | chr6: 124909272-124909291 | | |
| Tnfaip3 | chr10: 19002796-19002815 | Lag3 | chr6: 124909399-124909418 | | |
| Tnfaip3 | chr10: 19006981-19007000 | Lag3 | chr6: 124909228-124909247 | | |

TABLE 6A

| Human Genome Coordinates | | | | | |
|---|---|---|---|---|---|
| Target | Coordinates | Target | Coordinates | Target | Coordinates |
| BCL2L11 | chr2: 111123809-111123828 | PBRM1 | chr3:52554752-52554771 | CALM2 | chr2:47167608-47167627 |
| BCL2L11 | chr2: 111142346-111142365 | PBRM1 | chr3:52603635-52603654 | CALM2 | chr2:47162389-47162408 |
| BCL2L11 | chr2:111150125-111150144 | PBRM1 | chr3:52634703-52634722 | CALM2 | chr2:47162623-47162642 |
| BCL2L11 | chr2:111164161-111164180 | PBRM1 | chr3:52662232-52662251 | CALM2 | chr2:47161766-47161785 |
| BCL2L11 | chr2:111123880-111123899 | PBRM1 | chr3:52609796-52609815 | CALM2 | chr2:47161806-47161825 |
| BCL2L11 | chr2:111142303-111142322 | PBRM1 | chr3:52554720-52554739 | CALM2 | chr2:47162544-47162563 |
| BCL2L11 | chr2:111128637-111128656 | PBRM1 | chr3:52668623-52668642 | CALM2 | chr2:47167482-47167501 |
| BCL2L11 | chr2:111124067-111124086 | PBRM1 | chr3:52679663-52679682 | CALM2 | chr2:47162606-47162625 |
| BCL2L11 | chr2:111150032-111150051 | PBRM1 | chr3:52617272-52617291 | CALM2 | chr2:47162351-47162370 |
| BCL2L11 | chr2:111153772-111153791 | PBRM1 | chr3:52678502-52678521 | CALM2 | chr2:47162279-47162298 |
| BCL2L11 | chr2:111124106-111124125 | PBRM1 | chr3:52558272-52558291 | CALM2 | chr2:47172416-47172435 |
| BCL2L11 | chr2:111123866-111123885 | PBRM1 | chr3:52668512-52668531 | SERPINA3 | chr14:94614673-94614692 |
| BCL2L11 | chr2:111130128-111130147 | PBRM1 | chr3:52643284-52643303 | SERPINA3 | chr14:94619278-94619297 |
| BCL2L11 | chr2:111123761-111123780 | PBRM1 | chr3:52558266-52558285 | SERPINA3 | chr14:94614582-94614601 |
| BCL2L11 | chr2:111150081-111150100 | PBRM1 | chr3:52634800-52634819 | SERPINA3 | chr14:94619423-94619442 |
| BCL2L11 | chr2:111123790-111123809 | PBRM1 | chr3:52603596-52603615 | SERPINA3 | chr14:94614528-94614547 |
| BCL2L11 | chr2:111153779-111153798 | PBRM1 | chr3:52643330-52643349 | SERPINA3 | chr14:94614599-94614618 |
| BCL2L11 | chr2:111124008-111124027 | PBRM1 | chr3:52651751-52651770 | SERPINA3 | chr14:94614744-94614763 |
| BCL2L11 | chr2:111123848-111123867 | WDR6 | chr3:49008972-49008991 | SERPINA3 | chr14:94614944-94614963 |
| BCL2L11 | chr2:111123849-111123868 | WDR6 | chr3:49011963-49011982 | SERPINA3 | chr14:94614885-94614904 |
| CHIC2 | chr4:54064267-54064286 | WDR6 | chr3:49011741-49011760 | SERPINA3 | chr14:94614692-94614711 |
| CHIC2 | chr4:54049066-54049085 | WDR6 | chr3:49014895-49014914 | SEMA7A | chr15:74417586-74417605 |
| CHIC2 | chr4:54048982-54049001 | WDR6 | chr3:49012228-49012247 | SEMA7A | chr15:74416690-74416709 |
| CHIC2 | chr4:54064276-54064295 | WDR6 | chr3:49007462-49007481 | SEMA7A | chr15:74417405-74417424 |
| CHIC2 | chr4:54014101-54014120 | WDR6 | chr3:49012620-49012639 | SEMA7A | chr15:74416640-74416659 |
| CHIC2 | chr4:54013870-54013889 | WDR6 | chr3:49012948-49012967 | SEMA7A | chr15:74415947-74415966 |
| CHIC2 | chr4:54049029-54049048 | RBM39 | chr20:35729298-35729317 | SEMA7A | chr15:74411646-74411665 |
| CHIC2 | chr4:54049258-54049277 | RBM39 | chr20:35738973-35738992 | SEMA7A | chr15:74417429-74417448 |
| CHIC2 | chr4:54064203-54064222 | RBM39 | chr20:35725067-35725086 | SEMA7A | chr15:74414850-74414869 |
| CHIC2 | chr4:54064222-54064241 | RBM39 | chr20:35714187-35714206 | SEMA7A | chr15:74417393-74417412 |
| CHIC2 | chr4:54014065-54014084 | RBM39 | chr20:35716784-35716803 | DHODH | chr16:72014466-72014485 |
| CHIC2 | chr4:54064183-54064202 | RBM39 | chr20:35739528-35739547 | DHODH | chr16:72008782-72008801 |
| FLI1 | chr11:128772938-128772957 | RBM39 | chr20:35734223-35734242 | DHODH | chr16:72012120-72012139 |
| FLI1 | chr11:128810556-128810575 | RBM39 | chr20:35735042-35735061 | DHODH | chr16:72012061-72012080 |
| FLI1 | chr11:128768268-128768287 | RBM39 | chr20:35724711-35724730 | DHODH | chr16:72022430-72022449 |
| FLI1 | chr11:128772807-128772826 | RBM39 | chr20:35729482-35729501 | DHODH | chr16:72014503-72014522 |
| FLI1 | chr11:128807189-128807208 | RBM39 | chr20:35731997-35732016 | DHODH | chr16:72014529-72014548 |
| FLI1 | chr11:128768230-128768249 | RBM39 | chr20:35731969-35731988 | DHODH | chr16:72012094-72012113 |

TABLE 6A-continued

Human Genome Coordinates

| Target | Coordinates | Target | Coordinates | Target | Coordinates |
|---|---|---|---|---|---|
| FLI1 | chr11:128807207-128807226 | RBM39 | chr20:35740826-35740845 | DHODH | chr16:72012147-72012166 |
| FLI1 | chr11:128810519-128810538 | RBM39 | chr20:35716771-35716790 | DHODH | chr16:72017036-72017055 |
| FLI1 | chr11:128810490-128810509 | RBM39 | chr20:35707976-35707995 | DHODH | chr16:72008781-72008800 |
| FLI1 | chr11:128810665-128810684 | RBM39 | chr20:35734220-35734239 | DHODH | chr16:72012216-72012235 |
| FLI1 | chr11:128772978-128772997 | RBM39 | chr20:35707942-35707961 | DHODH | chr16:72014491-72014510 |
| FLI1 | chr11:128772894-128772913 | RBM39 | chr20:35729478-35729497 | DHODH | chr16:72008781-72008800 |
| PCBP1 | chr2:70087872-70087891 | RBM39 | chr20:35740555-35740574 | DHODH | chr16:72014548-72014567 |
| PCBP1 | chr2:70087909-70087928 | RBM39 | chr20:35736543-35736562 | UMPS | chr3:124738139-124738158 |
| PCBP1 | chr2:70087790-70087809 | RBM39 | chr20:35739531-35739550 | UMPS | chr3:124730574-124730593 |
| PCBP1 | chr2:70087821-70087840 | RBM39 | chr20:35732003-35732022 | UMPS | chr3:124737663-124737682 |
| PCBP1 | chr2:70087998-70088017 | RBM39 | chr20:35714241-35714260 | UMPS | chr3:124737918-124737937 |
| PCBP1 | chr2:70088588-70088607 | RBM39 | chr20:35736551-35736570 | UMPS | chr3:124735177-124735196 |
| PCBP1 | chr2:70088106-70088125 | E2F8 | chr11:19234923-19234942 | GNAS | chr20:58895661-58895680 |
| PCBP1 | chr2:70087940-70087959 | E2F8 | chr11:19234390-19234409 | GNAS | chr20:58903685-58903704 |
| PCBP1 | chr2:70088307-70088326 | E2F8 | chr11:19237345-19237364 | GNAS | chr20:58905460-58905479 |
| PCBP1 | chr2:70088200-70088219 | E2F8 | chr11:19235005-19235024 | GNAS | chr20:58840352-58840371 |
| PCBP1 | chr2:70088063-70088082 | E2F8 | chr11:19225425-19225444 | GNAS | chr20:58840096-58840115 |
| PCBP1 | chr2:70087845-70087864 | E2F8 | chr11:19237329-19237348 | GNAS | chr20:58840253-58840272 |
| | | E2F8 | chr11:19234967-19234986 | GNAS | chr20:58891819-58891838 |
| | | E2F8 | chr11:19234422-19234441 | GNAS | chr20:58891756-58891775 |
| | | E2F8 | chr11:19237906-19237925 | GNAS | chr20:58891768-58891787 |
| | | E2F8 | chr11:19237980-19237999 | GNAS | chr20:58840195-58840214 |
| | | E2F8 | chr11:19232290-19232309 | GNAS | chr20:58891728-58891747 |
| | | E2F8 | chr11:19229509-19229528 | GNAS | chr20:58840198-58840217 |

TABLE 6B

Murine Genome Coordinates

| Target | Coordinates | Target | Coordinates | Target | Coordinates |
|---|---|---|---|---|---|
| Bcl2l11 | chr2: 128128713-128128732 | Fli1 | chr9: 32461444-32461463 | Wdr6 | chr9: 108578530-108578549 |
| Bcl2l11 | chr2: 128147115-128147134 | Fli1 | chr9: 32461386-32461405 | Wdr6 | chr9: 108576565-108576584 |
| Bcl2l11 | chr2: 128128731-128128750 | Fli1 | chr9: 32461401-32461420 | Wdr6 | chr9: 108578514-108578533 |
| Bcl2l11 | chr2: 128147173-128147192 | Fli1 | chr9: 32465687-32465706 | Wdr6 | chr9: 108578497-108578516 |
| Bcl2l11 | chr2: 128128648-128128667 | Fli1 | chr9: 32461420-32461439 | Wdr6 | chr9: 108576511-108576530 |
| Bcl2l11 | chr2: 128128660-128128679 | Fli1 | chr9: 32424186-32424205 | Dhodh | chr8: 109596082-109596101 |
| Bcl2l11 | chr2: 128147091-128147110 | Fli1 | chr9: 32461239-32461258 | Dhodh | chr8: 109601459-109601478 |
| Bcl2l11 | chr2: 128128682-128128701 | Fli1 | chr9: 32424232-32424251 | Dhodh | chr8: 109603453-109603472 |
| Bcl2l11 | chr2: 128128640-128128659 | Pcbp1 | chr6: 86525508-86525527 | Dhodh | chr8: 109603306-109603325 |

TABLE 6B-continued

Murine Genome Coordinates

| Target | Coordinates | Target | Coordinates | Target | Coordinates |
|---|---|---|---|---|---|
| Bcl2l11 | chr2: 128147141-128147160 | Pcbp1 | chr6: 86524927-86524946 | Dhodh | chr8: 109603364-109603383 |
| Bcl2l11 | chr2: 128158269-128158288 | Pcbp1 | chr6: 86525842-86525861 | Dhodh | chr8: 109603351-109603370 |
| Bcl2l11 | chr2: 128158233-128158252 | Pcbp1 | chr6: 86525525-86525544 | Dhodh | chr8: 109596173-109596192 |
| Bcl2l11 | chr2: 128147129-128147148 | Pcbp1 | chr6: 86525608-86525627 | Dhodh | chr8: 109601503-109601522 |
| Bcl2l11 | chr2: 128128753-128128772 | Pcbp1 | chr6: 86525731-86525750 | Gnas | chr2: 174334196-174334215 |
| Bcl2l11 | chr2: 128158301-128158320 | Pcbp1 | chr6: 86525676-86525695 | Gnas | chr2: 174345476-174345495 |
| Bcl2l11 | chr2: 128147086-128147105 | Pcbp1 | chr6: 86525148-86525167 | Gnas | chr2: 174346023-174346042 |
| Bcl2l11 | chr2: 128128730-128128749 | Pbrm1 | 14: 31040494-31040513 | Gnas | chr2: 174341872-174341891 |
| Bcl2l11 | chr2: 128128992-128129011 | Pbrm1 | 14: 31038941-31038960 | Gnas | chr2: 174345749-174345768 |
| Chic2 | chr5: 75027179-75027198 | Pbrm1 | 14: 31061547-31061566 | Gnas | chr2: 174345419-174345438 |
| Chic2 | chr5: 75044295-75044314 | Pbrm1 | 14: 31036055-31036074 | Gnas | chr2: 174334251-174334270 |
| Chic2 | chr5: 75044192-75044211 | Pbrm1 | 14: 31067548-31067567 | Gnas | chr2: 174345768-174345787 |
| Chic2 | chr5: 75011480-75011499 | Pbrm1 | 14: 31027510-31027529 | | |
| Chic2 | chr5: 75044214-75044233 | Pbrm1 | 14: 31067943-31067962 | | |
| Chic2 | chr5: 75011437-75011456 | Pbrm1 | 14: 31030854-31030873 | | |
| Chic2 | chr5: 75027108-75027127 | | | | |
| Chic2 | chr5: 75044244-75044263 | | | | |

TABLE 6C

Human Genome Coordinates

| Target | Coordinates | Target | Coordinates | Target | Coordinates |
|---|---|---|---|---|---|
| ZC3H12A | Chr1: 37480274_37480293 | ZC3H12A | Chr1: 37482857_37482876 | ZC3H12A | Chr1: 37483381_37483400 |
| ZC3H12A | Chr1: 37482967_37482986 | ZC3H12A | Chr1: 37475578_37475597 | ZC3H12A | Chr1: 37482899_37482918 |
| ZC3H12A | Chr1: 37482922_37482941 | ZC3H12A | Chr1: 37480329_37480348 | ZC3H12A | Chr1: 37480373_37480392 |
| ZC3H12A | Chr1: 37480273_37480292 | ZC3H12A | Chr1: 37480288_37480307 | ZC3H12A | Chr1: 37481847_37481866 |
| ZC3H12A | Chr1: 37482886_37482905 | ZC3H12A | Chr1: 37481600_37481619 | ZC3H12A | Chr1: 37483330_37483349 |
| ZC3H12A | Chr1: 37483185_37483204 | ZC3H12A | Chr1: 37483212_37483231 | ZC3H12A | Chr1: 37483065_37483084 |
| ZC3H12A | Chr1: 37475817_37475836 | ZC3H12A | Chr1: 37483337_37483356 | ZC3H12A | Chr1: 37482499_37482518 |
| ZC3H12A | Chr1: 37483033_37483052 | ZC3H12A | Chr1: 37475542_37475561 | ZC3H12A | Chr1: 37483105_37483124 |
| ZC3H12A | Chr1: 37480408_37480427 | ZC3H12A | Chr1: 37483197_37483216 | ZC3H12A | Chr1: 37475631_37475650 |
| ZC3H12A | Chr1: 37483026_37483045 | ZC3H12A | Chr1: 37482730_37482749 | ZC3H12A | Chr1: 37483530_37483549 |
| ZC3H12A | Chr1: 37483463_37483482 | ZC3H12A | Chr1: 37475599_37475618 | ZC3H12A | Chr1: 37483407_37483426 |
| ZC3H12A | Chr1: 37480362_37480381 | ZC3H12A | Chr1: 37483262_37483281 | ZC3H12A | Chr1: 37483308_37483327 |
| ZC3H12A | Chr1: 37482962_37482981 | ZC3H12A | Chr1: 37482790_37482809 | ZC3H12A | Chr1: 37482853_37482872 |
| ZC3H12A | Chr1: 37475775_37475794 | ZC3H12A | Chr1: 37482719_37482738 | ZC3H12A | Chr1: 37482934_37482953 |
| ZC3H12A | Chr1: 37475509_37475528 | ZC3H12A | Chr1: 37482860_37482879 | ZC3H12A | Chr1: 37475591_37475610 |
| ZC3H12A | Chr1: 37475722_37475741 | ZC3H12A | Chr1: 37483443_37483462 | ZC3H12A | Chr1: 37475826_37475845 |
| ZC3H12A | Chr1: 37475818_37475837 | ZC3H12A | Chr1: 37483558_37483577 | ZC3H12A | Chr1: 37475865_37475884 |
| ZC3H12A | Chr1: 37482966_37482985 | ZC3H12A | Chr1: 37481599_37481618 | ZC3H12A | Chr1: 37481784_37481803 |
| ZC3H12A | Chr1: 37480388_37480407 | ZC3H12A | Chr1: 37475845_37475864 | ZC3H12A | Chr1: 37480322_37480341 |
| ZC3H12A | Chr1: 37483142_37483161 | ZC3H12A | Chr1: 37475730_37475749 | ZC3H12A | Chr1: 37475664_37475683 |
| ZC3H12A | Chr1: 37482448_37482467 | ZC3H12A | Chr1: 37482524_37482543 | ZC3H12A | Chr1: 37475757_37475776 |
| ZC3H12A | Chr1: 37483049_37483068 | ZC3H12A | Chr1: 37482849_37482868 | ZC3H12A | Chr1: 37483385_37483404 |
| ZC3H12A | Chr1: 37482905_37482924 | ZC3H12A | Chr1: 37475529_37475548 | ZC3H12A | Chr1: 37482933_37482952 |
| ZC3H12A | Chr1: 37482733_37482752 | ZC3H12A | Chr1: 37475664_37475683 | ZC3H12A | Chr1: 37475866_37475885 |
| ZC3H12A | Chr1: 37480423_37480442 | ZC3H12A | Chr1: 37482972_37482991 | ZC3H12A | Chr1: 37475843_37475862 |
| ZC3H12A | Chr1: 37482456_37482475 | ZC3H12A | Chr1: 37483321_37483340 | ZC3H12A | Chr1: 37475797_37475816 |
| ZC3H12A | Chr1: 37483551_37483570 | ZC3H12A | Chr1: 37482984_37483003 | ZC3H12A | Chr1: 37475642_37475661 |
| ZC3H12A | Chr1: 37481767_37481786 | ZC3H12A | Chr1: 37475807_37475826 | ZC3H12A | Chr1: 37483270_37483289 |
| ZC3H12A | Chr1: 37475715_37475734 | ZC3H12A | Chr1: 37483213_37483232 | ZC3H12A | Chr1: 37483024_37483043 |
| ZC3H12A | Chr1: 37483377_37483396 | ZC3H12A | Chr1: 37482427_37482446 | ZC3H12A | Chr1: 37483201_37483220 |
| ZC3H12A | Chr1: 37475593_37475612 | ZC3H12A | Chr1: 37483104_37483123 | ZC3H12A | Chr1: 37482447_37482466 |
| ZC3H12A | Chr1: 37475875_37475894 | ZC3H12A | Chr1: 37482879_37482898 | ZC3H12A | Chr1: 37483253_37483272 |

TABLE 6C-continued

Human Genome Coordinates

| Target | Coordinates | Target | Coordinates | Target | Coordinates |
| --- | --- | --- | --- | --- | --- |
| ZC3H12A | Chr1: 37475534_37475553 | ZC3H12A | Chr1: 37483409_37483428 | ZC3H12A | Chr1: 37483429_37483448 |
| ZC3H12A | Chr1: 37482764_37482783 | ZC3H12A | Chr1: 37482752_37482771 | ZC3H12A | Chr1: 37483195_37483214 |
| ZC3H12A | Chr1: 37475869_37475888 | ZC3H12A | Chr1: 37480391_37480410 | ZC3H12A | Chr1: 37481648_37481667 |
| ZC3H12A | Chr1: 37483437_37483456 | ZC3H12A | Chr1: 37475694_37475713 | ZC3H12A | Chr1: 37483424_37483443 |
| ZC3H12A | Chr1: 37475598_37475617 | ZC3H12A | Chr1: 37482458_37482477 | ZC3H12A | Chr1: 37475580_37475599 |
| ZC3H12A | Chr1: 37482438_37482457 | ZC3H12A | Chr1: 37475774_37475793 | ZC3H12A | Chr1: 37482980_37482999 |
| ZC3H12A | Chr1: 37483257_37483276 | ZC3H12A | Chr1: 37475574_37475593 | ZC3H12A | Chr1: 37480408_37480427 |
| ZC3H12A | Chr1: 37483263_37483282 | ZC3H12A | Chr1: 37475803_37475822 | ZC3H12A | Chr1: 37483405_37483424 |
| ZC3H12A | Chr1: 37482545_37482564 | ZC3H12A | Chr1: 37481605_37481624 | ZC3H12A | Chr1: 37475740_37475759 |
| ZC3H12A | Chr1: 37483015_37483034 | ZC3H12A | Chr1: 37482437_37482456 | ZC3H12A | Chr1: 37480387_37480406 |
| ZC3H12A | Chr1: 37481595_37481614 | ZC3H12A | Chr1: 37482825_37482844 | ZC3H12A | Chr1: 37483507_37483526 |
| ZC3H12A | Chr1: 37482923_37482942 | ZC3H12A | Chr1: 37483595_37483614 | ZC3H12A | Chr1: 37483110_37483129 |
| ZC3H12A | Chr1: 37483143_37483162 | ZC3H12A | Chr1: 37483510_37483529 | ZC3H12A | Chr1: 37483325_37483344 |
| ZC3H12A | Chr1: 37482348_37482367 | ZC3H12A | Chr1: 37483283_37483302 | ZC3H12A | Chr1: 37481692_37481711 |
| ZC3H12A | Chr1: 37483018_37483037 | ZC3H12A | Chr1: 37482446_37482465 | ZC3H12A | Chr1: 37475826_37475845 |
| ZC3H12A | Chr1: 37482612_37482631 | ZC3H12A | Chr1: 37475700_37475719 | ZC3H12A | Chr1: 37483098_37483117 |
| ZC3H12A | Chr1: 37475613_37475632 | ZC3H12A | Chr1: 37475721_37475740 | ZC3H12A | Chr1: 37481758_37481777 |
| ZC3H12A | Chr1: 37475563_37475582 | ZC3H12A | Chr1: 37475628_37475647 | ZC3H12A | Chr1: 37480320_37480339 |
| ZC3H12A | Chr1: 37475535_37475554 | ZC3H12A | Chr1: 37482848_37482867 | ZC3H12A | Chr1: 37483380_37483399 |
| ZC3H12A | Chr1: 37482843_37482862 | ZC3H12A | Chr1: 37483134_37483153 | ZC3H12A | Chr1: 37483011_37483030 |
| ZC3H12A | Chr1: 37480424_37480443 | ZC3H12A | Chr1: 37475543_37475562 | ZC3H12A | Chr1: 37483509_37483528 |
| ZC3H12A | Chr1: 37482606_37482625 | ZC3H12A | Chr1: 37482799_37482818 | ZC3H12A | Chr1: 37483509_37483528 |
| ZC3H12A | Chr1: 37483098_37483117 | ZC3H12A | Chr1: 37483296_37483315 | ZC3H12A | Chr1: 37482768_37482787 |
| ZC3H12A | Chr1: 37483508_37483527 | ZC3H12A | Chr1: 37483332_37483351 | ZC3H12A | Chr1: 37475804_37475823 |
| ZC3H12A | Chr1: 37483559_37483578 | ZC3H12A | Chr1: 37483600_37483619 | ZC3H12A | Chr1: 37475808_37475827 |
| ZC3H12A | Chr1: 37483256_37483275 | ZC3H12A | Chr1: 37482410_37482429 | ZC3H12A | Chr1: 37475859_37475878 |
| ZC3H12A | Chr1: 37475936_37475955 | ZC3H12A | Chr1: 37481718_37481737 | ZC3H12A | Chr1: 37482973_37482992 |
| ZC3H12A | Chr1: 37475607_37475626 | ZC3H12A | Chr1: 37483395_37483414 | ZC3H12A | Chr1: 37475634_37475653 |
| ZC3H12A | Chr1: 37475809_37475828 | ZC3H12A | Chr1: 37482428_37482447 | ZC3H12A | Chr1: 37475854_37475873 |
| ZC3H12A | Chr1: 37483186_37483205 | ZC3H12A | Chr1: 37475562_37475581 | ZC3H12A | Chr1: 37480334_37480353 |
| ZC3H12A | Chr1: 37481747_37481766 | ZC3H12A | Chr1: 37483500_37483519 | ZC3H12A | Chr1: 37480414_37480433 |
| ZC3H12A | Chr1: 37482734_37482753 | ZC3H12A | Chr1: 37475827_37475846 | ZC3H12A | Chr1: 37480316_37480335 |
| ZC3H12A | Chr1: 37483278_37483297 | ZC3H12A | Chr1: 37483586_37483605 | ZC3H12A | Chr1: 37482971_37482990 |
| ZC3H12A | Chr1: 37482332_37482351 | ZC3H12A | Chr1: 37483089_37483108 | ZC3H12A | Chr1: 37482781_37482800 |
| ZC3H12A | Chr1: 37483109_37483128 | ZC3H12A | Chr1: 37483419_37483438 | ZC3H12A | Chr1: 37483173_37483192 |
| ZC3H12A | Chr1: 37475633_37475652 | ZC3H12A | Chr1: 37480285_37480304 | ZC3H12A | Chr1: 37482391_37482410 |
| ZC3H12A | Chr1: 37482591_37482610 | ZC3H12A | Chr1: 37483256_37483275 | ZC3H12A | Chr1: 37482392_37482411 |
| ZC3H12A | Chr1: 37483271_37483290 | ZC3H12A | Chr1: 37483420_37483439 | ZC3H12A | Chr1: 37482936_37482955 |
| ZC3H12A | Chr1: 37483603_37483622 | ZC3H12A | Chr1: 37475691_37475710 | ZC3H12A | Chr1: 37483408_37483427 |
| ZC3H12A | Chr1: 37482504_37482523 | ZC3H12A | Chr1: 37483419_37483438 | ZC3H12A | Chr1: 37481779_37481798 |
| ZC3H12A | Chr1: 37483252_37483271 | ZC3H12A | Chr1: 37475918_37475937 | ZC3H12A | Chr1: 37483206_37483225 |
| ZC3H12A | Chr1: 37483119_37483138 | ZC3H12A | Chr1: 37475589_37475608 | ZC3H12A | Chr1: 37482561_37482580 |
| ZC3H12A | Chr1: 37482343_37482362 | ZC3H12A | Chr1: 37482362_37482381 | ZC3H12A | Chr1: 37481745_37481764 |
| ZC3H12A | Chr1: 37483144_37483163 | ZC3H12A | Chr1: 37482566_37482585 | ZC3H12A | Chr1: 37475802_37475821 |
| ZC3H12A | Chr1: 37483213_37483232 | ZC3H12A | Chr1: 37482963_37482982 | ZC3H12A | Chr1: 37483494_37483513 |
| ZC3H12A | Chr1: 37482981_37483000 | ZC3H12A | Chr1: 37483420_37483439 | ZC3H12A | Chr1: 37483371_37483390 |
| ZC3H12A | Chr1: 37482789_37482808 | ZC3H12A | Chr1: 37483139_37483158 | ZC3H12A | Chr1: 37482552_37482571 |
| ZC3H12A | Chr1: 37483159_37483178 | ZC3H12A | Chr1: 37483619_37483638 | ZC3H12A | Chr1: 37475491_37475510 |
| ZC3H12A | Chr1: 37482349_37482368 | ZC3H12A | Chr1: 37481764_37481783 | ZC3H12A | Chr1: 37482479_37482498 |
| ZC3H12A | Chr1: 37483602_37483621 | ZC3H12A | Chr1: 37475650_37475669 | ZC3H12A | Chr1: 37483140_37483159 |
| ZC3H12A | Chr1: 37481596_37481615 | ZC3H12A | Chr1: 37483405_37483424 | ZC3H12A | Chr1: 37483313_37483332 |
| ZC3H12A | Chr1: 37482537_37482556 | ZC3H12A | Chr1: 37483037_37483056 | ZC3H12A | Chr1: 37483458_37483477 |
| ZC3H12A | Chr1: 37482370_37482389 | ZC3H12A | Chr1: 37483211_37483230 | ZC3H12A | Chr1: 37483320_37483339 |
| ZC3H12A | Chr1: 37475546_37475565 | ZC3H12A | Chr1: 37475537_37475556 | ZC3H12A | Chr1: 37483204_37483223 |
| ZC3H12A | Chr1: 37482598_37482617 | ZC3H12A | Chr1: 37475756_37475775 | ZC3H12A | Chr1: 37475792_37475811 |
| ZC3H12A | Chr1: 37483146_37483165 | ZC3H12A | Chr1: 37482403_37482422 | ZC3H12A | Chr1: 37483475_37483494 |
| ZC3H12A | Chr1: 37475812_37475831 | ZC3H12A | Chr1: 37482455_37482474 | ZC3H12A | Chr1: 37475577_37475596 |
| ZC3H12A | Chr1: 37483400_37483419 | ZC3H12A | Chr1: 37480311_37480330 | ZC3H12A | Chr1: 37475787_37475806 |
| ZC3H12A | Chr1: 37475703_37475722 | ZC3H12A | Chr1: 37482586_37482605 | ZC3H12A | Chr1: 37483574_37483593 |
| ZC3H12A | Chr1: 37483418_37483437 | ZC3H12A | Chr1: 37483099_37483118 | ZC3H12A | Chr1: 37480284_37480303 |
| ZC3H12A | Chr1: 37480284_37480303 | ZC3H12A | Chr1: 37483342_37483361 | ZC3H12A | Chr1: 37482369_37482388 |
| ZC3H12A | Chr1: 37482800_37482819 | ZC3H12A | Chr1: 37481823_37481842 | ZC3H12A | Chr1: 37483384_37483403 |
| ZC3H12A | Chr1: 37475721_37475740 | ZC3H12A | Chr1: 37482777_37482796 | ZC3H12A | Chr1: 37483425_37483444 |
| ZC3H12A | Chr1: 37482715_37482734 | ZC3H12A | Chr1: 37482412_37482431 | ZC3H12A | Chr1: 37482582_37482601 |
| ZC3H12A | Chr1: 37480281_37480300 | ZC3H12A | Chr1: 37483604_37483623 | ZC3H12A | Chr1: 37483153_37483172 |
| ZC3H12A | Chr1: 37482491_37482510 | ZC3H12A | Chr1: 37483438_37483457 | ZC3H12A | Chr1: 37482935_37482954 |
| ZC3H12A | Chr1: 37483497_37483516 | ZC3H12A | Chr1: 37482445_37482464 | ZC3H12A | Chr1: 37483378_37483397 |
| ZC3H12A | Chr1: 37475899_37475918 | ZC3H12A | Chr1: 37483331_37483350 | ZC3H12A | Chr1: 37482952_37482971 |
| ZC3H12A | Chr1: 37475889_37475908 | ZC3H12A | Chr1: 37483111_37483130 | ZC3H12A | Chr1: 37483399_37483418 |
| ZC3H12A | Chr1: 37482375_37482394 | ZC3H12A | Chr1: 37482847_37482866 | ZC3H12A | Chr1: 37483309_37483328 |
| ZC3H12A | Chr1: 37475741_37475760 | ZC3H12A | Chr1: 37483249_37483268 | ZC3H12A | Chr1: 37483200_37483219 |
| ZC3H12A | Chr1: 37482900_37482919 | ZC3H12A | Chr1: 37481754_37481773 | ZC3H12A | Chr1: 37481641_37481660 |
| ZC3H12A | Chr1: 37482442_37482461 | ZC3H12A | Chr1: 37475684_37475703 | ZC3H12A | Chr1: 37481656_37481675 |
| ZC3H12A | Chr1: 37481644_37481663 | ZC3H12A | Chr1: 37482519_37482538 | ZC3H12A | Chr1: 37483036_37483055 |
| ZC3H12A | Chr1: 37482464_37482483 | ZC3H12A | Chr1: 37482475_37482494 | ZC3H12A | Chr1: 37483474_37483493 |
| ZC3H12A | Chr1: 37482994_37483013 | ZC3H12A | Chr1: 37482613_37482632 | ZC3H12A | Chr1: 37483004_37483023 |

TABLE 6C-continued

| Target | Coordinates | Target | Coordinates | Target | Coordinates |
|---|---|---|---|---|---|
| ZC3H12A | Chr1: 37483437__37483456 | ZC3H12A | Chr1: 37482939__37482958 | ZC3H12A | Chr1: 37481846__37481865 |
| ZC3H12A | Chr1: 37482736__37482755 | ZC3H12A | Chr1: 37475541__37475560 | ZC3H12A | Chr1: 37483205__37483224 |
| ZC3H12A | Chr1: 37482538__37482557 | ZC3H12A | Chr1: 37481763__37481782 | ZC3H12A | Chr1: 37483406__37483425 |
| ZC3H12A | Chr1: 37483515__37483534 | ZC3H12A | Chr1: 37483231__37483250 | ZC3H12A | Chr1: 37480336__37480355 |
| ZC3H12A | Chr1: 37475874__37475893 | ZC3H12A | Chr1: 37482953__37482972 | ZC3H12A | Chr1: 37481716__37481735 |
| ZC3H12A | Chr1: 37483145__37483164 | ZC3H12A | Chr1: 37482407__37482426 | ZC3H12A | Chr1: 37480335__37480354 |
| ZC3H12A | Chr1: 37482587__37482606 | ZC3H12A | Chr1: 37475808__37475827 | ZC3H12A | Chr1: 37481659__37481678 |
| ZC3H12A | Chr1: 37475482__37475501 | ZC3H12A | Chr1: 37481620__37481639 | ZC3H12A | Chr1: 37475809__37475828 |
| ZC3H12A | Chr1: 37475844__37475863 | ZC3H12A | Chr1: 37475592__37475611 | ZC3H12A | Chr1: 37482565__37482584 |
| ZC3H12A | Chr1: 37480415__37480434 | ZC3H12A | Chr1: 37483156__37483175 | ZC3H12A | Chr1: 37482491__37482510 |
| ZC3H12A | Chr1: 37481709__37481728 | ZC3H12A | Chr1: 37480329__37480348 | ZC3H12A | Chr1: 37483379__37483398 |
| ZC3H12A | Chr1: 37483366__37483385 | ZC3H12A | Chr1: 37475573__37475592 | ZC3H12A | Chr1: 37481654__37481673 |
| ZC3H12A | Chr1: 37475627__37475646 | ZC3H12A | Chr1: 37483198__37483217 | ZC3H12A | Chr1: 37482567__37482586 |
| ZC3H12A | Chr1: 37482447__37482466 | ZC3H12A | Chr1: 37483557__37483576 | ZC3H12A | Chr1: 37481614__37481633 |
| ZC3H12A | Chr1: 37481758__37481777 | ZC3H12A | Chr1: 37482892__37482911 | ZC3H12A | Chr1: 37482562__37482581 |
| ZC3H12A | Chr1: 37483560__37483579 | ZC3H12A | Chr1: 37483334__37483353 | ZC3H12A | Chr1: 37475868__37475887 |
| ZC3H12A | Chr1: 37475869__37475888 | ZC3H12A | Chr1: 37481708__37481727 | ZC3H12A | Chr1: 37482557__37482576 |
| ZC3H12A | Chr1: 37481655__37481674 | ZC3H12A | Chr1: 37483063__37483082 | ZC3H12A | Chr1: 37483511__37483530 |
| ZC3H12A | Chr1: 37481645__37481664 | ZC3H12A | Chr1: 37482998__37483017 | ZC3H12A | Chr1: 37475615__37475634 |
| ZC3H12A | Chr1: 37483016__37483035 | ZC3H12A | Chr1: 37482942__37482961 | ZC3H12A | Chr1: 37483333__37483352 |
| ZC3H12A | Chr1: 37475838__37475857 | ZC3H12A | Chr1: 37475508__37475527 | ZC3H12A | Chr1: 37482840__37482859 |
| ZC3H12A | Chr1: 37482850__37482869 | ZC3H12A | Chr1: 37482371__37482390 | ZC3H12A | Chr1: 37483545__37483564 |
| ZC3H12A | Chr1: 37475510__37475529 | ZC3H12A | Chr1: 37483119__37483138 | ZC3H12A | Chr1: 37482830__37482849 |
| ZC3H12A | Chr1: 37483510__37483529 | ZC3H12A | Chr1: 37482798__37482817 | ZC3H12A | Chr1: 37482444__37482463 |
| ZC3H12A | Chr1: 37483064__37483083 | ZC3H12A | Chr1: 37475859__37475878 | ZC3H12A | Chr1: 37482571__37482590 |
| ZC3H12A | Chr1: 37483149__37483168 | ZC3H12A | Chr1: 37483401__37483420 | ZC3H12A | Chr1: 37482553__37482572 |
| ZC3H12A | Chr1: 37483449__37483468 | ZC3H12A | Chr1: 37482851__37482870 | ZC3H12A | Chr1: 37483543__37483562 |
| ZC3H12A | Chr1: 37483264__37483283 | ZC3H12A | Chr1: 37475524__37475543 | ZC3H12A | Chr1: 37483542__37483561 |
| ZC3H12A | Chr1: 37475508__37475527 | ZC3H12A | Chr1: 37475601__37475620 | ZC3H12A | Chr1: 37482575__37482594 |
| ZC3H12A | Chr1: 37480415__37480434 | ZC3H12A | Chr1: 37475815__37475834 | ZC3H12A | Chr1: 37475855__37475874 |
| ZC3H12A | Chr1: 37482918__37482937 | ZC3H12A | Chr1: 37482801__37482820 | ZC3H12A | Chr1: 37482572__37482591 |
| ZC3H12A | Chr1: 37482474__37482493 | ZC3H12A | Chr1: 37475544__37475563 | Zc3h12a | chr1: 125122335-125122354 |
| ZC3H12A | Chr1: 37483232__37483251 | ZC3H12A | Chr1: 37483010__37483029 | Zc3h12a | chr1: 125121083-125121102 |
| ZC3H12A | Chr1: 37475732__37475751 | ZC3H12A | Chr1: 37483077__37483096 | Zc3h12a | chr1: 125120961-125120980 |
| ZC3H12A | Chr1: 37481602__37481621 | ZC3H12A | Chr1: 37482404__37482423 | Zc3h12a | chr1: 125122390-125122409 |
| ZC3H12A | Chr1: 37480289__37480308 | ZC3H12A | Chr1: 37475692__37475711 | Zc3h12a | chr1: 125120373-125120392 |
| ZC3H12A | Chr1: 37483165__37483184 | ZC3H12A | Chr1: 37483596__37483615 | Zc3h12a | chr1: 125122250-125122269 |
| ZC3H12A | Chr1: 37483248__37483267 | ZC3H12A | Chr1: 37483372__37483391 | Zc3h12a | chr1: 125122375-125122394 |
| ZC3H12A | Chr1: 37483078__37483097 | ZC3H12A | Chr1: 37481596__37481615 | Zc3h12a | chr1: 125120975-125120994 |
| ZC3H12A | Chr1: 37483017__37483036 | ZC3H12A | Chr1: 37480370__37480389 | | |
| ZC3H12A | Chr1: 37483174__37483193 | ZC3H12A | Chr1: 37480377__37480396 | | |

TABLE 6D

Murine Genome Coordinates

| Target | Coordinates |
|---|---|
| Zc3h12a | chr1: 125122335-125122354 |
| Zc3h12a | chr1: 125121083-125121102 |
| Zc3h12a | chr1: 125120961-125120980 |
| Zc3h12a | chr1: 125122390-125122409 |
| Zc3h12a | chr1: 125120373-125120392 |
| Zc3h12a | chr1: 125122250-125122269 |
| Zc3h12a | chr1: 125122375-125122394 |
| Zc3h12a | chr1: 125120975-125120994 |

TABLE 6E

Human Genome Coordinates

| Target | Coordinates |
|---|---|
| MAP4K1 | chr19: 38617794-38617813 |
| MAP4K1 | chr19: 38612617-38612636 |
| MAP4K1 | chr19: 38599957-38599976 |
| MAP4K1 | chr19: 38617616-38617635 |
| MAP4K1 | chr19: 38607904-38607923 |
| MAP4K1 | chr19: 38613865-38613884 |
| MAP4K1 | chr19: 38607916-38607935 |
| MAP4K1 | chr19: 38617828-38617847 |
| MAP4K1 | chr19: 38616225-38616244 |
| MAP4K1 | chr19: 38610007-38610026 |
| MAP4K1 | chr19: 38599964-38599983 |
| MAP4K1 | chr19: 38612614-38612633 |
| MAP4K1 | chr19: 38617365-38617384 |

TABLE 6F

| Murine Genome Coordinates | |
|---|---|
| Target | Coordinates |
| Map4k1 | chr7: 28983466-28983485 |
| Map4k1 | chr7: 28983244-28983263 |
| Map4k1 | chr7: 28983478-28983497 |
| Map4k1 | chr7: 28983003-28983022 |
| Map4k1 | chr7: 28983420-28983439 |
| Map4k1 | chr7: 28983436-28983455 |
| Map4k1 | chr7: 28983405-28983424 |
| Map4k1 | chr7: 28983214-28983233 |
| Map4k1 | chr7: 28984113-28984132 |
| Map4k1 | chr7: 28984134-28984153 |
| Map4k1 | chr7: 28983019-28983038 |
| Map4k1 | chr7: 28986802-28986821 |
| Map4k1 | chr7: 28983446-28983465 |
| Map4k1 | chr7: 28983220-28983239 |
| Map4k1 | chr7: 28983466-28983485 |
| Map4k1 | chr7: 28983478-28983497 |

TABLE 6G

| Human Genome Coordinates | |
|---|---|
| Target | Coordinates |
| NR4A3 | chr9: 99826780-99826799 |
| NR4A3 | chr9: 99828951-99828970 |
| NR4A3 | chr9: 99828105-99828124 |
| NR4A3 | chr9: 99826768-99826787 |
| NR4A3 | chr9: 99828319-99828338 |
| NR4A3 | chr9: 99832766-99832785 |
| NR4A3 | chr9: 99828263-99828282 |

TABLE 6G-continued

| Human Genome Coordinates | |
|---|---|
| Target | Coordinates |
| NR4A3 | chr9: 99828909-99828928 |
| NR4A3 | chr9: 99828489-99828508 |
| NR4A3 | chr9: 99828437-99828456 |
| NR4A3 | chr9: 99828669-99828688 |
| NR4A3 | chr9: 99832703-99832722 |

TABLE 6H

| Murine Genome Coordinates | |
|---|---|
| Target | Coordinates |
| Nr4a3 | chr4: 48051580-48051599 |
| Nr4a3 | chr4: 48052171-48052190 |
| Nr4a3 | chr4: 48055944-48055963 |
| Nr4a3 | chr4: 48056028-48056047 |
| Nr4a3 | chr4: 48051515-48051534 |
| Nr4a3 | chr4: 48052131-48052150 |
| Nr4a3 | chr4: 48051303-48051322 |
| Nr4a3 | chr4: 48052115-48052134 |
| Nr4a3 | chr4: 48051287-48051306 |
| Nr4a3 | chr4: 48051580-48051599 |
| Nr4a3 | chr4: 48052171-48052190 |
| Nr4a3 | chr4: 48051348-48051367 |
| Nr4a3 | chr4: 48051255-48051274 |
| Nr4a3 | chr4: 48051366-48051385 |
| Nr4a3 | chr4: 48056024-48056043 |
| Nr4a3 | chr4: 48055983-48056002 |

---

The invention claimed is:

1. A human tumor infiltrating lymphocyte (TIL) comprising (a) a modified endogenous ZC3H12A gene and (b) a Cas endonuclease and/or a guide RNA (gRNA), wherein
ZC3H12A protein expression and/or function is reduced in the human TIL, relative to ZC3H12A protein expression and/or function in an unmodified human TIL expressing an endogenous ZC3H12A gene, and
anti-tumor efficacy of the human TIL is increased, relative to anti-tumor efficacy of an unmodified human TIL expressing an endogenous ZC3H12A gene.

2. The human TIL of claim 1, wherein the modified endogenous ZC3H12A gene comprises an insertion, deletion, and/or mutation.

3. The human TIL of claim 1, wherein the Cas endonuclease is:
   (a) a wild-type Cas protein comprising two enzymatically active domains;
   (b) a Cas nickase mutant comprising one enzymatically active domain;
   (c) a deactivated Cas protein (dCas) associated with a heterologous protein; or
   (d) a Cas ortholog.

4. The human TIL of claim 3, wherein the Cas endonuclease is a wild-type Cas9 protein comprising two enzymatically active domains.

5. The human TIL of claim 1, wherein the gRNA comprises a targeting domain sequence that hybridizes to a target sequence in the endogenous ZC3H12A gene.

6. The human TIL of claim 5, wherein the target sequence is selected from the group consisting of SEQ ID NOs: 1065-1264.

7. The human TIL of claim 5, wherein the gRNA targeting domain sequence is encoded by a sequence selected from the group consisting of SEQ ID NOs: 1065-1264.

8. The human TIL of claim 1, further comprising an exogenous transgene expressing an immune activating molecule selected from the group consisting of a cytokine, a chemokine, a co-stimulatory molecule, an activating peptide, and an antibody or an antigen-binding fragment thereof.

9. The human TIL of claim 1, further comprising a modified endogenous target gene selected from the group consisting of IKZF1, IKZF3, GATA3, BCL3, TNIP1, TNFAIP3, NFKBIA, SMAD2, TGFBR1, TGFBR2, TANK, FOXP3, RC3H1, TRAF6, IKZF2, CBLB, PPP2R2D, NRP1, HAVCR2, LAG3, TIGIT, CTLA4, PTPN6, PDCD1, BCOR, BCL2L11, FLI1, CALM2, DHODH, UMPS, RBM39, SEMA7A, CHIC2, PCBP1, PBRM1, WDR6, E2F8, SERPINA3, GNAS, MAP4K1 and NR4A3.

10. The human TIL of claim 9, further comprising a modified endogenous TGFBR2 gene.

11. The human TIL of claim 1, comprising the Cas endonuclease and the gRNA.

12. The human TIL of claim 11, wherein the Cas endonuclease is a wild-type Cas9 protein comprising two enzymatically active domains.

13. The human TIL of claim 12, wherein the gRNA comprises a targeting domain sequence that hybridizes to a target sequence in the endogenous ZC3H12A gene.

14. The human TIL of claim 13, wherein the target sequence is selected from the group consisting of SEQ ID NOs: 1065-1264.

15. The human TIL of claim 13, wherein the gRNA targeting domain sequence is encoded by a sequence selected from the group consisting of SEQ ID NOs: 1065-1264.

16. A pharmaceutical composition comprising the human TIL of claim 1.

* * * * *